US012706175B2

(12) United States Patent
Dzakula et al.

(10) Patent No.: US 12,706,175 B2
(45) **Date of Patent: *Aug. 11, 2026**

(54) METHODS AND PROCESSES FOR NON-INVASIVE ASSESSMENT OF GENETIC VARIATIONS

(71) Applicant: Sequenom, Inc., San Diego, CA (US)

(72) Inventors: Zeljko Dzakula, San Diego, CA (US); Amin R. Mazloom, San Diego, CA (US); Cosmin Deciu, San Diego, CA (US); Huiquan Wang, San Diego, CA (US)

(73) Assignee: SEQUENOM, INC., San Diego, CA (US)

( * ) Notice: Subject to any disclaimer, the term of this patent is extended or adjusted under 35 U.S.C. 154(b) by 1084 days.

This patent is subject to a terminal disclaimer.

(21) Appl. No.: 16/698,678

(22) Filed: Nov. 27, 2019

(65) Prior Publication Data

US 2020/0160934 A1 May 21, 2020

Related U.S. Application Data

(63) Continuation of application No. 13/797,508, filed on Mar. 12, 2013, now Pat. No. 10,497,461.

(60) Provisional application No. 61/663,482, filed on Jun. 22, 2012.

(51) Int. Cl.

*G16B 20/10* (2019.01)
*C12Q 1/6809* (2018.01)
*G16B 20/00* (2019.01)
*G16B 20/20* (2019.01)

(52) U.S. Cl.

CPC ........... *G16B 20/10* (2019.02); *C12Q 1/6809* (2013.01); *G16B 20/00* (2019.02); *G16B 20/20* (2019.02); *C12Q 2535/122* (2013.01); *C12Q 2537/16* (2013.01)

(58) Field of Classification Search

None

See application file for complete search history.

(56) References Cited

U.S. PATENT DOCUMENTS 4,683,195 A 7/1987 Mullins et al.
4,683,202 A 7/1987 Mullis et al.
5,075,212 A 12/1991 Rotbart
5,091,652 A 2/1992 Mathies et al.
5,432,054 A 7/1995 Saunders et al.
5,445,934 A 8/1995 Fodor et al.
5,670,325 A 9/1997 Lapidus et al.
5,720,928 A 2/1998 Schwartz et al.
5,786,146 A 7/1998 Herman et al.
5,795,714 A 8/1998 Cantor et al.
5,928,870 A 7/1999 Lapidus et al.
5,939,598 A 8/1999 Kucherlapati et al.
6,015,714 A 1/2000 Baldarelli et al.
6,090,550 A 7/2000 Collinge et al.
6,100,029 A 8/2000 Lapidus et al.
6,214,558 B1 4/2001 Shuber et al.
6,214,560 B1 4/2001 Yguerabide et al.
6,235,475 B1 5/2001 Brenner
6,258,540 B1 7/2001 Lo et al.
6,263,286 B1 7/2001 Gilmanshin et al.
6,403,311 B1 6/2002 Chan
6,566,101 B1 5/2003 Shuber et al.
6,617,133 B1 9/2003 Noda et al.
6,772,070 B2 8/2004 Gilmanshin et al.
6,818,395 B1 11/2004 Quake et al.
6,927,028 B2 8/2005 Dennis et al.
6,936,422 B2 8/2005 El Solh et al.
7,005,264 B2 2/2006 Su
7,169,560 B2 1/2007 Lapidus et al.
7,279,337 B2 10/2007 Zhu
7,282,337 B1 10/2007 Harris
7,947,454 B2 5/2011 Akeson et al.
7,960,105 B2 6/2011 Schwartz et al.
7,972,858 B2 7/2011 Meller et al.
8,688,328 B2 4/2014 Okada et al.
8,688,388 B2 4/2014 Dzakula et al.
9,367,663 B2 6/2016 Deciu et al.
9,984,198 B2 5/2018 Deciu et al.
10,196,681 B2 2/2019 Deciu et al.
10,323,268 B2 6/2019 Deciu et al.
10,424,394 B2 9/2019 Deciu et al.
10,497,461 B2 12/2019 Dzakula et al.
10,930,368 B2 2/2021 Dzakula et al.
11,437,121 B2 9/2022 Deciu et al.
11,492,254 B2 11/2022 Harale et al.

(Continued)

FOREIGN PATENT DOCUMENTS

JP 2014-534507 A 12/2014
WO 2000/006770 2/2000

(Continued)

OTHER PUBLICATIONS

Strumm, M, Hagen A, Becker R, Hofmann W, et al. Noninvasive prenatal detection of chromosomal aneuploidies using different next generation sequencing strategies and algorithms. Prenat Diagn. Jun. 2012;32(6):569-77. (Year: 2012).*

Fan, H. C. (2010). Molecular counting: From noninvasive prenatal diagnostics to whole-genome haplotyping (Order No. 28124287). Available from ProQuest Dissertations & Theses Global. (2440931542). (Year: 2010).*

Lo YM, Chiu RW. Genomic analysis of fetal nucleic acids in maternal blood. Annu Rev Genomics Hum Genet. 2012; 13:285-306. (Year: 2012).*

Bianchi DW, Platt LD, Goldberg JD, Abuhamad AZ, Sehnert AJ, Rava RP; MatErnal BLood IS Source to Accurately diagnose fetal aneuploidy (MELISSA) Study Group. Genome-wide fetal aneuploidy detection by maternal plasma DNA sequencing. Obstet Gynecol. May 2012;119(5):890-901 (Year: 2012).*

Benjamini, Yuval, and Terence P Speed. "Summarizing and Correcting the GC Content Bias in High-Throughput Sequencing." Nucleic acids research 40.10 (2012): e72-e72. Web. with supplimental (Year: 2012).*

(Continued)

*Primary Examiner* — Karlheinz R. Skowronek
*Assistant Examiner* — Joseph Pulliam
(74) *Attorney, Agent, or Firm* — LOZA & LOZA, LLP

(57) ABSTRACT

Provided herein are methods, processes and apparatuses for non-invasive assessment of genetic variations.

28 Claims, 153 Drawing Sheets

(56) References Cited

U.S. PATENT DOCUMENTS 11,492,659 B2 11/2022 Deciu et al.
11,560,586 B2 1/2023 Deciu et al.
11,697,849 B2 7/2023 Deciu et al.
2001/0014850 A1 8/2001 Gilmanshin et al.
2001/0049102 A1 12/2001 Huang et al.
2002/0006621 A1 1/2002 Bianchi
2002/0045176 A1 4/2002 Lo et al.
2002/0110818 A1 8/2002 Chan
2002/0119469 A1 8/2002 Shuber et al.
2002/0164629 A1 11/2002 Quake et al.
2003/0013101 A1 1/2003 Balasubramanian
2003/0082600 A1 5/2003 Olek et al.
2003/0180779 A1 9/2003 Lofton-Day et al.
2003/0207326 A1 11/2003 Su et al.
2003/0232346 A1 12/2003 Su et al.
2004/0081993 A1 4/2004 Cantor et al.
2004/0110208 A1 6/2004 Chan et al.
2004/0137470 A1 7/2004 Dhallan
2005/0019784 A1 1/2005 Su et al.
2005/0095599 A1 5/2005 Pittaro et al.
2005/0112590 A1 5/2005 Boom et al.
2005/0147980 A1 7/2005 Berlin et al.
2005/0164241 A1 7/2005 Hahn et al.
2005/0227278 A1 10/2005 Wall
2005/0287592 A1 12/2005 Kless
2006/0046258 A1 3/2006 Lapidus et al.
2006/0063171 A1 3/2006 Akeson et al.
2006/0068440 A1 3/2006 Chan et al.
2006/0252071 A1 11/2006 Lo et al.
2007/0065823 A1 3/2007 Dressman et al.
2007/0202525 A1 8/2007 Quake et al.
2008/0020390 A1 1/2008 Mitchell et al.
2008/0070792 A1 3/2008 Stoughton et al.
2008/0081330 A1 4/2008 Kahvejian
2008/0138809 A1 6/2008 Kapur et al.
2008/0187915 A1 8/2008 Polonsky et al.
2008/0233575 A1 9/2008 Harris et al.
2009/0026082 A1 1/2009 Rothberg et al.
2009/0029377 A1 1/2009 Lo et al.
2009/0075252 A1 3/2009 Harris et al.
2009/0129647 A1 5/2009 Dimitrova et al.
2009/0191565 A1 7/2009 Lapidus et al.
2009/0197257 A1 8/2009 Harris
2009/0317817 A1 12/2009 Oeth et al.
2009/0317818 A1 12/2009 Ehrich et al.
2010/0105049 A1 4/2010 Ehrich et al.
2010/0109197 A1 5/2010 Hansen et al.
2010/0112575 A1 5/2010 Fan et al.
2010/0112590 A1 5/2010 Lo et al.
2010/0138165 A1 6/2010 Fan et al.
2010/0151471 A1 6/2010 Faham et al.
2010/0216151 A1 8/2010 Lapidus et al.
2010/0216153 A1 8/2010 Lapidus et al.
2010/0261285 A1 10/2010 Goldstein et al.
2010/0310421 A1 12/2010 Oliver et al.
2010/0330557 A1 12/2010 Yakhini et al.
2011/0086769 A1 4/2011 Oliphant et al.
2011/0112575 A1 5/2011 Tochimura et al.
2011/0151442 A1 6/2011 Fan et al.
2011/0159601 A1 6/2011 Golovchenko et al.
2011/0171634 A1 7/2011 Xiao et al.
2011/0174625 A1 7/2011 Akeson et al.
2011/0177498 A1 7/2011 Clarke et al.
2011/0177517 A1 7/2011 Rava et al.
2011/0201507 A1 8/2011 Rava et al.
2011/0224087 A1 9/2011 Quake
2011/0230358 A1 9/2011 Rava
2011/0288780 A1 11/2011 Rabinowitz et al.
2011/0294699 A1 12/2011 Lee et al.
2011/0312503 A1 12/2011 Chuu et al.
2011/0319272 A1 12/2011 Fan
2012/0046877 A1 2/2012 Hyland et al.
2012/0122701 A1 5/2012 Ryan et al.
2012/0165203 A1 6/2012 Quake et al.
2012/0184449 A1 7/2012 Hixson et al.
2012/0214678 A1 8/2012 Rava et al.
2012/0264115 A1 10/2012 Rava
2012/0270212 A1 10/2012 Rabinowitz et al.
2012/0270739 A1 10/2012 Rava et al.
2013/0012399 A1 1/2013 Meyers
2013/0022977 A1 1/2013 Lapidus et al.
2013/0034546 A1 2/2013 Rava et al.
2013/0085681 A1 4/2013 Deciu et al.
2013/0096011 A1 4/2013 Rava et al.
2013/0130921 A1 5/2013 Gao et al.
2013/0130923 A1 5/2013 Ehrich et al.
2013/0150253 A1 6/2013 Deciu et al.
2013/0196317 A1 8/2013 Lapidus et al.
2013/0237431 A1 9/2013 Lo et al.
2013/0245961 A1 9/2013 Lo et al.
2013/0261983 A1 10/2013 Dzakula et al.
2013/0288244 A1 10/2013 Deciu et al.
2013/0304392 A1 11/2013 Deciu et al.
2013/0309666 A1 11/2013 Deciu et al.
2013/0310260 A1 11/2013 Kim et al.
2013/0325360 A1 12/2013 Deciu et al.
2013/0338933 A1 12/2013 Deciu et al.
2014/0100792 A1 4/2014 Deciu et al.
2014/0180594 A1 6/2014 Kim et al.
2014/0235474 A1 8/2014 Tang et al.
2014/0242588 A1 8/2014 Van Den Boom et al.
2014/0322709 A1 10/2014 Lapidus et al.
2015/0005176 A1 1/2015 Kim et al.
2015/0100244 A1 4/2015 Hannum
2015/0347676 A1 12/2015 Zhao et al.
2016/0034640 A1 2/2016 Zhao et al.
2016/0110497 A1 4/2016 Dzakula et al.
2016/0224724 A1 8/2016 Zhao et al.
2016/0292356 A1 10/2016 Kim et al.
2016/0319335 A1 11/2016 Deciu et al.
2019/0005188 A1 1/2019 Deciu et al.
2019/0276874 A1 9/2019 Deciu et al.
2019/0309351 A1 10/2019 Deciu et al.
2020/0160934 A1 5/2020 Dzakula et al.
2021/0174894 A1 6/2021 Dzakula et al.
2022/0383977 A1 12/2022 Deciu et al.

FOREIGN PATENT DOCUMENTS

WO 2001/032887 5/2001
WO 2002/042496 5/2002
WO 2003/000920 1/2003
WO 2003/106620 12/2003
WO 2005/023091 A3 6/2005
WO 2006/056480 6/2006
WO 2007/140417 12/2007
WO 2007/147063 12/2007
WO 2008024080 A1 2/2008
WO 2008/121828 10/2008
WO 2009/007743 1/2009
WO 2009/007743 A1 1/2009
WO 2009/032779 3/2009
WO 2009/032781 3/2009
WO 2009/046445 4/2009
WO 2010/004265 1/2010
WO 2010/033578 3/2010
WO 2010/033639 3/2010
WO 2010/056728 A1 5/2010
WO 2010/059731 5/2010
WO 2010/065470 A2 6/2010
WO 2010/115016 10/2010
WO 2011/034631 3/2011
WO 2011/038327 3/2011
WO 2011/050147 A1 4/2011
WO 2011/057094 5/2011
WO 2011/087760 7/2011
WO 2011/090556 7/2011
WO 2011/090558 7/2011
WO 2011/090559 7/2011
WO 2011/091063 7/2011
WO 2011/102998 8/2011
WO 2011/143659 A2 11/2011
WO 2011/146632 A1 11/2011
WO 2012/012703 A2 1/2012

(56) References Cited

FOREIGN PATENT DOCUMENTS

| | | |
|---|---|---|
| WO | 2012/088348 A2 | 6/2012 |
| WO | 2012/088456 A2 | 6/2012 |
| WO | 2012/103031 A2 | 8/2012 |
| WO | 2012/108920 A1 | 8/2012 |
| WO | 2012/118745 A1 | 9/2012 |
| WO | 2012149042 A2 | 11/2012 |
| WO | 2012/177792 A2 | 12/2012 |
| WO | 2013/000100 A1 | 1/2013 |
| WO | 2013/052907 A2 | 4/2013 |
| WO | 2013/052913 A2 | 4/2013 |
| WO | 2013/055817 A1 | 4/2013 |
| WO | 2013/109981 A1 | 7/2013 |
| WO | 2013/177086 | 11/2013 |
| WO | 2013/192562 | 12/2013 |
| WO | 2014/039556 | 3/2014 |
| WO | 2014/055774 | 4/2014 |
| WO | 2014/055790 A2 | 4/2014 |
| WO | 2014/116598 | 7/2014 |
| WO | 2014/165596 A1 | 10/2014 |
| WO | 2014/190286 A2 | 11/2014 |
| WO | 2015/040591 | 3/2015 |
| WO | 2015/051163 | 4/2015 |
| WO | 2015/054080 | 4/2015 |
| WO | 2015/183872 | 12/2015 |
| WO | 2016/019042 | 2/2016 |

OTHER PUBLICATIONS

Genzyme Genetics: Explaning Test Results/Karyotypes to Parents "https://www.imdsa.org/Resources/Documents/Information/ Karyotypes.pdf" web 2011 (Year: 2011).*

"Sequenom CMM's MaterniT21 PLUS LDT Now Reporting on Gender-Specific Chromosomal Abnormalities", Sequenom, Inc., Feb. 4, 2013, 3 pages.

Office Action dated Jul. 19, 2022 in U.S. Appl. No. 16/215,254, filed Dec. 10, 2018, 9 pages.

Wang et al., Next generation sequencing has lower sequence coverage and poorer SNP-detection capability in the regulatory regions, Scientific Reports, 1:55 Aug. 5, 2011, pp. 1-7.

Benjamini et al., "Estimation and correction for GC-content bias in high throughput sequencing," Department of Statistics, University of California at Berkeley, dated Jun. 24, 2011, 27 pages.

EP Extended Search Report in European Appln. No. 21182355.4, dated Dec. 6, 2021, 13 pages.

Office Action dated Aug. 1, 2017 in U.S. Appl. No. 13/797,508, filed Mar. 12, 2013 and published as US 2013-0261983 on Oct. 3, 2013, 13 pages.

Office Action dated Dec. 9, 2021 in U.S. Appl. No. 15/959,880, filed Apr. 23, 2018 and published as US-2019-0005188-A1 on Jan. 3, 2019, 9 pages.

Office Action dated Apr. 26, 2016 in U.S. Appl. No. 13/797,508, filed Mar. 12, 2013 and published as US 2013-0261983 on Oct. 3, 2013, 12 pages.

Office Action dated Aug. 12, 2021 in U.S. Appl. No. 15/959,880, filed Apr. 23, 2018 and published as US-2019-0005188 on Jan. 3, 2019, 16 pages.

Office Action dated Aug. 22, 2013 in U.S. Appl. No. 13/797,508, filed Mar. 12, 2013 and published as US 2013-0261983 on Oct. 3, 2013, 17 pages.

Office Action dated Dec. 26, 2013 in U.S. Appl. No. 13/797,508, filed Mar. 12, 2013 and published as US 2013-0261983 on Oct. 3, 2013, 9 pages.

Office Action dated Feb. 27, 2017 in U.S. Appl. No. 13/797,508, filed Mar. 12, 2013 and published as US 2013-0261983 on Oct. 3, 2013, 12 pages.

Office Action dated Jan. 19, 2018 in U.S. Appl. No. 13/797,930, filed Oct. 6, 2016 and published as US 2013-0325360 on Dec. 5, 2013, 10 pages.

Office Action dated Jul. 28, 2014 in U.S. Appl. No. 13/797,508, filed Mar. 12, 2013 and published as US 2013-0261983 on Oct. 3, 2013, 7 pages.

Office Action dated Mar. 6, 2019 in U.S. Appl. No. 15/149,045, filed May 6, 2016 and published as US 2016-0319335 A1 Nov. 3, 2016, 9 pages.

Office Action dated Mar. 19, 2015 in U.S. Appl. No. 13/797,508, filed Mar. 12, 2013 and published as US 2013-0261983 on Oct. 3, 2013, 10 pages.

Office Action dated Mar. 8, 2018 in U.S. Appl. No. 13/797,508, filed Mar. 12, 2013 and published as US 2013-0261983 on Oct. 3, 2013, 12 pages.

Office Action dated Mar. 8, 2018 in U.S. Appl. No. 13/829,164, filed Mar. 14, 2013 and published as US 2013-0288244 on Oct. 31, 2014, 12 pages.

Office Action dated Oct. 1, 2018 in U.S. Appl. No. 15/149,045, filed May 6, 2016 and published as US 2016-0319335 A1 Nov. 3, 2016, 18 pages.

Office Action dated Sep. 8, 2015 in U.S. Appl. No. 13/797,508, filed Mar. 12, 2013 and published as US 2013-0261983 on Oct. 3, 2013, 9 pages.

Office Action dated May 27, 2022 in U.S. Appl. No. 15/959,880, filed Apr. 23, 2018 and published as US-2019-0005188 on Jan. 3, 2019.

Berry et al., "Household Chaos and Children's Cognitive and Socio-Emotional Development in Early Childhood: Does Childcare Play a Buffering Role?", Early Childhood Research Quarterly, 2016, 34:115-127.

Clark et al., "Performance Comparison of Exome DNA Sequencing Technologies", Nature Biotechnology, 2011, 29(10):908-914.

Kircher et al., "Double Indexing Overcomes Inaccuracies in Multiplex Sequencing on the Illumina Platform", Nucleic Acids Research, 2011, 40(1): 8 pages.

Laird Peter W., "Principles and Challenges of Genome-wide DNA Methylation Analysis", Nature Reviews Genetics, Mar. 2010, 11:191-203.

Lo YM, "Non-Invasive Prenatal Diagnosis by Massively Parallel Sequencing of Maternal Plasma DNA", Open Biology, 2012, 2:(20086):5 pages.

Skelton et al., "The Norma Cluster (ACO3627): II. the near Infrared K_s-Band Luminosity Function", Monthly Notices of the Royal Astronomical Society, 2009, 396:2367-2378.

Tong et al., "Generation of Mirage Effect by Heated Carbon Nanotube Thin Film", Journal of Applied Physics, Jun. 2014, 115:244905-1-244905-9.

Notice of Allowance in U.S. Appl. No. 17/109,723 dated Feb. 9, 2026, 13 pages.

Office Action dated May 27, 2022 in U.S. Appl. No. 16/395,658, filed Apr. 26, 2019 and published as US-2019-0309351-A1 on Oct. 10, 2019, 8 pages.

Office Action dated Feb. 22, 2022 in U.S. Appl. No. 16/215,254, filed Dec. 10, 2018 and published as US 2019-0276874 A1 on Sep. 12, 2019, 15 pages.

U.S. Appl. No. 12/727,824, Final Office Action mailed on Nov. 5, 2018, 18 pages.

U.S. Appl. No. 12/727,824, Non-Final Office Action mailed on Mar. 29, 2018, 17 pages.

U.S. Appl. No. 13/797,508, Notice of Allowance mailed on Jul. 17, 2019, 16 pages.

U.S. Appl. No. 13/797,930, Notice of Allowance mailed on Apr. 27, 2018, 2 pages.

U.S. Appl. No. 13/829,164, Notice of Allowance mailed on Sep. 10, 2018, 9 pages.

U.S. Appl. No. 14/781,987, Final Office Action mailed on Sep. 6, 2019, 18 pages.

U.S. Appl. No. 14/781,987, Final Office Action mailed on Nov. 12, 2019, 19 pages.

U.S. Appl. No. 14/781,987, Non-Final Office Action mailed on Mar. 7, 2019, 14 pages.

U.S. Appl. No. 14/781,987, Notice of Allowance mailed on Sep. 3, 2020, 16 pages.

U.S. Appl. No. 15/959,880, Notice of Allowance mailed on Dec. 22, 2021, 20 pages.

U.S. Appl. No. 15/959,880, Notice of Allowance mailed on Feb. 15, 2022, 20 pages.

(56) References Cited

OTHER PUBLICATIONS

U.S. Appl. No. 16/215,254, Corrected Notice of Allowability mailed on Oct. 4, 2022, 3 pages.
U.S. Appl. No. 16/395,658, Notice of Allowance mailed on Sep. 22, 2022, 8 pages.
Ajay et al., Accurate and Comprehensive Sequencing of Personal Genomes, Genome Research, vol. 21, No. 9, Sep. 2011, pp. 1498-1505.
Chiu et al., Patterned Deposition of Cells and Proteins onto Surfaces by Using Three-Dimensional Microfluidic Systems, PNAS, vol. 97, No. 6, Mar. 14, 2000, pp. 2408-2413.
Finney et al., Molecular Cloning of PCR Products, Current Protocols in Molecular Biology, Supplement 56, Nov. 2001, pp. 15.4.1-15.4.11.
Gargis et al., Assuring the Quality of Next-generation Sequencing in Clinical Laboratory Practice, Nature Biotechnology, vol. 30, No. 11, Nov. 8, 2012, pp. 1033-1036.
Lo et al., Rapid Clearance of fetal DNA from Maternal Plasma, American Journal of Human Genetics, vol. 64, Jan. 1999, pp. 218-224.
Okamura et al., Detection of a Novel DNA Virus (TTV) Sequence in Peripheral Blood Mononuclear Cells, Journal of Medical Virology, vol. 58, 1999, pp. 174-177.
Pollack et al., A Less Risky Down Syndrome Test is Developed, New York Times, Available online at https://www.nytimes.com/2011/10/18/business/sequenom-test-for-down-syndrome-raises-hopes-and-questions.html, Oct. 17, 2011, 3 pages.
Sambrook et al., Molecular Cloning: A Laboratory Manual, Second Edition, Cold Spring Harbor Laboratory Press, 1989, 30 pages.
U.S. Appl. No. 17/109,723, Non-Final Office Action mailed on Jun. 18, 2025, 17 pages.
Zimmerman, et al., "Real-time quantitative polymerase chain reaction measurement of male fetal DNA in maternal plasma", Methods Mol Med, 132, 2007, 43-9.
Office Action mailed in U.S. Appl. No. 13/829,164, filed Mar. 14, 2013 and published as US 2013-0288244 on Oct. 31, 2014, Apr. 27, 2016.
Office Action mailed in U.S. Appl. No. 13/933,935, filed Jul. 2, 2013 and published as US 2013-0304392 on Nov. 14, 2013, Apr. 27, 2016.
Office Action mailed in U.S. Appl. No. 14/187,876, filed Feb. 24, 2014 and published as US 2014-0322709 on Oct. 30, 2014, May 29, 2015.
Office Action mailed in U.S. Appl. No. 13/333,842, filed Dec. 21, 2011 and published as US 2012/0184449 on Jul. 19, 2012, Jan. 17, 2014.
Invitation to Pay Additional Fees and Partial Search Report mailed in International Application No. PCT/US2012/059592 filed: Oct. 10, 2012, Jan. 18, 2013.
Office Action mailed in U.S. Appl. No. 13/933,935, filed Jul. 2, 2013 and published as US 2013-0304392 on Nov. 14, 2013, Jan. 30, 2014.
International Preliminary Report on Patentability and Written Opinion mailed in International Application No. PCT/US2012/043388, filed Jun. 20, 2012 and published as WO 2012/177792 on Dec. 27, 2012, Jan. 9, 2014.
Office Action mailed in U.S. Appl. No. 13/669,136, filed Nov. 5, 2012 and published as US 2013-0085681 on Apr. 4, 2013, Oct. 17, 2013.
Office Action mailed in U.S. Appl. No. 13/656,328, filed Oct. 19, 2012 and published as US 2013-0103320 on Apr. 25, 2013, Oct. 18, 2013.
Office Action mailed in U.S. Appl. No. 13/754,817, filed Jan. 30, 2013 and published as US 2013-0150253 on Jun. 13, 2013, Oct. 6, 2014.
International Search Report (PCT Search Report and Written Opinion) mailed in International Application No. PCT/US2013/063287, filed Oct. 3, 2013, Dec. 13, 2013.
International Search Report (PCT Search Report and Written Opinion mailed in International Application No. PCT/US2014/039389, filed on May 23, 2014 and published as WO 2014/190286 on Nov. 27, 2014, Dec. 17, 2014.
International Preliminary Report on Patentability in International Application No. PCT/US2013/047131 filed on Jun. 21, 2013, and published as WO 2013/192562 on Dec. 27, 2013, Dec. 31, 2014.
Office Action dated Dec. 7, 2016 in U.S. Appl. No. 12/727,824, filed Mar. 19, 2010 and published as US 2010-0216153 on Aug. 26, 2010, Dec. 7, 2016.
Human Genome Mutations, D. N. Cooper and M. Krawczak, BIOS Publishers, 1993.
Office Action mailed in U.S. Appl. No. 13/669,136 filed on: Nov. 5, 2012 and published as: US 2013-0085681 on Apr. 4, 2013, Feb. 15, 2013.
International Search Report (PCT Search Report and Written Opinion) mailed in International Application No. PCT/US2014/058885 filed on Oct. 2, 2014, Feb. 18, 2015.
Office Action mailed in U.S. Appl. No. 13/656,328 filed Oct. 19, 2012, not yet published, Feb. 20, 2013.
International Preliminary Report on Patentability mailed in International Application No. PCT/US2012/059123, filed on Oct. 5, 2012 and published as WO 2013/052913 on Apr. 11, 2013, Feb. 27, 2014.
Zhou, et al., "Recent Patents of Nanopore DNA Sequencing Technology: Progress and Challenges", Recent Patents on DNA & Gene Sequences, 4, 2010, 192-201.
Office Action dated Oct. 6, 2016 in U.S. Appl. No. 13/797,930, filed Mar. 12, 2013 and published as US 2013-0325360 on Dec. 5, 2013, Feb. 27, 2017.
Zhou, et al., "Detection of DNA copy number abnormality by microarray expression analysis", Hum. Genet., 114, 2004, 464-467.
International Search Report (PCT Search Report and Written Opinion) mailed in International Application No. PCT/US2012/059592 filed: Oct. 10, 2012, Mar. 6, 2013.
International Search Report (PCT Search Report and Written Opinion) mailed in International Application No. PCT/US2013/063314, filed on Oct. 3, 2013 and published as WO 2014/055790 on Apr. 10, 2014, Apr. 2, 2014.
DNAcopy [online], [retrieved on Apr. 24, 2013], retrieved from the internet <URL:* >http://bioconductor.org/packages/Z.12/bioc/htmI/DNAcopy.html, Apr. 24, 2013.
International Preliminary Report on Patentability and Written Opinion mailed in International Application No. PCT/US2012/059592, filed on Oct. 10, 2012 and published as WO 2013/055817 on Apr. 18, 2013, Apr. 24, 2014.
Data Sheet: Illumina Sequencing: TruSeq RNA and DNA Sample Preparation Kits v2, Publication No. 970-2009-039, Apr. 27, 2011.
International Search Report (PCT Search Report and Written Opinion) mailed in International Application No.: PCT/US2012/043388 filed: Jun. 20, 2012 and published as: WO 12/177792 Dec. 27, 2012, Apr. 5, 2013.
Office Action mailed in U.S. Appl. No. 13/754,817, filed on Jan. 30, 2013 and published as US 2013-0150253 on Jun. 13, 2013, Apr. 7, 2014.
Office Action mailed in U.S. Appl. No. 13/333,842 filed: Dec. 21, 2011 and published as:-2012/0184449 on: Jul. 19, 2012, May 3, 2013.
Office Action mailed in U.S. Appl. No. 13/754,817 filed: Jan. 30, 2013, May 7, 2013.
International Search Report (PCT Search Report and Written Opinion) mailed in International Application No. PCT/US2014/012369, filed Jan. 21, 2014, May 9, 2014.
Office Action dated Jun. 12, 2017 in U.S. Appl. No. 12/727,824, filed Mar. 19,2010 and published as US 2010-0216153 on Aug. 26, 2010 , Jun. 12, 2017.
International Preliminary Report on Patentability mailed in International Application No. PCT/US2012/059114, filed on Oct. 5, 2012 and published as WO 2013/052907 on Apr. 11, 2013, Jun. 9, 2014.
International Search Report (PCT Search Report and Written Opinion) mailed in International Application No. PCT/US2014/032687, filed on Apr. 2, 2014, Jul. 14, 2014.

(56) References Cited

OTHER PUBLICATIONS

Office Action mailed in U.S. Appl. No. 13/782,857, Jul. 27, 2015.
Zhong, et al., "Elevation of both maternal and fetal extracellular circulating deoxyribonucleic acid concentrations in the plasma of pregnant women with preeclampsia", Am. J. Obstet. Gynecol., 184, 2001, 414-419.
Invitation to Pay Additional Fees and Partial Search Report mailed in International Application No. PCT/US2012/059123 filed: Oct. 5, 2012 and published as: WO/2013/052913 on Apr. 11, 2013, Jul. 3, 2013.
International Search Report (PCT Search Report and Written Opinion) mailed in International Application No. PCT/US2013/022290 filed: Jan. 18, 2013, and published as: WO/2013/109981 on Jul. 25, 2013, Jul. 4, 2013.
International Search Report and Written Opinion in International Application No. PCT/US2013/022290 filed: Jan. 18, 2013, and published as: WO/2013/109981 on Jul. 25, 2013, Jul. 4, 2013.
Zhong, et al., "Cell-free fetal DNA in the maternal circulation does not stem from the transplacental passage of fetal erythroblasts", Molecular Human Reproduction, 8(9), 2002, 864-870.
Zhong, et al., "CelI-free DNA in urine: a marker for kidney graft rejection, but not for prenatal diagnosis?", Annals New York Academy of Sciences, 2001, 250-257.
Office Action dated Jul. 14, 2017 in U.S. Appl. No. 13/797,930, filed Mar. 12,2013 and published as US 2013-0325360 on Dec. 5, 2013, Aug. 1, 2017.
Office Action mailed in U.S. Appl. No. 13/669,136, filed Nov. 5, 2012 and published as US 2013-0085681 on Apr. 4, 2013, Aug. 13, 2014.
Office Action mailed in U.S. Appl. No. 13/829,164, filed Mar. 14, 2013 and published as US 2013-0288244 on Oct. 31, 2014, Aug. 13, 2014.
Office Action mailed in U.S. Appl. No. 13/933,935, filed Jul. 2, 2013 and published as US 2013-0304392 on Nov. 14, 2013, Aug. 14, 2014.
Zhao, et al., "Quantification and application of the placental epigenetic signature of the RASSF1A gene in maternal plasma", Pretat Diag, 30(8) doi:10.1002/pd.2546, 2010, 778-782.
Office Action mailed in U.S. Appl. No. 13/829,164, filed Mar. 14, 2013, Sep. 11, 2013.
Office Action mailed in U.S. Appl. No. 13/656,328, filed Oct. 19, 2012 and published as US 2013-0103320 on Apr. 25, 2013, Sep. 12, 2013.
International Search Report (PCT Search Report and Written Opinion) mailed in International Application No. PCT/US2013/047131, filed on Jun. 21, 2013 and published as WO 2013/192562 on Dec. 27, 2013, Sep. 18, 2013.
International Search Report (PCT Search Report and Written Opinion) mailed in International Application No. PCT/U82014/043497, filed on Jun. 20, 2014, Sep. 24, 2014.
International Search Report (PCT Search Report and Written Opinion) mailed in International Application No. PCT/US2011/066639 filed: Dec. 21, 2011 and published as: WO 12/088348 Jun. 28, 2012, Sep. 26, 2012.
International Search Report (PCT Search Report and Written Opinion) mailed in International Application No. PCT/US2012/059114, filed on Oct. 5, 2012 and published as WO/2013/052907 on Apr. 11, 2013, Sep. 9, 2013.
International Search Report (PCT Search Report and Written Opinion) mailed in International Application No. PCT/US2012/059123, filed on Oct. 5, 2012 and published as WO/2013/052913 on Apr. 11, 2013, Sep. 9, 2013.
International Preliminary Report on Patentability received in International Application No. PCT/US2014/012369, filed Jan. 21, 2014 and published as WO 2014/116598 on Jul. 31, 2014, Aug. 6, 2015
Extended European Search Report received in European Application No. EP117450502, filed on Feb. 9, 2011 and published as EP 2 536 852 on Dec. 26, 2012, Dec. 2, 2015.
International Preliminary Report on Patentability received in International Application No. PCT/US2014/039389, filed on May 23, 2014 and published as WO 2014/190286 on Nov. 27, 2014, Dec. 3, 2015.
Office Action mailed in U.S. Appl. No. 13/669,136, filed Nov. 5, 2012 and published as US 2013-0085681 on Apr. 4, 2013, Feb. 1, 2016.
Office Action mailed in U.S. Appl. No. 13/797,930, filed Mar. 12, 2013 and published as US 2013-0325360 on Dec. 5, 2013, Feb. 12, 2016.
Office Action mailed in U.S. Appl. No. 14/812,432, filed Jul. 29, 2015 and published as US 2016-0034640 on Feb. 4, 2016, Feb. 23, 2016.
International Search Report and Written Opinion mailed in International Application No. PCT/US2015/042701, filed on Jul. 29, 2015, Jan. 5, 2016.
International Search Report and Written Opinion in International Application No. PCT/US2014/039389 filed on May 23, 2014, and published as WO 2014/190286 on Nov. 27, 2014, mailed Dec. 17, 2014.
Office Action received in U.S. Appl. No. 13/829,373, filed Mar. 14, 2013 and published as US 2013-0338933 on Dec. 19, 2013, Mar. 3, 2016.
Invitation to Pay Additional Fees and Partial International Search Report received in International Application No. PCT/U82015/042701, filed on Jul. 29, 2015, Oct. 14, 2015.
International Search Report and Written Opinion received in International Application No. PCT/US2015/032550, filed on May 27, 2015 and published as WO 2015/183872 on Dec. 3, 2015, Oct. 2, 2015.
Office Action received in U.S. Appl. No. 13/781,530, filed Feb. 28, 2013 and published as US 2014-0100792 on Apr. 10, 2014, Oct. 22, 2015.
Office Action received in U.S. Appl. No. 13/333,842, filed Dec. 21, 2011 and published as US 2012/0184449 on Jul. 19, 2012, Oct. 27, 2015.
International Search Report (PCT Search Report and Written Opinion mailed in PCT Application No. PCT/ US2011/024132), Aug. 8, 2011, 15 pages.
Office Action dated Aug. 2, 2017 in U.S. Appl. No. 13/829,164, filed Mar. 14, 2013 and published as US 2013-0288244 on Oct. 31, 2014.
Office Action dated Feb. 17, 2017 in U.S. Appl. No. 13/829,164, filed Mar. 14, 2013 and published as US 2013-0288244 on Oct. 31, 2014.
Office Action dated Mar. 22, 2016 in U.S. Appl. No. 12/727,824, filed Mar. 19,2010 and published as US 2010-0216153 on Aug. 26, 2010.
International Preliminary Report on Patentability mailed on Apr. 14, 2016 in International Application No. PCT/US2014/058885, filed on Oct. 2, 2014 and published as WO 2015/051163 on Apr. 9, 2015.
International Preliminary Report on Patentability mailed on Apr. 21, 2016 in International Application No. PCT/US2014/059156, filed on Oct. 3, 2014 and published as WO 2015/054080 on Apr. 16, 2015.
Office Action dated: Aug. 22, 2013 in U.S. Appl. No. 13/619,039 filed: Sep. 14, 2012 and published as: US 2013/0022977 on: Jan. 24, 2013.
Office Action dated: Jan. 10, 2013 in U.S. Appl. No. 13/619,039 filed: Sep. 14, 2012 and published as: US 2013/0022977 on: Jan. 24, 2013.
Office Action dated: Jul. 14, 2014 in U.S. Appl. No. 12/727,824 filed Sep. 13,2012 and published as: US 2010/0216153 on: Aug. 26,2010
Office Action dated: Oct. 18, 2011 in U.S. Appl. No. 12/727,824 filed: Sep. 13,2012 and published as: US 2010/0216153 on: Aug. 26, 2010.
Office Action dated: May 16, 2011 in U.S. Appl. No. 12/727,824 filed:Sep. 13, 2012 and published as: US 2010/0216153 on: Aug. 26, 2010.
Office Action dated: Feb. 25, 2015 in U.S. Appl. No. 12/727,824 filed: Sep. 13, 2012 and published as: US 2010/0216153 on: Aug. 26, 2010.

(56) References Cited

OTHER PUBLICATIONS

Supplementary Partial European Search Report dated Aug. 10, 2015 in European Application No.: EP11745050.2, filed on Feb. 9, 2011 and published as EP 2 536 852 on Dec. 26, 2012.
Office Action dated Aug. 27, 2015 in U.S. Appl. No. 13/933,935, filed Jul. 2, 2013 and published as US 2013-0304392 on Nov. 14, 2013.
Office Action dated Sep. 1, 2015 in U.S. Appl. No. 13/829,164, filed Mar. 14, 2013 and published as US 2013-0288244 on Oct. 31, 2014.
Office Action dated Sep. 8, 2015 in U.S. Appl. No. 13/669,136, filed Nov. 5, 2012 and published as US 2013- 0085681 on Apr. 4, 2013.
Office Action dated Sep. 18, 2015 in U.S. Appl. No. 12/727,824, filed Mar. 19, 2010 and published as US 2010-0216153 on Aug. 26, 2010.
Office Action dated Sep. 22, 2015 in U.S. Appl. No. 13/779,638, filed Feb. 27, 2013 and published as US 2013-0309666 on Nov. 21, 2013.
Office Action dated Sep. 28, 2015 in U.S. Appl. No. 14/187,876, filed Feb. 24, 2014 and published as US 2014-0322709 on Oct. 30, 2014.
Office Action dated Oct. 2, 2015 in U.S. Appl. No. 13/754,817, filed Jan. 30, 2013 and published as US 2013-0150253 on Jun. 13, 2013.
Office Action dated Oct. 2, 2015 in U.S. Appl. No. 13/782,883, filed Mar. 1, 2013 and published as US 2014-0180594 on Jun. 26, 2014 filed on Mar. 1, 2013 and published as US 2014-0180594 on Jun. 26, 2014.
International Preliminary Report on Patentability mailed on Oct. 15, 2015 inInternational Application No. PCT/US2014/032687, filed on Apr. 2, 2014 and published as WO 2014/165596 on Oct. 9, 2014.
Office Action dated Apr. 16, 2015 in U.S. Appl. No. 13/669,136, filed Nov. 5, 2012 and published as US 2013-0085681 on Apr. 4, 2013.
Office Action dated Apr. 16, 2015 in U.S. Appl. No. 13/933,935, filed Jul. 2, 2013 and published as US 2013-0304392 on Nov. 14, 2013.
International Preliminary Report on Patentability mailed on Apr. 16, 2015 in International Application No. PCT/U82013/063314, filed on Oct. 3, 2013 and published as WO 2014/055790 on Apr. 10, 2014.
International Preliminary Report on Patentability mailed on Apr. 16, 2015 in International Application No. PCT/U82013/063287, filed Oct. 3, 2013.
Office Action dated Apr. 17, 2015 in U.S. Appl, No. 13/829,164, filed Mar. 14, 2013 and published as US 2013-0288244 on Oct. 31, 2014.
Office Action dated Apr. 21, 2015 in U.S. Appl. No. 13/754,817, filed Jan. 30, 2013 and published as US 2013-0150253 on Jun. 13, 2013.
Office Action dated May 12, 2015 in U.S. Appl. No. 13/669,136, filed Nov. 5, 2012 and published as US 2013-0085681 on Apr. 4, 2013.
Office Action dated May 13, 2015 in U.S. Appl. No. 13/333,842, filed Dec. 21, 2011 and published as US 2012/0184449 on Jul. 19, 2012.
International Preliminary Report on Patentability mailed on Jul. 31, 2014 in International Application No. PCT/US2013/022290, filed on Jan. 18, 2013 and published as WO 2013/109981 on Jul. 25, 2013.
Office Action dated Jan. 27, 2014 in U.S. Appl. No. 13/829,164, filed Mar. 14, 2013 and published as US 2013-0288244 on Oct. 31, 2014.
Office Action mailed on Oct. 16, 2013 in U.S. Appl. No. 13/933,935, filed Jul. 2, 2013 and published as US 2013-0304392 on Nov. 14, 2013.
Office Action dated Sep. 12, 2013 in U.S. Appl. No. 13/669,136, filed Nov. 5, 2012 and published as: US 2013-0085681 on Apr. 4, 2013.
Product Sheet for: Nextera™ DNA Sample Prep Kit (Illumina®—Compatible), Cat. Nos. GA09115, GA091120, GA0911-50, GA0911-96, and GABC0950, from: Epicentre, an Illumina Company, Literature #307, Jun. 2011, 9 pages.
"Hybridization with Radioactive Probes", Current Protocols in Molecular Biology, John Wiley & Sons, N.Y., 1989, 6.31-6.36.
"International Human Genome Sequencing Consortium Initial sequencing and analysis of the human genome", Nature, vol. 409, 2001, 860-921.
Office Action in U.S. Appl. No. 13/782,857, filed Mar. 1, 2013 and published as US 2013-0310260 on Nov. 21, 2013, Mar. 11, 2016.
"PCT International Search Report and Written Opinion of the international Searching Authority for International Application No. PCT/US11/24132 mailed Aug. 8, 2011", 15 pages.
"The international SNP Map Working group", Nature, vol. 409, 2001, 928-933.
Adinolfi, et al., "Rapid detection of aneuploidies by microsatellite and the quantitative fluorescent polymerase chain reaction", Prenat. Diagn. 17(13), 1997, 1299-311.
Agarwal, et al., "Commercial landscape of noninvasive prenatal testing in the United States", Prenatal Diagnosis, 33(6), 2013, 521-531.
Akeson, et al., "Microsecond Time-Scale Discrimination Among Polycytidylic Acid, Polyadenylic Acid, and Polyuridylic Acid as Homopolymers or as Segments Within Single RNA Molecules", Biophysical Journal, vol. 77, Dec. 1999, 3227-3233.
Alkan, et al., "Personalized copy number and segmental duplication maps using next generation sequencing", Nat Genet, 41(10), Oct. 30, 2009, 1061-7 and Supplementary Information 1-68.
Amicucci, et al., "Prenatal Diagnosis of Myotonic Dystrophy Using Fetal DNA Obtained from Maternal Plasma", Clin. Chem. 46, 2000, 301-302.
Anantha, et al., "Porphyrin binding to quadrupled T4G4", Biochemistry., 37(9), Mar. 3, 1998, 2709-14.
Armour, et al., "Measurement of locus copy number by hybridisation with amplifiable probes", Nucleic Acids Res., 28(2), Jan. 15, 2000, 605-9.
Armour, et al., "The detection of large deletions or duplications in genomic DNA", Hum Mutat, 20(5), Nov. 2002, 325-37.
Ashkenasy, et al., "Recognizing a Single Base in an Individual DNA Strand: A Step Toward Nanopore DNA Sequencing", Angew Chem Int Ed Engl., 44(9), Feb. 18, 2005, 1401-1404.
Ashoor, et al., "Chromosome-selective sequencing of maternal plasma cell-free DNA for first-trimester detection of trisomy 21 and trisomy 18", Am J Obstet Gynecol, 206(4), Apr. 2012, 322.e1-5.
Aston, et al., "Optical mapping and its potential for large-scale sequencing project", Trends Biotechnol. 17(7), 1999, 297-302.
Aston, et al., "Optical mapping: an approach for fine mapping", Methods Enzymol. 303, 1999, 55-73.
Avent, et al., "Non-invasive diagnosis of fetal sex; utilization of free fetal DNA in maternal", Prenatal Diagnosis, 26, 2006, 598-603.
Avent, , "Refining noninvasive prenatal diagnosis with single-molecule next-generation sequencing", Clinical Chemistry, 58:4, 2012, 657-658.
Beaucage, et al., "Deoxynucleoside phosphoramidites—A new class of key intermediates for deoxypolynucleotide synthesis", Tetrahedron Letters, 22(20), 1981, 1859-1862.
Benjamini, et al., "Summarizing and correcting the GC content bias in high-throughput sequencing", Nucleic Acids Research, 40(10):e72, Feb 9, 2012, 1-14.
Berger, et al., "Universal bases for hybridization, replication and chain termination", Nucleic Acids Res. 28(15), 2000, 2911-2914.
Bergstrom, et al., "Synthesis, Structure, and Deoxyribonucleic Acid Sequencing with a Universal Nucleoside: 1-(2'-Deoxy-.beta.-D-ribofuranosyl)-3-nitropyrrole", J. Am. Chem. Soc. 117, 1995, 1201-1209.
Zhao, et al., "Detection of fetal subchromosomal abnormalities by sequencing circulating cell-free DNA from maternal plasma", Clinical Chemistry, 61(4), 2015, 608-616.
Bianchi, et al., "Isolation of fetal DNA from nucleated erythrocytes in maternal blood", Medical Sciences, vol. 87, 1990, 3279-3283.
Boeva, et al., "Control-free calling of copy number alterations in deep-sequencing data using GC-content normalization", Bioinformatics, 27(2), 2011, 268-269.

(56) References Cited

OTHER PUBLICATIONS

Bollen, , "Bioconductor: Microarray versus next-generation sequencing tool sets", retrieved from the internet: http://dspace.library.uu.nl/bitstream/handle/1874/290489/Sander_Bollen_writing_assignment.pdf, Sep. 23, 2015.
Borsenberger, et al., "Chemically Labeled Nucleotides and Oligonucleotides Encode DNA IS. P./ for Sensing with Nanopores", J. Am. Chem. Soc., 131, 2009, 7530-7531.
Branton, et al., "The potential and challenges of nanopore sequencing", Nature Biotechnology, vol. 26, No. 10, Oct. 2008, 1146-1153.
Braslavsky, et al., "Sequence information can be obtained from single DNA molecules", PNAS, 100(7), Apr. 1, 2003, 3960-3964.
Brizot, et al., "Maternal serum hCG and fetal nuchal translucency thickness for the prediction of fetal trisomies in the first trimester of pregnancy", Br J Obstet Gynaecol.; 102(2), Feb. 1995, 127-32.
Brizot, et al., "Maternal serum pregnancy-associated plasma protein A and fetal nuchal translucency thickness for the prediction of fetal trisomies in early pregnancy", Obstet Gynecol., 84(6), Dec. 1994, 918-22.
Brown, et al., "A step-by-step guide to non-linear regression analysis of experimental data using a Microsoft Excel spreadsheet Computer Methods and Programs", Biomedicine vol. 65, 2001, pp. 191-200.
Brown, et al., "Synthesis and duplex stability of oligonucleotides cotnaining adenine-guanine analogues", Carbohydrate Research, 216, 1991, 129-139.
Brown, et al., "Validation of QF-PCR for prenatal aneuploidy screening in the United States", Prenat Diagn, 26(11), 2006, 1068-74.
Bruch, et al., "Trophoblast-like cells sorted from peripheral maternal blood using flow cytometry: A multiparametric study involving transmission electron microscopy and fetal DNA amplification", Prenatal Diagnosis, vol. 11, 1991, pp 787-798.
Brunger, , "Free R value: a novel statistical quantity for assessing the accuracy of crystal", Nature 355, doi:10.1038/355472a0, Jan. 30, 1992, 472-475.
Bullard, et al., "Evaluation of statistical methods for normalization and differential expression in mRNA-Seq experiments", Bioinformatics, 11:94, 2010, 1-13.
Burlingame, et al., Anal. Chem. 70, 1998, 647R-716R.
Campbell, et al., "Identification of somatically acquired rearrangements in cancer using genome-wide massively parallel paried-end sequencing", Nat Genet. 40(6), doi: 10.1038/ng.128. Epub 2008 Apr. 27, Jun. 2008, 722-9.
Canick, et al., "A New Prenatal Blood Test for Down Syndrome (RNA)", found on the internet at: clinicaltrials.gov/show/A15NCT00877292, Jul. 2012.
Canick, et al., "DNA sequencing of maternal plasma to identify Down syndrome and other trisomies in multiple gestations", Prenatal Diagnosis, vol. 32, 2012, 730-734.
Canick, et al., "The impact of maternal plasma DNA fetal fraction on next generation sequencing tests for common fetal aneuploidies", Prenat. Diagn. 33(7), 2013, 667-674.
Cann, et al., "A heterodimeric DNA polymerase: evidence that members of Euryarchaeota possess a distinct DNA polymerase", Proc. Natl. Acad. Sci. USA 95, 1998, 14250-14255.
Cariello, et al., "Fidelity of Thermococcus litoralis DNA polymerase (Vent) in PCR determined by denaturing gradient gel electrophoresis", Nucleic Acids Res. 19(15), Aug. 11, 1991, 4193-8.
Carlson, et al., "Molecular Definition of 22q11 Deletions in 151 Velo- Cardio-Facial Syndrome Patients", The American Journal of Human Genetics, Volume 61, Issue 3, Sep. 1, 1997, 620-629.
Chan, et al., "Size Distributions of maternal and fetal DNA in Maternal Plasma", Clin. Chem 50(1), Jan. 2004, 88-92.
Chandrananda, , "Investigating and correcting plasma DNA sequencing coverage bias to enhance aneuploidy discovery", PloS One, 9:e86993, 2014.
Chen, et al., "A method for noninvasive detection of fetal large deletions/duplications by low coverage massively parallel sequencing", Prenatal Diagnosis 33(6) and supplementary material pp. 1-6, 2013, 584-590.
Chen, et al., "Noninvasive Prenatal Diagnosis of Fetal Trisomy 18 and Trisomy 13 by Maternal Plasma DNA Sequencing", PLoS ONE, vol. 6, Issue 7, Jul. 2011, e21791.
Chiang, et al., "High-resolution mapping of copy-number alterations with massively parallel sequencing", Nature Methods, vol. 6, No. 1 (2009), published online: doi:10.1038/nmeth.1276, 1/2009, 99-103.
Chien, et al., "Deoxyribonucleic acid polymerase from the extreme thermophile Thermus aquaticus", J. Bacteoriol, 127, 1976, 1550-1557.
Chim, et al., "Systematic search for placental DNA-methylation markers on chromosome 21: toward a maternal plasma-based epigenetic test for fetal trisomy 21", Clin Chem 54(3), 2008, 500-11.
Chiu, et al., "Maternal Plasma DNA Analysis with Massively Parallel Sequencing by Ligation for Noninvasive Prenatal Diagnosis of Trisomy 21", Clinical Chemistry 56:3, 2010, 459-463.
Chiu, et al., "Non-invasive prenatal assessment of trisomy 21 by multiplexed maternal plasma DNA sequencing: large scale validity study", BMJ 342, Jan. 11, 2011, c7401.
Chiu, et al., "Noninvasive prenatal diagnosis of fetal chromosomal aneuploidy by massively parallel genomic sequencing of DNA in maternal plasma", PNAS, vol. 105, No. 51, Dec. 23, 2008, pp. 20458-20463.
Zhang, et al., "A single cell level based method for copy number variation analysis by low coverage massively parallel sequencing", PLoS ONE 8(1), doi:10.1371/journal.pone.0054236, 2013, e54236.
Chiu, et al., "Prenatal exclusion of thalassaemia major by examination of maternal plasma", Lancet 360, 2002, 998-1000.
Chu, et al., "Statistical model for whole genome sequencing and its application to minimally invasive of fetal genetic disease", Bioinformatics 25(10), May 15, 2009, 1244-1250.
Chung, et al., "Discovering transcription factor binding sites in highly repetitive regions of genomes with multi-read analysis of ChIP-Seq data", PLoS Computational Biology, 7(7):e1002111, 2011.
Cohen, et al., "GC Composition of the Human Genome: In Search of Isochores", Mole Biol. Evol., 22(5), 2005, 1260-1272.
Costa, , "Fetal RHO genotyping in maternal serum during the first trimester of pregnancy", British Journal of Haematology, vol. 119, 2002, 255-260.
Costa, et al., "New Strategy for Prenatal Diagnosis of X-Linked Disorders", N. Engl. J. Med., 346, 2002, 1502.
Cunningham et al., , "Williams Obstetrics", McGraw-Hill Professional, 2002, p. 942.
D'Alton, , "Prenatal diagnostic procedures", Semin Perinatal.; 18(3), Jun. 1994, 140-62.
Dan, et al., "Clinical application of massively parallel sequencing-based prenatal noninvasive fetal trisomy test for trisomies 21 and 18 in 11,105 pregnancies with mixed risk factors", Prenatal Diagnosis, 32, 2012, 1225-1232.
Dan, et al., "Prenatal detection of aneuploidy and imbalanced chromosomal arrangements by massively parallel sequencing", PLoS ONE 7(2), 2012, e27835.
Davanos, et al., "Relative quantitation of cell-free fetal DNA in maternal plasma using autosomal DNA markers", Clinica Chimica Acta, 412, 2011, 1539-1543.
Deamer, et al., "Nanopores and nucleic acids: prospects for ultrarapid sequencing", Trends Biotechnol, 18(4), 2000, 147-151.
Derrien, et al., "Fast Computation and Applications of Genome Mappability", PLoS ONE 7(1), doi:10.1371/journal.pone.0030377, Jan. 19, 2012, e30377.
Dhallan, et al., "Methods to Increase the Percentage of Free Fetal DNA Recovered From the Maternal Circulation", J. Am. Med. Soc., vol. 291, No. 9, Mar. 2004, 1114-1119.
Diaz, et al., "Accuracy of replication in the polymerase chain reaction. Comparison between Thermotoga maritima DNA polymerase and Thermus aquaticus DNA polymerase", Diaz RS, Sabino EC. Braz J. Med. Res, 31, 1998, p. 1239.

(56) References Cited

OTHER PUBLICATIONS

Ding, et al., “A high-throughput gene expression analysis technique using competitive PCR and matrix-assisted laser desorption ionization time-of-flight MS”, Proc Natl Acad Sci USA, 100, 2003, 3059-3064.
Dohm, J.C. et al., “Substantial biases in ultra-short read data sets from high-throughput DNA sequencing”, Nucleic Acids Res., 36(16); doi: 10.1093/nar/gkn425., Jul. 28, 2008, e105.
Donoho, et al., “WaveLab and Reproducible Research”, Stanford University, Stanford CA 94305, USA, 1995, 1-27.
Drmanac, et al., “Sequencing by hybridization: towards an automated sequencing of one million m13 clones arrayed on membranes”, Electrophoresis 13, 1992, 566-573.
Edelmann, et al., “A common molecular basis for rearrangement disorders on chromosome 22q11”, Hum Mol Genet, 8(7), 1999, 1157-67.
Egger, et al., “Reverse transcription multiplex PCR for differentiation between polio- and enteroviruses from clinical and environmental samples”, J Clin Microbial; 33(6), Jun. 1995, 1442-7.
Ehrich, , “Noninvasive detection of fetal trisomy 21 by sequencing of DNA in maternal blood: a study in a clinical setting”, Am J Obstet Gynecol, 204(3), Mar. 2011, 205.el-11.
Eiben, et al., “First-trimester screening: an overview”, J Histochem Cytochem.; 53(3), Mar. 2005, 281-3.
Ensenauer, et al., “Microduplication 22q11.2, an emerging syndrome: clinical, cytogenetic, and molecular analysis of thirteen patients”, Am J Hum Genet, 73(5), 2003, 1027-40.
Fan, et al., “Analysis of the size distributions of fetal and maternal cell-free DNA by paired-end sequencing”, Clin. Chem 56(8), Aug. 1, 2020, 1279-1286.
Fan, et al., “Noninvasive diagnosis of fetal aneuploidy by shotgun sequencing DNA from maternal blood”, Proceedings of the National Academy of Sciences, vol. 105, No. 42, also available at: http://www.pnas.org/cgi/doi/10.1073/pnas.0808319105, Oct. 21, 2008, 16266-71.
Fan, et al., “Sensitivity of noninvasive prenatal detection of fetal aneuploidy from maternal plasma using shotgun sequencing is limited only by counting statistics”, PLoS One 5(5), May 3, 2010, e10439.
Forabosco, et al., “Incidence of non-age-dependent chromosomal abnormalities: a population-based study on 88965 amniocenteses”, European Journal of Human Genetics 17, 2009, 897-903.
Gebhard, et al., “Genomewide profiling of CpG methylation identifies novel targets of aberrant hypermethylation in myeloid leukemia”, Cancer Res, 66, 2006, 6118-6128.
Goya et al., “SNVMix: predicting single nucleotide variants from next generation sequencing of tumors”, Bioinformatics, 26, 2010, 730-736.
Grati, , “Chromosomal Mosaicism in Human Feta-Placental Development: Implications for Prenatal Diagnosis”, J. Clin. Med. 3, 2014, 809-837.
Haar, , “Zur Theorie der orthogonalen Funktionensysteme”, Mathematische Annalen, 69(3), English translation “On the Theory of Orthogonal Function Systems” 1-37, 1910, 331-371.
Hahn, et al., “Cell-free nucleic acids as potential markers for preeclampsia”, Placenta 32 Suppl: 817-820, Suppl:S17-20. doi: 10.1016/j.placenta.2010.06.018, Feb. 2011.
Harris, et al., “Single-Molecule DNA Sequencing of a Viral Genome”, Science 320, Apr. 4, 2008, 106-109 and Suppl. Materials 1-25.
Herzenberg, et al., “Fetal cells in the blood of pregnant women: Detection and enrichment by fluorescence-activated cell sorting”, Proc. Natl. Acad. Sci. 76, 1979, 1453-1455.
Hill, , “Gen-Probe Transcription-Mediated Amplification: System Principles”, httl://www.gen-probe.com/pdfs/tma_whiteppr.pdf, Jan. 1996.
Hinds, et al., “Whole-Genome Patterns of Common DNA Variation in Three Human Populations”, Science, vol. 307, Feb. 18, 2005, 1072-1079.
Hinnisdaels, et al., “Direct cloning of PCR products amplified with Pwo DNA polymerase”, Biotechniques, 20, 1996, 186-188.
Hsu, et al., “A model-based circular binary segmentation algorithm for the analysis of array CGH data”, BMC Research Notes, vol 4, BioMed Central Ltd., Oct. 10, 2011, 394.
Hsu, et al., “Denoising array-based comparative genomic hybridization data using wavelets”, Biostatistics (Oxford, England), vol. 6, No. 2, 2005, 211-226.
Huber, et al., “High-resolution liquid chromatography of DNA fragments on non-porous poly(styrene-divinylbenzene) particles”, Nucleic Acids Res., vol. 21, No. 5, 11 Mar. 1993, 1061-1066.
Hudecova, et al., “Maternal plasma fetal DNA fractions in pregnancies with low and high risks for fetal chromosomal aneuploidies”, PLoS One 9(2), 2014, e88484.
Hudson, et al., “An STS-based map of the human genome”, Science 270, 1995, 1945-1954.
Hulten, et al., “Rapid and simple prenatal diagnosis of common chromosome disorders:advantages and disadvantages of the molecular methods FISH and QF-PCR”, Reproduction, 126(3), Sep. 2003, 279-97.
Hupe, et al., “Analysis of array CGH data: from signal ratio to gain and loss of DNA regions”, Bioinformatics, 20, 2004, 3413-3422.
Huse, et al., “Accuracy and quality of massively parallel DNA pyrosequencing”, Genome Biology, vol. 8, Issue 7, Article R143, 2007, 9 pages.
Ingersoll, et al., “Comparison of gene expression profiles between human and mouse monocyte subsets”, www.bloodjournal.ord, Jun. 7, 2017.
Innis, et al., “PCR Protocols: A Guide to Methods and Applications”, 1990, pp. v-x.
James, , “Mathematics Dictionary”, Fifth Edition, Chapman & Hall, International Thomson Publishing, 1992, 266-267_270.
Jauch, et al., “Reconstruction if genomic rearrangements in great apes and gibbons by chromosome painting”, Proc. Natl. Acad. Sci. USA, vol. 89, Sep. 1992, 8611-8615.
Jensen, et al., “Detection of Microdeletion 22q11.2 in a Fetus by Next-Generation Sequencing of Maternal Plasma”, Clinical Chemistry 58:7; doi:10.1373/clinchem.2011.180794, May 4, 2012, 1148-1151.
Jensen, et al., “High-Throughput Massively Parallel Sequencing for Fetal Aneuploidy Detection from Maternal Plasma”, PLoS ONE, 8(3), Mar. 6, 2013, e57381.
Jiang, P. et al., “FetalQuant: deducing fractional fetal DNA concentration from massively parallel sequencing of DNA in maternal plasma”, Bioinformatics, vol. 28, No. 22, 2012, 2883-2890.
Jing, et al., Proc Natl Acad Sci USA, 95(14), 1998, 8046-51.
Johnston, et al., “Autoradiography using storage phosphor technology”, Electrophoresis 11 (5), May 1990, 355-360.
Joos, et al., “Covalent attachment of hybridizable oligonucleotides to glass supports”, Analytical Biochemistry, 247, 1997, 96-101.
Jorgez, et al., “Improving Enrichment of circulating fetal DNA for genetic testing: size fractionation followed by whole gene amplification”, Fetal Diagnosis and Therapy, Karger Basel, CH, Vol. 25, No. 3, 2009, pp. 314-319.
Juncosa-Ginesta, et al., “Improved efficiency in site-directed mutagenesis by PCR using a Pyrococcus sp. GB-D polymerase”, Biotechniques, 16, 1994, 820-823.
Jurinke, et al., “MALDI-TOF mass spectrometry: a versatile tool for high-performance DNA analysis”, Mol. Biotechnol., 26, 2004, 147-164.
Kalinina, et al., “Nanoliter scale PCR with TaqMan detection”, Nucleic Acids Res.; 25(10), May 15, 1997, 1999-2004.
Kato, et al., “A New Packing for Separation of DNA Restriction Fragments by High Performance Liquid Chromatography”, J. Biochem., vol. 95, No. 1, 1984, 83-86.
Khandjian, , “UV crosslinking of RNA to nylon membrane enhances hybridization signals”, Mol. Bio. Rep, 11, 1986, 107-115.
Kim, et al., “Determination of fetal DNA fraction from the plasma of pregnant women using sequence read counts”, Prenat. Diagn. 35(8), 2015, pp. 810-815.
Kim, et al., “Identification of significant regional genetic variations using continuous CNV values”, Genomics 94, 2009, 317-323.
Kitzman, et al., “Noninvasive Whole-Genome Sequencing of a Human Fetus”, Science Translation Medicine, 4(137), 2012, 115-122.

(56) References Cited

OTHER PUBLICATIONS

Kornberg and Baker, , "DNA Replication 2nd edition", W. H. Freeman, New York, N.Y., 1991.
Kulkarni, et al., "Global DNA methylation patterns in placenta and its association with maternal hypertension in pre-eclampsia", DNA Cell Biol. 2011 Feb;30(2) doi:10.1089/dna.2010.1084, Epub Nov. 2, 2010, 79-84.
Lai, et al., "A shotgun optical map of the entire Plasmodium falciparum genome", Nat Genet, 23(3), 1999, 309-13.
Lai, et al., "Comparative Analysis of Algorithms for identifying amplifications and deletions in array CGH data", Bioinformatics, 21(19), 2005, 3763-3770.
Langmead, et al., "Ultrafast and memory-efficient alignment of short DNA sequences to the human genome", Genome Biology, vol. 10, 2009, R251-R2510.
Larsson, et al., "Reference values for clinical chemistry tests during normal pregnancy", BJOG Vol. 115, 2008, 874-88.
Lecomte, et al., "Selective inactivation of the 3' to 5' exonuclease activity of *Escherichia coli* DNA polymerase I by heat", Polynucleotides Res. 11, 1983, 7505-7515.
Leek, et al., "Tackling the widespread and critical impact of batch effects in high-throughput data", Nature Reviews Genetics 11, 2010, 733-739.
Lefkowitz, et al., "Clinical validation of a noninvasive prenatal test for genomewide detection of fetal copy number variants", American Journal of Obstetrics & Gynecology, 80002-9378(16)00318-5. doi: 10.1016/j.ajog.2016.02.030. [Epub ahead of print], Dec. 2, 2015.
Levin, , "It's prime time for reverse transcriptase", Cell 88, 1997, pp 5-8.
LI, et al., "Detection of paternally inherited fetal point mutations for beta- thalassemia using size-fractionated cell-free DNA in maternal plasma", J. Amer. Med. Assoc., vol. 293, Feb. 16, 2005, 843-849.
LI, H. et al., "Mapping short DNA sequencing reads and calling varients using mapping quality scores", Genome Res. 2008 18, Aug. 19, 2009, 1851-1858.
Liao, et al., "Noninvasive prenatal diagnosis of fetal trisomy 21 by allelic ratio analysis using targeted massively parallel sequencing of maternal plasma DNA", PLos ONE, www.plosone.org, vol. 7, Issue 5, May 2012, e38154, 8 pages.
Liao, et al., "Targeted Massively parallel sequencing of maternal plasma DNA permits efficient and unbiased detection of fetal alleles", Clinical Chemistry 57:1, 2011, 92-101.
Lichtensen, et al., "Circulating Nucleic Acids and Apoptosis", Annals New York Academy of Sciences, 2001, 239-249.
Lin, et al., "Synthesis and duplex stability of oligonucleotides containing cytosine-thymine analogues", Nucleic Acids Res., vol. 17, No. 24, 1989, 10373-10383.
Lin, et al., "Synthesis of oligodeoxyribonucleotides containing degenerate bases and their use as primers in the polymerase chain reaction", Nucleic Acids Res. vol. 20 No. 19, 1992, 5149-5152.
Liu, et al., "CUSHAW: a CUDA compatible short read aligner to large genomes based on the Burrows-Wheeler transform", Bloinformatics, 28(14), 2012, 1830-1837.
Lo, et al., "Digital PCR for the molecular detection of fetal chromosomal aneuploidy", Proc Natl Acad Sci USA. 104(32), Aug. 7, 2007, 13116-13121.
Lo, , "Fetal DNA in maternal plasma: application to non-invasive blood group genotyping of the fetus", Transfus Clin Bioi, vol. 8, 2001, 306-310.
Lo, et al., "Increased fetal DNA concentrations in the plasma of pregnant women carrying fetuses with trisomy 21", Clinical Chemistry 45:10, 1999, 1747-51.
Lo, et al., "Maternal Plasma DNA Sequencing Reveals The Genome-Wide Genetic And Mutational Profile Of The Fetus", Sci Transl Med. 2(61):, Dec. 8 , 2010, 61ra91.
Lo, et al., "Prenatal diagnosis of fetal RhD Status by molecular analysis of maternal plasma", The New England Journal of Medicine, vol. 339, Dec. 10, 1998, 1734-1738.
LO, et al., "Presence of fetal DNA in maternal plasma and serum", Lancet. 350(9076), Aug. 19, 1997, 485-487.
Lo, et al., "Quantative Abnormalities of Fetal NDA in Maternal Serum in Preeclampsia", Clin. Chem, 45, 1999, 184-188.
Lo, et al., "Quantitative analysis of fetal DNA in maternal plasma and serum: implications for noninvasive prenatal diagnosis", Am J Hum Genet 62(4), Apr. 1998, 768-775.
Lo, et al., "Recent advances in fetal nucleic acids in maternal plasma", J Histochem Cytochem. 53(3), Mar. 2005, 293-6.
Lo, Y.M. Dennis et al., "Plasma placental RNA allelic ratio permits noninvasive prenatial chromosomal aneuploidy detection", Nature Medicine, vol. 13, No. 2, Feb. 2007, 218-223.
Loakes, et al., "5-Niroindole as an universal base analogue", NAR, 22, 1994, 4039-4043.
Lun, et al., "Microfluidics digital PCR Reveals a Higher than expected fraction of fetal DNA in maternal plasma", Clinical Chemistry, vol. 54, No. 10, Oct. 1, 2008, 1664-1672.
Lundberg, et al., "High-fidelity amplification using a thermostable DNA polymerase isolated from Pyrococcus furiosus", Gene, 108, 1991, pp. 1-6.
Mann, et al., "Development and implementation of a new rapid aneuploidy diagnostic service within the UK National Health Service and implications for the future of prenatal diagnosis", Lancet.; 358(9287), Sep. 29, 2001, 1057-61.
Mansfield, et al., "Termination rates after prenatal diagnosis of Down syndrome, spina bifida, anencephaly, and Turner and Klinefelter syndromes: a systematic literature review", Prenatal Diagnosis 19, 1999, 808-812.
Margulies, et al., "An initial strategy for the systematic identification of functional elements in the human genome by low-redundancy comparative sequencing", PNAS vol. 102 (13), Mar. 29, 2005, 4795-4800.
Margulies, et al., "Genome sequencing in microfabricated high-density picolitre reactors", Nature, vol. 437, 2005, 376-380 and Supplemental Materials.
Mazloom, , "Gender Prediction with Bowtie Alignments using Male Specific Regions", May 10, 2012.
Metzker, , "Sequencing technologies—the next generation", Nat Rev Genet. 1(1) doi: 10.1038/m92626. Epub 2009 Dec. 8, Jan. 2010, p. 31-46.
Metzker, M.L. , "Applications of Next-Generation Sequencing: Sequencing technologies-the next generation", Nature Reviews Genetics, Nature Publishing Group, GB, vol. 11(1), Jan. 1, 2010, 31-46.
Miller, et al., "ReadDepth: A Parallel R Package for Detecting Copy Number Alterations from Short Sequencing Reads", PLoS One, vol. 6, Issue 1: e16327, Jan. 2011.
Mitchell, et al., "Chemical tags facilitate the sensing of individual DNA strands with nanopores", Angew. Chem. Int. Ed. 47, 2008, 5565.
Moudrianakis, et al., Proc Natl Acad Sci USA; 53, Mar. 1965, 564-71.
Mujezinovic, et al., "Procedure-related complications of amniocentesis and chorionic villous sampling: a systematic review", Obstetrics & Gynecology 110, 2007, 687-694.
Myers, et al., "Reverse transcription and DNA amplification by a Thermus thermophilus DNA polymerase", Biochemistry, 30, 1991, 7661-7666.
Nankano, et al., "Single molecule PCR using water-in-oil emulsion", Journal of Biotechnology vol. 102, 2003, 117-124.
Nason, , "Wavelet methods in Statistics, table of contents", R. Springer, New York ISBN: 978-0-387-75960-9 (Print) 978-0-387-75961-6 (Online), 2008.
National Human Genome Research I, , "Chromosomes fact sheet", http://www.genome.gov/26524120, downloaded Sep. 9, 2015.
Needham-Vandevanter, et al., "Characterization of an Adduct between 00-1065 and a defined oligodeoxynucleotide duplex", Nucleic Acids Research 12(15), 1984, 6159-6168.
Nevin, , "Future direction of medical genetics", The Ulster Medical Journal, vol. 70, No. 1, 2001, 1-2.
NG, et al., "mRNA of placental origin is readily detectable in maternal plasma", Proc. Nat. Acad. Sci., vol. 100, No. 8, 2003, 4748-4753.

(56) References Cited

OTHER PUBLICATIONS

NG, et al., "The Concentration of Circulating Corticotropin-releasing Hormone mRNA in Maternal Plasma ls Increased in Preecla[mu]psia", Clin. Chem., vol. 49:5, 2003, 727-731.
Nguyen, et al., "Denoising of Array-Based DNA Copy Number Data Using The Dual-tree Complex Wavelet Transform", Bioinformatics and Bioengineering, 2007. BIBE 2007. Proceedings of the 7th IEEE International Conference on IEEE, Piscataway, NJ, USA, Oct. 1, 2007, 137 -144.
Nichols, et al., "A Universal Nucleoside for Uses at Ambiguous Sites in DNA Primers", Nature 369, 1994, 492.
Nicolaides, et al., "One-stop clinic for assessment of risk of chromosomal defects at 12 weeks of gestation", J Matern Fetal Neonatal Med.; 12(1), Jul. 2002, 9-18.
Yuk, et al., "Genomic Analysis of Fetal Nucleic Acids in Maternal Blood", Annual Review of Genomics and Human Genetics, 13, May 29, 2012, 285-306.
Nolte, , "Branched DNA signal amplification for direct quantitation of nucleic acid sequences in clinical specimens", Adv Clin Chem.; 33, 1998, 201-35.
Nordstrom, et al., "Characterization of bacteriophage T7 DNA polymerase purified to homogeneity by antithioredoxin immunoadsorbent chromatography", J. Bioi. Chem. 256, 1981, 3112-3117.
Nygren, et al., "Quantification of Fetal DNA by Use of Methylation-Based DNA Discrimination", Clinical Chemistry, 56:10, 2010, 1627-1635.
Oh, et al., "CAM: A web tool for combining array CGH and microarray gene expression", Computers in Biology and Medicine 40, 2010, 781-785.
Ohno, , "Sex chromosomes and Sex-linked Genes", Berlin, Springer, 1967, 111.
Olshen, et al., "Circular binary segmentation for the analysis of array-based DNA copy number data", Biostatistics, 5(4), Oct. 2004, 557-572.
Omont, et al., "Gene-based bin analysis of genome-wide association studies", BMC Proceedings 2 (Suppl 4), 2008, S6.
Oroskar, et al., "Detection of immobilized amplicons by ELISA-like techniques", Clinical Chemistry 42, 1996, 1547-1555.
Oudejans, et al., "Detection of Chromosome 21-encoded mRANA of Placental Origin in Maternal Plasma", Clinical Chemistry, vol. 49, 2003, 1445-1449.
Palomaki, et al., "DNA sequencing of maternal plasma reliably identifies trisomy 18 and trisomy 13 as well as Down syndrome: an international collaborative study", Genet Med, 14, 2012, 296-305.
Palomaki, et al., "DNA sequencing of maternal plasma to detect Down syndrome: an international clinical validation study", Genet Med., 13(11), Nov. 2011, 913-920.
Pandya, et al., "Screening for fetal trisomies by maternal age and fetal nuchal translucency thickness at 10 to 14 weeks of gestation", Br J Obstet Gynaecol.; 102(12), Nov. 1995, 957-62.
Pearson, et al., "High-Performance Anion-Exchange Chromatography of OIigonucIeotides", J. Chrom., 255, 1983, 137-149.
Pekalska, et al., "Classifiers for dissimilarity-based pattern recognition", 15th International Conference on Pattern Recognition (ICPR'OO), vol. 2, Barcelona, Spain, Sep. 3-8, 2000, 12-16.
Pertl, et al., "Rapid molecular method for prenatal detection of Down's syndrome", Lancet; 343(8907), May 14, 1994, 1197-8.
Peters, D. et al., "Noninvasive Prenatal Diagnosis of a Fetal Microdeletion Syndrome", New England Journal of Medicine 365;19, Correspondence, Nov. 10 2011, 1847-1848.
Poon, et al., "Differential DNA Methylation between Fetus and Mother as a Strategy for Detecting Fetal DNA in Maternal Plasma", Clin. Chem, vol. 48, No. 1, 2002, 35-41.
Purnell, et al., "Discrimination of single base substitutions in a DNA strand immobilized in a biological nanopore", ACS Nano, 3, 2009, p. 2533
Pushkarev, et al., "Single-molecule sequencing of an individual human genome", Nat Biotechnol. 27(9):, Sep. 2009, 847-50.
QU, et al., "Analysis of drug-DNA binding data", Methods Enzymol.; 321, 2000, 353-69.
Robin, et al., "Defining the clinical spectrum of deletion 22q11.2", J Pediatr, 147(1), 2005, 90-6.
Romero, et al., "Diagnostic Molecular Biology: Principles and Applications", Pershing et al, eds., Mayo Foundation, Rochester, Minn., 1993, 401-406.
Romiguier, et al., "Contrasting GC-content dynamics across 33 mammalian genomes: relationship with life-history traits and chromosome sizes", Genome Research, 20, 2010, 1001-1009.
Ross, et al., "The DNA sequence of the human X chromosome", Nature, 434(7031), Mar. 17, 2005, 325-337.
Roth, et al., "JointSNVMix: a probabilistic model for accurate detection of somatic mutations in normal/tumour paired next-generation sequencing data", Bioinformatics, 28, 2012, 907-913.
Saito, et al., "Prenatal DNA diagnosis of a singlegene disorder from maternal plasma", Lancet 356, 2000, 1170.
Saito-Hisaminato, et al., "Genome-wide profiling of gene expression in 29 normal human tissues with a cDNA microarray", DNA Research, 2002, 35-45.
Sambrook, et al., "Molecular Cloning: A Laboratory Manual", Chapter 10, 3rd Edition, Cold Spring Harbor Laboratory, New York, 2001.
Schouten, et al., "Relative quantification of 40 nucleic acid sequences by multiplex ligationdependent probe amplification", Nucleic Acids Research, 30(12), 2002, e57, 1-13.
Schwinger, et al., "Clinical utility gene card for: DiGeorge syndrome, velocardiofacial syndrome, Shprintzen syndrome, chromosome 22q11.2 deletion syndrome (22q11.2, TBX1)", European Journal of Human Genetics,18, published online Feb. 3, 2010, 2010.
Sehnert, et al., "Optimal Detection of Fetal Chromosomal Abnormalities by Massively Parallel DNA Sequencing of Cell-Free Fetal DNA from Maternal Blood", Clinical Chemistry, July 2011, vol. 57 No. 7, E-pub on Apr. 25, 2011 as doi:10.1373/clinchem. 2011165910., Apr. 25, 2011, 1042-1049.
Sekizawa, et al., "Cell-free Fetal DNA is increased in Plasma of Women with Hyperemisis Gravidarum", Clin. Chem. 47, 2001, 2164-2165.
Shaffer, et al., "Variation in the decision to terminate pregnancy in the setting of fetal aneuploidy", Prenatal Diagnosis, 26, 2006, 667-671.
Shah, et al., "Mutational evolution in a Iobular breast tumour profiled at single nucleotide resolution", Nature, 461, 2009, 809-813.
Shen, et al., "A hidden Markov model for copy number variant prediction from whole genome resequencing data", BMC Bioinformatics,12(Suppl 6):54, 2011, 1-7.
Shendure, et al., "Next-generation DNA sequencing", Nature Biotechnology 26(10), 2008, 1135-1145.
Sherman, et al., "Epidemiology of Down syndrome", Ment Retard Dev Disabil Res Rev 13(3), 2007, 221-7.
Shin, et al., "Prevalence of Down syndrome among children and adolescents in 10 regions of the United States", Pediatrics, 124(6), 2009, 1565-71.
Skaletsy, et al., "The male-specific region of the human Y chromosome is a mosaic of discrete sequence classes", Nature, 423(6942), Jun. 19, 2003, 825-37.
Slater, et al., "Rapid, high throughput prenatal detection of aneuploidy using a novel quantitative method (MLPA)", J Med Genet, 40(12), Dec. 2003, 907-12.
SMID, , "Evaluation of Different Approaches for Fetal DNA Analysis from Maternal Plasma and Nucleated Blood Cells", Clinical Chemistry, vol. 45, No. 8, 1999, 1570-1572.
Smith, et al., "Direct Mechanical Measurements of the Elasticity of Single DNA Molecules by Using Magnetic Beads", Science, 258, 1992, p. 1122.
Snijders, et al., "Assembly of microarrays for genome-wide measurement of DNA copy number", Nat Genet; 29(3), Nov. 2001, 263-4.
Snijders, et al., "First-trimester ultrasound screening for chromosomal defects", Ultrasound Obstet Gynecol.; 7(3), Mar. 1996, 216-26.

(56) References Cited

OTHER PUBLICATIONS

Smijder, et al., "UK multicentre project on assessment of risk of trisomy 21 by maternal age and fetal nuchal-translucency thickness at 10-14 weeks of gestation. Fetal Medicine Foundation First Trimester Screening Group", Lancet.; 352(9125), Aug. 1, 1998, 343-6.
Soni, et al., "Progress toward Ultrafast DNA Sequencing Using Solid-State Nanopores", Clin Chem, 53(11), 2007, 1996-2001.
Sparks, et al., "Non-invasive prenatal detection and selective analysis of cell-free DNA obtained from maternal blood: evaluation for trisomy 21 and trisomy 18", American Journal of Obstetrics and Gynecology, doi: 10.1016/j.ajog.2012.01.030, Jan. 30, 2012, 33 pages.
Sparks, et al., "Selective analysis of cell-free DNA in maternal blood for evaluation of fetal trisomy", Prenat Diagn. 32(1), Jan. 2012, 3-9.
Srinivasan, et al., "Noninvasive Detection of Fetal Subchromosome Abnormalities via Deep Sequencing of Maternal Plasma", The American Journal of Human Genetics, vol. 92, No. 2, Feb. 7, 2013, 167-176.
Stagi, et al., "Bone density and metabolism in subjects with microdeletion of chromosome 22q11 (del22q11)", Eur J Endocrinol, 163(2), 2010, 329-37.
Stanghellini, et al., "Quantitation of fetal DNA in maternal serum during the first trimester of pregnancy by the use of a DAZ repetitive probe", Mol Hum Reprod, 12(9), 2006, 587-91.
Stenesh, et al., "DNA polymerase from mesophilic and thermophilic bacteria. III. Lack of fidelity in the replication of synthetic polydeoxyribonucleotides by DNA polymerase from *Bacillus licheniformis* and *Bacillus stearothermophilus*", Biochim Biophys Acta 475, 1977, 32-41.
Stoddart, et al., "Single-nucleotide discrimination in immobilized DNA oligonucleotides with a biological nanopore", PNAS, vol. 106, No. 19, May 12, 2009, 7702-7707.
Strachan, , "The Human Genome", BIOS Scientific Publishers, 1992.
Tabor, et al., "Randomised controlled trial of genetic amniocentesis in 4606 low-risk women", Lancet, 1(8493), 1986, 1287-93.
Takagi, et al., "Characterization of DNA polymerase from Pyrococcus sp. strain KOD1 and its application to PCR", Appl. Environ. Microbial. 63(11), 1997, 4504-4510.
Taylor, et al., "Characterization of chemisorbed monolayers by surface potential measurements", J. Phys. D: Appl. Phys., 24, 1991, p. 1443.
Timp, et al., "Nanopore Sequencing: Electrical Measurements of the Code of Life", IEEE Trans Nanotechnol., 9(3), May 1, 2010, 281-294.
Trapnell, et al., "How to map billions of short reads onto genomes", Nat. Biotechnol. 27(5), 2009, pp. 455-457.
Van Den Berghe, et al., "A new characteristic karyotypic anomaly in lymphoproliferative disorders", Cancer, 44, 1979, 188-95.
Vetlman, et al., "High-throughput analysis of subtelomeric chromosome rearrangements by use of array-based comparative genomic hybridization", Am J Hum Genet.; 70(5). Epub 2002 Apr. 9, May 2002, 1269-76.
Venkatraman, et al., "A faster circular binary segmentation algorithm for the analysis of array CGH data", Bioinformatics, 23, 6, 2007, 657-63.
Verbeck, et al., in the Journal of Biomolecular Techniques, vol. 13, Issue 2, 56-61.
Verma, et al., "Rapid and simple prenatal DNA diagnosis of Down's syndrome", Lancet; 352(9121), Jul. 4, 1998, 9-12.
Verma, , "The reverse transcriptase", Biochim Biophys Acta 473(1), Mar. 21, 1977, pp 1-38.
Vincent, et al., "Helicase-dependent isothermal DNA amplification", EMBO Rep 5, Epub Jul. 9, 2004, 795-800.
Voelkerding, et al., "Next-Generation Sequencing: From Basic Research to Diagnostics", Clinical Chemistry 55:4, 2009, 641-658.
Vogelstein, et al., "Digital PCR", PNAS USA, vol. 96, Aug. 3, 1999, 9236-9241.
Wang, et al., "A novel stationary wavelet denoising algorithm for array- based DNA copy number data", International Journal of Bioinformatics Research and Applications, vol. 3, No. 2, 2007, 206-222.
Wapner, et al., "First-trimester screening for trisomies 21 and 18", N Engl J Med.; 349(15), Oct. 9, 2003, 1405-13.
WaveThresh, , "Wavelets statistics and transforms", retrieved from the internet <URL:*>http://cran.r-project.org/web/packages/wavethresh/index.html<> and a detailed description of WaveThresh (Package 'wavethresh', Apr. 2, 2013, retrieved from the internet <URL:*>http://cran.rproject.org/web/packages/w, Apr. 24, 2013.
Wei, et al., "Detection and Quantification by Homogenous PCR of Cell-free Fetal DNA in Maternal Plasma", Clinical Chemistry, vol. 47, No. 2, 2001, 336-338.
WillenBrock, et al., "A comparison study: applying segmentation to array CGH data for downstream analyses", Bioinformatics, 21(22):, Nov. 15, 2005, 4084-91.
Wright, et al., "The use of cell-free fetal nucleic acids in maternal blood for non-invasive prenatal diagnosis", Hum Reprod Update. 15(1), Jan. 1, 2009, 139-151.
Wu, et al., "Genetic and environmental influences on blood pressure and body mass index in Han Chinese: a twin study", Hypertens Res. Hypertens Res 34: advance online publication, Nov. 4, 2010, Feb. 2011, 173-179.
Wu, et al., "Reverse Transcriptas", CRC Grit. Rev Biochem. 3(3), Jan. 1975, pp. 289-347.
Xie, et al., "CNV-seq, a new method to detect copy number variation using high-thoughput sequencing", BMC Bioinformatics, 10:80, 2009, 9 pages.
Yershov, et al., "DNA analysis and diagnostics on oligonucleotide microchips", PNAS US 93, 1996, 4913-4918.
Yoon, et al., "Sensitive and accurate detection of copy number variants using read depth of coverage", Genome Research, vol. 19, 2009, 1586-1592.
Yu, et al., "Noninvasive Prenatal Molecular Karyotyping from Maternal Plasma", PLOS One, vol. 8, Issue 4, Apr. 2013, e60968.
Yu, et al., "Size-based molecular diagnostics using plasma DNA for noninvasive prenatal testing", PNAS USA 111(23), 2014, pp. 8583-8588.
Office Action in U.S. Appl. No. 17/933,938 dated Jun. 3, 2026, 26 pages.

* cited by examiner

Fetal fraction estimates based on Chr 21 vs. measured fetal fractions.

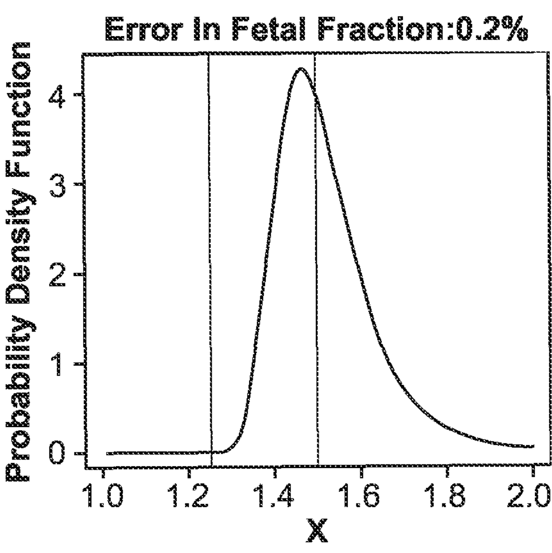
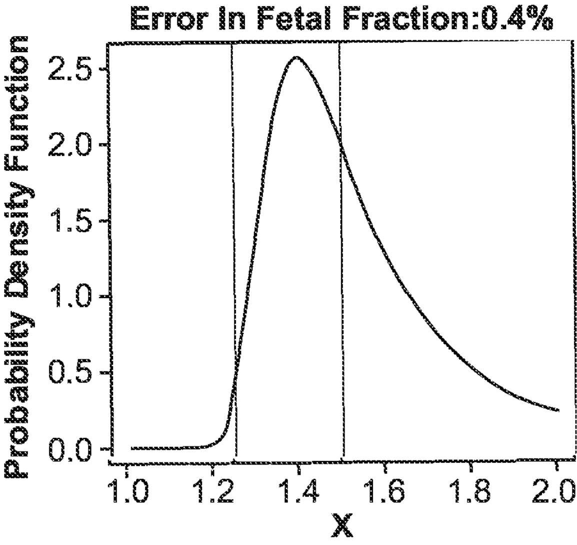
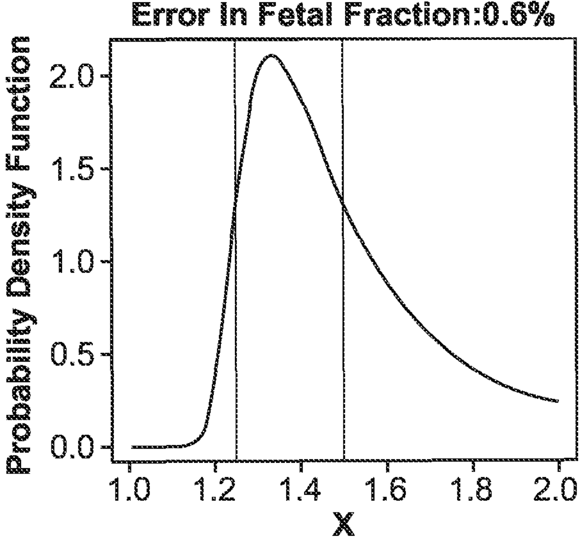
FIG. 42

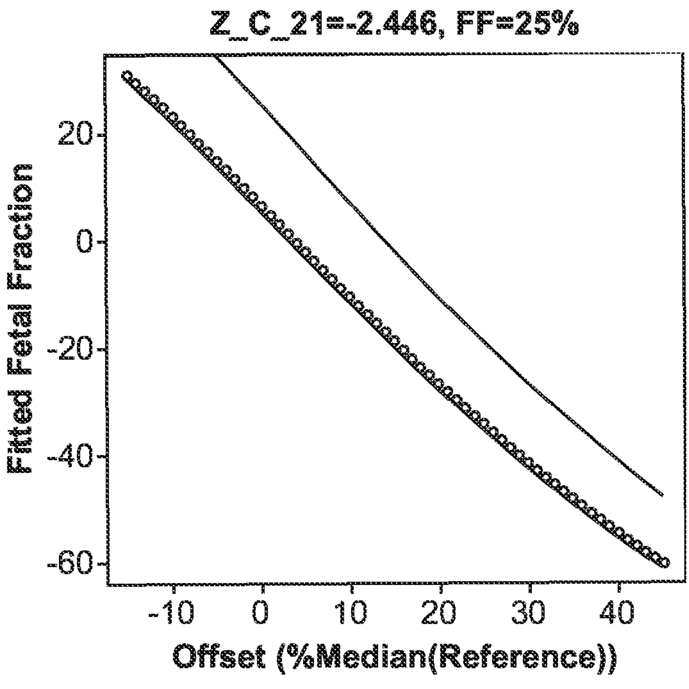
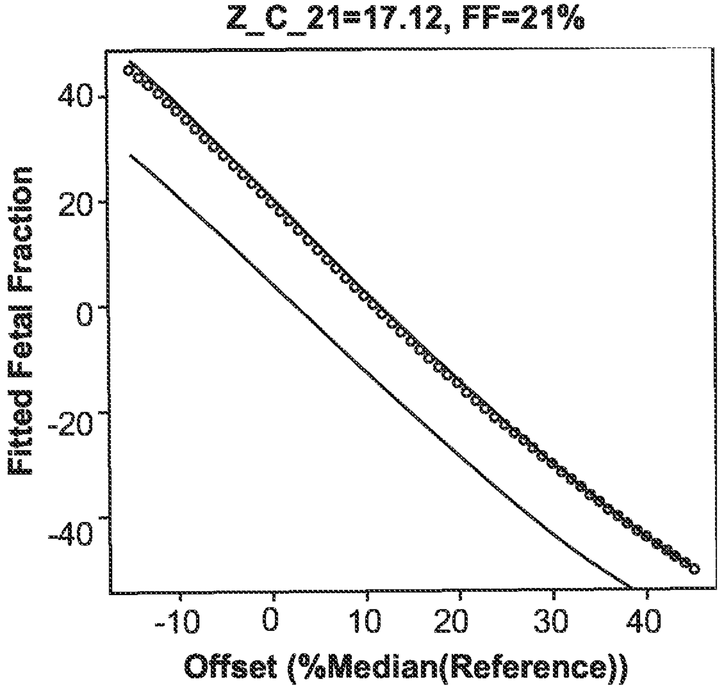
FIG. 50

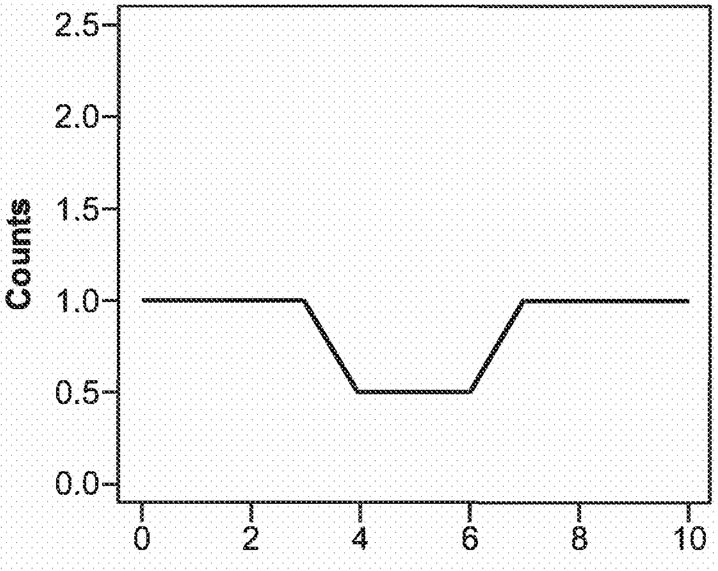
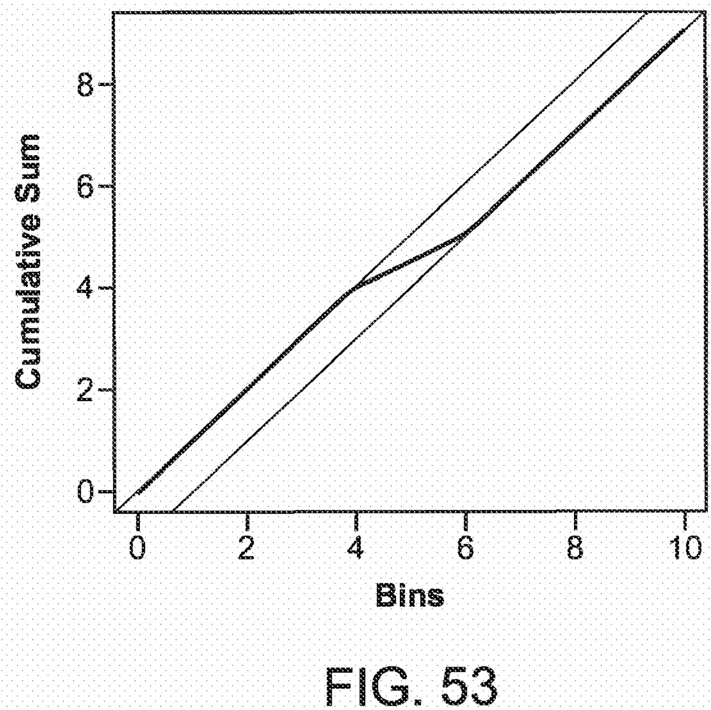
FIG. 53

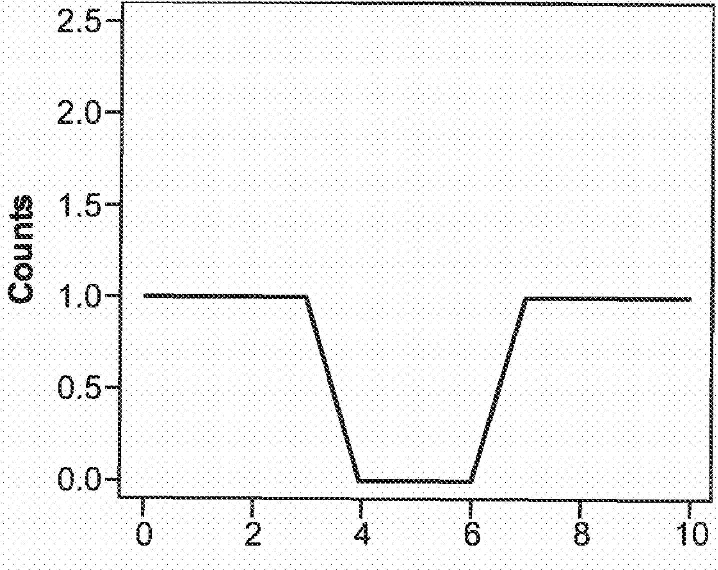
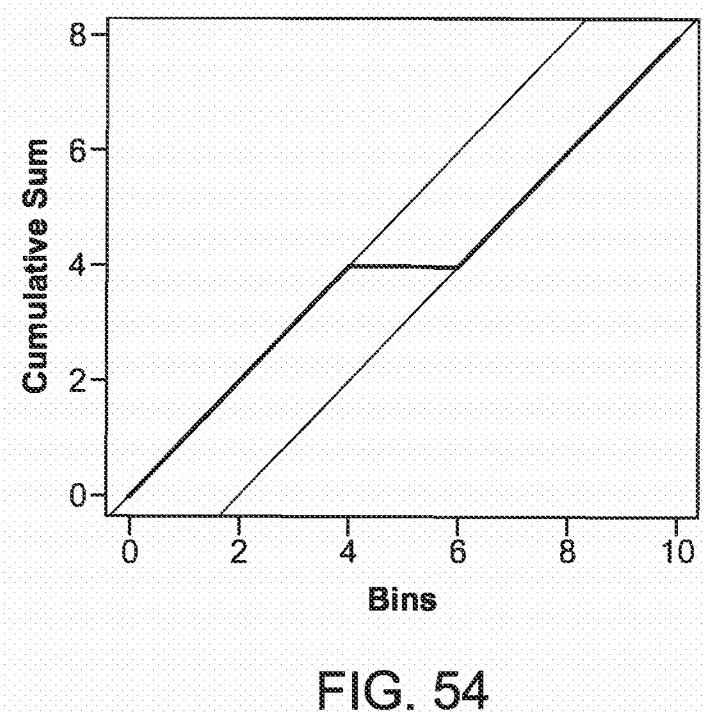
FIG. 54

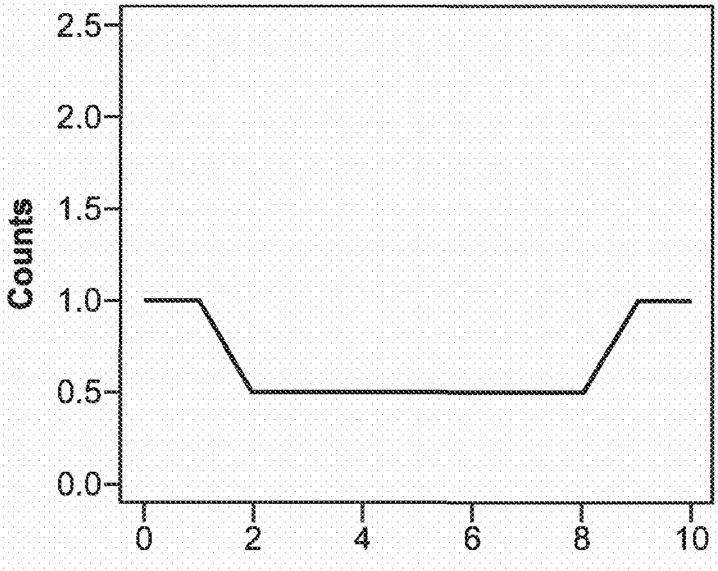
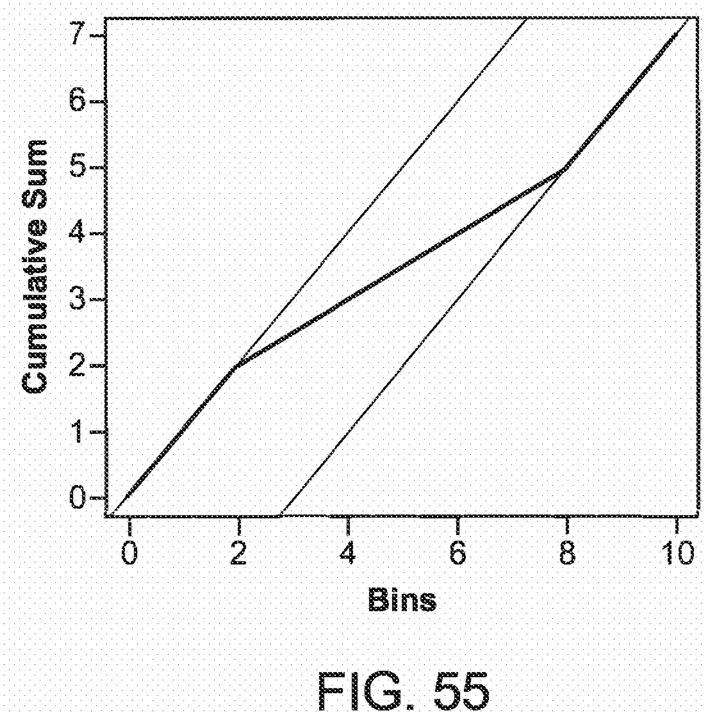
FIG. 55

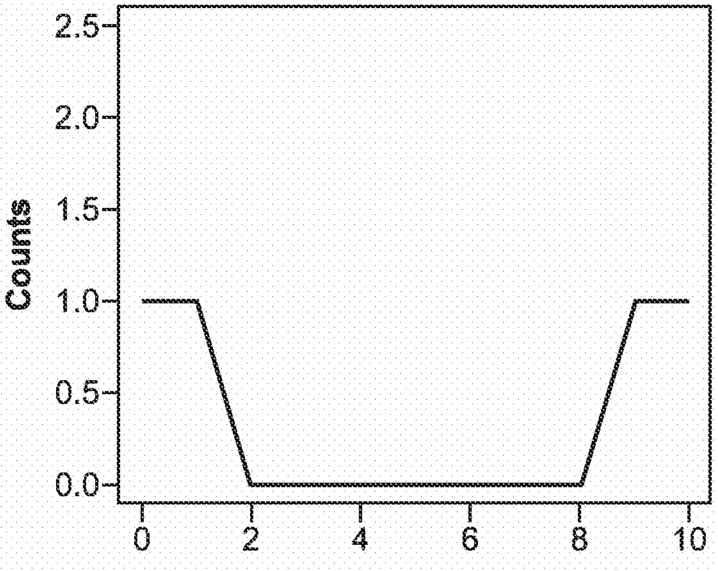
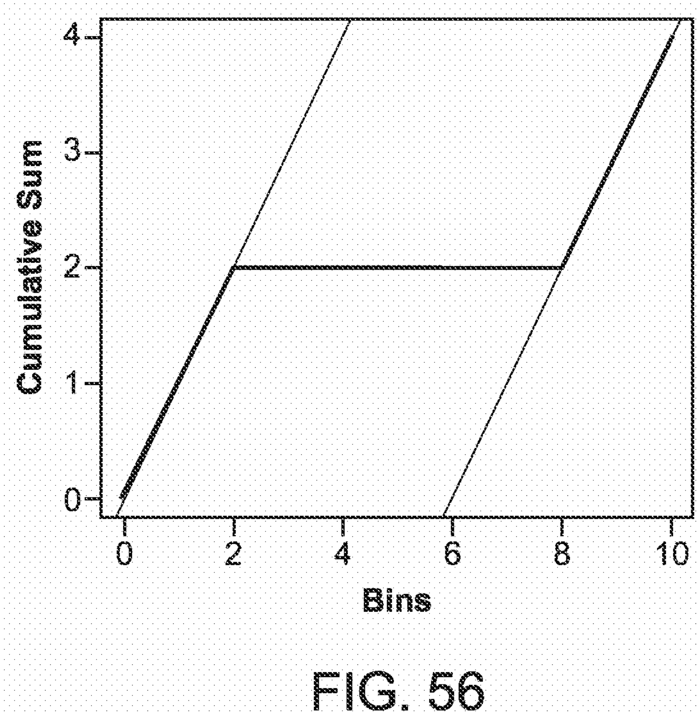
FIG. 56

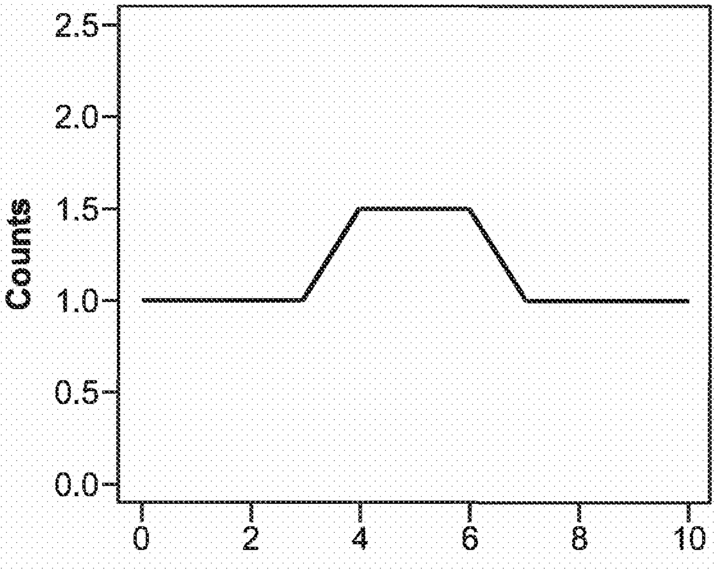
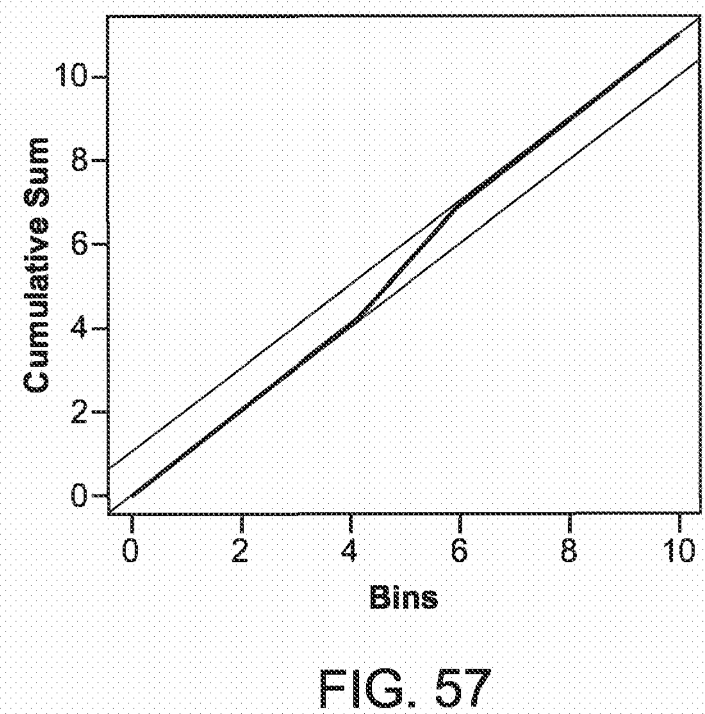
FIG. 57

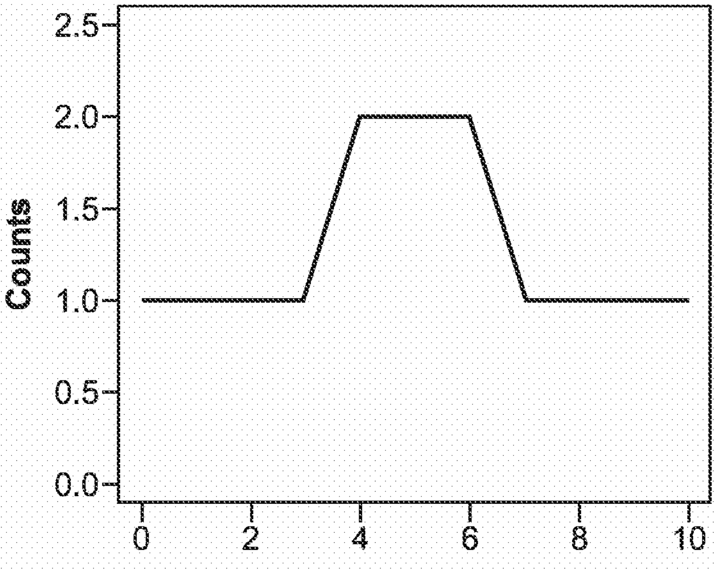
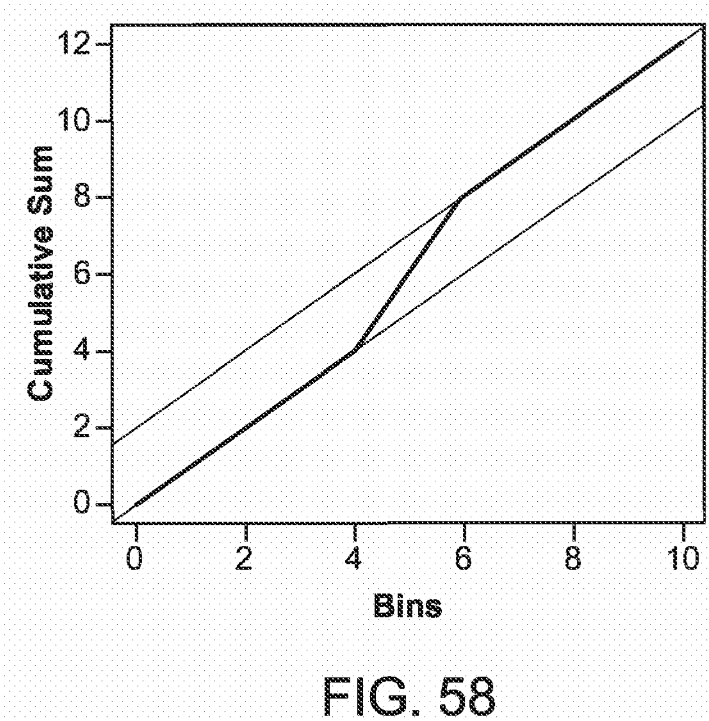
FIG. 58

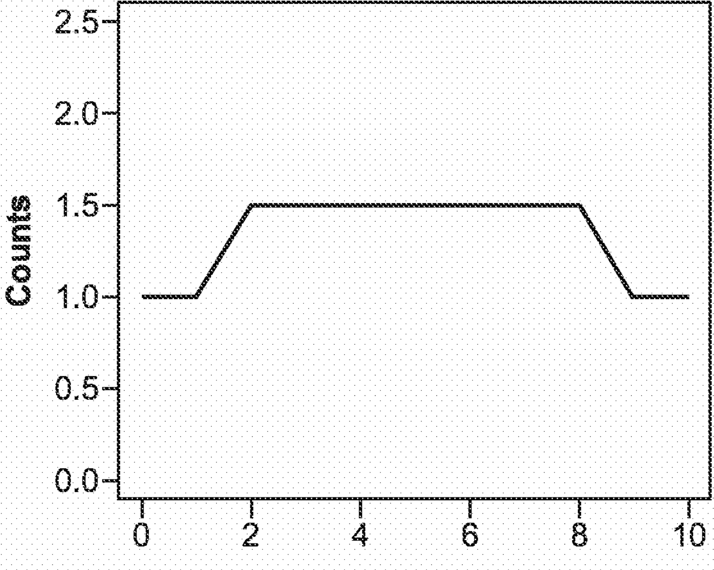
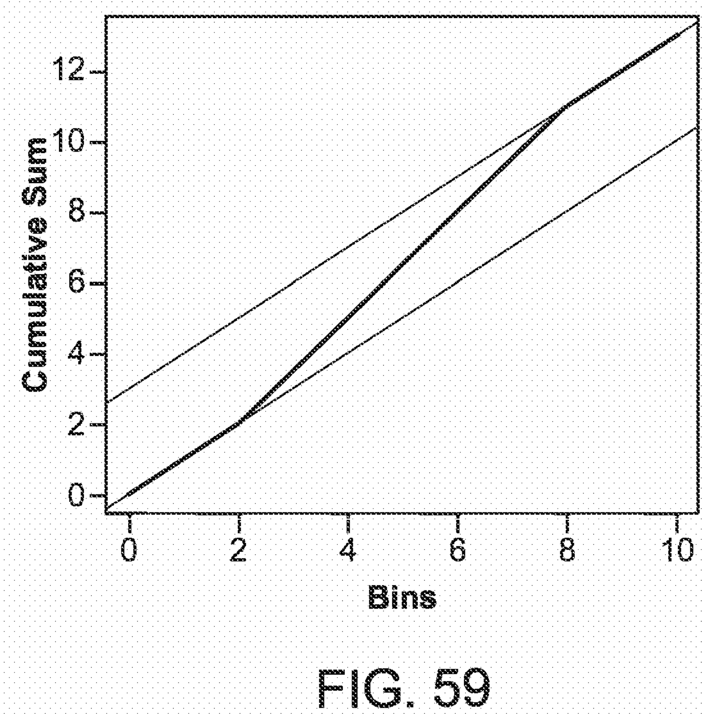
FIG. 59

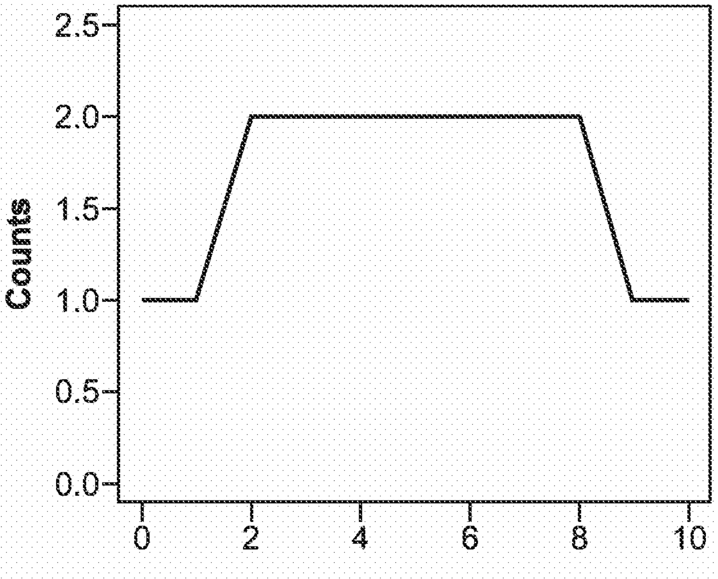
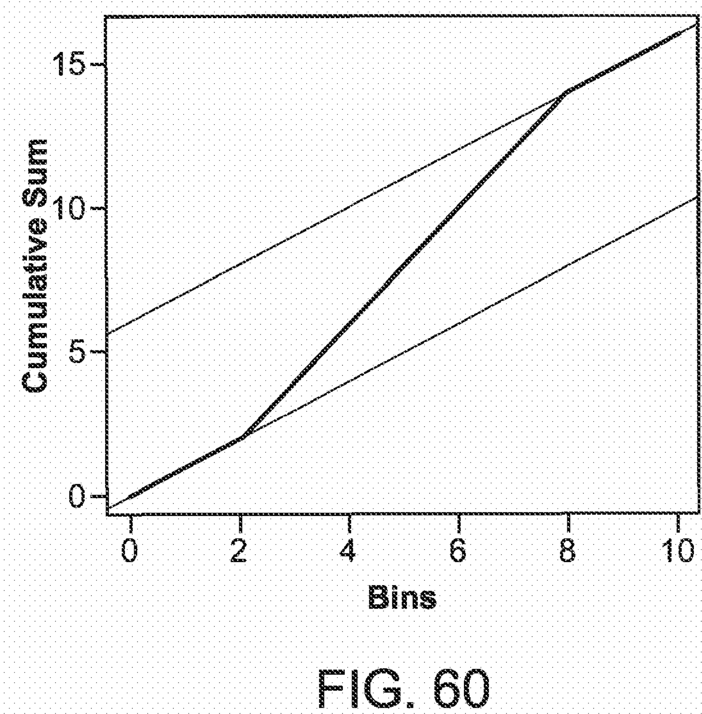
FIG. 60

Chromosomal Level
2.0
1.0
0.0
Trisomy: L=1 + F/2
54500 55000 55500 56000 56500 57000 57500
Chr 20, 21, 22 (50 kbp bins)

Frequency
12
10
8
6
4
2
0
0.134
0.136
0.138
0.140
Slopes

| SCA Category | Phenotypes | Prevalence |
|---|---|---|
| **45,X** | 2.5% of affected develop to full term, abnormal growth pattern, short in stature, possible mental retardation, sterile | Female 1:3000 |
| **47,XXX** | No severe phenotype, mild learning difficulties | Female 1:1000 |
| **47,XXY or XY/XXY Mosaic** | Infertile, tall, abnormal testis development, deficiency in secondary male sex characteristics | Male 1:600 |
| **47,XYY** | Tall, higher level of testosterone, prone to acne | 1:1000 |

FIG. 136

| Demographic | Median | Range |
|---|---|---|
| **Maternal Age, years (n=411)** | 36 | 19 - 47 |
| **Gestational Age, weeks (n=411)** | 17 | 8 - 29 |
| **Body Mass Index (n=408)** | 24.8 | 16.4 - 49.6 |
| **Variable** | Percent | $N_{affected}$ / $N_{total}$ |
| **Ethnicity** | | |
| African American / Black | 7.5 | 31 / 411 |
| American Indian / Alaska Native | 0.7 | 3 / 411 |
| Asian | 18.5 | 76 / 411 |
| Caucasian / White | 58.4 | 240 / 411 |
| Hispanic | 5.1 | 21 / 411 |
| Multiracial | 0.2 | 1 / 411 |
| Not Specified | 9.5 | 39 / 411 |
| **Procedure** | | |
| Genetic Amniocentesis (Non-Transplacental) | 63.7 | 262 / 411 |
| Genetic Amniocentesis (Transplacental) | 9.5 | 39 / 411 |
| CVS | 26 | 107 / 411 |
| Not Specified | 0.7 | 3 / 411 |
| **Indication for Testing** | | |
| Advanced Maternal Age | 61.8 | 254 / 411 |
| Family History of Aneuploidy | 4.9 | 20 / 411 |
| Ultrasound Abnormality | 22.6 | 93 / 411 |
| 1st Trimester Positive Serum Screening | 9.2 | 38 / 411 |
| 1st Trimester Positive Sequential Serum Screening | 1.2 | 5 / 411 |
| 2nd Trimester Positive Serum Screening | 23.6 | 97 / 411 |
| 2nd Trimester Triple/Quad Positive Serum Screening | 5.8 | 24 / 411 |
| Other | 4.1 | 17 / 411 |
| **Confirmation** | | |
| Karyotype | 63.5 | 261 / 411 |
| FISH | 0.2 | 1 / 411 |
| Both | 36.3 | 149 / 411 |

FIG. 137

Karyotype Result

Number (%) from the training dataset

| Test Result | XX | X | XXX | XY | XXY | XYY | Total |
|---|---|---|---|---|---|---|---|
| **XX** | *720 (94.4)* | 0 | 0 | 4 ( 0.5) | 0 | 0 | 724 |
| **X** | 3 ( 0.4) | *8 (100)* | 0 | 0 | 0 | 0 | 11 |
| **XXX** | 1 ( 0.1) | 0 | *4 (100)* | 0 | 0 | 0 | 5 |
| **XY** | 4 ( 0.5) | 0 | 0 | *718 (99.4)* | 0 | 0 | 722 |
| **XXY** | 0 | 0 | 0 | 0 | *6 (100)* | 0 | 6 |
| **XYY** | 0 | 0 | 0 | 0 | 0 | *1 (100)* | 1 |
| **Not Reported** | 35 ( 4.8) | 1 ( 12.5) | 1 ( 25) | 56 ( 7.8) | 2 ( 33) | 0 | 95 |
| **Total** | 763 | 9 | 5 | 778 | 8 | 1 | 1564 |

Number (%) from the validation dataset

| Test Result | XX | X | XXX | XY | XXY | XYY | Total |
|---|---|---|---|---|---|---|---|
| **XX** | *167 (97.1)* | 1( 5.5) | 0 | 1 ( 0.5) | 0 | 0 | 169 |
| **X** | 1 ( 0.6) | *17(94.4)* | 0 | 0 | 0 | 0 | 18 |
| **XXX** | 0 | 0 | *1 (100)* | 0 | 0 | 0 | 1 |
| **XY** | 4 ( 2.3) | 0 | 0 | *191 (99.5)* | 0 | 0 | 194 |
| **XXY** | 0 | 0 | 0 | 0 | *5 (100)* | 0 | 5 |
| **XYY** | 0 | 0 | 0 | 0 | 0 | *2 (100)* | 2 |
| **Not Reported** | 4 ( 2.3) | 3(16.7) | 0 | 13 ( 6.8) | 0 | 1 ( 50) | 21 |
| **Total** | 176 | 21 | 1 | 205 | 5 | 3 | 411 |

Number (%) from both datasets

| Test Result | XX | X | XXX | XY | XXY | XYY | Total |
|---|---|---|---|---|---|---|---|
| **XX** | *887 (98.5)* | 1 ( 4) | 0 | 5 ( 0.5) | 0 | 0 | 893 |
| **X** | 4 ( 0.4) | *25 ( 96)* | 0 | 0 | 0 | 0 | 29 |
| **XXX** | 1 ( 0.1) | 0 | *5 (100)* | 0 | 0 | 0 | 6 |
| **XY** | 8 ( 0.9) | 0 | 0 | *909 (99.4)* | 0 | 0 | 917 |
| **XXY** | 0 | 0 | 0 | 0 | *11 (100)* | 0 | 11 |
| **XYY** | 0 | 0 | 0 | 0 | 0 | *3 (100)* | 3 |
| **Not Reported** | 39 ( 4.3) | 4(15.4) | 1 ( 20) | 69 ( 7.5) | 2 ( 18) | 1 ( 33) | 116 |
| **Total** | 939 | 30 | 6 | 983 | 13 | 4 | 1975 |

FIG. 138

```
################################################################################
complement <- function( superSet, subSet ) {
  complementarySet <- which( is.na( match( superSet, subSet ) ) );
  return( superSet[ complementarySet ] );
} # complement

# PATH: C:\SEQUENOM_PROJECTS\USEFUL_SCRIPTS\
# FILE: SEX_ANEUPLOIDY_PERUN_LDTv2_BOWTIE.r
# AUTHOR: Zeljko Jovan Dzakula
# DATE: 8/24/2012

source( "C:/SEQUENOM_PROJECTS/USEFUL_SCRIPTS/complement.r" );

################################################################################
piecewiseChromosomalRepresentation <- function( normalizedProfile, retainAutosomes, chrBins, specialBins=c() ) {
  norm <- sum(
    normalizedProfile[ as.character( retainAutosomes ) ], na.rm=TRUE );
  #
  totalChrLevel <- sum(
    normalizedProfile[ as.character( chrBins ) ], na.rm=TRUE );
  if ( length( specialBins ) > 0 ) {
    specialChrLevel <- sum(
      normalizedProfile[ as.character( specialBins ) ], na.rm=TRUE );
    trimmedChrLevel <- totalChrLevel - specialChrLevel;
    #
    specialChrMAD <- mad(
      normalizedProfile[ as.character( specialBins ) ], na.rm=TRUE );
    trimmedChrMAD <- mad( normalizedProfile[ complement( as.character(
      chrBins ), as.character( specialBins ) ) ], na.rm=TRUE );
    #
    delta <- specialChrLevel / length( specialBins ) -
        trimmedChrLevel / ( length( chrBins ) - length( specialBins ) );
    sigma <- sqrt(
      trimmedChrMAD * trimmedChrMAD / ( length( chrBins ) - length( specialBins ) ) +
      specialChrMAD * specialChrMAD / length( specialBins ) );
    if ( abs( delta ) / sigma > 3 ) {
      totalChrLevel <- trimmedChrLevel * ( 1 + length( specialBins ) / length( chrBins ) );
    } else {
      # Do nothing
    } # if delta/sigma else
    #
  } else {
    # Do nothing
  } # if length else
  return( totalChrLevel / norm );
} # piecewiseChromosomalRepresentation
```

FIG. 149

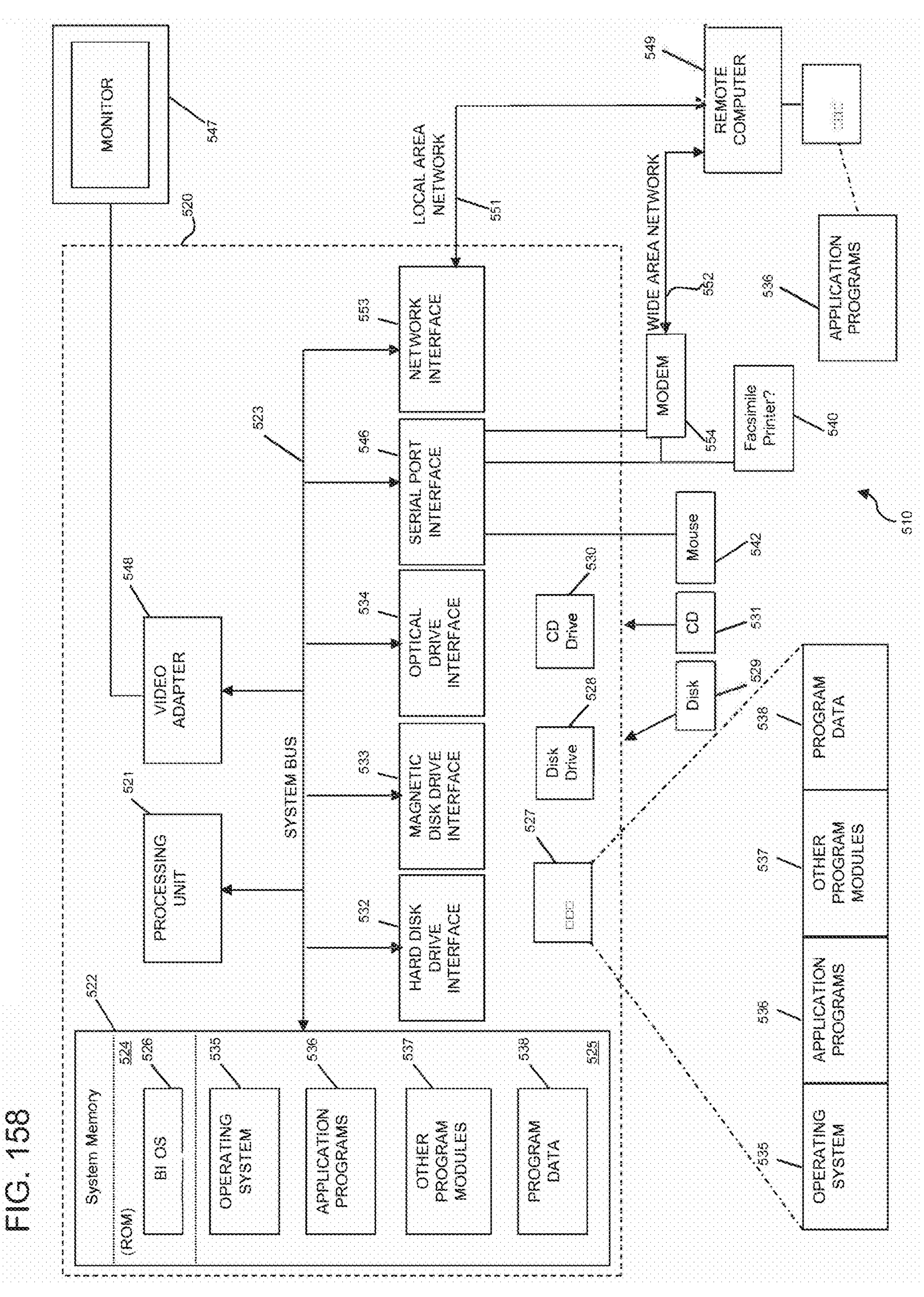
FIG. 158
System Memory
(ROM)
524
526
BI OS
535
OPERATING SYSTEM
536
APPLICATION PROGRAMS
537
OTHER PROGRAM MODULES
538
PROGRAM DATA
525
522
520
521
PROCESSING UNIT
SYSTEM BUS
523
548
VIDEO ADAPTER
MONITOR
547
532
HARD DISK DRIVE INTERFACE
533
MAGNETIC DISK DRIVE INTERFACE
534
OPTICAL DRIVE INTERFACE
546
SERIAL PORT INTERFACE
553
NETWORK INTERFACE
LOCAL AREA NETWORK
551
WIDE AREA NETWORK
552
MODEM
554
549
REMOTE COMPUTER
Facsimile Printer?
540
536
APPLICATION PROGRAMS
Mouse
542
CD
531
Disk
529
CD Drive
530
Disk Drive
528
527
510
535
OPERATING SYSTEM
536
APPLICATION PROGRAMS
537
OTHER PROGRAM MODULES
538
PROGRAM DATA

METHODS AND PROCESSES FOR NON-INVASIVE ASSESSMENT OF GENETIC VARIATIONS

RELATED PATENT APPLICATIONS

This patent application is a continuation of U.S. patent application Ser. No. 13/797,508 filed on Mar. 12, 2013, entitled METHODS AND PROCESSES FOR NON-INVASIVE ASSESSMENT OF GENETIC VARIATIONS, naming Zeljko Dzakula, Cosmin Deciu, Amin Mazloom, and Huiquan Wang as inventors, which claims the benefit of U.S. provisional patent application No. 61/663,482 filed on Jun. 22, 2012, entitled METHODS AND PROCESSES FOR NON-INVASIVE ASSESSMENT OF GENETIC VARIATIONS, naming Zeljko Dzakula, Cosmin Deciu, Amin Mazloom, and Huiquan Wang as inventors. The entire contents of the foregoing applications are incorporated herein by reference, including all text, tables and drawings.

FIELD

Technology provided herein relates in part to methods, processes and apparatuses for non-invasive assessment of genetic variations.

BACKGROUND

Genetic information of living organisms (e.g., animals, plants and microorganisms) and other forms of replicating genetic information (e.g., viruses) is encoded in deoxyribonucleic acid (DNA) or ribonucleic acid (RNA). Genetic information is a succession of nucleotides or modified nucleotides representing the primary structure of chemical or hypothetical nucleic acids. In humans, the complete genome contains about 30,000 genes located on twenty-four (24) chromosomes (see The Human Genome, T. Strachan, BIOS Scientific Publishers, 1992). Each gene encodes a specific protein, which after expression via transcription and translation fulfills a specific biochemical function within a living cell.

Many medical conditions are caused by one or more genetic variations. Certain genetic variations cause medical conditions that include, for example, hemophilia, thalassemia, Duchenne Muscular Dystrophy (DMD), Huntington's Disease (HD), Alzheimer's Disease and Cystic Fibrosis (CF) (Human Genome Mutations, D. N. Cooper and M. Krawczak, BIOS Publishers, 1993). Such genetic diseases can result from an addition, substitution, or deletion of a single nucleotide in DNA of a particular gene. Certain birth defects are caused by a chromosomal abnormality, also referred to as an aneuploidy, such as Trisomy 21 (Down's Syndrome), Trisomy 13 (Patau Syndrome), Trisomy 18 (Edward's Syndrome), Monosomy X (Turner's Syndrome) and certain sex chromosome aneuploidies such as Klinefelter's Syndrome (XXY), for example. Another genetic variation is fetal gender, which can often be determined based on sex chromosomes X and Y. Some genetic variations may predispose an individual to, or cause, any of a number of diseases such as, for example, diabetes, arteriosclerosis, obesity, various autoimmune diseases and cancer (e.g., colorectal, breast, ovarian, lung).

Identifying one or more genetic variations or variances can lead to diagnosis of, or determining predisposition to, a particular medical condition. Identifying a genetic variance can result in facilitating a medical decision and/or employing a helpful medical procedure. Identification of one or more genetic variations or variances sometimes involves the analysis of cell-free DNA.

Cell-free DNA (CF-DNA) is composed of DNA fragments that originate from cell death and circulate in peripheral blood. High concentrations of CF-DNA can be indicative of certain clinical conditions such as cancer, trauma, burns, myocardial infarction, stroke, sepsis, infection, and other illnesses. Additionally, cell-free fetal DNA (CFF-DNA) can be detected in the maternal bloodstream and used for various noninvasive prenatal diagnostics.

The presence of fetal nucleic acid in maternal plasma allows for non-invasive prenatal diagnosis through the analysis of a maternal blood sample. For example, quantitative abnormalities of fetal DNA in maternal plasma can be associated with a number of pregnancy-associated disorders, including preeclampsia, preterm labor, antepartum hemorrhage, invasive placentation, fetal Down syndrome, and other fetal chromosomal aneuploidies. Hence, fetal nucleic acid analysis in maternal plasma can be a useful mechanism for the monitoring of fetomaternal well-being.

SUMMARY

Provided, in some aspects, are methods for identifying the presence or absence of a sex chromosome aneuploidy in a fetus, comprising (a) obtaining counts of sequence reads mapped to sections of a reference genome, which sequence reads are reads of circulating cell-free nucleic acid from a pregnant female bearing a fetus; (b) determining a guanine and cytosine (GC) bias for each of the sections of the reference genome for multiple samples from a fitted relation for each sample between (i) the counts of the sequence reads mapped to each of the sections of the reference genome, and (ii) GC content for each of the sections; (c) calculating a genomic section level for each of the sections of the reference genome from a fitted relation between the GC bias and the counts of the sequence reads mapped to each of the sections of the reference genome, thereby providing calculated genomic section levels; and (d) identifying the presence or absence of a sex chromosome aneuploidy for the fetus according to the calculated genomic section levels.

Also provided, in some aspects, are methods for determining fetal gender, comprising (a) obtaining counts of sequence reads mapped to sections of a reference genome, which sequence reads are reads of circulating cell-free nucleic acid from a pregnant female bearing a fetus; (b) determining a guanine and cytosine (GC) bias for each of the sections of the reference genome for multiple samples from a fitted relation for each sample between (i) the counts of the sequence reads mapped to each of the sections of the reference genome, and (ii) GC content for each of the sections; (c) calculating a genomic section level for each of the sections of the reference genome from a fitted relation between the GC bias and the counts of the sequence reads mapped to each of the sections of the reference genome, thereby providing calculated genomic section levels; and (d) determining fetal gender according to the calculated genomic section levels.

Also provided, in some aspects, are methods for determining sex chromosome karyotype in a fetus, comprising (a) obtaining counts of sequence reads mapped to sections of a reference genome, which sequence reads are reads of circulating cell-free nucleic acid from a pregnant female bearing a fetus; (b) determining a guanine and cytosine (GC) bias for each of the sections of the reference genome for multiple samples from a fitted relation for each sample between (i)

the counts of the sequence reads mapped to each of the sections of the reference genome, and (ii) GC content for each of the sections; (c) calculating a genomic section level for each of the sections of the reference genome from a fitted relation between the GC bias and the counts of the sequence reads mapped to each of the sections of the reference genome, thereby providing calculated genomic section levels; and (d) determining sex chromosome karyotype for the fetus according to the calculated genomic section levels.

Also provided, in some aspects, are methods for identifying the presence or absence of a sex chromosome aneuploidy in a fetus, comprising (a) obtaining counts of sequence reads mapped to sections of a reference genome, which sequence reads are reads of circulating cell-free nucleic acid from a pregnant female bearing a fetus; (b) determining an experimental bias for each of the sections of the reference genome for multiple samples from a fitted relation for each sample between (i) the counts of the sequence reads mapped to each of the sections of the reference genome, and (ii) a mapping feature for each of the sections; (c) calculating a genomic section level for each of the sections of the reference genome from a fitted relation between the experimental bias and the counts of the sequence reads mapped to each of the sections of the reference genome, thereby providing calculated genomic section levels; and (d) identifying the presence or absence of a sex chromosome aneuploidy for the fetus according to the calculated genomic section levels.

Also provided, in some aspects, are methods for for determining fetal gender, comprising (a) obtaining counts of sequence reads mapped to sections of a reference genome, which sequence reads are reads of circulating cell-free nucleic acid from a pregnant female bearing a fetus; (b) determining an experimental bias for each of the sections of the reference genome for multiple samples from a fitted relation for each sample between (i) the counts of the sequence reads mapped to each of the sections of the reference genome, and (ii) a mapping feature for each of the sections; (c) calculating a genomic section level for each of the sections of the reference genome from a fitted relation between the experimental bias and the counts of the sequence reads mapped to each of the sections of the reference genome, thereby providing calculated genomic section levels; and (d) determining fetal gender according to the calculated genomic section levels.

Also provided, in some aspects, are methods for determining sex chromosome karyotype in a fetus, comprising (a) obtaining counts of sequence reads mapped to sections of a reference genome, which sequence reads are reads of circulating cell-free nucleic acid from a pregnant female bearing a fetus; (b) determining an experimental bias for each of the sections of the reference genome for multiple samples from a fitted relation for each sample between (i) the counts of the sequence reads mapped to each of the sections of the reference genome, and (ii) a mapping feature for each of the sections; (c) calculating a genomic section level for each of the sections of the reference genome from a fitted relation between the experimental bias and the counts of the sequence reads mapped to each of the sections of the reference genome, thereby providing calculated genomic section levels; and (d) determining sex chromosome karyotype for the fetus according to the calculated genomic section levels.

Also provided, in some aspects, are systems comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to (a) determine an experimental bias for each of the sections of the reference genome for multiple samples from a fitted relation for each sample between (i) the counts of the sequence reads mapped to each of the sections of the reference genome, and (ii) a mapping feature for each of the sections; (b) calculate a genomic section level for each of the sections of the reference genome from a fitted relation between the experimental bias and the counts of the sequence reads mapped to each of the sections of the reference genome, thereby providing calculated genomic section levels; and (c) identify the presence or absence of a sex chromosome aneuploidy for the fetus, determine fetal gender, and/or determine sex chromosome karyotype for the fetus according to the calculated genomic section levels.

Also provided, in some aspects, are apparatuses comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to (a) determine an experimental bias for each of the sections of the reference genome for multiple samples from a fitted relation for each sample between (i) the counts of the sequence reads mapped to each of the sections of the reference genome, and (ii) a mapping feature for each of the sections; (b) calculate a genomic section level for each of the sections of the reference genome from a fitted relation between the experimental bias and the counts of the sequence reads mapped to each of the sections of the reference genome, thereby providing calculated genomic section levels; and (c) identify the presence or absence of a sex chromosome aneuploidy for the fetus, determine fetal gender, and/or determine sex chromosome karyotype for the fetus according to the calculated genomic section levels.

Also provided, in some aspects, are computer program products tangibly embodied on a computer-readable medium, comprising instructions that when executed by one or more processors are configured to: (a) access counts of nucleotide sequence reads mapped to genomic sections of a reference genome, which sequence reads are reads of circulating cell-free nucleic acid from a pregnant female bearing a fetus; (b) determine an experimental bias for each of the sections of the reference genome for multiple samples from a fitted relation for each sample between (i) the counts of the sequence reads mapped to each of the sections of the reference genome, and (ii) a mapping feature for each of the sections; (c) calculate a genomic section level for each of the sections of the reference genome from a fitted relation between the experimental bias and the counts of the sequence reads mapped to each of the sections of the reference genome, thereby providing calculated genomic section levels; and (d) identify the presence or absence of a sex chromosome aneuploidy for the fetus, determine fetal gender, and/or determine sex chromosome karyotype for the fetus according to the calculated genomic section levels.

Certain aspects of the technology are described further in the following description, examples, claims and drawings.

BRIEF DESCRIPTION OF THE DRAWINGS

The drawings illustrate aspects of the technology and are not limiting. For clarity and ease of illustration, the drawings are not made to scale and, in some instances, various aspects may be shown exaggerated or enlarged to facilitate an understanding of particular embodiments.

In FIG. 6, the two bottom traces show a patient with a large deletion in chromosome 18. See Example 1 for experimental details and results.

FIG. 42 graphically illustrates probability distributions for fitted ploidy at different levels of errors in measured fetal fractions. The top panel in FIG. 42 sets measured fetal fraction error to 0.2%. The middle panel in FIG. 42 sets measured fetal fraction error to 0.4%. The bottom panel in FIG. 42 sets measured fetal fraction error to 0.6%. See Example 2 for experimental details and results.

FIG. 50 graphically illustrates fitted fetal fraction as a function of the systematic offset, obtained for a euploid and for a triploid data set.

Example 3 addresses FIG. 52 to 61F.

Figure 52:
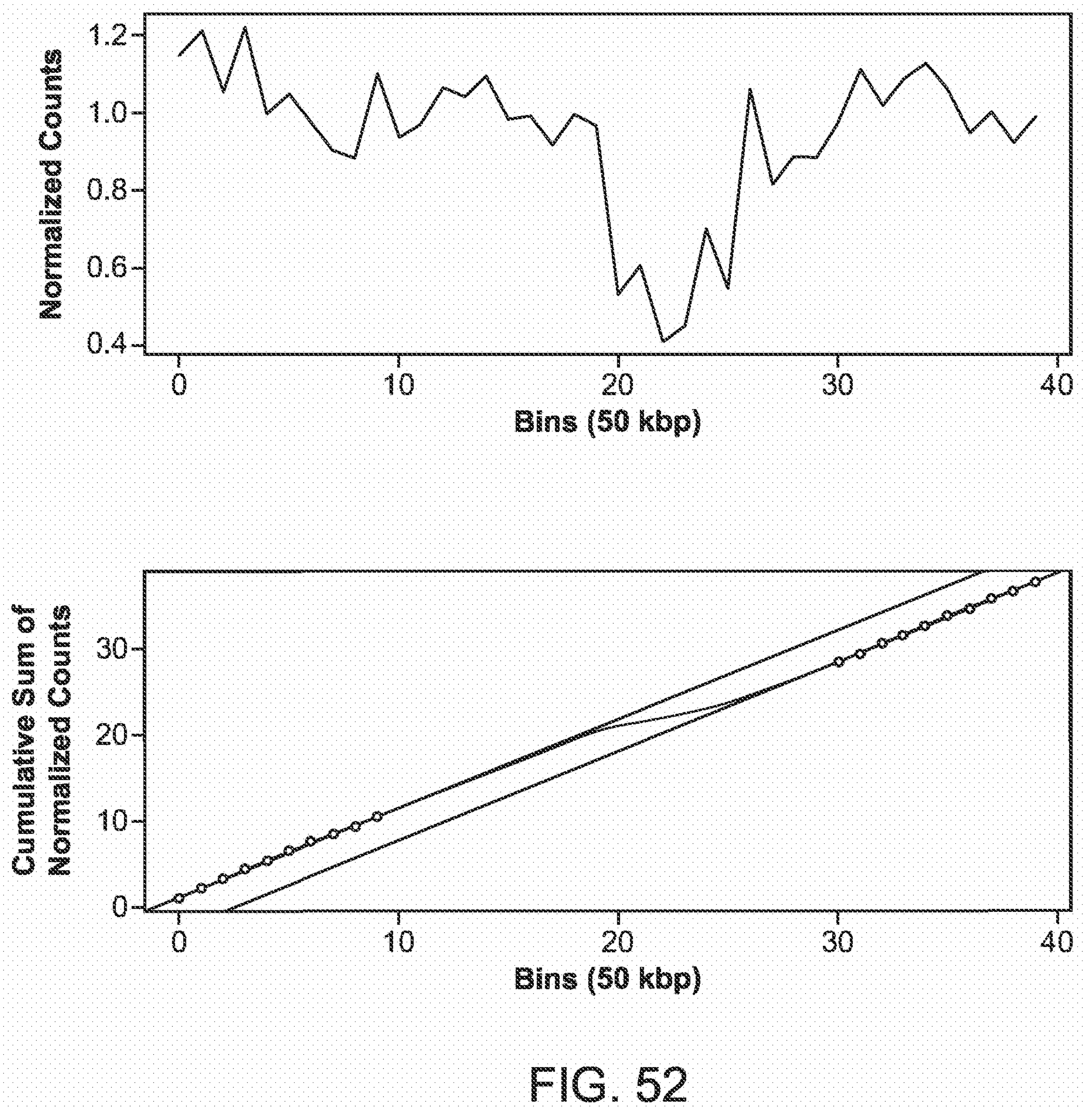
Figure 61A:
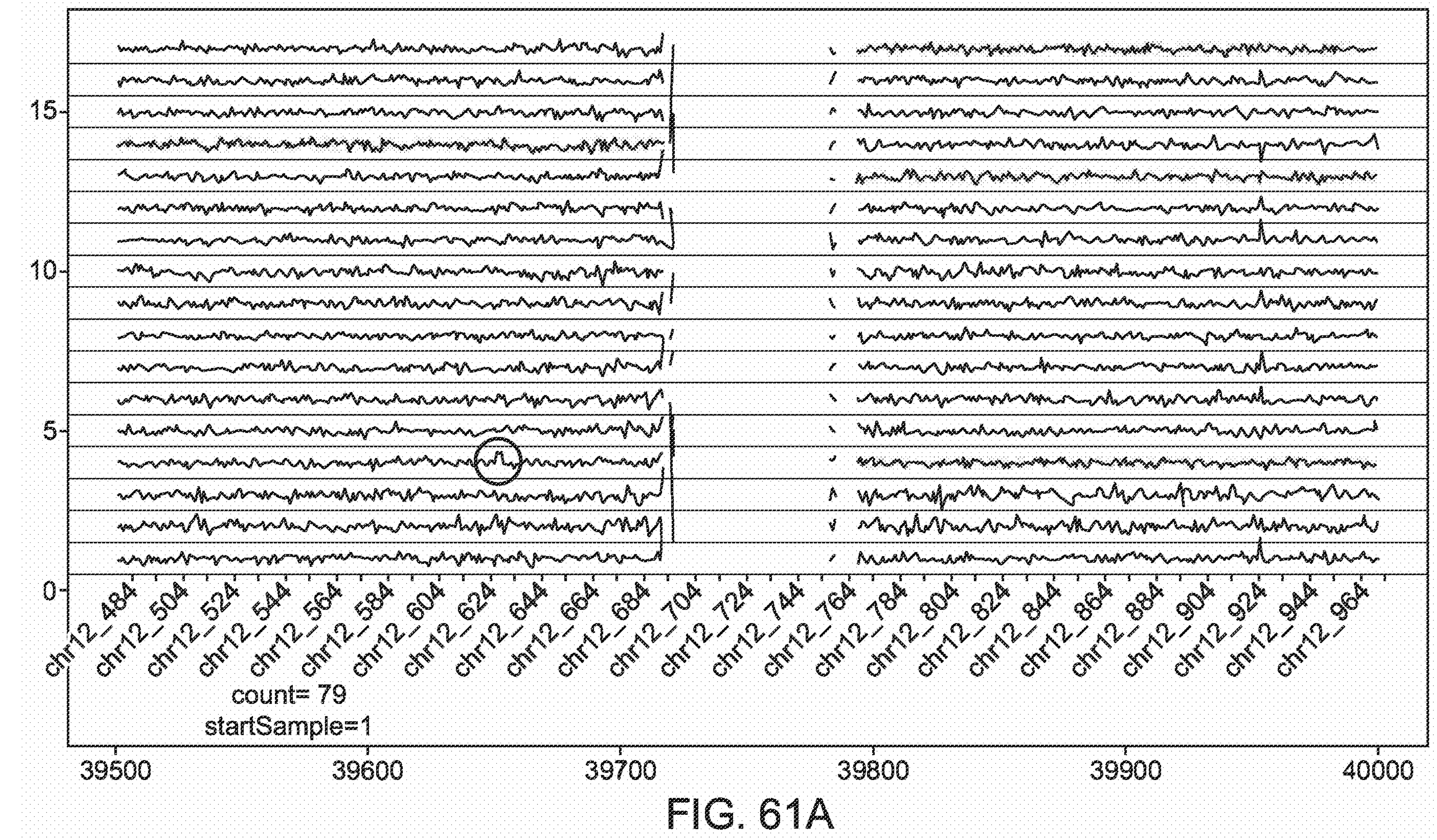
Figure 61B:
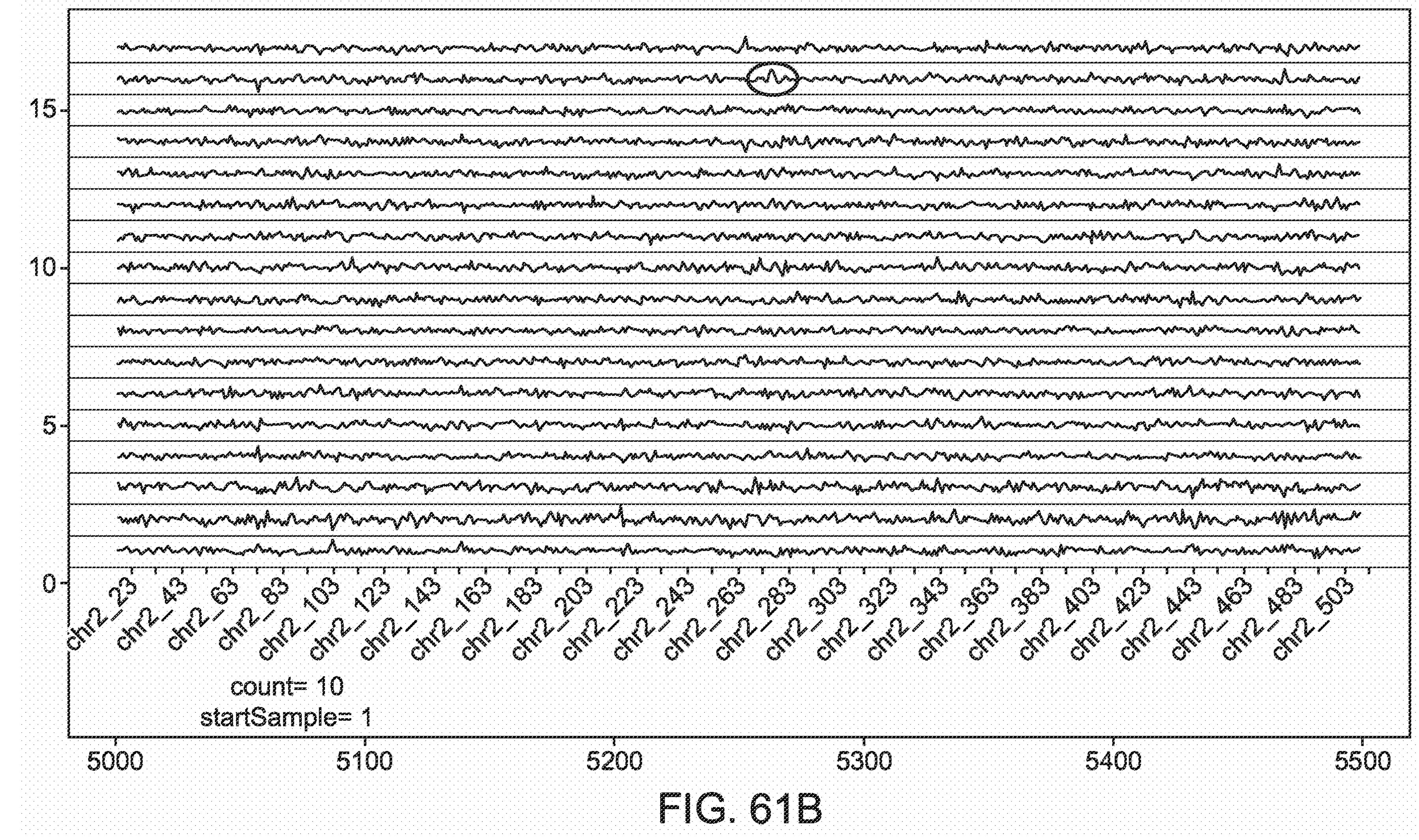
Figure 61C:
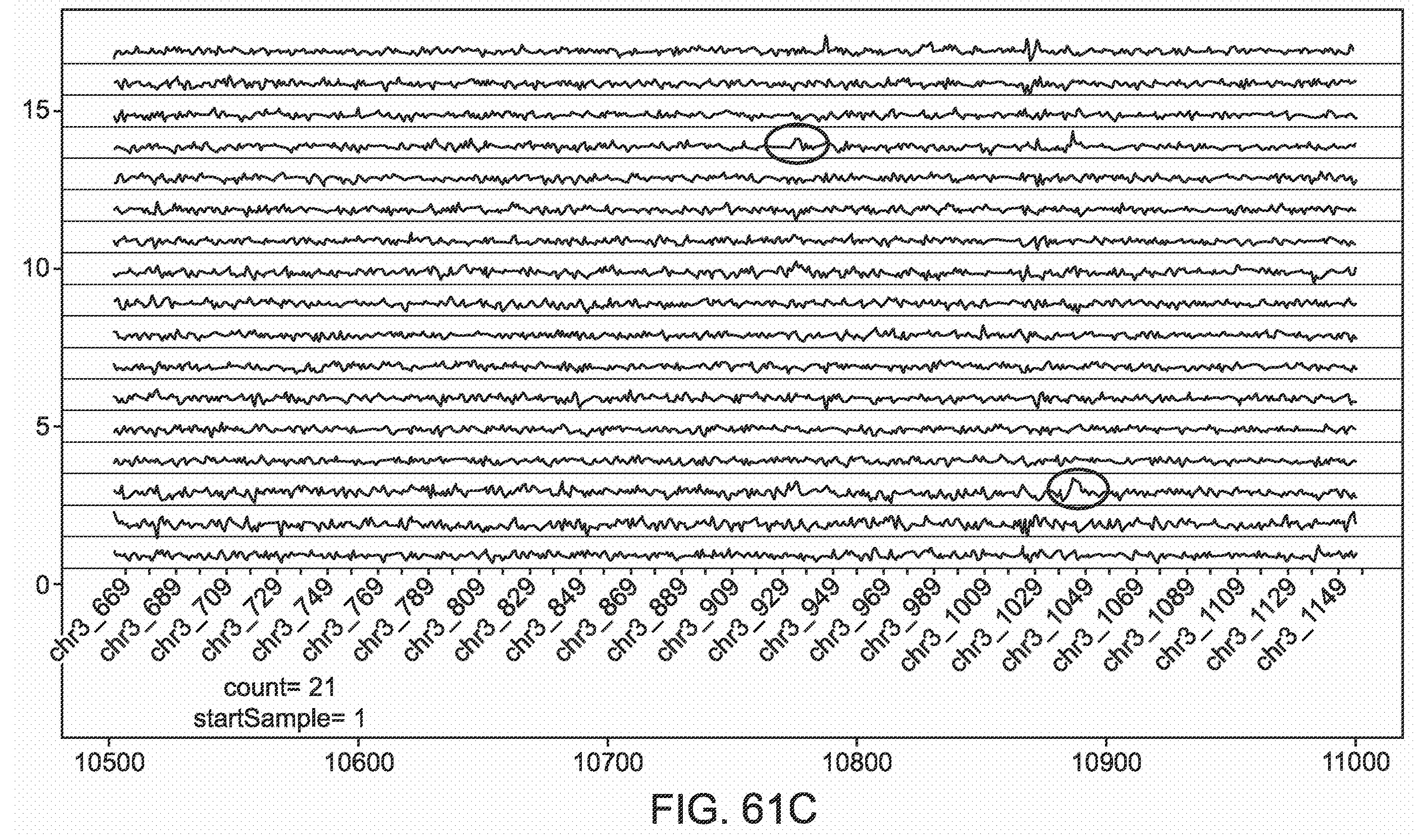
Figure 61D:
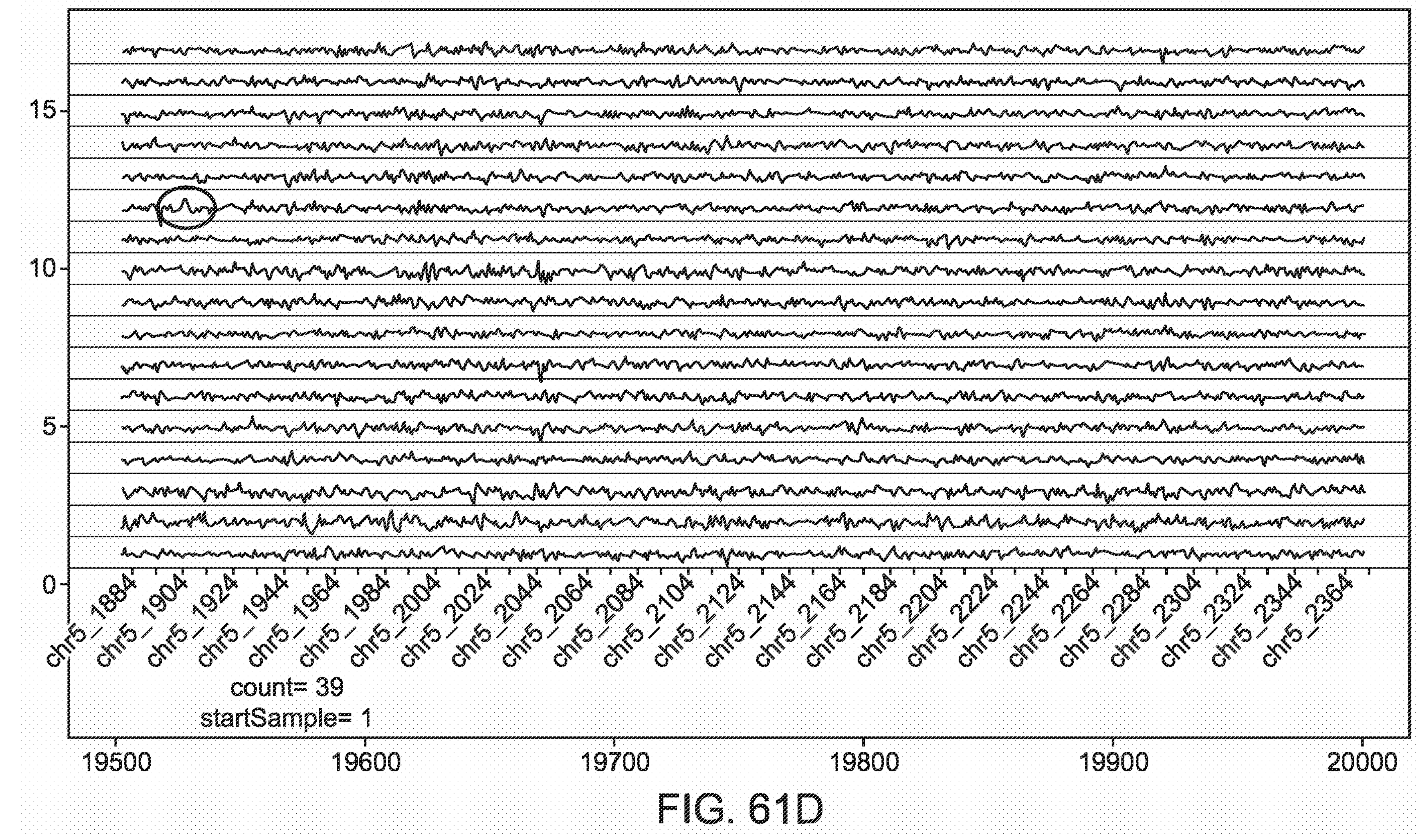
Figure 61E:
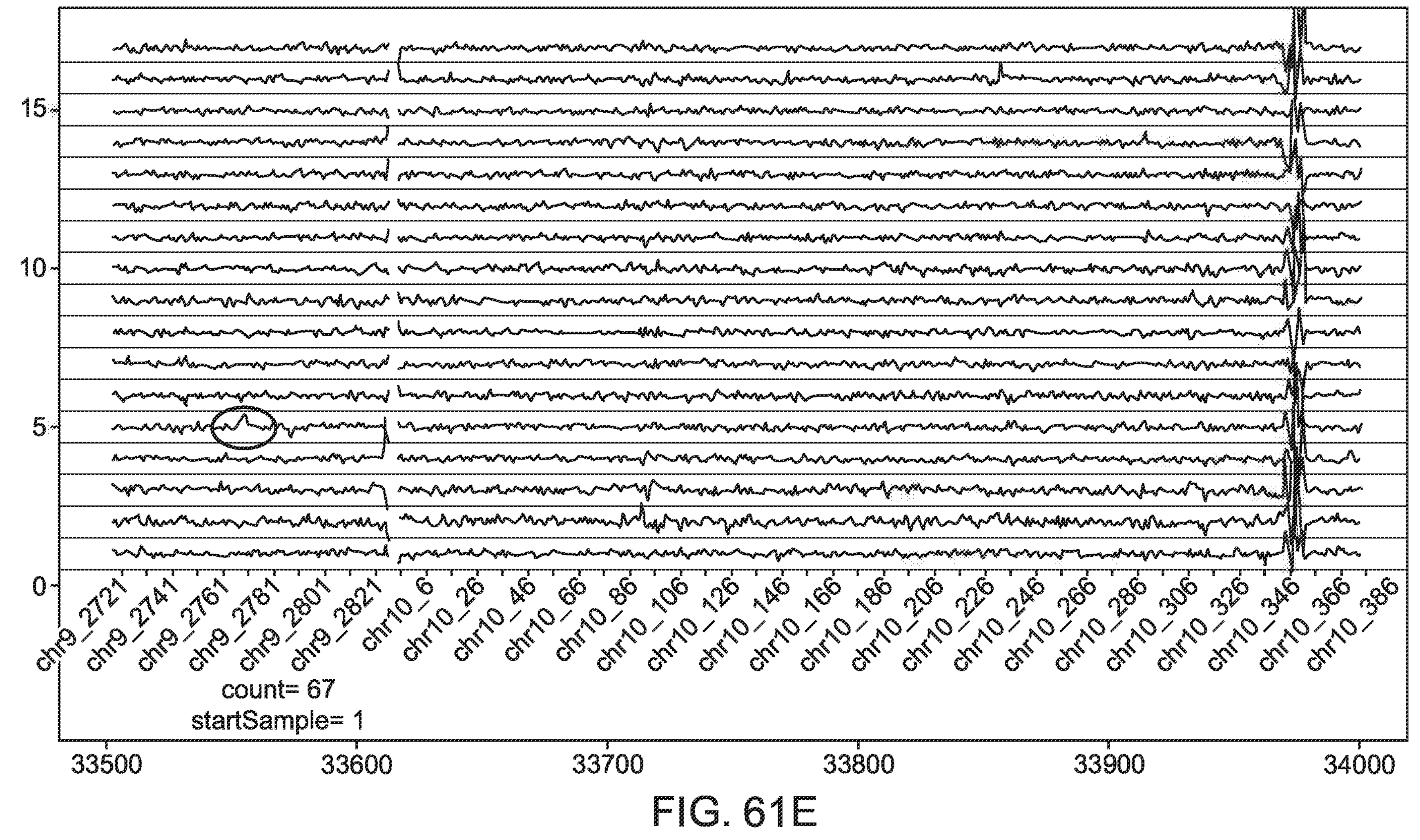
Figure 61F:
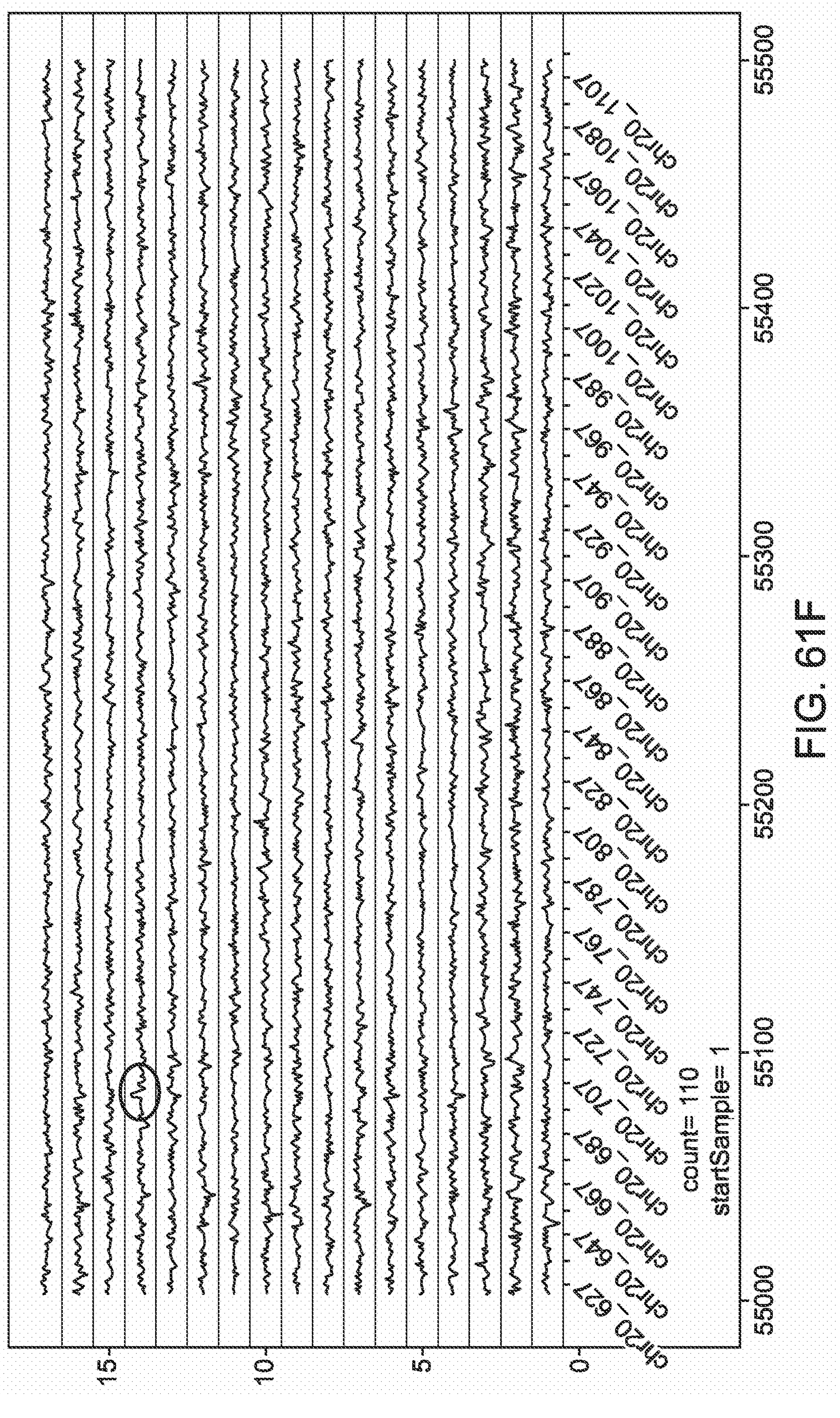

FIG. 52 graphically illustrates an example of application of the cumulative sum algorithm to a heterozygous maternal microdeletion in chromosome 12, bin 1457. The difference between the intercepts associated with the left and the right linear models is 2.92, indicating that the heterozygous deletion is 6 bins wide.

FIG. 53 graphically illustrates a hypothetical heterozygous deletion, approximately 2 genomic sections wide, and its associated cumulative sum profile. The difference between the left and the right intercepts is −1.

FIG. 54 graphically illustrates a hypothetical homozygous deletion, approximately 2 genomic sections wide, and its associated cumulative sum profile. The difference between the left and the right intercepts is −2.

FIG. 55 graphically illustrates a hypothetical heterozygous deletion, approximately 6 genomic sections wide, and its associated cumulative sum profile. The difference between the left and the right intercepts is −3.

FIG. 56 graphically illustrates a hypothetical homozygous deletion, approximately 6 genomic sections wide, and its associated cumulative sum profile. The difference between the left and the right intercepts is −6.

FIG. 57 graphically illustrates a hypothetical heterozygous duplication, approximately 2 genomic sections wide, and its associated cumulative sum profile. The difference between the left and the right intercepts is 1.

FIG. 58 graphically illustrates a hypothetical homozygous duplication, approximately 2 genomic sections wide, and its associated cumulative sum profile. The difference between the left and the right intercepts is 2.

FIG. 59 graphically illustrates a hypothetical heterozygous duplication, approximately 6 genomic sections wide, and its associated cumulative sum profile. The difference between the left and the right intercepts is 3.

FIG. 60 graphically illustrates a hypothetical homozygous duplication, approximately 6 genomic sections wide, and its associated cumulative sum profile. The difference between the left and the right intercepts is 6.

FIG. 61A-F graphically illustrate candidates for fetal heterozygous duplications in data obtained from women and infant clinical studies with high fetal fraction values (40-50%). To rule out the possibility that the aberrations originate from the mother and not the fetus, independent maternal profiles were used. The profile elevation in the affected regions is approximately 1.25, in accordance with the fetal fraction estimates.

Figures 62, 63:
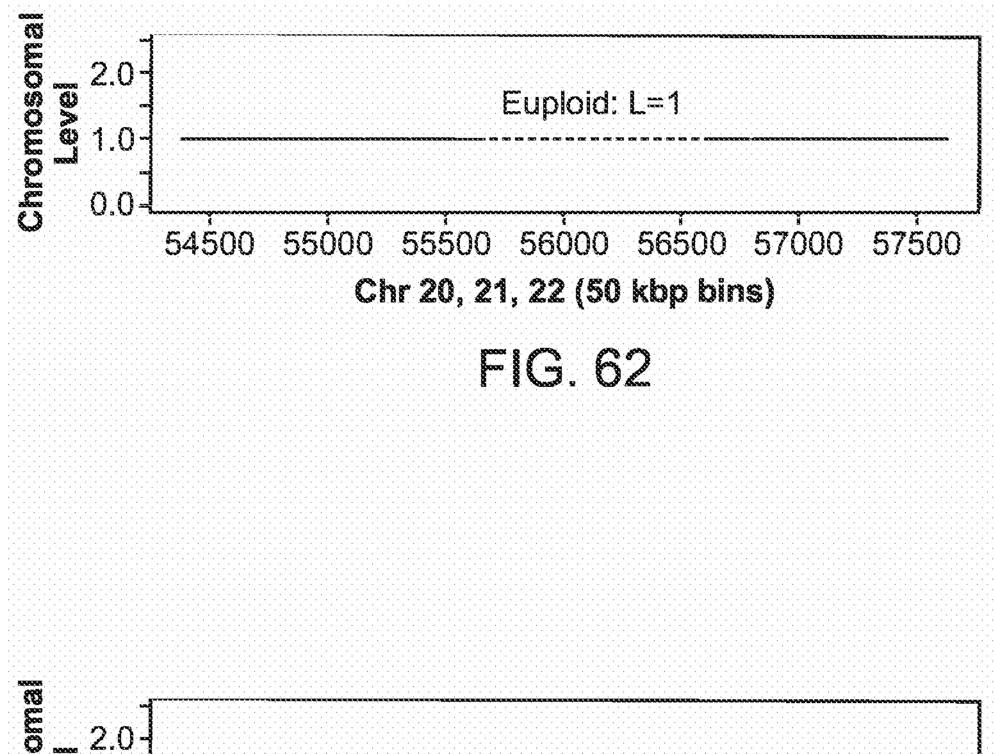

FIG. 62 shows a profile of elevations for Chr20, Chr21 (~55750 to ~56750) and Chr22 obtained from a pregnant female bearing a euploid fetus.

FIG. 63 shows a profile of elevations for Chr20, Chr21 (~55750 to ~56750) and Chr22 obtained from a pregnant female bearing a trisomy 21 fetus.

Figures 64, 65:
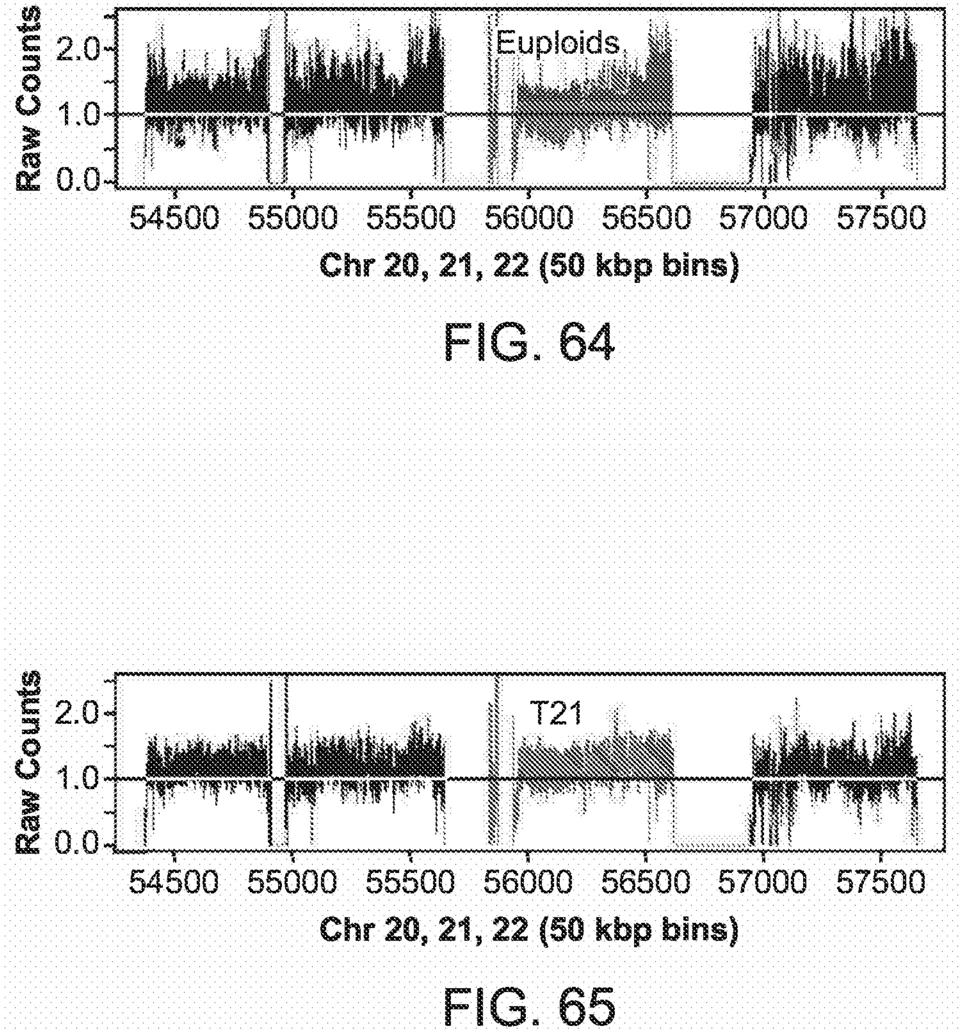

FIG. 64 shows a profile of raw counts for Chr20, Chr21 (~55750 to ~56750) and Chr22 obtained from a pregnant female bearing a euploid fetus.

FIG. 65 shows a profile of raw counts for Chr20, Chr21 (~55750 to ~56750) and Chr22 obtained from a pregnant female bearing a trisomy 21 fetus.

Figure 66:
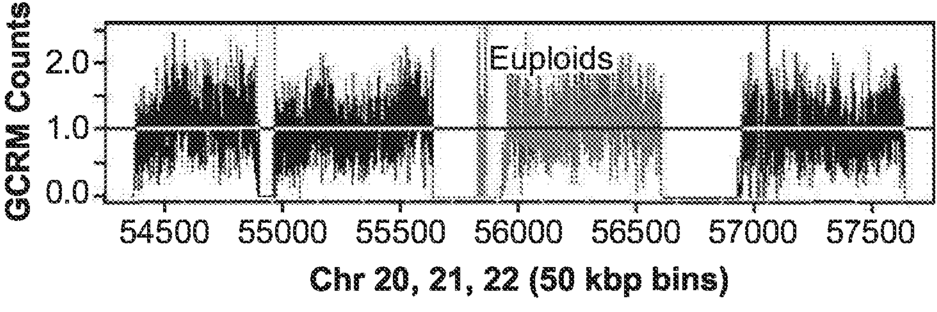

FIG. 66 shows a profile of normalized counts for Chr20, Chr21 (~55750 to ~56750) and Chr22 obtained from a pregnant female bearing a euploid fetus.

Figure 67:
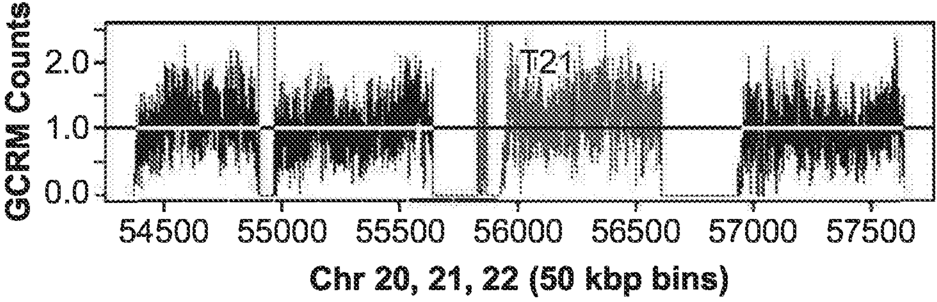

FIG. 67 shows a profile of normalized counts for Chr20, Chr21 (~55750 to ~56750) and Chr22 obtained from a pregnant female bearing a trisomy 21 fetus.

Figures 68, 69:
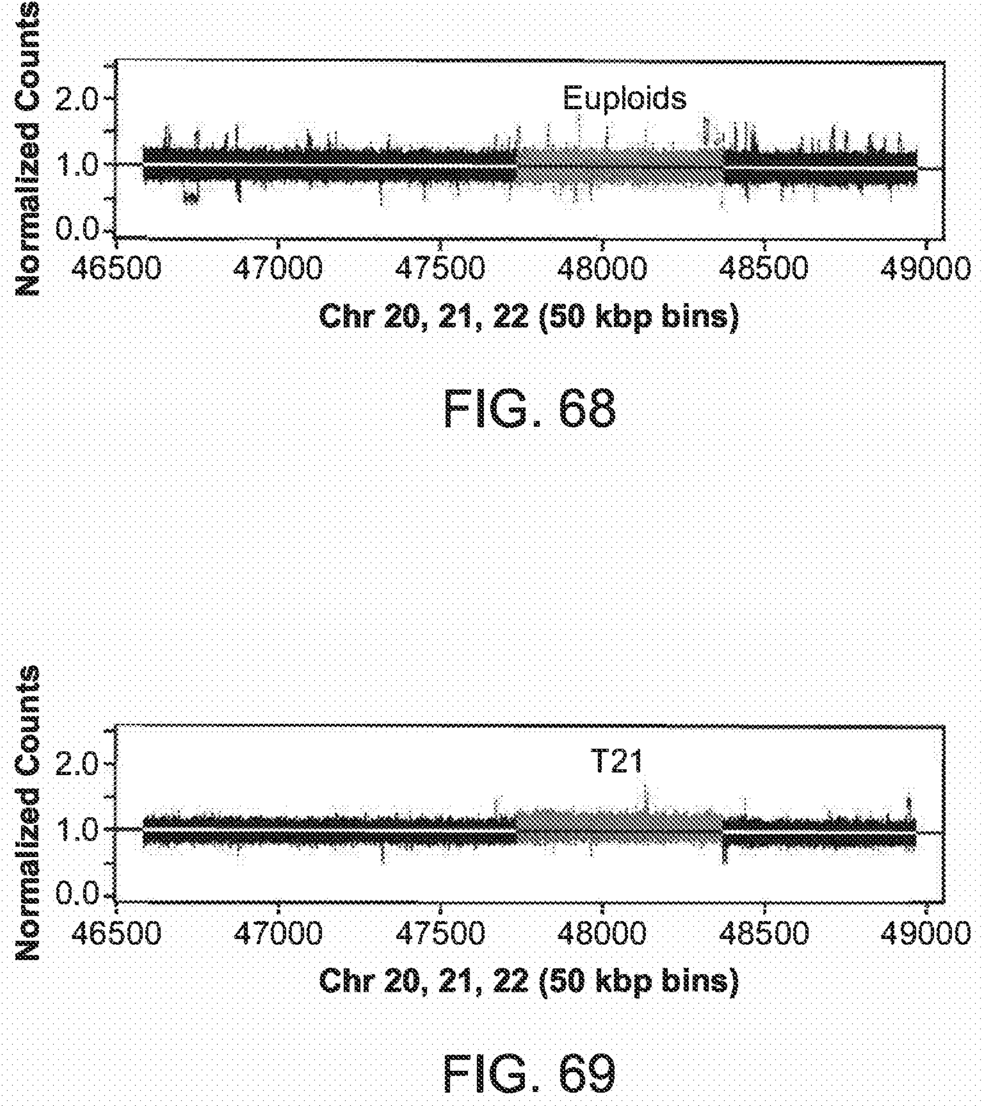

FIG. 68 shows a profile of normalized counts for Chr20, Chr21 (~47750 to ~48375) and Chr22 obtained from a pregnant female bearing a euploid fetus.

FIG. 69 shows a profile of normalized counts for Chr20, Chr21 (~47750 to ~48375) and Chr22 obtained from a pregnant female bearing a trisomy 21 fetus.

Figure 70:
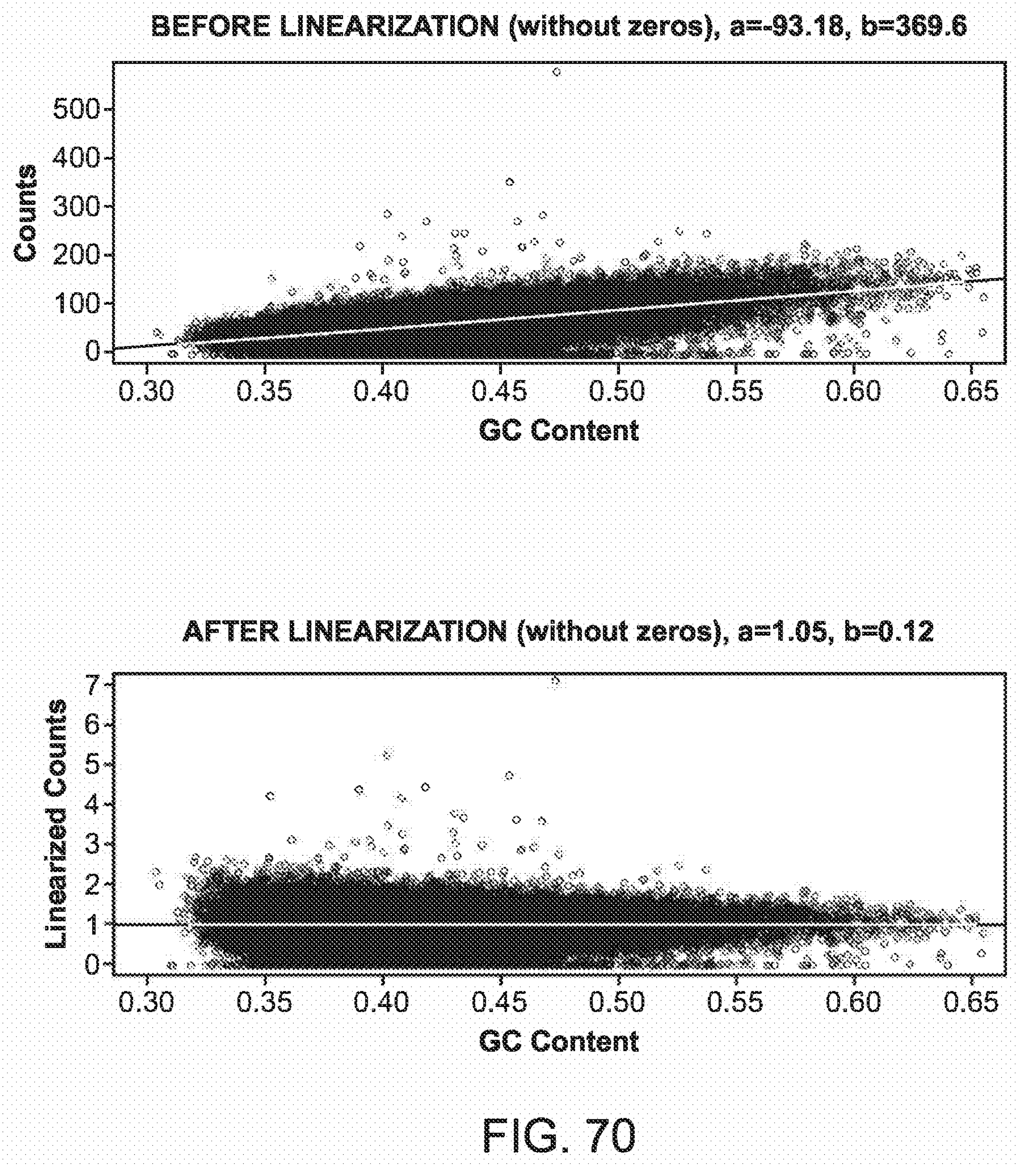

FIG. 70 shows a graph of counts (y axis) versus GC content (X axis) before LOESS GC correction (upper panel) and after LOESS GC (lower panel).

Figure 71:
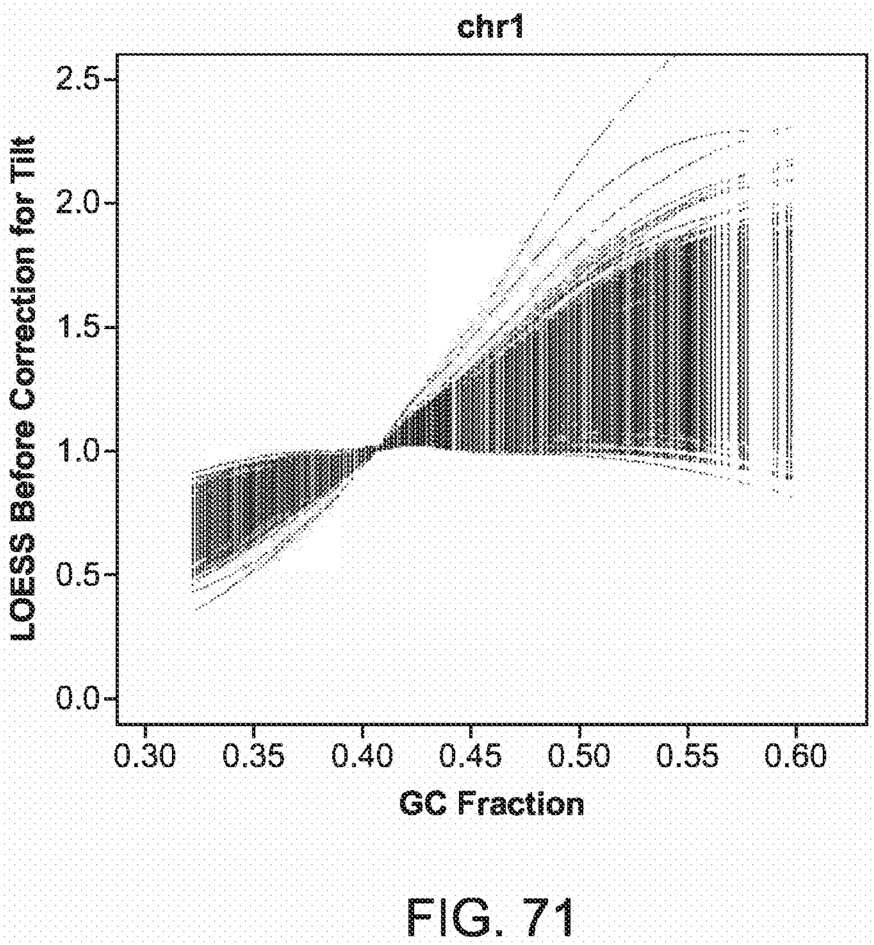

FIG. 71 shows a graph of counts normalized by LOESS GC (Y axis) versus GC fraction for multiple samples of chromosome 1.

Figure 72:
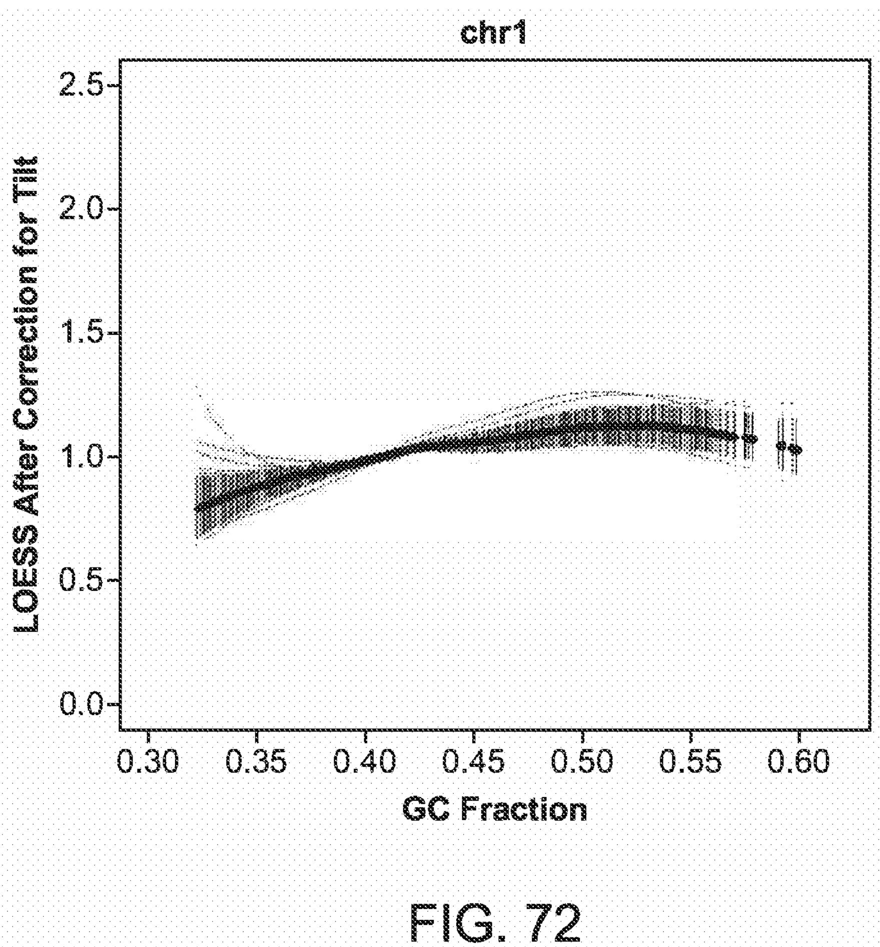

FIG. 72 shows a graph of counts normalized by LOESS GC and corrected for tilt (Y axis) versus GC fraction (X axis) for multiple samples of chromosome 1.

Figure 73:
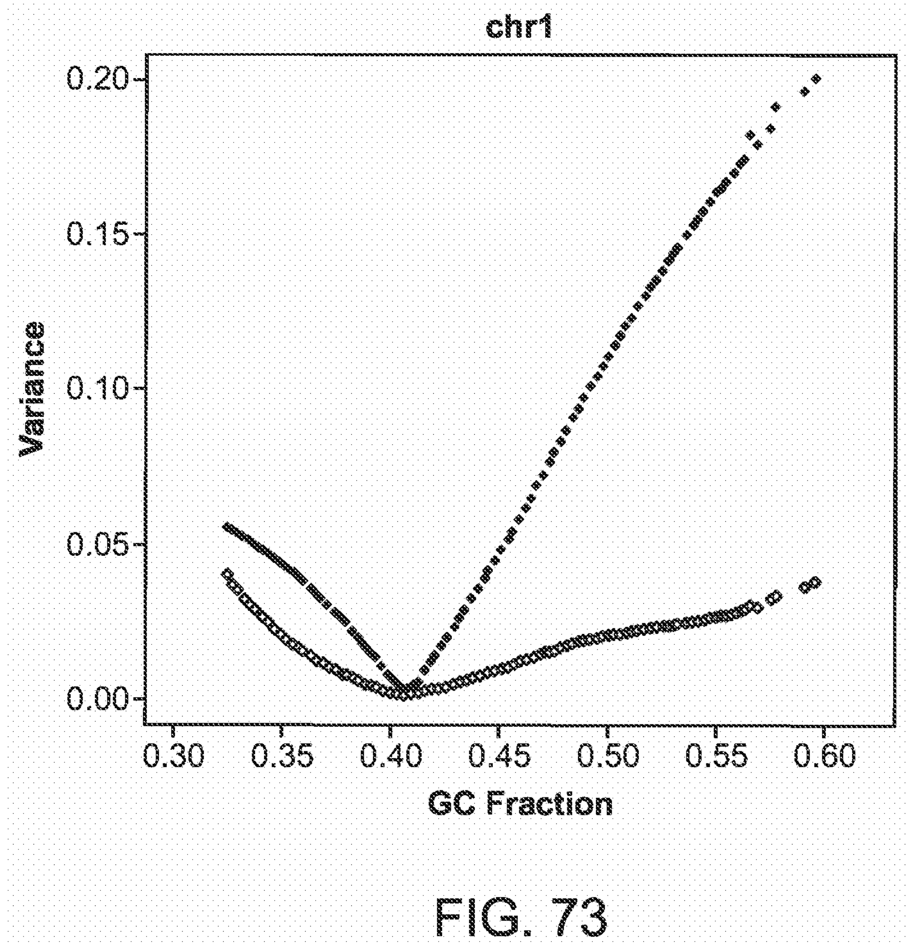

FIG. 73 shows a graph of variance (Y-axis) versus GC fraction (X axis) for chromosome 1 before tilting (black filled circles) and after tilting (open circles).

Figure 74:
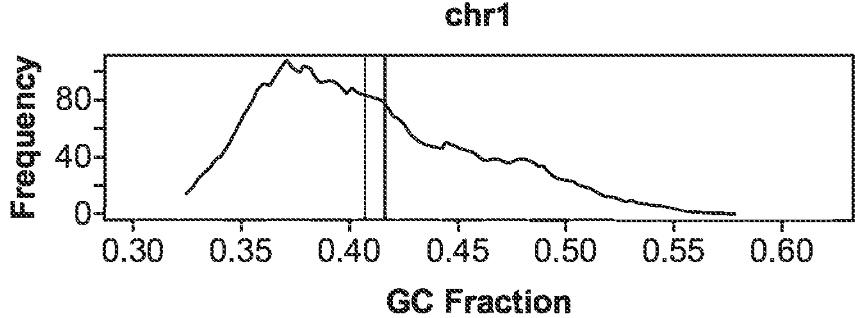

FIG. 74 shows a graph of frequency (Y-axis) versus GC fraction (X axis) for chromosome as well as a median (left vertical line) and mean (right vertical line).

Figures 75A, 75B:
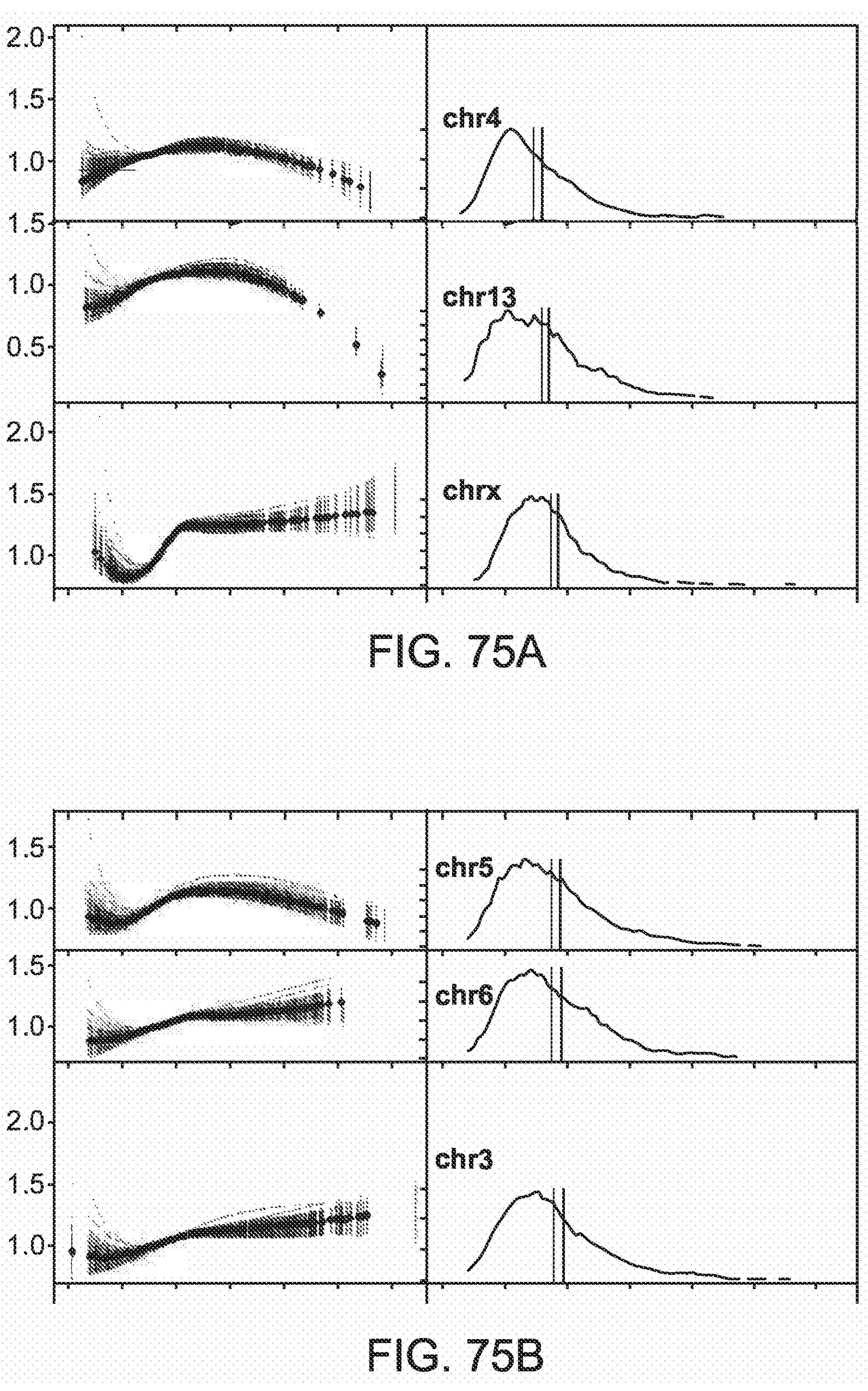
Figures 75C, 75D:
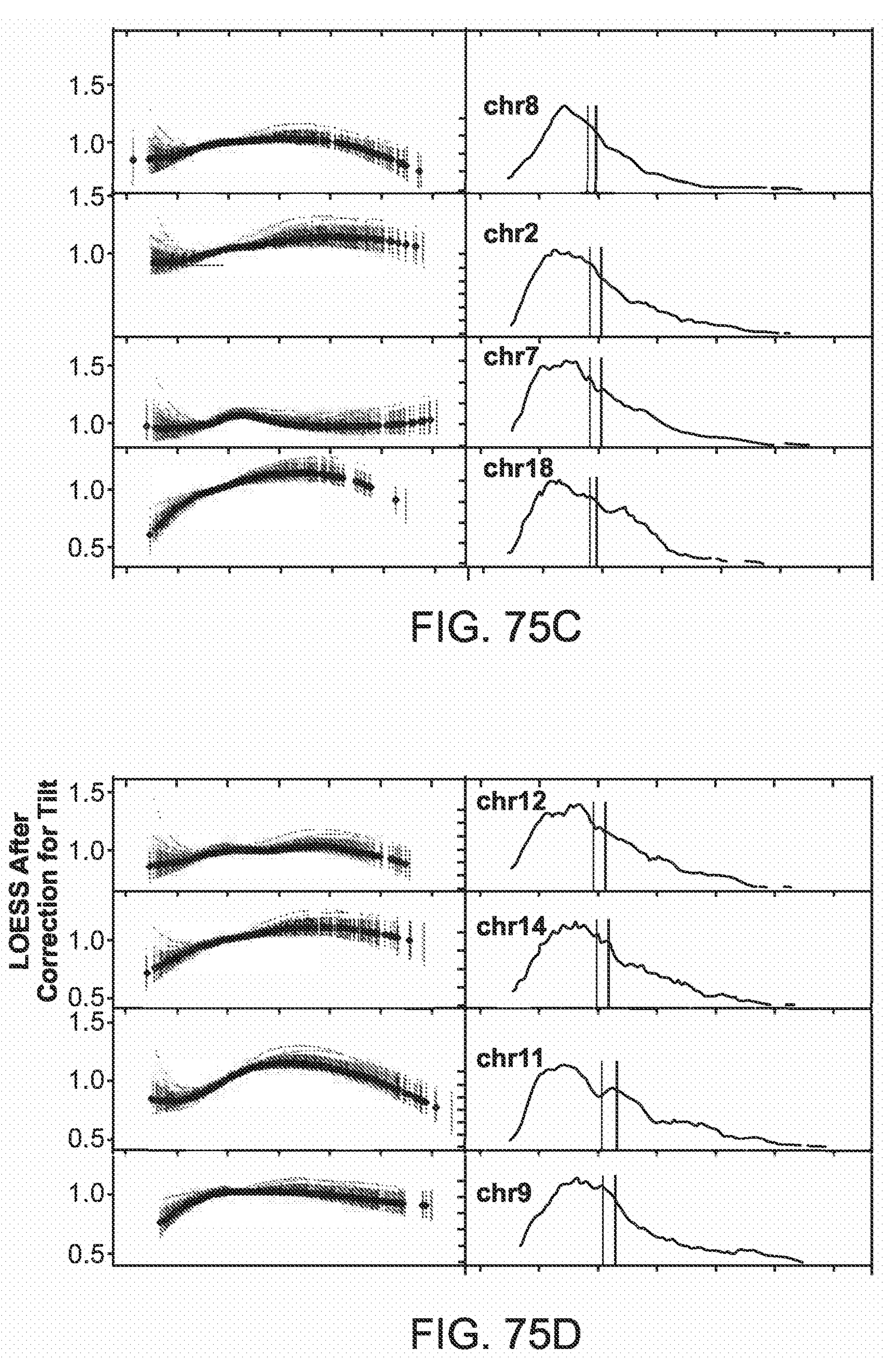
Figures 75E, 75F:
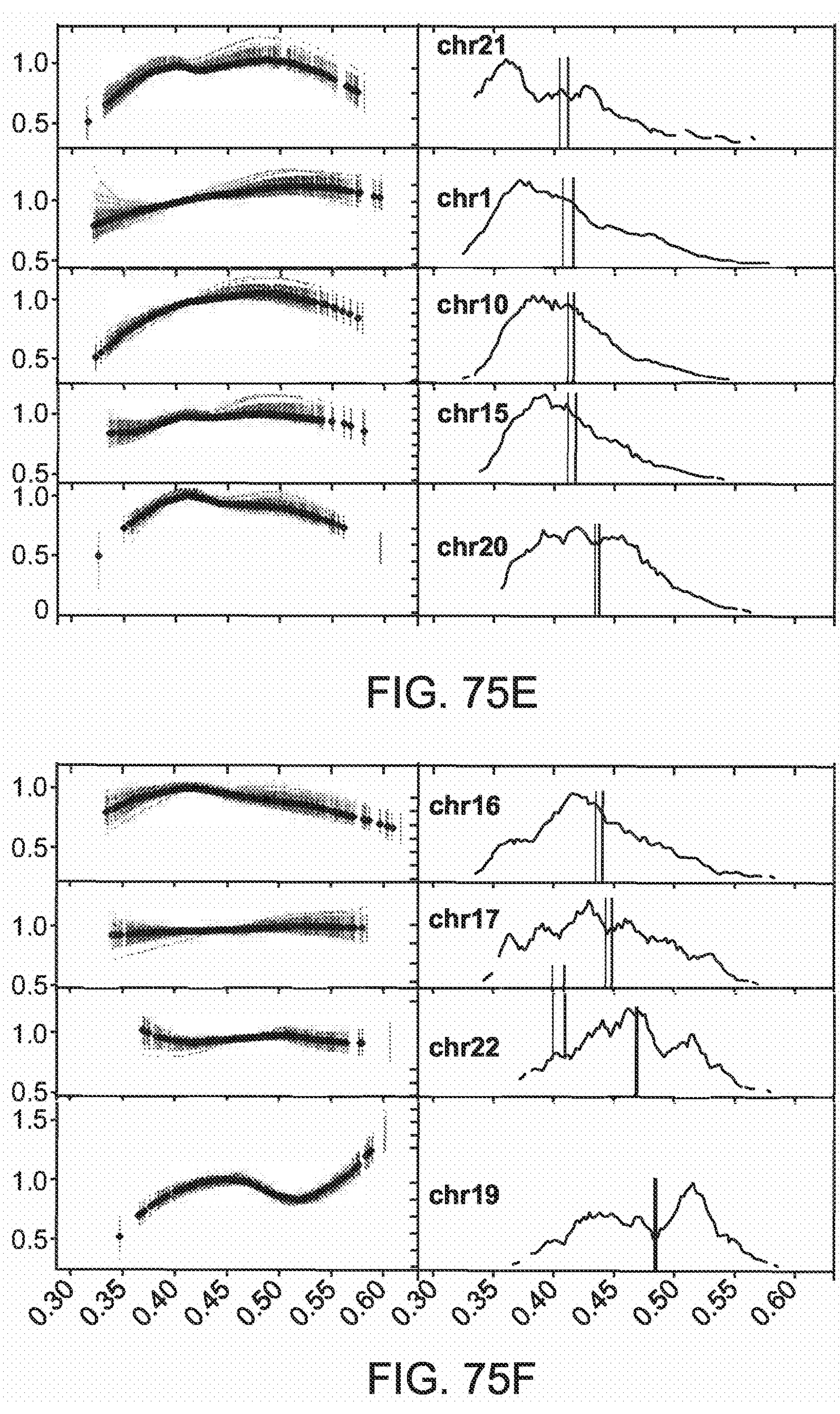

FIG. 75A-F shows a graph of counts normalized by LOESS GC and corrected for tilt (Y axis) versus GC fraction (X axis) left panels and frequency (Y-axis) versus GC fraction (X axis)(right panels) for chromosomes 4, 15 and X (FIG. 75A, listed from top to bottom), chromosomes 5, 6 and 3 (FIG. 75B, listed from top to bottom), chromosomes 8, 2, 7 and 18 (FIG. 75C, listed from top to bottom), chromosomes 12, 14, 11 and 9 (FIG. 75D, listed from top to bottom), chromosomes 21, 1, 10, 15 and 20 (FIG. 75E, listed from top to bottom) and chromosomes 16, 17, 22 and 19 (FIG. 75F, listed from top to bottom). Median values (left vertical line) and mean values (right vertical line) are indicated in the right panels.

Figure 76:
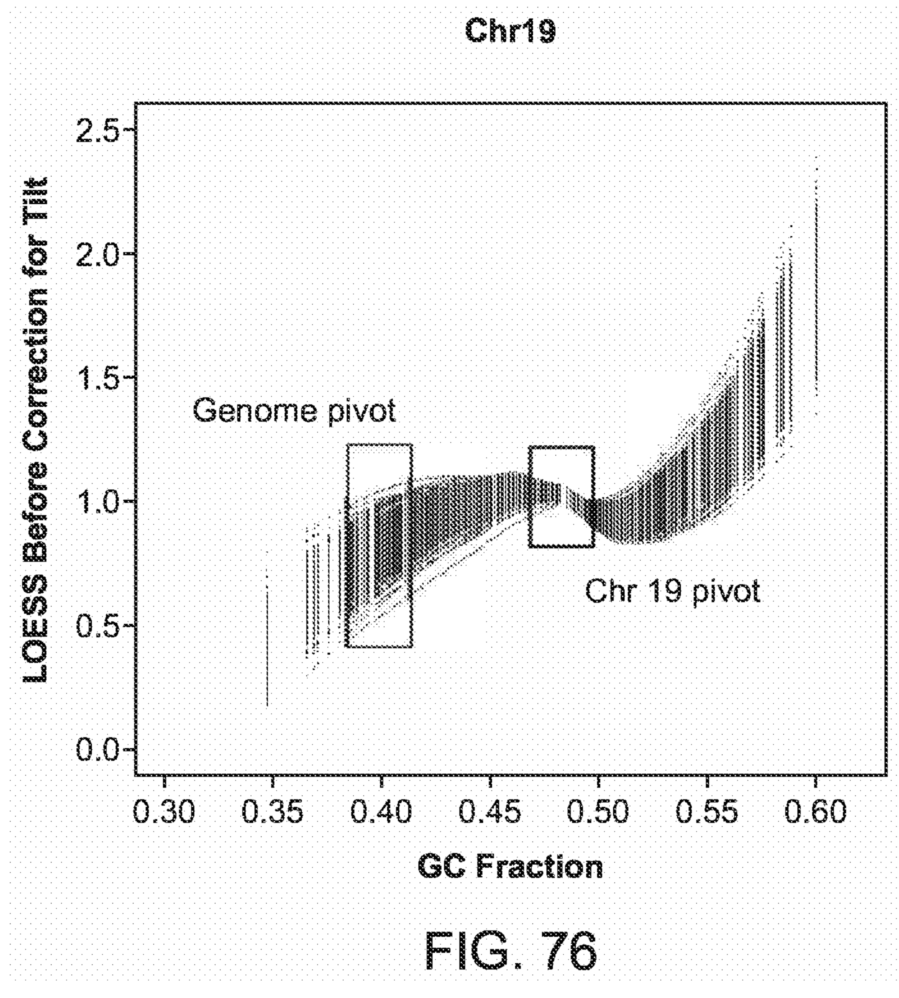

FIG. 76 shows a graph of counts normalized by LOESS GC and corrected for tilt (Y axis) versus GC fraction (X axis) for chromosome 19. The chromosome pivot is shown in the right boxed regions and the genome pivot is shown in the left boxed region.

Figure 77:
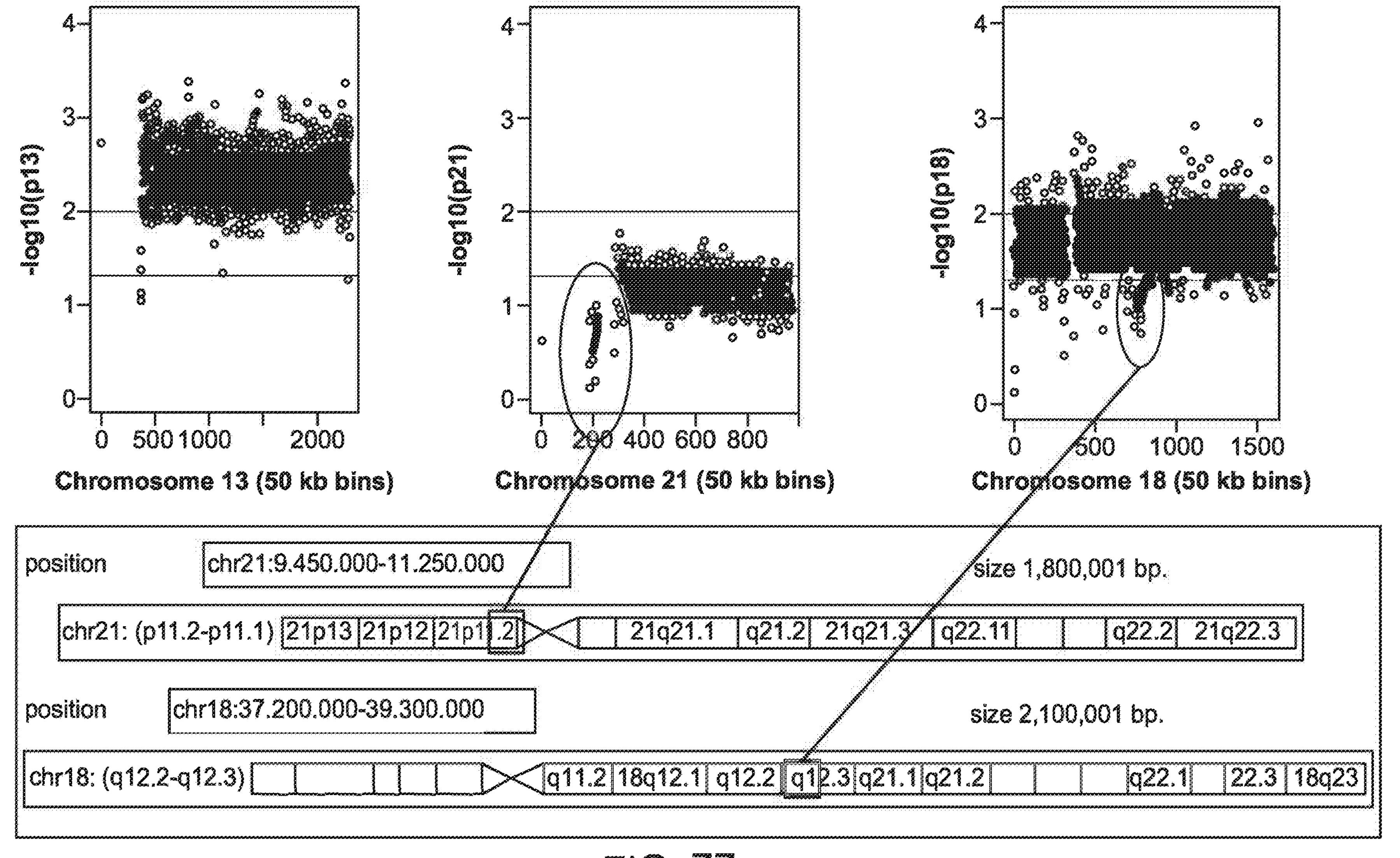

FIG. 77 shows a graph of p-value (Y axis) versus bins (X-axis) for chromosomes 13 (top right), 21 (top middle), and 18 (top right). The chromosomal position of certain bins is shown in the bottom panel.

Figure 78:
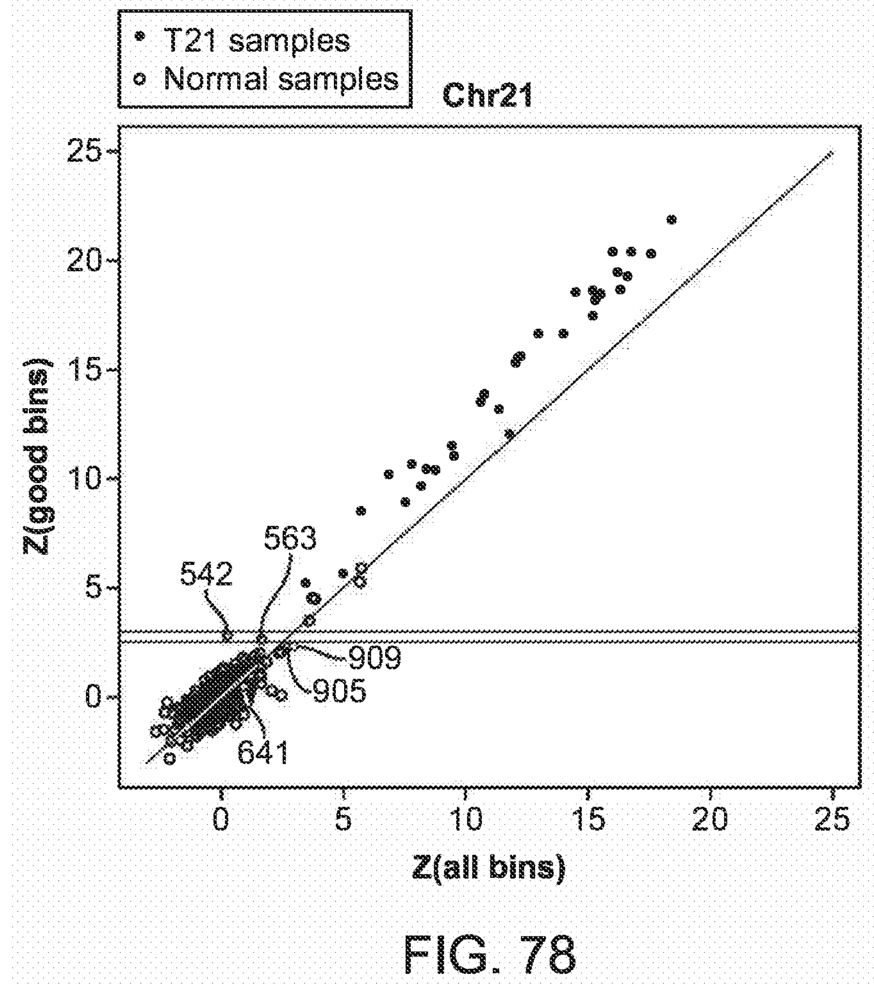

FIG. 78 shows the Z-score for chromosome 21 where uninformative bins were excluded from the Z-score calculation (Y-axis) and Z-score for chromosome 21 for all bins (X-axis). Trisomy 21 cases are indicated by filled circles. Euploids are indicated by open circles.

Figure 79:
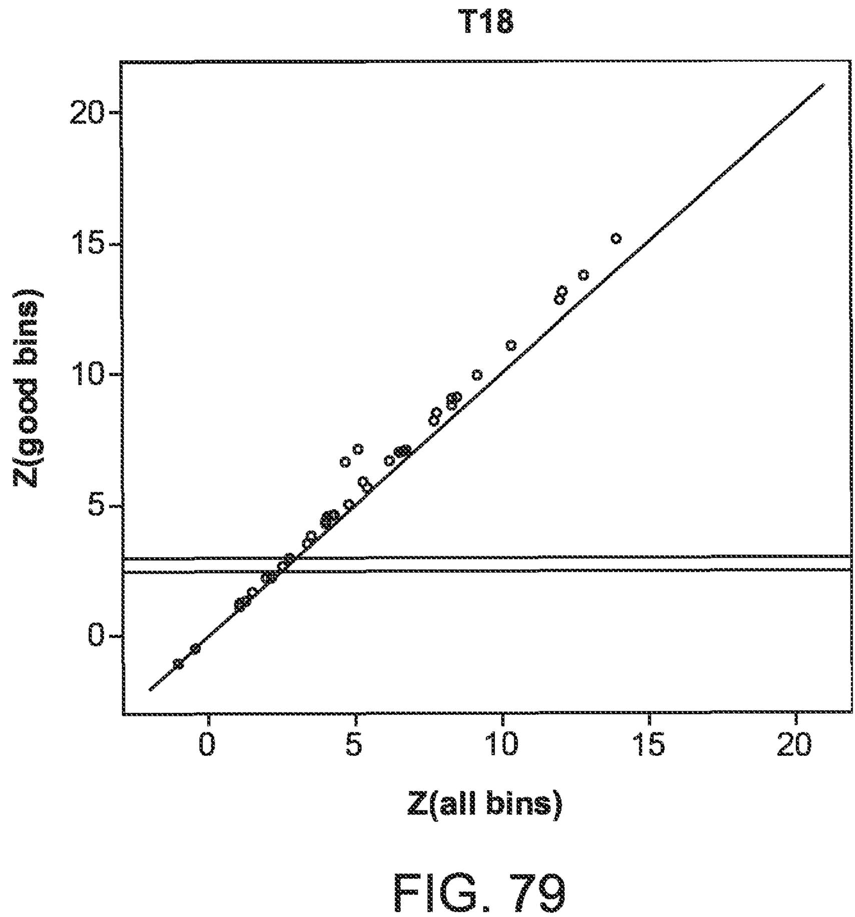

FIG. 79 shows the Z-score for chromosome 18 where uninformative bins were excluded from the Z-score calculation (Y-axis) and Z-score for chromosome 18 for all bins (X-axis).

Figure 80:
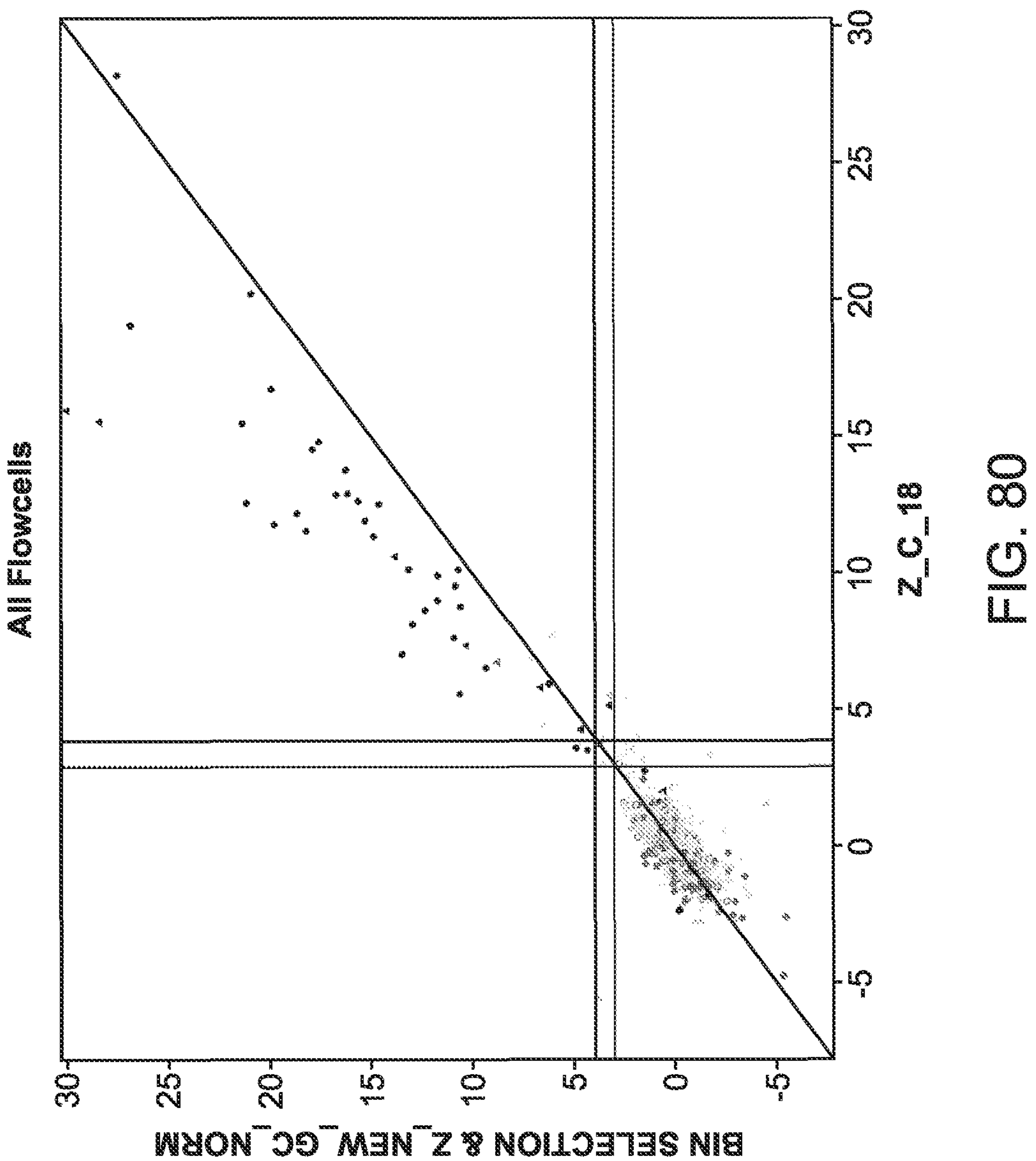

FIG. 80 shows a graph of selected bins (Y axis) verse all bins (X axis) for chromosome 18.

Figure 81:
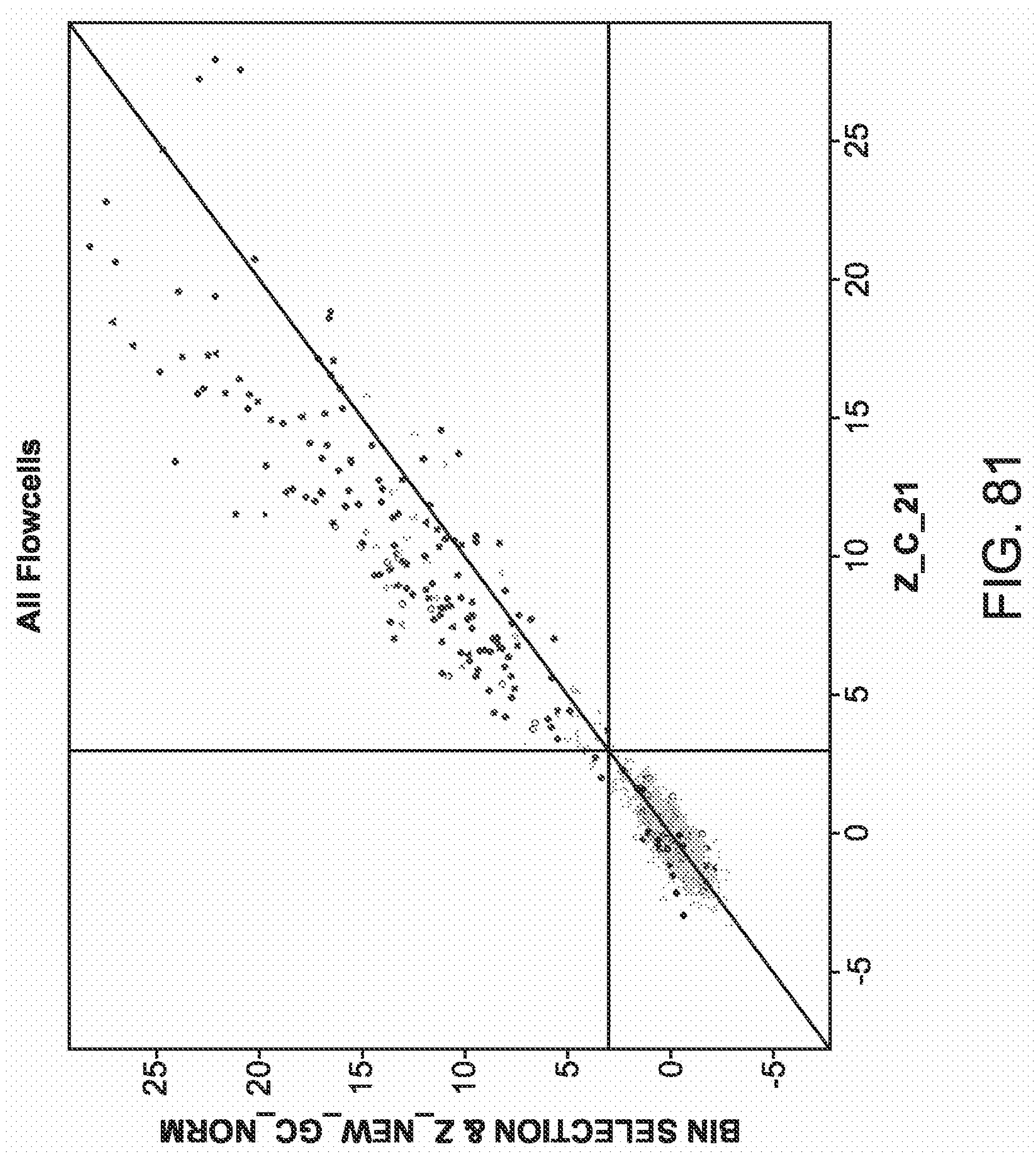

FIG. 81 shows a graph of selected bins (Y axis) verse all bins (X axis) for chromosome 21.

Figure 82:
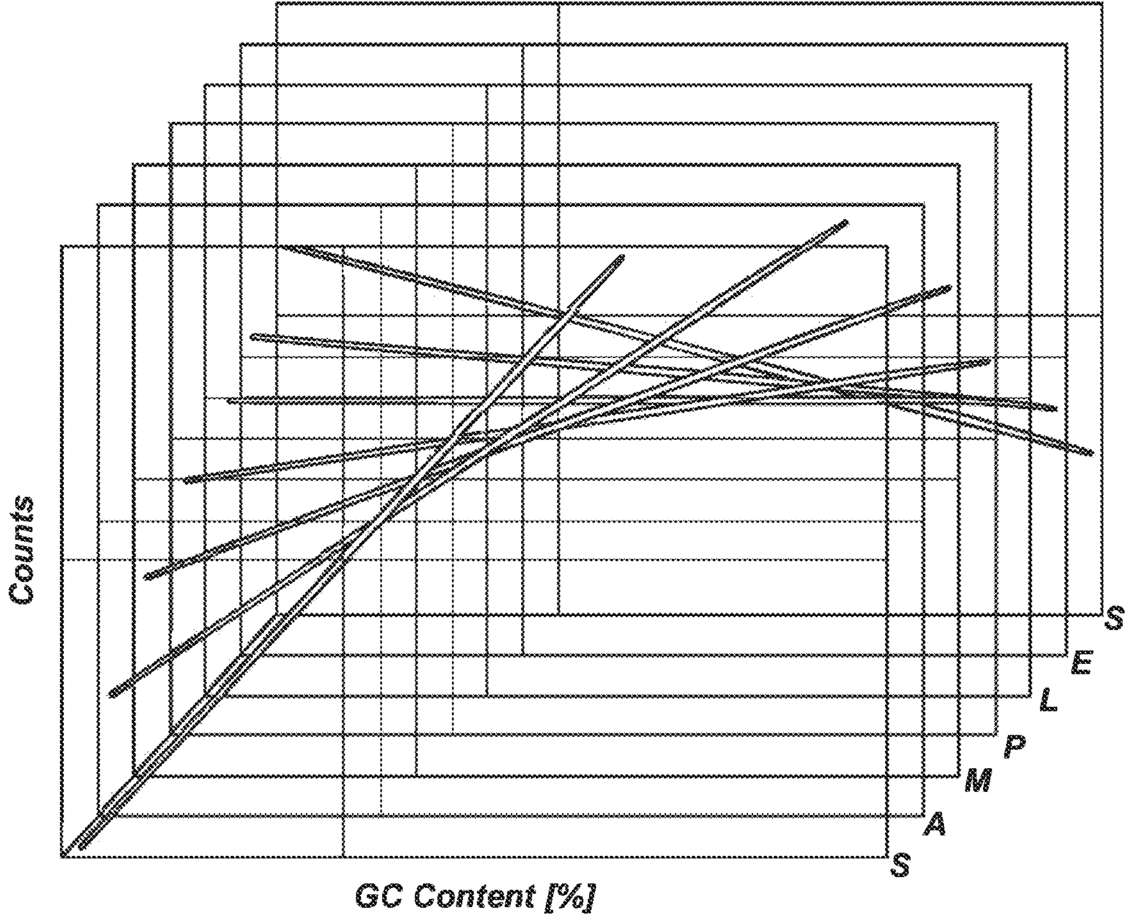

FIG. 82 shows a graph of counts (Y axis) verse GC content (X axis) for 7 samples.

Figure 83:
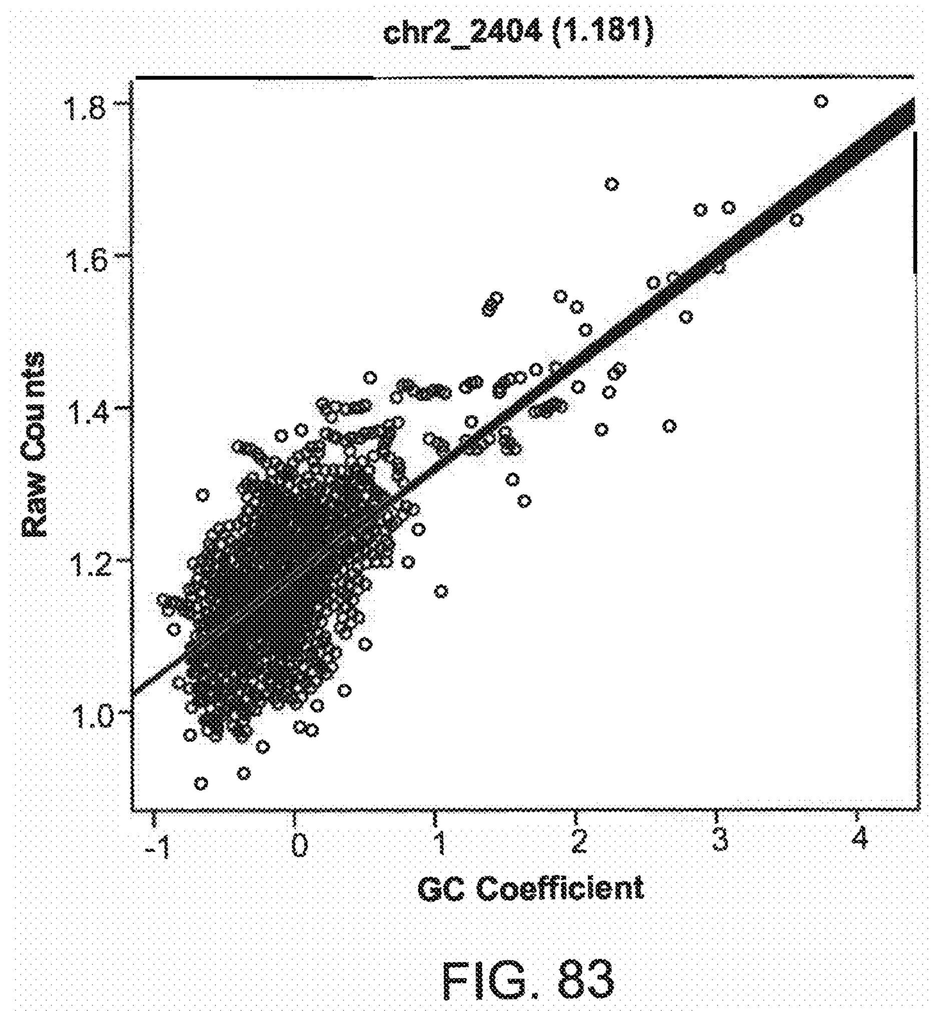

FIG. 83 shows a graph of raw counts (Y axis) verse GC bias coefficients (X axis).

Figures 84, 85:
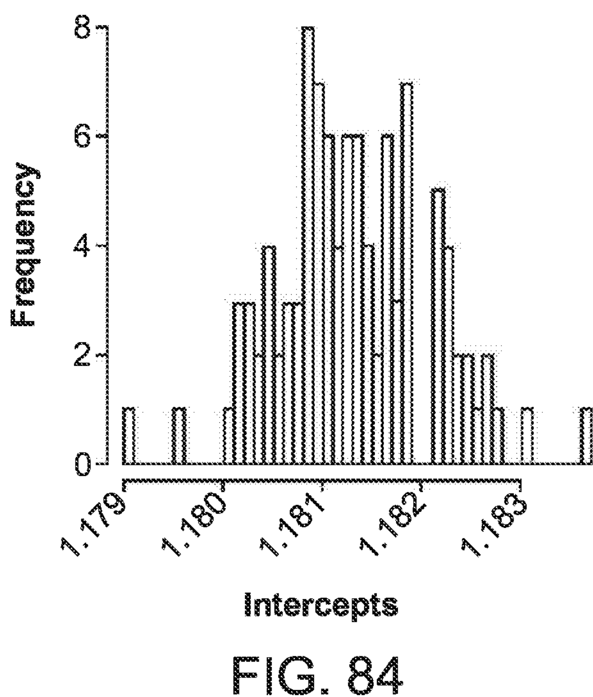

FIG. 84 shows a graph of frequency (Y axis) verse intercepts (X axis).

FIG. 85 shows a graph of frequency (Y axis) verse slopes (X axis).

Figure 86:
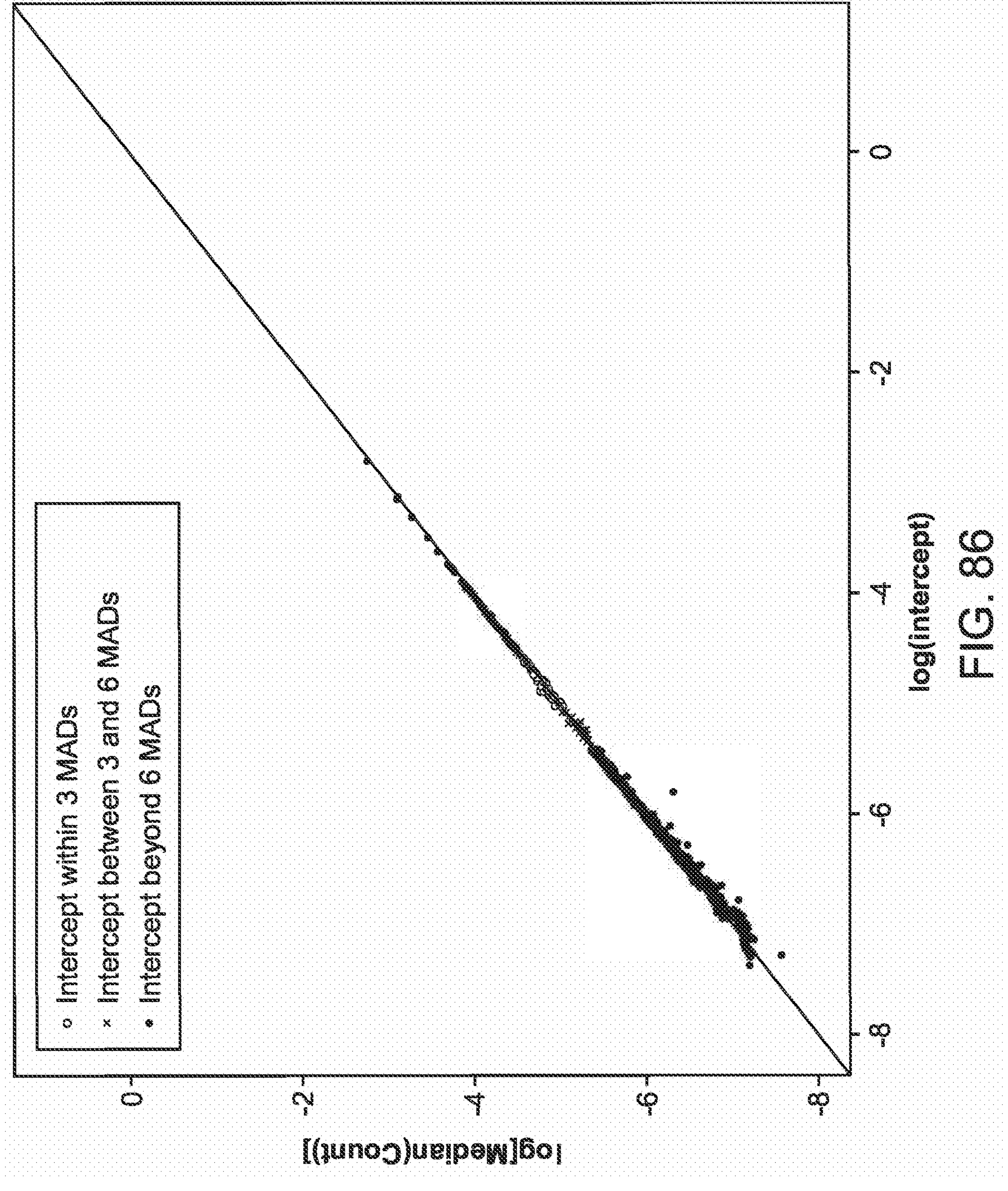

FIG. 86 shows a graph of Log Median Count (Y axis) verse Log Intercept (X axis).

Figure 87:
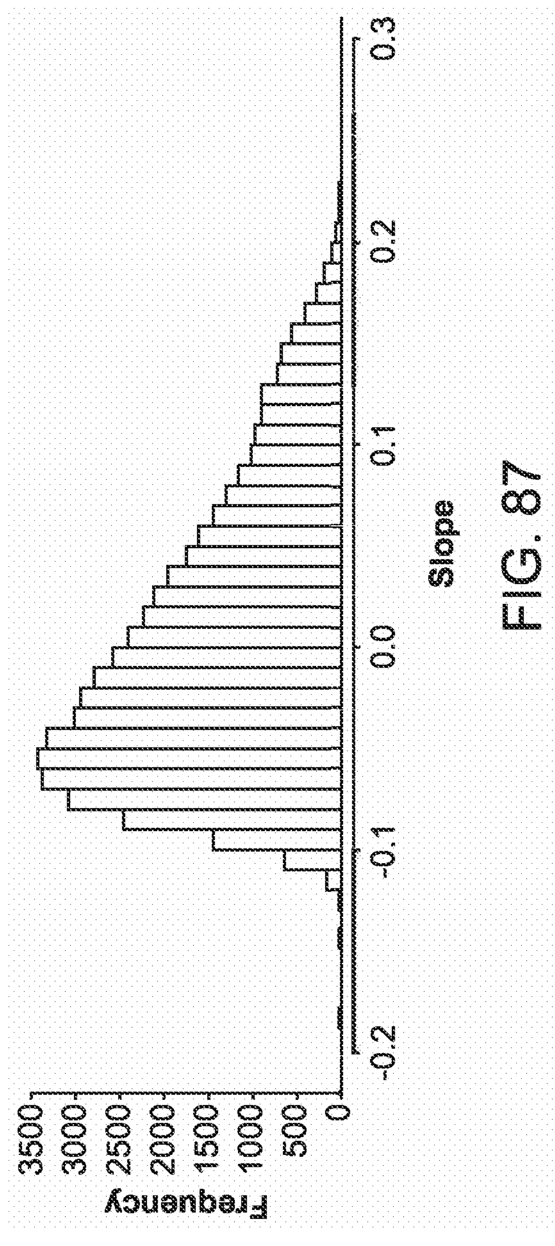

FIG. 87 shows a graph of frequency (Y axis) verse slope (X axis).

Figure 88:
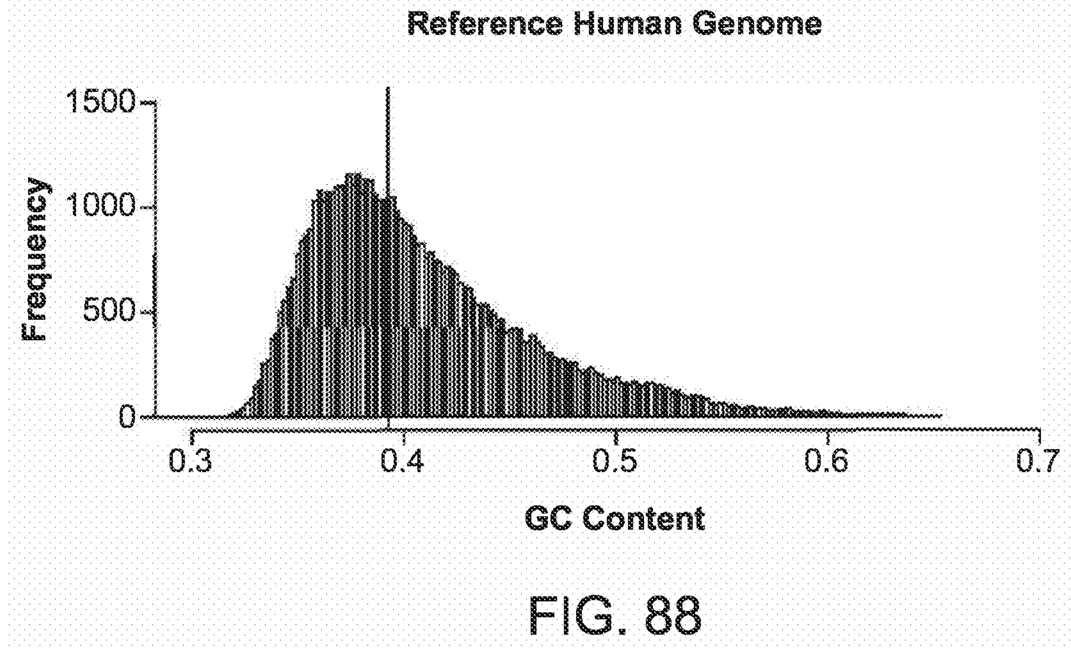

FIG. 88 shows a graph of frequency (Y axis) verse GC content (X axis).

Figure 89:
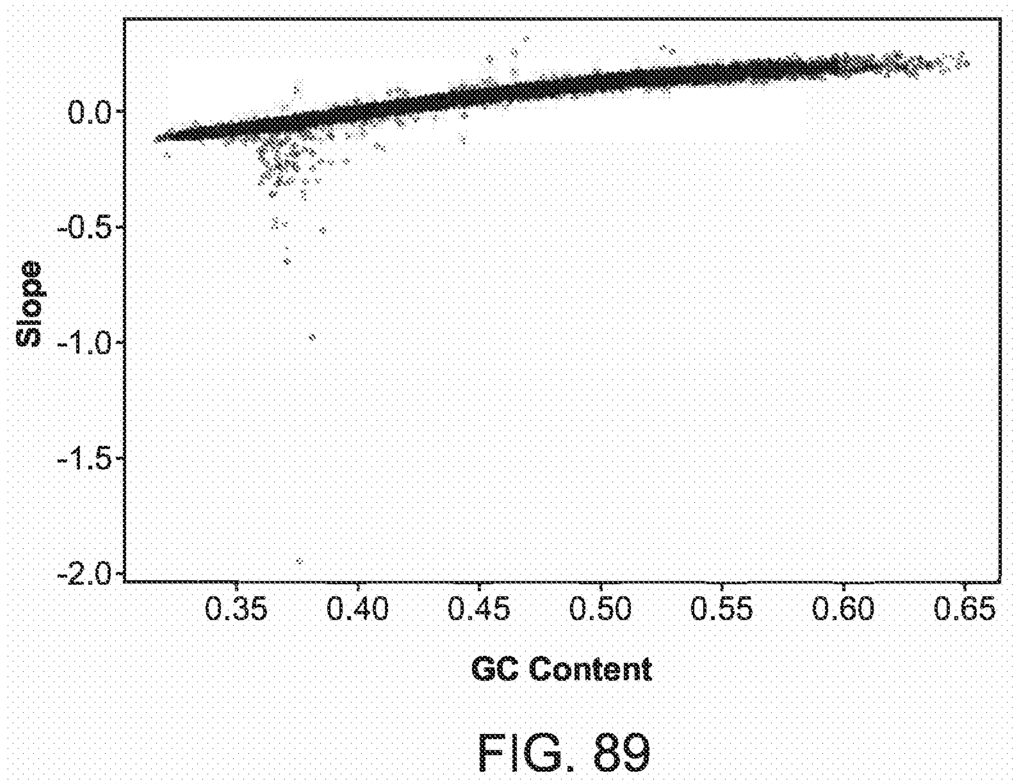

FIG. 89 shows a graph of slope (Y axis) verse GC content (X axis).

Figure 90:
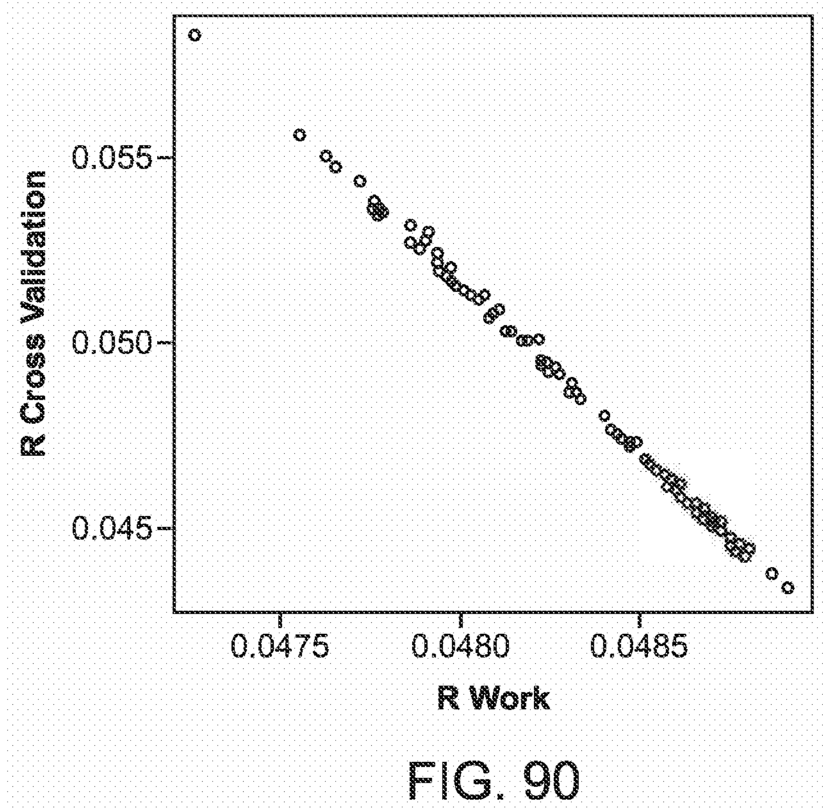

FIG. 90 shows a graph of cross-validation errors (Y axis) verse R work (X axis) for bins chr2_2404.

Figure 91:
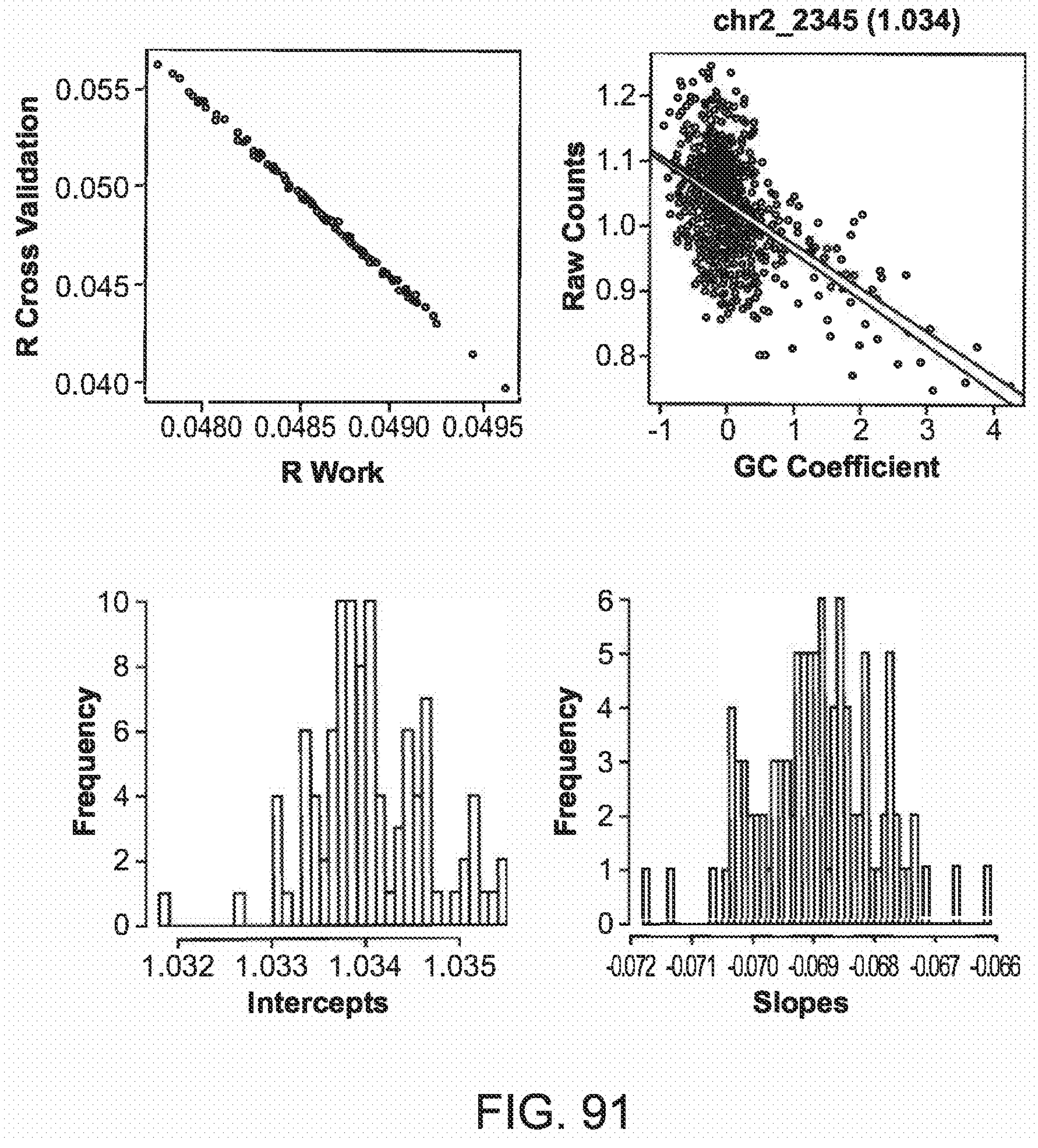

FIG. 91 shows a graph of cross-validation errors (Y axis) verse R work (X axis) (Top Left), raw counts (Y axis) verse GC bias coefficients (X axis)(Top Right), frequency (Y axis) verse intercepts (X axis) (Bottom Left), and frequency (Y axis) verse slope (X axis)(Bottom Right) for bins chr2_2345.

Figure 92:
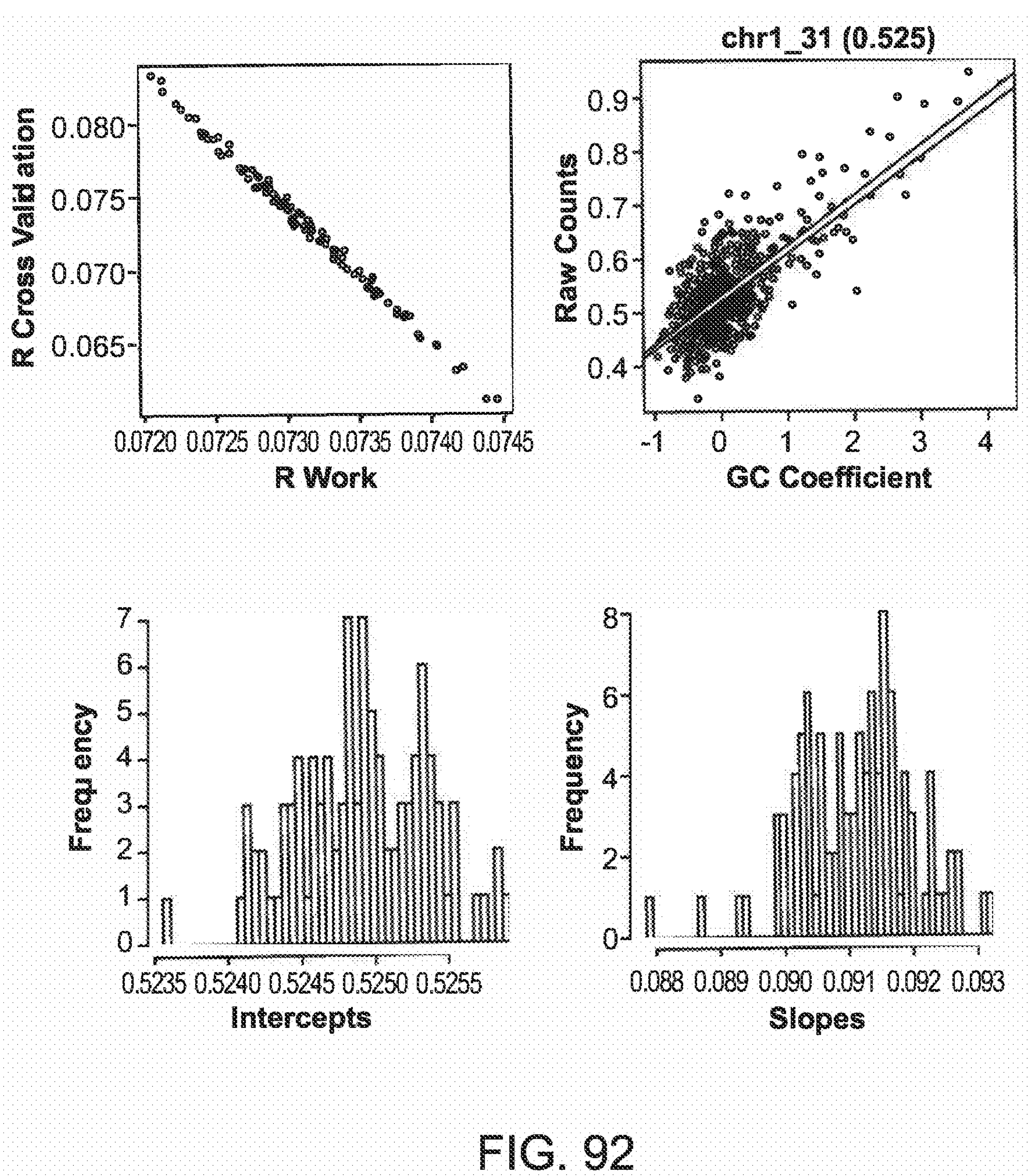

FIG. 92 shows a graph of cross-validation errors (Y axis) verse R work (X axis) (Top Left), raw counts (Y axis) verse GC bias coefficients (X axis)(Top Right), frequency (Y axis) verse intercepts (X axis) (Bottom Left), and frequency (Y axis) verse slope (X axis)(Bottom Right) for bins chr1_31.

Figure 93:
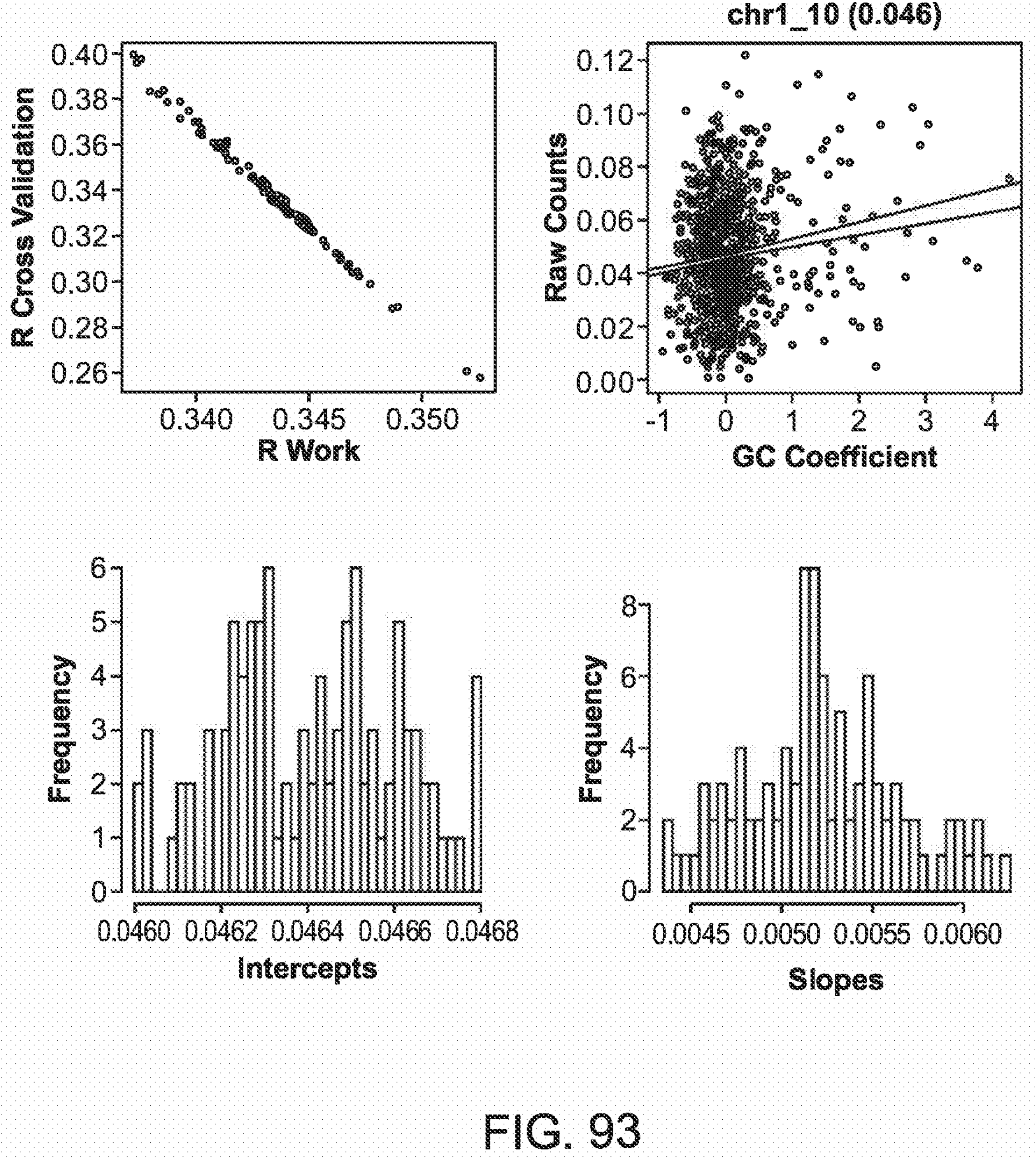

FIG. 93 shows a graph of cross-validation errors (Y axis) verse R work (X axis) (Top Left), raw counts (Y axis) verse GC bias coefficients (X axis)(Top Right), frequency (Y axis) verse intercepts (X axis) (Bottom Left), and frequency (Y axis) verse slope (X axis)(Bottom Right) for bins chr1_10.

Figure 94:
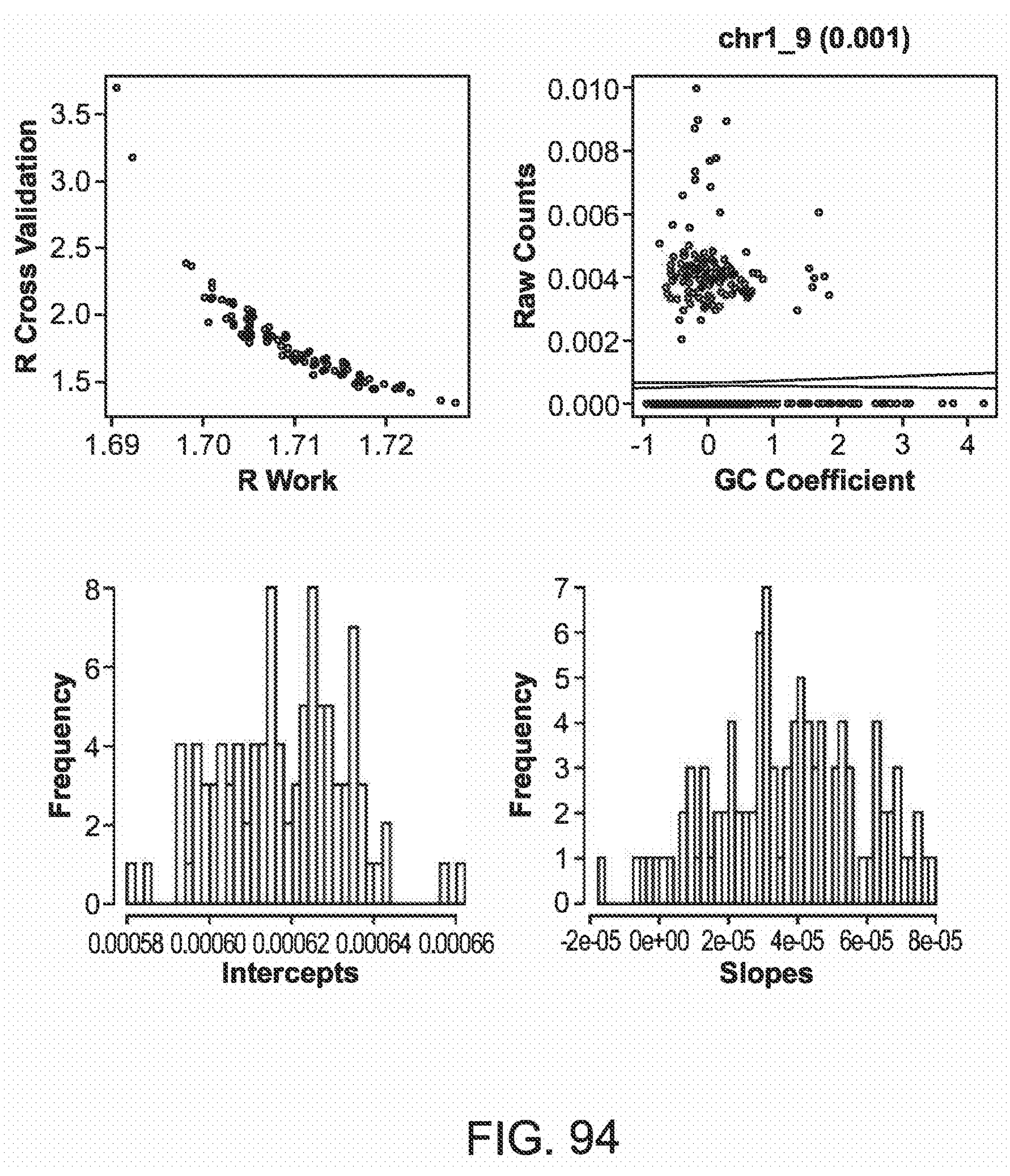

FIG. 94 shows a graph of cross-validation errors (Y axis) verse R work (X axis) (Top Left), raw counts (Y axis) verse GC bias coefficients (X axis)(Top Right), frequency (Y axis) verse intercepts (X axis) (Bottom Left), and frequency (Y axis) verse slope (X axis)(Bottom Right) for bins chr1_9.

Figure 95:
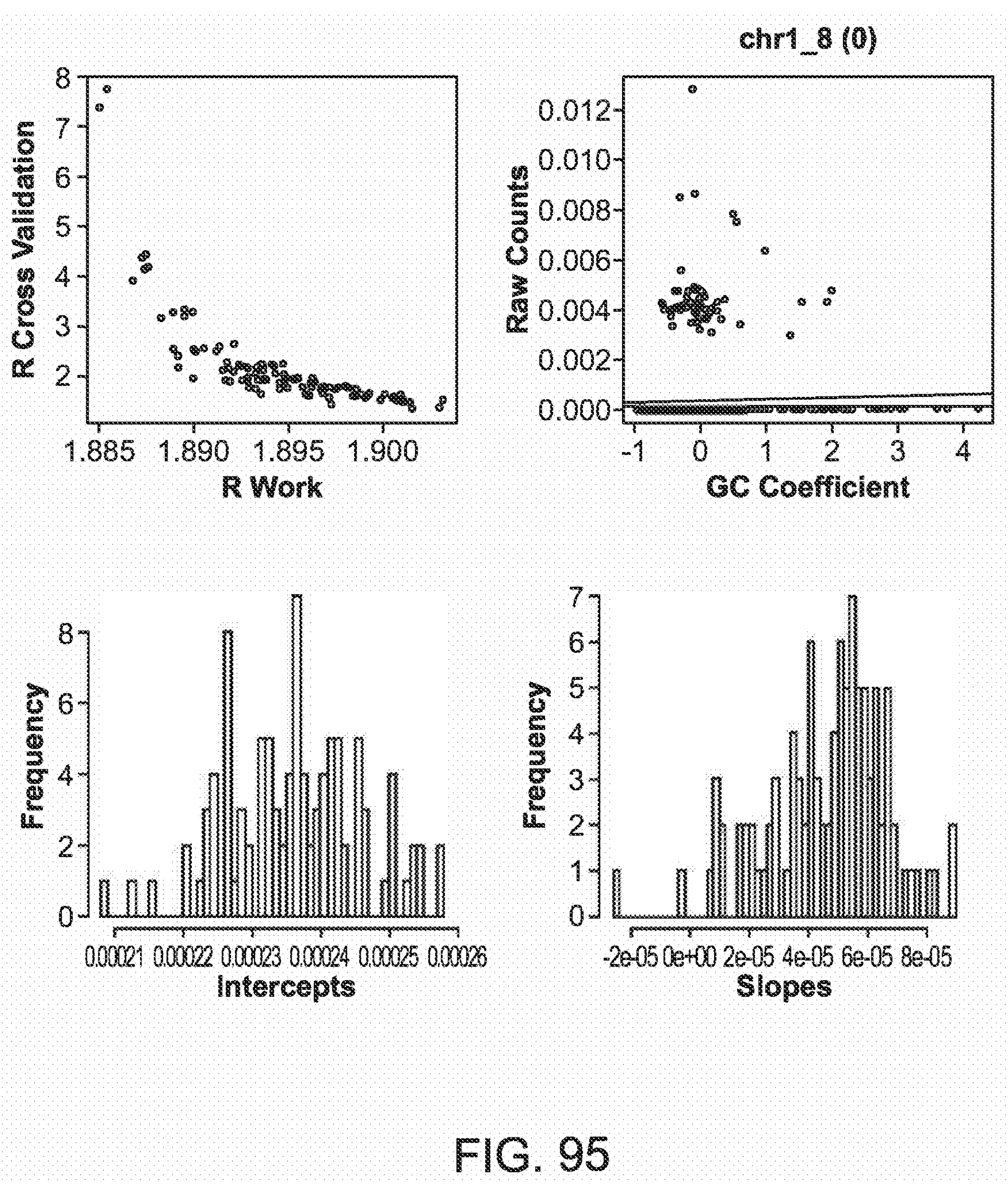

FIG. 95 shows a graph of cross-validation errors (Y axis) verse R work (X axis) (Top Left), raw counts (Y axis) verse GC bias coefficients (X axis)(Top Right), frequency (Y axis)

verse intercepts (X axis) (Bottom Left), and frequency (Y axis) verse slope (X axis)(Bottom Right) for bins chr1_8.

Figure 96:
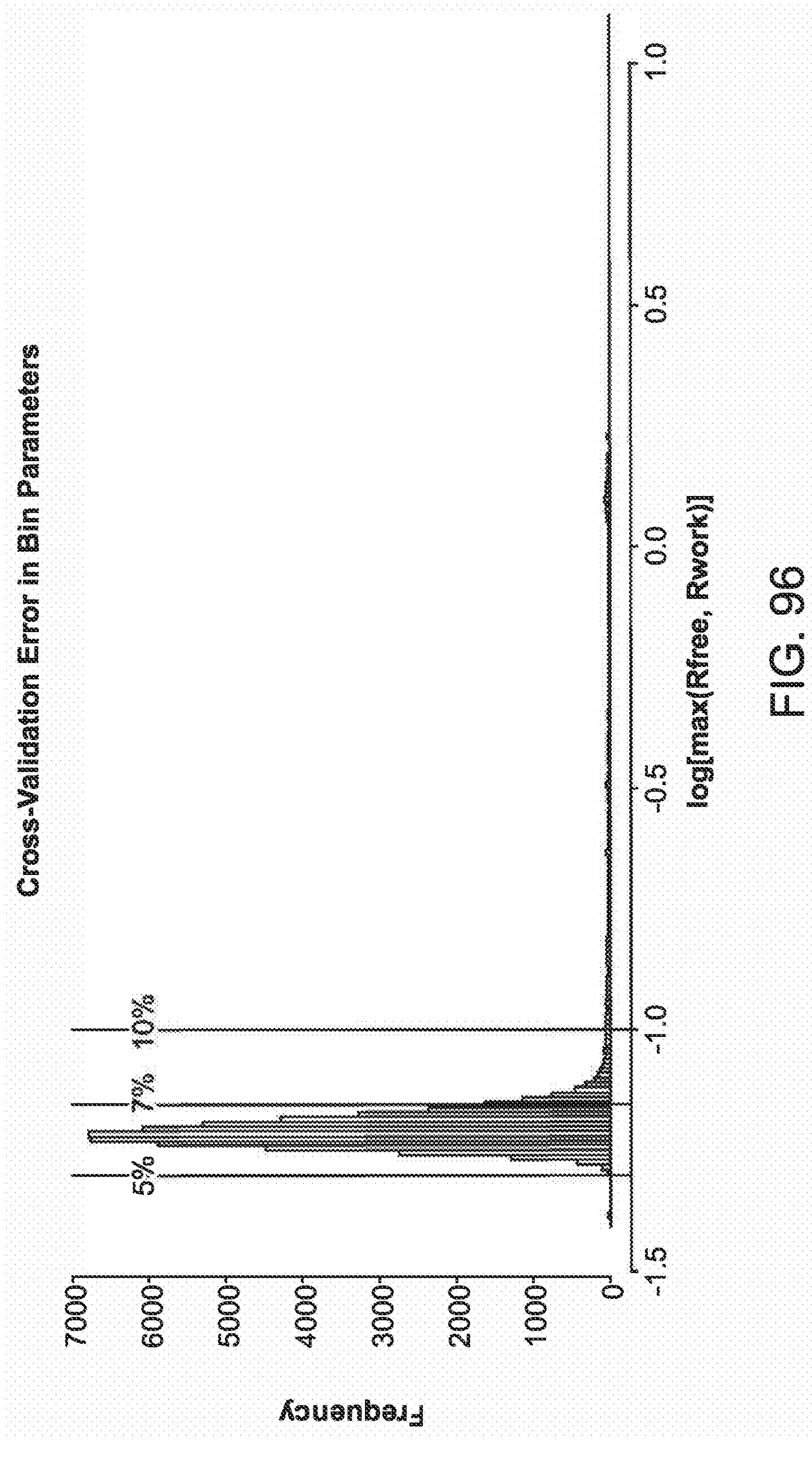

FIG. 96 shows a graph of frequency (Y axis) verse max($R_{cv}$, $R_{work}$) (X axis).

Figure 97:
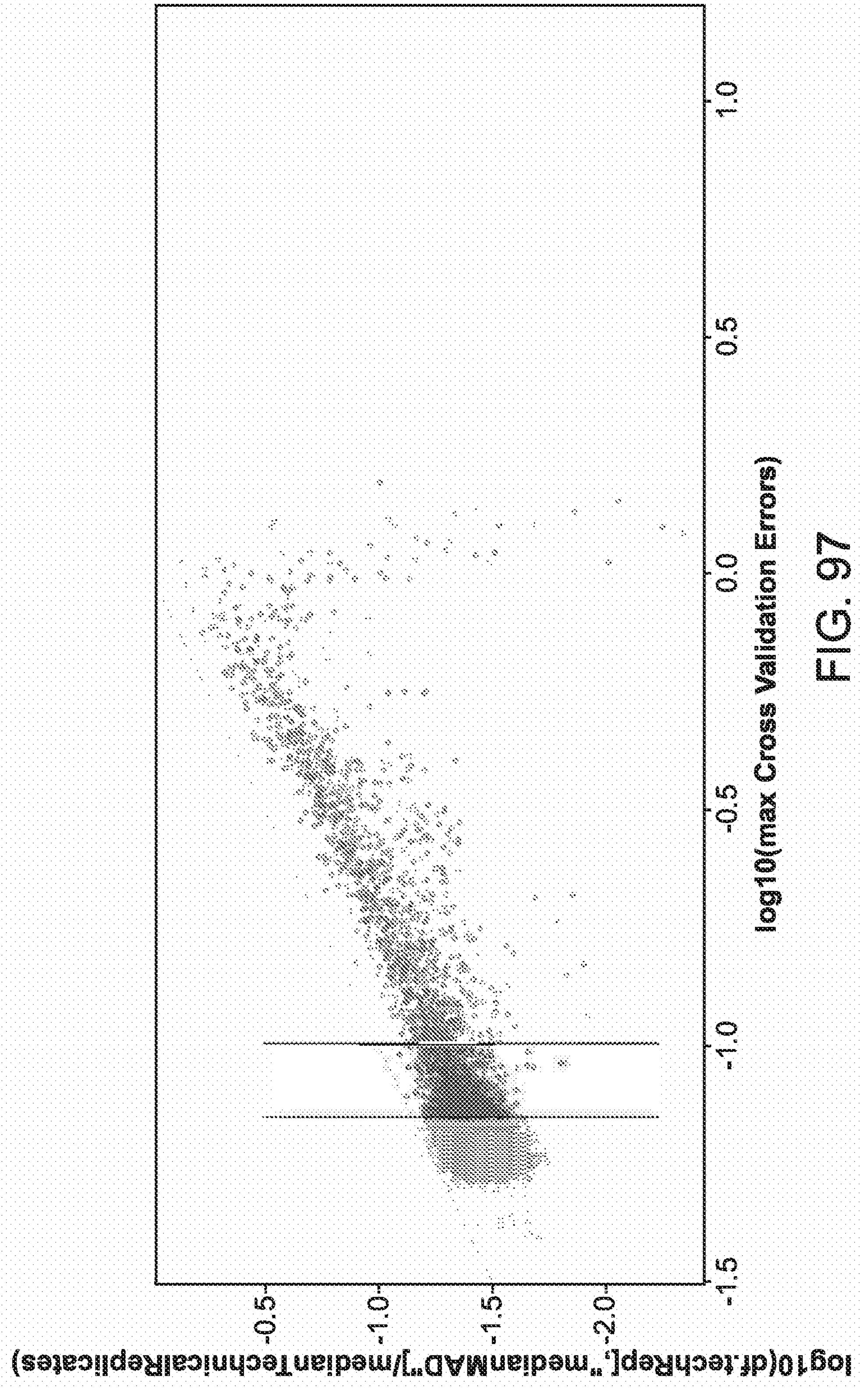

FIG. 97 shows a graph of technical replicates (X axis) verse Log 10 cross-validation errors (X axis).

Figure 98:
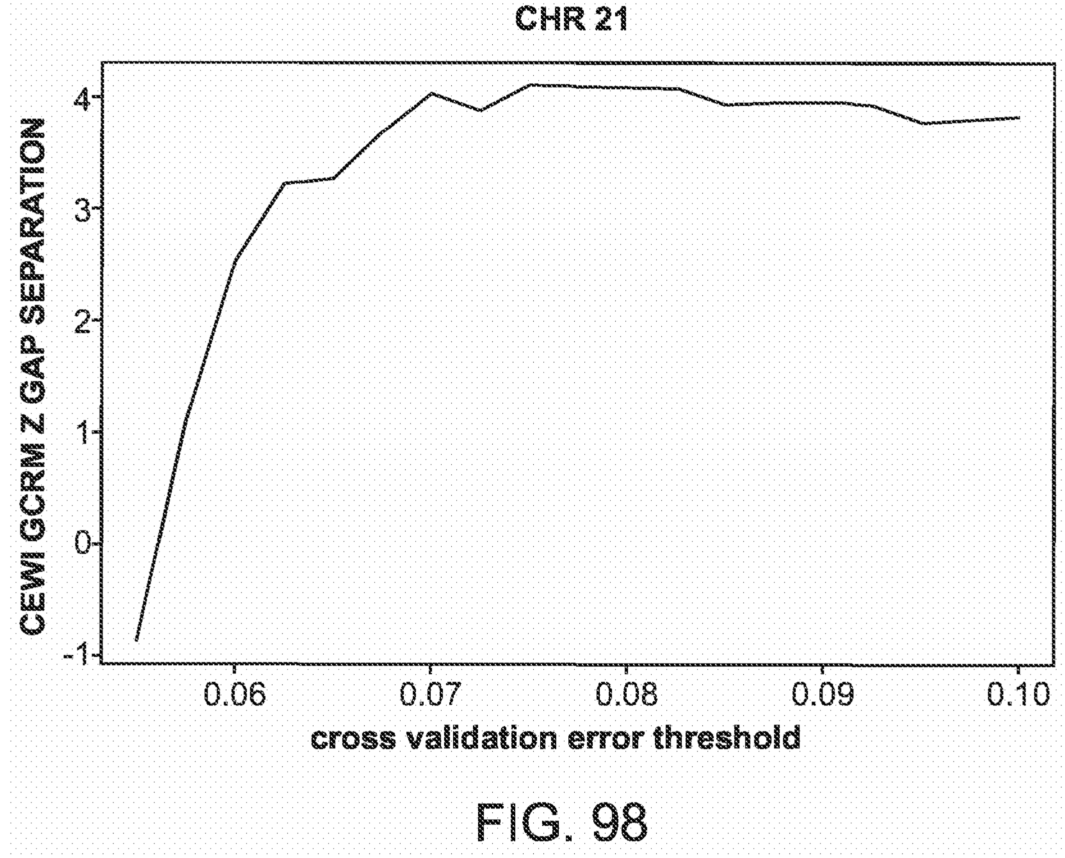

FIG. 98 shows a graph of Z score gap separation (Y axis) verse cross validation error threshold (X axis) for Chr21.

Figures 99A, 99B:
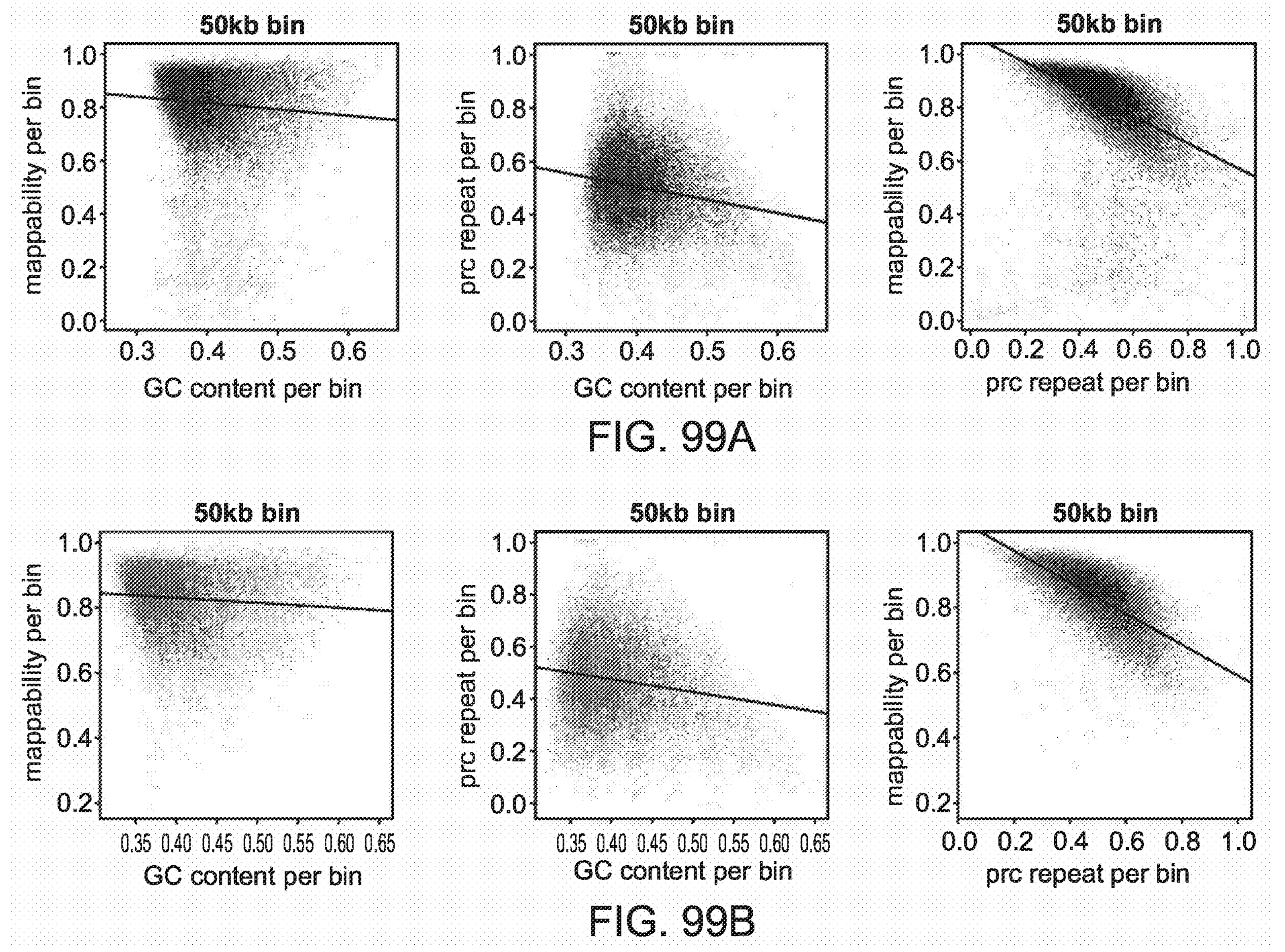

FIG. 99A (all bins) and FIG. 99B (cross-validated bins) demonstrates that the bin selection described in example 4 mostly removes bins with low mappability.

Figure 100:
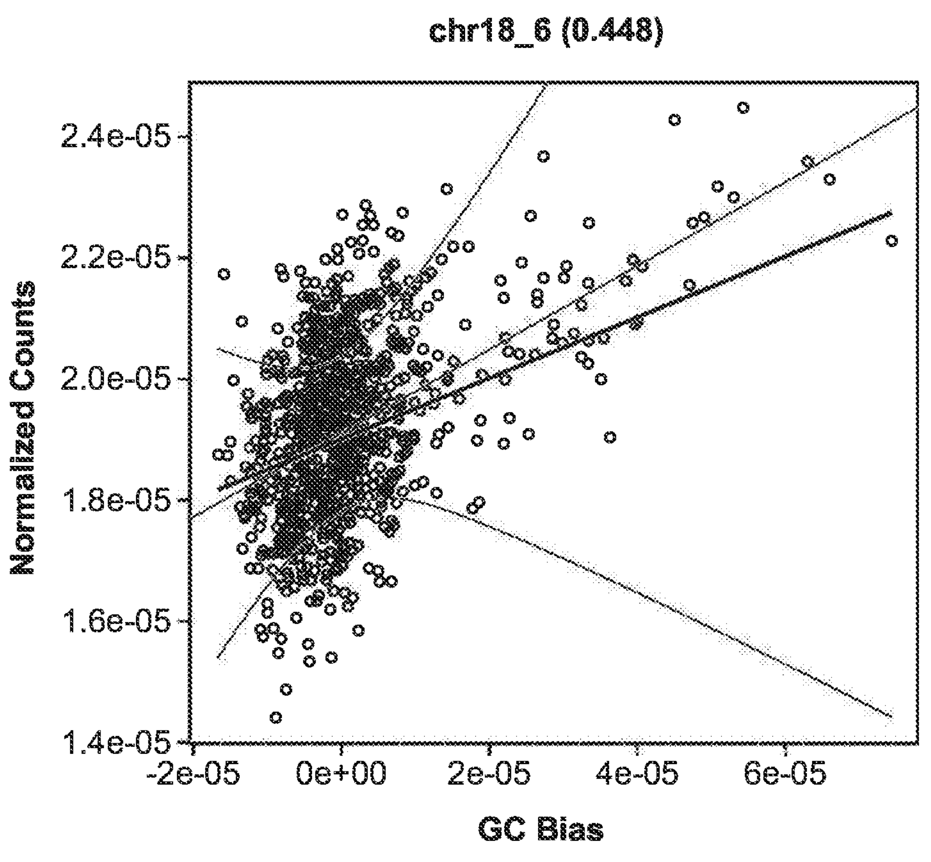

FIG. 100 shows a graph of normalized counts (Y axis) verse GC (X axis) bias for Chr18_6.

Figure 101:
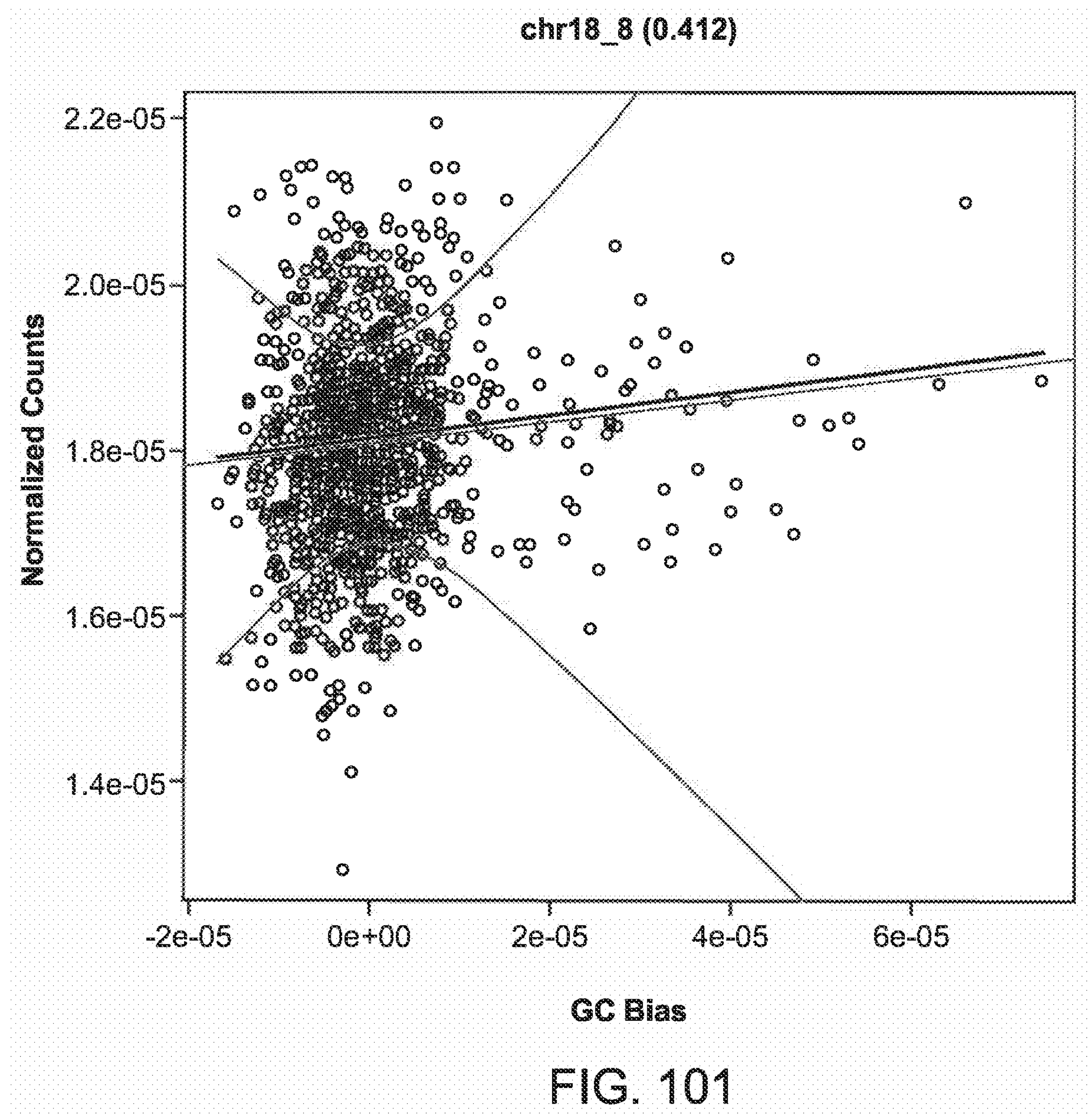

FIG. 101 show a graph of normalized counts (Y axis) verse GC bias (X axis) for Chr18_8.

Figure 102:
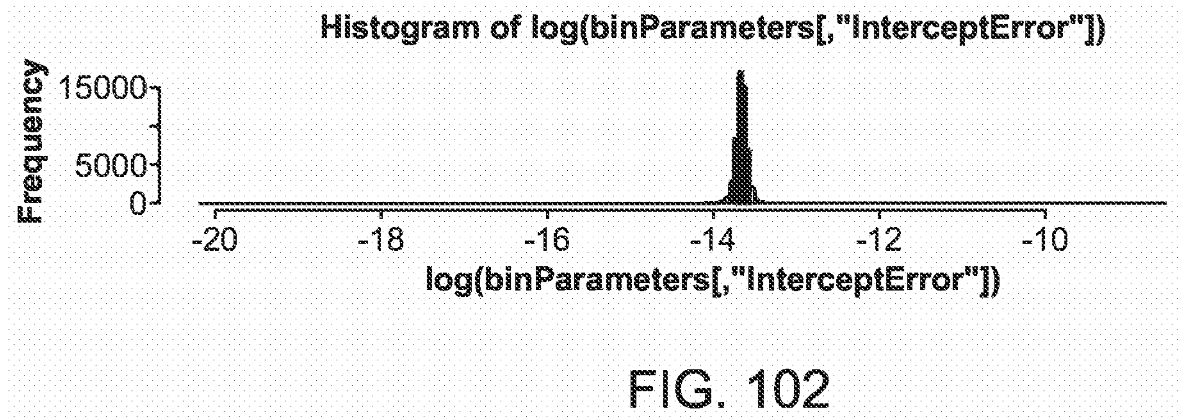

FIG. 102 shows a histogram of frequency (Y axis) verse intercept error (X axis).

Figure 103:
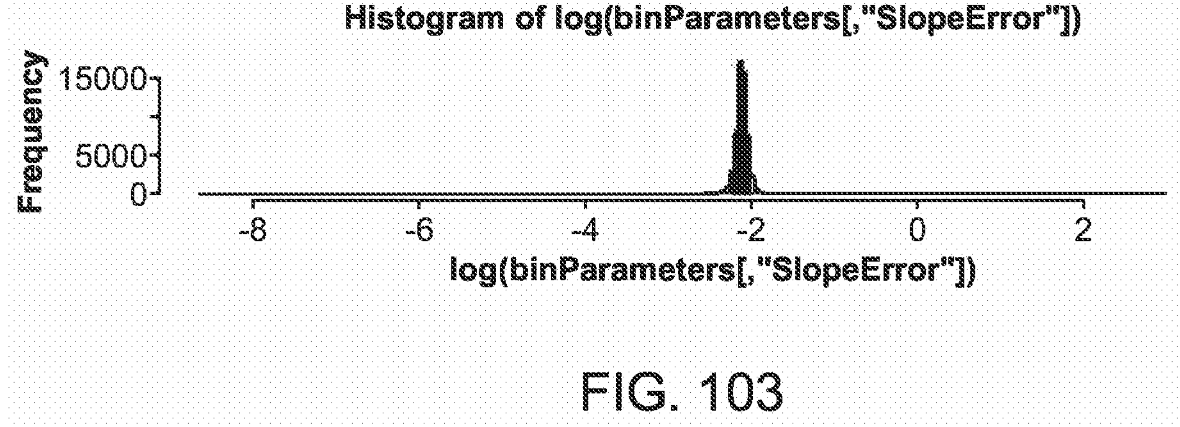

FIG. 103 shows a histogram of frequency (Y axis) verse slope error (X axis).

Figure 104:
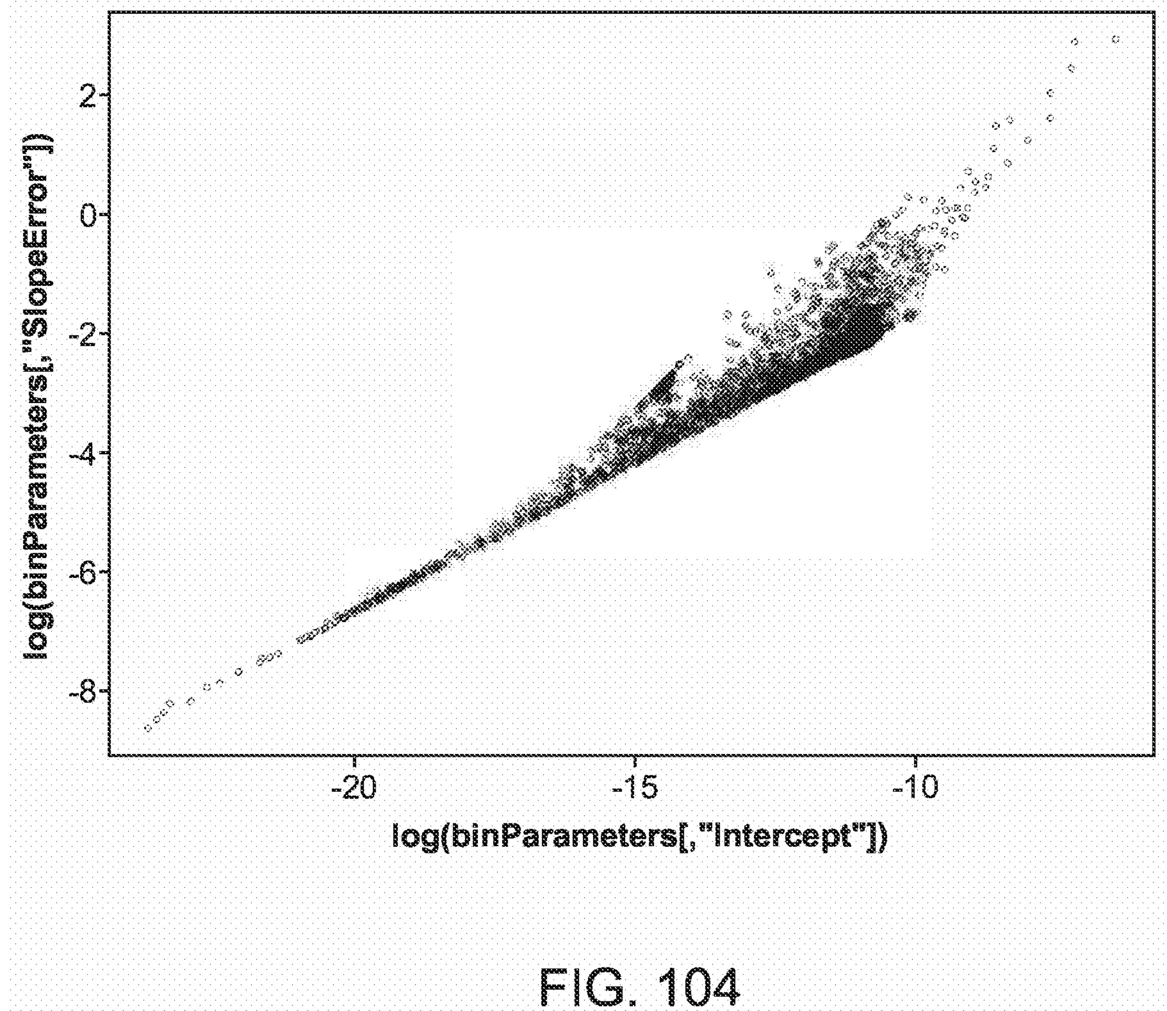

FIG. 104 shows a graph of slope error (Y axis) verse intercept (X axis).

Figure 105:
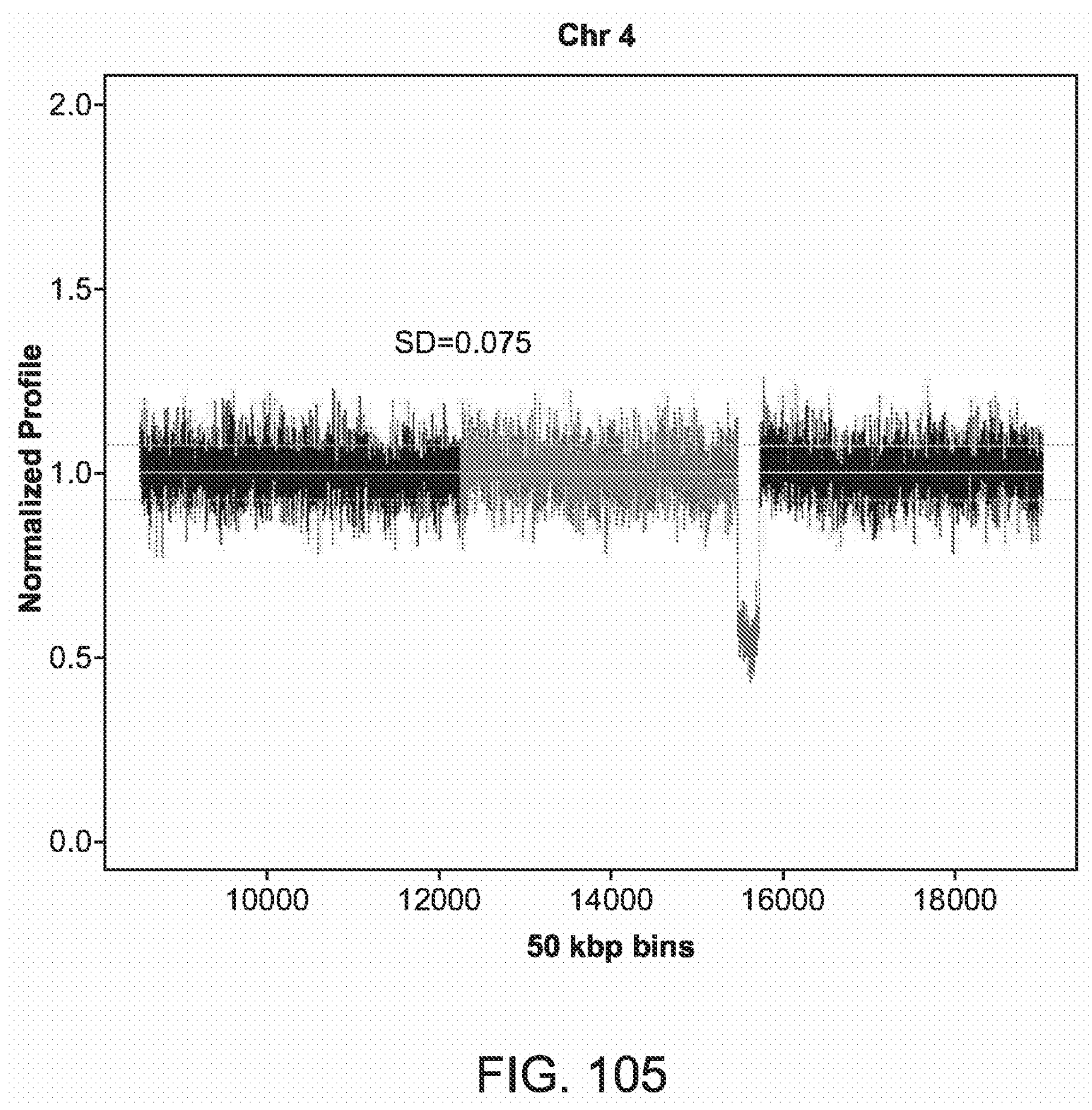

FIG. 105 shows a normalized profile that includes Chr4 (about 12400 to about 15750) with elevation (Y axis) and bin number (X axis).

Figure 106:
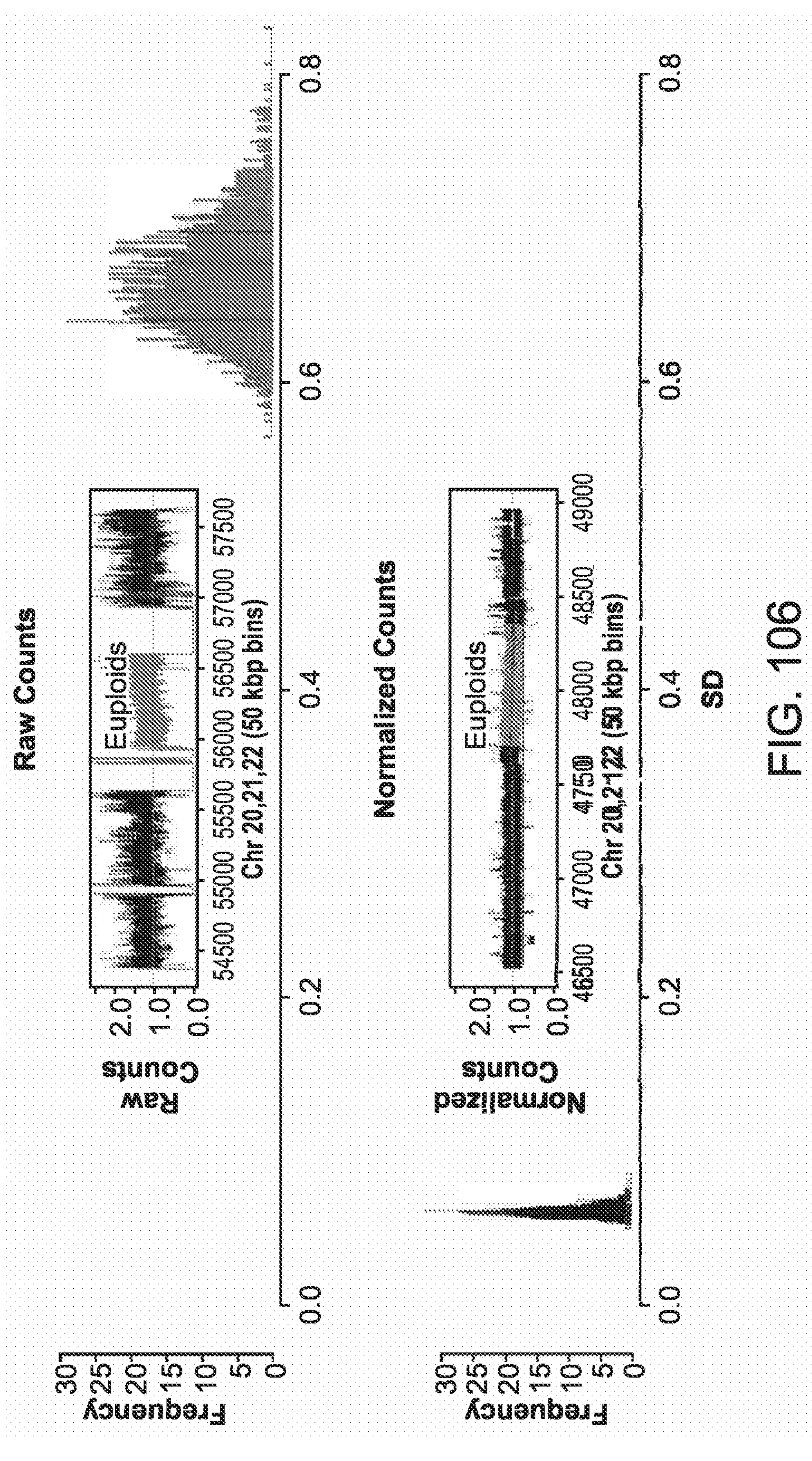

FIG. 106 shows a profile of raw counts (Top Panel) and normalized counts (Bottom Panel) for Chr20, Chr21 and Chr22. Also shown is a distribution of standard deviations (X axis) verse frequency (Y axis) for the profiles before (top) and after (bottom) PERUN normalization.

Figure 107:
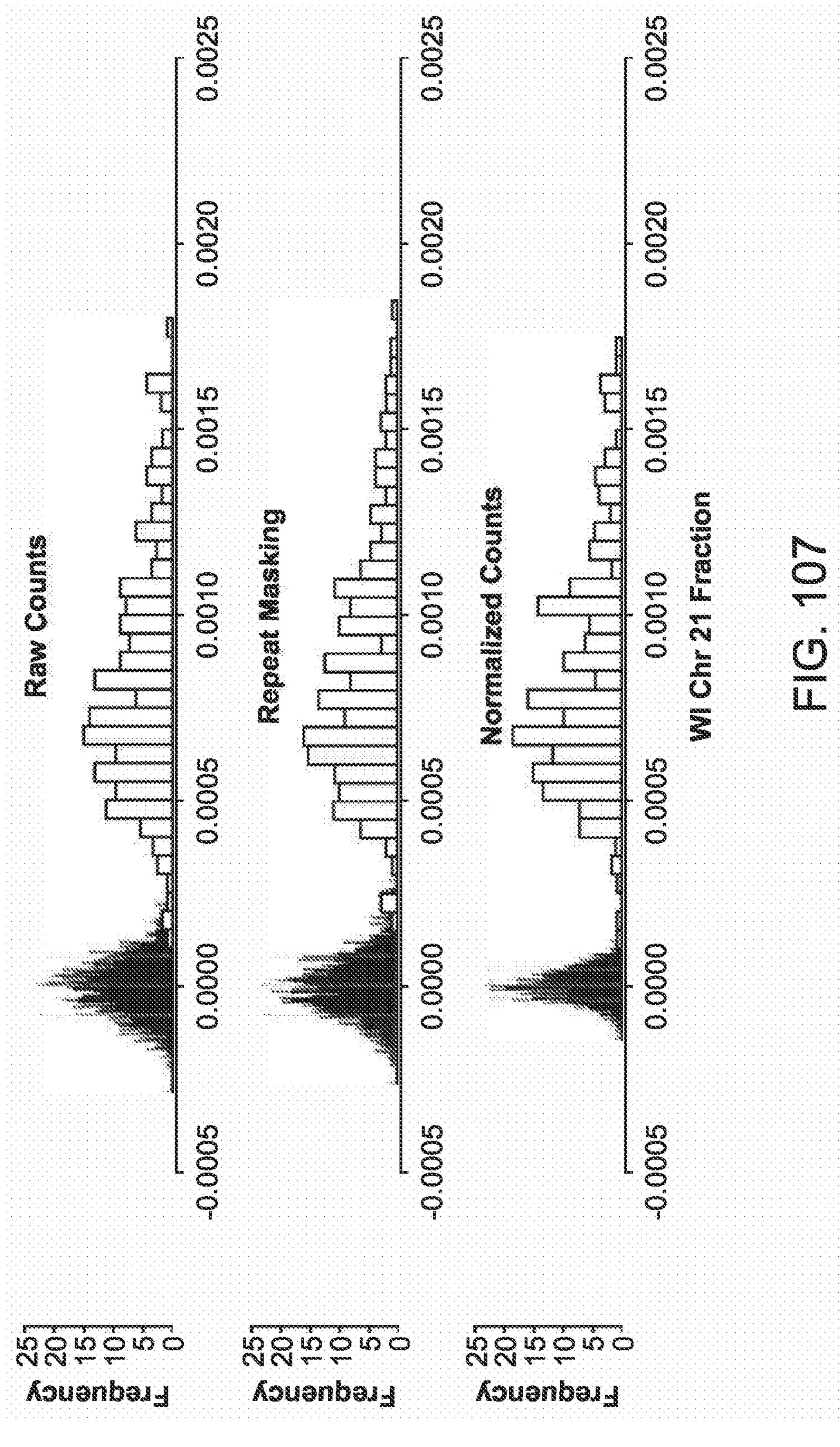

FIG. 107 shows a distribution of chromosome representations for euploids and trisomy cases for raw counts (top), repeat masking (middle) and normalized counts (bottom).

Figure 108:
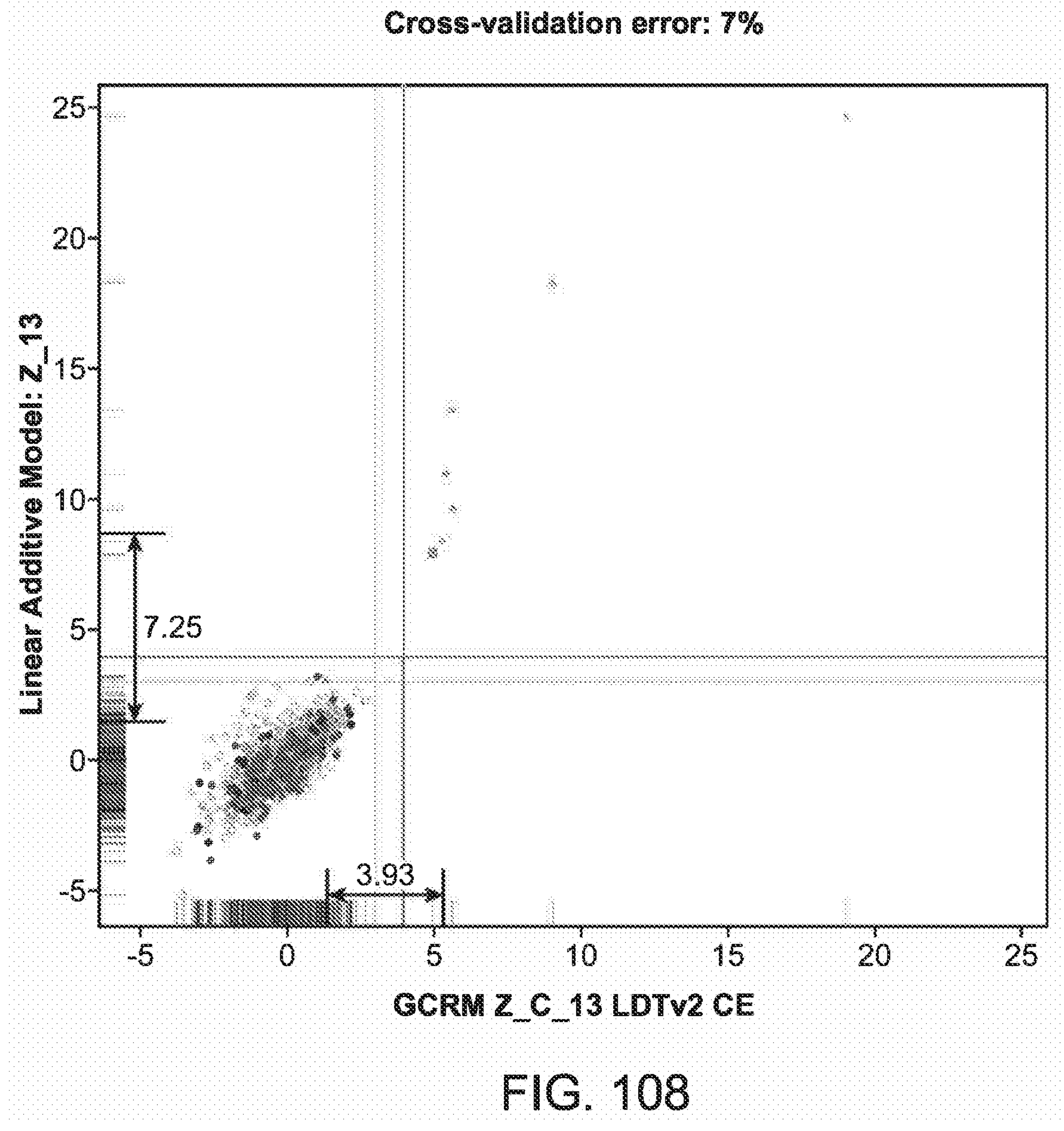

FIG. 108 shows a graph of results obtained with a linear additive model (Y axis) verse a GCRM for Chr13.

Figure 109:
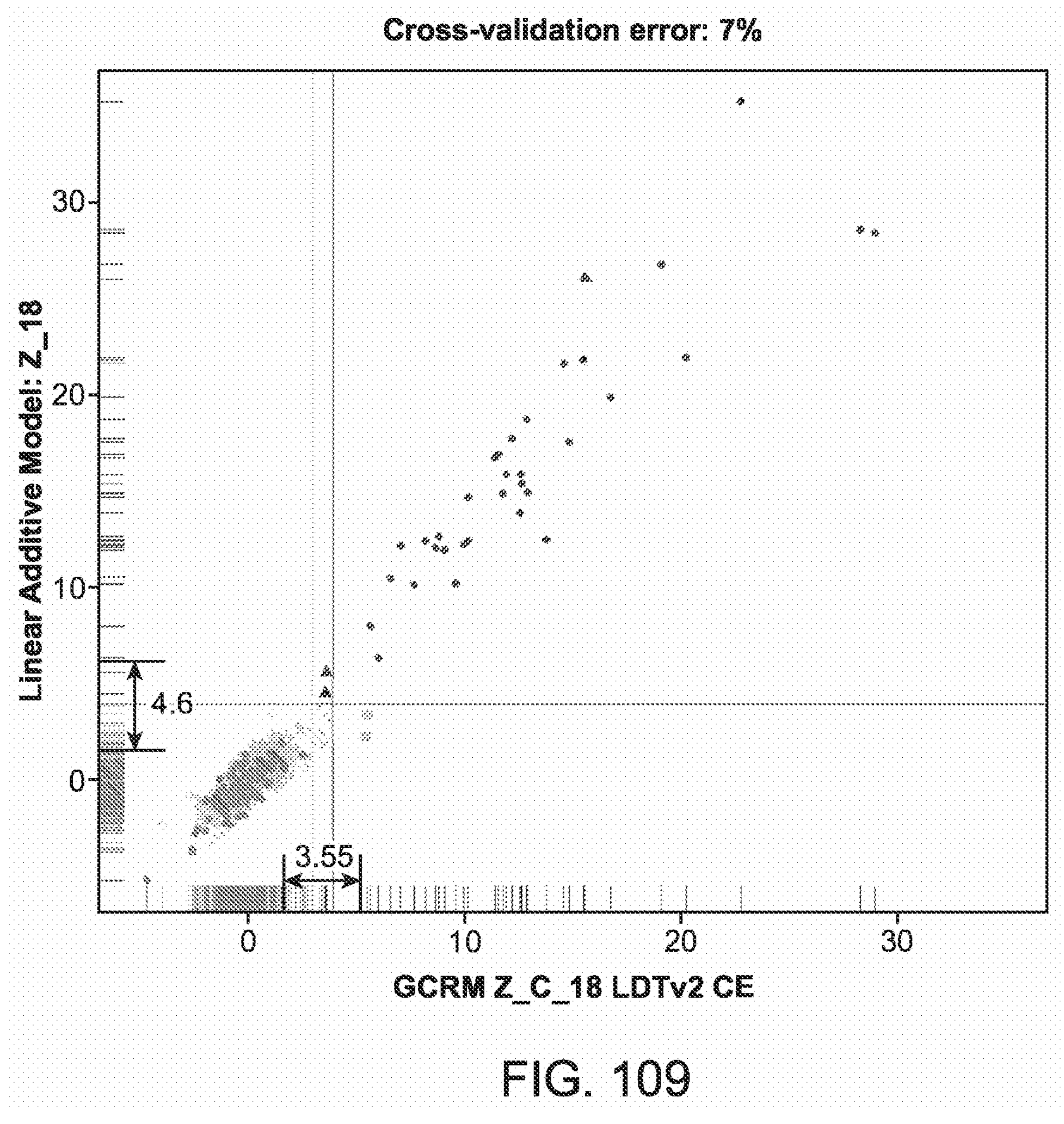

FIG. 109 shows a graph of results obtained with a linear additive model (Y axis) verse a GCRM for Chr18.

Figure 110:
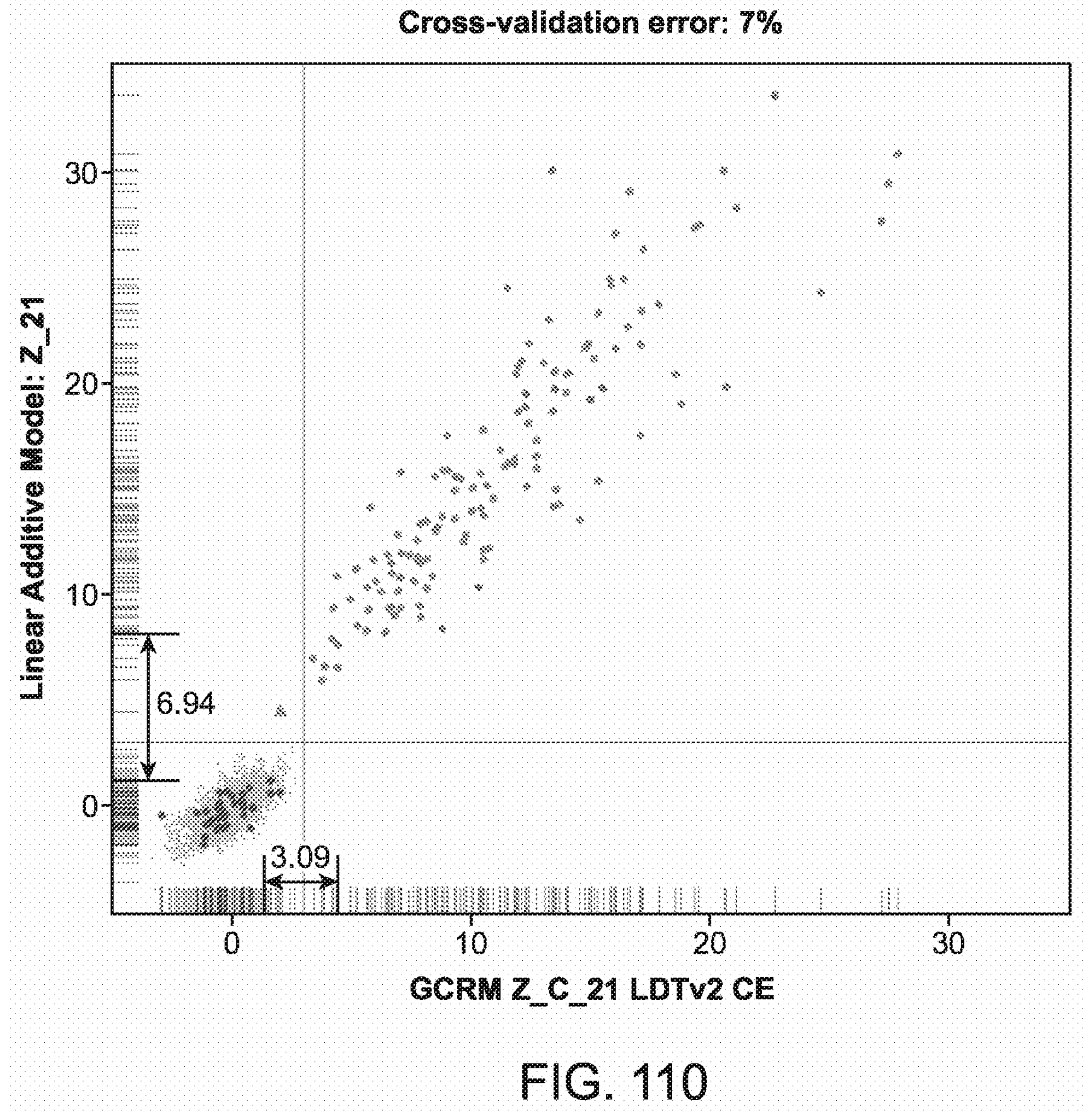
Figure 111:
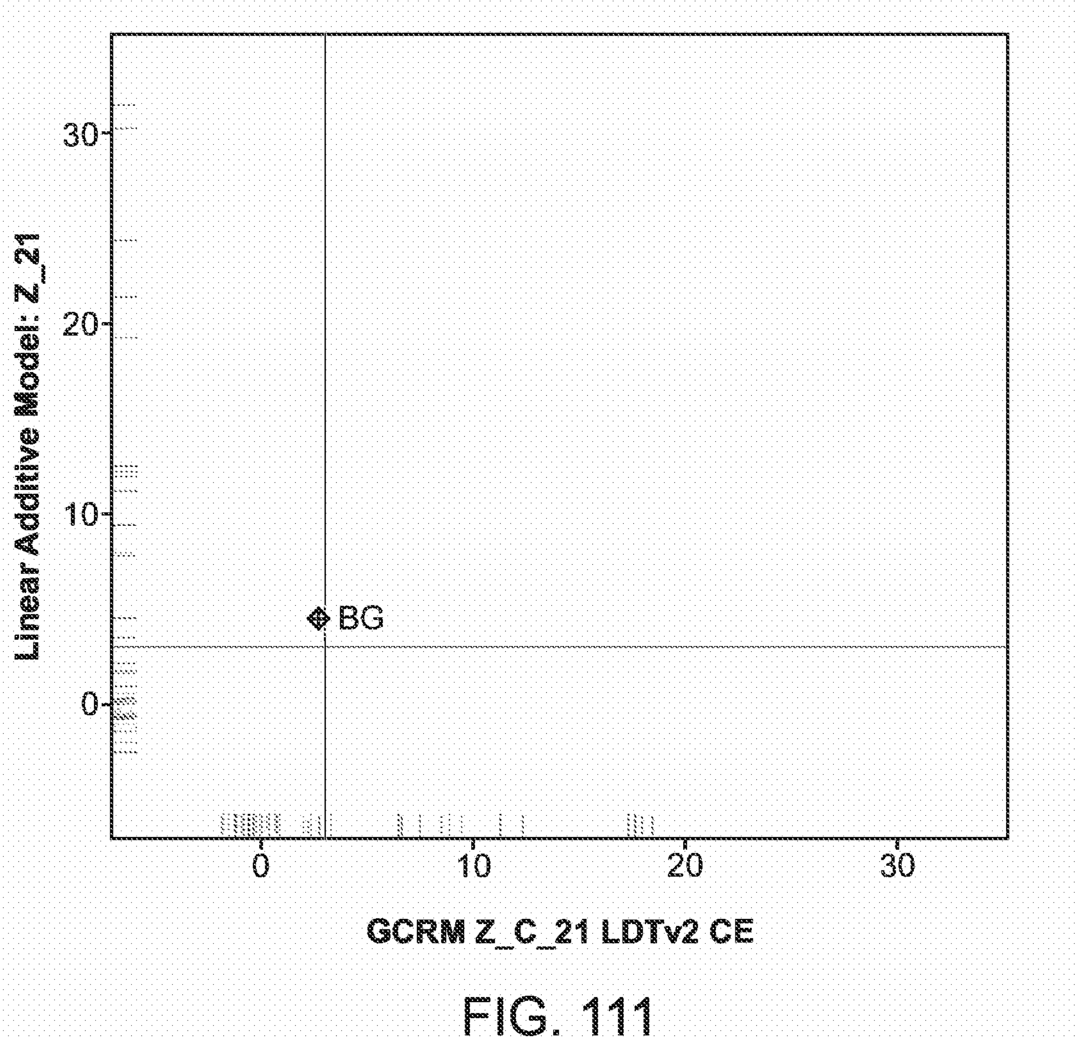

FIG. 110 and FIG. 111 show a graph of results obtained with a linear additive model (Y axis) verse a GCRM for Chr21.

Figures 112A, 112B, 112C:
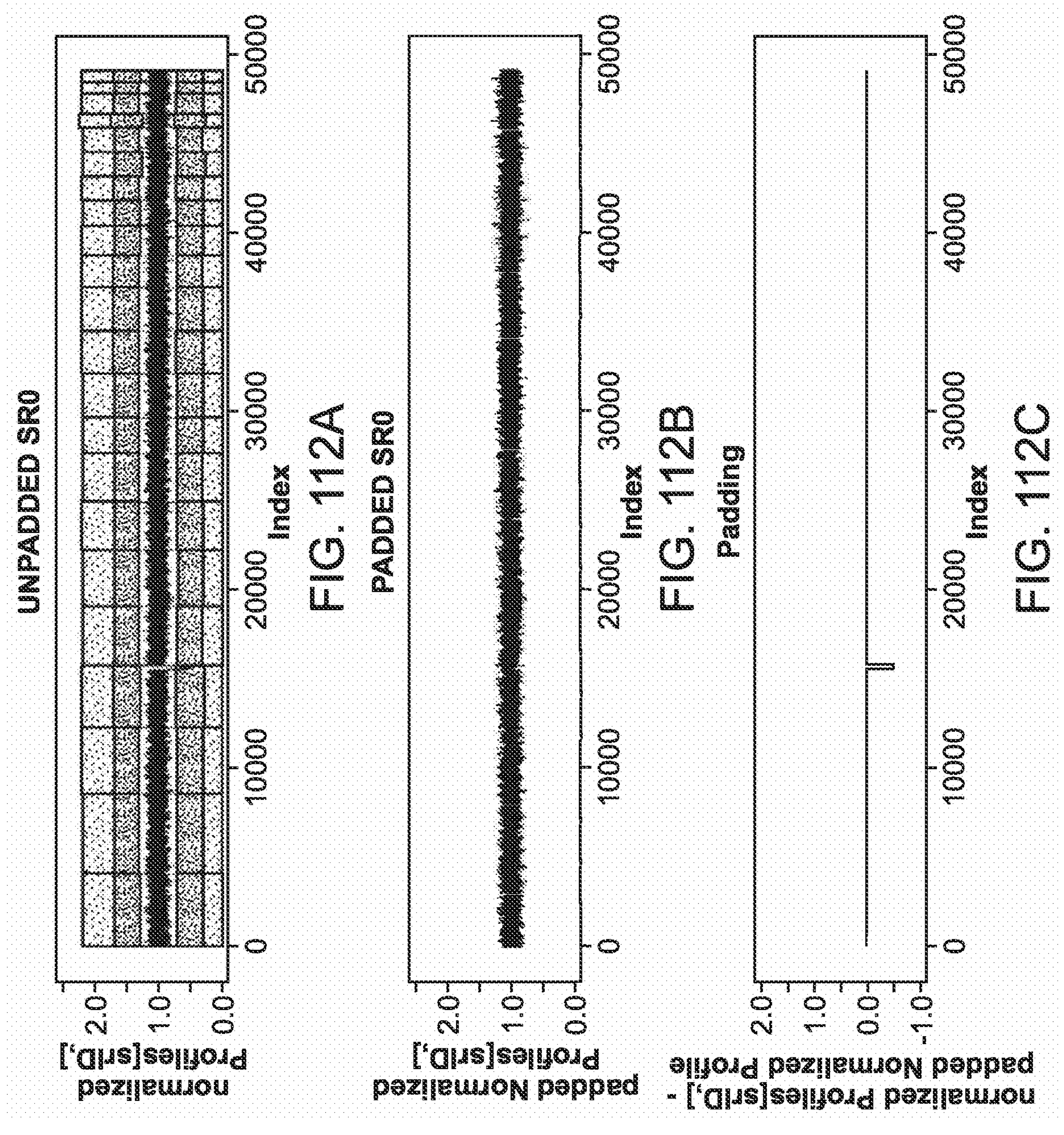

FIG. 112A-C illustrates padding of a normalized autosomal profile for a euploid WI sample. FIG. 112A is an example of an unpadded profile. FIG. 112B is an example of a padded profile. FIG. 112C is an example of a padding correction (e.g., an adjusted profile, an adjusted elevation).

Figures 113A, 113B, 113C:
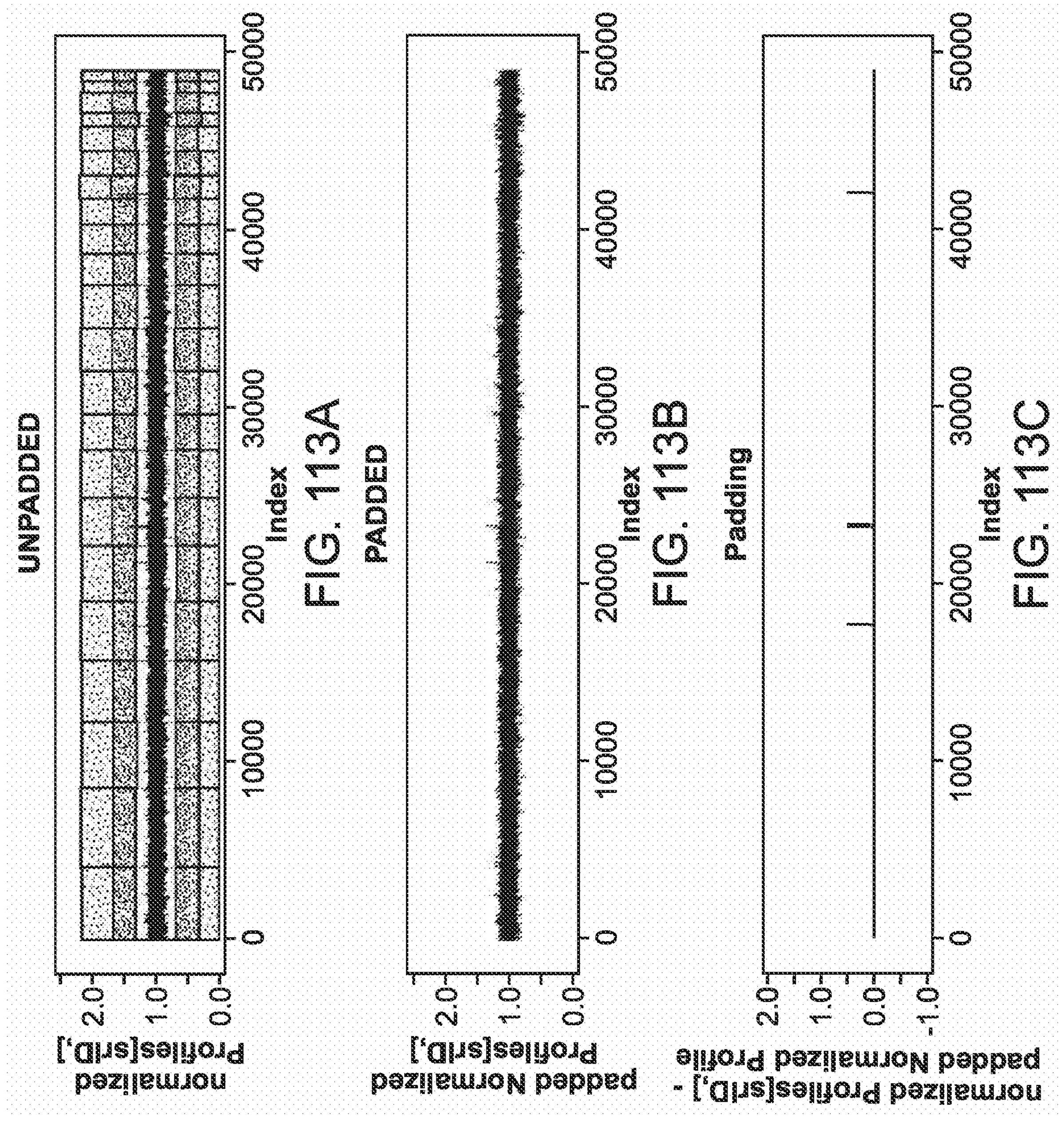

FIG. 113A-C illustrates padding of a normalized autosomal profile for a euploid WI sample. FIG. 113A is an example of an unpadded profile. FIG. 113B is an example of a padded profile. FIG. 113C is an example of a padding correction (e.g., an adjusted profile, an adjusted elevation).

Figures 114A, 114B, 114C:
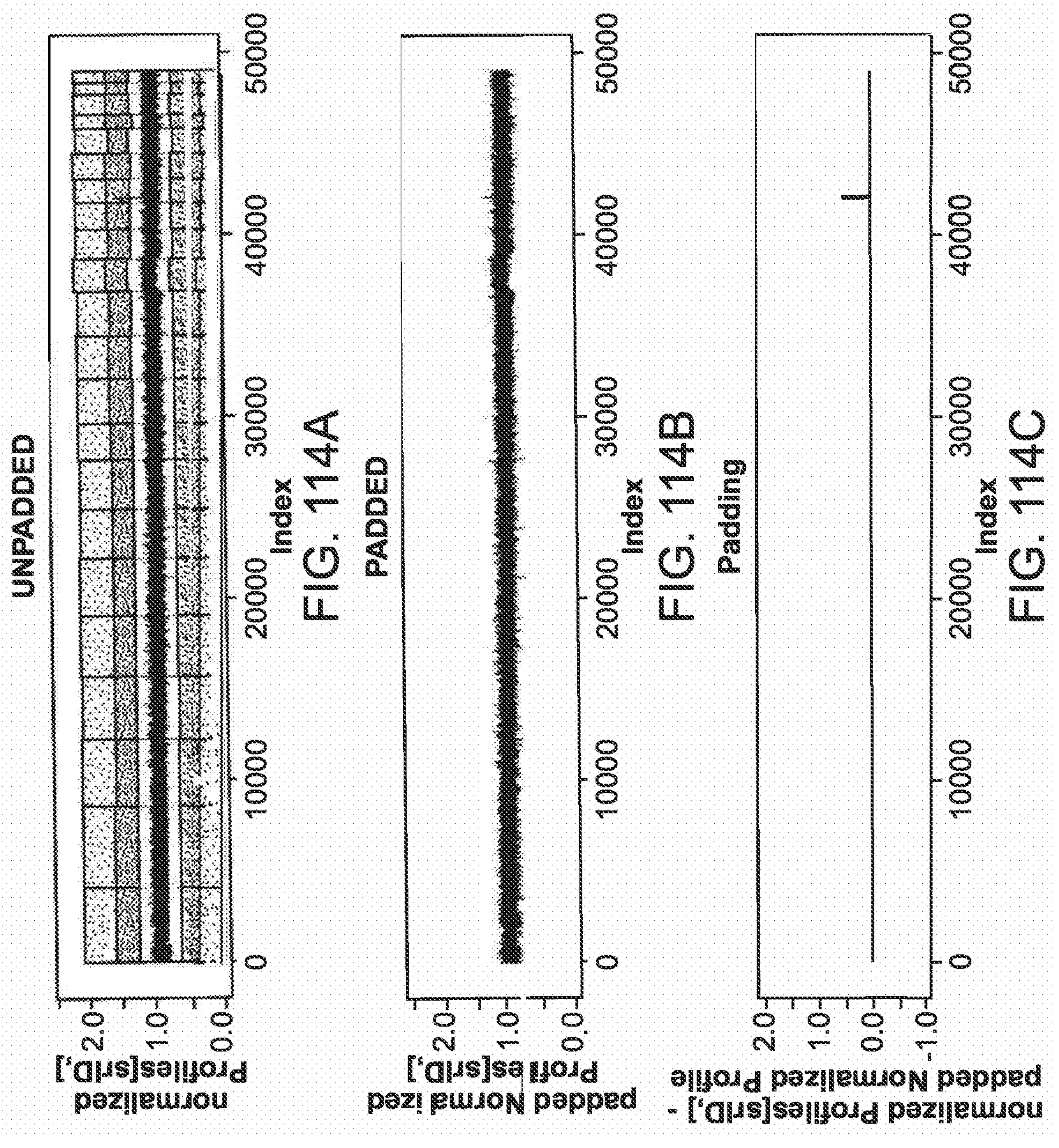

FIG. 114A-C illustrates padding of a normalized autosomal profile for a trisomy 13 WI sample. FIG. 114A is an example of an unpadded profile. FIG. 114B is an example of a padded profile. FIG. 114C is an example of a padding correction (e.g., an adjusted profile, an adjusted elevation).

Figures 115A, 115B, 115C:
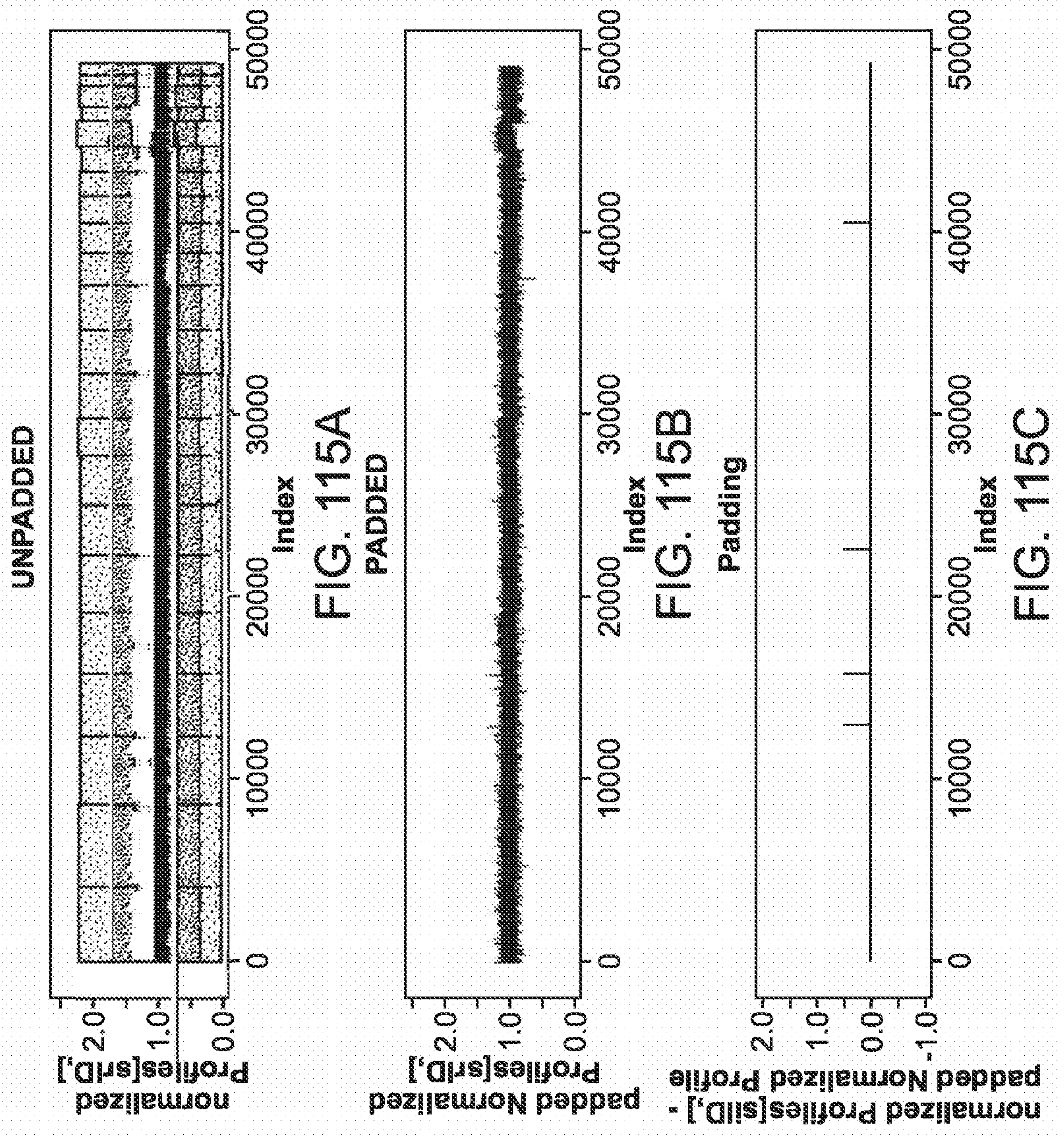
Figures 116, 117:
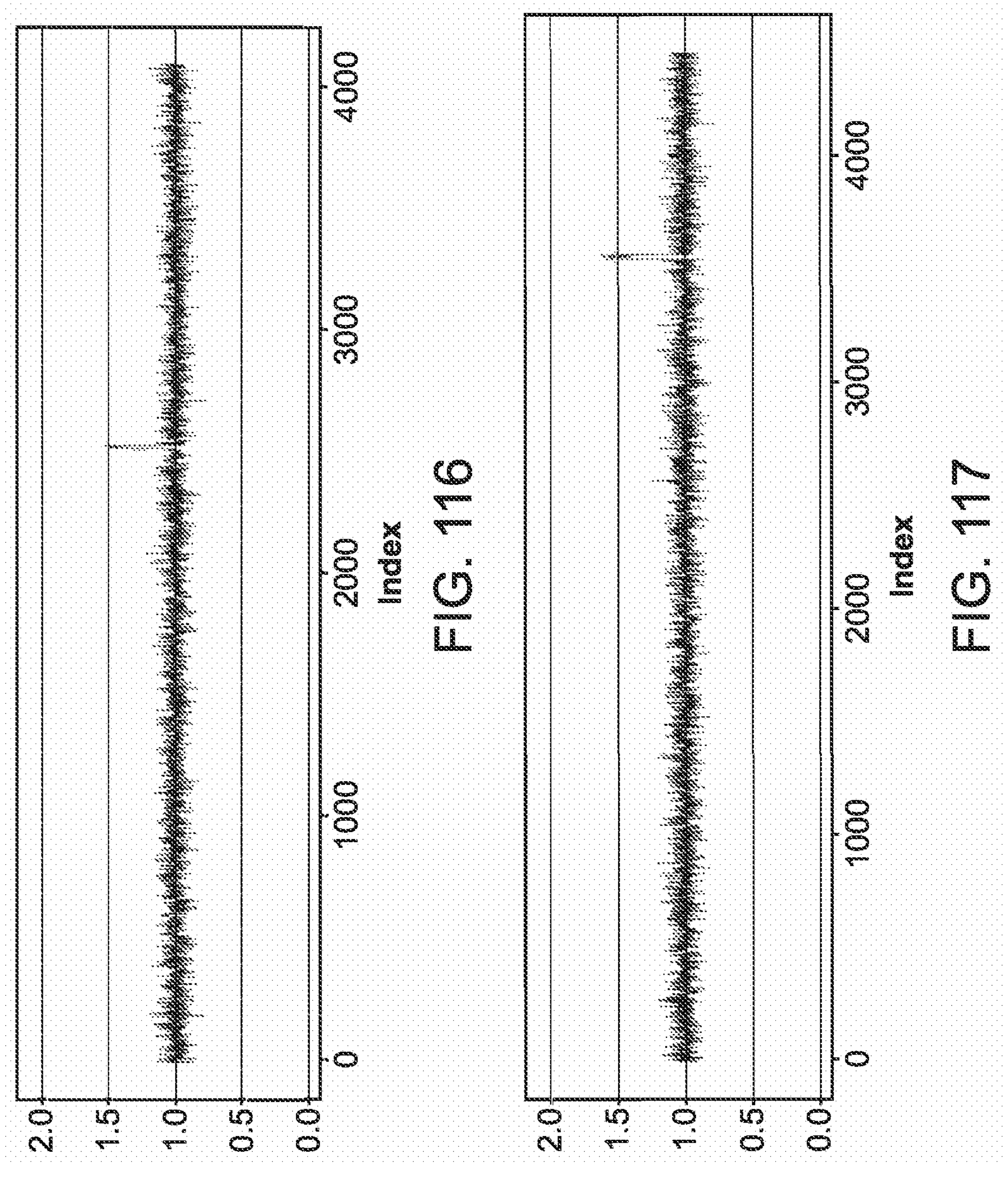
Figures 118, 119:
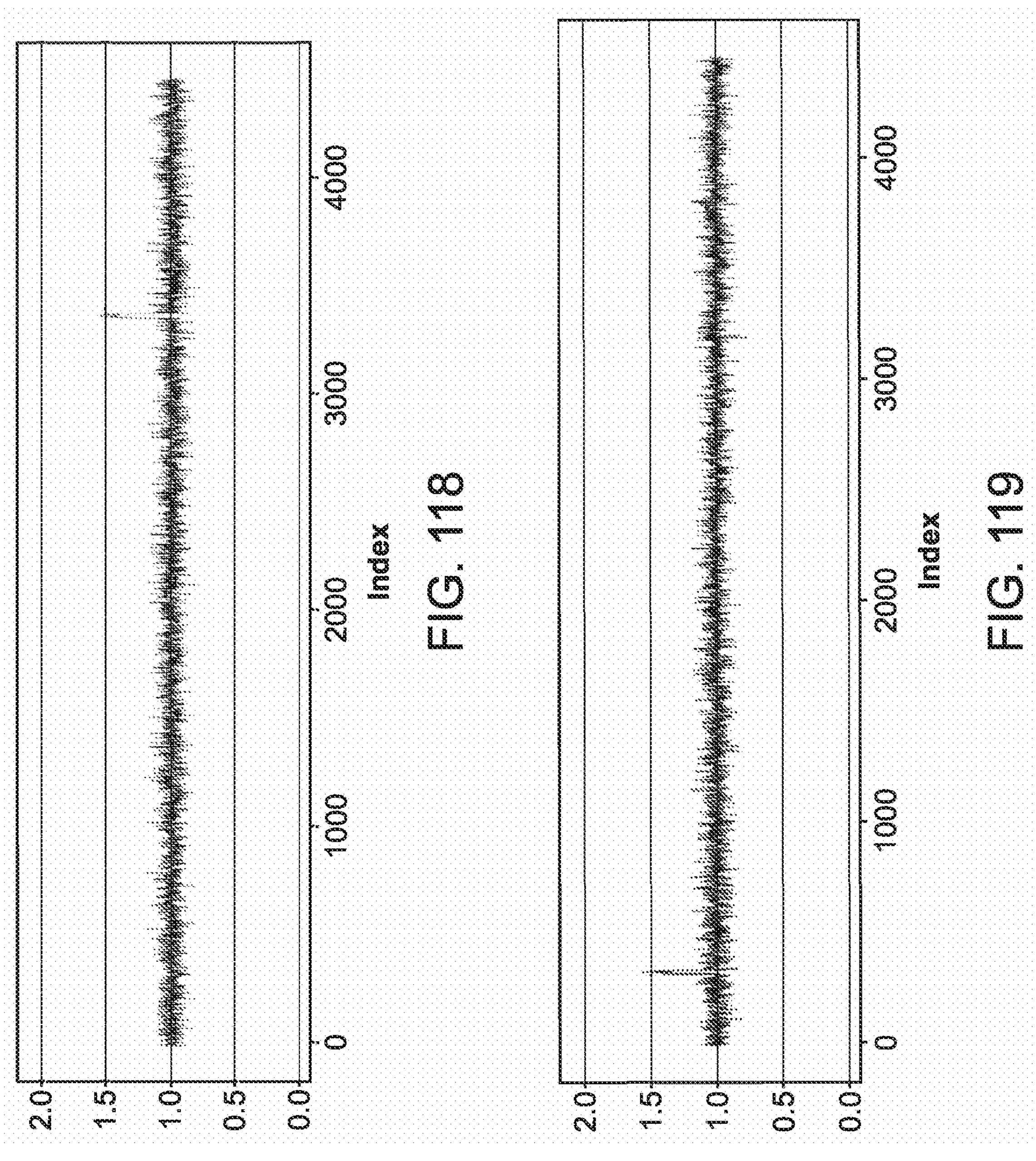
Figures 120, 121:
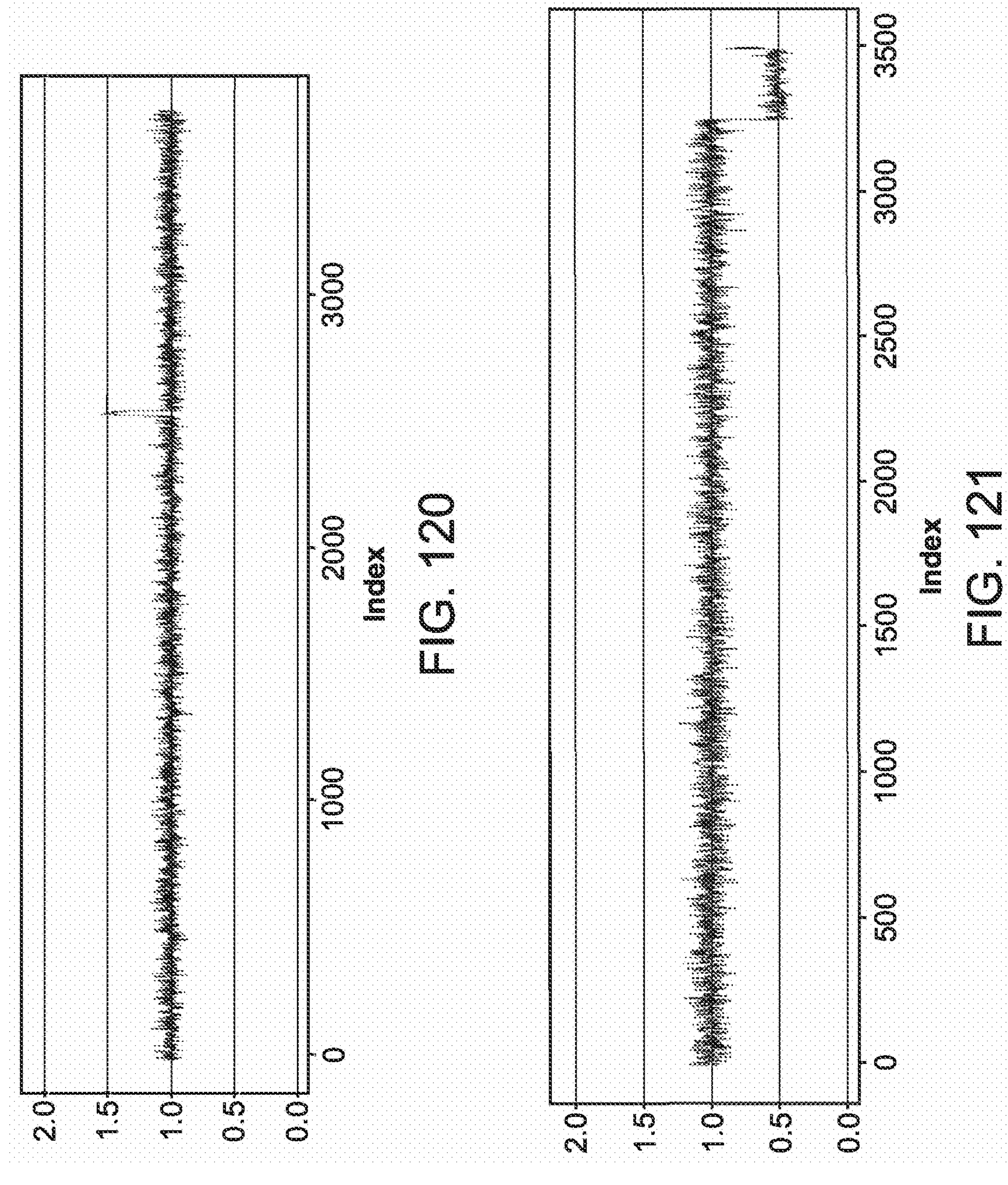
Figures 122, 123:
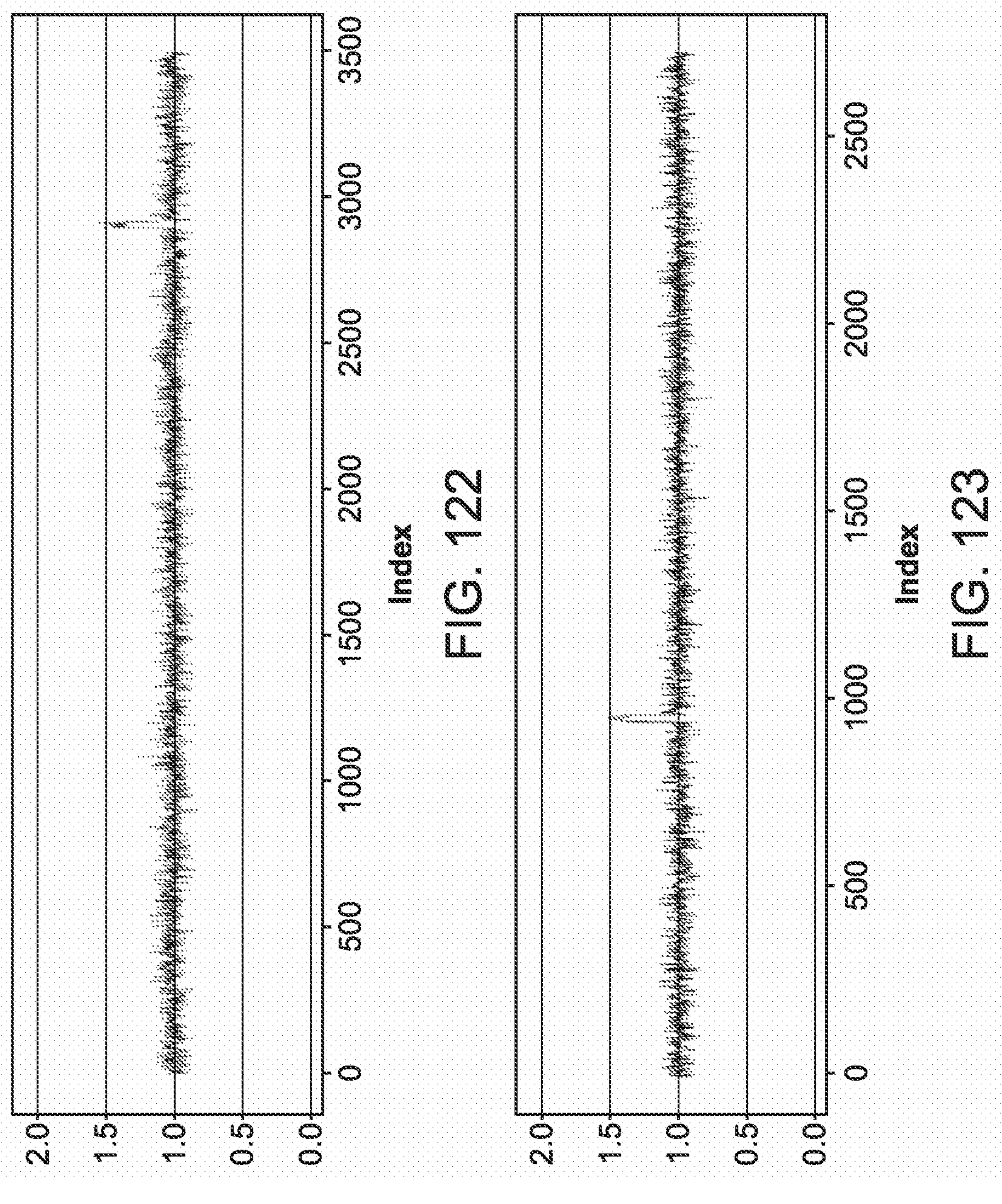
Figures 124, 125:
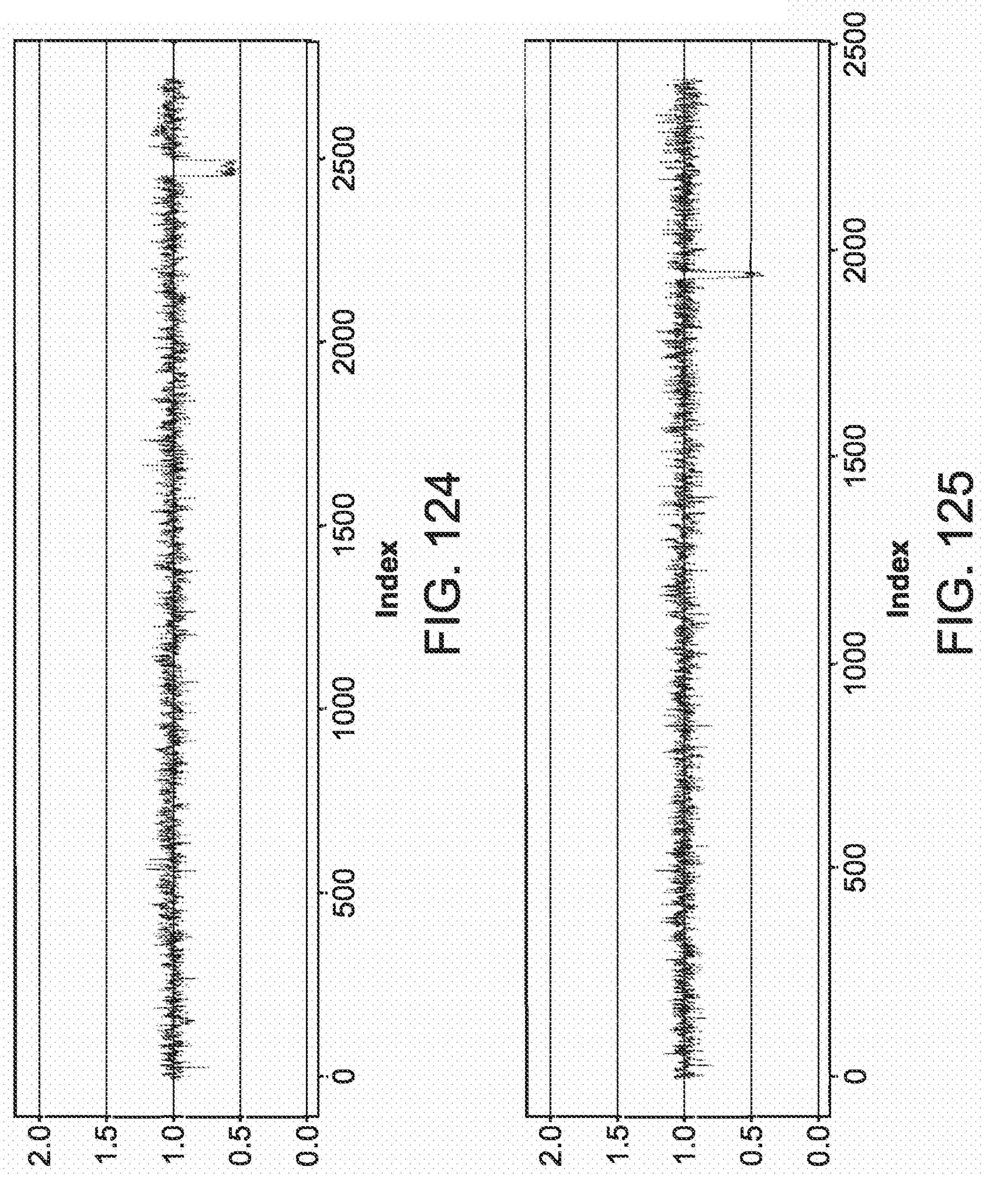
Figures 126, 127:
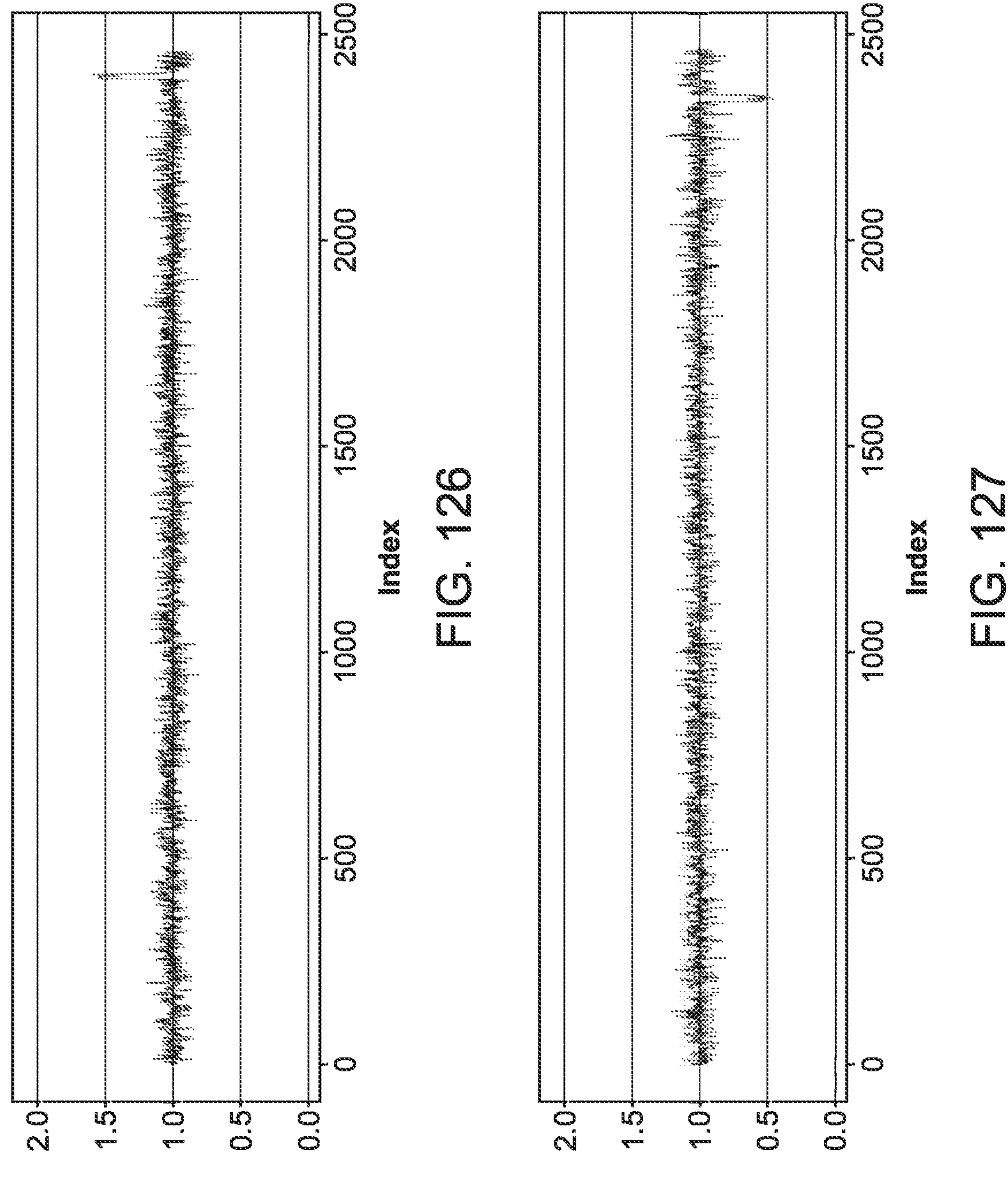
Figures 128, 129:
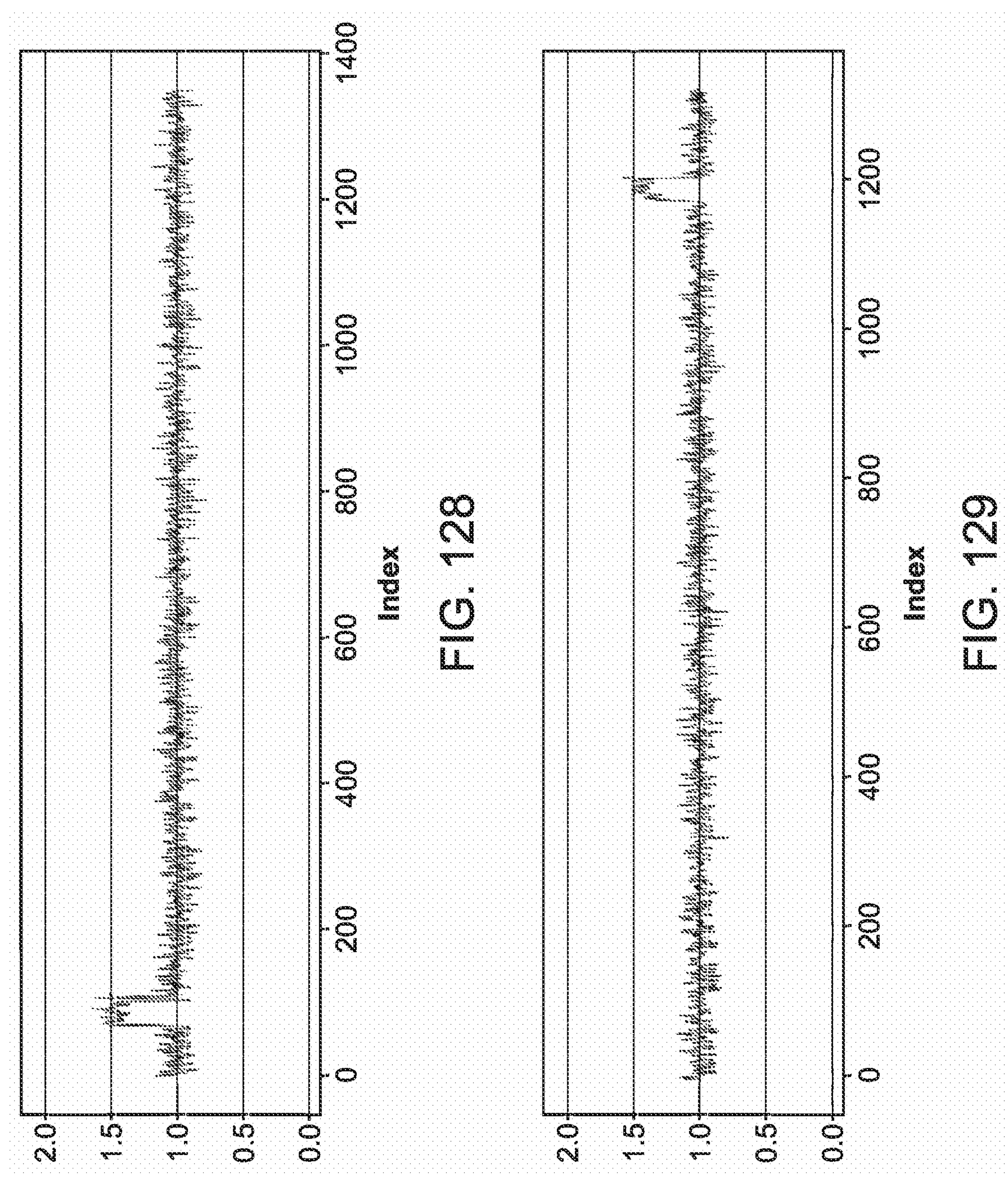
Figures 130, 131:
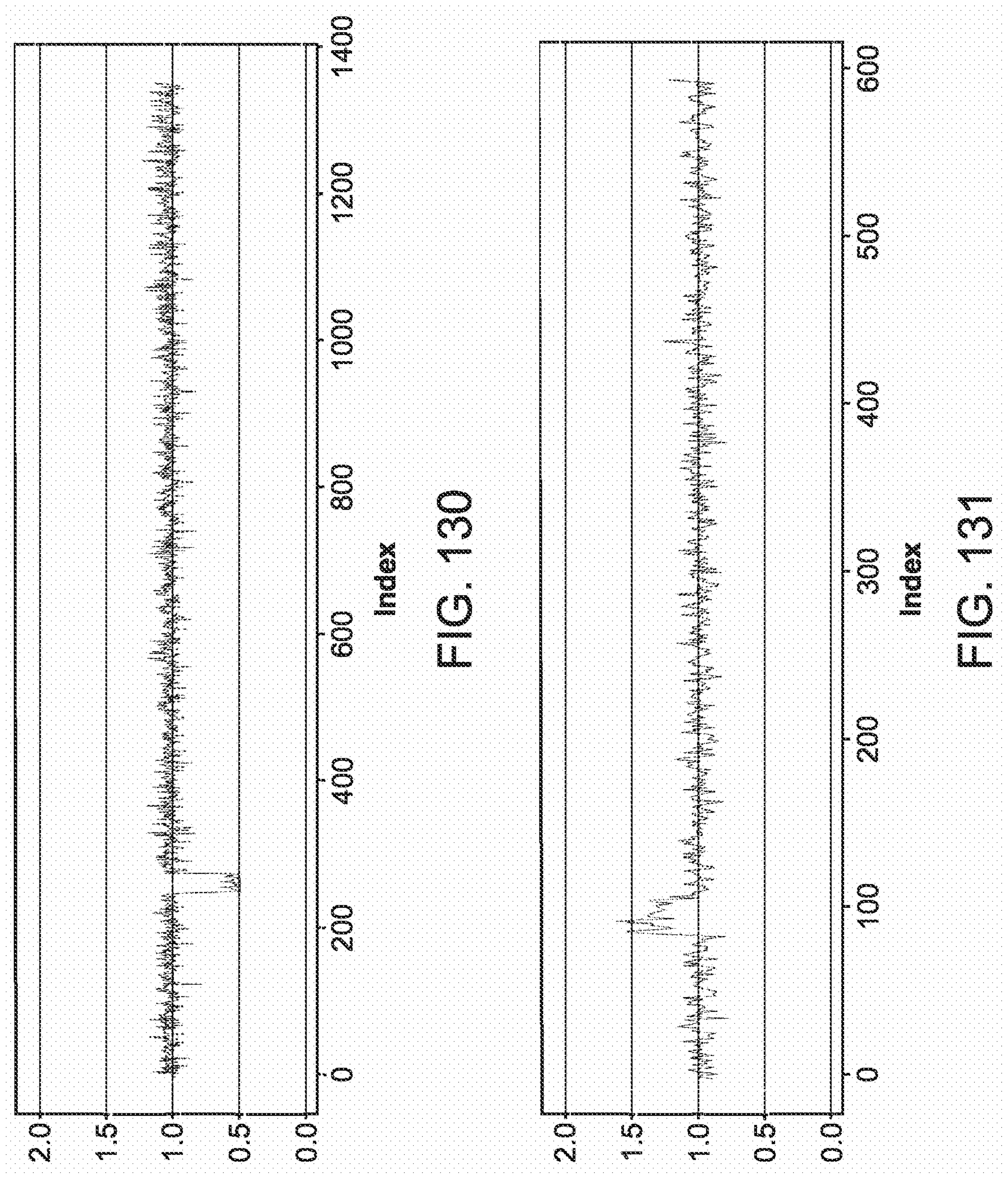

FIG. 115A-C illustrates padding of a normalized autosomal profile for a trisomy 18 WI sample. FIG. 115A is an example of an unpadded profile. FIG. 115B is an example of a padded profile. FIG. 115C is an example of a padding correction (e.g., an adjusted profile, an adjusted elevation).

FIGS. 116-120, 122, 123, 126, 128, 129 and 131 show a maternal duplication within a profile.

FIGS. 121, 124, 125, 127 and 130 show a maternal deletion within a profile.

Figure 132:
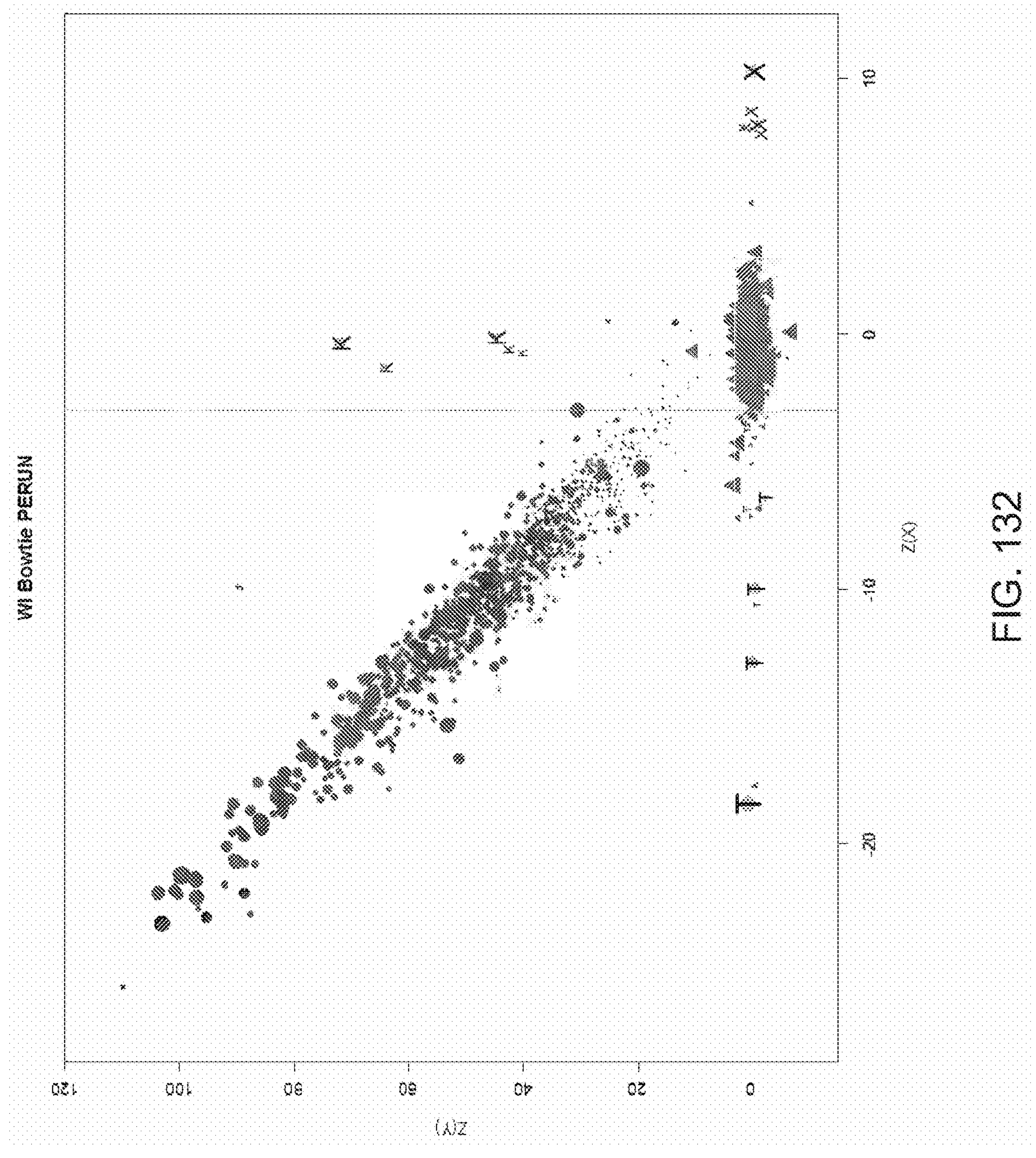

FIG. 132 shows a plot of chromosome Y Z-scores (Z(Y); y-axis) versus chromosome X Z-scores (Z(X); x-axis). Solid circles indicate euploid male fetuses (XY); solid triangles indicate euploid female fetuses (XX); X indicates Triple X Syndrome (XXX); T indicates Turner Syndrome (X); K indicates Klinefelter Syndrome (XXY); and J indicates Jacobs Syndrome (XYY). The size of each plot point is proportional to fetal fraction for each sample.

Figure 133:
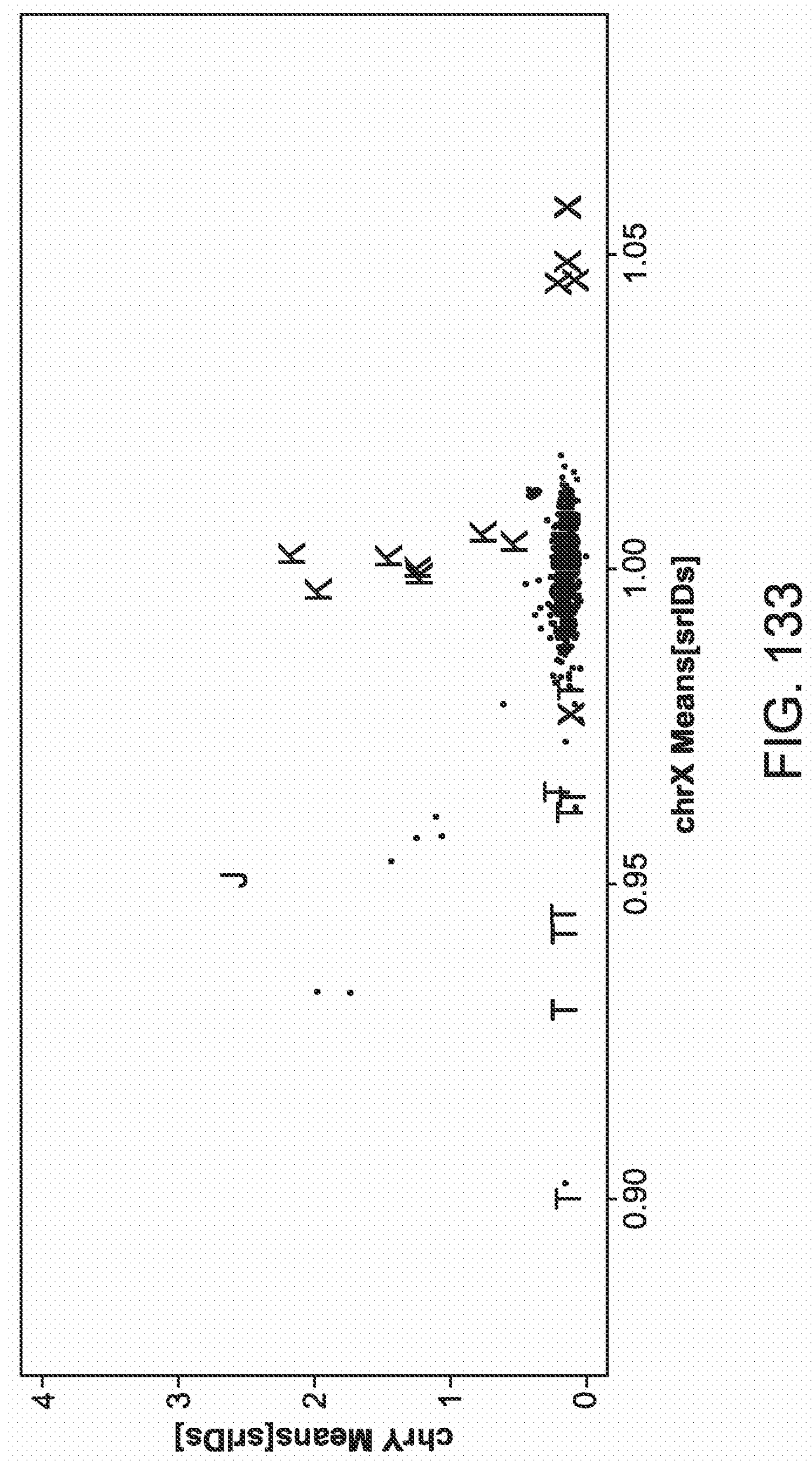

FIG. 133 shows a plot of chromosome Y means (chrYMeans[srIDs]; y-axis) versus chromosome X means (chrXMeans[srIDs]; x-axis). Samples were uniquely identified by strings (i.e., sequences of characters; each sample was assigned a unique combination of characters as an identifier) called SR IDs, and stored in array srIDs (i.e., collection of sample data). chrYMeans[srIDs] is an array containing mean elevations (e.g., mean L values) within chromosome Y and chrXMeans[srIDs] is an array containing mean elevations (e.g., mean L values) within chromosome X. Each element of the two arrays is named according to the SR ID of the corresponding sample. Open circles indicate euploid female fetuses (XX); X indicates Triple X Syndrome (XXX); T indicates Turner Syndrome (X); K indicates Klinefelter Syndrome (XXY); and J indicates Jacobs Syndrome (XYY).

Figure 134:
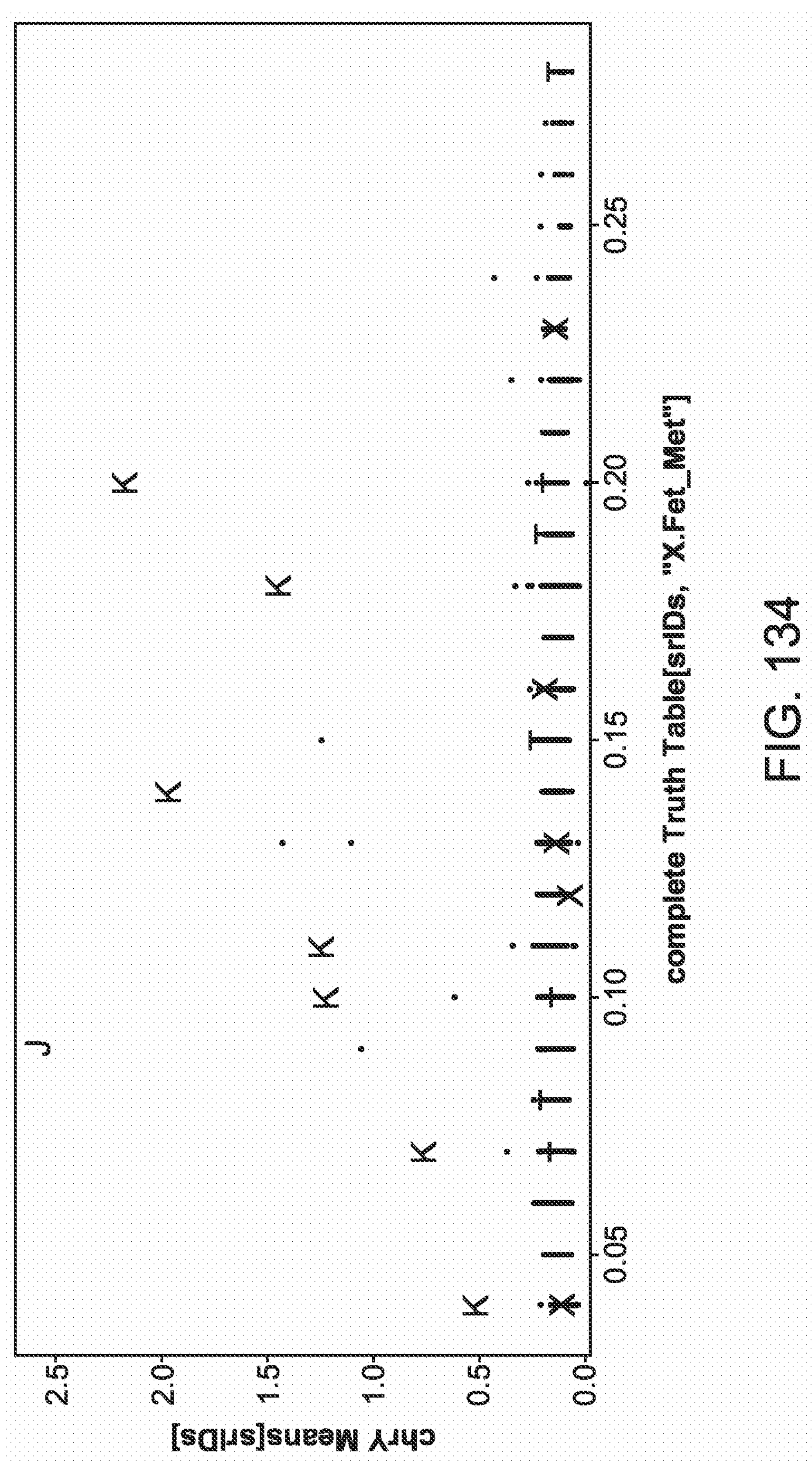

FIG. 134 shows a plot of chromosome Y means (chrYMeans[srIDs]; y-axis) versus complete truth table (complete Truth Table[srIDs, "X Fet_Met" ]; x-axis). chrYMeans [srIDs] is an array containing mean elevations within chromosome Y and complete Truth Table[srIDs, "X Fet_Met" ] is a table containing demographic data (e.g., karyotype data, measured fetal fractions, total number of counts, library concentrations, and other details). The table contains FQA measurements of the fetal fractions in the column X Fet_Met. The syntax complete Truth Table[srIDs, "X Fet_Met" ] extracts the column with fetal fractions for all samples. Open circles indicate euploid female fetuses (XX); X indicates Triple X Syndrome (XXX); T indicates Turner Syndrome (X); K indicates Klinefelter Syndrome (XXY); and J indicates Jacobs Syndrome (XYY).

Figure 135:
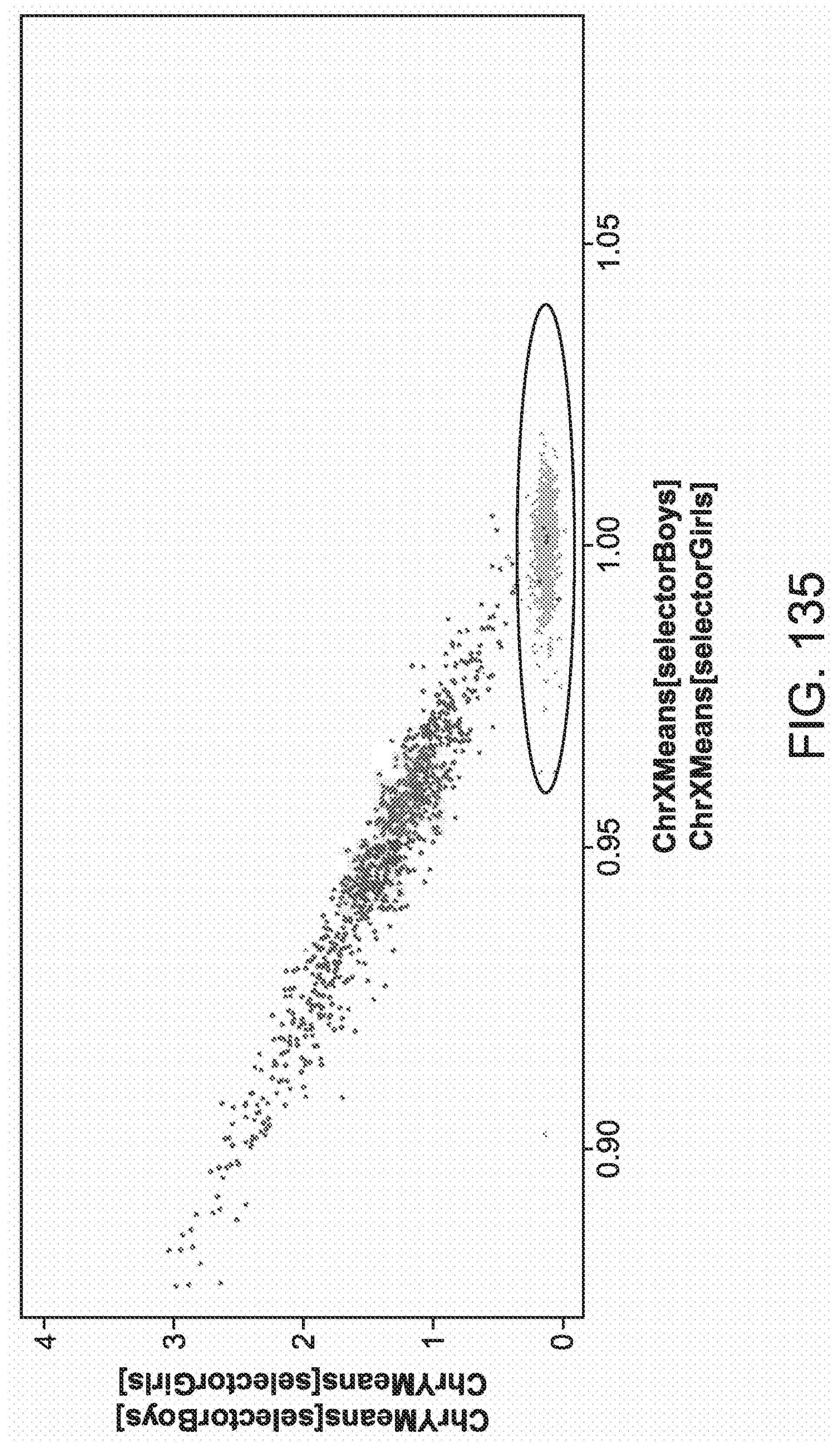

FIG. 135 shows a plot of chromosome Y means (chrYMeans[selectorBoys]; chrYMeans[selectorGirls]; y-axis) versus chromosome X means (chrYMeans[selectorBoys]; chrYMeans[selectorGirls; x-axis). This figure represents an overlay of two selectors: selectorBoys for male pregnancies and selectorGirls for female pregnancies. The coordinates of the origin are defined by median elevations (e.g., sequence read counts or derivatives thereof) of chromosome X (ChrX) and chromosome Y (ChrY) for female pregnancies. Most data points representing female pregnancies were found within the ellipse centered at the origin. The length of the vertical axis of the ellipse is the median absolute deviation (MAD) of the mean ChrY elevation for girls, multiplied by 3. The length of the horizontal axis of the ellipse is MAD of the mean ChrX elevation in girls, multiplied by 3. Male pregnancies were distinguished from female pregnancies in both dimensions. Data points outside of the ellipse and along the diagonal that follows decreasing ChrX elevation and increasing ChrY elevation corresponded to male pregnancies.

FIG. 136 presents a table containing phenotypes and prevalence of certain sex chromosome aneuploidies (SCA).

FIG. 137 presents a table containing demographics data for 411 analyzed samples from a validation cohort. For some patients not all information was available and some patients had more than one indication.

FIG. 138 presents a table containing sex chromosome results for a training set, a validation set and the combined datasets. Italicized values indicate those results where the karyotype and test result agreed. Percentages were calculated with respect to the number of reported samples.

Figure 139:
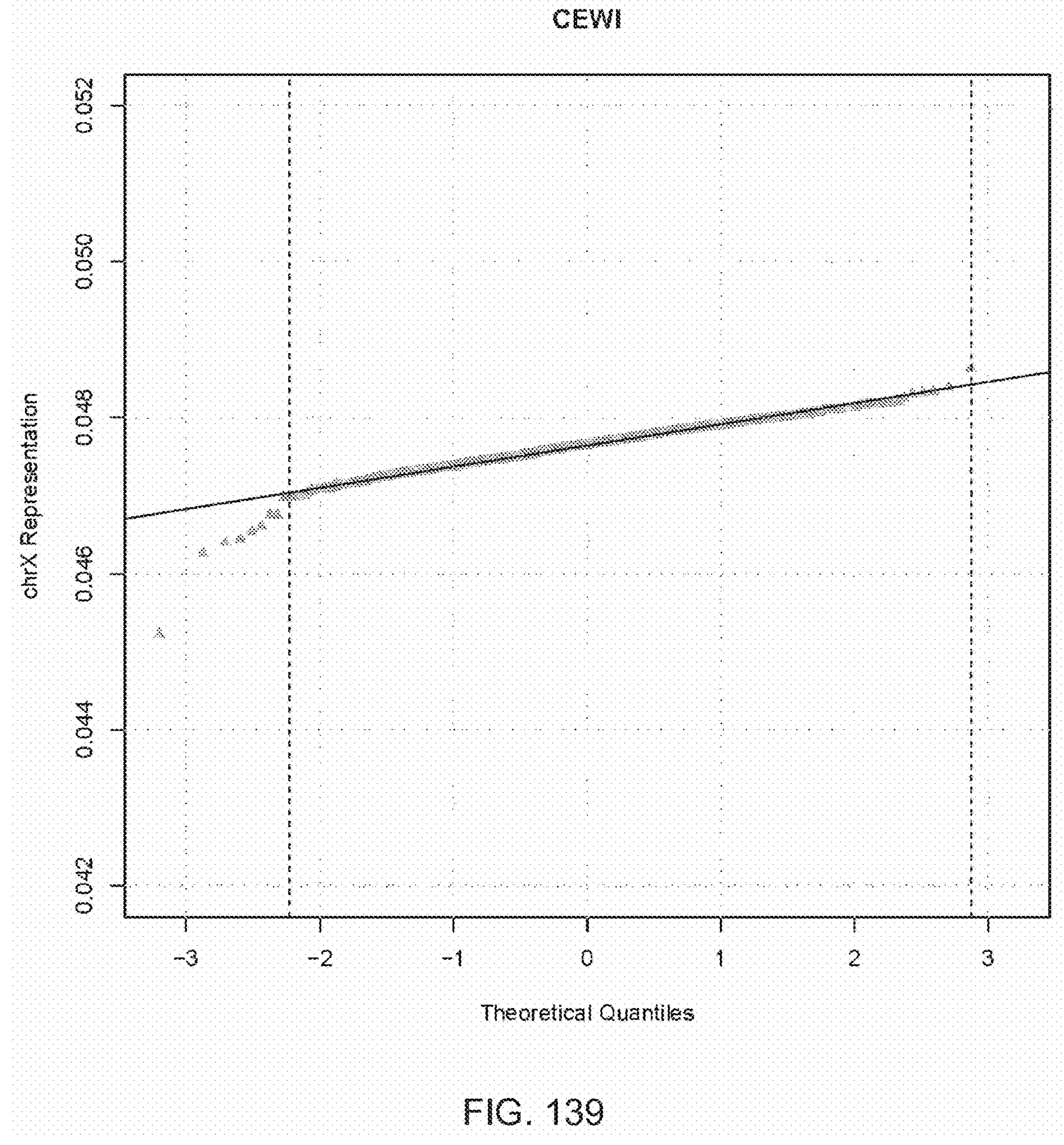

FIG. 139 shows a quintile comparison between the theoretical normal distribution and a distribution of chromosome X representations observed in female pregnancies (i.e., pregnant females carrying female fetuses) from the training cohort. Standard normal quintiles and observed chromosome X quintiles are shown along the abscissa (x axis) and ordinate (y axis), respectively. The solid line connects the first and the third quartiles of the chromosome X.

Figure 140:
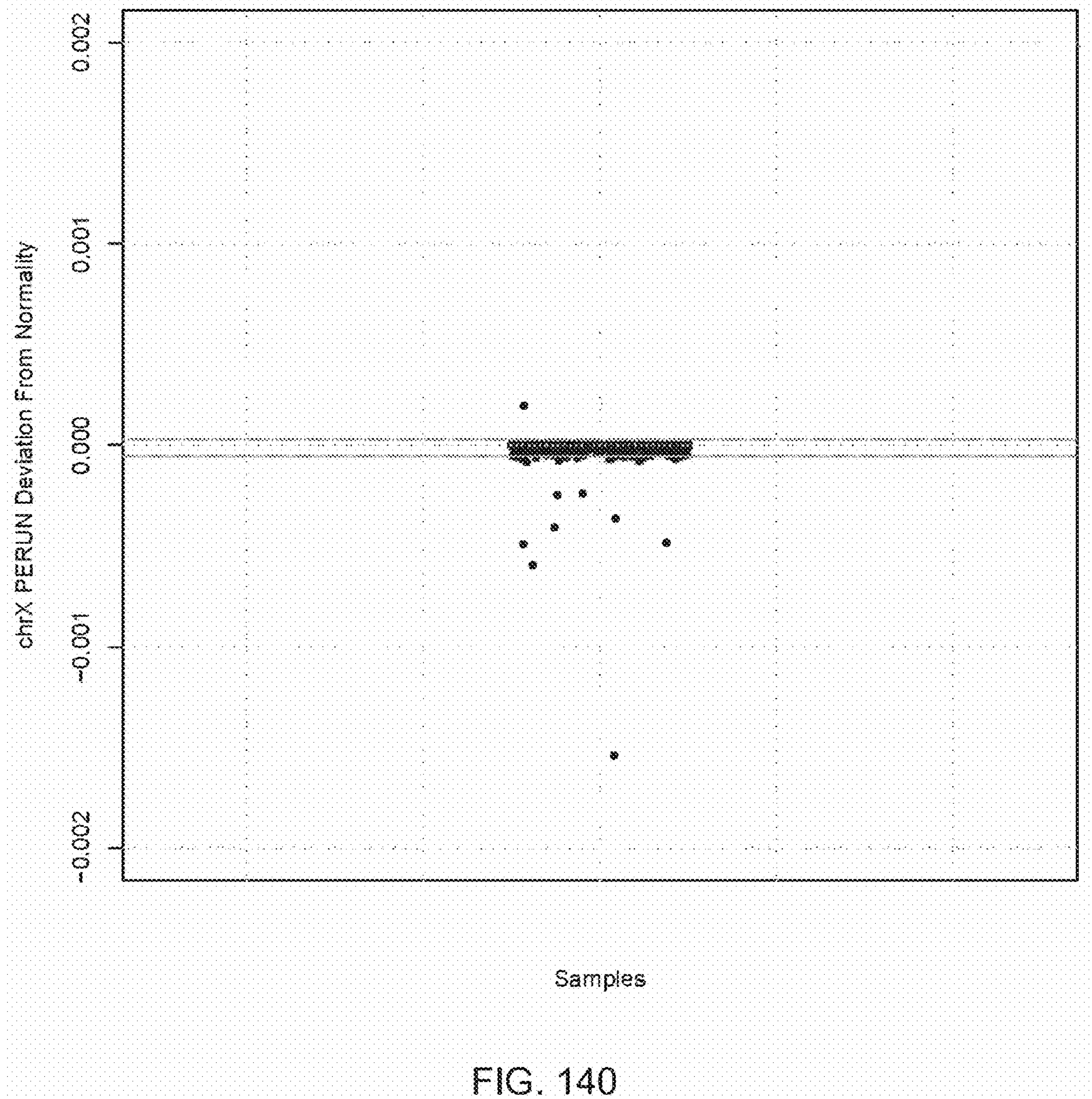

FIG. 140 shows a distribution of the residuals of female chromosome X representations. The residuals were estimated from the linear model trained on the interquartile range of the female cohort.

Figure 141:
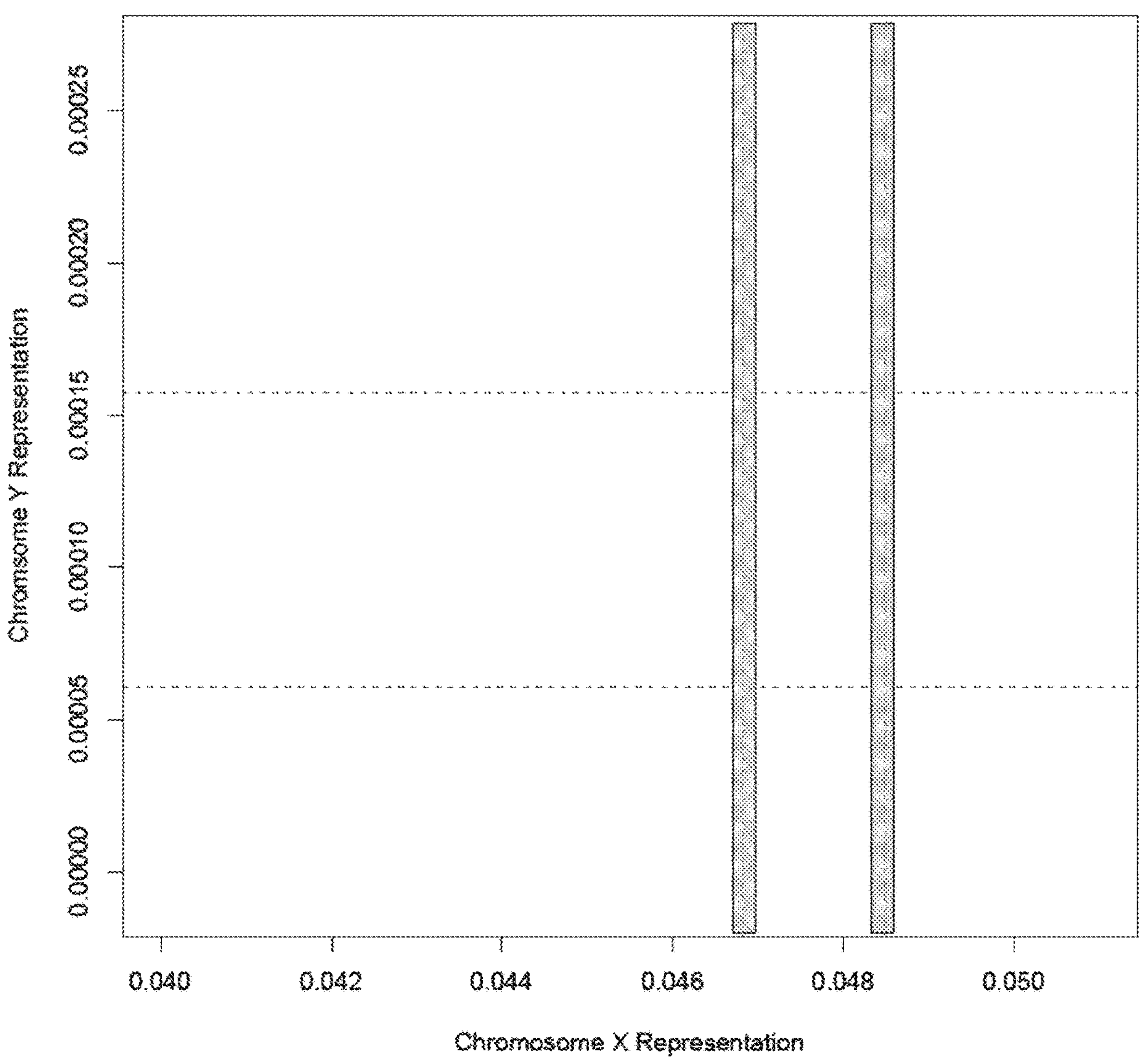

FIG. 141 shows a coordinate system for chromosome X representations versus chromosome Y representations. Shaded vertical regions delineate no-call zones (i.e., non-reportable zones) for female fetal sex aneuploidy classification. Vertical dotted lines within the two shaded zones represent the 45,X (left, $Z_X=-3$) and 47,XXX (right, $Z_X=3$) cutoffs.

Figure 142:
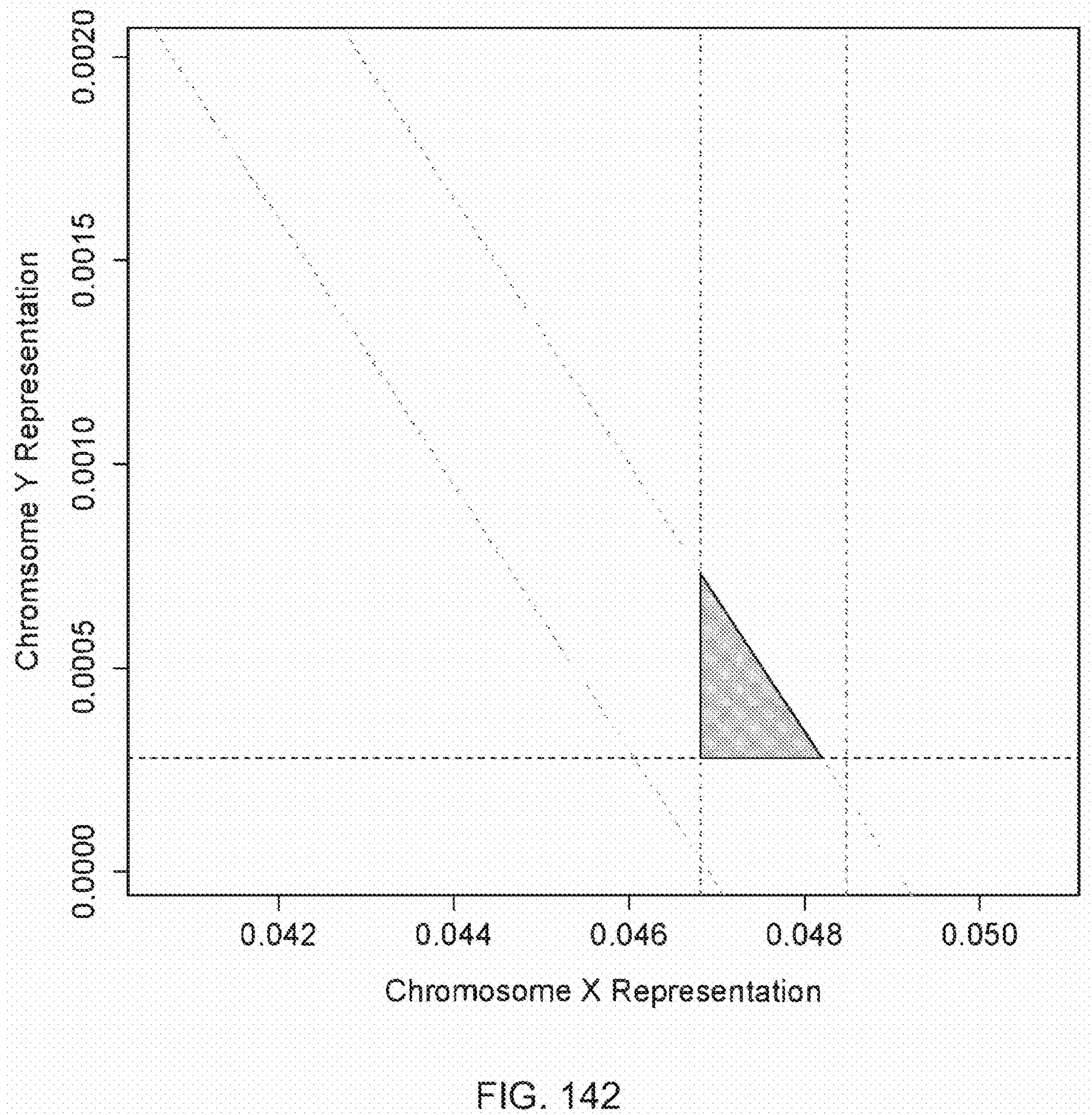

FIG. 142 shows a coordinate system for chromosome X representations versus chromosome Y representations. The shaded triangular region delineates male pregnancies (pregnant females carrying a male fetuses) deemed non-reportable for sex chromosomal aneuploidies. The dotted horizontal line depicts the 0.15% percentile of male euploid control samples spiked with 4% fetal fraction. The vertical dotted lines correspond to $Z_X=-3$ and $Z_X=3$.

Figure 143:
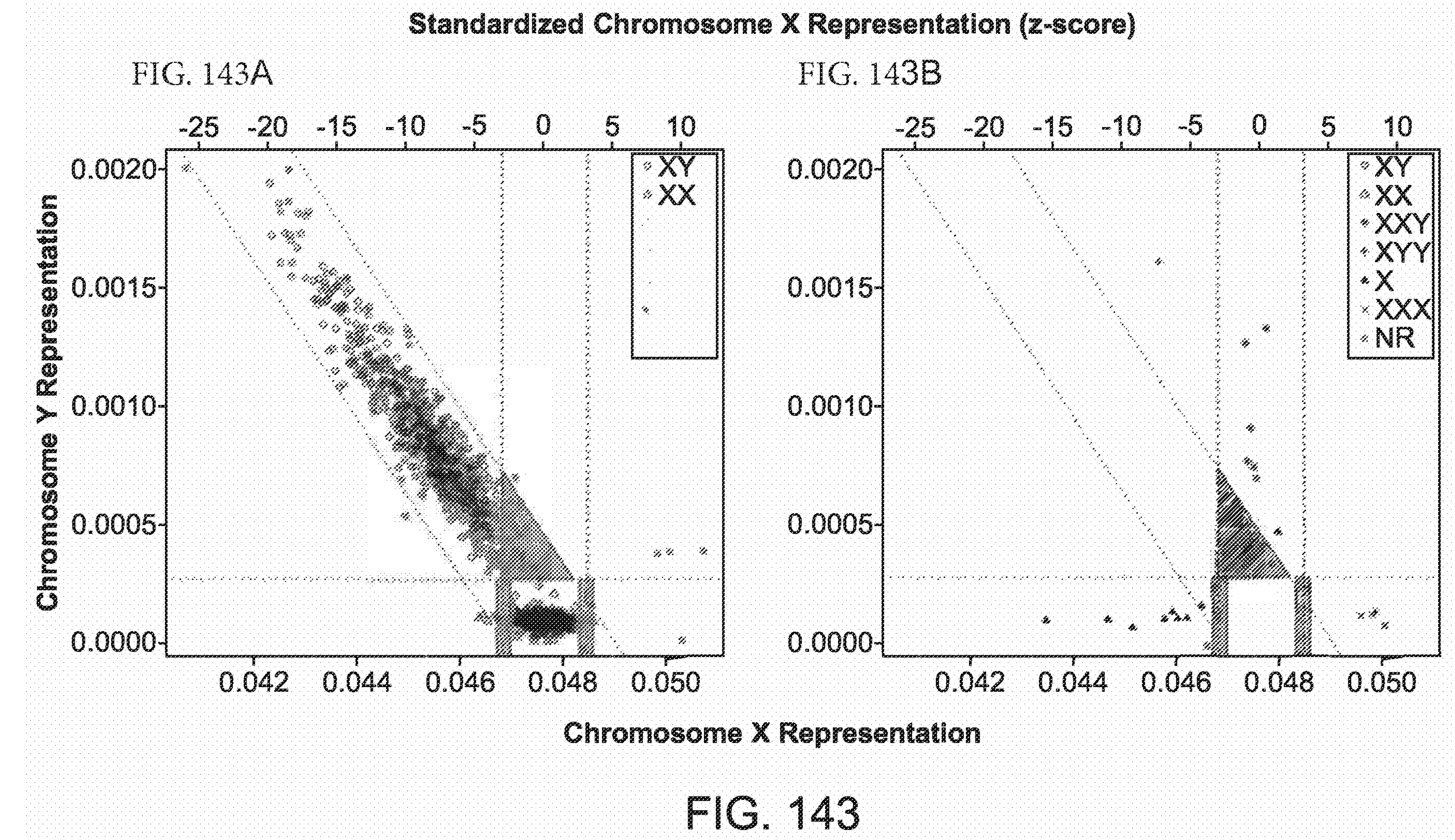
Figure 143:
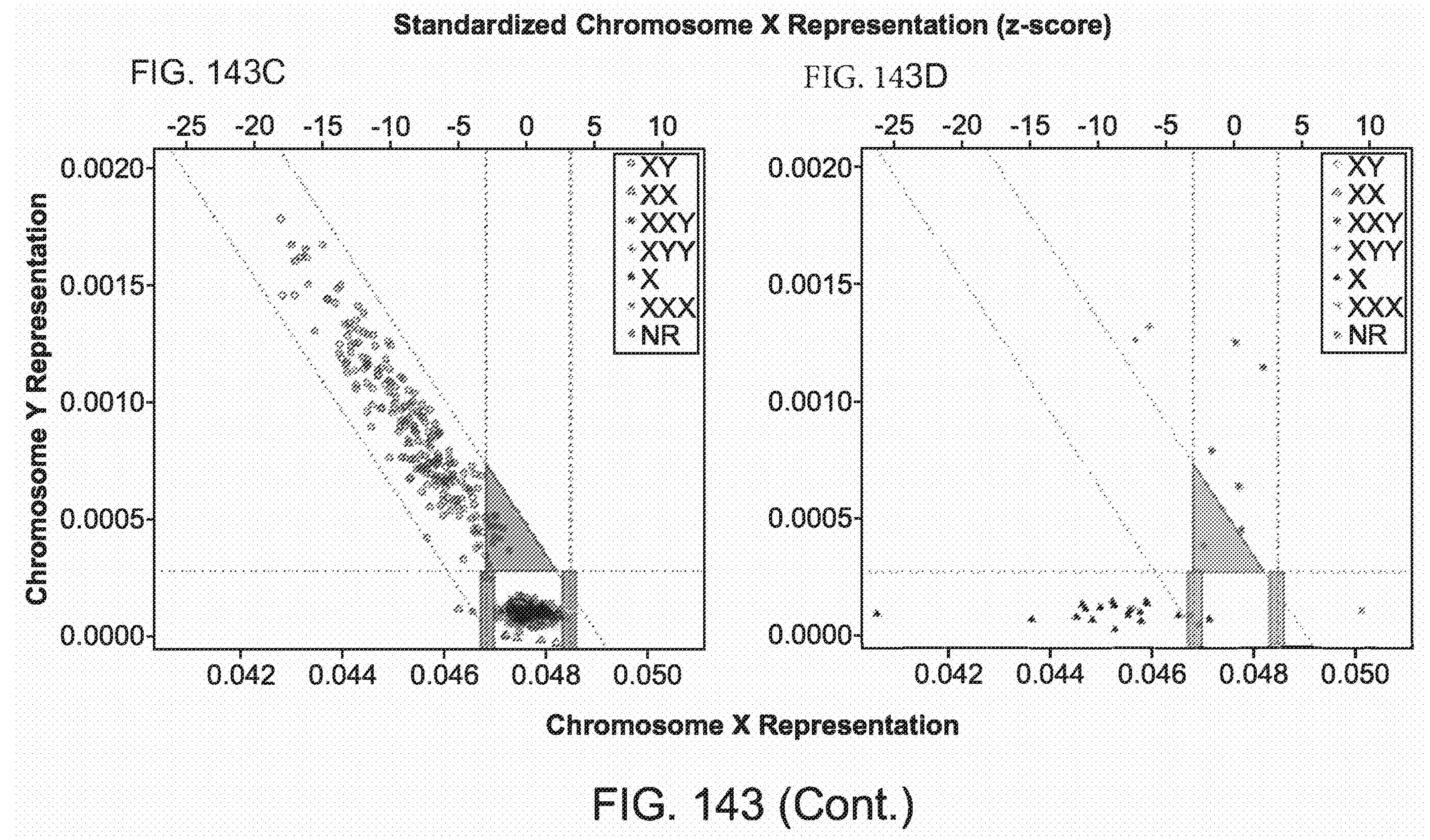

FIG. 143 shows a distribution of chromosome X representations and chromosome Y representations. Panels A and C show a distribution of data for unaffected samples in a training set and validation set, respectively. Panels B and D contain data for affected samples from the training set and the validation set, respectively. The shaded areas mark certain regions in which sex chromosome aneuploidy (SCA) was not reportable. Chromosome X representation is shown on a standardized scale.

Figure 144:
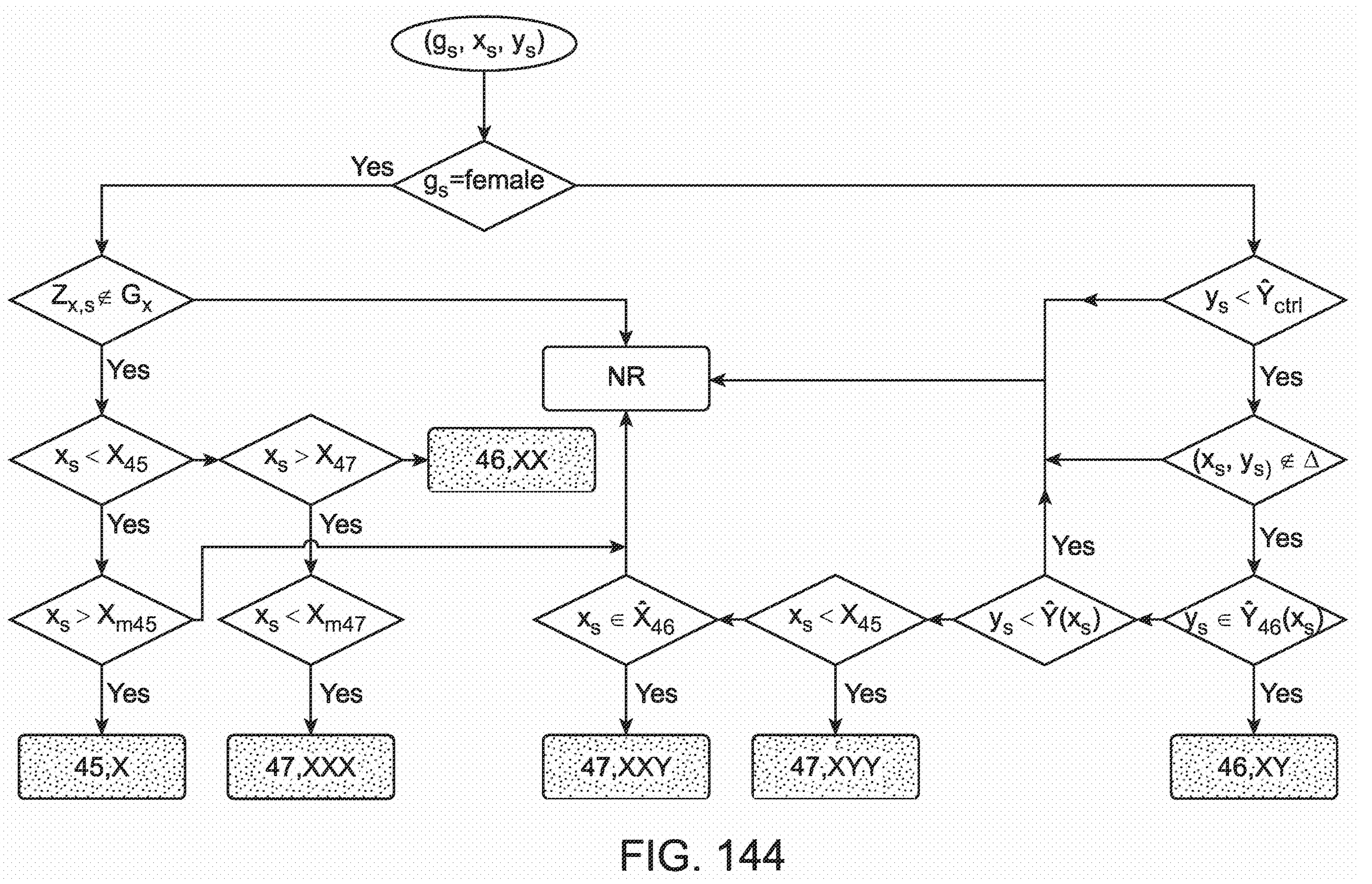

FIG. 144 shows a decision tree used in a sex chromosome aneuploidy (SCA) algorithm (the variables are described in Table 2 of Example 11).

Figure 145:
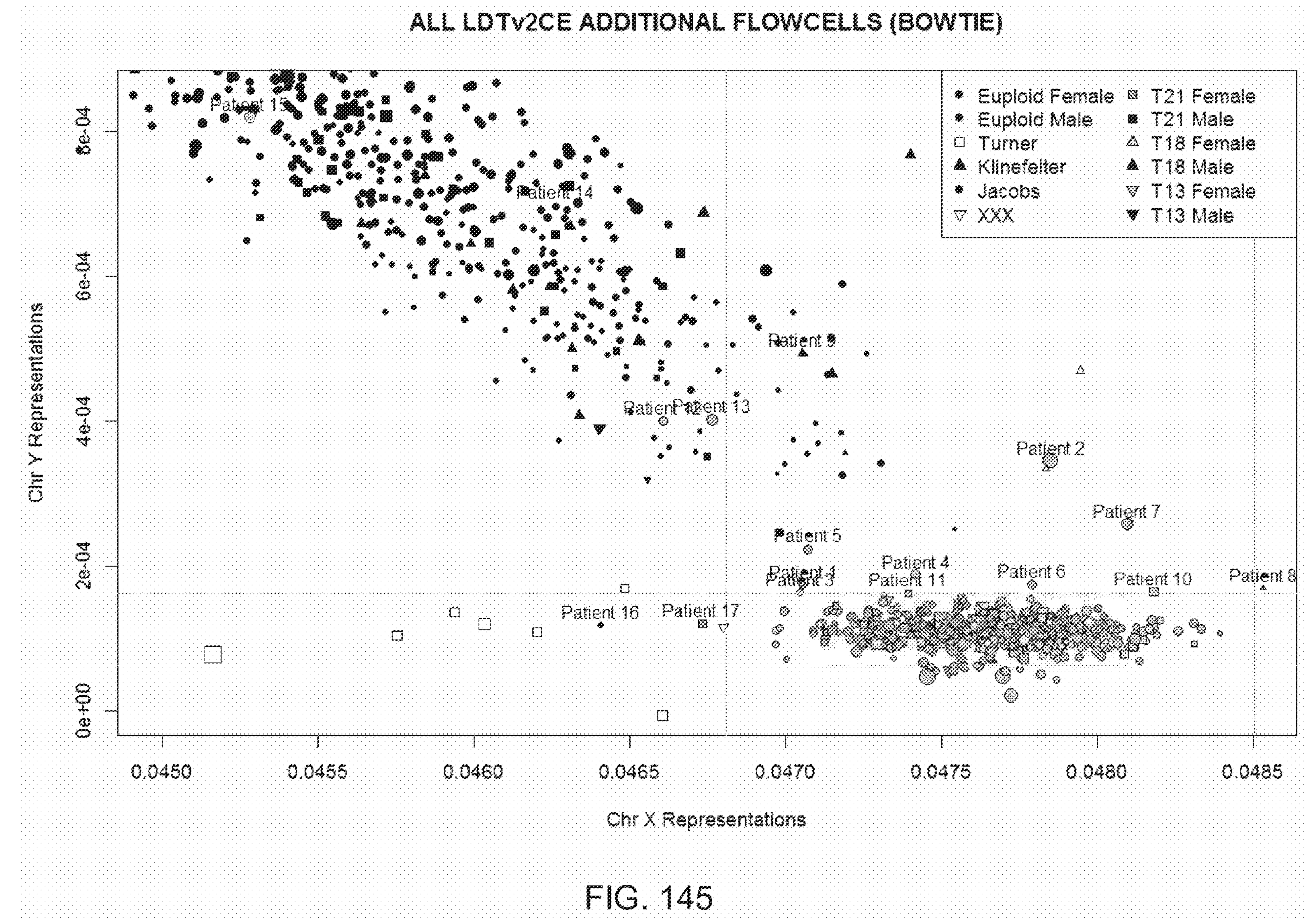

FIG. 145 shows a distribution of chromosome X representations and chromosome Y representations. LDTv2CE female pregnancies with elevated ChrY signal are labeled with a patient number.

Figure 146:
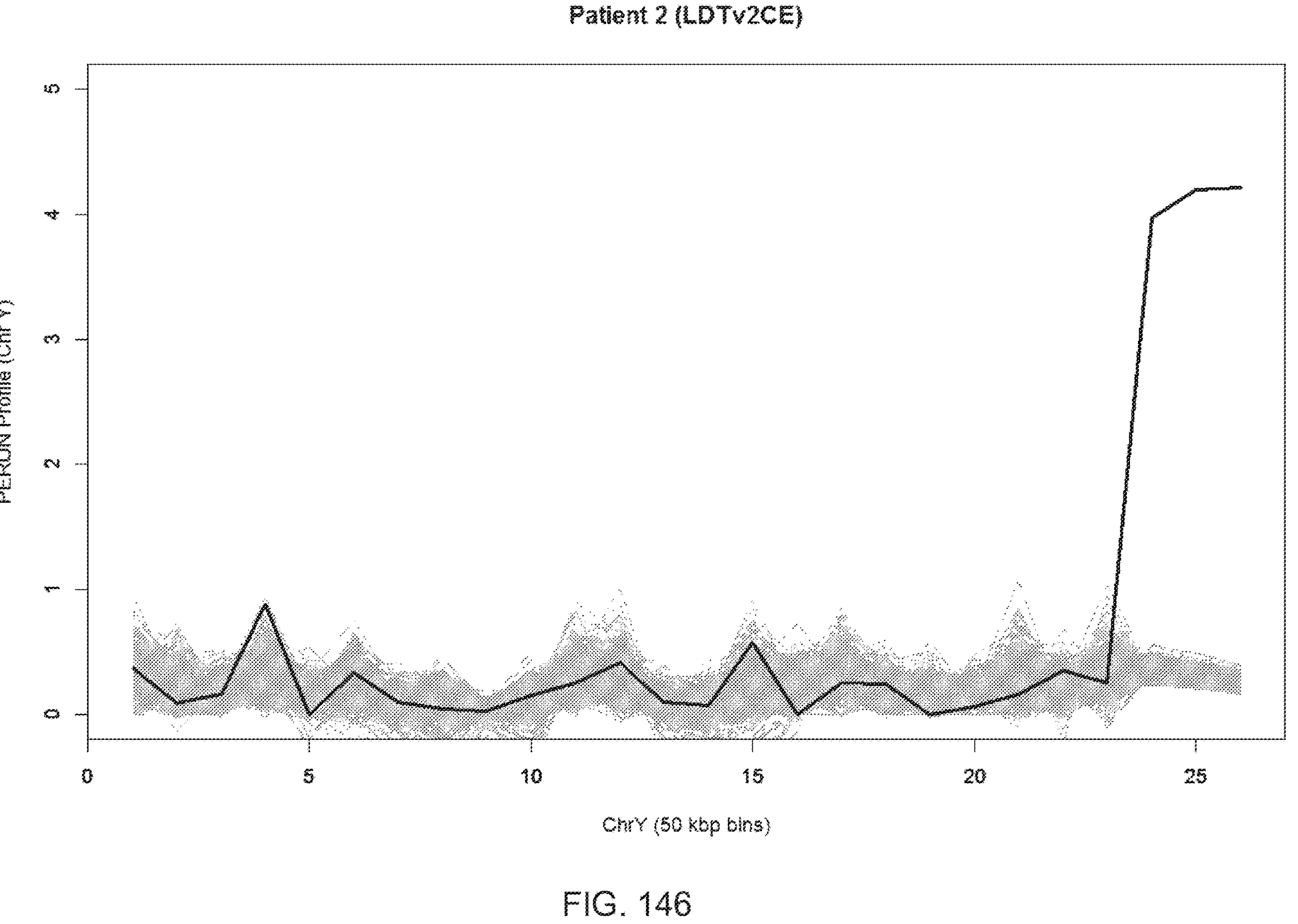

FIG. 146 shows PERUN profiles of ChrY in LDTv2CE female pregnancies. The shaded area is a collection of represent PERUN profiles of ChrY in LDTv2CE female pregnancies that do not exhibit elevated ChrY representation. The bold line is a PERUN profile of ChrY for Patient 2, an LDTv2CE sample with elevated ChrY representation. Only the last three bins (chrY_1176, chrY_1177, and chrY_1178) in the Patient 2 profile are elevated, while the rest of the Patient 2 profile is consistent with the profiles observed in a great majority of female LDTv2CE pregnancies.

Figure 147:
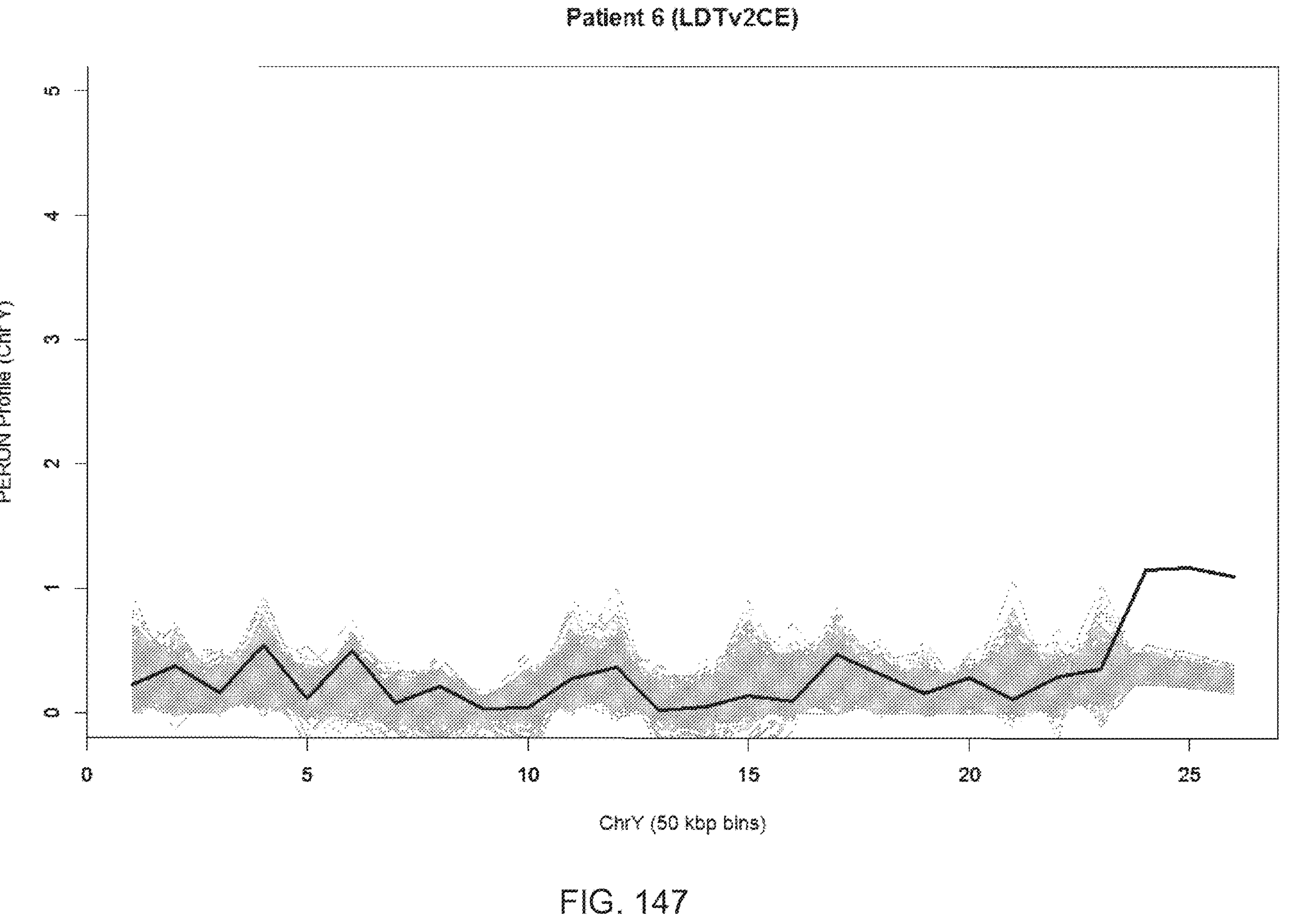

FIG. 147 shows PERUN profiles of ChrY in LDTv2CE female pregnancies. The shaded area is a collection of represent PERUN profiles of ChrY in LDTv2CE female pregnancies that do not exhibit elevated ChrY representation. The bold line is a PERUN profile of ChrY for Patient 6, an LDTv2CE sample with elevated ChrY representation.

Figure 148:
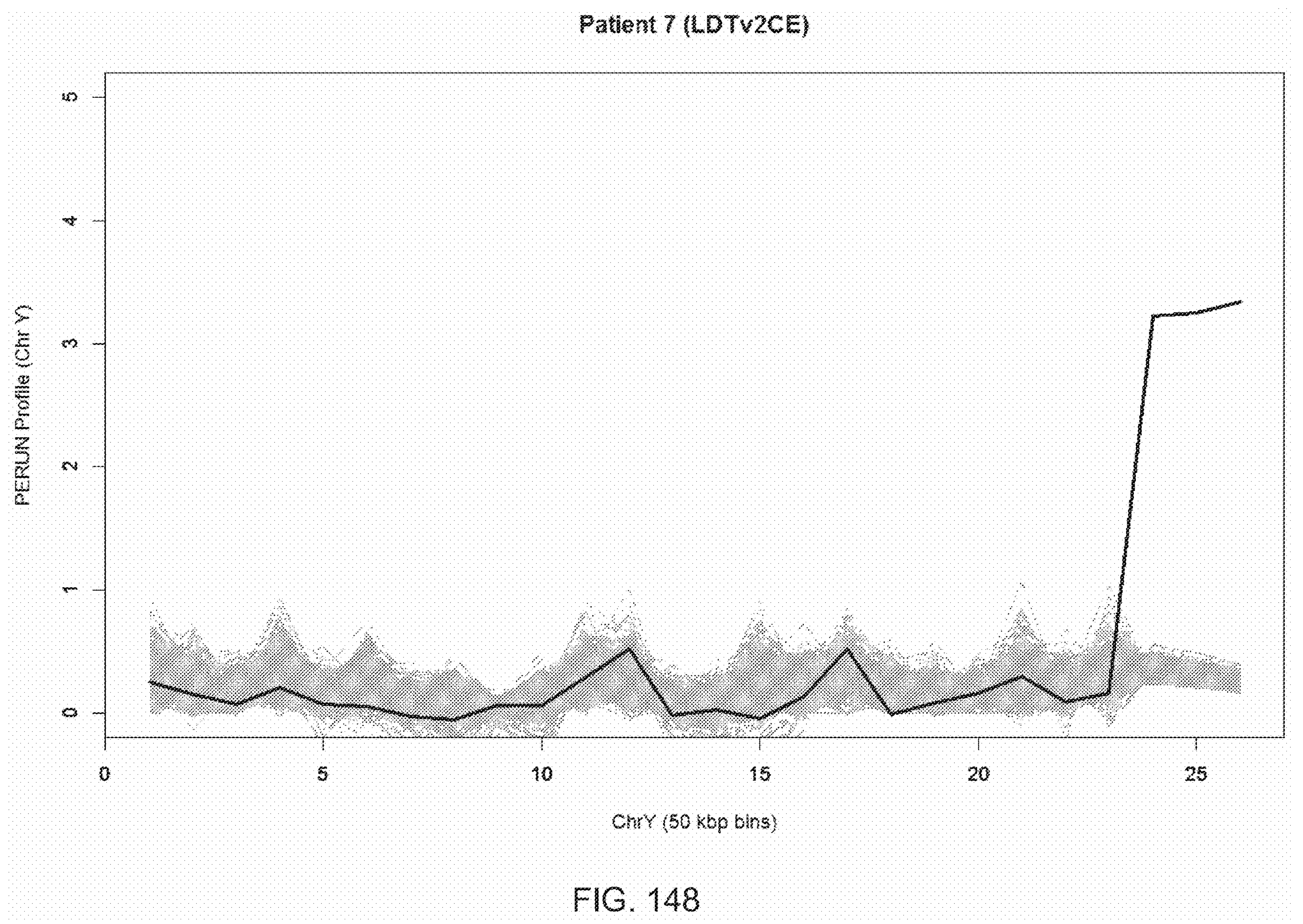

FIG. 148 shows PERUN profiles of ChrY in LDTv2CE female pregnancies. The shaded area is a collection of represent PERUN profiles of ChrY in LDTv2CE female pregnancies that do not exhibit elevated ChrY representation. The bold line is a PERUN profile of ChrY for Patient 7, an LDTv2CE sample with elevated ChrY representation.

FIG. 149 shows an R-script used for evaluating chromosome Y representations in female pregnancies that had elevated bins chrY_1176, chrY_1177, and chrY_1178.

Figure 150:
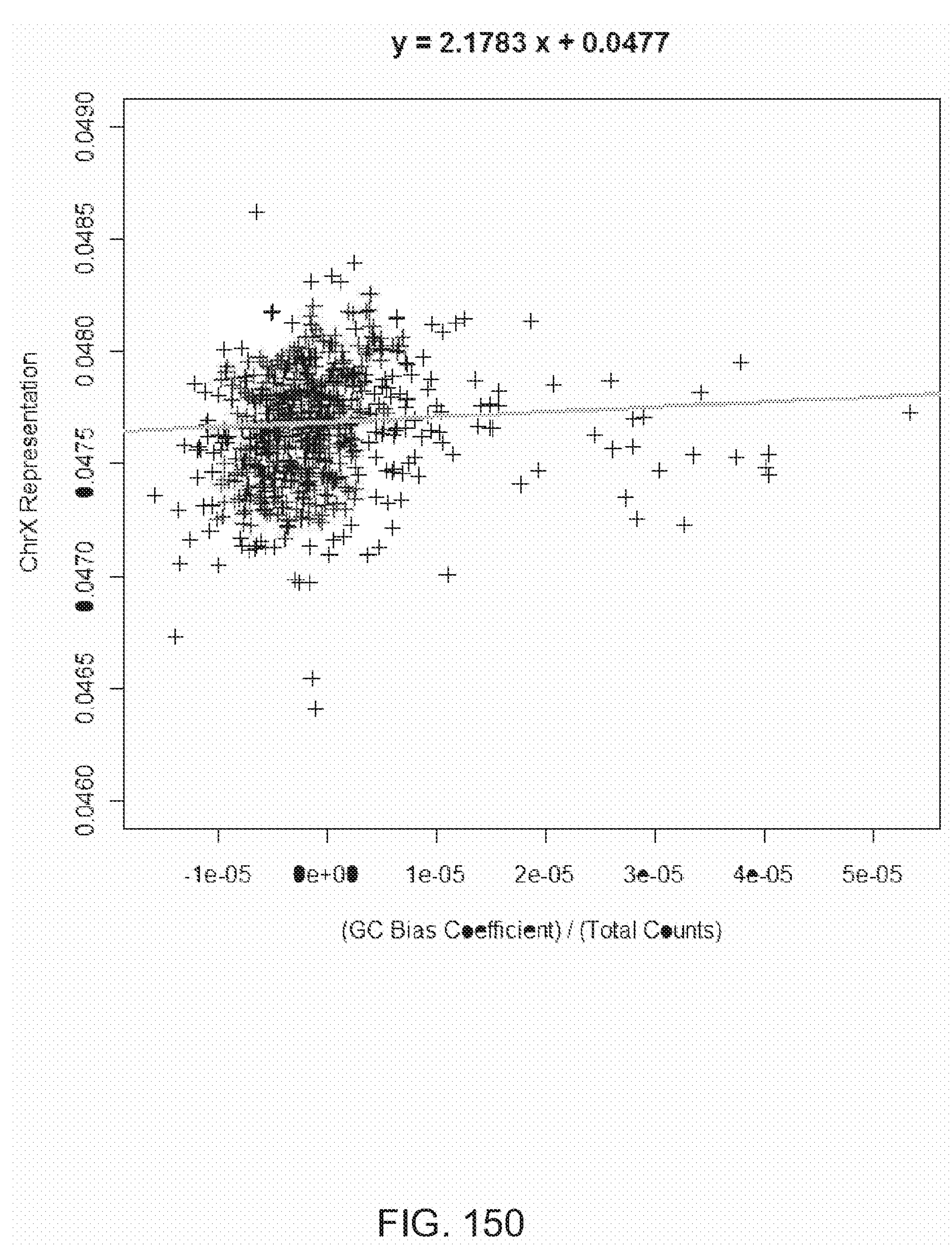

FIG. 150 shows a correlation of ChrX representations with GC bias coefficients. Female LDTv2CE pregnancies are shown. A chromosomal representation was obtained as the sum of PERUN chromosomal elevations of all selected ChrX bins, divided by the sum of PERUN chromosomal elevations of all selected autosomal bins. No secondary GC bias correction was applied to either ChrX bin elevations or ChrX representations. The solid diagonal line represents the regression between GC coefficients (scaled with respect to total counts) and ChrX representations. Coefficients of the linear regression are listed above the graph.

Figure 151:
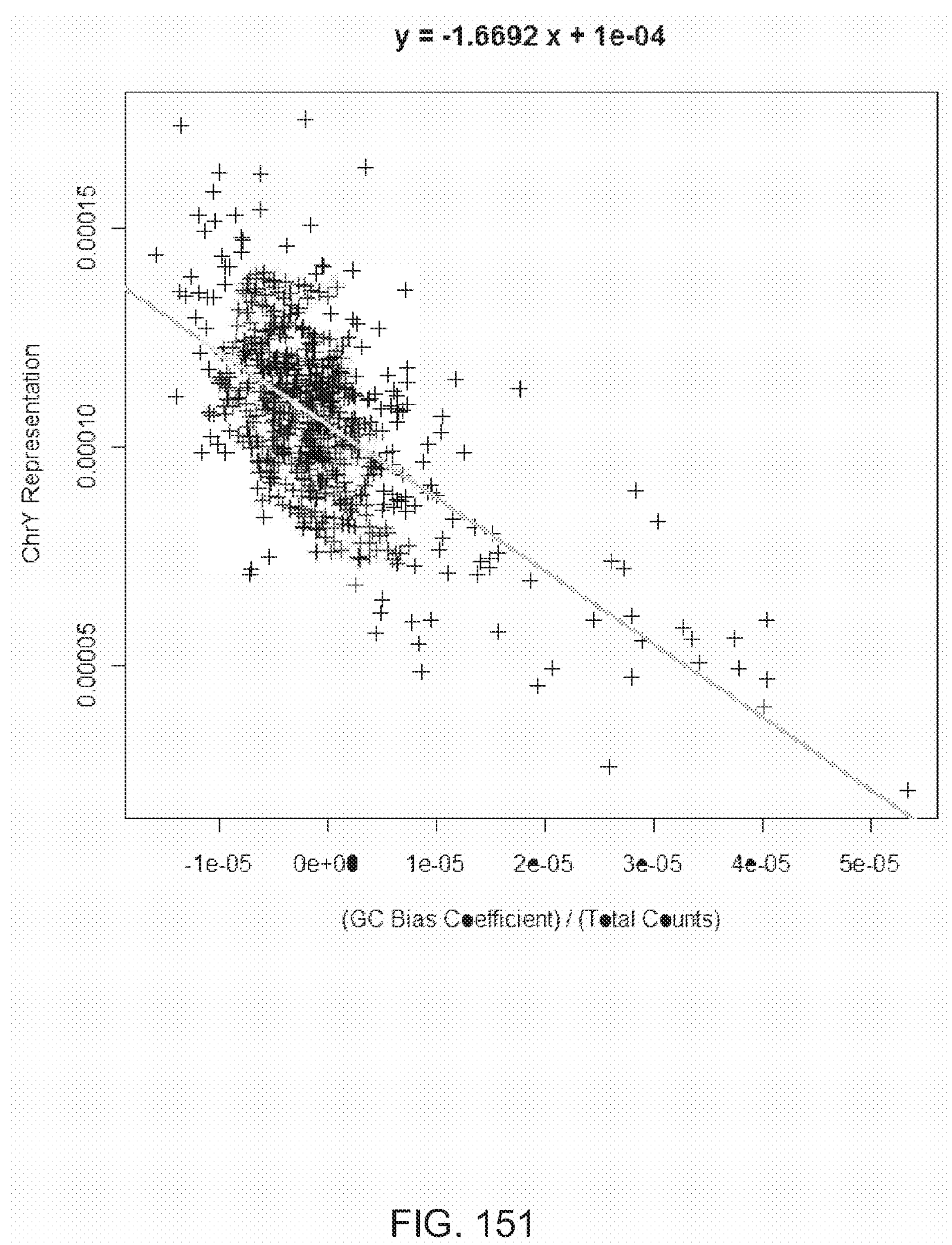

FIG. 151 shows a correlation of ChrY representations with GC bias coefficients. Female LDTv2CE pregnancies are shown. A chromosomal representation was obtained as the sum of PERUN chromosomal elevations of all selected ChrY bins, divided by the sum of PERUN chromosomal elevations of all selected autosomal bins. No secondary GC bias correction was applied to either ChrY bin elevations or the ChrY representations. The three bins preceding the PAR2 region of ChrY were treated as described in Example 13. The solid diagonal line represents the regression between GC coefficients (scaled with respect to total counts) and ChrY representations. Coefficients of the linear regression are listed above the graph.

Figure 152:
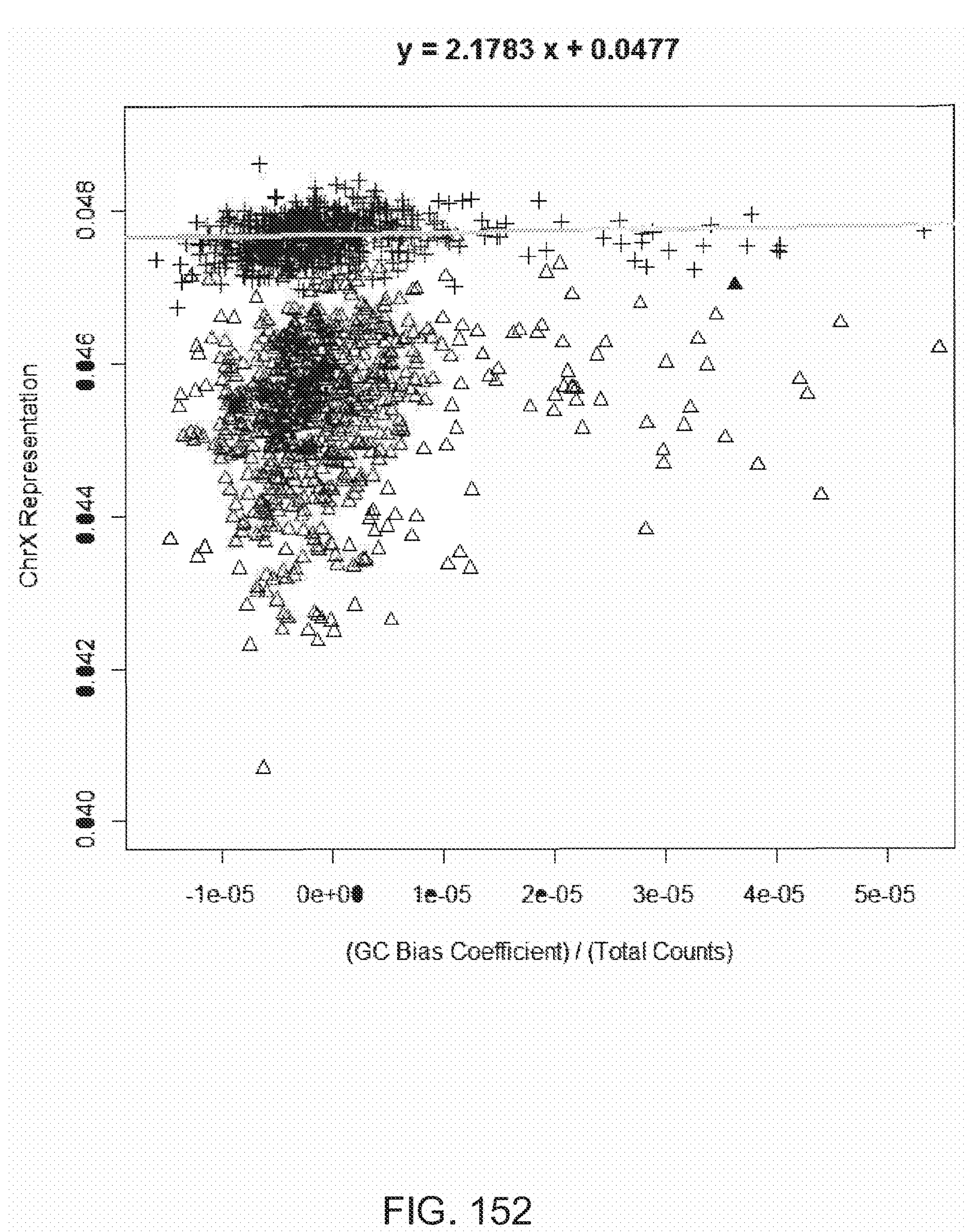

FIG. 152 shows ChrX representations vs. GC bias coefficients for all LDTv2CE pregnancies, including both female (crosses) and male fetuses (triangles). Chromosomal representations were obtained as described for FIG. 150.

Figure 153:
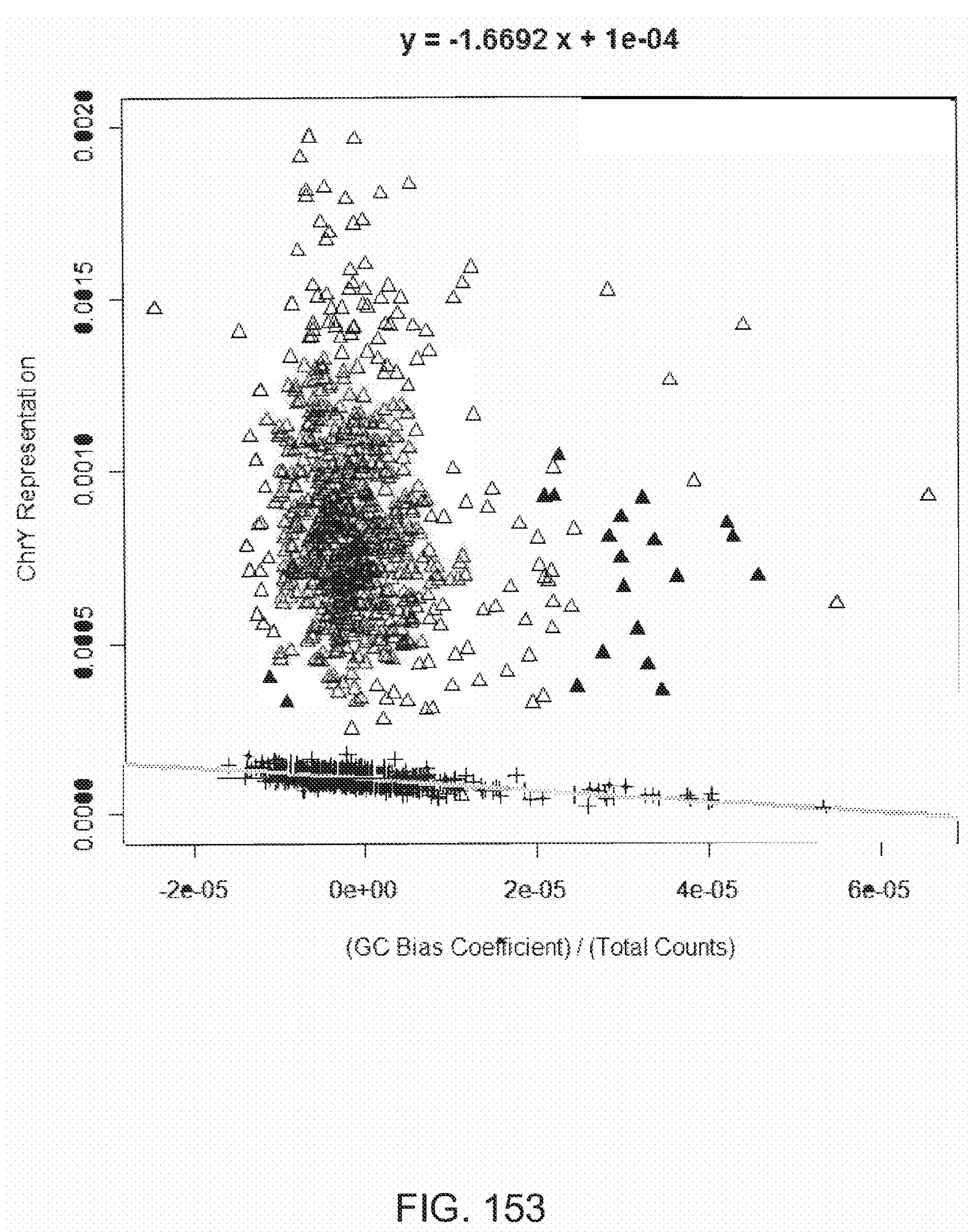

FIG. 153 shows ChrY representations vs. GC bias coefficients for all LDTv2CE pregnancies, including both female (crosses) and male fetuses (triangles). Chromosomal representations were obtained as described for FIG. 151.

Figure 154:
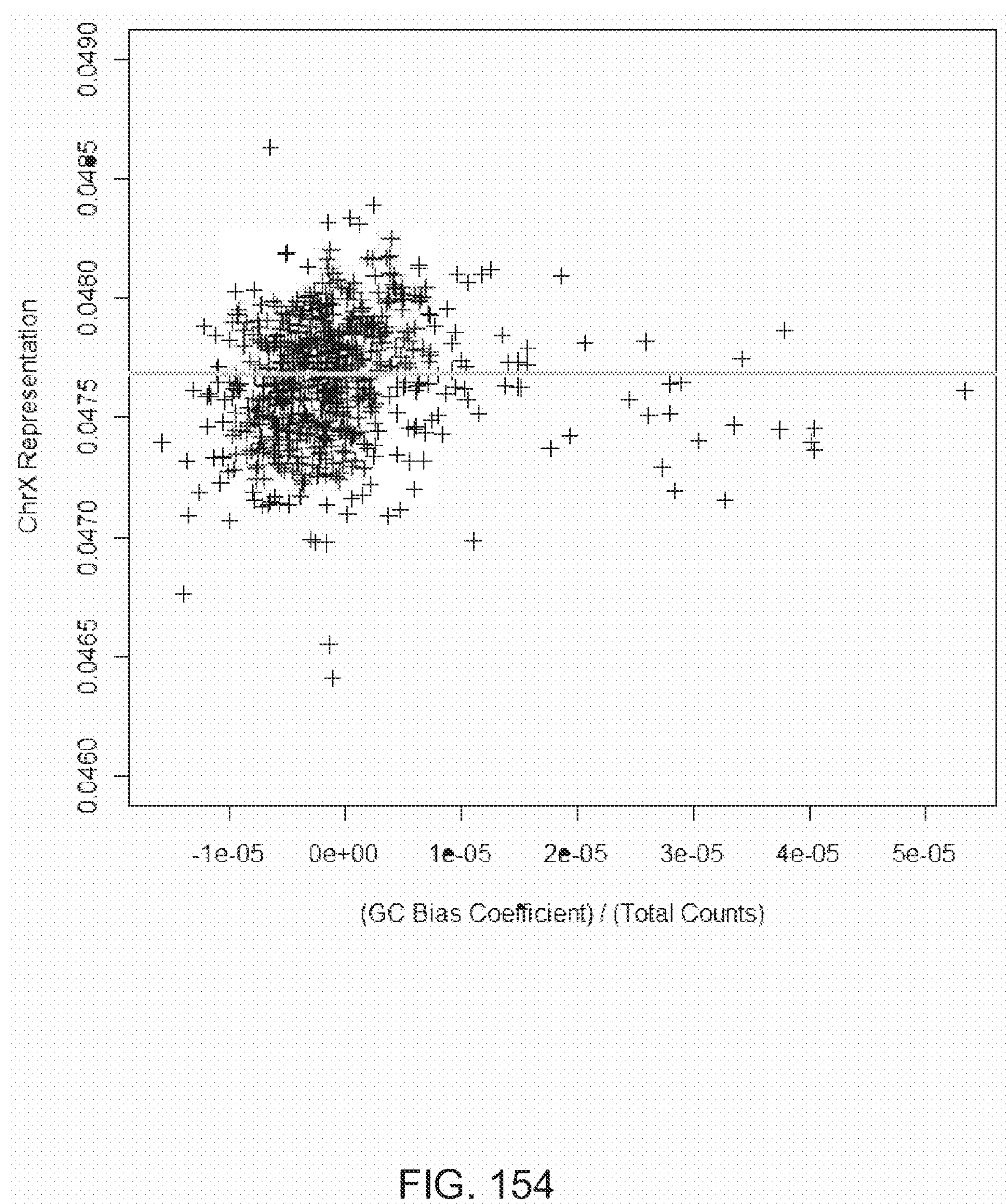

FIG. 154 shows a correlation of GC-corrected ChrX representations with GC bias coefficients. Female LDTv2CE pregnancies are shown. A chromosomal representation was obtained as the sum of PERUN chromosomal elevations of all selected ChrX bins, divided by the sum of PERUN chromosomal elevations of all selected autosomal bins, and then adjusted for GC bias as described in Example 14.

Figure 155:
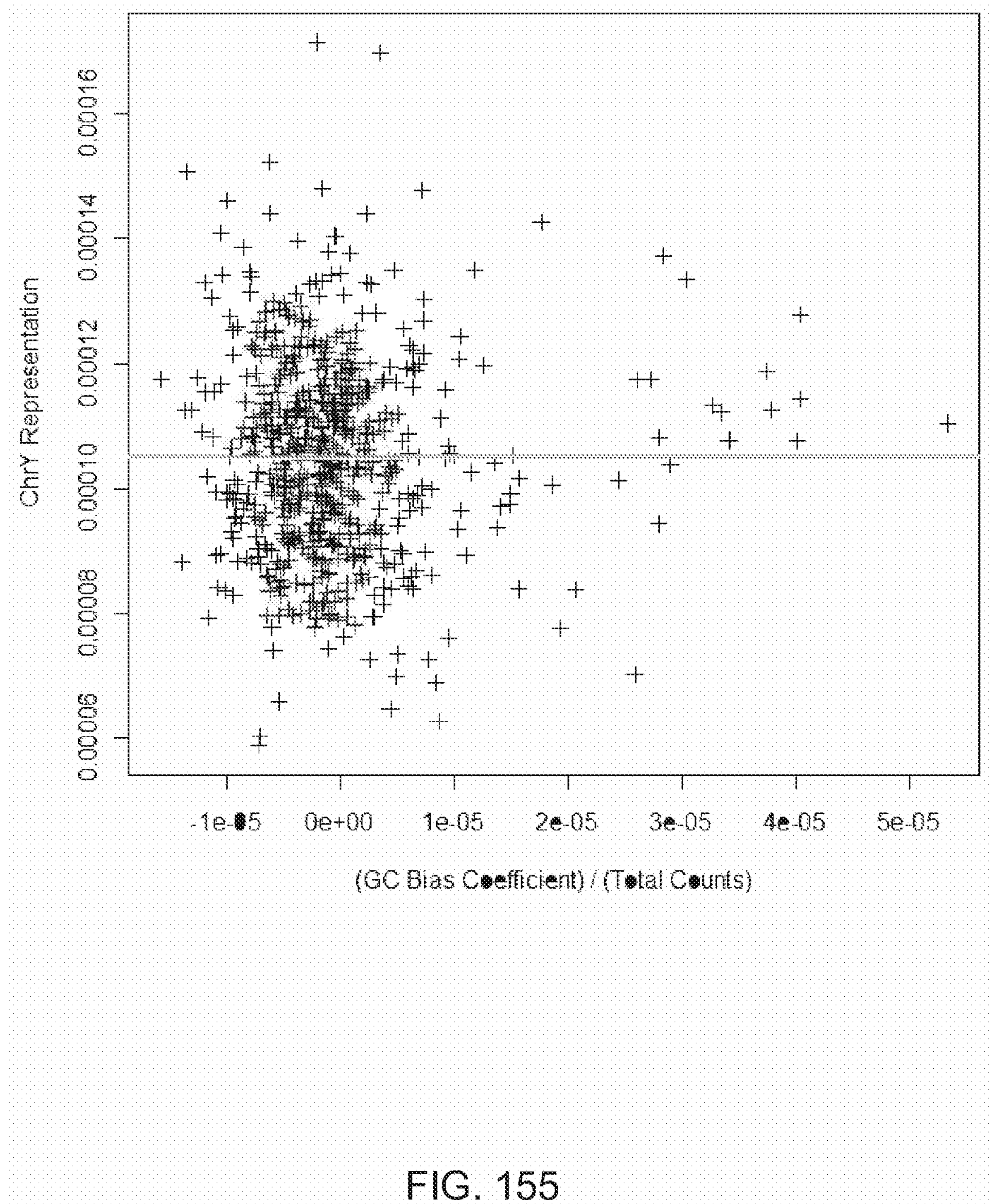

FIG. 155 shows GC-corrected ChrY representations vs. GC bias coefficients. Female LDTv2CE pregnancies are shown. A chromosomal representation was obtained as the sum of PERUN chromosomal elevations of all selected ChrY bins, divided by the sum of PERUN chromosomal elevations of all selected autosomal bins. The three bins preceding the PAR2 region of ChrY were treated as described in Example 13. ChrY representations were adjusted for GC bias as described in Example 14.

Figure 156:
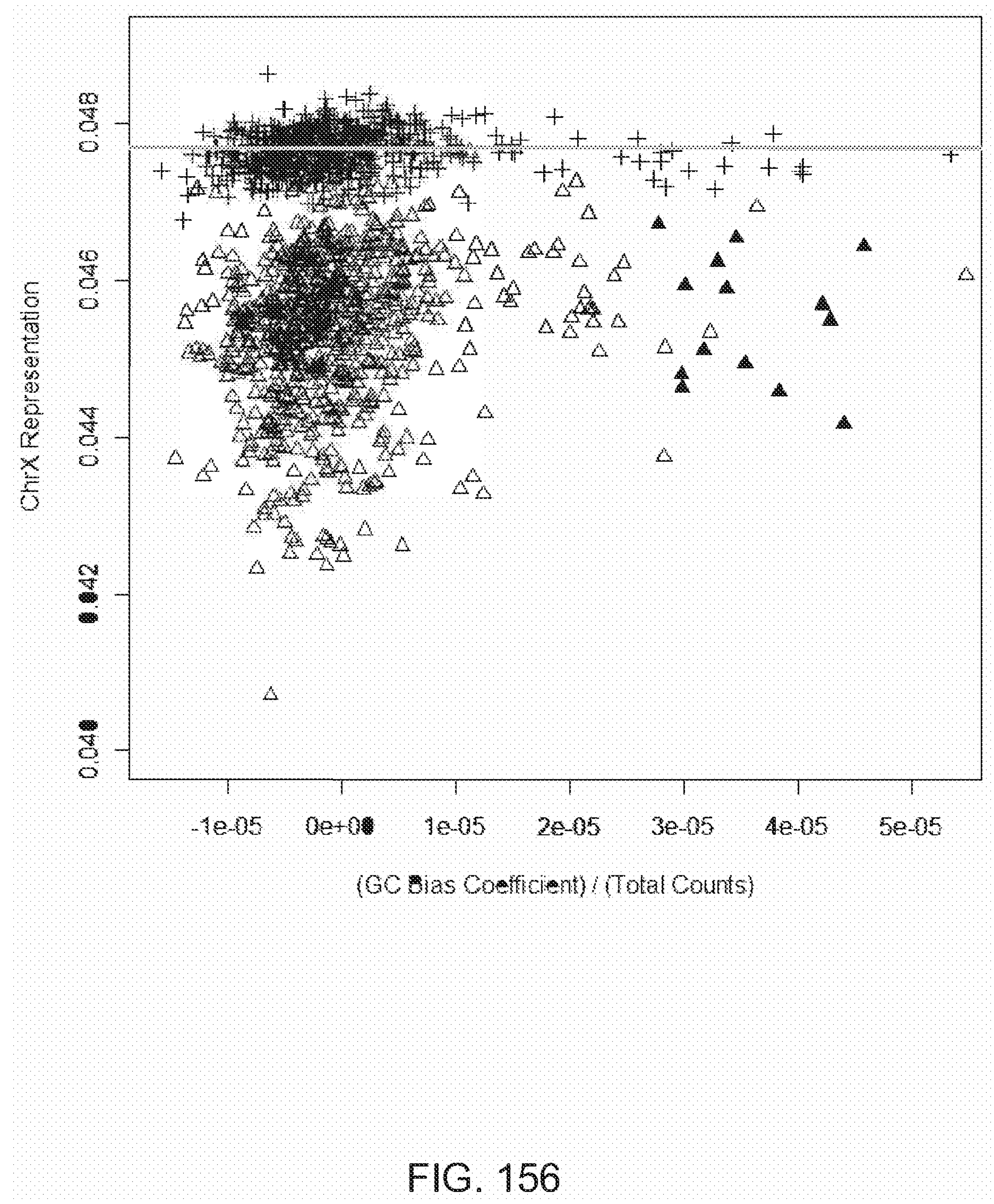

FIG. 156 shows GC-corrected ChrX representations vs. GC bias coefficients for all LDTv2CE pregnancies, including both female fetuses (crosses) and male fetuses (triangles). Chromosomal representations were obtained as described for FIG. 154.

Figure 157:
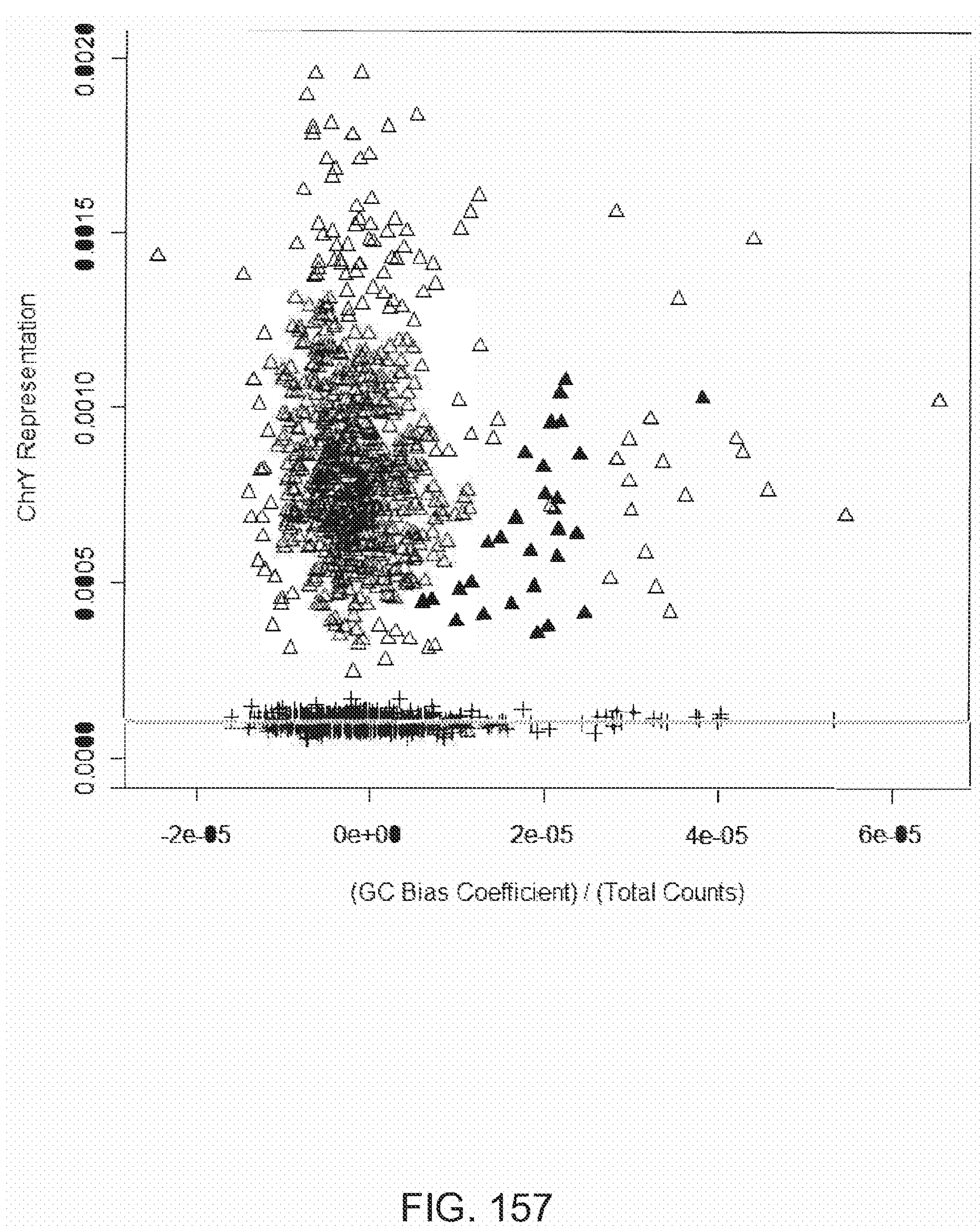

FIG. 157 shows GC-corrected ChrY representations vs. GC bias coefficients for all LDTv2CE pregnancies, including both female fetuses (crosses) and male fetuses (triangles). Chromosomal representations were obtained as described for FIG. 155.

FIG. 158 shows an illustrative embodiment of a system in which certain embodiments of the technology may be implemented.

DETAILED DESCRIPTION

Provided are methods, processes and apparatuses useful for identifying a genetic variation. Identifying a genetic variation sometimes comprises detecting a copy number variation and/or sometimes comprises adjusting an elevation comprising a copy number variation. In some embodiments, an elevation is adjusted providing an identification of one or more genetic variations or variances with a reduced likelihood of a false positive or false negative diagnosis. In some embodiments, identifying a genetic variation by a method described herein can lead to a diagnosis of, or determining a predisposition to, a particular medical condition. Identifying a genetic variance can result in facilitating a medical decision and/or employing a helpful medical procedure.

Also provided are methods, processes and apparatuses useful for identifying a genetic variation of a sex chromosome. In some embodiments, a method comprises determining sex chromosome karyotype, identifying a sex chromosome aneuploidy and/or determining fetal gender. A number of clinical disorders have been linked to copy number variations of sex chromosomes or segments thereof. For example, some sex chromosome aneuploidy (SCA) conditions include, but are not limited to, Turner syndrome [45,X], Trisomy X [47,XXX], Klinefelter syndrome [47, XXY], and [47,XYY] syndrome (sometimes referred to as Jacobs syndrome). In certain populations, sex chromosome aneuploidies can occur in approximately 0.3% of all live births. The population prevalence of SCAs (as a whole) often surpasses the birth prevalence of autosomal chromosomal abnormalities (e.g., trisomies 21, 18, or 13). SCAs are not lethal in most cases and their phenotypic features often are less severe than autosomal chromosomal abnormalities. SCAs may account for nearly one half of all chromosomal abnormalities in humans, and, in certain populations, one out of every 400 phenotypically normal humans (0.25%) can have some form of SCA. FIG. 136 lists the prevalence of certain forms of SCA.

Sex chromosome variations can be detected using ccf DNA and massively parallel sequencing (MPS). Detection of sex chromosome variations sometimes is based on quantification of chromosomal dosages. Typically, if the measured deviation originates from the fetus, it is proportional to the fraction of fetal DNA in the maternal plasma. Certain methods for noninvasive detection of sex chromosome variations can possess a number of additional challenges when compared to the detection of autosomal aneuploidies. Among these are sequencing bias associated with genomic GC composition and the sequence similarity between chromosomes X and Y, leading to mapping challenges. Moreover, two chromosomes (i.e., X and Y) typically are assessed simultaneously amid a background of presumably normal maternal sex chromosomes and the sex of the fetus is typically unknown. In addition, homology between chromosome Y and other chromosomes reduces the signal-to-noise ratio and the small size of the Y chromosome can result in large variations in its measured representations. Further, the unknown presence of possible maternal and/or fetal mosaicism can hinder optimal quantification of chromosomal representations and can impede sex chromosome variation detection. Provided herein are methods for noninvasively determining sex chromosome variations that overcome such challenges and provide highly accurate results.

Samples

Provided herein are methods and compositions for analyzing nucleic acid. In some embodiments, nucleic acid fragments in a mixture of nucleic acid fragments are analyzed. A mixture of nucleic acids can comprise two or more nucleic acid fragment species having different nucleotide sequences, different fragment lengths, different origins (e.g., genomic origins, fetal vs. maternal origins, cell or tissue origins, sample origins, subject origins, and the like), or combinations thereof.

Nucleic acid or a nucleic acid mixture utilized in methods and apparatuses described herein often is isolated from a sample obtained from a subject. A subject can be any living or non-living organism, including but not limited to a human, a non-human animal, a plant, a bacterium, a fungus or a protist. Any human or non-human animal can be selected, including but not limited to mammal, reptile, avian, amphibian, fish, ungulate, ruminant, bovine (e.g., cattle), equine (e.g., horse), caprine and ovine (e.g., sheep, goat), swine (e.g., pig), camelid (e.g., camel, llama, alpaca), monkey, ape (e.g., gorilla, chimpanzee), ursid (e.g., bear), poultry, dog, cat, mouse, rat, fish, dolphin, whale and shark. A subject may be a male or female (e.g., woman).

Nucleic acid may be isolated from any type of suitable biological specimen or sample (e.g., a test sample). A sample or test sample can be any specimen that is isolated or obtained from a subject (e.g., a human subject, a pregnant female). Non-limiting examples of specimens include fluid or tissue from a subject, including, without limitation, umbilical cord blood, chorionic villi, amniotic fluid, cerebrospinal fluid, spinal fluid, lavage fluid (e.g., bronchoalveolar, gastric, peritoneal, ductal, ear, arthroscopic), biopsy sample (e.g., from pre-implantation embryo), celocentesis sample, fetal nucleated cells or fetal cellular remnants, washings of female reproductive tract, urine, feces, sputum, saliva, nasal mucous, prostate fluid, lavage, semen, lymphatic fluid, bile, tears, sweat, breast milk, breast fluid, embryonic cells and fetal cells (e.g. placental cells). In some embodiments, a biological sample is a cervical swab from a subject. In some embodiments, a biological sample may be blood and sometimes plasma or serum. As used herein, the term "blood" encompasses whole blood or any fractions of blood, such as serum and plasma as conventionally defined, for example. Blood or fractions thereof often comprise nucleosomes (e.g., maternal and/or fetal nucleosomes). Nucleosomes comprise nucleic acids and are sometimes cell-free or intracellular. Blood also comprises buffy coats. Buffy coats are sometimes isolated by utilizing a ficoll gradient. Buffy coats can comprise white blood cells (e.g., leukocytes, T-cells, B-cells, platelets, and the like). In certain instances, buffy coats comprise maternal and/or fetal nucleic acid. Blood plasma refers to the fraction of whole blood resulting from centrifugation of blood treated with anticoagulants. Blood serum refers to the watery portion of fluid remaining after a blood sample has coagulated. Fluid or tissue samples often are collected in accordance with standard protocols hospitals or clinics generally follow. For blood, an appropriate amount of peripheral blood (e.g., between 3-40 milliliters) often is collected and can be stored according to standard procedures prior to or after preparation. A fluid or tissue sample from which nucleic acid is extracted may be acellular (e.g., cell-free). In some embodiments, a fluid or tissue sample may contain cellular elements or cellular remnants. In some embodiments fetal cells or cancer cells may be included in the sample.

A sample often is heterogeneous, by which is meant that more than one type of nucleic acid species is present in the sample. For example, heterogeneous nucleic acid can include, but is not limited to, (i) fetal derived and maternal derived nucleic acid, (ii) cancer and non-cancer nucleic acid, (iii) pathogen and host nucleic acid, and more generally, (iv) mutated and wild-type nucleic acid. A sample may be heterogeneous because more than one cell type is present, such as a fetal cell and a maternal cell, a cancer and non-cancer cell, or a pathogenic and host cell. In some embodiments, a minority nucleic acid species and a majority nucleic acid species is present.

For prenatal applications of technology described herein, fluid or tissue sample may be collected from a female at a gestational age suitable for testing, or from a female who is being tested for possible pregnancy. Suitable gestational age may vary depending on the prenatal test being performed. In certain embodiments, a pregnant female subject sometimes is in the first trimester of pregnancy, at times in the second trimester of pregnancy, or sometimes in the third trimester of pregnancy. In certain embodiments, a fluid or tissue is collected from a pregnant female between about 1 to about 45 weeks of fetal gestation (e.g., at 1-4, 4-8, 8-12, 12-16, 16-20, 20-24, 24-28, 28-32, 32-36, 36-40 or 40-44 weeks of fetal gestation), and sometimes between about 5 to about 28 weeks of fetal gestation (e.g., at 6, 7, 8, 9, 10, 11, 12, 13, 14, 15, 16, 17, 18, 19, 20, 21, 22, 23, 24, 25, 26 or 27 weeks of fetal gestation). In some embodiments, a fluid or tissue sample is collected from a pregnant female during or just after (e.g., 0 to 72 hours after) giving birth (e.g., vaginal or non-vaginal birth (e.g., surgical delivery)).

Nucleic Acid Isolation and Processing

Nucleic acid may be derived from one or more sources (e.g., cells, serum, plasma, buffy coat, lymphatic fluid, skin, soil, and the like) by methods known in the art. Cell lysis procedures and reagents are known in the art and may generally be performed by chemical (e.g., detergent, hypotonic solutions, enzymatic procedures, and the like, or combination thereof), physical (e.g., French press, sonication, and the like), or electrolytic lysis methods. Any suitable lysis procedure can be utilized. For example, chemical methods generally employ lysing agents to disrupt cells and extract the nucleic acids from the cells, followed by treatment with chaotropic salts. Physical methods such as freeze/thaw followed by grinding, the use of cell presses and the like also are useful. High salt lysis procedures also are commonly used. For example, an alkaline lysis procedure may be utilized. The latter procedure traditionally incorporates the use of phenol-chloroform solutions, and an alternative phenol-chloroform-free procedure involving three solutions can be utilized. In the latter procedures, one solution can contain 15 mM Tris, pH 8.0; 10 mM EDTA and 100 ug/ml Rnase A; a second solution can contain 0.2N NaOH and 1% SDS; and a third solution can contain 3M KOAc, pH 5.5. These procedures can be found in Current Protocols in Molecular Biology, John Wiley & Sons, N.Y., 6.3.1-6.3.6 (1989), incorporated herein in its entirety.

The terms "nucleic acid" and "nucleic acid molecule" are used interchangeably. The terms refer to nucleic acids of any composition form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing base analogs, sugar analogs and/or a non-native backbone and the like), RNA/DNA hybrids and polyamide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes herein (e.g., linear, circular, supercoiled, single-stranded, double-stranded and the like). A nucleic acid may be, or may be from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid in some embodiments can be from a single chromosome or fragment thereof (e.g., a nucleic acid sample may be from one chromosome of a sample obtained from a diploid organism). Nucleic acids sometimes comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. A nucleic acid may be prepared using a nucleic acid obtained from a subject as a template.

Nucleic acid may be isolated at a different time point as compared to another nucleic acid, where each of the samples is from the same or a different source. A nucleic acid may be from a nucleic acid library, such as a cDNA or RNA library, for example. A nucleic acid may be a result of nucleic acid purification or isolation and/or amplification of nucleic acid molecules from the sample. Nucleic acid provided for processes described herein may contain nucleic acid from one sample or from two or more samples (e.g., from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more samples).

Nucleic acids can include extracellular nucleic acid in certain embodiments. The term "extracellular nucleic acid" as used herein can refer to nucleic acid isolated from a source having substantially no cells and also is referred to as "cell-free" nucleic acid and/or "cell-free circulating" nucleic acid. Extracellular nucleic acid can be present in and obtained from blood (e.g., from the blood of a pregnant female). Extracellular nucleic acid often includes no detectable cells and may contain cellular elements or cellular remnants. Non-limiting examples of acellular sources for extracellular nucleic acid are blood, blood plasma, blood serum and urine. As used herein, the term "obtain cell-free circulating sample nucleic acid" includes obtaining a sample directly (e.g., collecting a sample, e.g., a test sample) or obtaining a sample from another who has collected a sample. Without being limited by theory, extracellular nucleic acid may be a product of cell apoptosis and cell breakdown, which provides basis for extracellular nucleic acid often having a series of lengths across a spectrum (e.g., a "ladder").

Extracellular nucleic acid can include different nucleic acid species, and therefore is referred to herein as "heterogeneous" in certain embodiments. For example, blood serum or plasma from a person having cancer can include nucleic acid from cancer cells and nucleic acid from non-cancer cells. In another example, blood serum or plasma from a pregnant female can include maternal nucleic acid and fetal nucleic acid. In some instances, fetal nucleic acid sometimes is about 5% to about 50% of the overall nucleic acid (e.g., about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, or 49% of the total nucleic acid is fetal nucleic acid). In some embodiments, the majority of fetal nucleic acid in nucleic acid is of a length of about 500 base pairs or less (e.g., about 80, 85, 90, 91, 92, 93, 94, 95, 96, 97, 98, 99 or 100% of fetal nucleic acid is of a length of about 500 base pairs or less). In some embodiments, the majority of fetal nucleic acid in nucleic acid is of a length of about 250 base pairs or less (e.g., about 80, 85, 90, 91, 92, 93, 94, 95, 96, 97, 98, 99 or 100% of fetal nucleic acid is of a length of about 250 base pairs or less). In some embodiments, the majority of fetal nucleic acid in nucleic acid is of a length of about 200 base pairs or less (e.g., about 80, 85, 90, 91, 92, 93, 94, 95, 96, 97, 98, 99 or 100% of fetal nucleic acid is of a length of about 200 base pairs or less). In some embodiments, the majority of fetal nucleic acid in nucleic acid is of a length of about 150 base pairs or less (e.g., about 80, 85, 90, 91, 92, 93, 94, 95, 96, 97, 98, 99 or 100% of fetal nucleic acid is of a length of about 150 base pairs or less). In some embodiments, the majority of fetal nucleic acid in nucleic acid is of a length of about 100 base pairs or less (e.g., about 80, 85, 90, 91, 92, 93, 94, 95, 96, 97, 98, 99 or 100% of fetal nucleic acid is of a length of about 100 base pairs or less). In some embodiments, the majority of fetal nucleic acid in nucleic acid is of a length of about 50 base pairs or less (e.g., about 80, 85, 90, 91, 92, 93, 94, 95, 96, 97, 98, 99 or 100% of fetal nucleic acid is of a length of about 50 base pairs or less). In some embodiments, the majority of fetal nucleic acid in nucleic acid is of a length of about 25 base pairs or less (e.g., about 80, 85, 90, 91, 92, 93, 94, 95, 96, 97, 98, 99 or 100% of fetal nucleic acid is of a length of about 25 base pairs or less).

Nucleic acid may be provided for conducting methods described herein without processing of the sample(s) containing the nucleic acid, in certain embodiments. In some embodiments, nucleic acid is provided for conducting methods described herein after processing of the sample(s) containing the nucleic acid. For example, a nucleic acid can be extracted, isolated, purified, partially purified or amplified from the sample(s). The term "isolated" as used herein refers to nucleic acid removed from its original environment (e.g., the natural environment if it is naturally occurring, or a host cell if expressed exogenously), and thus is altered by human intervention (e.g., "by the hand of man") from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate) than the amount of non-nucleic acid components present prior to subjecting the nucleic acid to a purification procedure. A composition comprising purified nucleic acid may be about 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. The term "purified" as used herein can refer to a nucleic acid provided that contains fewer nucleic acid species than in the sample source from which the nucleic acid is derived. A composition comprising purified nucleic acid may be about 90%, 91%, 92%, 93%, 94%, 95%, 96%, 97%, 98%, 99% or greater than 99% free of other nucleic acid species. For example, fetal nucleic acid can be purified from a mixture comprising maternal and fetal nucleic acid. In certain examples, nucleosomes comprising small fragments of fetal nucleic acid can be purified from a mixture of larger nucleosome complexes comprising larger fragments of maternal nucleic acid.

The term "amplified" as used herein refers to subjecting a target nucleic acid in a sample to a process that linearly or exponentially generates amplicon nucleic acids having the same or substantially the same nucleotide sequence as the target nucleic acid, or segment thereof. The term "amplified" as used herein can refer to subjecting a target nucleic acid (e.g., in a sample comprising other nucleic acids) to a process that selectively and linearly or exponentially generates amplicon nucleic acids having the same or substantially the same nucleotide sequence as the target nucleic acid, or segment thereof. The term "amplified" as used herein can refer to subjecting a population of nucleic acids to a process that non-selectively and linearly or exponentially generates amplicon nucleic acids having the same or substantially the same nucleotide sequence as nucleic acids, or portions thereof, that were present in the sample prior to amplification. In some embodiments, the term "amplified" refers to a method that comprises a polymerase chain reaction (PCR).

Nucleic acid also may be processed by subjecting nucleic acid to a method that generates nucleic acid fragments, in certain embodiments, before providing nucleic acid for a process described herein. In some embodiments, nucleic acid subjected to fragmentation or cleavage may have a nominal, average or mean length of about 5 to about 10,000 base pairs, about 100 to about 1,000 base pairs, about 100 to about 500 base pairs, or about 10, 15, 20, 25, 30, 35, 40, 45, 50, 55, 60, 65, 70, 75, 80, 85, 90, 95, 100, 200, 300, 400, 500, 600, 700, 800, 900, 1000, 2000, 3000, 4000, 5000, 6000, 7000, 8000 or 9000 base pairs. Fragments can be generated by a suitable method known in the art, and the average, mean or nominal length of nucleic acid fragments can be controlled by selecting an appropriate fragment-generating procedure. In certain embodiments, nucleic acid of a relatively shorter length can be utilized to analyze sequences that contain little sequence variation and/or contain relatively large amounts of known nucleotide sequence information. In some embodiments, nucleic acid of a relatively longer length can be utilized to analyze sequences that contain greater sequence variation and/or contain relatively small amounts of nucleotide sequence information.

Nucleic acid fragments may contain overlapping nucleotide sequences, and such overlapping sequences can facilitate construction of a nucleotide sequence of the non-fragmented counterpart nucleic acid, or a segment thereof. For example, one fragment may have subsequences x and y and another fragment may have subsequences y and z, where x, y and z are nucleotide sequences that can be 5 nucleotides in length or greater. Overlap sequence y can be utilized to facilitate construction of the x-y-z nucleotide sequence in nucleic acid from a sample in certain embodiments. Nucleic acid may be partially fragmented (e.g., from an incomplete or terminated specific cleavage reaction) or fully fragmented in certain embodiments.

Nucleic acid can be fragmented by various methods known in the art, which include without limitation, physical, chemical and enzymatic processes. Non-limiting examples of such processes are described in U.S. Patent Application Publication No. 20050112590 (published on May 26, 2005, entitled "Fragmentation-based methods and systems for sequence variation detection and discovery," naming Van Den Boom et al.). Certain processes can be selected to generate non-specifically cleaved fragments or specifically cleaved fragments. Non-limiting examples of processes that can generate non-specifically cleaved fragment nucleic acid include, without limitation, contacting nucleic acid with apparatus that expose nucleic acid to shearing force (e.g., passing nucleic acid through a syringe needle; use of a French press); exposing nucleic acid to irradiation (e.g., gamma, x-ray, UV irradiation; fragment sizes can be controlled by irradiation intensity); boiling nucleic acid in water (e.g., yields about 500 base pair fragments) and exposing nucleic acid to an acid and base hydrolysis process.

As used herein, "fragmentation" or "cleavage" refers to a procedure or conditions in which a nucleic acid molecule, such as a nucleic acid template gene molecule or amplified product thereof, may be severed into two or more smaller nucleic acid molecules. Such fragmentation or cleavage can be sequence specific, base specific, or nonspecific, and can be accomplished by any of a variety of methods, reagents or conditions, including, for example, chemical, enzymatic, physical fragmentation.

As used herein, "fragments", "cleavage products", "cleaved products" or grammatical variants thereof, refers to nucleic acid molecules resultant from a fragmentation or cleavage of a nucleic acid template gene molecule or amplified product thereof. While such fragments or cleaved products can refer to all nucleic acid molecules resultant from a cleavage reaction, typically such fragments or cleaved products refer only to nucleic acid molecules resultant from a fragmentation or cleavage of a nucleic acid template gene molecule or the segment of an amplified product thereof containing the corresponding nucleotide sequence of a nucleic acid template gene molecule. For example, an amplified product can contain one or more nucleotides more than the amplified nucleotide region of a nucleic acid template sequence (e.g., a primer can contain "extra" nucleotides such as a transcriptional initiation sequence, in addition to nucleotides complementary to a nucleic acid template gene molecule, resulting in an amplified product containing "extra" nucleotides or nucleotides not corresponding to the amplified nucleotide region of the nucleic acid template gene molecule). Accordingly, fragments can include fragments arising from portions of amplified nucleic acid molecules containing, at least in part, nucleotide sequence information from or based on the representative nucleic acid template molecule.

As used herein, the term "complementary cleavage reactions" refers to cleavage reactions that are carried out on the same nucleic acid using different cleavage reagents or by altering the cleavage specificity of the same cleavage reagent such that alternate cleavage patterns of the same target or reference nucleic acid or protein are generated. In certain embodiments, nucleic acid may be treated with one or more specific cleavage agents (e.g., 1, 2, 3, 4, 5, 6, 7, 8, 9, 10 or more specific cleavage agents) in one or more reaction vessels (e.g., nucleic acid is treated with each specific cleavage agent in a separate vessel).

Nucleic acid may be specifically cleaved or non-specifically cleaved by contacting the nucleic acid with one or more enzymatic cleavage agents (e.g., nucleases, restriction enzymes). The term "specific cleavage agent" as used herein refers to an agent, sometimes a chemical or an enzyme that can cleave a nucleic acid at one or more specific sites. Specific cleavage agents often cleave specifically according to a particular nucleotide sequence at a particular site. Non-specific cleavage agents often cleave nucleic acids at non-specific sites or degrade nucleic acids. Non-specific cleavage agents often degrade nucleic acids by removal of nucleotides from the end (either the 5' end, 3' end or both) of a nucleic acid strand.

Any suitable non-specific or specific enzymatic cleavage agent can be used to cleave or fragment nucleic acids. A suitable restriction enzyme can be used to cleave nucleic acids, in some embodiments. Examples of enzymatic cleavage agents include without limitation endonucleases (e.g., DNase (e.g., DNase I, II); RNase (e.g., RNase E, F, H, P); Cleavase™ enzyme; Taq DNA polymerase; *E. coli* DNA polymerase I and eukaryotic structure-specific endonucleases; murine FEN-1 endonucleases; type I, II or III restriction endonucleases such as Acc I, Afl III, Alu I, Alw44 I, Apa I, Asn I, Ava I, Ava II, BamH I, Ban II, Bcl I, Bgl I. Bgl II, Bin I, Bsm I, BssH II, BstE II, Cfo I, Cla I, Dde I, Dpn I, Dra I, EclX I, EcoR I, EcoR I, EcoR II, EcoR V, Hae II, Hae II, Hind II, Hind III, Hpa I, Hpa II, Kpn I, Ksp I, Mlu I, MIuN I, Msp I, Nci I, Nco I, Nde I, Nde II, Nhe I, Not I, Nru I, Nsi I, Pst I, Pvu I, Pvu II, Rsa I, Sac I, Sal I, Sau3A I, Sca I, ScrF I, Sfi I, Sma I, Spe I, Sph I, Ssp I, Stu I, Sty I, Swa I, Taq I, Xba I, Xho I; glycosylases (e.g., uracil-DNA glycosylase (UDG), 3-methyladenine DNA glycosylase, 3-methyladenine DNA glycosylase II, pyrimidine hydrate-DNA glycosylase, FaPy-DNA glycosylase, thymine mismatch-DNA glycosylase, hypoxanthine-DNA glycosylase, 5-Hydroxymethyluracil DNA glycosylase (HmUDG), 5-Hydroxymethylcytosine DNA glycosylase, or 1,N6-etheno-adenine DNA glycosylase); exonucleases (e.g., exonuclease III); ribozymes, and DNAzymes. Nucleic acid may be treated with a chemical agent, and the modified nucleic acid may be cleaved. In non-limiting examples, nucleic acid may be treated with (i) alkylating agents such as methylnitrosourea that generate several alkylated bases, including N3-methyladenine and N3-methylguanine, which are recognized and cleaved by alkyl purine DNA-glycosylase; (ii) sodium bisulfite, which causes deamination of cytosine residues in DNA to form uracil residues that can be cleaved by uracil N-glycosylase; and (iii) a chemical agent that converts guanine to its oxidized form, 8-hydroxyguanine, which can be cleaved by formamidopyrimidine DNA N-glycosylase. Examples of chemical cleavage processes include without limitation alkylation, (e.g., alkylation of phosphorothioate-modified nucleic acid); cleavage of acid lability of P3'-N5'-phosphoroamidate-containing nucleic acid; and osmium tetroxide and piperidine treatment of nucleic acid.

Nucleic acid also may be exposed to a process that modifies certain nucleotides in the nucleic acid before providing nucleic acid for a method described herein. A process that selectively modifies nucleic acid based upon the methylation state of nucleotides therein can be applied to nucleic acid, for example. In addition, conditions such as high temperature, ultraviolet radiation, x-radiation, can induce changes in the sequence of a nucleic acid molecule. Nucleic acid may be provided in any form useful for conducting a sequence analysis or manufacture process described herein, such as solid or liquid form, for example. In certain embodiments, nucleic acid may be provided in a liquid form optionally comprising one or more other components, including without limitation one or more buffers or salts.

Nucleic acid may be single or double stranded. Single stranded DNA, for example, can be generated by denaturing double stranded DNA by heating or by treatment with alkali, for example. Nucleic acid sometimes is in a D-loop structure, formed by strand invasion of a duplex DNA molecule by an oligonucleotide or a DNA-like molecule such as peptide nucleic acid (PNA). D loop formation can be facilitated by addition of *E. coli* RecA protein and/or by alteration of salt concentration, for example, using methods known in the art.

Determining Fetal Nucleic Acid Content

The amount of fetal nucleic acid (e.g., concentration, relative amount, absolute amount, copy number, and the like) in nucleic acid is determined in some embodiments. In some embodiments, the amount of fetal nucleic acid in a sample is referred to as "fetal fraction". In some embodiments, "fetal fraction" refers to the fraction of fetal nucleic acid in circulating cell-free nucleic acid in a sample (e.g., a blood sample, a serum sample, a plasma sample) obtained from a pregnant female. In some embodiments, a method in which a genetic variation is determined also can comprise determining fetal fraction. Determining fetal fraction can be performed in a suitable manner, non-limiting examples of which include methods described below.

In some embodiments, the amount of fetal nucleic acid is determined according to markers specific to a male fetus (e.g., Y-chromosome STR markers (e.g., DYS 19, DYS 385, DYS 392 markers); RhD marker in RhD-negative females), allelic ratios of polymorphic sequences, or according to one or more markers specific to fetal nucleic acid and not maternal nucleic acid (e.g., differential epigenetic biomarkers (e.g., methylation; described in further detail below) between mother and fetus, or fetal RNA markers in maternal blood plasma (see e.g., Lo, 2005, Journal of Histochemistry and Cytochemistry 53 (3): 293-296)).

Determination of fetal nucleic acid content (e.g., fetal fraction) sometimes is performed using a fetal quantifier assay (FQA) as described, for example, in U.S. Patent Application Publication No. 2010/0105049, which is hereby incorporated by reference. This type of assay allows for the detection and quantification of fetal nucleic acid in a maternal sample based on the methylation status of the nucleic acid in the sample. The amount of fetal nucleic acid from a maternal sample sometimes can be determined relative to the total amount of nucleic acid present, thereby providing the percentage of fetal nucleic acid in the sample. The copy number of fetal nucleic acid sometimes can be determined in a maternal sample. The amount of fetal nucleic acid sometimes can be determined in a sequence-specific (or locus-specific) manner and sometimes with sufficient sensitivity to allow for accurate chromosomal dosage analysis (for example, to detect the presence or absence of a fetal aneuploidy or other genetic variation).

A fetal quantifier assay (FQA) can be performed in conjunction with any method described herein. Such an assay can be performed by any method known in the art and/or described in U.S. Patent Application Publication No. 2010/0105049, such as, for example, by a method that can distinguish between maternal and fetal DNA based on differential methylation status, and quantify (i.e. determine the amount of) the fetal DNA. Methods for differentiating nucleic acid based on methylation status include, but are not limited to, methylation sensitive capture, for example, using a MBD2-Fc fragment in which the methyl binding domain of MBD2 is fused to the Fc fragment of an antibody (MBD-FC) (Gebhard et al. (2006) Cancer Res. 66(12):6118-28); methylation specific antibodies; bisulfite conversion methods, for example, MSP (methylation-sensitive PCR), COBRA, methylation-sensitive single nucleotide primer extension (Ms-SNuPE) or Sequenom MassCLEAVE™ technology; and the use of methylation sensitive restriction enzymes (e.g., digestion of maternal DNA in a maternal sample using one or more methylation sensitive restriction enzymes thereby enriching the fetal DNA). Methyl-sensitive enzymes also can be used to differentiate nucleic acid based on methylation status, which, for example, can preferentially or substantially cleave or digest at their DNA recognition sequence if the latter is non-methylated. Thus, an unmethylated DNA sample will be cut into smaller fragments than a methylated DNA sample and a hypermethylated DNA sample will not be cleaved. Except where explicitly stated, any method for differentiating nucleic acid based on methylation status can be used with the compositions and methods of the technology herein. The amount of fetal DNA can be determined, for example, by introducing one or more competitors at known concentrations during an amplification reaction. Determining the amount of fetal DNA also can be done, for example, by RT-PCR, primer extension, sequencing and/or counting. In certain instances, the amount of nucleic acid can be determined using BEAMing technology as described in U.S. Patent Application Publication No. 2007/0065823. In some embodiments, the restriction efficiency can be determined and the efficiency rate is used to further determine the amount of fetal DNA.

A fetal quantifier assay (FQA) sometimes can be used to determine the concentration of fetal DNA in a maternal sample, for example, by the following method: a) determine the total amount of DNA present in a maternal sample; b) selectively digest the maternal DNA in a maternal sample using one or more methylation sensitive restriction enzymes thereby enriching the fetal DNA; c) determine the amount of fetal DNA from step b); and d) compare the amount of fetal DNA from step c) to the total amount of DNA from step a), thereby determining the concentration of fetal DNA in the maternal sample. The absolute copy number of fetal nucleic acid in a maternal sample sometimes can be determined, for example, using mass spectrometry and/or a system that uses a competitive PCR approach for absolute copy number measurements. See for example, Ding and Cantor (2003) Proc. Natl. Acad. Sci. USA 100:3059-3064, and U.S. Patent Application Publication No. 2004/0081993, both of which are hereby incorporated by reference.

Fetal fraction sometimes can be determined based on allelic ratios of polymorphic sequences (e.g., single nucleotide polymorphisms (SNPs)), such as, for example, using a method described in U.S. Patent Application Publication No. 2011/0224087, which is hereby incorporated by reference. In such a method, nucleotide sequence reads are obtained for a maternal sample and fetal fraction is determined by comparing the total number of nucleotide sequence reads that map to a first allele and the total number of nucleotide sequence reads that map to a second allele at an informative polymorphic site (e.g., SNP) in a reference genome. Fetal alleles can be identified, for example, by their relative minor contribution to the mixture of fetal and maternal nucleic acids in the sample when compared to the major contribution to the mixture by the maternal nucleic acids. Accordingly, the relative abundance of fetal nucleic acid in a maternal sample can be determined as a parameter of the total number of unique sequence reads mapped to a target nucleic acid sequence on a reference genome for each of the two alleles of a polymorphic site.

The amount of fetal nucleic acid in extracellular nucleic acid can be quantified and used in conjunction with a method provided herein. Thus, in certain embodiments, methods of the technology described herein comprise an additional step of determining the amount of fetal nucleic acid. The amount of fetal nucleic acid can be determined in a nucleic acid sample from a subject before or after processing to prepare sample nucleic acid. In certain embodiments, the amount of fetal nucleic acid is determined in a sample after sample nucleic acid is processed and prepared, which amount is utilized for further assessment. In some embodiments, an outcome comprises factoring the fraction of fetal nucleic acid in the sample nucleic acid (e.g., adjusting counts, removing samples, making a call or not making a call).

The determination step can be performed before, during, at any one point in a method described herein, or after certain (e.g., aneuploidy detection) methods described herein. For example, to achieve an aneuploidy determination method with a given sensitivity or specificity, a fetal nucleic acid quantification method may be implemented prior to, during or after aneuploidy determination to identify those samples with greater than about 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25% or more fetal nucleic acid. In some embodiments, samples determined as having a certain threshold amount of fetal nucleic acid (e.g., about 15% or more fetal nucleic acid; about 4% or more fetal nucleic acid) are further analyzed for the presence or absence of aneuploidy or genetic variation, for example. In certain embodiments, determinations of, for example, the presence or absence of aneuploidy are selected (e.g., selected and communicated to a patient) only for samples having a certain threshold amount of fetal nucleic acid (e.g., about 15% or more fetal nucleic acid; about 4% or more fetal nucleic acid).

In some embodiments, the determination of fetal fraction or determining the amount of fetal nucleic acid is not required or necessary for identifying the presence or absence of a chromosome aneuploidy. In some embodiments, identifying the presence or absence of a chromosome aneuploidy does not require the sequence differentiation of fetal versus maternal DNA. This is because the summed contribution of both maternal and fetal sequences in a particular chromosome, chromosome portion or segment thereof is analyzed, in some embodiments. In some embodiments, identifying the presence or absence of a chromosome aneuploidy does not rely on a priori sequence information that would distinguish fetal DNA from maternal DNA.

Enriching for a Subpopulation of Nucleic Acid

In some embodiments, nucleic acid (e.g., extracellular nucleic acid) is enriched or relatively enriched for a subpopulation or species of nucleic acid. Nucleic acid subpopulations can include, for example, fetal nucleic acid, maternal nucleic acid, nucleic acid comprising fragments of a particular length or range of lengths, or nucleic acid from a particular genome region (e.g., single chromosome, set of chromosomes, and/or certain chromosome regions). Such enriched samples can be used in conjunction with a method provided herein. Thus, in certain embodiments, methods of the technology comprise an additional step of enriching for a subpopulation of nucleic acid in a sample, such as, for example, fetal nucleic acid. In some embodiments, a method for determining fetal fraction described above also can be used to enrich for fetal nucleic acid. In certain embodiments, maternal nucleic acid is selectively removed (partially, substantially, almost completely or completely) from the sample. In some embodiments, enriching for a particular low copy number species nucleic acid (e.g., fetal nucleic acid) may improve quantitative sensitivity. Methods for enriching a sample for a particular species of nucleic acid are described, for example, in U.S. Pat. No. 6,927,028, International Patent Application Publication No. WO2007/140417, International Patent Application Publication No. WO2007/147063, International Patent Application Publication No. WO2009/032779, International Patent Application Publication No. WO2009/032781, International Patent Application Publication No. WO2010/033639, International Patent Application Publication No. WO2011/034631, International Patent Application Publication No. WO2006/056480, and International Patent Application Publication No. WO2011/143659, all of which are incorporated by reference herein.

In some embodiments, nucleic acid is enriched for certain target fragment species and/or reference fragment species. In some embodiments, nucleic acid is enriched for a specific nucleic acid fragment length or range of fragment lengths using one or more length-based separation methods described below. In some embodiments, nucleic acid is enriched for fragments from a select genomic region (e.g., chromosome) using one or more sequence-based separation methods described herein and/or known in the art. Certain methods for enriching for a nucleic acid subpopulation (e.g., fetal nucleic acid) in a sample are described in detail below.

Some methods for enriching for a nucleic acid subpopulation (e.g., fetal nucleic acid) that can be used with a method described herein include methods that exploit epigenetic differences between maternal and fetal nucleic acid. For example, fetal nucleic acid can be differentiated and separated from maternal nucleic acid based on methylation differences. Methylation-based fetal nucleic acid enrichment methods are described in U.S. Patent Application Publication No. 2010/0105049, which is incorporated by reference herein. Such methods sometimes involve binding a sample nucleic acid to a methylation-specific binding agent (methyl-CpG binding protein (MBD), methylation specific antibodies, and the like) and separating bound nucleic acid from unbound nucleic acid based on differential methylation status. Such methods also can include the use of methylation-sensitive restriction enzymes (as described above; e.g., HhaI and HpaII), which allow for the enrichment of fetal nucleic acid regions in a maternal sample by selectively digesting nucleic acid from the maternal sample with an enzyme that selectively and completely or substantially digests the maternal nucleic acid to enrich the sample for at least one fetal nucleic acid region.

Another method for enriching for a nucleic acid subpopulation (e.g., fetal nucleic acid) that can be used with a method described herein is a restriction endonuclease enhanced polymorphic sequence approach, such as a method described in U.S. Patent Application Publication No. 2009/0317818, which is incorporated by reference herein. Such methods include cleavage of nucleic acid comprising a non-target allele with a restriction endonuclease that recognizes the nucleic acid comprising the non-target allele but not the target allele; and amplification of uncleaved nucleic acid but not cleaved nucleic acid, where the uncleaved, amplified nucleic acid represents enriched target nucleic acid (e.g., fetal nucleic acid) relative to non-target nucleic acid (e.g., maternal nucleic acid). In some embodiments, nucleic acid may be selected such that it comprises an allele having a polymorphic site that is susceptible to selective digestion by a cleavage agent, for example.

Some methods for enriching for a nucleic acid subpopulation (e.g., fetal nucleic acid) that can be used with a method described herein include selective enzymatic degradation approaches. Such methods involve protecting target sequences from exonuclease digestion thereby facilitating the elimination in a sample of undesired sequences (e.g., maternal DNA). For example, in one approach, sample nucleic acid is denatured to generate single stranded nucleic acid, single stranded nucleic acid is contacted with at least one target-specific primer pair under suitable annealing conditions, annealed primers are extended by nucleotide polymerization generating double stranded target sequences, and digesting single stranded nucleic acid using a nuclease that digests single stranded (i.e., non-target) nucleic acid. In some embodiments, the method can be repeated for at least one additional cycle. In some embodiments, the same target-specific primer pair is used to prime each of the first and second cycles of extension, and in some embodiments, different target-specific primer pairs are used for the first and second cycles.

Some methods for enriching for a nucleic acid subpopulation (e.g., fetal nucleic acid) that can be used with a method described herein include massively parallel signature sequencing (MPSS) approaches. MPSS typically is a solid phase method that uses adapter (i.e., tag) ligation, followed by adapter decoding, and reading of the nucleic acid sequence in small increments. Tagged PCR products are typically amplified such that each nucleic acid generates a PCR product with a unique tag. Tags are often used to attach the PCR products to microbeads. After several rounds of ligation-based sequence determination, for example, a sequence signature can be identified from each bead. Each signature sequence (MPSS tag) in a MPSS dataset is analyzed, compared with all other signatures, and all identical signatures are counted.

In some embodiments, certain MPSS-based enrichment methods can include amplification (e.g., PCR)-based approaches. In some embodiments, loci-specific amplification methods can be used (e.g., using loci-specific amplification primers). In some embodiments, a multiplex SNP allele PCR approach can be used. In some embodiments, a multiplex SNP allele PCR approach can be used in combination with uniplex sequencing. For example, such an approach can involve the use of multiplex PCR (e.g., MASSARRAY system) and incorporation of capture probe sequences into the amplicons followed by sequencing using, for example, the Illumina MPSS system. In some embodiments, a multiplex SNP allele PCR approach can be used in combination with a three-primer system and indexed sequencing. For example, such an approach can involve the use of multiplex PCR (e.g., MASSARRAY system) with primers having a first capture probe incorporated into certain loci-specific forward PCR primers and adapter sequences incorporated into loci-specific reverse PCR primers, to thereby generate amplicons, followed by a secondary PCR to incorporate reverse capture sequences and molecular index barcodes for sequencing using, for example, the Illumina MPSS system. In some embodiments, a multiplex SNP allele PCR approach can be used in combination with a four-primer system and indexed sequencing. For example, such an approach can involve the use of multiplex PCR (e.g., MASSARRAY system) with primers having adaptor sequences incorporated into both loci-specific forward and loci-specific reverse PCR primers, followed by a secondary PCR to incorporate both forward and reverse capture sequences and molecular index barcodes for sequencing using, for example, the Illumina MPSS system. In some embodiments, a microfluidics approach can be used. In some embodiments, an array-based microfluidics approach can be used. For example, such an approach can involve the use of a microfluidics array (e.g., Fluidigm) for amplification at low plex and incorporation of index and capture probes, followed by sequencing. In some embodiments, an emulsion microfluidics approach can be used, such as, for example, digital droplet PCR.

In some embodiments, universal amplification methods can be used (e.g., using universal or non-loci-specific amplification primers). In some embodiments, universal amplification methods can be used in combination with pull-down approaches. In some embodiments, a method can include biotinylated ultramer pull-down (e.g., biotinylated pull-down assays from Agilent or IDT) from a universally amplified sequencing library. For example, such an approach can involve preparation of a standard library, enrichment for selected regions by a pull-down assay, and a secondary universal amplification step. In some embodiments, pull-down approaches can be used in combination with ligation-based methods. In some embodiments, a method can include biotinylated ultramer pull down with sequence specific adapter ligation (e.g., HALOPLEX PCR, Halo Genomics). For example, such an approach can involve the use of selector probes to capture restriction enzyme-digested fragments, followed by ligation of captured products to an adaptor, and universal amplification followed by sequencing. In some embodiments, pull-down approaches can be used in combination with extension and ligation-based methods. In some embodiments, a method can include molecular inversion probe (MIP) extension and ligation. For example, such an approach can involve the use of molecular inversion probes in combination with sequence adapters followed by universal amplification and sequencing. In some embodiments, complementary DNA can be synthesized and sequenced without amplification.

In some embodiments, extension and ligation approaches can be performed without a pull-down component. In some embodiments, a method can include loci-specific forward and reverse primer hybridization, extension and ligation. Such methods can further include universal amplification or complementary DNA synthesis without amplification, followed by sequencing. Such methods can reduce or exclude background sequences during analysis, in some embodiments.

In some embodiments, pull-down approaches can be used with an optional amplification component or with no amplification component. In some embodiments, a method can include a modified pull-down assay and ligation with full incorporation of capture probes without universal amplification. For example, such an approach can involve the use of modified selector probes to capture restriction enzyme-digested fragments, followed by ligation of captured products to an adaptor, optional amplification, and sequencing. In some embodiments, a method can include a biotinylated pull-down assay with extension and ligation of adaptor sequence in combination with circular single stranded ligation. For example, such an approach can involve the use of selector probes to capture regions of interest (i.e., target sequences), extension of the probes, adaptor ligation, single stranded circular ligation, optional amplification, and sequencing. In some embodiments, the analysis of the sequencing result can separate target sequences form background.

In some embodiments, nucleic acid is enriched for fragments from a select genomic region (e.g., chromosome) using one or more sequence-based separation methods described herein. Sequence-based separation generally is based on nucleotide sequences present in the fragments of interest (e.g., target and/or reference fragments) and substantially not present in other fragments of the sample or present in an insubstantial amount of the other fragments (e.g., 5% or less). In some embodiments, sequence-based separation can generate separated target fragments and/or separated reference fragments. Separated target fragments and/or separated reference fragments typically are isolated away from the remaining fragments in the nucleic acid sample. In some embodiments, the separated target fragments and the separated reference fragments also are isolated away from each other (e.g., isolated in separate assay compartments). In some embodiments, the separated target fragments and the separated reference fragments are isolated together (e.g., isolated in the same assay compartment). In some embodiments, unbound fragments can be differentially removed or degraded or digested.

In some embodiments, a selective nucleic acid capture process is used to separate target and/or reference fragments away from the nucleic acid sample. Commercially available nucleic acid capture systems include, for example, Nimblegen sequence capture system (Roche NimbleGen, Madison, WI); Illumina BEADARRAY platform (Illumina, San Diego, CA); Affymetrix GENECHIP platform (Affymetrix, Santa Clara, CA); Agilent SureSelect Target Enrichment System (Agilent Technologies, Santa Clara, CA); and related platforms. Such methods typically involve hybridization of a capture oligonucleotide to a segment or all of the nucleotide sequence of a target or reference fragment and can include use of a solid phase (e.g., solid phase array) and/or a solution based platform. Capture oligonucleotides (sometimes referred to as "bait") can be selected or designed such that they preferentially hybridize to nucleic acid fragments from selected genomic regions or loci (e.g., one of chromosomes 21, 18, 13, X or Y, or a reference chromosome).

In some embodiments, nucleic acid is enriched for a particular nucleic acid fragment length, range of lengths, or lengths under or over a particular threshold or cutoff using one or more length-based separation methods. Nucleic acid fragment length typically refers to the number of nucleotides in the fragment. Nucleic acid fragment length also is sometimes referred to as nucleic acid fragment size. In some embodiments, a length-based separation method is performed without measuring lengths of individual fragments. In some embodiments, a length based separation method is performed in conjunction with a method for determining length of individual fragments. In some embodiments, length-based separation refers to a size fractionation procedure where all or part of the fractionated pool can be isolated (e.g., retained) and/or analyzed. Size fractionation procedures are known in the art (e.g., separation on an array, separation by a molecular sieve, separation by gel electrophoresis, separation by column chromatography (e.g., size-exclusion columns), and microfluidics-based approaches). In some embodiments, length-based separation approaches can include fragment circularization, chemical treatment (e.g., formaldehyde, polyethylene glycol (PEG)), mass spectrometry and/or size-specific nucleic acid amplification, for example.

Certain length-based separation methods that can be used with methods described herein employ a selective sequence tagging approach, for example. The term "sequence tagging" refers to incorporating a recognizable and distinct sequence into a nucleic acid or population of nucleic acids. The term "sequence tagging" as used herein has a different meaning than the term "sequence tag" described later herein. In such sequence tagging methods, a fragment size species (e.g., short fragments) nucleic acids are subjected to selective sequence tagging in a sample that includes long and short nucleic acids. Such methods typically involve performing a nucleic acid amplification reaction using a set of nested primers which include inner primers and outer primers. In some embodiments, one or both of the inner can be tagged to thereby introduce a tag onto the target amplification product. The outer primers generally do not anneal to the short fragments that carry the (inner) target sequence. The inner primers can anneal to the short fragments and generate an amplification product that carries a tag and the target sequence. Typically, tagging of the long fragments is inhibited through a combination of mechanisms which include, for example, blocked extension of the inner primers by the prior annealing and extension of the outer primers. Enrichment for tagged fragments can be accomplished by any of a variety of methods, including for example, exonuclease digestion of single stranded nucleic acid and amplification of the tagged fragments using amplification primers specific for at least one tag.

Another length-based separation method that can be used with methods described herein involves subjecting a nucleic acid sample to polyethylene glycol (PEG) precipitation. Examples of methods include those described in International Patent Application Publication Nos. WO2007/140417 and WO2010/115016. This method in general entails contacting a nucleic acid sample with PEG in the presence of one or more monovalent salts under conditions sufficient to substantially precipitate large nucleic acids without substantially precipitating small (e.g., less than 300 nucleotides) nucleic acids.

Another size-based enrichment method that can be used with methods described herein involves circularization by ligation, for example, using circligase. Short nucleic acid fragments typically can be circularized with higher efficiency than long fragments. Non-circularized sequences can be separated from circularized sequences, and the enriched short fragments can be used for further analysis.

Obtaining Sequence Reads

In some embodiments, nucleic acids (e.g., nucleic acid fragments, sample nucleic acid, cell-free nucleic acid) may be sequenced. In some embodiments, a full or substantially full sequence is obtained and sometimes a partial sequence is obtained. In some embodiments, a nucleic acid is not sequenced, and the sequence of a nucleic acid is not determined by a sequencing method, when performing a method described herein. Sequencing, mapping and related analytical methods are known in the art (e.g., United States Patent Application Publication US2009/0029377, incorporated by reference). Certain aspects of such processes are described hereafter.

As used herein, "reads" (i.e., "a read", "a sequence read") are short nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads).

In some embodiments the nominal, average, mean or absolute length of single-end reads sometimes is about 20 contiguous nucleotides to about 50 contiguous nucleotides, sometimes about 30 contiguous nucleotides to about 40 contiguous nucleotides, and sometimes about 35 contiguous nucleotides or about 36 contiguous nucleotides. In some embodiments, the nominal, average, mean or absolute length of single-end reads is about 20 to about 30 bases in length. In some embodiments, the nominal, average, mean or absolute length of single-end reads is about 24 to about 28 bases in length. In some embodiments, the nominal, average, mean or absolute length of single-end reads is about 21, 22, 23, 24, 25, 26, 27, 28 or about 29 bases in length.

In certain embodiments, the nominal, average, mean or absolute length of the paired-end reads sometimes is about 10 contiguous nucleotides to about 50 contiguous nucleotides (e.g., about 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 or 49 nucleotides in length), sometimes is about 15 contiguous nucleotides to about 25 contiguous nucleotides, and sometimes is about 17 contiguous nucleotides, about 18 contiguous nucleotides, about 20 contiguous nucleotides, about 25 contiguous nucleotides, about 36 contiguous nucleotides or about 45 contiguous nucleotides.

Reads generally are representations of nucleotide sequences in a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Sequence reads obtained from the blood of a pregnant female can be reads from a mixture of fetal and maternal nucleic acid. A mixture of relatively short reads can be transformed by processes described herein into a representation of a genomic nucleic acid present in the pregnant female and/or in the fetus. A mixture of relatively short reads can be transformed into a representation of a copy number variation (e.g., a maternal and/or fetal copy number variation), genetic variation or an aneuploidy, for example. Reads of a mixture of maternal and fetal nucleic acid can be transformed into a representation of a composite chromosome or a segment thereof comprising features of one or both maternal and fetal chromosomes. In certain embodiments, "obtaining" nucleic acid sequence reads of a sample from a subject and/or "obtaining" nucleic acid sequence reads of a biological specimen from one or more reference persons can involve directly sequencing nucleic acid to obtain the sequence information. In some embodiments, "obtaining" can involve receiving sequence information obtained directly from a nucleic acid by another.

Sequence reads can be mapped and the number of reads or sequence tags mapping to a specified nucleic acid region (e.g., a chromosome, a bin, a genomic section) are referred to as counts. In some embodiments, counts can be manipulated or transformed (e.g., normalized, combined, added, filtered, selected, averaged, derived as a mean, the like, or a combination thereof). In some embodiments, counts can be transformed to produce normalized counts. Normalized counts for multiple genomic sections can be provided in a profile (e.g., a genomic profile, a chromosome profile, a profile of a segment of a chromosome). One or more different elevations in a profile also can be manipulated or transformed (e.g., counts associated with elevations can be normalized) and elevations can be adjusted.

In some embodiments, one nucleic acid sample from one individual is sequenced. In certain embodiments, nucleic acid samples from two or more biological samples, where each biological sample is from one individual or two or more individuals, are pooled and the pool is sequenced. In the latter embodiments, a nucleic acid sample from each biological sample often is identified by one or more unique identification tags.

In some embodiments, a fraction of the genome is sequenced, which sometimes is expressed in the amount of the genome covered by the determined nucleotide sequences (e.g., "fold" coverage less than 1). When a genome is sequenced with about 1-fold coverage, roughly 100% of the nucleotide sequence of the genome is represented by reads. A genome also can be sequenced with redundancy, where a given region of the genome can be covered by two or more reads or overlapping reads (e.g., "fold" coverage greater than 1). In some embodiments, a genome is sequenced with about 0.01-fold to about 100-fold coverage, about 0.2-fold to 20-fold coverage, or about 0.2-fold to about 1-fold coverage (e.g., about 0.02-, 0.03-, 0.04-, 0.05-, 0.06-, 0.07-, 0.08-, 0.09-, 0.1-, 0.2-, 0.3-, 0.4-, 0.5-, 0.6-, 0.7-, 0.8-, 0.9-, 1-, 2-, 3-, 4-, 5-, 6-, 7-, 8-, 9-, 10-, 15-, 20-, 30-, 40-, 50-, 60-, 70-, 80-, 90-fold coverage).

In certain embodiments, a subset of nucleic acid fragments is selected prior to sequencing. In certain embodiments, hybridization-based techniques (e.g., using oligonucleotide arrays) can be used to first select for nucleic acid sequences from certain chromosomes (e.g., a potentially aneuploid chromosome and other chromosome(s) not involved in the aneuploidy tested). In some embodiments, nucleic acid can be fractionated by size (e.g., by gel electrophoresis, size exclusion chromatography or by microfluidics-based approach) and in certain instances, fetal nucleic acid can be enriched by selecting for nucleic acid having a lower molecular weight (e.g., less than 300 base pairs, less than 200 base pairs, less than 150 base pairs, less than 100 base pairs). In some embodiments, fetal nucleic acid can be enriched by suppressing maternal background nucleic acid, such as by the addition of formaldehyde. In some embodiments, a portion or subset of a pre-selected set of nucleic acid fragments is sequenced randomly. In some embodiments, the nucleic acid is amplified prior to sequencing. In some embodiments, a portion or subset of the nucleic acid is amplified prior to sequencing.

In some embodiments, a sequencing library is prepared prior to or during a sequencing process. Methods for preparing a sequencing library are known in the art and commercially available platforms may be used for certain applications. Certain commercially available library platforms may be compatible with certain nucleotide sequencing processes described herein. For example, one or more commercially available library platforms may be compatible with a sequencing by synthesis process. In some embodiments, a ligation-based library preparation method is used (e.g., ILLUMINA TRUSEQ, Illumina, San Diego CA). Ligation-based library preparation methods typically use a methylated adaptor design which can incorporate an index sequence at the initial ligation step and often can be used to prepare samples for single-read sequencing, paired-end sequencing and multiplexed sequencing. In some embodiments, a transposon-based library preparation method is used (e.g., EPICENTRE NEXTERA, Epicentre, Madison WI). Transposon-based methods typically use in vitro transposition to simultaneously fragment and tag DNA in a single-tube reaction (often allowing incorporation of platform-specific tags and optional barcodes), and prepare sequencer-ready libraries.

Any sequencing method suitable for conducting methods described herein can be utilized. In some embodiments, a high-throughput sequencing method is used. High-throughput sequencing methods generally involve clonally amplified DNA templates or single DNA molecules that are sequenced in a massively parallel fashion within a flow cell (e.g. as described in Metzker M Nature Rev 11:31-46 (2010); Volkerding et al. Clin Chem 55:641-658 (2009)). Such sequencing methods also can provide digital quantitative information, where each sequence read is a countable "sequence tag" or "count" representing an individual clonal DNA template, a single DNA molecule, bin or chromosome. Next generation sequencing techniques capable of sequencing DNA in a massively parallel fashion are collectively referred to herein as "massively parallel sequencing" (MPS). High-throughput sequencing technologies include, for example, sequencing-by-synthesis with reversible dye terminators, sequencing by oligonucleotide probe ligation, pyrosequencing and real time sequencing. Non-limiting examples of MPS include Massively Parallel Signature Sequencing (MPSS), Polony sequencing, Pyrosequencing, Illumina (Solexa) sequencing, SOLiD sequencing, Ion semiconductor sequencing, DNA nanoball sequencing, Helioscope single molecule sequencing, single molecule real time (SMRT) sequencing, nanopore sequencing, ION Torrent and RNA polymerase (RNAP) sequencing.

Systems utilized for high-throughput sequencing methods are commercially available and include, for example, the Roche 454 platform, the Applied Biosystems SOLID platform, the Helicos True Single Molecule DNA sequencing technology, the sequencing-by-hybridization platform from Affymetrix Inc., the single molecule, real-time (SMRT) technology of Pacific Biosciences, the sequencing-by-synthesis platforms from 454 Life Sciences, Illumina/Solexa and Helicos Biosciences, and the sequencing-by-ligation platform from Applied Biosystems. The ION TORRENT technology from Life technologies and nanopore sequencing also can be used in high-throughput sequencing approaches.

In some embodiments, first generation technology, such as, for example, Sanger sequencing including the automated Sanger sequencing, can be used in a method provided herein. Additional sequencing technologies that include the use of developing nucleic acid imaging technologies (e.g. transmission electron microscopy (TEM) and atomic force microscopy (AFM)), also are contemplated herein. Examples of various sequencing technologies are described below.

A nucleic acid sequencing technology that may be used in a method described herein is sequencing-by-synthesis and reversible terminator-based sequencing (e.g. Illumina's Genome Analyzer; Genome Analyzer II; HISEQ 2000; HISEQ 2500 (Illumina, San Diego CA)). With this technology, millions of nucleic acid (e.g. DNA) fragments can be sequenced in parallel. In one example of this type of sequencing technology, a flow cell is used which contains an optically transparent slide with 8 individual lanes on the surfaces of which are bound oligonucleotide anchors (e.g., adaptor primers). A flow cell often is a solid support that can be configured to retain and/or allow the orderly passage of reagent solutions over bound analytes. Flow cells frequently are planar in shape, optically transparent, generally in the millimeter or sub-millimeter scale, and often have channels or lanes in which the analyte/reagent interaction occurs.

In certain sequencing by synthesis procedures, for example, template DNA (e.g., circulating cell-free DNA (ccfDNA)) sometimes can be fragmented into lengths of several hundred base pairs in preparation for library generation. In some embodiments, library preparation can be performed without further fragmentation or size selection of the template DNA (e.g., ccfDNA). Sample isolation and library generation may be performed using automated methods and apparatus, in certain embodiments. Briefly, template DNA is end repaired by a fill-in reaction, exonuclease reaction or a combination of a fill-in reaction and exonuclease reaction. The resulting blunt-end repaired template DNA is extended by a single nucleotide, which is complementary to a single nucleotide overhang on the 3' end of an adapter primer, and often increases ligation efficiency. Any complementary nucleotides can be used for the extension/overhang nucleotides (e.g., A/T, C/G), however adenine frequently is used to extend the end-repaired DNA, and thymine often is used as the 3' end overhang nucleotide.

In certain sequencing by synthesis procedures, for example, adapter oligonucleotides are complementary to the flow-cell anchors, and sometimes are utilized to associate the modified template DNA (e.g., end-repaired and single nucleotide extended) with a solid support, such as the inside surface of a flow cell, for example. In some embodiments, the adapter also includes identifiers (i.e., indexing nucleotides, or "barcode" nucleotides (e.g., a unique sequence of nucleotides usable as an identifier to allow unambiguous identification of a sample and/or chromosome)), one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing). Identifiers or nucleotides contained in an adapter often are six or more nucleotides in length, and frequently are positioned in the adaptor such that the identifier nucleotides are the first nucleotides sequenced during the sequencing reaction. In certain embodiments, identifier nucleotides are associated with a sample but are sequenced in a separate sequencing reaction to avoid compromising the quality of sequence reads. Subsequently, the reads from the identifier sequencing and the DNA template sequencing are linked together and the reads de-multiplexed. After linking and de-multiplexing the sequence reads and/or identifiers can be further adjusted or processed as described herein.

In certain sequencing by synthesis procedures, utilization of identifiers allows multiplexing of sequence reactions in a flow cell lane, thereby allowing analysis of multiple samples per flow cell lane. The number of samples that can be analyzed in a given flow cell lane often is dependent on the number of unique identifiers utilized during library preparation and/or probe design. Non limiting examples of commercially available multiplex sequencing kits include Illumina's multiplexing sample preparation oligonucleotide kit and multiplexing sequencing primers and PhiX control kit (e.g., Illumina's catalog numbers PE-400-1001 and PE-400-1002, respectively). A method described herein can be performed using any number of unique identifiers (e.g., 4, 8, 12, 24, 48, 96, or more). The greater the number of unique identifiers, the greater the number of samples and/or chromosomes, for example, that can be multiplexed in a single flow cell lane. Multiplexing using 12 identifiers, for example, allows simultaneous analysis of 96 samples (e.g., equal to the number of wells in a 96 well microwell plate) in an 8 lane flow cell. Similarly, multiplexing using 48 identifiers, for example, allows simultaneous analysis of 384 samples (e.g., equal to the number of wells in a 384 well microwell plate) in an 8 lane flow cell.

In certain sequencing by synthesis procedures, adapter-modified, single-stranded template DNA is added to the flow cell and immobilized by hybridization to the anchors under limiting-dilution conditions. In contrast to emulsion PCR, DNA templates are amplified in the flow cell by "bridge" amplification, which relies on captured DNA strands "arching" over and hybridizing to an adjacent anchor oligonucleotide. Multiple amplification cycles convert the single-molecule DNA template to a clonally amplified arching "cluster," with each cluster containing approximately 1000 clonal molecules. Approximately $50\times10^6$ separate clusters can be generated per flow cell. For sequencing, the clusters are denatured, and a subsequent chemical cleavage reaction and wash leave only forward strands for single-end sequencing. Sequencing of the forward strands is initiated by hybridizing a primer complementary to the adapter sequences, which is followed by addition of polymerase and a mixture of four differently colored fluorescent reversible dye terminators. The terminators are incorporated according to sequence complementarity in each strand in a clonal cluster. After incorporation, excess reagents are washed away, the clusters are optically interrogated, and the fluorescence is recorded. With successive chemical steps, the reversible dye terminators are unblocked, the fluorescent labels are cleaved and washed away, and the next sequencing cycle is performed. This iterative, sequencing-by-synthesis process sometimes requires approximately 2.5 days to generate read lengths of 36 bases. With $50 \times 10^6$ clusters per flow cell, the overall sequence output can be greater than 1 billion base pairs (Gb) per analytical run.

Another nucleic acid sequencing technology that may be used with a method described herein is 454 sequencing (Roche). 454 sequencing uses a large-scale parallel pyrosequencing system capable of sequencing about 400-600 megabases of DNA per run. The process typically involves two steps. In the first step, sample nucleic acid (e.g. DNA) is sometimes fractionated into smaller fragments (300-800 base pairs) and polished (made blunt at each end). Short adaptors are then ligated onto the ends of the fragments. These adaptors provide priming sequences for both amplification and sequencing of the sample-library fragments. One adaptor (Adaptor B) contains a 5'-biotin tag for immobilization of the DNA library onto streptavidin-coated beads. After nick repair, the non-biotinylated strand is released and used as a single-stranded template DNA (sstDNA) library. The sstDNA library is assessed for its quality and the optimal amount (DNA copies per bead) needed for emPCR is determined by titration. The sstDNA library is immobilized onto beads. The beads containing a library fragment carry a single sstDNA molecule. The bead-bound library is emulsified with the amplification reagents in a water-in-oil mixture. Each bead is captured within its own microreactor where PCR amplification occurs. This results in bead-immobilized, clonally amplified DNA fragments.

In the second step of 454 sequencing, single-stranded template DNA library beads are added to an incubation mix containing DNA polymerase and are layered with beads containing sulfurylase and luciferase onto a device containing pico-liter sized wells. Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing exploits the release of pyrophosphate (PPi) upon nucleotide addition. PPi is converted to ATP by ATP sulfurylase in the presence of adenosine 5' phosphosulfate. Luciferase uses ATP to convert luciferin to oxyluciferin, and this reaction generates light that is discerned and analyzed (see, for example, Margulies, M. et al. Nature 437:376-380 (2005)).

Another nucleic acid sequencing technology that may be used in a method provided herein is Applied Biosystems' SOLiD™ technology. In SOLiD™ sequencing-by-ligation, a library of nucleic acid fragments is prepared from the sample and is used to prepare clonal bead populations. With this method, one species of nucleic acid fragment will be present on the surface of each bead (e.g. magnetic bead). Sample nucleic acid (e.g. genomic DNA) is sheared into fragments, and adaptors are subsequently attached to the 5' and 3' ends of the fragments to generate a fragment library. The adapters are typically universal adapter sequences so that the starting sequence of every fragment is both known and identical. Emulsion PCR takes place in microreactors containing all the necessary reagents for PCR. The resulting PCR products attached to the beads are then covalently bound to a glass slide. Primers then hybridize to the adapter sequence within the library template. A set of four fluorescently labeled di-base probes compete for ligation to the sequencing primer. Specificity of the di-base probe is achieved by interrogating every 1st and 2nd base in each ligation reaction. Multiple cycles of ligation, detection and cleavage are performed with the number of cycles determining the eventual read length. Following a series of ligation cycles, the extension product is removed and the template is reset with a primer complementary to the n−1 position for a second round of ligation cycles. Often, five rounds of primer reset are completed for each sequence tag. Through the primer reset process, each base is interrogated in two independent ligation reactions by two different primers. For example, the base at read position 5 is assayed by primer number 2 in ligation cycle 2 and by primer number 3 in ligation cycle 1. Another nucleic acid sequencing technology that may be used in a method described herein is the Helicos True Single Molecule Sequencing (tSMS). In the tSMS technique, a polyA sequence is added to the 3' end of each nucleic acid (e.g. DNA) strand from the sample. Each strand is labeled by the addition of a fluorescently labeled adenosine nucleotide. The DNA strands are then hybridized to a flow cell, which contains millions of oligo-T capture sites that are immobilized to the flow cell surface. The templates can be at a density of about 100 million templates/$cm^2$. The flow cell is then loaded into a sequencing apparatus and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are detected by imaging the flow cell surface. After imaging, a cleavage step removes the fluorescent label, and the process is repeated with other fluorescently labeled nucleotides until the desired read length is achieved. Sequence information is collected with each nucleotide addition step (see, for example, Harris T. D. et al., Science 320:106-109 (2008)).

Another nucleic acid sequencing technology that may be used in a method provided herein is the single molecule, real-time (SMRT™) sequencing technology of Pacific Biosciences. With this method, each of the four DNA bases is attached to one of four different fluorescent dyes. These dyes are phospholinked. A single DNA polymerase is immobilized with a single molecule of template single stranded DNA at the bottom of a zero-mode waveguide (ZMW). A ZMW is a confinement structure which enables observation of incorporation of a single nucleotide by DNA polymerase against the background of fluorescent nucleotides that rapidly diffuse in an out of the ZMW (in microseconds). It takes several milliseconds to incorporate a nucleotide into a growing strand. During this time, the fluorescent label is excited and produces a fluorescent signal, and the fluorescent tag is cleaved off. Detection of the corresponding fluorescence of the dye indicates which base was incorporated. The process is then repeated.

Another nucleic acid sequencing technology that may be used in a method described herein is ION TORRENT (Life Technologies) single molecule sequencing which pairs semiconductor technology with a simple sequencing chemistry to directly translate chemically encoded information (A, C, G, T) into digital information (0, 1) on a semiconductor chip. ION TORRENT uses a high-density array of micro-machined wells to perform nucleic acid sequencing in a massively parallel way. Each well holds a different DNA molecule. Beneath the wells is an ion-sensitive layer and beneath that an ion sensor. Typically, when a nucleotide is incorporated into a strand of DNA by a polymerase, a hydrogen ion is released as a byproduct. If a nucleotide, for example a C, is added to a DNA template and is then incorporated into a strand of DNA, a hydrogen ion will be released. The charge from that ion will change the pH of the solution, which can be detected by an ion sensor. A sequencer can call the base, going directly from chemical information to digital information. The sequencer then sequentially floods the chip with one nucleotide after another. If the next nucleotide that floods the chip is not a match, no voltage change will be recorded and no base will be called. If there are two identical bases on the DNA strand, the voltage will be double, and the chip will record two identical bases called. Because this is direct detection (i.e. detection without scanning, cameras or light), each nucleotide incorporation is recorded in seconds.

Another nucleic acid sequencing technology that may be used in a method described herein is the chemical-sensitive field effect transistor (CHEMFET) array. In one example of this sequencing technique, DNA molecules are placed into reaction chambers, and the template molecules can be hybridized to a sequencing primer bound to a polymerase. Incorporation of one or more triphosphates into a new nucleic acid strand at the 3' end of the sequencing primer can be detected by a change in current by a CHEMFET sensor. An array can have multiple CHEMFET sensors. In another example, single nucleic acids are attached to beads, and the nucleic acids can be amplified on the bead, and the individual beads can be transferred to individual reaction chambers on a CHEMFET array, with each chamber having a CHEMFET sensor, and the nucleic acids can be sequenced (see, for example, U.S. Patent Application Publication No. 2009/0026082).

Another nucleic acid sequencing technology that may be used in a method described herein is electron microscopy. In one example of this sequencing technique, individual nucleic acid (e.g. DNA) molecules are labeled using metallic labels that are distinguishable using an electron microscope. These molecules are then stretched on a flat surface and imaged using an electron microscope to measure sequences (see, for example, Moudrianakis E. N. and Beer M. Proc Natl Acad Sci USA. 1965 March; 53:564-71). In some embodiments, transmission electron microscopy (TEM) is used (e.g. Halcyon Molecular's TEM method). This method, termed Individual Molecule Placement Rapid Nano Transfer (IMPRNT), includes utilizing single atom resolution transmission electron microscope imaging of high-molecular weight (e.g. about 150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA (see, for example, International Patent Application No. WO 2009/046445).

Other sequencing methods that may be used to conduct methods herein include digital PCR and sequencing by hybridization. Digital polymerase chain reaction (digital PCR or dPCR) can be used to directly identify and quantify nucleic acids in a sample. Digital PCR can be performed in an emulsion, in some embodiments. For example, individual nucleic acids are separated, e.g., in a microfluidic chamber device, and each nucleic acid is individually amplified by PCR. Nucleic acids can be separated such that there is no more than one nucleic acid per well. In some embodiments, different probes can be used to distinguish various alleles (e.g. fetal alleles and maternal alleles). Alleles can be enumerated to determine copy number. In sequencing by hybridization, the method involves contacting a plurality of polynucleotide sequences with a plurality of polynucleotide probes, where each of the plurality of polynucleotide probes can be optionally tethered to a substrate. The substrate can be a flat surface with an array of known nucleotide sequences, in some embodiments. The pattern of hybridization to the array can be used to determine the polynucleotide sequences present in the sample. In some embodiments, each probe is tethered to a bead, e.g., a magnetic bead or the like. Hybridization to the beads can be identified and used to identify the plurality of polynucleotide sequences within the sample.

In some embodiments, nanopore sequencing can be used in a method described herein. Nanopore sequencing is a single-molecule sequencing technology whereby a single nucleic acid molecule (e.g. DNA) is sequenced directly as it passes through a nanopore. A nanopore is a small hole or channel, of the order of 1 nanometer in diameter. Certain transmembrane cellular proteins can act as nanopores (e.g. alpha-hemolysin). Nanopores sometimes can be synthesized (e.g. using a silicon platform). Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree and generates characteristic changes to the current. The amount of current which can pass through the nanopore at any given moment therefore varies depending on whether the nanopore is blocked by an A, a C, a G, a T, or in some instances, methyl-C. The change in the current through the nanopore as the DNA molecule passes through the nanopore represents a direct reading of the DNA sequence. A nanopore sometimes can be used to identify individual DNA bases as they pass through the nanopore in the correct order (see, for example, Soni G V and Meller A. Clin. Chem. 53: 1996-2001 (2007); International Patent Application No. WO2010/004265).

There are a number of ways that nanopores can be used to sequence nucleic acid molecules. In some embodiments, an exonuclease enzyme, such as a deoxyribonuclease, is used. In this case, the exonuclease enzyme is used to sequentially detach nucleotides from a nucleic acid (e.g. DNA) molecule. The nucleotides are then detected and discriminated by the nanopore in order of their release, thus reading the sequence of the original strand. For such an embodiment, the exonuclease enzyme can be attached to the nanopore such that a proportion of the nucleotides released from the DNA molecule is capable of entering and interacting with the channel of the nanopore. The exonuclease can be attached to the nanopore structure at a site in close proximity to the part of the nanopore that forms the opening of the channel. The exonuclease enzyme sometimes can be attached to the nanopore structure such that its nucleotide exit trajectory site is orientated towards the part of the nanopore that forms part of the opening.

In some embodiments, nanopore sequencing of nucleic acids involves the use of an enzyme that pushes or pulls the nucleic acid (e.g. DNA) molecule through the pore. In this case, the ionic current fluctuates as a nucleotide in the DNA molecule passes through the pore. The fluctuations in the current are indicative of the DNA sequence. For such an embodiment, the enzyme can be attached to the nanopore structure such that it is capable of pushing or pulling the target nucleic acid through the channel of a nanopore without interfering with the flow of ionic current through the pore. The enzyme can be attached to the nanopore structure at a site in close proximity to the part of the structure that forms part of the opening. The enzyme can be attached to the subunit, for example, such that its active site is orientated towards the part of the structure that forms part of the opening.

In some embodiments, nanopore sequencing of nucleic acids involves detection of polymerase bi-products in close proximity to a nanopore detector. In this case, nucleoside phosphates (nucleotides) are labeled so that a phosphate labeled species is released upon the addition of a polymerase to the nucleotide strand and the phosphate labeled species is detected by the pore. Typically, the phosphate species contains a specific label for each nucleotide. As nucleotides are sequentially added to the nucleic acid strand, the bi-products of the base addition are detected. The order that the phosphate labeled species are detected can be used to determine the sequence of the nucleic acid strand.

The length of the sequence read is often associated with the particular sequencing technology. High-throughput methods, for example, provide sequence reads that can vary in size from tens to hundreds of base pairs (bp). Nanopore sequencing, for example, can provide sequence reads that can vary in size from tens to hundreds to thousands of base pairs. In some embodiments, the sequence reads are of a mean, median or average length of about 15 bp to 900 bp long (e.g. about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median, mode or average length of about 1000 bp or more.

In some embodiments, chromosome-specific sequencing is performed. In some embodiments, chromosome-specific sequencing is performed utilizing DANSR (digital analysis of selected regions). Digital analysis of selected regions enables simultaneous quantification of hundreds of loci by cfDNA-dependent catenation of two locus-specific oligonucleotides via an intervening 'bridge' oligo to form a PCR template. In some embodiments, chromosome-specific sequencing is performed by generating a library enriched in chromosome-specific sequences. In some embodiments, sequence reads are obtained only for a selected set of chromosomes. In some embodiments, sequence reads are obtained only for chromosomes 21, 18 and 13.

In some embodiments, nucleic acids may include a fluorescent signal or sequence tag information. Quantification of the signal or tag may be used in a variety of techniques such as, for example, flow cytometry, quantitative polymerase chain reaction (qPCR), gel electrophoresis, gene-chip analysis, microarray, mass spectrometry, cytofluorimetric analysis, fluorescence microscopy, confocal laser scanning microscopy, laser scanning cytometry, affinity chromatography, manual batch mode separation, electric field suspension, sequencing, and combination thereof.

Sequencing Module

Sequencing and obtaining sequencing reads can be provided by a sequencing module or by an apparatus comprising a sequencing module. A "sequence receiving module" as used herein is the same as a "sequencing module". An apparatus comprising a sequencing module can be any apparatus that determines the sequence of a nucleic acid from a sequencing technology known in the art. In certain embodiments, an apparatus comprising a sequencing module performs a sequencing reaction known in the art. A sequencing module generally provides a nucleic acid sequence read according to data from a sequencing reaction (e.g., signals generated from a sequencing apparatus). In some embodiments, a sequencing module or an apparatus comprising a sequencing module is required to provide sequencing reads. In some embodiments a sequencing module can receive, obtain, access or recover sequence reads from another sequencing module, computer peripheral, operator, server, hard drive, apparatus or from a suitable source. In some embodiments, a sequencing module can manipulate sequence reads. For example, a sequencing module can align, assemble, fragment, complement, reverse complement, error check, or error correct sequence reads. An apparatus comprising a sequencing module can comprise at least one processor. In some embodiments, sequencing reads are provided by an apparatus that includes a processor (e.g., one or more processors) which processor can perform and/or implement one or more instructions (e.g., processes, routines and/or subroutines) from the sequencing module. In some embodiments, sequencing reads are provided by an apparatus that includes multiple processors, such as processors coordinated and working in parallel. In some embodiments, a sequencing module operates with one or more external processors (e.g., an internal or external network, server, storage device and/or storage network (e.g., a cloud)). In some embodiments, a sequencing module gathers, assembles and/or receives data and/or information from another module, apparatus, peripheral, component or specialized component (e.g., a sequencer). In some embodiments, sequencing reads are provided by an apparatus comprising one or more of the following: one or more flow cells, a camera, a photo detector, a photo cell, fluid handling components, a printer, a display (e.g., an LED, LCT or CRT) and the like. Often a sequencing module receives, gathers and/or assembles sequence reads. In some embodiments, a sequencing module accepts and gathers input data and/or information from an operator of an apparatus. For example, sometimes an operator of an apparatus provides instructions, a constant, a threshold value, a formula or a predetermined value to a module. In some embodiments, a sequencing module can transform data and/or information that it receives into a contiguous nucleic acid sequence. In some embodiments, a nucleic acid sequence provided by a sequencing module is printed or displayed. In some embodiments, sequence reads are provided by a sequencing module and transferred from a sequencing module to an apparatus or an apparatus comprising any suitable peripheral, component or specialized component. In some embodiments, data and/or information are provided from a sequencing module to an apparatus that includes multiple processors, such as processors coordinated and working in parallel. In some embodiments, data and/or information related to sequence reads can be transferred from a sequencing module to any other suitable module. A sequencing module can transfer sequence reads to a mapping module or counting module, in some embodiments.

Mapping Reads

Mapping nucleotide sequence reads (i.e., sequence information from a fragment whose physical genomic position is unknown) can be performed in a number of ways, and often comprises alignment of the obtained sequence reads with a matching sequence in a reference genome (e.g., Li et al., "Mapping short DNA sequencing reads and calling variants using mapping quality score," Genome Res., 2008 Aug. 19.) In such alignments, sequence reads generally are aligned to a reference sequence and those that align are designated as being "mapped" or a "sequence tag." In some embodiments, a mapped sequence read is referred to as a "hit" or a "count". In some embodiments, mapped sequence reads are grouped together according to various parameters and assigned to particular genomic sections, which are discussed in further detail below.

As used herein, the terms "aligned", "alignment", or "aligning" refer to two or more nucleic acid sequences that can be identified as a match (e.g., 100% identity) or partial match. Alignments can be done manually or by a computer algorithm, examples including the Efficient Local Alignment of Nucleotide Data (ELAND) computer program distributed as part of the Illumina Genomics Analysis pipeline. The alignment of a sequence read can be a 100% sequence match. In some embodiments, an alignment is less than a 100% sequence match (i.e., non-perfect match, partial match, partial alignment). In some embodiments an alignment is about a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% match. In some embodiments, an alignment comprises a mismatch. In some embodiments, an alignment comprises 1, 2, 3, 4 or 5 mismatches. Two or more sequences can be aligned using either strand. In some embodiments, a nucleic acid sequence is aligned with the reverse complement of another nucleic acid sequence.

Various computational methods can be used to map each sequence read to a genomic section. Non-limiting examples of computer algorithms that can be used to align sequences include, without limitation, BLAST, BLITZ, FASTA, BOWTIE 1, BOWTIE 2, ELAND, MAQ, PROBEMATCH, SOAP or SEQMAP, or variations thereof or combinations thereof. In some embodiments, sequence reads can be aligned with sequences in a reference genome. In some embodiments, sequence reads can be found and/or aligned with sequences in nucleic acid databases known in the art including, for example, GenBank, dbEST, dbSTS, EMBL (European Molecular Biology Laboratory) and DDBJ (DNA Databank of Japan). BLAST or similar tools can be used to search the identified sequences against a sequence database. Search hits can then be used to sort the identified sequences into appropriate genomic sections (described hereafter), for example.

The term "sequence tag" is herein used interchangeably with the term "mapped sequence tag" to refer to a sequence read that has been specifically assigned i.e. mapped, to a larger sequence e.g. a reference genome, by alignment. Mapped sequence tags are uniquely mapped to a reference genome i.e. they are assigned to a single location to the reference genome. Tags that can be mapped to more than one location on a reference genome i.e. tags that do not map uniquely, are not included in the analysis. A "sequence tag" can be a nucleic acid (e.g. DNA) sequence (i.e. read) assigned specifically to a particular genomic section and/or chromosome (i.e. one of chromosomes 1-22, X or Y for a human subject). A sequence tag may be repetitive or non-repetitive within a single segment of the reference genome (e.g., a chromosome). In some embodiments, repetitive sequence tags are eliminated from further analysis (e.g. quantification). In some embodiments, a read may uniquely or non-uniquely map to sections in the reference genome. A read is considered to be "uniquely mapped" if it aligns with a single sequence in the reference genome. A read is considered to be "non-uniquely mapped" if it aligns with two or more sequences in the reference genome. In some embodiments, non-uniquely mapped reads are eliminated from further analysis (e.g. quantification). A certain, small degree of mismatch (0-1) may be allowed to account for single nucleotide polymorphisms that may exist between the reference genome and the reads from individual samples being mapped, in certain embodiments. In some embodiments, no degree of mismatch is allowed for a read to be mapped to a reference sequence.

As used herein, the term "reference genome" can refer to any particular known, sequenced or characterized genome, whether partial or complete, of any organism or virus which may be used to reference identified sequences from a subject. For example, a reference genome used for human subjects as well as many other organisms can be found at the National Center for Biotechnology Information at world wide web universal source code address ncbi.nlm.nih.gov. A "genome" refers to the complete genetic information of an organism or virus, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. In some embodiments, a reference genome comprises sequences assigned to chromosomes.

In certain embodiments, where a sample nucleic acid is from a pregnant female, a reference sequence sometimes is not from the fetus, the mother of the fetus or the father of the fetus, and is referred to herein as an "external reference." A maternal reference may be prepared and used in some embodiments. A reference sometimes is prepared from maternal nucleic acid (e.g., cellular nucleic acid). When a reference from the pregnant female is prepared ("maternal reference sequence") based on an external reference, reads from DNA of the pregnant female that contains substantially no fetal DNA often are mapped to the external reference sequence and assembled. In certain embodiments the external reference is from DNA of an individual having substantially the same ethnicity as the pregnant female. A maternal reference sequence may not completely cover the maternal genomic DNA (e.g., it may cover about 50%, 60%, 70%, 80%, 90% or more of the maternal genomic DNA), and the maternal reference may not perfectly match the maternal genomic DNA sequence (e.g., the maternal reference sequence may include multiple mismatches).

In some embodiments, mappability is assessed for a genomic region (e.g., genomic section, genomic portion, bin). Mappability is the ability to unambiguously align a nucleotide sequence read to a section of a reference genome, typically up to a specified number of mismatches, including, for example, 0, 1, 2 or more mismatches. For a given genomic region, the expected mappability can be estimated using a sliding-window approach of a preset read length and averaging the resulting read-level mappability values. Genomic regions comprising stretches of unique nucleotide sequence sometimes have a high mappability value.

In some embodiments, a mapping feature is assessed for a genomic region (e.g., genomic section, genomic portion, bin). Mapping features can include any feature of a genomic region can directly of indirectly influence mapping of sequence reads thereto. Mapping features can include, for example, a measure of mappability, nucleotide sequence, nucleotide composition, location within the genome, location within a chromosome, proximity to certain regions within a chromosome, and the like. In some embodiments, a mapping feature can be a measure of mappability for the genomic region. In some embodiments, a mapping feature can be GC content of the genomic region. In some embodiments, a mapping feature can influence experimental bias (e.g., mappability bias, GC bias) for certain genomic regions, as described in further detail herein.

Mapping Module

Sequence reads can be mapped by a mapping module or by an apparatus comprising a mapping module, which mapping module generally maps reads to a reference genome or segment thereof. A mapping module can map sequencing reads by a suitable method known in the art. In some embodiments, a mapping module or an apparatus comprising a mapping module is required to provide mapped sequence reads. An apparatus comprising a mapping module can comprise at least one processor. In some embodiments, mapped sequencing reads are provided by an apparatus that includes a processor (e.g., one or more processors) which processor can perform and/or implement one or more instructions (e.g., processes, routines and/or subroutines) from the mapping module. In some embodiments, sequencing reads are mapped by an apparatus that includes multiple processors, such as processors coordinated and working in parallel. In some embodiments, nucleic acid fragment length is determined based on the mapped sequence reads (e.g., paired-end reads) by an apparatus that includes multiple processors, such as processors coordinated and working in parallel. In some embodiments, a mapping module operates with one or more external processors (e.g., an internal or external network, server, storage device and/or storage network (e.g., a cloud)). An apparatus may comprise a mapping module and a sequencing module. In some embodiments, sequence reads are mapped by an apparatus comprising one or more of the following: one or more flow cells, a camera, fluid handling components, a printer, a display (e.g., an LED, LCT or CRT) and the like. A mapping module can receive sequence reads from a sequencing module, in some embodiments. Mapped sequencing reads can be transferred from a mapping module to a counting module or a normalization module, in some embodiments.

Genomic Sections

In some embodiments, mapped sequence reads (i.e. sequence tags) are grouped together according to various parameters and assigned to particular genomic sections. Often, the individual mapped sequence reads can be used to identify an amount of a genomic section present in a sample. In some embodiments, the amount of a genomic section can be indicative of the amount of a larger sequence (e.g. a chromosome) in the sample. The term "genomic section" can also be referred to herein as a "sequence window", "section", "bin", "locus", "region", "partition", "portion" (e.g., portion of a reference genome, portion of a chromosome) or "genomic portion." In some embodiments, a genomic section is an entire chromosome, portion of a chromosome, portion of a reference genome, multiple chromosome portions, multiple chromosomes, portions from multiple chromosomes, and/or combinations thereof. In some embodiments, a genomic section is predefined based on specific parameters. In some embodiments, a genomic section is arbitrarily defined based on partitioning of a genome (e.g., partitioned by size, portions, contiguous regions, contiguous regions of an arbitrarily defined size, and the like).

In some embodiments, a genomic section is delineated based on one or more parameters which include, for example, length or a particular feature or features of the sequence. Genomic sections can be selected, filtered and/or removed from consideration using any suitable criteria know in the art or described herein. In some embodiments, a genomic section is based on a particular length of genomic sequence. In some embodiments, a method can include analysis of multiple mapped sequence reads to a plurality of genomic sections. Genomic sections can be approximately the same length or the genomic sections can be different lengths. In some embodiments, genomic sections are of about equal length. In some embodiments genomic sections of different lengths are adjusted or weighted. In some embodiments, a genomic section is about 10 kilobases (kb) to about 100 kb, about 20 kb to about 80 kb, about 30 kb to about 70 kb, about 40 kb to about 60 kb, and sometimes about 50 kb. In some embodiments, a genomic section is about 10 kb to about 20 kb. A genomic section is not limited to contiguous runs of sequence. Thus, genomic sections can be made up of contiguous and/or non-contiguous sequences. A genomic section is not limited to a single chromosome. In some embodiments, a genomic section includes all or part of one chromosome or all or part of two or more chromosomes. In some embodiments, genomic sections may span one, two, or more entire chromosomes. In addition, the genomic sections may span joint or disjointed portions of multiple chromosomes.

In some embodiments, genomic sections can be particular chromosome portion in a chromosome of interest, such as, for example, chromosomes where a genetic variation is assessed (e.g. an aneuploidy of chromosomes 13, 18 and/or 21 or a sex chromosome). A genomic section can also be a pathogenic genome (e.g. bacterial, fungal or viral) or fragment thereof. Genomic sections can be genes, gene fragments, regulatory sequences, introns, exons, and the like.

In some embodiments, a genome (e.g. human genome) is partitioned into genomic sections based on the information content of the regions. The resulting genomic regions may contain sequences for multiple chromosomes and/or may contain sequences for portions of multiple chromosomes. In some embodiments, the partitioning may eliminate similar locations across the genome and only keep unique regions. The eliminated regions may be within a single chromosome or may span multiple chromosomes. The resulting genome is thus trimmed down and optimized for faster alignment, often allowing for focus on uniquely identifiable sequences.

In some embodiments, the partitioning may down weight similar regions. The process for down weighting a genomic section is discussed in further detail below. In some embodiments, the partitioning of the genome into regions transcending chromosomes may be based on information gain produced in the context of classification. For example, the information content may be quantified using the p-value profile measuring the significance of particular genomic locations for distinguishing between groups of confirmed normal and abnormal subjects (e.g. euploid and aneuploid (e.g. trisomy) subjects, respectively). In some embodiments, the partitioning of the genome into regions transcending chromosomes may be based on any other criterion, such as, for example, speed/convenience while aligning tags, high or low GC content, uniformity of GC content, other measures of sequence content (e.g. fraction of individual nucleotides, fraction of pyrimidines or purines, fraction of natural vs. non-natural nucleic acids, fraction of methylated nucleotides, and CpG content), methylation state, duplex melting temperature, amenability to sequencing or PCR, uncertainty value assigned to individual bins, and/or a targeted search for particular features.

A "segment" of a chromosome generally is part of a chromosome, and typically is a different part of a chromosome than a genomic section (e.g., bin). A segment of a chromosome sometimes is in a different region of a chromosome than a genomic section, sometimes does not share a polynucleotide with a genomic section, and sometimes includes a polynucleotide that is in a genomic section. A segment of a chromosome often contains a larger number of nucleotides than a genomic section (e.g., a segment sometimes includes a genomic section), and sometimes a segment of a chromosome contains a smaller number of nucleotides than a genomic section (e.g., a segment sometimes is within a genomic section).

Sex Chromosome Genomic Sections

In some embodiments, nucleotide sequence reads are mapped to genomic sections on one or more sex chromosomes (i.e., chromosome X, chromosome Y). Chromosome X and chromosome Y genomic sections can be selected based on certain criteria including cross-validation parameters, error parameters, mappability, repeatability, male versus female separation and/or any other feature described herein for genomic sections.

In some embodiments, chromosome X and/or chromosome Y genomic sections are selected based, in part, on a measure of error for each genomic section. In some embodiments, a measure of error is calculated for counts of sequence reads mapped to some or all of the sections of a reference genome. In some instances, counts of sequence reads are removed or weighted for certain sections of the reference genome according to a threshold of the measure of error. In some embodiments, the threshold is selected according to a standard deviation gap between a first genomic section level and a second genomic section level. Such a gap can be about 1.0 or greater. For example, a standard deviation gap can be about 1.0, 1.5, 2.0, 2.5, 3.0, 3.1, 3.2, 3.3, 3.4, 3.5, 3.6, 3.7, 3.8, 3.9, 4.0, 4.5, 5.0 or greater. In certain embodiments, the standard deviation gap can be about 3.5 or greater. In some embodiments, the measure of error is represented by an R factor (e.g., based on cross validation experiments as described herein). In some embodiments, counts of sequence reads for a section of the reference genome (e.g., a section on chromosome X and/or chromosome Y) having an R factor value of about 5% or greater are removed prior to a normalization process, such as a normalization process described herein. For example, counts of sequence reads for a section of the reference genome having an R factor value of about 5.0%, 5.5%, 6.0%, 6.5%, 6.6%, 6.7%, 6.8%, 6.9%, 7.0%, 7.1%, 7.2%, 7.3%, 7.4%, 7.5%, 8.0%, 8.5%, 9.0%, 9.5%, 10.0% or greater can be removed prior to a normalization process. In some embodiments, counts of sequence reads for a section of the reference genome having an R factor value of about 7.0% or greater are removed prior to a normalization process. In some embodiments, counts of sequence reads for a section of the reference genome having an R factor value of between about 7.0% to about 10.0% are removed prior to a normalization process.

In some embodiments, the reference genome comprises genomic sections of chromosome Y. In some embodiments a selected set of chromosome Y sections are used for certain methods described herein. Chromosome Y bins sometimes are selected based on parameters derived from adult male controls. In certain embodiments, chromosome Y bins are selected according to a particular degree of male versus female separation. For example, bins having sequence read counts in male pregnancies that exceed sequence read counts for female pregnancies by a particular value or factor may be selected. A factor may be 2 or more. For example, a factor may be 2, 3, 4, 5, 6, 7, 8, 9, 10 or more. In some embodiments, bins having sequence read counts in male pregnancies that exceed sequence read counts for female pregnancies by a factor of 6 or more are selected.

In some embodiments, chromosome Y bins are selected that may be informative for gender determination and/or detecting the presence or absence of a sex aneuploidy. Informative chromosome Y bins can be identified, in some embodiments, by generating euploid count profiles. In some embodiments, the euploid count profiles are normalized. In some embodiments, the euploid count profiles are normalized according to the PERUN procedure described herein. In some embodiments, the euploid count profiles are GCRM normalized. In some embodiments, the euploid count profiles are not normalized (e.g., raw counts are used). Euploid count profiles can be segregated according to fetal gender. For each chromosome Y section, the median, mean, mode or other statistical manipulation, and the MAD, standard deviation or other measure of error can be evaluated separately for each subset. In some embodiments, the median and MAD are evaluated separately for each subset. The two medians and MADs, for example, can be combined to yield a single, genomic section-specific t-statistics value, which can be determined according Equation β:

$$t = \frac{Y_m - Y_f}{\sqrt{\frac{S_m^2}{N_m} + \frac{S_f^2}{N_f}}} \quad \text{Equation } \beta$$

where:

t=t-value for a given ChrY bin.

$N_m$=the number of male euploid pregnancies.

$Y_m$=median PERUN-normalized counts evaluated for all $N_m$ male pregnancies for a given ChrY bin. The median can be replaced with mean, in certain instances. The PERUN-normalized counts can be replaced by raw counts or GCRM counts or any other unnormalized or normalized counts.

$S_m$=MAD PERUN-normalized counts evaluated for all $N_m$ male pregnancies for a given ChrY bin. The MAD can be replaced with standard deviation, in certain instances. The PERUN-normalized counts can be replaced by raw counts or GCRM counts or any other unnormalized or normalized counts.

$N_f$=The number of female euploid pregnancies.

$Y_f$=Median PERUN-normalized counts evaluated for all $N_f$ female pregnancies for a given ChrY bin. The median can be replaced with mean, in certain instances. The PERUN-normalized counts can be replaced by raw counts or GCRM counts or any other unnormalized or normalized counts.

$S_f$=MAD PERUN-normalized counts evaluated for all $N_f$ female pregnancies for a given ChrY bin. The MAD can be replaced with standard deviation, in certain instances. The PERUN-normalized counts can be replaced by raw counts or GCRM counts or any other unnormalized or normalized counts.

A bin can be selected if the t-value is greater than or equal to a certain cutoff value. In some embodiments, bins having t-values greater than or equal to 10 are selected. For example, bins having t-values greater than or equal to 20, 30, 35, 40, 45, 46, 47, 48, 49, 50, 51, 52, 53, 54, 55, 60, 65, 70, 80, 90 or 100 can be selected In some embodiments, a bin can be selected if the t-value is greater than or equal to 50 (t≥50).

In some embodiments, about 10 to about 500 or more sections of chromosome Y can be selected. For example, about 10, 11, 12, 13, 14, 15, 16, 17, 18, 19, 20, 21, 22, 23, 24, 25, 26, 27, 28, 29, 30, 31, 32, 33, 34, 35, 40, 45, 50, 55, 60, 65, 70, 75, 80, 85, 90, 95, 100, 200, 210, 220, 230, 300, 400, 500 or more sections of chromosome Y can be selected. In some embodiments, about 20 or more sections of chromosome Y are selected. In some embodiments, 26 chromosome Y bins are selected. In some embodiments, about 220 or more sections of chromosome Y are selected. In some embodiments, 226 chromosome Y bins are selected. In some embodiments, chromosome Y bins are chosen from among the genomic sections of Table 3. In some embodiments, chromosome Y bins comprise one or more of ChrY_1176, ChrY_1177, and ChrY_1176. In some embodiments, chromosome Y bins do not comprise one or more of ChrY_1176, ChrY_1177, and/or ChrY_1176. Whether or not such bins are included in a method herein is described in Example 13.

In some embodiments, the reference genome comprises genomic sections of chromosome X. In some embodiments a selected set of chromosome X sections are used for certain methods described herein. Certain sections of chromosome X may be selected according to R factor values as described above and/or mappability and repeatability filtering. In some embodiments, about 1000 to about 3000 or more sections of chromosome X can be selected. For example, about 1000, 1500, 2000, 2100, 2200, 2300, 2400, 2500, 2600, 2700, 2800, 2900, 300, or more sections of chromosome X can be selected. In some embodiments, about 2750 or more sections of chromosome X are selected. In some embodiments, about 2800 sections of chromosome X are selected. In some embodiments, about 2350 or more sections of chromosome X are selected. In some embodiments, about 2382 sections of chromosome X are selected.

Counts

Sequence reads that are mapped or partitioned based on a selected feature or variable can be quantified to determine the number and/or amount of reads that are mapped to a genomic section (e.g., bin, partition, genomic portion, portion of a reference genome, portion of a chromosome and the like), in some embodiments. In some embodiments, the amount or quantity of sequence reads that are mapped to a genomic section are termed counts (e.g., a count). An "amount" can be a density, relative level, sum, measure, value or other qualitative or quantitative representation. Often a count is associated with a genomic section. For example, an "amount of reads" can be the number of reads mapped to a genomic section (e.g., bin). In some embodiments, counts for two or more genomic sections (e.g., a set of genomic sections) are mathematically manipulated (e.g., averaged, added, normalized, the like or a combination thereof). In some embodiments a count is determined from some or all of the sequence reads mapped to (i.e., associated with) a genomic section. In certain embodiments, a count is determined from a pre-defined subset of mapped sequence reads. Pre-defined subsets of mapped sequence reads can be defined or selected utilizing any suitable feature or variable. In some embodiments, pre-defined subsets of mapped sequence reads can include from 1 to n sequence reads, where n represents a number equal to the sum of all sequence reads generated from a test subject or reference subject sample.

In some embodiments, a count is derived from sequence reads that are processed or manipulated by a suitable method, operation or mathematical process known in the art. In some embodiments, a count is derived from sequence reads associated with a genomic section where some or all of the sequence reads are weighted, removed, filtered, normalized, adjusted, averaged, derived as a mean, added, or subtracted or processed by a combination thereof. In some embodiments, a count is derived from raw sequence reads and or filtered sequence reads. A count (e.g., counts) can be determined by a suitable method, operation or mathematical process. In some embodiments, a count value is determined by a mathematical process. In some embodiments, a count value is an average, mean or sum of sequence reads mapped to a genomic section. Often a count is a mean number of counts. In some embodiments, a count is associated with an uncertainty value. Counts can be processed (e.g., normalized) by a method known in the art and/or as described herein (e.g., bin-wise normalization, normalization by GC content, linear and nonlinear least squares regression, GC LOESS, LOWESS, PERUN, RM, GCRM, cQn and/or combinations thereof).

Counts (e.g., raw, filtered and/or normalized counts) can be processed and normalized to one or more elevations. Elevations and profiles are described in greater detail hereafter. In some embodiments, counts can be processed and/or normalized to a reference elevation. Reference elevations are addressed later herein. Counts processed according to an elevation (e.g., processed counts) can be associated with an uncertainty value (e.g., a calculated variance, an error, standard deviation, p-value, mean absolute deviation, etc.). An uncertainty value typically defines a range above and below an elevation. A value for deviation can be used in place of an uncertainty value, and non-limiting examples of measures of deviation include standard deviation, average absolute deviation, median absolute deviation, standard score (e.g., Z-score, Z-value, normal score, standardized variable) and the like.

Counts are often obtained from a nucleic acid sample from a pregnant female bearing a fetus. Counts of nucleic acid sequence reads mapped to a genomic section often are counts representative of both the fetus and the mother of the fetus (e.g., a pregnant female subject). In some embodiments, some of the counts mapped to a genomic section are from a fetal genome and some of the counts mapped to the same genomic section are from the maternal genome.

Counting Module

Counts can be provided by a counting module or by an apparatus comprising a counting module. A counting module can determine, assemble, and/or display counts according to a counting method known in the art. A counting module generally determines or assembles counts according to counting methodology known in the art. In some embodiments, a counting module or an apparatus comprising a counting module is required to provide counts. An apparatus comprising a counting module can comprise at least one processor. In some embodiments, counts are provided by an apparatus that includes a processor (e.g., one or more processors) which processor can perform and/or implement one or more instructions (e.g., processes, routines and/or subroutines) from the counting module. In some embodiments, reads are counted by an apparatus that includes multiple processors, such as processors coordinated and working in parallel. In some embodiments, a counting module operates with one or more external processors (e.g., an internal or external network, server, storage device and/or storage network (e.g., a cloud)). In some embodiments, reads are counted by an apparatus comprising one or more of the following: a sequencing module, a mapping module, one or more flow cells, a camera, fluid handling components, a printer, a display (e.g., an LED, LCT or CRT) and the like. A counting module can receive data and/or information from a sequencing module and/or a mapping module, transform the data and/or information and provide counts (e.g., counts mapped to genomic sections). A counting module can receive mapped sequence reads from a mapping module. A counting module can receive normalized mapped sequence reads from a mapping module or from a normalization module. A counting module can transfer data and/or information related to counts (e.g., counts, assembled counts and/or displays of counts) to any other suitable apparatus, peripheral, or module. In some embodiments, data and/or information related to counts are transferred from a counting module to a normalization module, a plotting module, a categorization module and/or an outcome module.

Data Processing

Mapped sequence reads and/or fragments that have been counted are referred to herein as raw data, since the data represents unmanipulated counts (e.g., raw counts). In some embodiments, sequence read data and/or fragment count data in a data set can be processed further (e.g., mathematically and/or statistically manipulated) and/or displayed to facilitate providing an outcome. Processed counts sometimes can be referred to as a derivative of counts. Non-limiting examples of a derivative of counts includes normalized counts, levels, elevations, profiles and the like and combinations of the foregoing. Any suitable normalization method can be utilized to normalize counts, such as, for example, a normalization method described herein. In certain embodiments, data sets, including larger data sets, may benefit from pre-processing to facilitate further analysis. Pre-processing of data sets sometimes involves removal of redundant and/or uninformative genomic sections or bins (e.g., bins with uninformative data, redundant mapped reads, genomic sections or bins with zero median counts, over represented or under represented sequences). Without being limited by theory, data processing and/or preprocessing may (i) remove noisy data, (ii) remove uninformative data, (iii) remove redundant data, (iv) reduce the complexity of larger data sets, and/or (v) facilitate transformation of the data from one form into one or more other forms. The terms "pre-processing" and "processing" when utilized with respect to data or data sets are collectively referred to herein as "processing". Processing can render data more amenable to further analysis, and can generate an outcome in some embodiments.

The term "noisy data" as used herein refers to (a) data that has a significant variance between data points when analyzed or plotted, (b) data that has a significant standard deviation (e.g., greater than 3 standard deviations), (c) data that has a significant standard error of the mean, the like, and combinations of the foregoing. Noisy data sometimes occurs due to the quantity and/or quality of starting material (e.g., nucleic acid sample), and sometimes occurs as part of processes for preparing, replicating, separating, or amplifying DNA used to generate sequence reads and/or fragment counts. In certain embodiments, noise results from certain sequences being over represented when prepared using PCR-based methods. Methods described herein can reduce or eliminate the contribution of noisy data, and therefore reduce the effect of noisy data on the provided outcome.

The terms "uninformative data", "uninformative bins", and "uninformative genomic sections" as used herein refer to genomic sections, or data derived therefrom, having a numerical value that is significantly different from a predetermined threshold value or falls outside a predetermined cutoff range of values. The terms "threshold" and "threshold value" herein refer to any number that is calculated using a qualifying data set and serves as a limit of diagnosis of a genetic variation (e.g. a copy number variation, an aneuploidy, a chromosomal aberration, and the like). In some embodiments, a threshold is exceeded by results obtained by methods described herein and a subject is diagnosed with a genetic variation (e.g. trisomy 21, sex chromosome aneuploidy). A threshold value or range of values often is calculated by mathematically and/or statistically manipulating sequence read data (e.g., from a reference and/or subject), in some embodiments, and in certain embodiments, sequence read data manipulated to generate a threshold value or range of values is sequence read data (e.g., from a reference and/or subject). In some embodiments, an uncertainty value is determined. An uncertainty value generally is a measure of variance or error and can be any suitable measure of variance or error. An uncertainty value can be a standard deviation, standard error, calculated variance, p-value, or mean absolute deviation (MAD), in some embodiments. In some embodiments an uncertainty value can be calculated according to a formula in Example 6.

Any suitable procedure can be utilized for processing data sets described herein. Non-limiting examples of procedures suitable for use for processing data sets include filtering, normalizing, weighting, monitoring peak heights, monitoring peak areas, monitoring peak edges, determining area ratios, mathematical processing of data, statistical processing of data, application of statistical algorithms, analysis with fixed variables, analysis with optimized variables, plotting data to identify patterns or trends for additional processing, the like and combinations of the foregoing. In some embodiments, data sets are processed based on various features (e.g., GC content, redundant mapped reads, centromere regions, telomere regions, the like and combinations thereof) and/or variables (e.g., fetal gender, maternal age, maternal ploidy, percent contribution of fetal nucleic acid, the like or combinations thereof). In certain embodiments, processing data sets as described herein can reduce the complexity and/or dimensionality of large and/or complex data sets. A non-limiting example of a complex data set includes sequence read data generated from one or more test subjects and a plurality of reference subjects of different ages and ethnic backgrounds. In some embodiments, data sets can include from thousands to millions of sequence reads for each test and/or reference subject.

Data processing can be performed in any number of steps, in certain embodiments. For example, data may be processed using only a single processing procedure in some embodiments, and in certain embodiments data may be processed using 1 or more, 5 or more, 10 or more or 20 or more processing steps (e.g., 1 or more processing steps, 2 or more processing steps, 3 or more processing steps, 4 or more processing steps, 5 or more processing steps, 6 or more processing steps, 7 or more processing steps, 8 or more processing steps, 9 or more processing steps, 10 or more processing steps, 11 or more processing steps, 12 or more processing steps, 13 or more processing steps, 14 or more processing steps, 15 or more processing steps, 16 or more processing steps, 17 or more processing steps, 18 or more processing steps, 19 or more processing steps, or 20 or more processing steps). In some embodiments, processing steps may be the same step repeated two or more times (e.g., filtering two or more times, normalizing two or more times), and in certain embodiments, processing steps may be two or more different processing steps (e.g., filtering, normalizing; normalizing, monitoring peak heights and edges; filtering, normalizing, normalizing to a reference, statistical manipulation to determine p-values, and the like), carried out simultaneously or sequentially. In some embodiments, any suitable number and/or combination of the same or different processing steps can be utilized to process sequence read data to facilitate providing an outcome. In certain embodiments, processing data sets by the criteria described herein may reduce the complexity and/or dimensionality of a data set.

In some embodiments, one or more processing steps can comprise one or more filtering steps. The term "filtering" as used herein refers to removing genomic sections or bins from consideration. Bins can be selected for removal based on any suitable criteria, including but not limited to redundant data (e.g., redundant or overlapping mapped reads), non-informative data (e.g., bins with zero median counts), bins with over represented or under represented sequences, noisy data, the like, or combinations of the foregoing. A filtering process often involves removing one or more bins from consideration and subtracting the counts in the one or more bins selected for removal from the counted or summed counts for the bins, chromosome or chromosomes, or genome under consideration. In some embodiments, bins can be removed successively (e.g., one at a time to allow evaluation of the effect of removal of each individual bin), and in certain embodiments all bins marked for removal can be removed at the same time. In some embodiments, genomic sections characterized by a variance above or below a certain level are removed, which sometimes is referred to herein as filtering "noisy" genomic sections. In certain embodiments, a filtering process comprises obtaining data points from a data set that deviate from the mean profile elevation of a genomic section, a chromosome, or segment of a chromosome by a predetermined multiple of the profile variance, and in certain embodiments, a filtering process comprises removing data points from a data set that do not deviate from the mean profile elevation of a genomic section, a chromosome or segment of a chromosome by a predetermined multiple of the profile variance. In some embodiments, a filtering process is utilized to reduce the number of candidate genomic sections analyzed for the presence or absence of a genetic variation. Reducing the number of candidate genomic sections analyzed for the presence or absence of a genetic variation (e.g., micro-deletion, micro-duplication) often reduces the complexity and/or dimensionality of a data set, and sometimes increases the speed of searching for and/or identifying genetic variations and/or genetic aberrations by two or more orders of magnitude.

Normalization

In some embodiments, one or more processing steps can comprise one or more normalization steps. Normalization can be performed by a suitable method known in the art. In some embodiments, normalization comprises adjusting values measured on different scales to a notionally common scale. In some embodiments, normalization comprises a sophisticated mathematical adjustment to bring probability distributions of adjusted values into alignment. In some embodiments, normalization comprises aligning distributions to a normal distribution. In some embodiments, normalization comprises mathematical adjustments that allow comparison of corresponding normalized values for different datasets in a way that eliminates the effects of certain gross influences (e.g., error and anomalies). In some embodiments, normalization comprises scaling. Normalization sometimes comprises division of one or more data sets by a predetermined variable or formula. Non-limiting examples of normalization methods include bin-wise normalization, normalization by GC content, linear and nonlinear least squares regression, LOESS, GC LOESS, LOWESS (locally weighted scatterplot smoothing), PERUN, repeat masking (RM), GC-normalization and repeat masking (GCRM), cQn and/or combinations thereof. In some embodiments, the determination of a presence or absence of a genetic variation (e.g., an aneuploidy) utilizes a normalization method (e.g., bin-wise normalization, normalization by GC content, linear and nonlinear least squares regression, LOESS, GC LOESS, LOWESS (locally weighted scatterplot smoothing), PERUN, repeat masking (RM), GC-normalization and repeat masking (GCRM), cQn, a normalization method known in the art and/or a combination thereof).

For example, LOESS is a regression modeling method known in the art that combines multiple regression models in a k-nearest-neighbor-based meta-model. LOESS is sometimes referred to as a locally weighted polynomial regression. GC LOESS, in some embodiments, applies an LOESS model to the relation between fragment count (e.g., sequence reads, counts) and GC composition for genomic sections. Plotting a smooth curve through a set of data points using LOESS is sometimes called an LOESS curve, particularly when each smoothed value is given by a weighted quadratic least squares regression over the span of values of the y-axis scattergram criterion variable. For each point in a data set, the LOESS method fits a low-degree polynomial to a subset of the data, with explanatory variable values near the point whose response is being estimated. The polynomial is fitted using weighted least squares, giving more weight to points near the point whose response is being estimated and less weight to points further away. The value of the regression function for a point is then obtained by evaluating the local polynomial using the explanatory variable values for that data point. The LOESS fit is sometimes considered complete after regression function values have been computed for each of the data points. Many of the details of this method, such as the degree of the polynomial model and the weights, are flexible.

Any suitable number of normalizations can be used. In some embodiments, data sets can be normalized 1 or more, 5 or more, 10 or more or even 20 or more times. Data sets can be normalized to values (e.g., normalizing value) representative of any suitable feature or variable (e.g., sample data, reference data, or both). Non-limiting examples of types of data normalizations that can be used include normalizing raw count data for one or more selected test or reference genomic sections to the total number of counts mapped to the chromosome or the entire genome on which the selected genomic section or sections are mapped; normalizing raw count data for one or more selected genomic sections to a median reference count for one or more genomic sections or the chromosome on which a selected genomic section or segments is mapped; normalizing raw count data to previously normalized data or derivatives thereof; and normalizing previously normalized data to one or more other predetermined normalization variables. Normalizing a data set sometimes has the effect of isolating statistical error, depending on the feature or property selected as the predetermined normalization variable. Normalizing a data set sometimes also allows comparison of data characteristics of data having different scales, by bringing the data to a common scale (e.g., predetermined normalization variable). In some embodiments, one or more normalizations to a statistically derived value can be utilized to minimize data differences and diminish the importance of outlying data. Normalizing genomic sections, or bins, with respect to a normalizing value sometimes is referred to as "bin-wise normalization".

In certain embodiments, a processing step comprising normalization includes normalizing to a static window, and in some embodiments, a processing step comprising normalization includes normalizing to a moving or sliding window. The term "window" as used herein refers to one or more genomic sections chosen for analysis, and sometimes used as a reference for comparison (e.g., used for normalization and/or other mathematical or statistical manipulation). The term "normalizing to a static window" as used herein refers to a normalization process using one or more genomic sections selected for comparison between a test subject and reference subject data set. In some embodiments the selected genomic sections are utilized to generate a profile. A static window generally includes a predetermined set of genomic sections that do not change during manipulations and/or analysis. The terms "normalizing to a moving window" and "normalizing to a sliding window" as used herein refer to normalizations performed to genomic sections localized to the genomic region (e.g., immediate genetic surrounding, adjacent genomic section or sections, and the like) of a selected test genomic section, where one or more selected test genomic sections are normalized to genomic sections immediately surrounding the selected test genomic section. In certain embodiments, the selected genomic sections are utilized to generate a profile. A sliding or moving window normalization often includes repeatedly moving or sliding to an adjacent test genomic section, and normalizing the newly selected test genomic section to genomic sections immediately surrounding or adjacent to the newly selected test genomic section, where adjacent windows have one or more genomic sections in common. In certain embodiments, a plurality of selected test genomic sections and/or chromosomes can be analyzed by a sliding window process.

In some embodiments, normalizing to a sliding or moving window can generate one or more values, where each value represents normalization to a different set of reference genomic sections selected from different regions of a genome (e.g., chromosome). In certain embodiments, the one or more values generated are cumulative sums (e.g., a numerical estimate of the integral of the normalized count profile over the selected genomic section, domain (e.g., part of chromosome), or chromosome). The values generated by the sliding or moving window process can be used to generate a profile and facilitate arriving at an outcome. In some embodiments, cumulative sums of one or more genomic sections can be displayed as a function of genomic position. Moving or sliding window analysis sometimes is used to analyze a genome for the presence or absence of micro-deletions and/or micro-insertions. In certain embodiments, displaying cumulative sums of one or more genomic sections is used to identify the presence or absence of regions of genetic variation (e.g., micro-deletions, micro-duplications). In some embodiments, moving or sliding window analysis is used to identify genomic regions containing micro-deletions and in certain embodiments, moving or sliding window analysis is used to identify genomic regions containing micro-duplications.

A particularly useful normalization methodology for reducing error associated with nucleic acid indicators is referred to herein as Parameterized Error Removal and Unbiased Normalization (PERUN; described, for example, in U.S. patent application Ser. No. 13/669,136, which is incorporated by reference in its entirety, and in International Application No. PCT/US12/59123, which is incorporated by reference in its entirety). PERUN methodology can be applied to a variety of nucleic acid indicators (e.g., nucleic acid sequence reads) for the purpose of reducing effects of error that confound predictions based on such indicators.

For example, PERUN methodology can be applied to nucleic acid sequence reads from a sample and reduce the effects of error that can impair nucleic acid elevation determinations (e.g., genomic section elevation determinations). Such an application is useful for using nucleic acid sequence reads to assess the presence or absence of a genetic variation in a subject manifested as a varying elevation of a nucleotide sequence (e.g., genomic section). Non-limiting examples of variations in genomic sections are chromosome aneuploidies (e.g., trisomy 21, trisomy 18, trisomy 13, sex chromosome aneuploidies) and presence or absence of a sex chromosome (e.g., XX in females versus XY in males). A trisomy of an autosome (e.g., a chromosome other than a sex chromosome) can be referred to as an affected autosome. An aneuploidy (e.g., trisomy, monosomy) of a sex chromosome (e.g., chromosome X, chromosome Y) can be referred to as an affected sex chromosome. Other non-limiting examples of variations in genomic section elevations include microdeletions, microinsertions, duplications and mosaicism.

In certain applications, PERUN methodology can reduce experimental bias by normalizing nucleic acid indicators for particular genomic groups, the latter of which are referred to as bins. Bins include a suitable collection of nucleic acid indicators, a non-limiting example of which includes a length of contiguous nucleotides, which is referred to herein as a genomic section or portion of a reference genome. Bins can include other nucleic acid indicators as described herein. In such applications, PERUN methodology generally normalizes nucleic acid indicators at particular bins across a number of samples in three dimensions. A detailed description of particular PERUN applications is described in Example 4 and Example 5 herein.

In certain embodiments, PERUN methodology includes calculating a genomic section elevation for each bin from a fitted relation between (i) experimental bias for a bin of a reference genome to which sequence reads are mapped and (ii) counts of sequence reads mapped to the bin. Experimental bias for each of the bins can be determined across multiple samples according to a fitted relation for each sample between (i) the counts of sequence reads mapped to each of the bins, and (ii) a mapping feature fore each of the bins. This fitted relation for each sample can be assembled for multiple samples in three dimensions. The assembly can be ordered according to the experimental bias in certain embodiments (e.g., FIG. 82, Example 4), although PERUN methodology may be practiced without ordering the assembly according to the experimental bias.

A relation can be generated by a method known in the art. A relation in two dimensions can be generated for each sample in certain embodiments, and a variable probative of error, or possibly probative of error, can be selected for one or more of the dimensions. A relation can be generated, for example, using graphing software known in the art that plots a graph using values of two or more variables provided by a user. A relation can be fitted using a method known in the art (e.g., graphing software). Certain relations can be fitted by linear regression, and the linear regression can generate a slope value and intercept value. Certain relations sometimes are not linear and can be fitted by a non-linear function, such as a parabolic, hyperbolic or exponential function, for example.

In PERUN methodology, one or more of the fitted relations may be linear. For an analysis of cell-free circulating nucleic acid from pregnant females, where the experimental bias is GC bias and the mapping feature is GC content, the fitted relation for a sample between the (i) the counts of sequence reads mapped to each bin, and (ii) GC content for each of the bins, can be linear. For the latter fitted relation, the slope pertains to GC bias, and a GC bias coefficient can be determined for each bin when the fitted relations are assembled across multiple samples. In such embodiments, the fitted relation for multiple samples and a bin between (i) GC bias coefficient for the bin, and (ii) counts of sequence reads mapped to bin, also can be linear. An intercept and slope can be obtained from the latter fitted relation. In such applications, the slope addresses sample-specific bias based on GC-content and the intercept addresses a bin-specific attenuation pattern common to all samples. PERUN methodology can significantly reduce such sample-specific bias and bin-specific attenuation when calculating genomic section elevations for providing an outcome (e.g., presence or absence of genetic variation; determination of fetal sex).

Thus, application of PERUN methodology to sequence reads across multiple samples in parallel can significantly reduce error caused by (i) sample-specific experimental bias (e.g., GC bias) and (ii) bin-specific attenuation common to samples. Other methods in which each of these two sources of error are addressed separately or serially often are not able to reduce these as effectively as PERUN methodology. Without being limited by theory, it is expected that PERUN methodology reduces error more effectively in part because its generally additive processes do not magnify spread as much as generally multiplicative processes utilized in other normalization approaches (e.g., GC-LOESS).

Additional normalization and statistical techniques may be utilized in combination with PERUN methodology. An additional process can be applied before, after and/or during employment of PERUN methodology. Non-limiting examples of processes that can be used in combination with PERUN methodology are described hereafter.

In some embodiments, a secondary normalization or adjustment of a genomic section elevation for GC content can be utilized in conjunction with PERUN methodology. A suitable GC content adjustment or normalization procedure can be utilized (e.g., GC-LOESS, GCRM). In certain embodiments, a particular sample can be identified for application of an additional GC normalization process. For example, application of PERUN methodology can determine GC bias for each sample, and a sample associated with a GC bias above a certain threshold can be selected for an additional GC normalization process. In such embodiments, a predetermined threshold elevation can be used to select such samples for additional GC normalization.

In certain embodiments, a bin filtering or weighting process can be utilized in conjunction with PERUN methodology. A suitable bin filtering or weighting process can be utilized and non-limiting examples are described herein. Examples 4 and 5 describe utilization of R-factor measures of error for bin filtering.

Normalization for Sex Chromosomes

In some embodiments, sequence read counts that map to one or more sex chromosomes (i.e., chromosome X, chromosome Y) are normalized. In some embodiments, normalization involves determining an experimental bias for genomic sections of a reference genome. In some embodiments, experimental bias can be determined for multiple samples from a first fitted relation (e.g., fitted linear relation, fitted non-linear relation) for each sample between counts of sequence reads mapped to each of the genomic sections of a reference genome and a mapping feature (e.g., GC content) for each of the genomic sections. The slope of a fitted relation (e.g., linear relation) generally is determined by linear regression, as described herein. In some embodiments, each experimental bias is represented by an experimental bias coefficient. Experimental bias coefficient is the slope of a linear relationship between, for example, (i) counts of sequence reads mapped to each of the sections of a reference genome, and (ii) a mapping feature for each of the sections. In some embodiments, experimental bias can comprise an experimental bias curvature estimation.

In some embodiments, a method further comprises calculating a genomic section level (e.g., elevation) for each of the genomic sections from a second fitted relation (e.g., fitted linear relation, fitted non-linear relation) between the experimental bias and the counts of sequence reads mapped to each of the genomic sections and the slope of the relation can be determined by linear regression. For example, if the first fitted relation is linear and the second fitted relation is linear, genomic section level $L_i$ can be determined for each of the sections of the reference genome according to Equation α:

$$L_i = (m_i - G_i S) I^{-1} \quad \text{Equation } \alpha$$

where $G_i$ is the experimental bias, I is the intercept of the second fitted relation, S is the slope of the second relation, $m_i$ is measured counts mapped to each section of the reference genome and i is a sample.

In some embodiments, a secondary normalization process is applied to one or more calculated genomic section levels. In some embodiments, the secondary normalization comprises GC normalization and sometimes comprises use of the PERUN methodology. An example of a secondary normalization is described in Example 14.

GC Bias Module

Determining GC bias (e.g., determining GC bias for each of the portions of a reference genome (e.g., genomic sections)) can be provided by a GC bias module (e.g., by an apparatus comprising a GC bias module). In some embodiments, a GC bias module is required to provide a determination of GC bias. In some embodiments, a GC bias module provides a determination of GC bias from a fitted relationship (e.g., a fitted linear relationship) between counts of sequence reads mapped to each of the sections of a reference genome and GC content of each portion. An apparatus comprising a GC bias module can comprise at least one processor. In some embodiments, GC bias determinations (i.e., GC bias data) are provided by an apparatus that includes a processor (e.g., one or more processors) which processor can perform and/or implement one or more instructions (e.g., processes, routines and/or subroutines) from the GC bias module. In some embodiments, GC bias data is provided by an apparatus that includes multiple processors, such as processors coordinated and working in parallel. In some embodiments, a GC bias module operates with one or more external processors (e.g., an internal or external network, server, storage device and/or storage network (e.g., a cloud)). In some embodiments, GC bias data is provided by an apparatus comprising one or more of the following: one or more flow cells, a camera, fluid handling components, a printer, a display (e.g., an LED, LCT or CRT) and the like. A GC bias module can receive data and/or information from a suitable apparatus or module. In some embodiments, a GC bias module can receive data and/or information from a sequencing module, a normalization module, a weighting module, a mapping module or counting module. A GC bias module sometimes is part of a normalization module (e.g., PERUN normalization module). A GC bias module can receive sequencing reads from a sequencing module, mapped sequencing reads from a mapping module and/or counts from a counting module, in some embodiments. Often a GC bias module receives data and/or information from an apparatus or another module (e.g., a counting module), transforms the data and/or information and provides GC bias data and/or information (e.g., a determination of GC bias, a linear fitted relationship, and the like). GC bias data and/or information can be transferred from a GC bias module to an elevation module, filtering module, comparison module, a normalization module, a weighting module, a range setting module, an adjustment module, a categorization module, and/or an outcome module, in certain embodiments.

Elevation Module

Determining elevations (e.g., levels) and/or calculating genomic section elevations (e.g., genomic section levels) for sections of a reference genome can be provided by an elevation module (e.g., by an apparatus comprising an elevation module). In some embodiments, an elevation module is required to provide an elevation or a calculated genomic section level. In some embodiments, an elevation module provides an elevation from a fitted relationship (e.g., a fitted linear relationship) between a GC bias and counts of sequence reads mapped to each of the sections of a reference genome. In some embodiments, an elevation module calculates a genomic section level as part of PERUN. In some embodiments, an elevation module provides a genomic section level (i.e., $L_i$) according to equation $L_i=(m_i-G_iS)I^{-1}$ where $G_i$ is the GC bias, $m_i$ is measured counts mapped to each section of a reference genome, i is a sample, and I is the intercept and S is the slope of the a fitted relationship (e.g., a fitted linear relationship) between a GC bias and counts of sequence reads mapped to each of the sections of a reference genome. An apparatus comprising an elevation module can comprise at least one processor. In some embodiments, an elevation determination (i.e., level data) is provided by an apparatus that includes a processor (e.g., one or more processors) which processor can perform and/or implement one or more instructions (e.g., processes, routines and/or subroutines) from the level module. In some embodiments, level data is provided by an apparatus that includes multiple processors, such as processors coordinated and working in parallel. In some embodiments, an elevation module operates with one or more external processors (e.g., an internal or external network, server, storage device and/or storage network (e.g., a cloud)). In some embodiments, level data is provided by an apparatus comprising one or more of the following: one or more flow cells, a camera, fluid handling components, a printer, a display (e.g., an LED, LCT or CRT) and the like. An elevation module can receive data and/or information from a suitable apparatus or module. In some embodiments, an elevation module can receive data and/or information from a GC bias module, a sequencing module, a normalization module, a weighting module, a mapping module or counting module. An elevation module can receive sequencing reads from a sequencing module, mapped sequencing reads from a mapping module and/or counts from a counting module, in some embodiments. An elevation module sometimes is part of a normalization module (e.g., PERUN normalization module). Often an elevation module receives data and/or information from an apparatus or another module (e.g., a GC bias module), transforms the data and/or information and provides level data and/or information (e.g., a determination of level, a linear fitted relationship, and the like). Level data and/or information can be transferred from an elevation module to a comparison module, a normalization module, a weighting module, a range setting module, an adjustment module, a categorization module, a module in a normalization module and/or an outcome module, in certain embodiments.

Filtering Module

Filtering genomic sections can be provided by a filtering module (e.g., by an apparatus comprising a filtering module). In some embodiments, a filtering module is required to provide filtered genomic section data (e.g., filtered genomic sections) and/or to remove genomic sections from consideration. In some embodiments, a filtering module removes counts mapped to a genomic section from consideration. In some embodiments, a filtering module removes counts mapped to a genomic section from a determination of an elevation or a profile. In some embodiments a filtering module filters genomic sections according to one or more of: a FLR, an amount of reads derived from CCF fragments less than a first selected fragment length, GC content (e.g., GC content of a genomic section), number of exons (e.g., number of exons in a genomic section), the like and combinations thereof. A filtering module can filter data (e.g., reads, counts, counts mapped to genomic sections, genomic sections, genomic section elevations, normalized counts, raw counts, and the like) by one or more filtering procedures known in the art or described herein. An apparatus comprising a filtering module can comprise at least one processor. In some embodiments, filtered data is provided by an apparatus that includes a processor (e.g., one or more processors) which processor can perform and/or implement one or more instructions (e.g., processes, routines and/or subroutines) from the filtering module. In some embodiments, filtered data is provided by an apparatus that includes multiple processors, such as processors coordinated and working in parallel. In some embodiments, a filtering module operates with one or more external processors (e.g., an internal or external network, server, storage device and/or storage network (e.g., a cloud)). In some embodiments, filtered data is provided by an apparatus comprising one or more of the following: one or more flow cells, a camera, fluid handling components, a printer, a display (e.g., an LED, LCT or CRT) and the like. A filtering module can receive data and/or information from a suitable apparatus or module. In some embodiments, a filtering module can receive data and/or information from a sequencing module, a normalization module, a weighting module, a mapping module or counting module. A filtering module can receive sequencing reads from a sequencing module, mapped sequencing reads from a mapping module and/or counts from a counting module, in some embodiments. Often a filtering module receives data and/or information from another apparatus or module, transforms the data and/or information and provides filtered data and/or information (e.g., filtered counts, filtered values, filtered genomic sections, and the like). Filtered data and/or information can be transferred from a filtering module to a comparison module, a normalization module, a weighting module, a range setting module, an adjustment module, a categorization module, and/or an outcome module, in certain embodiments.

Weighting Module

Weighting genomic sections can be provided by a weighting module (e.g., by an apparatus comprising a weighting module). In some embodiments, a weighting module is required to weight genomics sections and/or provide weighted genomic section values. A weighting module can weight genomic sections by one or more weighting procedures known in the art or described herein. An apparatus comprising a weighting module can comprise at least one processor. In some embodiments, weighted genomic sections are provided by an apparatus that includes a processor (e.g., one or more processors) which processor can perform and/or implement one or more instructions (e.g., processes, routines and/or subroutines) from the weighting module. In some embodiments, weighted genomic sections are provided by an apparatus that includes multiple processors, such as processors coordinated and working in parallel. In some embodiments, a weighting module operates with one or more external processors (e.g., an internal or external network, server, storage device and/or storage network (e.g., a cloud)). In some embodiments, weighted genomic sections are provided by an apparatus comprising one or more of the following: one or more flow cells, a camera, fluid handling components, a printer, a display (e.g., an LED, LCT or CRT) and the like. A weighting module can receive data and/or information from a suitable apparatus or module. In some embodiments, a weighting module can receive data and/or information from a sequencing module, a normalization module, a filtering module, a mapping module and/or a counting module. A weighting module can receive sequencing reads from a sequencing module, mapped sequencing reads from a mapping module and/or counts from a counting module, in some embodiments. In some embodiments a weighting module receives data and/or information from another apparatus or module, transforms the data and/or information and provides data and/or information (e.g., weighted genomic sections, weighted values, and the like). Weighted genomic section data and/or information can be transferred from a weighting module to a comparison module, a normalization module, a filtering module, a range setting module, an adjustment module, a categorization module, and/or an outcome module, in certain embodiments.

In some embodiments, a normalization technique that reduces error associated with insertions, duplications and/or deletions (e.g., maternal and/or fetal copy number variations), is utilized in conjunction with PERUN methodology.

Genomic section elevations calculated by PERUN methodology can be utilized directly for providing an outcome. In some embodiments, genomic section elevations can be utilized directly to provide an outcome for samples in which fetal fraction is about 2% to about 6% or greater (e.g., fetal fraction of about 4% or greater). Genomic section elevations calculated by PERUN methodology sometimes are further processed for the provision of an outcome. In some embodiments, calculated genomic section elevations are standardized. In certain embodiments, the sum, mean or median of calculated genomic section elevations for a test genomic section (e.g., chromosome 21) can be divided by the sum, mean or median of calculated genomic section elevations for genomic sections other than the test genomic section (e.g., autosomes other than chromosome 21), to generate an experimental genomic section elevation. An experimental genomic section elevation or a raw genomic section elevation can be used as part of a standardization analysis, such as calculation of a Z-score or Z-value. A Z-score can be generated for a sample by subtracting an expected genomic section elevation from an experimental genomic section elevation or raw genomic section elevation and the resulting value may be divided by a standard deviation for the samples. Resulting Z-scores can be distributed for different samples and analyzed, or can be related to other variables, such as fetal fraction and others, and analyzed, to provide an outcome, in certain embodiments.

As noted herein, PERUN methodology is not limited to normalization according to GC bias and GC content per se, and can be used to reduce error associated with other sources of error. A non-limiting example of a source of non-GC content bias is mappability. When normalization parameters other than GC bias and content are addressed, one or more of the fitted relations may be non-linear (e.g., hyperbolic, exponential). Where experimental bias is determined from a non-linear relation, for example, an experimental bias curvature estimation may be analyzed in some embodiments.

PERUN methodology can be applied to a variety of nucleic acid indicators. Non-limiting examples of nucleic acid indicators are nucleic acid sequence reads and nucleic acid elevations at a particular location on a microarray. Non-limiting examples of sequence reads include those obtained from cell-free circulating DNA, cell-free circulating RNA, cellular DNA and cellular RNA. PERUN methodology can be applied to sequence reads mapped to suitable reference sequences, such as genomic reference DNA, cellular reference RNA (e.g., transcriptome), and portions thereof (e.g., part(s) of a genomic complement of DNA or RNA transcriptome, part(s) of a chromosome).

Thus, in certain embodiments, cellular nucleic acid (e.g., DNA or RNA) can serve as a nucleic acid indicator. Cellular nucleic acid reads mapped to reference genome portions can be normalized using PERUN methodology.

Cellular nucleic acid sometimes is an association with one or more proteins, and an agent that captures protein-associated nucleic acid can be utilized to enrich for the latter, in some embodiments. An agent in certain embodiments is an antibody or antibody fragment that specifically binds to a protein in association with cellular nucleic acid (e.g., an antibody that specifically binds to a chromatin protein (e.g., histone protein)). Processes in which an antibody or antibody fragment is used to enrich for cellular nucleic acid bound to a particular protein sometimes are referred to chromatin immunoprecipitation (ChIP) processes. ChIP-enriched nucleic acid is a nucleic acid in association with cellular protein, such as DNA or RNA for example. Reads of ChIP-enriched nucleic acid can be obtained using technology known in the art. Reads of ChIP-enriched nucleic acid can be mapped to one or more portions of a reference genome, and results can be normalized using PERUN methodology for providing an outcome.

Thus, provided in certain embodiments are methods for calculating with reduced bias genomic section elevations for a test sample, comprising: (a) obtaining counts of sequence reads mapped to bins of a reference genome, which sequence reads are reads of cellular nucleic acid from a test sample obtained by isolation of a protein to which the nucleic acid was associated; (b) determining experimental bias for each of the bins across multiple samples from a fitted relation between (i) the counts of the sequence reads mapped to each of the bins, and (ii) a mapping feature for each of the bins; and (c) calculating a genomic section elevation for each of the bins from a fitted relation between the experimental bias and the counts of the sequence reads mapped to each of the bins, thereby providing calculated genomic section elevations, whereby bias in the counts of the sequence reads mapped to each of the bins is reduced in the calculated genomic section elevations.

In certain embodiments, cellular RNA can serve as nucleic acid indicators. Cellular RNA reads can be mapped to reference RNA portions and normalized using PERUN methodology for providing an outcome. Known sequences for cellular RNA, referred to as a transcriptome, or a segment thereof, can be used as a reference to which RNA reads from a sample can be mapped. Reads of sample RNA can be obtained using technology known in the art. Results of RNA reads mapped to a reference can be normalized using PERUN methodology for providing an outcome.

Thus, provided in some embodiments are methods for calculating with reduced bias genomic section elevations for a test sample, comprising: (a) obtaining counts of sequence reads mapped to bins of reference RNA (e.g., reference transcriptome or segment(s) thereof), which sequence reads are reads of cellular RNA from a test sample; (b) determining experimental bias for each of the bins across multiple samples from a fitted relation between (i) the counts of the sequence reads mapped to each of the bins, and (ii) a mapping feature for each of the bins; and (c) calculating a genomic section elevation for each of the bins from a fitted relation between the experimental bias and the counts of the sequence reads mapped to each of the bins, thereby providing calculated genomic section elevations, whereby bias in the counts of the sequence reads mapped to each of the bins is reduced in the calculated genomic section elevations.

In some embodiments, microarray nucleic acid levels can serve as nucleic acid indicators. Nucleic acid levels across samples for a particular address, or hybridizing nucleic acid, on an array can be analyzed using PERUN methodology, thereby normalizing nucleic acid indicators provided by microarray analysis. In this manner, a particular address or hybridizing nucleic acid on a microarray is analogous to a bin for mapped nucleic acid sequence reads, and PERUN methodology can be used to normalize microarray data to provide an improved outcome.

Thus, provided in certain embodiments are methods for reducing microarray nucleic acid level error for a test sample, comprising: (a) obtaining nucleic acid levels in a microarray to which test sample nucleic acid has been associated, which microarray includes an array of capture nucleic acids; (b) determining experimental bias for each of the capture nucleic acids across multiple samples from a fitted relation between (i) the test sample nucleic acid levels associated with each of the capture nucleic acids, and (ii) an association feature for each of the capture nucleic acids; and (c) calculating a test sample nucleic acid level for each of the capture nucleic acids from a fitted relation between the experimental bias and the levels of the test sample nucleic acid associated with each of the capture nucleic acids, thereby providing calculated levels, whereby bias in the levels of test sample nucleic acid associated with each of the capture nucleic acids is reduced in the calculated levels. The association feature mentioned above can be any feature correlated with hybridization of a test sample nucleic acid to a capture nucleic acid that gives rise to, or may give rise to, error in determining the level of test sample nucleic acid associated with a capture nucleic acid.

Normalization Module

Normalized data (e.g., normalized counts) can be provided by a normalization module (e.g., by an apparatus comprising a normalization module). In some embodiments, a normalization module is required to provide normalized data (e.g., normalized counts) obtained from sequencing reads. A normalization module can normalize data (e.g., counts, filtered counts, raw counts) by one or more normalization procedures known in the art. An apparatus comprising a normalization module can comprise at least one processor. In some embodiments, normalized data is provided by an apparatus that includes a processor (e.g., one or more processors) which processor can perform and/or implement one or more instructions (e.g., processes, routines and/or subroutines) from the normalization module. In some embodiments, normalized data is provided by an apparatus that includes multiple processors, such as processors coordinated and working in parallel. In some embodiments, a normalization module operates with one or more external processors (e.g., an internal or external network, server, storage device and/or storage network (e.g., a cloud)). In some embodiments, normalized data is provided by an apparatus comprising one or more of the following: one or more flow cells, a camera, fluid handling components, a printer, a display (e.g., an LED, LCT or CRT) and the like. A normalization module can receive data and/or information from a suitable apparatus or module. In some embodiments, a normalization module can receive data and/or information from a sequencing module, a normalization module, a mapping module or counting module. A normalization module can receive sequencing reads from a sequencing module, mapped sequencing reads from a mapping module and/or counts from a counting module, in some embodiments. Often a normalization module receives data and/or information from another apparatus or module, transforms the data and/or information and provides normalized data and/or information (e.g., normalized counts, normalized values, normalized reference values (NRVs), and the like). Normalized data and/or information can be transferred from a normalization module to a comparison module, a normalization module, a range setting module, an adjustment module, a categorization module, and/or an outcome module, in certain embodiments. In some embodiments, normalized counts (e.g., normalized mapped counts) are transferred to an expected representation module and/or to an experimental representation module from a normalization module.

In some embodiments, a processing step comprises a weighting. The terms "weighted", "weighting" or "weight function" or grammatical derivatives or equivalents thereof, as used herein, refer to a mathematical manipulation of a portion or all of a data set sometimes utilized to alter the influence of certain data set features or variables with respect to other data set features or variables (e.g., increase or decrease the significance and/or contribution of data contained in one or more genomic sections or bins, based on the quality or usefulness of the data in the selected bin or bins). A weighting function can be used to increase the influence of data with a relatively small measurement variance, and/or to decrease the influence of data with a relatively large measurement variance, in some embodiments. For example, bins with under represented or low quality sequence data can be "down weighted" to minimize the influence on a data set, whereas selected bins can be "up weighted" to increase the influence on a data set. A non-limiting example of a weighting function is [1/(standard deviation)$^2$]. A weighting step sometimes is performed in a manner substantially similar to a normalizing step. In some embodiments, a data set is divided by a predetermined variable (e.g., weighting variable). A predetermined variable (e.g., minimized target function, Phi) often is selected to weigh different parts of a data set differently (e.g., increase the influence of certain data types while decreasing the influence of other data types).

In certain embodiments, a processing step can comprise one or more mathematical and/or statistical manipulations. Any suitable mathematical and/or statistical manipulation, alone or in combination, may be used to analyze and/or manipulate a data set described herein. Any suitable number of mathematical and/or statistical manipulations can be used. In some embodiments, a data set can be mathematically and/or statistically manipulated 1 or more, 5 or more, 10 or more or 20 or more times. Non-limiting examples of mathematical and statistical manipulations that can be used include addition, subtraction, multiplication, division, algebraic functions, least squares estimators, curve fitting, differential equations, rational polynomials, double polynomials, orthogonal polynomials, z-scores, p-values, chi values, phi values, analysis of peak elevations, determination of peak edge locations, calculation of peak area ratios, analysis of median chromosomal elevation, calculation of mean absolute deviation, sum of squared residuals, mean, standard deviation, standard error, the like or combinations thereof. A mathematical and/or statistical manipulation can be performed on all or a portion of sequence read data, or processed products thereof. Non-limiting examples of data set variables or features that can be statistically manipulated include raw counts, filtered counts, normalized counts, peak heights, peak widths, peak areas, peak edges, lateral tolerances, P-values, median elevations, mean elevations, count distribution within a genomic region, relative representation of nucleic acid species, the like or combinations thereof.

In some embodiments, a processing step can include the use of one or more statistical algorithms. Any suitable statistical algorithm, alone or in combination, may be used to analyze and/or manipulate a data set described herein. Any suitable number of statistical algorithms can be used. In some embodiments, a data set can be analyzed using 1 or more, 5 or more, 10 or more or 20 or more statistical algorithms. Non-limiting examples of statistical algorithms suitable for use with methods described herein include decision trees, counternulls, multiple comparisons, omnibus test, Behrens-Fisher problem, bootstrapping, Fisher's method for combining independent tests of significance, null hypothesis, type I error, type II error, exact test, one-sample Z test, two-sample Z test, one-sample t-test, paired t-test, two-sample pooled t-test having equal variances, two-sample unpooled t-test having unequal variances, one-proportion z-test, two-proportion z-test pooled, two-proportion z-test unpooled, one-sample chi-square test, two-sample F test for equality of variances, confidence interval, credible interval, significance, meta analysis, simple linear regression, robust linear regression, the like or combinations of the foregoing. Non-limiting examples of data set variables or features that can be analyzed using statistical algorithms include raw counts, filtered counts, normalized counts, peak heights, peak widths, peak edges, lateral tolerances, P-values, median elevations, mean elevations, count distribution within a genomic region, relative representation of nucleic acid species, the like or combinations thereof.

In certain embodiments, a data set can be analyzed by utilizing multiple (e.g., 2 or more) statistical algorithms (e.g., least squares regression, principle component analysis, linear discriminant analysis, quadratic discriminant analysis, bagging, neural networks, support vector machine models, random forests, classification tree models, K-nearest neighbors, logistic regression and/or loss smoothing) and/or mathematical and/or statistical manipulations (e.g., referred to herein as manipulations). The use of multiple manipulations can generate an N-dimensional space that can be used to provide an outcome, in some embodiments. In certain embodiments, analysis of a data set by utilizing multiple manipulations can reduce the complexity and/or dimensionality of the data set. For example, the use of multiple manipulations on a reference data set can generate an N-dimensional space (e.g., probability plot) that can be used to represent the presence or absence of a genetic variation, depending on the genetic status of the reference samples (e.g., positive or negative for a selected genetic variation). Analysis of test samples using a substantially similar set of manipulations can be used to generate an N-dimensional point for each of the test samples. The complexity and/or dimensionality of a test subject data set sometimes is reduced to a single value or N-dimensional point that can be readily compared to the N-dimensional space generated from the reference data. Test sample data that fall within the N-dimensional space populated by the reference subject data are indicative of a genetic status substantially similar to that of the reference subjects. Test sample data that fall outside of the N-dimensional space populated by the reference subject data are indicative of a genetic status substantially dissimilar to that of the reference subjects. In some embodiments, references are euploid or do not otherwise have a genetic variation or medical condition.

After data sets have been counted, optionally filtered and normalized, the processed data sets can be further manipulated by one or more filtering and/or normalizing procedures, in some embodiments. A data set that has been further manipulated by one or more filtering and/or normalizing procedures can be used to generate a profile, in certain embodiments. The one or more filtering and/or normalizing procedures sometimes can reduce data set complexity and/or dimensionality, in some embodiments. An outcome can be provided based on a data set of reduced complexity and/or dimensionality.

Non-limiting examples of genomic section filtering is provided herein in Example 4 with respect to PERUN methods. Genomic sections may be filtered based on, or based on part on, a measure of error. A measure of error comprising absolute values of deviation, such as an R-factor, can be used for genomic section removal or weighting in certain embodiments. An R-factor, in some embodiments, is defined as the sum of the absolute deviations of the predicted count values from the actual measurements divided by the predicted count values from the actual measurements (e.g., Equation B herein). While a measure of error comprising absolute values of deviation may be used, a suitable measure of error may be alternatively employed. In certain embodiments, a measure of error not comprising absolute values of deviation, such as a dispersion based on squares, may be utilized. In some embodiments, genomic sections are filtered or weighted according to a measure of mappability (e.g., a mappability score; Example 5). A genomic section sometimes is filtered or weighted according to a relatively low number of sequence reads mapped to the genomic section (e.g., 0, 1, 2, 3, 4, 5 reads mapped to the genomic section). Genomic sections can be filtered or weighted according to the type of analysis being performed. For example, for chromosome 13, 18 and/or 21 aneuploidy analysis, sex chromosomes may be filtered, and only autosomes, or a subset of autosomes, may be analyzed.

In particular embodiments, the following filtering process may be employed. The same set of genomic sections (e.g., bins) within a given chromosome (e.g., chromosome 21) are selected and the number and/or amount of reads in affected and unaffected samples are compared. The gap relates trisomy 21 and euploid samples and it involves a set of genomic sections covering most of chromosome 21. The set of genomic sections is the same between euploid and T21 samples. The distinction between a set of genomic sections and a single section is not crucial, as a genomic section can be defined. The same genomic region is compared in different patients. This process can be utilized for a trisomy analysis, such as for T13 or T18 in addition to, or instead of, T21.

In particular embodiments, the following filtering process may be employed. The same set of genomic sections (e.g., bins) within a given sex chromosome (e.g., chromosome X, chromosome Y) are selected and the number and/or amount of reads in affected and unaffected samples are compared. The gap relates sex chromosome aneuploid and euploid samples and it involves a set of genomic sections covering most of chromosome X and/or chromosome Y. The set of genomic sections is the same between euploid and affected samples. The distinction between a set of genomic sections and a single section is not crucial, as a genomic section can be defined. The same genomic region is compared in different patients. This process can be utilized for a sex chromosome aneuploidy analysis, such as for X0, XXX, XXY, and XYY, for example.

After data sets have been counted, optionally filtered and normalized, the processed data sets can be manipulated by weighting, in some embodiments. One or more genomic sections can be selected for weighting to reduce the influence of data (e.g., noisy data, uninformative data) contained in the selected genomic sections, in certain embodiments, and in some embodiments, one or more genomic sections can be selected for weighting to enhance or augment the influence of data (e.g., data with small measured variance) contained in the selected genomic sections. In some embodiments, a data set is weighted utilizing a single weighting function that decreases the influence of data with large variances and increases the influence of data with small variances. A weighting function sometimes is used to reduce the influence of data with large variances and augment the influence of data with small variances (e.g., [1/(standard deviation)$^2$]). In some embodiments, a profile plot of processed data further manipulated by weighting is generated to facilitate classification and/or providing an outcome. An outcome can be provided based on a profile plot of weighted data Filtering or weighting of genomic sections can be performed at one or more suitable points in an analysis. For example, genomic sections may be filtered or weighted before or after sequence reads are mapped to portions of a reference genome. Genomic sections may be filtered or weighted before or after an experimental bias for individual genome portions is determined in some embodiments. In certain embodiments, genomic sections may be filtered or weighted before or after genomic section elevations are calculated.

After data sets have been counted, optionally filtered, normalized, and optionally weighted, the processed data sets can be manipulated by one or more mathematical and/or statistical (e.g., statistical functions or statistical algorithm) manipulations, in some embodiments. In certain embodiments, processed data sets can be further manipulated by calculating Z-scores for one or more selected genomic sections, chromosomes, or portions of chromosomes. In some embodiments, processed data sets can be further manipulated by calculating P-values. Formulas for calculating Z-scores and P-values are presented in Example 1. In certain embodiments, mathematical and/or statistical manipulations include one or more assumptions pertaining to ploidy and/or fetal fraction. In some embodiments, a profile plot of processed data further manipulated by one or more statistical and/or mathematical manipulations is generated to facilitate classification and/or providing an outcome. An outcome can be provided based on a profile plot of statistically and/or mathematically manipulated data. An outcome provided based on a profile plot of statistically and/or mathematically manipulated data often includes one or more assumptions pertaining to ploidy and/or fetal fraction.

In certain embodiments, multiple manipulations are performed on processed data sets to generate an N-dimensional space and/or N-dimensional point, after data sets have been counted, optionally filtered and normalized. An outcome can be provided based on a profile plot of data sets analyzed in N-dimensions.

In some embodiments, data sets are processed utilizing one or more peak elevation analysis, peak width analysis, peak edge location analysis, peak lateral tolerances, the like, derivations thereof, or combinations of the foregoing, as part of or after data sets have processed and/or manipulated. In some embodiments, a profile plot of data processed utilizing one or more peak elevation analysis, peak width analysis, peak edge location analysis, peak lateral tolerances, the like, derivations thereof, or combinations of the foregoing is generated to facilitate classification and/or providing an outcome. An outcome can be provided based on a profile plot of data that has been processed utilizing one or more peak elevation analysis, peak width analysis, peak edge location analysis, peak lateral tolerances, the like, derivations thereof, or combinations of the foregoing.

In some embodiments, the use of one or more reference samples known to be free of a genetic variation in question can be used to generate a reference median count profile, which may result in a predetermined value representative of the absence of the genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for the selected genomic section or sections is expected to vary significantly from the predetermined value for non-affected genomic locations. In certain embodiments, the use of one or more reference samples known to carry the genetic variation in question can be used to generate a reference median count profile, which may result in a predetermined value representative of the presence of the genetic variation, and often deviates from a predetermined value in areas corresponding to the genomic location in which a test subject does not carry the genetic variation. In test subjects not at risk for, or suffering from a medical condition associated with a genetic variation, the numerical value for the selected genomic section or sections is expected to vary significantly from the predetermined value for affected genomic locations.

In some embodiments, analysis and processing of data can include the use of one or more assumptions. A suitable number or type of assumptions can be utilized to analyze or process a data set. Non-limiting examples of assumptions that can be used for data processing and/or analysis include maternal ploidy, fetal contribution, prevalence of certain sequences in a reference population, ethnic background, prevalence of a selected medical condition in related family members, parallelism between raw count profiles from different patients and/or runs after GC-normalization and repeat masking (e.g., GCRM), identical matches represent PCR artifacts (e.g., identical base position), assumptions inherent in a fetal quantifier assay (e.g., FQA), assumptions regarding twins (e.g., if 2 twins and only 1 is affected the effective fetal fraction is only 50% of the total measured fetal fraction (similarly for triplets, quadruplets and the like)), fetal cell free DNA (e.g., cfDNA) uniformly covers the entire genome, the like and combinations thereof.

In those instances where the quality and/or depth of mapped sequence reads does not permit an outcome prediction of the presence or absence of a genetic variation at a desired confidence level (e.g., 95% or higher confidence level), based on the normalized count profiles, one or more additional mathematical manipulation algorithms and/or statistical prediction algorithms, can be utilized to generate additional numerical values useful for data analysis and/or providing an outcome. The term "normalized count profile" as used herein refers to a profile generated using normalized counts. Examples of methods that can be used to generate normalized counts and normalized count profiles are described herein. As noted, mapped sequence reads that have been counted can be normalized with respect to test sample counts or reference sample counts. In some embodiments, a normalized count profile can be presented as a plot.

Profiles

In some embodiments, a processing step can comprise generating one or more profiles (e.g., profile plot) from various aspects of a data set or derivation thereof (e.g., product of one or more mathematical and/or statistical data processing steps known in the art and/or described herein). The term "profile" as used herein refers to a product of a mathematical and/or statistical manipulation of data that can facilitate identification of patterns and/or correlations in large quantities of data. A "profile" often includes values resulting from one or more manipulations of data or data sets, based on one or more criteria. A profile often includes multiple data points. Any suitable number of data points may be included in a profile depending on the nature and/or complexity of a data set. In certain embodiments, profiles may include 2 or more data points, 3 or more data points, 5 or more data points, 10 or more data points, 24 or more data points, 25 or more data points, 50 or more data points, 100 or more data points, 500 or more data points, 1000 or more data points, 5000 or more data points, 10,000 or more data points, or 100,000 or more data points.

In some embodiments, a profile is representative of the entirety of a data set, and in certain embodiments, a profile is representative of a portion or subset of a data set. That is, a profile sometimes includes or is generated from data points representative of data that has not been filtered to remove any data, and sometimes a profile includes or is generated from data points representative of data that has been filtered to remove unwanted data. In some embodiments, a data point in a profile represents the results of data manipulation for a genomic section. In certain embodiments, a data point in a profile includes results of data manipulation for groups of genomic sections. In some embodiments, groups of genomic sections may be adjacent to one another, and in certain embodiments, groups of genomic sections may be from different parts of a chromosome or genome.

Data points in a profile derived from a data set can be representative of any suitable data categorization. Non-limiting examples of categories into which data can be grouped to generate profile data points include: genomic sections based on size, genomic sections based on sequence features (e.g., GC content, AT content, position on a chromosome (e.g., short arm, long arm, centromere, telomere), and the like), levels of expression, chromosome, the like or combinations thereof. In some embodiments, a profile may be generated from data points obtained from another profile (e.g., normalized data profile renormalized to a different normalizing value to generate a renormalized data profile). In certain embodiments, a profile generated from data points obtained from another profile reduces the number of data points and/or complexity of the data set. Reducing the number of data points and/or complexity of a data set often facilitates interpretation of data and/or facilitates providing an outcome.

A profile often is a collection of normalized or non-normalized counts for two or more genomic sections. A profile often includes at least one elevation, and often comprises two or more elevations (e.g., a profile often has multiple elevations). An elevation generally is for a set of genomic sections having about the same counts or normalized counts. Elevations are described in greater detail herein. In some embodiments, a profile comprises one or more genomic sections, which genomic sections can be weighted, removed, filtered, normalized, adjusted, averaged, derived as a mean, added, subtracted, processed or transformed by any combination thereof. A profile often comprises normalized counts mapped to genomic sections defining two or more elevations, where the counts are further normalized according to one of the elevations by a suitable method. Often counts of a profile (e.g., a profile elevation) are associated with an uncertainty value.

A profile comprising one or more elevations can include a first elevation and a second elevation. In some embodiments, a first elevation is different (e.g., significantly different) than a second elevation. In some embodiments a first elevation comprises a first set of genomic sections, a second elevation comprises a second set of genomic sections and the first set of genomic sections is not a subset of the second set of genomic sections. In some embodiments, a first set of genomic sections is different than a second set of genomic sections from which a first and second elevation are determined. In some embodiments, a profile can have multiple first elevations that are different (e.g., significantly different, e.g., have a significantly different value) than a second elevation within the profile. In some embodiments, a profile comprises one or more first elevations that are significantly different than a second elevation within the profile and one or more of the first elevations are adjusted. In some embodiments, a profile comprises one or more first elevations that are significantly different than a second elevation within the profile, each of the one or more first elevations comprise a maternal copy number variation, fetal copy number variation, or a maternal copy number variation and a fetal copy number variation and one or more of the first elevations are adjusted. In some embodiments, a first elevation within a profile is removed from the profile or adjusted (e.g., padded). A profile can comprise multiple elevations that include one or more first elevations significantly different than one or more second elevations and often the majority of elevations in a profile are second elevations, which second elevations are about equal to one another. In some embodiments, greater than 50%, greater than 60%, greater than 70%, greater than 80%, greater than 90% or greater than 95% of the elevations in a profile are second elevations.

A profile sometimes is displayed as a plot. For example, one or more elevations representing counts (e.g., normalized counts) of genomic sections can be plotted and visualized. Non-limiting examples of profile plots that can be generated include raw count (e.g., raw count profile or raw profile), normalized count, bin-weighted, z-score, p-value, area ratio versus fitted ploidy, median elevation versus ratio between fitted and measured fetal fraction, principle components, the like, or combinations thereof. Profile plots allow visualization of the manipulated data, in some embodiments. In certain embodiments, a profile plot can be utilized to provide an outcome (e.g., area ratio versus fitted ploidy, median elevation versus ratio between fitted and measured fetal fraction, principle components). The terms "raw count profile plot" or "raw profile plot" as used herein refer to a plot of counts in each genomic section in a region normalized to total counts in a region (e.g., genome, genomic section, chromosome, chromosome bins or a segment of a chromosome). In some embodiments, a profile can be generated using a static window process, and in certain embodiments, a profile can be generated using a sliding window process.

A profile generated for a test subject sometimes is compared to a profile generated for one or more reference subjects, to facilitate interpretation of mathematical and/or statistical manipulations of a data set and/or to provide an outcome. In some embodiments, a profile is generated based on one or more starting assumptions (e.g., maternal contribution of nucleic acid (e.g., maternal fraction), fetal contribution of nucleic acid (e.g., fetal fraction), ploidy of reference sample, the like or combinations thereof). In certain embodiments, a test profile often centers around a predetermined value representative of the absence of a genetic variation, and often deviates from a predetermined value in areas corresponding to the genomic location in which the genetic variation is located in the test subject, if the test subject possessed the genetic variation. In test subjects at risk for, or suffering from a medical condition associated with a genetic variation, the numerical value for a selected genomic section is expected to vary significantly from the predetermined value for non-affected genomic locations. Depending on starting assumptions (e.g., fixed ploidy or optimized ploidy, fixed fetal fraction or optimized fetal fraction or combinations thereof) the predetermined threshold or cutoff value or threshold range of values indicative of the presence or absence of a genetic variation can vary while still providing an outcome useful for determining the presence or absence of a genetic variation. In some embodiments, a profile is indicative of and/or representative of a phenotype.

By way of a non-limiting example, normalized sample and/or reference count profiles can be obtained from raw sequence read data by (a) calculating reference median counts for selected chromosomes, genomic sections or segments thereof from a set of references known not to carry a genetic variation, (b) removal of uninformative genomic sections from the reference sample raw counts (e.g., filtering); (c) normalizing the reference counts for all remaining bins to the total residual number of counts (e.g., sum of remaining counts after removal of uninformative bins) for the reference sample selected chromosome or selected genomic location, thereby generating a normalized reference subject profile; (d) removing the corresponding genomic sections from the test subject sample; and (e) normalizing the remaining test subject counts for one or more selected genomic locations to the sum of the residual reference median counts for the chromosome or chromosomes containing the selected genomic locations, thereby generating a normalized test subject profile. In certain embodiments, an additional normalizing step with respect to the entire genome, reduced by the filtered genomic sections in (b), can be included between (c) and (d). A data set profile can be generated by one or more manipulations of counted mapped sequence read data. Some embodiments include the following. Sequence reads are mapped and the number of sequence tags mapping to each genomic bin are determined (e.g., counted). A raw count profile is generated from the mapped sequence reads that are counted. An outcome is provided by comparing a raw count profile from a test subject to a reference median count profile for chromosomes, genomic sections or segments thereof from a set of reference subjects known not to possess a genetic variation, in certain embodiments.

In some embodiments, sequence read data is optionally filtered to remove noisy data or uninformative genomic sections. After filtering, the remaining counts typically are summed to generate a filtered data set. A filtered count profile is generated from a filtered data set, in certain embodiments.

After sequence read data have been counted and optionally filtered, data sets can be normalized to generate elevations or profiles. A data set can be normalized by normalizing one or more selected genomic sections to a suitable normalizing reference value. In some embodiments, a normalizing reference value is representative of the total counts for the chromosome or chromosomes from which genomic sections are selected. In certain embodiments, a normalizing reference value is representative of one or more corresponding genomic sections, portions of chromosomes or chromosomes from a reference data set prepared from a set of reference subjects known not to possess a genetic variation. In some embodiments, a normalizing reference value is representative of one or more corresponding genomic sections, portions of chromosomes or chromosomes from a test subject data set prepared from a test subject being analyzed for the presence or absence of a genetic variation. In certain embodiments, the normalizing process is performed utilizing a static window approach, and in some embodiments the normalizing process is performed utilizing a moving or sliding window approach. In certain embodiments, a profile comprising normalized counts is generated to facilitate classification and/or providing an outcome. An outcome can be provided based on a plot of a profile comprising normalized counts (e.g., using a plot of such a profile).

Determining a Chromosome Representation

In some embodiments, elevations or levels of a collection of genomic sections (e.g., genomic sections for a chromosome of interest) are combined to generate a chromosome elevation. In some embodiments, chromosome elevation is expressed as a chromosome representation. Chromosome representation can be derived from any suitable quantification method, an example of which is provided in Example 9. Chromosome representations can be transformed, such as into Z-scores, as described herein. Thus, a derivative of a chromosome representation can be a Z-score transformation. Chromosome representation can be an expected chromosome representation (ECR) or a measured chromosome representation (MCR).

Expected Chromosome Representation (ECR)

In some embodiments, an expected chromosome representation (ECR, e.g., an expected euploid chromosome representation) is generated for a chromosome or segment thereof. An ECR is often for a euploid representation of a chromosome, or segment thereof. An ECR can be determined for an autosome or a sex chromosome. In some cases an ECR is determined for an affected autosome (e.g., in the case of a trisomy, e.g., chromosome 13 is the affected autosome in the case of a trisomy 13, chromosome 18 is the affected autosome in the case of trisomy 18, or chromosome 21 is the affected autosome in the case of a trisomy 21). An ECR for chromosome n, or segment thereof, can be referred to as an "expected n chromosome representation". For example, an ECR for chromosome X can be referred to as an "expected X chromosome representation". In some embodiments, an ECR is determined according to the number of genomic sections in a normalized count profile. In some cases the ECR for chromosome n is the ratio between the total number of genomic sections for chromosome n, or a segment thereof, and the total number of genomic sections in a profile (e.g., a profile of all autosomal chromosomes, a profile of most all autosomal chromosomes, a profile of a genome or segment of a genome). In some embodiments, an ECR is the ratio between the total area under an expected elevation representative of the genomic sections for chromosome n, or a segment thereof, and the total area under the expected elevation for all genomic sections of an entire profile (e.g., a profile of all autosomal chromosomes, a profile of most all autosomal chromosomes, a profile of a genome or segment of a genome). In some embodiments, an ECR is determined according to an expected median or mean value of an expected elevation and/or profile. In some embodiments, an ECR is determined for chromosome n, or a segment thereof, where chromosome n is an aneuploid chromosome (e.g., a trisomy). In some embodiments, an ECR is determined for chromosome X and/or chromosome Y for a pregnant female bearing a male or a female fetus. In some cases, an ECR is determined for chromosome X and/or chromosome Y for a pregnant female bearing a male or female fetus comprising a sex aneuploidy (e.g., Turner's Syndrome, Klinefelter syndrome, Jacobs syndrome, XXX syndrome). In some embodiments, an expected euploid chromosome representation for ChrX is the median or mean ChrX representation obtained from a female pregnancy or from a set of female pregnancies. In some embodiments, an expected chromosome representation for ChrX in a male pregnancy is the median or mean ChrX representation obtained from a female pregnancy or from a set of female pregnancies.

Measured Chromosome Representation (MCR)

In some embodiments, a measured (i.e., experimental) chromosome representation (MCR) is generated. Often an MCR is an experimentally derived value. An MCR can be referred to as an experimental chromosome representation. An MCR for chromosome n can be referred to as an "experimental n chromosome representation". For example, an MCR for chromosome X can be referred to as an "experimental X chromosome representation". Generally a "chromosome representation" herein refers to a measured chromosome representation. In some embodiments, an MCR is determined according to counts mapped to genomic sections of a chromosome or a segment thereof. In some embodiments, an MCR is determined from normalized counts. In some embodiments, an MCR is determined from raw counts. Often an MCR is determined from counts normalized by GC content, bin-wise normalization, GC LOESS, PERUN, GCRM, the like or a combination thereof. In some embodiments, an MCR is determined according to counts mapped to genomic sections of a sex chromosome (e.g., an X or Y chromosome) or a chromosome representing an aneuploidy (e.g., an affected autosome, a trisomy). In some embodiments, an MCR is determined according to a measured elevation of a chromosome or segment thereof. In some cases, an MCR for a chromosome can be determined according to a median, average or mean value of one or more elevations in a profile. In some embodiments, an MCR is determined according to counts mapped to genomic sections of a sex chromosome (e.g., an X or Y chromosome) for a pregnant female bearing a male or female fetus comprising a sex aneuploidy (e.g., Turner's Syndrome, Klinefelter syndrome, Jacobs syndrome, XXX syndrome). In some cases an MCR for chromosome n is the ratio between the total number of counts mapped to genomic sections of chromosome n, or a segment thereof, and the total number of counts mapped to genomic sections of all autosomal chromosomes represented in a profile (e.g., a profile of a genome or segment thereof) where chromosome n can be any chromosome. In some embodiments, an MCR for chromosome n is the ratio between the total area under an elevation representative of chromosome n, or a segment thereof, and the total area under an elevation of an entire profile (e.g., a profile of all autosomal chromosomes, a profile of most all autosomal chromosomes, a profile of a genome or segment of a genome).

Representation Module

In some embodiments, a chromosome representation is determined by a representation module. In some embodiments, an ECR is determined by an expected representation module. In some embodiments, an MCR is determined by a representation module. A representation module can be a representation module or an expected representation module. In some embodiments, a representation module determines one or more ratios. As used herein the term "ratio" refers to a numerical value (e.g., a number arrived at) by dividing a first numerical value by a second numerical value. For example, a ratio between A and B can be expressed mathematically as A/B or B/A and a numerical value for the ratio can be obtained by dividing A by B or by dividing B by A. In some cases, a representation module (e.g., a representation module) determines an MCR by generating a ratio of counts. In some embodiments, a representation module determines an MCR for an affected autosome (e.g., chromosome 13 in the case of a trisomy 13, chromosome 18 in the case of a trisomy 18 or chromosome 21 in the case of a trisomy 21). For example, sometimes a representation module (e.g., a representation module) determines an MCR by generating a ratio of counts mapped to genomic sections of chromosome n to the total number of counts mapped to genomic sections of all autosomal chromosomes represented in a profile. In some embodiments, a representation module (e.g., a representation module) determines an MCR by generating a ratio of counts mapped to genomic sections of a sex chromosome (e.g., chromosome X or Y) to the total number of counts mapped to genomic sections of all autosomal chromosomes represented in a profile. In some cases, a representation module (e.g., an expected representation module) determines an ECR by generating a ratio of genomic sections. In some embodiments, an expected representation module determines an ECR for an affected autosome (e.g., chromosome 13 the case of a trisomy 13, chromosome 18 in the case of a trisomy 18 or chromosome 21 in the case of a trisomy 21). For example, sometimes a representation module (e.g., an expected representation module) determines an ECR by generating a ratio of genomic sections for chromosome n to all autosomal genomic sections in a profile. In some embodiments, a representation module can provide a ratio of an MCR to an ECR. In some embodiments, a representation module or an apparatus comprising a representation module gathers, assembles, receives, provides and/or transfers data and/or information to or from another module, apparatus, component, peripheral or operator of an apparatus. For example, sometimes an operator of an apparatus provides a constant, a threshold value, a formula or a predetermined value to a representation module. A representation module can receive data and/or information from a sequencing module, sequencing module, mapping module, counting module, normalization module, comparison module, range setting module, categorization module, adjustment module, plotting module, outcome module, data display organization module and/or logic processing module. In some embodiments, normalized mapped counts are transferred to a representation module from a normalization module. In some embodiments, normalized mapped counts are transferred to an expected representation module from a normalization module. Data and/or information derived from or transformed by a representation module can be transferred from a representation module to a normalization module, comparison module, range setting module, categorization module, adjustment module, plotting module, outcome module, data display organization module, logic processing module, fetal fraction module or other suitable apparatus and/or module. An apparatus comprising a representation module can comprise at least one processor. In some embodiments, a representation is provided by an apparatus that includes a processor (e.g., one or more processors) which processor can perform and/or implement one or more instructions (e.g., processes, routines and/or subroutines) from the representation module. In some embodiments, a representation module operates with one or more external processors (e.g., an internal or external network, server, storage device and/or storage network (e.g., a cloud)).

Elevations

In some embodiments, a value is ascribed to an elevation (e.g. a number). An elevation can be determined by a suitable method, operation or mathematical process (e.g., a processed elevation). The term "level" as used herein is sometimes synonymous with the term "elevation" as used herein. The meaning of the term "level" as used herein sometimes refers to an amount. A determination of the meaning of the term "level" can be determined from the context in which it is used. For example, the term "level", when used in the context of a substance or composition (e.g., level of RNA, plexing level) often refers to an amount. The term "level", when used in the context of uncertainty (e.g., level of error, level of confidence, level of deviation, level of uncertainty) often refers to an amount. The term "level", when used in the context of genomic sections, profiles, reads and/or counts also is referred to herein as an elevation.

An elevation often is, or is derived from, counts (e.g., normalized counts) for a set of genomic sections. In some embodiments, an elevation of a genomic section is substantially equal to the total number of counts mapped to a genomic section (e.g., normalized counts). Often an elevation is determined from counts that are processed, transformed or manipulated by a suitable method, operation or mathematical process known in the art. In some embodiments, an elevation is derived from counts that are processed and non-limiting examples of processed counts include weighted, removed, filtered, normalized, adjusted, averaged, derived as a mean (e.g., mean elevation), added, subtracted, transformed counts or combination thereof. In some embodiments, an elevation comprises counts that are normalized (e.g., normalized counts of genomic sections). An elevation can be for counts normalized by a suitable process, non-limiting examples of which include bin-wise normalization, normalization by GC content, linear and nonlinear least squares regression, GC LOESS, LOWESS, PERUN, RM, GCRM, cQn, the like and/or combinations thereof. An elevation can comprise normalized counts or relative amounts of counts. In some embodiments, an elevation is for counts or normalized counts of two or more genomic sections that are averaged and the elevation is referred to as an average elevation. In some embodiments, an elevation is for a set of genomic sections having a mean count or mean of normalized counts which is referred to as a mean elevation. In some embodiments, an elevation is derived for genomic sections that comprise raw and/or filtered counts. In some embodiments, an elevation is based on counts that are raw. In some embodiments, an elevation is associated with an uncertainty value. An elevation for a genomic section, or a "genomic section elevation," is synonymous with a "genomic section level" herein.

Normalized or non-normalized counts for two or more elevations (e.g., two or more elevations in a profile) can sometimes be mathematically manipulated (e.g., added, multiplied, averaged, normalized, the like or combination thereof) according to elevations. For example, normalized or non-normalized counts for two or more elevations can be normalized according to one, some or all of the elevations in a profile. In some embodiments, normalized or non-normalized counts of all elevations in a profile are normalized according to one elevation in the profile. In some embodiments, normalized or non-normalized counts of a first elevation in a profile are normalized according to normalized or non-normalized counts of a second elevation in the profile.

Non-limiting examples of an elevation (e.g., a first elevation, a second elevation) are an elevation for a set of genomic sections comprising processed counts, an elevation for a set of genomic sections comprising a mean, median or average of counts, an elevation for a set of genomic sections comprising normalized counts, the like or any combination thereof. In some embodiments, a first elevation and a second elevation in a profile are derived from counts of genomic sections mapped to the same chromosome. In some embodiments, a first elevation and a second elevation in a profile are derived from counts of genomic sections mapped to different chromosomes.

In some embodiments an elevation is determined from normalized or non-normalized counts mapped to one or more genomic sections. In some embodiments, an elevation is determined from normalized or non-normalized counts mapped to two or more genomic sections, where the normalized counts for each genomic section often are about the same. There can be variation in counts (e.g., normalized counts) in a set of genomic sections for an elevation. In a set of genomic sections for an elevation there can be one or more genomic sections having counts that are significantly different than in other genomic sections of the set (e.g., peaks and/or dips). Any suitable number of normalized or non-normalized counts associated with any suitable number of genomic sections can define an elevation.

In some embodiments, one or more elevations can be determined from normalized or non-normalized counts of all or some of the genomic sections of a genome. Often an elevation can be determined from all or some of the normalized or non-normalized counts of a chromosome, or segment thereof. In some embodiments, two or more counts derived from two or more genomic sections (e.g., a set of genomic sections) determine an elevation. In some embodiments, two or more counts (e.g., counts from two or more genomic sections) determine an elevation. In some embodiments, counts from 2 to about 100,000 genomic sections determine an elevation. In some embodiments, counts from 2 to about 50,000, 2 to about 40,000, 2 to about 30,000, 2 to about 20,000, 2 to about 10,000, 2 to about 5000, 2 to about 2500, 2 to about 1250, 2 to about 1000, 2 to about 500, 2 to about 250, 2 to about 100 or 2 to about 60 genomic sections determine an elevation. In some embodiments counts from about 10 to about 50 genomic sections determine an elevation. In some embodiments counts from about 20 to about 40 or more genomic sections determine an elevation. In some embodiments, an elevation comprises counts from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60 or more genomic sections. In some embodiments, an elevation corresponds to a set of genomic sections (e.g., a set of genomic sections of a reference genome, a set of genomic sections of a chromosome or a set of genomic sections of a segment of a chromosome).

In some embodiments, an elevation is determined for normalized or non-normalized counts of genomic sections that are contiguous. In some embodiments, genomic sections (e.g., a set of genomic sections) that are contiguous represent neighboring segments of a genome or neighboring segments of a chromosome or gene. For example, two or more contiguous genomic sections, when aligned by merging the genomic sections end to end, can represent a sequence assembly of a DNA sequence longer than each genomic section. For example two or more contiguous genomic sections can represent of an intact genome, chromosome, gene, intron, exon or segment thereof. In some embodiments, an elevation is determined from a collection (e.g., a set) of contiguous genomic sections and/or non-contiguous genomic sections.

Significantly Different Elevations

In some embodiments, a profile of normalized counts comprises an elevation (e.g., a first elevation) significantly different than another elevation (e.g., a second elevation) within the profile. A first elevation may be higher or lower than a second elevation. In some embodiments, a first elevation is for a set of genomic sections comprising one or more reads comprising a copy number variation (e.g., a maternal copy number variation, fetal copy number variation, or a maternal copy number variation and a fetal copy number variation) and the second elevation is for a set of genomic sections comprising reads having substantially no copy number variation. In some embodiments, significantly different refers to an observable difference. In some embodiments, significantly different refers to statistically different or a statistically significant difference. A statistically significant difference is sometimes a statistical assessment of an observed difference. A statistically significant difference can be assessed by a suitable method in the art. Any suitable threshold or range can be used to determine that two elevations are significantly different. In some embodiments two elevations (e.g., mean elevations) that differ by about 0.01 percent or more (e.g., 0.01 percent of one or either of the elevation values) are significantly different. In some embodiments, two elevations (e.g., mean elevations) that differ by about 0.1 percent or more are significantly different. In some embodiments, two elevations (e.g., mean elevations) that differ by about 0.5 percent or more are significantly different. In some embodiments, two elevations (e.g., mean elevations) that differ by about 0.5, 0.75, 1, 1.5, 2, 2.5, 3, 3.5, 4, 4.5, 5, 5.5, 6, 6.5, 7, 7.5, 8, 8.5, 9, 9.5 or more than about 10% are significantly different. In some embodiments, two elevations (e.g., mean elevations) are significantly different and there is no overlap in either elevation and/or no overlap in a range defined by an uncertainty value calculated for one or both elevations. In some embodiments the uncertainty value is a standard deviation expressed as sigma. In some embodiments, two elevations (e.g., mean elevations) are significantly different and they differ by about 1 or more times the uncertainty value (e.g., 1 sigma). In some embodiments, two elevations (e.g., mean elevations) are significantly different and they differ by about 2 or more times the uncertainty value (e.g., 2 sigma), about 3 or more, about 4 or more, about 5 or more, about 6 or more, about 7 or more, about 8 or more, about 9 or more, or about 10 or more times the uncertainty value. In some embodiments, two elevations (e.g., mean elevations) are significantly different when they differ by about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0 times the uncertainty value or more. In some embodiments, the confidence level increases as the difference between two elevations increases. In some embodiments, the confidence level decreases as the difference between two elevations decreases and/or as the uncertainty value increases. For example, sometimes the confidence level increases with the ratio of the difference between elevations and the standard deviation (e.g., MADs).

In some embodiments, a first set of genomic sections often includes genomic sections that are different than (e.g., non-overlapping with) a second set of genomic sections. For example, sometimes a first elevation of normalized counts is significantly different than a second elevation of normalized counts in a profile, and the first elevation is for a first set of genomic sections, the second elevation is for a second set of genomic sections and the genomic sections do not overlap in the first set and second set of genomic sections. In some embodiments, a first set of genomic sections is not a subset of a second set of genomic sections from which a first elevation and second elevation are determined, respectively. In some embodiments, a first set of genomic sections is different and/or distinct from a second set of genomic sections from which a first elevation and second elevation are determined, respectively.

In some embodiments, a first set of genomic sections is a subset of a second set of genomic sections in a profile. For example, sometimes a second elevation of normalized counts for a second set of genomic sections in a profile comprises normalized counts of a first set of genomic sections for a first elevation in the profile and the first set of genomic sections is a subset of the second set of genomic sections in the profile. In some embodiments, an average, mean or median elevation is derived from a second elevation where the second elevation comprises a first elevation. In some embodiments, a second elevation comprises a second set of genomic sections representing an entire chromosome and a first elevation comprises a first set of genomic sections where the first set is a subset of the second set of genomic sections and the first elevation represents a maternal copy number variation, fetal copy number variation, or a maternal copy number variation and a fetal copy number variation that is present in the chromosome.

In some embodiments, a value of a second elevation is closer to the mean, average or median value of a count profile for a chromosome, or segment thereof, than the first elevation. In some embodiments, a second elevation is a mean elevation of a chromosome, a portion of a chromosome or a segment thereof. In some embodiments, a first elevation is significantly different from a predominant elevation (e.g., a second elevation) representing a chromosome, or segment thereof. A profile may include multiple first elevations that significantly differ from a second elevation, and each first elevation independently can be higher or lower than the second elevation. In some embodiments, a first elevation and a second elevation are derived from the same chromosome and the first elevation is higher or lower than the second elevation, and the second elevation is the predominant elevation of the chromosome. In some embodiments, a first elevation and a second elevation are derived from the same chromosome, a first elevation is indicative of a copy number variation (e.g., a maternal and/or fetal copy number variation, deletion, insertion, duplication) and a second elevation is a mean elevation or predominant elevation of genomic sections for a chromosome, or segment thereof.

In some embodiments, a read in a second set of genomic sections for a second elevation substantially does not include a genetic variation (e.g., a copy number variation, a maternal and/or fetal copy number variation). Often, a second set of genomic sections for a second elevation includes some variability (e.g., variability in elevation, variability in counts for genomic sections). In some embodiments, one or more genomic sections in a set of genomic sections for an elevation associated with substantially no copy number variation include one or more reads having a copy number variation present in a maternal and/or fetal genome. For example, sometimes a set of genomic sections include a copy number variation that is present in a small segment of a chromosome (e.g., less than 10 genomic sections) and the set of genomic sections is for an elevation associated with substantially no copy number variation. Thus a set of genomic sections that include substantially no copy number variation still can include a copy number variation that is present in less than about 10, 9, 8, 7, 6, 5, 4, 3, 2 or 1 genomic sections of an elevation.

In some embodiments, a first elevation is for a first set of genomic sections and a second elevation is for a second set of genomic sections and the first set of genomic sections and second set of genomic sections are contiguous (e.g., adjacent with respect to the nucleic acid sequence of a chromosome or segment thereof). In some embodiments, the first set of genomic sections and second set of genomic sections are not contiguous.

Relatively short sequence reads from a mixture of fetal and maternal nucleic acid can be utilized to provide counts which can be transformed into an elevation and/or a profile. Counts, elevations and profiles can be depicted in electronic or tangible form and can be visualized. Counts mapped to genomic sections (e.g., represented as elevations and/or profiles) can provide a visual representation of a fetal and/or a maternal genome, chromosome, or a portion or a segment of a chromosome that is present in a fetus and/or pregnant female.

Comparison Module

A first elevation can be identified as significantly different from a second elevation by a comparison module or by an apparatus comprising a comparison module. In some embodiments, a comparison module or an apparatus comprising a comparison module is required to provide a comparison between two elevations. In some embodiments, a comparison module compares genomic sections according to one or more of: a FLR, an amount of reads derived from CCF fragments less than a first selected fragment length, GC content (e.g., GC content of a genomic section), number of exons (e.g., number of exons in a genomic section), the like and combinations thereof. In some embodiments a comparison module compares sequence reads according to reads derived from fetal templates, maternal templates and/or reads derived from CCF fragment templates less than a first selected fragment length. An apparatus comprising a comparison module can comprise at least one processor. In some embodiments, elevations, FLR values, thresholds, and/or cut-off values are determined to be significantly different by an apparatus that includes a processor (e.g., one or more processors) which processor can perform and/or implement one or more instructions (e.g., processes, routines and/or subroutines) from the comparison module. In some embodiments, elevations, FRS values, thresholds, and/or cut-off values are determined to be significantly different by an apparatus that includes multiple processors, such as processors coordinated and working in parallel. In some embodiments, a comparison module operates with one or more external processors (e.g., an internal or external network, server, storage device and/or storage network (e.g., a cloud)). In some embodiments, elevations, FLR values, thresholds, and/or cut-off values are determined to be significantly different by an apparatus comprising one or more of the following: one or more flow cells, a camera, fluid handling components, a printer, a display (e.g., an LED, LCT or CRT) and the like. A comparison module can receive data and/or information from a suitable module. A comparison module can receive data and/or information from a sequencing module, a mapping module, a filtering module, a weighting module, a counting module, or a normalization module. A comparison module can receive normalized data and/or information from a normalization module. Data and/or information derived from, or transformed by, a comparison module can be transferred from a comparison module to a mapping module, a range setting module, a plotting module, an adjustment module, a categorization module or an outcome module. A comparison between two or more elevations and/or an identification of an elevation as significantly different from another elevation can be transferred from (e.g., provided to) a comparison module to a categorization module, range setting module or adjustment module.

Reference Elevation and Normalized Reference Value

In some embodiments, a profile comprises a reference elevation (e.g., an elevation used as a reference). Often a profile of normalized counts provides a reference elevation from which expected elevations and expected ranges are determined (see discussion below on expected elevations and ranges). A reference elevation often is for normalized counts of genomic sections comprising mapped reads from both a mother and a fetus. A reference elevation is often the sum of normalized counts of mapped reads from a fetus and a mother (e.g., a pregnant female). In some embodiments, a reference elevation is for genomic sections comprising mapped reads from a euploid mother and/or a euploid fetus. In some embodiments, a reference elevation is for genomic sections comprising mapped reads having a fetal genetic variation (e.g., an aneuploidy (e.g., a trisomy, a sex chromosome aneuploidy)), and/or reads having a maternal genetic variation (e.g., a copy number variation, insertion, deletion). In some embodiments, a reference elevation is for genomic sections that include substantially no maternal and/or fetal copy number variations. In some embodiments, a second elevation is used as a reference elevation. In some embodiments, a profile comprises a first elevation of normalized counts and a second elevation of normalized counts, the first elevation is significantly different from the second elevation and the second elevation is the reference elevation. In some embodiments, a profile comprises a first elevation of normalized counts for a first set of genomic sections, a second elevation of normalized counts for a second set of genomic sections, the first set of genomic sections includes mapped reads having a maternal and/or fetal copy number variation, the second set of genomic sections comprises mapped reads having substantially no maternal copy number variation and/or fetal copy number variation, and the second elevation is a reference elevation.

In some embodiments counts mapped to genomic sections for one or more elevations of a profile are normalized according to counts of a reference elevation. In some embodiments, normalizing counts of an elevation according to counts of a reference elevation comprise dividing counts of an elevation by counts of a reference elevation or a multiple or fraction thereof. Counts normalized according to counts of a reference elevation often have been normalized according to another process (e.g., PERUN) and counts of a reference elevation also often have been normalized (e.g., by PERUN). In some embodiments, the counts of an elevation are normalized according to counts of a reference elevation and the counts of the reference elevation are scalable to a suitable value either prior to or after normalizing. The process of scaling the counts of a reference elevation can comprise any suitable constant (i.e., number) and any suitable mathematical manipulation may be applied to the counts of a reference elevation.

A normalized reference value (NRV) is often determined according to the normalized counts of a reference elevation. Determining an NRV can comprise any suitable normalization process (e.g., mathematical manipulation) applied to the counts of a reference elevation where the same normalization process is used to normalize the counts of other elevations within the same profile. Determining an NRV often comprises dividing a reference elevation by itself. Determining an NRV often comprises dividing a reference elevation by a multiple of itself. Determining an NRV often comprises dividing a reference elevation by the sum or difference of the reference elevation and a constant (e.g., any number).

An NRV is sometimes referred to as a null value. An NRV can be any suitable value. In some embodiments, an NRV is any value other than zero. In some embodiments, an NRV is a whole number. In some embodiments, an NRV is a positive integer. In some embodiments, an NRV is 1, 10, 100 or 1000. Often, an NRV is equal to 1. In some embodiments, an NRV is equal to zero. The counts of a reference elevation can be normalized to any suitable NRV. In some embodiments, the counts of a reference elevation are normalized to an NRV of zero. Often the counts of a reference elevation are normalized to an NRV of 1.

Expected Elevations

An expected elevation is sometimes a pre-defined elevation (e.g., a theoretical elevation, predicted elevation). An "expected elevation" is sometimes referred to herein as a "predetermined elevation value". In some embodiments, an expected elevation is a predicted value for an elevation of normalized counts for a set of genomic sections that include a copy number variation. In some embodiments, an expected elevation is determined for a set of genomic sections that include substantially no copy number variation. An expected elevation can be determined for a chromosome ploidy (e.g., 0, 1, 2 (i.e., diploid), 3 or 4 chromosomes) or a microploidy (homozygous or heterozygous deletion, duplication, insertion or absence thereof). Often an expected elevation is determined for a maternal microploidy (e.g., a maternal and/or fetal copy number variation).

An expected elevation for a genetic variation or a copy number variation can be determined by any suitable manner. Often an expected elevation is determined by a suitable mathematical manipulation of an elevation (e.g., counts mapped to a set of genomic sections for an elevation). In some embodiments, an expected elevation is determined by utilizing a constant sometimes referred to as an expected elevation constant. An expected elevation for a copy number variation is sometimes calculated by multiplying a reference elevation, normalized counts of a reference elevation or an NRV by an expected elevation constant, adding an expected elevation constant, subtracting an expected elevation constant, dividing by an expected elevation constant, or by a combination thereof. Often an expected elevation (e.g., an expected elevation of a maternal and/or fetal copy number variation) determined for the same subject, sample or test group is determined according to the same reference elevation or NRV.

Often an expected elevation is determined by multiplying a reference elevation, normalized counts of a reference elevation or an NRV by an expected elevation constant where the reference elevation, normalized counts of a reference elevation or NRV is not equal to zero. In some embodiments, an expected elevation is determined by adding an expected elevation constant to reference elevation, normalized counts of a reference elevation or an NRV that is equal to zero. In some embodiments, an expected elevation, normalized counts of a reference elevation, NRV and expected elevation constant are scalable. The process of scaling can comprise any suitable constant (i.e., number) and any suitable mathematical manipulation where the same scaling process is applied to all values under consideration.

Expected Elevation Constant

An expected elevation constant can be determined by a suitable method. In some embodiments, an expected elevation constant is arbitrarily determined. Often an expected elevation constant is determined empirically. In some embodiments, an expected elevation constant is determined according to a mathematical manipulation. In some embodiments, an expected elevation constant is determined according to a reference (e.g., a reference genome, a reference sample, reference test data). In some embodiments, an expected elevation constant is predetermined for an elevation representative of the presence or absence of a genetic variation or copy number variation (e.g., a duplication, insertion or deletion). In some embodiments, an expected elevation constant is predetermined for an elevation representative of the presence or absence of a maternal copy number variation, fetal copy number variation, or a maternal copy number variation and a fetal copy number variation. An expected elevation constant for a copy number variation can be any suitable constant or set of constants.

In some embodiments, the expected elevation constant for a homozygous duplication (e.g., a homozygous duplication) can be from about 1.6 to about 2.4, from about 1.7 to about 2.3, from about 1.8 to about 2.2, or from about 1.9 to about 2.1. In some embodiments, the expected elevation constant for a homozygous duplication is about 1.6, 1.7, 1.8, 1.9, 2.0, 2.1, 2.2, 2.3 or about 2.4. Often the expected elevation constant for a homozygous duplication is about 1.90, 1.92, 1.94, 1.96, 1.98, 2.0, 2.02, 2.04, 2.06, 2.08 or about 2.10. Often the expected elevation constant for a homozygous duplication is about 2.

In some embodiments, the expected elevation constant for a heterozygous duplication (e.g., a homozygous duplication) is from about 1.2 to about 1.8, from about 1.3 to about 1.7, or from about 1.4 to about 1.6. In some embodiments, the expected elevation constant for a heterozygous duplication is about 1.2, 1.3, 1.4, 1.5, 1.6, 1.7 or about 1.8. Often the expected elevation constant for a heterozygous duplication is about 1.40, 1.42, 1.44, 1.46, 1.48, 1.5, 1.52, 1.54, 1.56, 1.58 or about 1.60. In some embodiments, the expected elevation constant for a heterozygous duplication is about 1.5.

In some embodiments, the expected elevation constant for the absence of a copy number variation (e.g., the absence of a maternal copy number variation and/or fetal copy number variation) is from about 1.3 to about 0.7, from about 1.2 to about 0.8, or from about 1.1 to about 0.9. In some embodiments, the expected elevation constant for the absence of a copy number variation is about 1.3, 1.2, 1.1, 1.0, 0.9, 0.8 or about 0.7. Often the expected elevation constant for the absence of a copy number variation is about 1.09, 1.08, 1.06, 1.04, 1.02, 1.0, 0.98, 0.96, 0.94, or about 0.92. In some embodiments, the expected elevation constant for the absence of a copy number variation is about 1.

In some embodiments, the expected elevation constant for a heterozygous deletion (e.g., a maternal, fetal, or a maternal and a fetal heterozygous deletion) is from about 0.2 to about 0.8, from about 0.3 to about 0.7, or from about 0.4 to about 0.6. In some embodiments, the expected elevation constant for a heterozygous deletion is about 0.2, 0.3, 0.4, 0.5, 0.6, 0.7 or about 0.8. Often the expected elevation constant for a heterozygous deletion is about 0.40, 0.42, 0.44, 0.46, 0.48, 0.5, 0.52, 0.54, 0.56, 0.58 or about 0.60. In some embodiments, the expected elevation constant for a heterozygous deletion is about 0.5.

In some embodiments, the expected elevation constant for a homozygous deletion (e.g., a homozygous deletion) can be from about −0.4 to about 0.4, from about −0.3 to about 0.3, from about −0.2 to about 0.2, or from about −0.1 to about 0.1. In some embodiments, the expected elevation constant for a homozygous deletion is about −0.4, −0.3, −0.2, −0.1, 0.0, 0.1, 0.2, 0.3 or about 0.4. Often the expected elevation constant for a homozygous deletion is about −0.1, −0.08, −0.06, −0.04, −0.02, 0.0, 0.02, 0.04, 0.06, 0.08 or about 0.10. Often the expected elevation constant for a homozygous deletion is about 0.

Expected Elevation Range

In some embodiments, the presence or absence of a genetic variation or copy number variation (e.g., a maternal copy number variation, fetal copy number variation, or a maternal copy number variation and a fetal copy number variation) is determined by an elevation that falls within or outside of an expected elevation range. An expected elevation range is often determined according to an expected elevation. In some embodiments, an expected elevation range is determined for an elevation comprising substantially no genetic variation or substantially no copy number variation. A suitable method can be used to determine an expected elevation range.

In some embodiments, an expected elevation range is defined according to a suitable uncertainty value calculated for an elevation. Non-limiting examples of an uncertainty value are a standard deviation, standard error, calculated variance, p-value, and mean absolute deviation (MAD). In some embodiments, an expected elevation range for a genetic variation or a copy number variation is determined, in part, by calculating the uncertainty value for an elevation (e.g., a first elevation, a second elevation, a first elevation and a second elevation). In some embodiments, an expected elevation range is defined according to an uncertainty value calculated for a profile (e.g., a profile of normalized counts for a chromosome or segment thereof). In some embodiments, an uncertainty value is calculated for an elevation comprising substantially no genetic variation or substantially no copy number variation. In some embodiments, an uncertainty value is calculated for a first elevation, a second elevation or a first elevation and a second elevation. In some embodiments an uncertainty value is determined for a first elevation, a second elevation or a second elevation comprising a first elevation.

An expected elevation range is sometimes calculated, in part, by multiplying, adding, subtracting, or dividing an uncertainty value by a constant (e.g., a predetermined constant) n. A suitable mathematical procedure or combination of procedures can be used. The constant n (e.g., predetermined constant n) is sometimes referred to as a confidence interval. A selected confidence interval is determined according to the constant n that is selected. The constant n (e.g., the predetermined constant n, the confidence interval) can be determined by a suitable manner. The constant n can be a number or fraction of a number greater than zero. The constant n can be a whole number. Often the constant n is a number less than 10. In some embodiments, the constant n is a number less than about 10, less than about 9, less than about 8, less than about 7, less than about 6, less than about 5, less than about 4, less than about 3, or less than about 2. In some embodiments, the constant n is about 10, 9.5, 9, 8.5, 8, 7.5, 7, 6.5, 6, 5.5, 5, 4.5, 4, 3.5, 3, 2.5, 2 or 1. The constant n can be determined empirically from data derived from subjects (a pregnant female and/or a fetus) with a known genetic disposition.

Often an uncertainty value and constant n defines a range (e.g., an uncertainty cutoff). For example, sometimes an uncertainty value is a standard deviation (e.g., +/−5) and is multiplied by a constant n (e.g., a confidence interval) thereby defining a range or uncertainty cutoff (e.g., 5n to −5n).

In some embodiments, an expected elevation range for a genetic variation (e.g., a maternal copy number variation, fetal copy number variation, or a maternal copy number variation and fetal copy number variation) is the sum of an expected elevation plus a constant n times the uncertainty (e.g., n×sigma (e.g., 6 sigma)). In some embodiments, the expected elevation range for a genetic variation or copy number variation designated by k can be defined by the formula:

$$(\text{Expected Elevation Range})_k = (\text{Expected Elevation})_k + n\sigma \quad \text{Formula R}$$

where σ is an uncertainty value, n is a constant (e.g., a predetermined constant) and the expected elevation range and expected elevation are for the genetic variation k (e.g., k=a heterozygous deletion, e.g., k=the absence of a genetic variation). For example, for an expected elevation equal to 1 (e.g., the absence of a copy number variation), an uncertainty value (i.e. σ) equal to +/−0.05, and n=3, the expected elevation range is defined as 1.15 to 0.85. In some embodiments, the expected elevation range for a heterozygous duplication is determined as 1.65 to 1.35 when the expected elevation for a heterozygous duplication is 1.5, n=3, and the uncertainty value σ is +/−0.05. In some embodiments the expected elevation range for a heterozygous deletion is determined as 0.65 to 0.35 when the expected elevation for a heterozygous duplication is 0.5, n=3, and the uncertainty value σ is +/−0.05. In some embodiments the expected elevation range for a homozygous duplication is determined as 2.15 to 1.85 when the expected elevation for a heterozygous duplication is 2.0, n=3 and the uncertainty value σ is +/−0.05. In some embodiments the expected elevation range for a homozygous deletion is determined as 0.15 to −0.15 when the expected elevation for a heterozygous duplication is 0.0, n=3 and the uncertainty value σ is +/−0.05.

In some embodiments, an expected elevation range for a homozygous copy number variation (e.g., a maternal, fetal or maternal and fetal homozygous copy number variation) is determined, in part, according to an expected elevation range for a corresponding heterozygous copy number variation. For example, sometimes an expected elevation range for a homozygous duplication comprises all values greater than an upper limit of an expected elevation range for a heterozygous duplication. In some embodiments, an expected elevation range for a homozygous duplication comprises all values greater than or equal to an upper limit of an expected elevation range for a heterozygous duplication. In some embodiments, an expected elevation range for a homozygous duplication comprises all values greater than an upper limit of an expected elevation range for a heterozygous duplication and less than the upper limit defined by the formula R where a is an uncertainty value and is a positive value, n is a constant and k is a homozygous duplication. In some embodiments, an expected elevation range for a homozygous duplication comprises all values greater than or equal to an upper limit of an expected elevation range for a heterozygous duplication and less than or equal to the upper limit defined by the formula R where σ is an uncertainty value, σ is a positive value, n is a constant and k is a homozygous duplication.

In some embodiments, an expected elevation range for a homozygous deletion comprises all values less than a lower limit of an expected elevation range for a heterozygous deletion. In some embodiments, an expected elevation range for a homozygous deletion comprises all values less than or equal to a lower limit of an expected elevation range for a heterozygous deletion. In some embodiments, an expected elevation range for a homozygous deletion comprises all values less than a lower limit of an expected elevation range for a heterozygous deletion and greater than the lower limit defined by the formula R where σ is an uncertainty value, σ is a negative value, n is a constant and k is a homozygous deletion. In some embodiments, an expected elevation range for a homozygous deletion comprises all values less than or equal to a lower limit of an expected elevation range for a heterozygous deletion and greater than or equal to the lower limit defined by the formula R where σ is an uncertainty value, σ is a negative value, n is a constant and k is a homozygous deletion.

An uncertainty value can be utilized to determine a threshold value. In some embodiments, a range (e.g., a threshold range) is obtained by calculating the uncertainty value determined from a raw, filtered and/or normalized counts. A range can be determined by multiplying the uncertainty value for an elevation (e.g. normalized counts of an elevation) by a predetermined constant (e.g., 1, 2, 3, 4, 5, 6, etc.) representing the multiple of uncertainty (e.g., number of standard deviations) chosen as a cutoff threshold (e.g., multiply by 3 for 3 standard deviations), whereby a range is generated, in some embodiments. A range can be determined by adding and/or subtracting a value (e.g., a predetermined value, an uncertainty value, an uncertainty value multiplied by a predetermined constant) to and/or from an elevation whereby a range is generated, in some embodiments. For example, for an elevation equal to 1, a standard deviation of +/−0.2, where σ predetermined constant is 3, the range can be calculated as (1+3(0.2)) to (1+3(−0.2)), or 1.6 to 0.4. A range sometimes can define an expected range or expected elevation range for a copy number variation. In certain embodiments, some or all of the genomic sections exceeding a threshold value, falling outside a range or falling inside a range of values, are removed as part of, prior to, or after a normalization process. In some embodiments, some or all of the genomic sections exceeding a calculated threshold value, falling outside a range or falling inside a range are weighted or adjusted as part of, or prior to the normalization or classification process. Examples of weighting are described herein. The terms "redundant data", and "redundant mapped reads" as used herein refer to sample derived sequence reads that are identified as having already been assigned to a genomic location (e.g., base position) and/or counted for a genomic section.

In some embodiments an uncertainty value is determined according to the formula below:

$$Z = \frac{L_A - L_O}{\sqrt{\frac{\sigma_A^2}{N_A} + \frac{\sigma_O^2}{N_O}}}$$

Where Z represents the standardized deviation between two elevations, L is the mean (or median) elevation and sigma is the standard deviation (or MAD). The subscript O denotes a segment of a profile (e.g., a second elevation, a chromosome, an NRV, a "euploid level", a level absent a copy number variation), and A denotes another segment of a profile (e.g., a first elevation, an elevation representing a copy number variation, an elevation representing an aneuploidy (e.g., a trisomy, a sex chromosome aneuploidy). The variable $N_o$ represents the total number of genomic sections in the segment of the profile denoted by the subscript O. $N_A$ represents the total number of genomic sections in the segment of the profile denoted by subscript A.

Categorizing a Copy Number Variation

An elevation (e.g., a first elevation) that significantly differs from another elevation (e.g., a second elevation) can often be categorized as a copy number variation (e.g., a maternal and/or fetal copy number variation, a fetal copy number variation, a deletion, duplication, insertion) according to an expected elevation range. In some embodiments, the presence of a copy number variation is categorized when a first elevation is significantly different from a second elevation and the first elevation falls within the expected elevation range for a copy number variation. For example, a copy number variation (e.g., a maternal and/or fetal copy number variation, a fetal copy number variation) can be categorized when a first elevation is significantly different from a second elevation and the first elevation falls within the expected elevation range for a copy number variation. In some embodiments, a heterozygous duplication (e.g., a maternal or fetal, or maternal and fetal, heterozygous duplication) or heterozygous deletion (e.g., a maternal or fetal, or maternal and fetal, heterozygous deletion) is categorized when a first elevation is significantly different from a second elevation and the first elevation falls within the expected elevation range for a heterozygous duplication or heterozygous deletion, respectively. In some embodiments, a homozygous duplication or homozygous deletion is categorized when a first elevation is significantly different from a second elevation and the first elevation falls within the expected elevation range for a homozygous duplication or homozygous deletion, respectively.

Range Setting Module

Expected ranges (e.g., expected elevation ranges) for various copy number variations (e.g., duplications, insertions and/or deletions) or ranges for the absence of a copy number variation can be provided by a range setting module or by an apparatus comprising a range setting module. In some embodiments, expected elevations are provided by a range setting module or by an apparatus comprising a range setting module. In some embodiments, a range setting module or an apparatus comprising a range setting module is required to provide expected elevations and/or ranges. In some embodiments, a range setting module gathers, assembles and/or receives data and/or information from another module or apparatus. In some embodiments, a range setting module or an apparatus comprising a range setting module provides and/or transfers data and/or information to another module or apparatus. In some embodiments, a range setting module accepts and gathers data and/or information from a component or peripheral. Often a range setting module gathers and assembles elevations, reference elevations, uncertainty values, and/or constants. In some embodiments, a range setting module accepts and gathers input data and/or information from an operator of an apparatus. For example, sometimes an operator of an apparatus provides a constant, a threshold value, a formula or a predetermined value to a module. An apparatus comprising a range setting module can comprise at least one processor. In some embodiments, expected elevations and expected ranges are provided by an apparatus that includes a processor (e.g., one or more processors) which processor can perform and/or implement one or more instructions (e.g., processes, routines and/or subroutines) from the range setting module. In some embodiments, expected ranges and elevations are provided by an apparatus that includes multiple processors, such as processors coordinated and working in parallel. In some embodiments, a range setting module operates with one or more external processors (e.g., an internal or external network, server, storage device and/or storage network (e.g., a cloud)). In some embodiments, expected ranges are provided by an apparatus comprising a suitable peripheral or component. A range setting module can receive normalized data from a normalization module or comparison data from a comparison module. Data and/or information derived from or transformed by a range setting module (e.g., set ranges, range limits, expected elevation ranges, thresholds, and/or threshold ranges) can be transferred from a range setting module to an adjustment module, an outcome module, a categorization module, plotting module or other suitable apparatus and/or module.

Categorization Module

A copy number variation (e.g., a maternal and/or fetal copy number variation, a fetal copy number variation, a duplication, insertion, deletion) can be categorized by a categorization module or by an apparatus comprising a categorization module. In some embodiments, a copy number variation (e.g., a maternal and/or fetal copy number variation) is categorized by a categorization module. In some embodiments, an elevation (e.g., a first elevation) determined to be significantly different from another elevation (e.g., a second elevation) is identified as representative of a copy number variation by a categorization module. In some embodiments, the absence of a copy number variation is determined by a categorization module. In some embodiments, a determination of a copy number variation can be determined by an apparatus comprising a categorization module. A categorization module can be specialized for categorizing a maternal and/or fetal copy number variation, a fetal copy number variation, a duplication, deletion or insertion or lack thereof or combination of the foregoing. For example, a categorization module that identifies a maternal deletion can be different than and/or distinct from a categorization module that identifies a fetal duplication. In some embodiments, a categorization module or an apparatus comprising a categorization module is required to identify a copy number variation or an outcome determinative of a copy number variation. An apparatus comprising a categorization module can comprise at least one processor. In some embodiments, a copy number variation or an outcome determinative of a copy number variation is categorized by an apparatus that includes a processor (e.g., one or more processors) which processor can perform and/or implement one or more instructions (e.g., processes, routines and/or subroutines) from the categorization module. In some embodiments, a copy number variation or an outcome determinative of a copy number variation is categorized by an apparatus that may include multiple processors, such as processors coordinated and working in parallel. In some embodiments, a categorization module operates with one or more external processors (e.g., an internal or external network, server, storage device and/or storage network (e.g., a cloud)). In some embodiments, a categorization module transfers or receives and/or gathers data and/or information to or from a component or peripheral. Often a categorization module receives, gathers and/or assembles counts, elevations, profiles, normalized data and/or information, reference elevations, expected elevations, expected ranges, uncertainty values, adjustments, adjusted elevations, plots, comparisons and/or constants. In some embodiments, a categorization module accepts and gathers input data and/or information from an operator of an apparatus. For example, sometimes an operator of an apparatus provides a constant, a threshold value, a formula or a predetermined value to a module. In some embodiments, data and/or information are provided by an apparatus that includes multiple processors, such as processors coordinated and working in parallel. In some embodiments, identification or categorization of a copy number variation or an outcome determinative of a copy number variation is provided by an apparatus comprising a suitable peripheral or component. In some embodiments, a categorization module gathers, assembles and/or receives data and/or information from another module or apparatus. A categorization module can receive normalized data from a normalization module, expected elevations and/or ranges from a range setting module, comparison data from a comparison module, plots from a plotting module, and/or adjustment data from an adjustment module. A categorization module can transform data and/or information that it receives into a determination of the presence or absence of a copy number variation. A categorization module can transform data and/or information that it receives into a determination that an elevation represents a genomic section comprising a copy number variation or a specific type of copy number variation (e.g., a maternal homozygous deletion). Data and/or information related to a copy number variation or an outcome determinative of a copy number variation can be transferred from a categorization module to a suitable apparatus and/or module. A copy number variation or an outcome determinative of a copy number variation categorized by methods described herein can be independently verified by further testing (e.g., by targeted sequencing of maternal and/or fetal nucleic acid).

Fetal Fraction Determination Based on Elevation

In some embodiments, a fetal fraction is determined according to an elevation categorized as representative of a maternal and/or fetal copy number variation. For example determining fetal fraction often comprises assessing an expected elevation for a maternal and/or fetal copy number variation utilized for the determination of fetal fraction. In some embodiments, a fetal fraction is determined for an elevation (e.g., a first elevation) categorized as representative of a copy number variation according to an expected elevation range determined for the same type of copy number variation. Often a fetal fraction is determined according to an observed elevation that falls within an expected elevation range and is thereby categorized as a maternal and/or fetal copy number variation. In some embodiments, a fetal fraction is determined when an observed elevation (e.g., a first elevation) categorized as a maternal and/or fetal copy number variation is different than the expected elevation determined for the same maternal and/or fetal copy number variation.

In some embodiments an elevation (e.g., a first elevation, an observed elevation), is significantly different than a second elevation, the first elevation is categorized as a maternal and/or fetal copy number variation, and a fetal fraction is determined according to the first elevation. In some embodiments, a first elevation is an observed and/or experimentally obtained elevation that is significantly different than a second elevation in a profile and a fetal fraction is determined according to the first elevation. In some embodiments, the first elevation is an average, mean or summed elevation and a fetal fraction is determined according to the first elevation. In some embodiments, a first elevation and a second elevation are observed and/or experimentally obtained elevations and a fetal fraction is determined according to the first elevation. In some instances a first elevation comprises normalized counts for a first set of genomic sections and a second elevation comprises normalized counts for a second set of genomic sections and a fetal fraction is determined according to the first elevation. In some embodiments, a first set of genomic sections of a first elevation includes a copy number variation (e.g., the first elevation is representative of a copy number variation) and a fetal fraction is determined according to the first elevation. In some embodiments, the first set of genomic sections of a first elevation includes a homozygous or heterozygous maternal copy number variation and a fetal fraction is determined according to the first elevation. In some embodiments, a profile comprises a first elevation for a first set of genomic sections and a second elevation for a second set of genomic sections, the second set of genomic sections includes substantially no copy number variation (e.g., a maternal copy number variation, fetal copy number variation, or a maternal copy number variation and a fetal copy number variation) and a fetal fraction is determined according to the first elevation.

In some embodiments an elevation (e.g., a first elevation, an observed elevation), is significantly different than a second elevation, the first elevation is categorized as for a maternal and/or fetal copy number variation, and a fetal fraction is determined according to the first elevation and/or an expected elevation of the copy number variation. In some embodiments, a first elevation is categorized as for a copy number variation according to an expected elevation for a copy number variation and a fetal fraction is determined according to a difference between the first elevation and the expected elevation. In some embodiments, an elevation (e.g., a first elevation, an observed elevation) is categorized as a maternal and/or fetal copy number variation, and a fetal fraction is determined as twice the difference between the first elevation and expected elevation of the copy number variation. In some embodiments, an elevation (e.g., a first elevation, an observed elevation) is categorized as a maternal and/or fetal copy number variation, the first elevation is subtracted from the expected elevation thereby providing a difference, and a fetal fraction is determined as twice the difference. In some embodiments, an elevation (e.g., a first elevation, an observed elevation) is categorized as a maternal and/or fetal copy number variation, an expected elevation is subtracted from a first elevation thereby providing a difference, and the fetal fraction is determined as twice the difference.

Often a fetal fraction is provided as a percent. For example, a fetal fraction can be divided by 100 thereby providing a percent value. For example, for a first elevation representative of a maternal homozygous duplication and having an elevation of 155 and an expected elevation for a maternal homozygous duplication having an elevation of 150, a fetal fraction can be determined as 10% (e.g., (fetal fraction=2×(155−150)).

In some embodiments a fetal fraction is determined from two or more elevations within a profile that are categorized as copy number variations. For example, sometimes two or more elevations (e.g., two or more first elevations) in a profile are identified as significantly different than a reference elevation (e.g., a second elevation, an elevation that includes substantially no copy number variation), the two or more elevations are categorized as representative of a maternal and/or fetal copy number variation and a fetal fraction is determined from each of the two or more elevations. In some embodiments, a fetal fraction is determined from about 3 or more, about 4 or more, about 5 or more, about 6 or more, about 7 or more, about 8 or more, or about 9 or more fetal fraction determinations within a profile. In some embodiments, a fetal fraction is determined from about 10 or more, about 20 or more, about 30 or more, about 40 or more, about 50 or more, about 60 or more, about 70 or more, about 80 or more, or about 90 or more fetal fraction determinations within a profile. In some embodiments, a fetal fraction is determined from about 100 or more, about 200 or more, about 300 or more, about 400 or more, about 500 or more, about 600 or more, about 700 or more, about 800 or more, about 900 or more, or about 1000 or more fetal fraction determinations within a profile. In some embodiments, a fetal fraction is determined from about 10 to about 1000, about 20 to about 900, about 30 to about 700, about 40 to about 600, about 50 to about 500, about 50 to about 400, about 50 to about 300, about 50 to about 200, or about 50 to about 100 fetal fraction determinations within a profile.

In some embodiments a fetal fraction is determined as the average or mean of multiple fetal fraction determinations within a profile. In some embodiments, a fetal fraction determined from multiple fetal fraction determinations is a mean (e.g., an average, a mean, a standard average, a median, a mode, a range, or the like) of multiple fetal fraction determinations. Often a fetal fraction determined from multiple fetal fraction determinations is a mean value determined by a suitable method known in the art or described herein. In some embodiments, a mean value of a fetal fraction determination is a weighted mean. In some embodiments, a mean value of a fetal fraction determination is an unweighted mean. A mean, median, mode or average fetal fraction determination (i.e., a mean, median, mode or average fetal fraction determination value) generated from multiple fetal fraction determinations is sometimes associated with an uncertainty value (e.g., a variance, standard deviation, MAD, or the like). Before determining a mean, median, mode or average fetal fraction value from multiple determinations, one or more deviant determinations are removed in some embodiments (described in greater detail herein).

Some fetal fraction determinations within a profile sometimes are not included in the overall determination of a fetal fraction (e.g., mean or average fetal fraction determination). In some embodiments, a fetal fraction determination is derived from a first elevation (e.g., a first elevation that is significantly different than a second elevation) in a profile and the first elevation is not indicative of a genetic variation. For example, some first elevations (e.g., spikes or dips) in a profile are generated from anomalies or unknown causes. Such values often generate fetal fraction determinations that differ significantly from other fetal fraction determinations obtained from true copy number variations. In some embodiments, fetal fraction determinations that differ significantly from other fetal fraction determinations in a profile are identified and removed from a fetal fraction determination. For example, some fetal fraction determinations obtained from anomalous spikes and dips are identified by comparing them to other fetal fraction determinations within a profile and are excluded from the overall determination of fetal fraction.

In some embodiments, an independent fetal fraction determination that differs significantly from a mean, median, mode or average fetal fraction determination is an identified, recognized and/or observable difference. In some embodiments, the term "differs significantly" can mean statistically different and/or a statistically significant difference. An "independent" fetal fraction determination can be a fetal fraction determined (e.g., in some instances a single determination) from a specific elevation categorized as a copy number variation. Any suitable threshold or range can be used to determine that a fetal fraction determination differs significantly from a mean, median, mode or average fetal fraction determination. In some embodiments, a fetal fraction determination differs significantly from a mean, median, mode or average fetal fraction determination and the determination can be expressed as a percent deviation from the average or mean value. In some embodiments, a fetal fraction determination that differs significantly from a mean, median, mode or average fetal fraction determination differs by about 10 percent or more. In some embodiments, a fetal fraction determination that differs significantly from a mean, median, mode or average fetal fraction determination differs by about 15 percent or more. In some embodiments, a fetal fraction determination that differs significantly from a mean, median, mode or average fetal fraction determination differs by about 15% to about 100% or more.

In some embodiments, a fetal fraction determination differs significantly from a mean, median, mode or average fetal fraction determination according to a multiple of an uncertainty value associated with the mean or average fetal fraction determination. Often an uncertainty value and constant n (e.g., a confidence interval) defines a range (e.g., an uncertainty cutoff). For example, sometimes an uncertainty value is a standard deviation for fetal fraction determinations (e.g., +/−5) and is multiplied by a constant n (e.g., a confidence interval) thereby defining a range or uncertainty cutoff (e.g., 5n to −5n, sometimes referred to as 5 sigma). In some embodiments, an independent fetal fraction determination falls outside a range defined by the uncertainty cutoff and is considered significantly different from a mean, median, mode or average fetal fraction determination. For example, for a mean value of 10 and an uncertainty cutoff of 3, an independent fetal fraction greater than 13 or less than 7 is significantly different. In some embodiments, a fetal fraction determination that differs significantly from a mean, median, mode or average fetal fraction determination differs by more than n times the uncertainty value (e.g., n×sigma) where n is about equal to or greater than 1, 2, 3, 4, 5, 6, 7, 8, 9 or 10. In some embodiments, a fetal fraction determination that differs significantly from a mean, median, mode or average fetal fraction determination differs by more than n times the uncertainty value (e.g., n×sigma) where n is about equal to or greater than 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0.

In some embodiments, an elevation is representative of a fetal and/or maternal microploidy. In some embodiments, an elevation (e.g., a first elevation, an observed elevation), is significantly different than a second elevation, the first elevation is categorized as a maternal and/or fetal copy number variation, and the first elevation and/or second elevation is representative of a fetal microploidy and/or a maternal microploidy. In some embodiments, a first elevation is representative of a fetal microploidy, In some embodiments, a first elevation is representative of a maternal microploidy. Often a first elevation is representative of a fetal microploidy and a maternal microploidy. In some embodiments, an elevation (e.g., a first elevation, an observed elevation), is significantly different than a second elevation, the first elevation is categorized as a maternal and/or fetal copy number variation, the first elevation is representative of a fetal and/or maternal microploidy and a fetal fraction is determined according to the fetal and/or maternal microploidy. In some instances a first elevation is categorized as a maternal and/or fetal copy number variation, the first elevation is representative of a fetal microploidy and a fetal fraction is determined according to the fetal microploidy. In some embodiments, a first elevation is categorized as a maternal and/or fetal copy number variation, the first elevation is representative of a maternal microploidy and a fetal fraction is determined according to the maternal microploidy. In some embodiments, a first elevation is categorized as a maternal and/or fetal copy number variation, the first elevation is representative of a maternal and a fetal microploidy and a fetal fraction is determined according to the maternal and fetal microploidy.

In some embodiments, a determination of a fetal fraction comprises determining a fetal and/or maternal microploidy. In some embodiments, an elevation (e.g., a first elevation, an observed elevation), is significantly different than a second elevation, the first elevation is categorized as a maternal and/or fetal copy number variation, a fetal and/or maternal microploidy is determined according to the first elevation and/or second elevation and a fetal fraction is determined. In some embodiments, a first elevation is categorized as a maternal and/or fetal copy number variation, a fetal microploidy is determined according to the first elevation and/or second elevation and a fetal fraction is determined according to the fetal microploidy. In some embodiments, a first elevation is categorized as a maternal and/or fetal copy number variation, a maternal microploidy is determined according to the first elevation and/or second elevation and a fetal fraction is determined according to the maternal microploidy. In some embodiments, a first elevation is categorized as a maternal and/or fetal copy number variation, a maternal and fetal microploidy is determined according to the first elevation and/or second elevation and a fetal fraction is determined according to the maternal and fetal microploidy.

A fetal fraction often is determined when the microploidy of the mother is different from (e.g., not the same as) the microploidy of the fetus for a given elevation or for an elevation categorized as a copy number variation. In some embodiments, a fetal fraction is determined when the mother is homozygous for a duplication (e.g., a microploidy of 2) and the fetus is heterozygous for the same duplication (e.g., a microploidy of 1.5). In some embodiments, a fetal fraction is determined when the mother is heterozygous for a duplication (e.g., a microploidy of 1.5) and the fetus is homozygous for the same duplication (e.g., a microploidy of 2) or the duplication is absent in the fetus (e.g., a microploidy of 1). In some embodiments, a fetal fraction is determined when the mother is homozygous for a deletion (e.g., a microploidy of 0) and the fetus is heterozygous for the same deletion (e.g., a microploidy of 0.5). In some embodiments, a fetal fraction is determined when the mother is heterozygous for a deletion (e.g., a microploidy of 0.5) and the fetus is homozygous for the same deletion (e.g., a microploidy of 0) or the deletion is absent in the fetus (e.g., a microploidy of 1).

In some embodiments, a fetal fraction cannot be determined when the microploidy of the mother is the same (e.g., identified as the same) as the microploidy of the fetus for a given elevation identified as a copy number variation. For example, for a given elevation where both the mother and fetus carry the same number of copies of a copy number variation, a fetal fraction is not determined, in some embodiments. For example, a fetal fraction cannot be determined for an elevation categorized as a copy number variation when both the mother and fetus are homozygous for the same deletion or homozygous for the same duplication. In some embodiments, a fetal fraction cannot be determined for an elevation categorized as a copy number variation when both the mother and fetus are heterozygous for the same deletion or heterozygous for the same duplication. In embodiments where multiple fetal fraction determinations are made for a sample, determinations that significantly deviate from a mean, median, mode or average value can result from a copy number variation for which maternal ploidy is equal to fetal ploidy, and such determinations can be removed from consideration.

In some embodiments the microploidy of a maternal copy number variation and fetal copy number variation is unknown. In some embodiments, in instances when there is no determination of fetal and/or maternal microploidy for a copy number variation, a fetal fraction is generated and compared to a mean, median, mode or average fetal fraction determination. A fetal fraction determination for a copy number variation that differs significantly from a mean, median, mode or average fetal fraction determination is sometimes because the microploidy of the mother and fetus are the same for the copy number variation. A fetal fraction determination that differs significantly from a mean, median, mode or average fetal fraction determination is often excluded from an overall fetal fraction determination regardless of the source or cause of the difference. In some embodiments, the microploidy of the mother and/or fetus is determined and/or verified by a method known in the art (e.g., by targeted sequencing methods).

Elevation Adjustments

In some embodiments, one or more elevations are adjusted. A process for adjusting an elevation often is referred to as padding. In some embodiments, multiple elevations in a profile (e.g., a profile of a genome, a chromosome profile, a profile of a portion or segment of a chromosome) are adjusted. In some embodiments, about 1 to about 10,000 or more elevations in a profile are adjusted. In some embodiments, about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 elevations in a profile are adjusted. In some embodiments, one elevation is adjusted. In some embodiments, an elevation (e.g., a first elevation of a normalized count profile) that significantly differs from a second elevation is adjusted. In some embodiments, an elevation categorized as a copy number variation is adjusted. In some embodiments, an elevation (e.g., a first elevation of a normalized count profile) that significantly differs from a second elevation is categorized as a copy number variation (e.g., a copy number variation, e.g., a maternal copy number variation) and is adjusted. In some embodiments, an elevation (e.g., a first elevation) is within an expected elevation range for a maternal copy number variation, fetal copy number variation, or a maternal copy number variation and a fetal copy number variation and the elevation is adjusted. In some embodiments, one or more elevations (e.g., elevations in a profile) are not adjusted. In some embodiments, an elevation (e.g., a first elevation) is outside an expected elevation range for a copy number variation and the elevation is not adjusted. Often, an elevation within an expected elevation range for the absence of a copy number variation is not adjusted. Any suitable number of adjustments can be made to one or more elevations in a profile. In some embodiments, one or more elevations are adjusted. In some embodiments, 2 or more, 3 or more, 5 or more, 6 or more, 7 or more, 8 or more, 9 or more and sometimes 10 or more elevations are adjusted.

In some embodiments, a value of a first elevation is adjusted according to a value of a second elevation. In some embodiments, a first elevation, identified as representative of a copy number variation, is adjusted to the value of a second elevation, where the second elevation is often associated with no copy number variation. In some instances, a value of a first elevation, identified as representative of a copy number variation, is adjusted so the value of the first elevation is about equal to a value of a second elevation.

An adjustment can comprise a suitable mathematical operation. In some embodiments, an adjustment comprises one or more mathematical operations. In some embodiments, an elevation is adjusted by normalizing, filtering, averaging, multiplying, dividing, adding or subtracting or combination thereof. In some embodiments, an elevation is adjusted by a predetermined value or a constant. In some embodiments, an elevation is adjusted by modifying the value of the elevation to the value of another elevation. For example, a first elevation may be adjusted by modifying its value to the value of a second elevation. A value in such instances may be a processed value (e.g., mean, normalized value and the like).

In some embodiments, an elevation is categorized as a copy number variation (e.g., a maternal copy number variation) and is adjusted according to a predetermined value referred to herein as a predetermined adjustment value (PAV). Often a PAV is determined for a specific copy number variation. Often a PAV determined for a specific copy number variation (e.g., homozygous duplication, homozygous deletion, heterozygous duplication, heterozygous deletion) is used to adjust an elevation categorized as a specific copy number variation (e.g., homozygous duplication, homozygous deletion, heterozygous duplication, heterozygous deletion). In some embodiments, an elevation is categorized as a copy number variation and is then adjusted according to a PAV specific to the type of copy number variation categorized. In some embodiments, an elevation (e.g., a first elevation) is categorized as a maternal copy number variation, fetal copy number variation, or a maternal copy number variation and a fetal copy number variation and is adjusted by adding or subtracting a PAV from the elevation. Often an elevation (e.g., a first elevation) is categorized as a maternal copy number variation and is adjusted by adding a PAV to the elevation. For example, an elevation categorized as a duplication (e.g., a maternal, fetal or maternal and fetal homozygous duplication) can be adjusted by adding a PAV determined for a specific duplication (e.g., a homozygous duplication) thereby providing an adjusted elevation. Often a PAV determined for a copy number duplication is a negative value. In some embodiments providing an adjustment to an elevation representative of a duplication by utilizing a PAV determined for a duplication results in a reduction in the value of the elevation. In some embodiments, an elevation (e.g., a first elevation) that significantly differs from a second elevation is categorized as a copy number deletion (e.g., a homozygous deletion, heterozygous deletion, homozygous duplication, homozygous duplication) and the first elevation is adjusted by adding a PAV determined for a copy number deletion. Often a PAV determined for a copy number deletion is a positive value. In some embodiments providing an adjustment to an elevation representative of a deletion by utilizing a PAV determined for a deletion results in an increase in the value of the elevation.

A PAV can be any suitable value. Often a PAV is determined according to and is specific for a copy number variation (e.g., a categorized copy number variation). In some embodiments, a PAV is determined according to an expected elevation for a copy number variation (e.g., a categorized copy number variation) and/or a PAV factor. A PAV sometimes is determined by multiplying an expected elevation by a PAV factor. For example, a PAV for a copy number variation can be determined by multiplying an expected elevation determined for a copy number variation (e.g., a heterozygous deletion) by a PAV factor determined for the same copy number variation (e.g., a heterozygous deletion). For example, PAV can be determined by the formula below:

$$PAV_k = (\text{Expected Elevation})_k \times (PAV\ \text{factor})_k$$

for the copy number variation k (e.g., k=a heterozygous deletion)

A PAV factor can be any suitable value. In some embodiments, a PAV factor for a homozygous duplication is between about −0.6 and about −0.4. In some embodiments, a PAV factor for a homozygous duplication is about −0.60, −0.59, −0.58, −0.57, −0.56, −0.55, −0.54, −0.53, −0.52, −0.51, −0.50, −0.49, −0.48, −0.47, −0.46, −0.45, −0.44, −0.43, −0.42, −0.41 and −0.40. Often a PAV factor for a homozygous duplication is about −0.5.

For example, for an NRV of about 1 and an expected elevation of a homozygous duplication equal to about 2, the PAV for the homozygous duplication is determined as about −1 according to the formula above. In this case, a first elevation categorized as a homozygous duplication is adjusted by adding about −1 to the value of the first elevation, for example.

In some embodiments, a PAV factor for a heterozygous duplication is between about −0.4 and about −0.2. In some embodiments, a PAV factor for a heterozygous duplication is about −0.40, −0.39, −0.38, −0.37, −0.36, −0.35, −0.34, −0.33, −0.32, −0.31, −0.30, −0.29, −0.28, −0.27, −0.26, −0.25, −0.24, −0.23, −0.22, −0.21 and −0.20. Often a PAV factor for a heterozygous duplication is about −0.33.

For example, for an NRV of about 1 and an expected elevation of a heterozygous duplication equal to about 1.5, the PAV for the homozygous duplication is determined as about −0.495 according to the formula above. In this case, a first elevation categorized as a heterozygous duplication is adjusted by adding about −0.495 to the value of the first elevation, for example.

In some embodiments, a PAV factor for a heterozygous deletion is between about 0.4 and about 0.2. In some embodiments, a PAV factor for a heterozygous deletion is about 0.40, 0.39, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21 and 0.20. Often a PAV factor for a heterozygous deletion is about 0.33.

For example, for an NRV of about 1 and an expected elevation of a heterozygous deletion equal to about 0.5, the PAV for the heterozygous deletion is determined as about 0.495 according to the formula above. In this case, a first elevation categorized as a heterozygous deletion is adjusted by adding about 0.495 to the value of the first elevation, for example.

In some embodiments, a PAV factor for a homozygous deletion is between about 0.6 and about 0.4. In some embodiments, a PAV factor for a homozygous deletion is about 0.60, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41 and 0.40. Often a PAV factor for a homozygous deletion is about 0.5.

For example, for an NRV of about 1 and an expected elevation of a homozygous deletion equal to about 0, the PAV for the homozygous deletion is determined as about 1 according to the formula above. In this case, a first elevation categorized as a homozygous deletion is adjusted by adding about 1 to the value of the first elevation, for example.

In some embodiments, a PAV is about equal to or equal to an expected elevation for a copy number variation (e.g., the expected elevation of a copy number variation).

In some embodiments, counts of an elevation are normalized prior to making an adjustment. In some embodiments, counts of some or all elevations in a profile are normalized prior to making an adjustment. For example, counts of an elevation can be normalized according to counts of a reference elevation or an NRV. In some embodiments, counts of an elevation (e.g., a second elevation) are normalized according to counts of a reference elevation or an NRV and the counts of all other elevations (e.g., a first elevation) in a profile are normalized relative to the counts of the same reference elevation or NRV prior to making an adjustment.

In some embodiments, an elevation of a profile results from one or more adjustments. In some embodiments, an elevation of a profile is determined after one or more elevations in the profile are adjusted. In some embodiments, an elevation of a profile is re-calculated after one or more adjustments are made.

In some embodiments, a copy number variation (e.g., a maternal copy number variation, fetal copy number variation, or a maternal copy number variation and a fetal copy number variation) is determined (e.g., determined directly or indirectly) from an adjustment. For example, an elevation in a profile that was adjusted (e.g., an adjusted first elevation) can be identified as a maternal copy number variation. In some embodiments, the magnitude of the adjustment indicates the type of copy number variation (e.g., heterozygous deletion, homozygous duplication, and the like). An adjusted elevation in a profile sometimes can be identified as representative of a copy number variation according to the value of a PAV for the copy number variation. For example, for a given profile, PAV is about −1 for a homozygous duplication, about −0.5 for a heterozygous duplication, about 0.5 for a heterozygous deletion and about 1 for a homozygous deletion. In the preceding example, an elevation adjusted by about −1 can be identified as a homozygous duplication, for example. In some embodiments, one or more copy number variations can be determined from a profile or an elevation comprising one or more adjustments.

In some embodiments, adjusted elevations within a profile are compared. In some embodiments, anomalies and errors are identified by comparing adjusted elevations. For example, often one or more adjusted elevations in a profile are compared and a particular elevation may be identified as an anomaly or error. In some embodiments, an anomaly or error is identified within one or more genomic sections making up an elevation. An anomaly or error may be identified within the same elevation (e.g., in a profile) or in one or more elevations that represent genomic sections that are adjacent, contiguous, adjoining or abutting. In some embodiments, one or more adjusted elevations are elevations of genomic sections that are adjacent, contiguous, adjoining or abutting where the one or more adjusted elevations are compared and an anomaly or error is identified. An anomaly or error can be a peak or dip in a profile or elevation where a cause of the peak or dip is known or unknown. In some embodiments adjusted elevations are compared and an anomaly or error is identified where the anomaly or error is due to a stochastic, systematic, random or user error. In some embodiments, adjusted elevations are compared and an anomaly or error is removed from a profile. In some embodiments, adjusted elevations are compared and an anomaly or error is adjusted.

Adjustment Module

In some embodiments, adjustments (e.g., adjustments to elevations or profiles) are made by an adjustment module or by an apparatus comprising an adjustment module. In some embodiments, an adjustment module or an apparatus comprising an adjustment module is required to adjust an elevation. An apparatus comprising an adjustment module can comprise at least one processor.

In some embodiments, an adjusted elevation is provided by an apparatus that includes a processor (e.g., one or more processors) which processor can perform and/or implement one or more instructions (e.g., processes, routines and/or subroutines) from the adjustment module. In some embodiments, an elevation is adjusted by an apparatus that may include multiple processors, such as processors coordinated and working in parallel. In some embodiments, an adjustment module operates with one or more external processors (e.g., an internal or external network, server, storage device and/or storage network (e.g., a cloud)). In some embodiments, an apparatus comprising an adjustment module gathers, assembles and/or receives data and/or information from another module or apparatus. In some embodiments, an apparatus comprising an adjustment module provides and/or transfers data and/or information to another module or apparatus.

In some embodiments, an adjustment module receives and gathers data and/or information from a component or peripheral. Often an adjustment module receives, gathers and/or assembles counts, elevations, profiles, reference elevations, expected elevations, expected elevation ranges, uncertainty values, adjustments and/or constants. Often an adjustment module receives gathers and/or assembles elevations (e.g., first elevations) that are categorized or determined to be copy number variations (e.g., a maternal copy number variation, fetal copy number variation, or a maternal copy number variation and a fetal copy number variation). In some embodiments, an adjustment module accepts and gathers input data and/or information from an operator of an apparatus. For example, sometimes an operator of an apparatus provides a constant, a threshold value, a formula or a predetermined value to a module. In some embodiments, data and/or information are provided by an apparatus that includes multiple processors, such as processors coordinated and working in parallel. In some embodiments, an elevation is adjusted by an apparatus comprising a suitable peripheral or component. An apparatus comprising an adjustment module can receive normalized data from a normalization module, ranges from a range setting module, comparison data from a comparison module, elevations identified (e.g., identified as a copy number variation) from a categorization module, and/or adjustment data from another adjustment module. An adjustment module can receive data and/or information, transform the received data and/or information and provide adjustments. Data and/or information derived from, or transformed by, an adjustment module can be transferred from an adjustment module to a categorization module or to a suitable apparatus and/or module. An elevation adjusted by methods described herein can be independently verified and/or adjusted by further testing (e.g., by targeted sequencing of maternal and or fetal nucleic acid).

Plotting Module

In some embodiments a count, an elevation, and/or a profile is plotted (e.g., graphed). In some embodiments, a plot (e.g., a graph) comprises an adjustment. In some embodiments, a plot comprises an adjustment of a count, an elevation, and/or a profile. In some embodiments, a count, an elevation, and/or a profile is plotted and a count, elevation, and/or a profile comprises an adjustment. Often a count, an elevation, and/or a profile is plotted and a count, elevation, and/or a profile are compared. In some embodiments, a copy number variation (e.g., an aneuploidy, copy number variation) is identified and/or categorized from a plot of a count, an elevation, and/or a profile. In some embodiments, an outcome is determined from a plot of a count, an elevation, and/or a profile. In some embodiments, a plot (e.g., a graph) is made (e.g., generated) by a plotting module or an apparatus comprising a plotting module. In some embodiments, a plotting module or an apparatus comprising a plotting module is required to plot a count, an elevation or a profile. A plotting module may display a plot or send a plot to a display (e.g., a display module). An apparatus comprising a plotting module can comprise at least one processor. In some embodiments, a plot is provided by an apparatus that includes a processor (e.g., one or more processors) which processor can perform and/or implement one or more instructions (e.g., processes, routines and/or subroutines) from the plotting module. In some embodiments, a plot is made by an apparatus that may include multiple processors, such as processors coordinated and working in parallel. In some embodiments, a plotting module operates with one or more external processors (e.g., an internal or external network, server, storage device and/or storage network (e.g., a cloud)). In some embodiments, an apparatus comprising a plotting module gathers, assembles and/or receives data and/or information from another module or apparatus. In some embodiments, a plotting module receives and gathers data and/or information from a component or peripheral. Often a plotting module receives, gathers, assembles and/or plots sequence reads, genomic sections, mapped reads, counts, elevations, profiles, reference elevations, expected elevations, expected elevation ranges, uncertainty values, comparisons, categorized elevations (e.g., elevations identified as copy number variations) and/or outcomes, adjustments and/or constants. In some embodiments, a plotting module accepts and gathers input data and/or information from an operator of an apparatus. For example, sometimes an operator of an apparatus provides a constant, a threshold value, a formula or a predetermined value to a plotting module. In some embodiments, data and/or information are provided by an apparatus that includes multiple processors, such as processors coordinated and working in parallel. In some embodiments, a count, an elevation and/or a profile is plotted by an apparatus comprising a suitable peripheral or component. An apparatus comprising a plotting module can receive normalized data from a normalization module, ranges from a range setting module, comparison data from a comparison module, categorization data from a categorization module, and/or adjustment data from an adjustment module. A plotting module can receive data and/or information, transform the data and/or information and provided plotted data. In some embodiments, an apparatus comprising a plotting module provides and/or transfers data and/or information to another module or apparatus. An apparatus comprising a plotting module can plot a count, an elevation and/or a profile and provide or transfer data and/or information related to the plotting to a suitable apparatus and/or module. Often a plotting module receives, gathers, assembles and/or plots elevations (e.g., profiles, first elevations) and transfers plotted data and/or information to and from an adjustment module and/or comparison module. Plotted data and/or information is sometimes transferred from a plotting module to a categorization module and/or a peripheral (e.g., a display or printer). In some embodiments, plots are categorized and/or determined to comprise a genetic variation (e.g., an aneuploidy) or a copy number variation (e.g., a maternal and/or fetal copy number variation). A count, an elevation and/or a profile plotted by methods described herein can be independently verified and/or adjusted by further testing (e.g., by targeted sequencing of maternal and or fetal nucleic acid).

In some embodiments, an outcome is determined according to one or more elevations. In some embodiments, a determination of the presence or absence of a genetic variation (e.g., a chromosome aneuploidy) is determined according to one or more adjusted elevations. In some embodiments, a determination of the presence or absence of a genetic variation (e.g., a chromosome aneuploidy) is determined according to a profile comprising 1 to about 10,000 adjusted elevations. Often a determination of the presence or absence of a genetic variation (e.g., a chromosome aneuploidy) is determined according to a profile comprising about 1 to about a 1000, 1 to about 900, 1 to about 800, 1 to about 700, 1 to about 600, 1 to about 500, 1 to about 400, 1 to about 300, 1 to about 200, 1 to about 100, 1 to about 50, 1 to about 25, 1 to about 20, 1 to about 15, 1 to about 10, or 1 to about 5 adjustments. In some embodiments, a determination of the presence or absence of a genetic variation (e.g., a chromosome aneuploidy) is determined according to a profile comprising about 1 adjustment (e.g., one adjusted elevation). In some embodiments, an outcome is determined according to one or more profiles (e.g., a profile of a chromosome or segment thereof) comprising one or more, 2 or more, 3 or more, 5 or more, 6 or more, 7 or more, 8 or more, 9 or more or sometimes 10 or more adjustments. In some embodiments, a determination of the presence or absence of a genetic variation (e.g., a chromosome aneuploidy) is determined according to a profile where some elevations in a profile are not adjusted. In some embodiments, a determination of the presence or absence of a genetic variation (e.g., a chromosome aneuploidy) is determined according to a profile where adjustments are not made.

In some embodiments, an adjustment of an elevation (e.g., a first elevation) in a profile reduces a false determination or false outcome. In some embodiments, an adjustment of an elevation (e.g., a first elevation) in a profile reduces the frequency and/or probability (e.g., statistical probability, likelihood) of a false determination or false outcome. A false determination or outcome can be a determination or outcome that is not accurate. A false determination or outcome can be a determination or outcome that is not reflective of the actual or true genetic make-up or the actual or true genetic disposition (e.g., the presence or absence of a genetic variation) of a subject (e.g., a pregnant female, a fetus and/or a combination thereof). In some embodiments, a false determination or outcome is a false negative determination. In some embodiments a negative determination or negative outcome is the absence of a genetic variation (e.g., aneuploidy, copy number variation). In some embodiments, a false determination or false outcome is a false positive determination or false positive outcome. In some embodiments a positive determination or positive outcome is the presence of a genetic variation (e.g., aneuploidy, copy number variation). In some embodiments, a determination or outcome is utilized in a diagnosis. In some embodiments, a determination or outcome is for a fetus.

Outcome

Methods described herein can provide a determination of the presence or absence of a genetic variation (e.g., fetal aneuploidy) for a sample, thereby providing an outcome (e.g., thereby providing an outcome determinative of the presence or absence of a genetic variation (e.g., fetal aneuploidy)). A genetic variation often includes a gain, a loss and/or alteration (e.g., duplication, deletion, fusion, insertion, mutation, reorganization, substitution or aberrant methylation) of genetic information (e.g., chromosomes, segments of chromosomes, polymorphic regions, translocated regions, altered nucleotide sequence, the like or combinations of the foregoing) that results in a detectable change in the genome or genetic information of a test subject with respect to a reference. Presence or absence of a genetic variation can be determined by transforming, analyzing and/or manipulating sequence reads that have been mapped to genomic sections (e.g., genomic bins).

Methods described herein sometimes determine presence or absence of a fetal aneuploidy (e.g., full chromosome aneuploidy, partial chromosome aneuploidy or segmental chromosomal aberration (e.g., mosaicism, deletion and/or insertion)) for a test sample from a pregnant female bearing a fetus. In some embodiments, methods described herein detect euploidy or lack of euploidy (non-euploidy) for a sample from a pregnant female bearing a fetus. Methods described herein sometimes detect trisomy for one or more chromosomes (e.g., chromosome 13, chromosome 18, chromosome 21 or combination thereof) or segment thereof. Methods described herein sometimes detect an aneuploidy for one or more sex chromosomes (e.g., chromosome X, chromosome Y) or segment thereof.

In some embodiments, presence or absence of a genetic variation (e.g., a fetal aneuploidy) is determined by a method described herein, by a method known in the art or by a combination thereof. Presence or absence of a genetic variation generally is determined from counts of sequence reads mapped to genomic sections of a reference genome. Counts of sequence reads utilized to determine presence or absence of a genetic variation sometimes are raw counts and/or filtered counts, and often are normalized counts. A suitable normalization process or processes can be used to generate normalized counts, non-limiting examples of which include bin-wise normalization, normalization by GC content, linear and nonlinear least squares regression, LOESS, GC LOESS, LOWESS, PERUN, RM, GCRM and combinations thereof. Normalized counts sometimes are expressed as one or more levels or elevations in a profile for a particular set or sets of genomic sections. Normalized counts sometimes are adjusted or padded prior to determining presence or absence of a genetic variation.

Presence or absence of a genetic variation (e.g., fetal aneuploidy) sometimes is determined without comparing counts for a set of genomic sections to a reference. Counts measured for a test sample and are in a test region (e.g., a set of genomic sections of interest) are referred to as "test counts" herein. Test counts sometimes are processed counts, averaged or summed counts, a representation, normalized counts, or one or more levels or elevations, as described herein. In some embodiments, test counts are averaged or summed (e.g., an average, mean, median, mode or sum is calculated) for a set of genomic sections, and the averaged or summed counts are compared to a threshold or range. Test counts sometimes are expressed as a representation, which can be expressed as a ratio or percentage of counts for a first set of genomic sections to counts for a second set of genomic sections. In some embodiments, the first set of genomic sections is for one or more test chromosomes (e.g., chromosome 13, chromosome 18, chromosome 21, or combination thereof) and sometimes the second set of genomic sections is for the genome or a part of the genome (e.g., autosomes or autosomes and sex chromosomes). In some embodiments, the first set of genomic sections is for one or more test chromosomes (e.g., chromosome X, chromosome Y, or combination thereof) and sometimes the second set of genomic sections is for the genome or a part of the genome (e.g., autosomes). In some embodiments, the first set of genomic sections is for one or more first regions of a test chromosomes (e.g., chromosome X, chromosome Y, or combination thereof) and sometimes the second set of genomic sections is for one or more second regions of a test chromosome (e.g., chromosome X, chromosome Y, or combination thereof) or the entire test chromosome. In some embodiments, a representation is compared to a threshold or range. In some embodiments, test counts are expressed as one or more levels or elevations for normalized counts over a set of genomic sections, and the one or more levels or elevations are compared to a threshold or range. Test counts (e.g., averaged or summed counts, representation, normalized counts, one or more levels or elevations) above or below a particular threshold, in a particular range or outside a particular range sometimes are determinative of the presence of a genetic variation or lack of euploidy (e.g., not euploidy). Test counts (e.g., averaged or summed counts, representation, normalized counts, one or more levels or elevations) below or above a particular threshold, in a particular range or outside a particular range sometimes are determinative of the absence of a genetic variation or euploidy.

Presence or absence of a genetic variation (e.g., fetal aneuploidy) sometimes is determined by comparing test counts (e.g., raw counts, filtered counts, averaged or summed counts, representation, normalized counts, one or more levels or elevations, for a set of genomic sections) to a reference. A reference can be a suitable determination of counts. Counts for a reference sometimes are raw counts, filtered counts, averaged or summed counts, representation, normalized counts, one or more levels or elevations, for a set of genomic sections. Reference counts often are counts for a euploid test region.

In certain embodiments, test counts sometimes are for a first set of genomic sections and a reference includes counts for a second set of genomic sections different than the first set of genomic sections. Reference counts sometimes are for a nucleic acid sample from the same pregnant female from which the test sample is obtained. In some embodiments, reference counts are for a nucleic acid sample from one or more pregnant females different than the female from which the test sample was obtained. In some embodiments, a first set of genomic sections is in chromosome 13, chromosome 18, chromosome 21, chromosome X, chromosome Y, segment thereof or combination of the foregoing, and the second set of genomic sections is in another chromosome or chromosomes or segment thereof. In a non-limiting example, where a first set of genomic sections is in chromosome 21 or segment thereof, a second set of genomic sections often is in another chromosome (e.g., chromosome 1, chromosome 13, chromosome 14, chromosome 18, chromosome 19, segment thereof or combination of the foregoing). A reference often is located in a chromosome or segment thereof that is typically euploid. For example, chromosome 1 and chromosome 19 often are euploid in fetuses owing to a high rate of early fetal mortality associated with chromosome 1 and chromosome 19 aneuploidies. A measure of deviation between the test counts and the reference counts can be generated.

In some embodiments, a reference comprises counts for the same set of genomic sections as for the test counts, where the counts for the reference are from one or more reference samples (e.g., often multiple reference samples from multiple reference subjects). A reference sample often is from one or more pregnant females different than the female from which a test sample is obtained. A measure of deviation between the test counts and the reference counts can be generated.

A suitable measure of deviation between test counts and reference counts can be selected, non-limiting examples of which include standard deviation, average absolute deviation, median absolute deviation, maximum absolute deviation, standard score (e.g., z-value, z-score, normal score, standardized variable) and the like. In some embodiments, reference samples are euploid for a test region and deviation between the test counts and the reference counts is assessed. A deviation of less than three between test counts and reference counts (e.g., 3-sigma for standard deviation) often is indicative of a euploid test region (e.g., absence of a genetic variation). A deviation of greater than three between test counts and reference counts often is indicative of a non-euploid test region (e.g., presence of a genetic variation). Test counts significantly below reference counts, which reference counts are indicative of euploidy, sometimes are determinative of a monosomy. Test counts significantly above reference counts, which reference counts are indicative of euploidy, sometimes are determinative of a trisomy or sex chromosome aneuploidy. A measure of deviation between test counts for a test sample and reference counts for multiple reference subjects can be plotted and visualized (e.g., z-score plot).

Any other suitable reference can be factored with test counts for determining presence or absence of a genetic variation (or determination of euploid or non-euploid) for a test region of a test sample. For example, a fetal fraction determination can be factored with test counts to determine the presence or absence of a genetic variation. A suitable process for quantifying fetal fraction can be utilized, non-limiting examples of which include a mass spectrometric process, sequencing process or combination thereof.

Laboratory personnel (e.g., a laboratory manager) can analyze values (e.g., test counts, reference counts, level of deviation) underlying a determination of the presence or absence of a genetic variation (or determination of euploid or non-euploid for a test region). For calls pertaining to presence or absence of a genetic variation that are close or questionable, laboratory personnel can re-order the same test, and/or order a different test (e.g., karyotyping and/or amniocentesis in the case of fetal aneuploidy and/or fetal gender determinations), that makes use of the same or different sample nucleic acid from a test subject.

A genetic variation sometimes is associated with medical condition. An outcome determinative of a genetic variation is sometimes an outcome determinative of the presence or absence of a condition (e.g., a medical condition), disease, syndrome or abnormality, or includes, detection of a condition, disease, syndrome or abnormality (e.g., non-limiting examples listed in Tables 1A and 1B). In some embodiments, a diagnosis comprises assessment of an outcome. An outcome determinative of the presence or absence of a condition (e.g., a medical condition), disease, syndrome or abnormality by methods described herein can sometimes be independently verified by further testing (e.g., by karyotyping and/or amniocentesis).

Analysis and processing of data can provide one or more outcomes. The term "outcome" as used herein can refer to a result of data processing that facilitates determining the presence or absence of a genetic variation (e.g., an aneuploidy, a copy number variation). In some embodiments, the term "outcome" as used herein refers to a conclusion that predicts and/or determines the presence or absence of a genetic variation (e.g., an aneuploidy, a copy number variation). In some embodiments, the term "outcome" as used herein refers to a conclusion that predicts and/or determines a risk or probability of the presence or absence of a genetic variation (e.g., an aneuploidy, a copy number variation) in a subject (e.g., a fetus). A diagnosis sometimes comprises use of an outcome. For example, a health practitioner may analyze an outcome and provide a diagnosis bases on, or based in part on, the outcome. In some embodiments, determination, detection or diagnosis of a condition, syndrome or abnormality (e.g., listed in Tables 1A and 1B) comprises use of an outcome determinative of the presence or absence of a genetic variation. In some embodiments, an outcome based on counted mapped sequence reads or transformations thereof is determinative of the presence or absence of a genetic variation. In certain embodiments, an outcome generated utilizing one or more methods (e.g., data processing methods) described herein is determinative of the presence or absence of one or more conditions, syndromes or abnormalities listed in Tables 1A and 1B. In some embodiments, a diagnosis comprises a determination of a presence or absence of a condition, syndrome or abnormality. Often a diagnosis comprises a determination of a genetic variation as the nature and/or cause of a condition, syndrome or abnormality. In some embodiments, an outcome is not a diagnosis. An outcome often comprises one or more numerical values generated using a processing method described herein in the context of one or more considerations of probability. A consideration of risk or probability can include, but is not limited to: an uncertainty value, a measure of variability, confidence level, sensitivity, specificity, standard deviation, coefficient of variation (CV) and/or confidence level, Z-scores, Chi values, Phi values, ploidy values, fitted fetal fraction, area ratios, median elevation, the like or combinations thereof. A consideration of probability can facilitate determining whether a subject is at risk of having, or has, a genetic variation, and an outcome determinative of a presence or absence of a genetic disorder often includes such a consideration.

An outcome sometimes is a phenotype. An outcome sometimes is a phenotype with an associated level of confidence (e.g., an uncertainty value, e.g., a fetus is positive for trisomy 21 with a confidence level of 99%; a fetus is positive for a sex chromosome aneuploidy with a confidence level of 99%; a pregnant female is carrying a male fetus with a confidence level of 95%; a test subject is negative for a cancer associated with a genetic variation at a confidence level of 95%). Different methods of generating outcome values sometimes can produce different types of results. Generally, there are four types of possible scores or calls that can be made based on outcome values generated using methods described herein: true positive, false positive, true negative and false negative. The terms "score", "scores", "call" and "calls" as used herein refer to calculating the probability that a particular genetic variation is present or absent in a subject/sample. The value of a score may be used to determine, for example, a variation, difference, or ratio of mapped sequence reads that may correspond to a genetic variation. For example, calculating a positive score for a selected genetic variation or genomic section from a data set, with respect to a reference genome can lead to an identification of the presence or absence of a genetic variation, which genetic variation sometimes is associated with a medical condition (e.g., cancer, preeclampsia, trisomy, monosomy, sex chromosome aneuploidy, and the like). In some embodiments, an outcome comprises an elevation, a profile and/or a plot (e.g., a profile plot). In those embodiments in which an outcome comprises a profile, a suitable profile or combination of profiles can be used for an outcome. Non-limiting examples of profiles that can be used for an outcome include z-score profiles, p-value profiles, chi value profiles, phi value profiles, the like, and combinations thereof An outcome generated for determining the presence or absence of a genetic variation sometimes includes a null result (e.g., a data point between two clusters, a numerical value with a standard deviation that encompasses values for both the presence and absence of a genetic variation, a data set with a profile plot that is not similar to profile plots for subjects having or free from the genetic variation being investigated). In some embodiments, an outcome indicative of a null result still is a determinative result, and the determination can include the need for additional information and/or a repeat of the data generation and/or analysis for determining the presence or absence of a genetic variation.

An outcome can be generated after performing one or more processing steps described herein, in some embodiments. In certain embodiments, an outcome is generated as a result of one of the processing steps described herein, and in some embodiments, an outcome can be generated after each statistical and/or mathematical manipulation of a data set is performed. An outcome pertaining to the determination of the presence or absence of a genetic variation can be expressed in a suitable form, which form comprises without limitation, a probability (e.g., odds ratio, p-value), likelihood, value in or out of a cluster, value over or under a threshold value, value within a range (e.g., a threshold range), value with a measure of variance or confidence, or risk factor, associated with the presence or absence of a genetic variation for a subject or sample. In certain embodiments, comparison between samples allows confirmation of sample identity (e.g., allows identification of repeated samples and/or samples that have been mixed up (e.g., mislabeled, combined, and the like)).

In some embodiments, an outcome comprises a value above or below a predetermined threshold or cutoff value (e.g., greater than 1, less than 1), and an uncertainty or confidence level associated with the value. In some embodiments, a predetermined threshold or cutoff value is an expected elevation or an expected elevation range. An outcome also can describe an assumption used in data processing. In certain embodiments, an outcome comprises a value that falls within or outside a predetermined range of values (e.g., a threshold range) and the associated uncertainty or confidence level for that value being inside or outside the range. In some embodiments, an outcome comprises a value that is equal to a predetermined value (e.g., equal to 1, equal to zero), or is equal to a value within a predetermined value range, and its associated uncertainty or confidence level for that value being equal or within or outside a range. An outcome sometimes is graphically represented as a plot (e.g., profile plot).

As noted above, an outcome can be characterized as a true positive, true negative, false positive or false negative. The term "true positive" as used herein refers to a subject correctly diagnosed as having a genetic variation. The term "false positive" as used herein refers to a subject wrongly identified as having a genetic variation. The term "true negative" as used herein refers to a subject correctly identified as not having a genetic variation. The term "false negative" as used herein refers to a subject wrongly identified as not having a genetic variation. Two measures of performance for any given method can be calculated based on the ratios of these occurrences: (i) a sensitivity value, which generally is the fraction of predicted positives that are correctly identified as being positives; and (ii) a specificity value, which generally is the fraction of predicted negatives correctly identified as being negative. The term "sensitivity" as used herein refers to the number of true positives divided by the number of true positives plus the number of false negatives, where sensitivity (sens) may be within the range of $0 \leq sens \leq 1$. Ideally, the number of false negatives equal zero or close to zero, so that no subject is wrongly identified as not having at least one genetic variation when they indeed have at least one genetic variation. Conversely, an assessment often is made of the ability of a prediction algorithm to classify negatives correctly, a complementary measurement to sensitivity. The term "specificity" as used herein refers to the number of true negatives divided by the number of true negatives plus the number of false positives, where sensitivity (spec) may be within the range of $0 \leq spec \leq 1$. Ideally, the number of false positives equal zero or close to zero, so that no subject is wrongly identified as having at least one genetic variation when they do not have the genetic variation being assessed.

In certain embodiments, one or more of sensitivity, specificity and/or confidence level are expressed as a percentage. In some embodiments, the percentage, independently for each variable, is greater than about 90% (e.g., about 90, 91, 92, 93, 94, 95, 96, 97, 98 or 99%, or greater than 99% (e.g., about 99.5%, or greater, about 99.9% or greater, about 99.95% or greater, about 99.99% or greater)). Coefficient of variation (CV) in some embodiments is expressed as a percentage, and sometimes the percentage is about 10% or less (e.g., about 10, 9, 8, 7, 6, 5, 4, 3, 2 or 1%, or less than 1% (e.g., about 0.5% or less, about 0.1% or less, about 0.05% or less, about 0.01% or less)). A probability (e.g., that a particular outcome is not due to chance) in certain embodiments is expressed as a Z-score, a p-value, or the results of a t-test. In some embodiments, a measured variance, confidence interval, sensitivity, specificity and the like (e.g., referred to collectively as confidence parameters) for an outcome can be generated using one or more data processing manipulations described herein. Specific examples of generating outcomes and associated confidence levels are described in the Example section.

A method that has sensitivity and specificity equaling one, or 100%, or near one (e.g., between about 90% to about 99%) sometimes is selected. In some embodiments, a method having a sensitivity equaling 1, or 100% is selected, and in certain embodiments, a method having a sensitivity near 1 is selected (e.g., a sensitivity of about 90%, a sensitivity of about 91%, a sensitivity of about 92%, a sensitivity of about 93%, a sensitivity of about 94%, a sensitivity of about 95%, a sensitivity of about 96%, a sensitivity of about 97%, a sensitivity of about 98%, or a sensitivity of about 99%). In some embodiments, a method having a specificity equaling 1, or 100% is selected, and in certain embodiments, a method having a specificity near 1 is selected (e.g., a specificity of about 90%, a specificity of about 91%, a specificity of about 92%, a specificity of about 93%, a specificity of about 94%, a specificity of about 95%, a specificity of about 96%, a specificity of about 97%, a specificity of about 98%, or a specificity of about 99%).

In some embodiments, a method for determining the presence or absence of a genetic variation (e.g., fetal aneuploidy) is performed with an accuracy of at least about 90% to about 100%. For example, the presence or absence of a genetic variation may be determined with an accuracy of at least about 91%, 92%, 93%, 94%, 95%, 96%, 97%, 98%, 99%, 99.1%, 99.2%, 99.3%, 99.4%, 99.5%, 99.6%, 99.7%, 99.8% or 99.9%. In some embodiments, the presence or absence of a genetic variation is determined with an accuracy that is about the same or higher than the accuracy using other methods of genetic variation determination (e.g., karyotype analysis). In some embodiments, the presence or absence of a genetic variation is determined with an accuracy having confidence interval (CI) of about 80% to about 100%. For example, the confidence interval (CI) can be about 81%, 82%, 83%, 84%, 85%, 86%, 87%, 88%, 89%, 90%, 91%, 92%, 93%, 94%, 95%, 96%, 97%, 98%, or 99%.

Outcome sometimes can be determined in terms of sequence tag density. "Sequence tag density" refers to the normalized value of sequence tags or reads for a defined genomic section where the sequence tag density is used for comparing different samples and for subsequent analysis. The value of the sequence tag density often is normalized within a sample. In some embodiments, normalization can be performed by counting the number of tags falling within each genomic section; obtaining a median value of the total sequence tag count for each chromosome; obtaining a median value of all of the autosomal values; and using this value as a normalization constant to account for the differences in total number of sequence tags obtained for different samples. A sequence tag density sometimes is about 1 for a disomic chromosome. Sequence tag densities can vary according to sequencing artifacts, most notably G/C bias, which can be corrected by use of an external standard or internal reference (e.g., derived from substantially all of the sequence tags (genomic sequences), which may be, for example, a single chromosome or a calculated value from all autosomes, in some embodiments). Thus, dosage imbalance of a chromosome or chromosomal regions can be inferred from the percentage representation of the locus among other mappable sequenced tags of the specimen. Dosage imbalance of a particular chromosome or chromosomal regions therefore can be quantitatively determined and be normalized. Methods for sequence tag density normalization and quantification are discussed in further detail below.

In some embodiments, a proportion of all of the sequence reads are from a sex chromosome (e.g., chromosome X, chromosome Y) or a chromosome involved in an aneuploidy (e.g., chromosome 13, chromosome 18, chromosome 21), and other sequence reads are from other chromosomes. By taking into account the relative size of the sex chromosome or chromosome involved in the aneuploidy (e.g., "target chromosome": chromosome 21) compared to other chromosomes, one could obtain a normalized frequency, within a reference range, of target chromosome-specific sequences, in some embodiments. If the fetus has an aneuploidy, for example, in a target chromosome, then the normalized frequency of the target chromosome-derived sequences is statistically greater than the normalized frequency of non-target chromosome-derived sequences, thus allowing the detection of the aneuploidy. The degree of change in the normalized frequency will be dependent on the fractional concentration of fetal nucleic acids in the analyzed sample, in some embodiments.

In some embodiments, presence or absence of a genetic variation (e.g., chromosome aneuploidy) is determined for a fetus. In such embodiments, presence or absence of a fetal genetic variation (e.g., fetal chromosome aneuploidy) is determined.

In certain embodiments, presence or absence of a genetic variation (e.g., chromosome aneuploidy) is determined for a sample. In such embodiments, presence or absence of a genetic variation in sample nucleic acid (e.g., chromosome aneuploidy) is determined. In some embodiments, a variation detected or not detected resides in sample nucleic acid from one source but not in sample nucleic acid from another source. Non-limiting examples of sources include placental nucleic acid, fetal nucleic acid, maternal nucleic acid, cancer cell nucleic acid, non-cancer cell nucleic acid, the like and combinations thereof. In non-limiting examples, a particular genetic variation detected or not detected (i) resides in placental nucleic acid but not in fetal nucleic acid and not in maternal nucleic acid; (ii) resides in fetal nucleic acid but not maternal nucleic acid; or (iii) resides in maternal nucleic acid but not fetal nucleic acid.

Outcome Pertaining to Sex Chromosomes

In some embodiments, an outcome pertains to a genetic variation of a sex chromosome. In some embodiments, an outcome is a determination of sex chromosome karyotype, detection of a sex chromosome aneuploidy and/or determination of fetal gender. Some sex chromosome aneuploidy (SCA) conditions include, but are not limited to, Turner syndrome [45,X], Trisomy X [47,XXX], Klinefelter syndrome [47,XXY], and [47,XYY] syndrome (sometimes referred to as Jacobs syndrome).

Assessments of sex chromosome variations, in some embodiments, are based on a segregation of sequence read count transformations for chromosome X and chromosome Y. Sequence read count transformations may include, for example, chromosome X representations and chromosome Y representations and/or Z-scores based on such representations. A two dimensional plot of nucleotide sequence read count transformations (e.g., Z scores based on PERUN normalized read counts) for chromosome X versus chromosome Y for a group of samples having various karyotypes (e.g., XX, XY, XXX, X, XXY, XYY) generates a planar field of plot points that can be carved into regions, each specific for a particular karyotype (an example is provided in FIG. 132). Determination of a sex chromosome karyotype, for example, for a given sample may be achieved by determining in which region of the planar field the plot point for that sample falls.

Certain methods described herein can be useful for generating plots having well-defined regions (e.g., with sharp boundaries, high resolution) for particular karyotype variations. Methods that can help generate high resolution plots include sequence read count normalization, selection of informative genomic sections (i.e., bins) for chromosome X and chromosome Y, establishment of non-reportable (i.e., "no call" zones), and additional normalization of chromosome X and chromosome Y elevations. Normalization of sequence reads and further normalization of elevations is described herein and may include PERUN normalization, for example, of sequence reads mapped to chromosome X and/or chromosome Y and/or elevations (e.g., chromosome representations) for chromosome X and/or Y. Selection of informative genomic sections for chromosome X and chromosome Y is described herein and may include, for example, evaluation of filtering parameters such as cross-validation parameters, mappability, repeatability and/or male versus female separation.

Transformation of sequence reads into two-dimensional plots, as described herein, can be useful for determining sex chromosome karyotype, determining fetal gender and/or detecting the presence or absence of a sex chromosome aneuploidy, often with high levels sensitivity and specificity. In some instances, sensitivity (i.e., true positives divided by the sum of true positives plus false negatives) and specificity (i.e., true negatives divided by the sum of true negatives plus false positives) may be described in terms of plot points and regions of the planar field. For example, a false negative might be a plot point representing a sample with a true karyotype A that falls outside of the region defined for karyotype A. Thus, a plot point lying outside of its karyotype region would, in some instances, decrease the sensitivity f or detection of the karyotype. A false positive might be a plot point representing a sample with a true karyotype B that falls inside the region defined for karyotype A. Thus, a plot point incorrectly lying inside a karyotype region would, in some instances, decrease the specificity for detection of the karyotype.

Certain regions of the planar field described above may be designated as non-reportable zones (i.e., "no call" zones). Samples having plot points that lie within such non-reportable zones may not be assigned an outcome (e.g., sex chromosome karyotype). Elimination of samples having plot points that lie within non-reportable zones can increase the overall accuracy (e.g., sensitivity and specificity) of a method herein. A non-reportable zone may comprise any area on the planar field where two or more karyotype regions overlap or have the potential to overlap. For example, a non-reportable zone may comprise a region on the planar field where plot points for X0 samples overlap or may overlap with XX samples; a region on the planar field where plot points for XX samples overlap or may overlap with X×X samples; a region on the planar field where plot points for XY samples overlap or may overlap with XYY samples; a region on the planar field where plot points for XX samples overlap or may overlap with X×Y samples; a region on the planar field where plot points for XY samples overlap or may overlap with X×Y samples; a region on the planar field where plot points for XY samples overlap or may overlap with XX samples and/or a region on the planar field where plot points for X×Y samples overlap or may overlap with XYY samples. Thus, non-reportable zones may be defined by cutoff values for certain karyotype designations. A description of example cutoff values for certain karyotype designations is provided in Table 2. Non-reportable zones also may comprise any area on the planar field that does not fall within a percentile range and/or confidence interval range for any or all karyotypes assayed.

In some embodiments, non-reportable zones are different depending on whether the sample is from a pregnant female carrying a female fetus (i.e., "female pregnancy") or is from a pregnant female carrying a male fetus (i.e., "male pregnancy"). Examples of non-reportable zones for female pregnancies are presented in FIG. 141. In some embodiments, a non-reportable zone may comprise an area surrounding a cutoff value. For example, on the $Z_x$ scale (i.e., for Z-scores of chromosome X representations), a non-reportable zone may comprise a region surrounding a cutoff value of −5 to 5 (e.g., −5, −4, −3, −2, −1, −0.5, 0.5, 1, 2, 3, 4, 5) and a region surrounding a cutoff value may comprise a range of values less than and/or greater than the selected cutoff value (e.g., −1, −0.9, −0.8, −0.7, −0.6, −0.5, −0.4, −0.3, −0.2, −0.1, −0.05, 0.05, 0.1, 0.2, 0.3, 0.4, 0.5, 0.6, 0.7, 0.8, 0.9, 1.0). In some embodiments, a non-reportable zone comprises a region with $Z_x$ values within −3.5 to −2.5 (i.e., −3±0.5). In some embodiments, a non-reportable zone comprises a region with $Z_x$ values within 2.5 to 3.5 (i.e., 3±0.5). In some embodiments, a non-reportable zone comprises a region with $Z_x$ values within −3.5 to −2.5 (i.e., −3±0.5) and a region with $Z_x$ values within 2.5 to 3.5 (i.e., 3±0.5).

In some embodiments, a non-reportable zone is defined by multiple boundaries. For male pregnancies, for example, a non-reportable zone is defined as an area where several cutoff values intersect. An example of such a zone is provided in FIG. 142. For example, a non-reportable zone may include an area defined by an X0 cutoff (e.g. $Z_x$=−3), XY upper confidence interval value (e.g., $99^{th}$ percentile) and XY control cutoff (e.g., 0.15). In some embodiments, a non-reportable zone includes a planar region below a certain percentile (e.g., 0.15) for euploid male (XY) control measurements.

In some embodiments the presence or absence of a particular sex chromosome aneuploidy can be detected using a method provided herein with a certain sensitivity and specificity. For example, Triple X Syndrome (XXX) may be detected with a sensitivity of about 75% or greater, 80% or greater, 85% or greater, 90% or greater, 95% or greater, 96% or greater, 97% or greater, 98% or greater, 99% or greater, or 100% and a specificity of about 75% or greater, 80% or greater, 85% or greater, 90% or greater, 95% or greater, 96% or greater, 97% or greater, 98% or greater, 99% or greater, or 100%. Turner Syndrome (X or X0) may be detected with a sensitivity of about 75% or greater, 80% or greater, 85% or greater, 90% or greater, 95% or greater, 96% or greater, 97% or greater, 98% or greater, 99% or greater, or 100% and a specificity of about 75% or greater, 80% or greater, 85% or greater, 90% or greater, 95% or greater, 96% or greater, 97% or greater, 98% or greater, 99% or greater, or 100%. Klinefelter Syndrome (XXY) may be detected with a sensitivity of about 75% or greater, 80% or greater, 85% or greater, 90% or greater, 95% or greater, 96% or greater, 97% or greater, 98% or greater, 99% or greater, or 100% and a specificity of about 75% or greater, 80% or greater, 85% or greater, 90% or greater, 95% or greater, 96% or greater, 97% or greater, 98% or greater, 99% or greater, or 100%. Jacobs Syndrome (XYY) may be detected with a sensitivity of about 75% or greater, 80% or greater, 85% or greater, 90% or greater, 95% or greater, 96% or greater, 97% or greater, 98% or greater, 99% or greater, or 100% and a specificity of about 75% or greater, 80% or greater, 85% or greater, 90% or greater, 95% or greater, 96% or greater, 97% or greater, 98% or greater, 99% or greater, or 100%.

In some embodiments the fetal gender can be determined using a method provided herein with a certain sensitivity and specificity. For example, an XX karyotype (euploid female fetus) may be determined with a sensitivity of about 90% or greater, 95% or greater, 96% or greater, 97% or greater, 98% or greater, 99% or greater, or 100% and a specificity of about 90% or greater, 95% or greater, 96% or greater, 97% or greater, 98% or greater, 99% or greater, or 100%. An XY karyotype (euploid male fetus) may be determined with a sensitivity of about 90% or greater, 95% or greater, 96% or greater, 97% or greater, 98% or greater, 99% or greater, or 100% and a specificity of about 90% or greater, 95% or greater, 96% or greater, 97% or greater, 98% or greater, 99% or greater, or 100%.

Outcome Module

The presence or absence of a genetic variation (an aneuploidy, a fetal aneuploidy, a copy number variation, a sex chromosome aneuploidy) can be identified by an outcome module or by an apparatus comprising an outcome module. In some embodiments, a genetic variation is identified by an outcome module. Often a determination of the presence or absence of an aneuploidy is identified by an outcome module. In some embodiments, an outcome determinative of a genetic variation (an aneuploidy, a copy number variation) can be identified by an outcome module or by an apparatus comprising an outcome module. An outcome module can be specialized for determining a specific genetic variation (e.g., a trisomy 13, a trisomy 18, a trisomy 21, a sex chromosome aneuploidy). For example, an outcome module that identifies a trisomy 21 can be different than and/or distinct from an outcome module that identifies a trisomy 18. In some embodiments, an outcome module or an apparatus comprising an outcome module is required to identify a genetic variation or an outcome determinative of a genetic variation (e.g., an aneuploidy, a copy number variation, fetal gender). An apparatus comprising an outcome module can comprise at least one processor. In some embodiments, a genetic variation or an outcome determinative of a genetic variation is provided by an apparatus that includes a processor (e.g., one or more processors) which processor can perform and/or implement one or more instructions (e.g., processes, routines and/or subroutines) from the outcome module. In some embodiments, a genetic variation or an outcome determinative of a genetic variation is identified by an apparatus that may include multiple processors, such as processors coordinated and working in parallel. In some embodiments, an outcome module operates with one or more external processors (e.g., an internal or external network, server, storage device and/or storage network (e.g., a cloud)). In some embodiments, an apparatus comprising an outcome module gathers, assembles and/or receives data and/or information from another module or apparatus. In some embodiments, an apparatus comprising an outcome module provides and/or transfers data and/or information to another module or apparatus. In some embodiments, an outcome module transfers, receives or gathers data and/or information to or from a component or peripheral. Often an outcome module receives, gathers and/or assembles counts, elevations, profiles, normalized data and/or information, reference elevations, expected elevations, expected ranges, uncertainty values, adjustments, adjusted elevations, plots, categorized elevations, comparisons and/or constants. In some embodiments, an outcome module accepts and gathers input data and/or information from an operator of an apparatus. For example, sometimes an operator of an apparatus provides a constant, a threshold value, a formula or a predetermined value to an outcome module. In some embodiments, data and/or information are provided by an apparatus that includes multiple processors, such as processors coordinated and working in parallel. In some embodiments, identification of a genetic variation or an outcome determinative of a genetic variation is provided by an apparatus comprising a suitable peripheral or component. An apparatus comprising an outcome module can receive normalized data from a normalization module, expected elevations and/or ranges from a range setting module, comparison data from a comparison module, categorized elevations from a categorization module, plots from a plotting module, and/or adjustment data from an adjustment module. An outcome module can receive data and/or information, transform the data and/or information and provide an outcome. An outcome module can provide or transfer data and/or information related to a genetic variation or an outcome determinative of a genetic variation to a suitable apparatus and/or module. A genetic variation or an outcome determinative of a genetic variation identified by methods described herein can be independently verified by further testing (e.g., by targeted sequencing of maternal and/or fetal nucleic acid).

After one or more outcomes have been generated, an outcome often is used to provide a determination of the presence or absence of a genetic variation and/or associated medical condition. An outcome typically is provided to a health care professional (e.g., laboratory technician or manager; physician or assistant). Often an outcome is provided by an outcome module. In some embodiments, an outcome is provided by a plotting module. In some embodiments, an outcome is provided on a peripheral or component of an apparatus. For example, sometimes an outcome is provided by a printer or display. In some embodiments, an outcome determinative of the presence or absence of a genetic variation is provided to a healthcare professional in the form of a report, and in certain embodiments the report comprises a display of an outcome value and an associated confidence parameter. Generally, an outcome can be displayed in a suitable format that facilitates determination of the presence or absence of a genetic variation and/or medical condition. Non-limiting examples of formats suitable for use for reporting and/or displaying data sets or reporting an outcome include digital data, a graph, a 2D graph, a 3D graph, and 4D graph, a picture, a pictograph, a chart, a bar graph, a pie graph, a diagram, a flow chart, a scatter plot, a map, a histogram, a density chart, a function graph, a circuit diagram, a block diagram, a bubble map, a constellation diagram, a contour diagram, a cartogram, spider chart, Venn diagram, nomogram, and the like, and combination of the foregoing. Various examples of outcome representations are shown in the drawings and are described in the Examples.

Generating an outcome can be viewed as a transformation of nucleic acid sequence reads into a representation of a subject's cellular nucleic acid, in certain embodiments. A representation of a subject's cellular nucleic acid often reflects a dosage or copy number for a particular chromosome or portion thereof, and the representation thereby often is a property of the subject's nucleic acid. Converting a multitude of relatively small sequence reads to a representation of a relatively large chromosome, for example, can be viewed as a transformation. As an illustration, in a process for generating a representation of chromosome 21, which is about 47 million bases in length, using reads of approximately 36 base pairs in length, many thousands of reads that are at least 100,000 times smaller than the chromosome are transformed into a representation of the significantly larger chromosome. Generating such a representation of a chromosome typically involves several manipulations of reads (e.g., mapping, filtering and/or normalizing) to arrive at a representation of the relatively large chromosome, as described herein. Multiple manipulations often are utilized, which can require the use of one or more computers, often multiple computers coordinated in parallel.

When providing a representation of a chromosome for a fetal chromosome using a sample from a pregnant female, such a transformation further is apparent given that the majority of reads often are from maternal nucleic acid and a minority of reads often is from fetal nucleic acid. Reads of maternal nucleic acid often dominate reads of fetal nucleic acid, and the majority of maternal nucleic acid reads often masks a representation of a fetal chromosome. A typically large background of maternal reads can obscure differences between fetal and maternal chromosome nucleic acid and obtaining a representation of a fetal chromosome against such a background involves a process that de-convolutes the contribution of maternal reads, as described herein.

In some embodiments, an outcome comprises a transformation of sequence reads from a first subject (e.g., a pregnant female), into a composite representation of structures (e.g., a genome, a chromosome or segment thereof), and a second transformation of the composite representation that yields a representation of a structure present in a first subject (e.g., a pregnant female) and/or a second subject (e.g., a fetus).

A transformative method herein sometimes comprises determining the presence or absence of a trisomic chromosome (i.e., chromosome trisomy) in a fetus (e.g., T21, T18 and/or T13) from nucleic acid reads in a sample obtained from a pregnant female subject carrying the fetus. A transformative method herein sometimes comprises determining the presence or absence of an aneuploid sex chromosome (i.e., sex chromosome aneuploidy) in a fetus (e.g., X0, XXX, XXY, XYY) from nucleic acid reads in a sample obtained from a pregnant female subject carrying the fetus. In some embodiments, a transformative method herein may comprise preparing (e.g., determining, visualizing, displaying, providing) a representation of a chromosome (e.g., chromosome copy number, chromosome dosage) for a fetus from nucleic acid reads in a sample obtained from a pregnant female subject carrying the fetus. In the latter embodiments, a representation of a chromosome for a fetus often is for chromosome 13, chromosome 18, chromosome 21, chromosome X and/or chromosome Y.

Use of Outcomes

A health care professional, or other qualified individual, receiving a report comprising one or more outcomes determinative of the presence or absence of a genetic variation can use the displayed data in the report to make a call regarding the status of the test subject or patient. The healthcare professional can make a recommendation based on the provided outcome, in some embodiments. A health care professional or qualified individual can provide a test subject or patient with a call or score with regards to the presence or absence of the genetic variation based on the outcome value or values and associated confidence parameters provided in a report, in some embodiments. In certain embodiments, a score or call is made manually by a healthcare professional or qualified individual, using visual observation of the provided report. In certain embodiments, a score or call is made by an automated routine, sometimes embedded in software, and reviewed by a healthcare professional or qualified individual for accuracy prior to providing information to a test subject or patient. The term "receiving a report" as used herein refers to obtaining, by a communication means, a written and/or graphical representation comprising an outcome, which upon review allows a healthcare professional or other qualified individual to make a determination as to the presence or absence of a genetic variation in a test subject or patient. The report may be generated by a computer or by human data entry, and can be communicated using electronic means (e.g., over the internet, via computer, via fax, from one network location to another location at the same or different physical sites), or by a other method of sending or receiving data (e.g., mail service, courier service and the like). In some embodiments the outcome is transmitted to a health care professional in a suitable medium, including, without limitation, in verbal, document, or file form. The file may be, for example, but not limited to, an auditory file, a computer readable file, a paper file, a laboratory file or a medical record file.

The term "providing an outcome" and grammatical equivalents thereof, as used herein also can refer to a method for obtaining such information, including, without limitation, obtaining the information from a laboratory (e.g., a laboratory file). A laboratory file can be generated by a laboratory that carried out one or more assays or one or more data processing steps to determine the presence or absence of the medical condition. The laboratory may be in the same location or different location (e.g., in another country) as the personnel identifying the presence or absence of the medical condition from the laboratory file. For example, the laboratory file can be generated in one location and transmitted to another location in which the information therein will be transmitted to the pregnant female subject. The laboratory file may be in tangible form or electronic form (e.g., computer readable form), in certain embodiments.

In some embodiments, an outcome can be provided to a health care professional, physician or qualified individual from a laboratory and the health care professional, physician or qualified individual can make a diagnosis based on the outcome. In some embodiments, an outcome can be provided to a health care professional, physician or qualified individual from a laboratory and the health care professional, physician or qualified individual can make a diagnosis based, in part, on the outcome along with additional data and/or information and other outcomes.

A healthcare professional or qualified individual, can provide a suitable recommendation based on the outcome or outcomes provided in the report. Non-limiting examples of recommendations that can be provided based on the provided outcome report includes, surgery, radiation therapy, chemotherapy, genetic counseling, after birth treatment solutions (e.g., life planning, long term assisted care, medicaments, symptomatic treatments), pregnancy termination, organ transplant, blood transfusion, the like or combinations of the foregoing. In some embodiments the recommendation is dependent on the outcome based classification provided (e.g., Down's syndrome, Turner syndrome, medical conditions associated with genetic variations in T13, medical conditions associated with genetic variations in T18).

Software can be used to perform one or more steps in the processes described herein, including but not limited to; counting, data processing, generating an outcome, and/or providing one or more recommendations based on generated outcomes, as described in greater detail hereafter.

Transformations

As noted above, data sometimes is transformed from one form into another form. The terms "transformed", "transformation", and grammatical derivations or equivalents thereof, as used herein refer to an alteration of data from a physical starting material (e.g., test subject and/or reference subject sample nucleic acid; test chromosome and/or reference chromosome; target fragments and/or reference fragments) into a digital representation of the physical starting material (e.g., sequence read data), and in some embodiments includes a further transformation into one or more numerical values or graphical representations of the digital representation that can be utilized to provide an outcome. In certain embodiments, the one or more numerical values and/or graphical representations of digitally represented data can be utilized to represent the appearance of a test subject's physical genome (e.g., virtually represent or visually represent the presence or absence of a genomic insertion, duplication or deletion; represent the presence or absence of a variation in the physical amount of a sequence, fragment, region or chromosome associated with medical conditions). A virtual representation sometimes is further transformed into one or more numerical values or graphical representations of the digital representation of the starting material. These procedures can transform physical starting material into a numerical value or graphical representation, or a representation of the physical appearance of a test subject's genome.

In some embodiments, transformation of a data set facilitates providing an outcome by reducing data complexity and/or data dimensionality. Data set complexity sometimes is reduced during the process of transforming a physical starting material into a virtual representation of the starting material (e.g., sequence reads representative of physical starting material). A suitable feature or variable can be utilized to reduce data set complexity and/or dimensionality. Non-limiting examples of features that can be chosen for use as a target feature for data processing include GC content, fragment size (e.g., length), fragment sequence, fetal gender prediction, identification of chromosomal aneuploidy, identification of particular genes or proteins, identification of cancer, diseases, inherited genes/traits, chromosomal abnormalities, a biological category, a chemical category, a biochemical category, a category of genes or proteins, a gene ontology, a protein ontology, co-regulated genes, cell signaling genes, cell cycle genes, proteins pertaining to the foregoing genes, gene variants, protein variants, co-regulated genes, co-regulated proteins, amino acid sequence, nucleotide sequence, protein structure data and the like, and combinations of the foregoing. Non-limiting examples of data set complexity and/or dimensionality reduction include; reduction of a plurality of sequence reads to profile plots, reduction of a plurality of sequence reads to numerical values (e.g., normalized values, Z-scores, p-values); reduction of multiple analysis methods to probability plots or single points; principle component analysis of derived quantities; and the like or combinations thereof.

Machines, Software and Interfaces

Certain processes and methods described herein (e.g., quantifying, mapping, normalizing, range setting, adjusting, categorizing, counting and/or determining sequence reads, counts, elevations (e.g., elevations) and/or profiles) often cannot be performed without a computer, processor, software, module or other apparatus. Methods described herein typically are computer-implemented methods, and one or more portions of a method sometimes are performed by one or more processors. Embodiments pertaining to methods described in this document generally are applicable to the same or related processes implemented by instructions in systems, apparatus and computer program products described herein. In some embodiments, processes and methods described herein (e.g., quantifying, counting and/or determining sequence reads, counts, elevations and/or profiles) are performed by automated methods. In some embodiments, an automated method is embodied in software, modules, processors, peripherals and/or an apparatus comprising the like, that determine sequence reads, counts, mapping, mapped sequence tags, elevations, profiles, normalizations, comparisons, range setting, categorization, adjustments, plotting, outcomes, transformations and identifications. As used herein, software refers to computer readable program instructions that, when executed by a processor, perform computer operations, as described herein.

Sequence reads, counts, elevations, and profiles derived from a test subject (e.g., a patient, a pregnant female) and/or from a reference subject can be further analyzed and processed to determine the presence or absence of a genetic variation. Sequence reads, counts, elevations and/or profiles sometimes are referred to as "data" or "data sets". In some embodiments, data or data sets can be characterized by one or more features or variables (e.g., sequence based [e.g., GC content, specific nucleotide sequence, the like], function specific [e.g., expressed genes, cancer genes, the like], location based [genome specific, chromosome specific, genomic section or bin specific], the like and combinations thereof). In certain embodiments, data or data sets can be organized into a matrix having two or more dimensions based on one or more features or variables. Data organized into matrices can be organized using any suitable features or variables. A non-limiting example of data in a matrix includes data that is organized by maternal age, maternal ploidy, and fetal contribution. In certain embodiments, data sets characterized by one or more features or variables sometimes are processed after counting.

Apparatuses, software and interfaces may be used to conduct methods described herein. Using apparatuses, software and interfaces, a user may enter, request, query or determine options for using particular information, programs or processes (e.g., mapping sequence reads, processing mapped data and/or providing an outcome), which can involve implementing statistical analysis algorithms, statistical significance algorithms, statistical algorithms, iterative steps, validation algorithms, and graphical representations, for example. In some embodiments, a data set may be entered by a user as input information, a user may download one or more data sets by a suitable hardware media (e.g., flash drive), and/or a user may send a data set from one system to another for subsequent processing and/or providing an outcome (e.g., send sequence read data from a sequencer to a computer system for sequence read mapping; send mapped sequence data to a computer system for processing and yielding an outcome and/or report).

A system typically comprises one or more apparatus. Each apparatus often comprises one or more of memory, one or more processors, and instructions. Where a system includes two or more apparatus, some or all of the apparatus may be located at the same location, some or all of the apparatus may be located at different locations, all of the apparatus may be located at one location and/or all of the apparatus may be located at different locations. Where a system includes two or more apparatus, some or all of the apparatus may be located at the same location as a user, some or all of the apparatus may be located at a location different than a user, all of the apparatus may be located at the same location as the user, and/or all of the apparatus may be located at one or more locations different than the user.

A system sometimes comprises a computing apparatus and a sequencing apparatus, where the sequencing apparatus is configured to receive physical nucleic acid and generate sequence reads, and the computing apparatus is configured to process the reads from the sequencing apparatus. The computing apparatus sometimes is configured to determine the presence or absence of a genetic variation (e.g., copy number variation; fetal chromosome aneuploidy) from the sequence reads.

A user may, for example, place a query to software which then may acquire a data set via internet access, and in certain embodiments, a programmable processor may be prompted to acquire a suitable data set based on given parameters. A programmable processor also may prompt a user to select one or more data set options selected by the processor based on given parameters. A programmable processor may prompt a user to select one or more data set options selected by the processor based on information found via the internet, other internal or external information, or the like. Options may be chosen for selecting one or more data feature selections, one or more statistical algorithms, one or more statistical analysis algorithms, one or more statistical significance algorithms, iterative steps, one or more validation algorithms, and one or more graphical representations of methods, apparatuses, or computer programs.

Systems addressed herein may comprise general components of computer systems, such as, for example, network servers, laptop systems, desktop systems, handheld systems, personal digital assistants, computing kiosks, and the like. A computer system may comprise one or more input means such as a keyboard, touch screen, mouse, voice recognition or other means to allow the user to enter data into the system. A system may further comprise one or more outputs, including, but not limited to, a display screen (e.g., CRT or LCD), speaker, FAX machine, printer (e.g., laser, ink jet, impact, black and white or color printer), or other output useful for providing visual, auditory and/or hardcopy output of information (e.g., outcome and/or report).

In a system, input and output means may be connected to a central processing unit which may comprise among other components, a microprocessor for executing program instructions and memory for storing program code and data. In some embodiments, processes may be implemented as a single user system located in a single geographical site. In certain embodiments, processes may be implemented as a multi-user system. In the case of a multi-user implementation, multiple central processing units may be connected by means of a network. The network may be local, encompassing a single department in one portion of a building, an entire building, span multiple buildings, span a region, span an entire country or be worldwide. The network may be private, being owned and controlled by a provider, or it may be implemented as an internet based service where the user accesses a web page to enter and retrieve information. Accordingly, in certain embodiments, a system includes one or more machines, which may be local or remote with respect to a user. More than one machine in one location or multiple locations may be accessed by a user, and data may be mapped and/or processed in series and/or in parallel. Thus, a suitable configuration and control may be utilized for mapping and/or processing data using multiple machines, such as in local network, remote network and/or "cloud" computing platforms.

A system can include a communications interface in some embodiments. A communications interface allows for transfer of software and data between a computer system and one or more external devices. Non-limiting examples of communications interfaces include a modem, a network interface (such as an Ethernet card), a communications port, a PCMCIA slot and card, and the like. Software and data transferred via a communications interface generally are in the form of signals, which can be electronic, electromagnetic, optical and/or other signals capable of being received by a communications interface. Signals often are provided to a communications interface via a channel. A channel often carries signals and can be implemented using wire or cable, fiber optics, a phone line, a cellular phone link, an RF link and/or other communications channels. Thus, in an example, a communications interface may be used to receive signal information that can be detected by a signal detection module.

Data may be input by a suitable device and/or method, including, but not limited to, manual input devices or direct data entry devices (DDEs). Non-limiting examples of manual devices include keyboards, concept keyboards, touch sensitive screens, light pens, mouse, tracker balls, joysticks, graphic tablets, scanners, digital cameras, video digitizers and voice recognition devices. Non-limiting examples of DDEs include bar code readers, magnetic strip codes, smart cards, magnetic ink character recognition, optical character recognition, optical mark recognition, and turnaround documents.

In some embodiments, output from a sequencing apparatus may serve as data that can be input via an input device. In certain embodiments, mapped sequence reads may serve as data that can be input via an input device. In certain embodiments, nucleic acid fragment size (e.g., length) may serve as data that can be input via an input device. In certain embodiments, output from a nucleic acid capture process (e.g., genomic region origin data) may serve as data that can be input via an input device. In certain embodiments, a combination of nucleic acid fragment size (e.g., length) and output from a nucleic acid capture process (e.g., genomic region origin data) may serve as data that can be input via an input device. In certain embodiments, output from a nucleic acid detection process (e.g., mass spectrometry, digital PCR, nanopore) may serve as data that can be input via an input device. In certain embodiments, simulated data is generated by an in silico process and the simulated data serves as data that can be input via an input device. The term "in silico" refers to research and experiments performed using a computer. In silico processes include, but are not limited to, mapping sequence reads and processing mapped sequence reads according to processes described herein.

A system may include software useful for performing a process described herein, and software can include one or more modules for performing such processes (e.g., sequencing module, logic processing module, data display organization module). The term "software" refers to computer readable program instructions that, when executed by a computer, perform computer operations. Instructions executable by the one or more processors sometimes are provided as executable code, that when executed, can cause one or more processors to implement a method described herein. A module described herein can exist as software, and instructions (e.g., processes, routines, subroutines) embodied in the software can be implemented or performed by a processor. For example, a module (e.g., a software module) can be a part of a program that performs a particular process or task. The term "module" refers to a self-contained functional unit that can be used in a larger apparatus or software system. A module can comprise a set of instructions for carrying out a function of the module. A module can transform data and/or information. Data and/or information can be in a suitable form. For example, data and/or information can be digital or analogue. Data and/or information sometimes can be packets, bytes, characters, or bits. In some embodiments, data and/or information can be any gathered, assembled or usable data or information. Non-limiting examples of data and/or information include a suitable media, pictures, video, sound (e.g. frequencies, audible or non-audible), numbers, constants, a value, objects, time, functions, instructions, maps, references, sequences, reads, mapped reads, elevations, ranges, thresholds, signals, displays, representations, or transformations thereof. A module can accept or receive data and/or information, transform the data and/or information into a second form, and provide or transfer the second form to an apparatus, peripheral, component or another module. A module can perform one or more of the following non-limiting functions: mapping sequence reads, providing counts, assembling genomic sections, providing or determining an elevation, providing a count profile, normalizing (e.g., normalizing reads, normalizing counts, and the like), providing a normalized count profile or elevations of normalized counts, comparing two or more elevations, providing uncertainty values, providing or determining expected elevations and expected ranges (e.g., expected elevation ranges, threshold ranges and threshold elevations), providing adjustments to elevations (e.g., adjusting a first elevation, adjusting a second elevation, adjusting a profile of a chromosome or a segment thereof, and/or padding), providing identification (e.g., identifying fetal gender, a copy number variation, genetic variation or aneuploidy), categorizing, plotting, and/or determining an outcome, for example. A processor can, in some instances, carry out the instructions in a module. In some embodiments, one or more processors are required to carry out instructions in a module or group of modules. A module can provide data and/or information to another module, apparatus or source and can receive data and/or information from another module, apparatus or source.

A computer program product sometimes is embodied on a tangible computer-readable medium, and sometimes is tangibly embodied on a non-transitory computer-readable medium. A module sometimes is stored on a computer readable medium (e.g., disk, drive) or in memory (e.g., random access memory). A module and processor capable of implementing instructions from a module can be located in an apparatus or in different apparatus. A module and/or processor capable of implementing an instruction for a module can be located in the same location as a user (e.g., local network) or in a different location from a user (e.g., remote network, cloud system). In embodiments in which a method is carried out in conjunction with two or more modules, the modules can be located in the same apparatus, one or more modules can be located in different apparatus in the same physical location, and one or more modules may be located in different apparatus in different physical locations.

An apparatus, in some embodiments, comprises at least one processor for carrying out the instructions in a module. Counts of sequence reads mapped to genomic sections of a reference genome sometimes are accessed by a processor that executes instructions configured to carry out a method described herein. Counts that are accessed by a processor can be within memory of a system, and the counts can be accessed and placed into the memory of the system after they are obtained. In some embodiments, an apparatus includes a processor (e.g., one or more processors) which processor can perform and/or implement one or more instructions (e.g., processes, routines and/or subroutines) from a module. In some embodiments, an apparatus includes multiple processors, such as processors coordinated and working in parallel. In some embodiments, an apparatus operates with one or more external processors (e.g., an internal or external network, server, storage device and/or storage network (e.g., a cloud)). In some embodiments, an apparatus comprises a module. In some embodiments, an apparatus comprises one or more modules. An apparatus comprising a module often can receive and transfer one or more of data and/or information to and from other modules. In some embodiments, an apparatus comprises peripherals and/or components. In some embodiments, an apparatus can comprise one or more peripherals or components that can transfer data and/or information to and from other modules, peripherals and/or components. In some embodiments, an apparatus interacts with a peripheral and/or component that provides data and/or information. In some embodiments, peripherals and components assist an apparatus in carrying out a function or interact directly with a module. Non-limiting examples of peripherals and/or components include a suitable computer peripheral, I/O or storage method or device including but not limited to scanners, printers, displays (e.g., monitors, LED, LCT or CRTs), cameras, microphones, pads (e.g., ipads, tablets), touch screens, smart phones, mobile phones, USB I/O devices, USB mass storage devices, keyboards, a computer mouse, digital pens, modems, hard drives, jump drives, flash drives, a processor, a server, CDs, DVDs, graphic cards, specialized I/O devices (e.g., sequencers, photo cells, photo multiplier tubes, optical readers, sensors, etc.), one or more flow cells, fluid handling components, network interface controllers, ROM, RAM, wireless transfer methods and devices (Bluetooth, WiFi, and the like,), the world wide web (www), the internet, a computer and/or another module.

One or more of a sequencing module, logic processing module and data display organization module can be utilized in a method described herein. In some embodiments, a logic processing module, sequencing module or data display organization module, or an apparatus comprising one or more such modules, gather, assemble, receive, provide and/or transfer data and/or information to or from another module, apparatus, component, peripheral or operator of an apparatus. For example, sometimes an operator of an apparatus provides a constant, a threshold value, a formula or a predetermined value to a logic processing module, sequencing module or data display organization module. A logic processing module, sequencing module or data display organization module can receive data and/or information from another module, non-limiting examples of which include a logic processing module, sequencing module, data display organization module, mapping module, counting module, normalization module, comparison module, range setting module, categorization module, adjustment module, plotting module, outcome module, data display organization module and/or logic processing module, the like or combination thereof. Data and/or information derived from or transformed by a logic processing module, sequencing module or data display organization module can be transferred from a logic processing module, sequencing module or data display organization module to a sequencing module, mapping module, counting module, normalization module, comparison module, range setting module, categorization module, adjustment module, plotting module, outcome module, data display organization module, logic processing module or other suitable apparatus and/or module. A sequencing module can receive data and/or information form a logic processing module and/or sequencing module and transfer data and/or information to a logic processing module and/or a mapping module, for example. In some embodiments, a logic processing module orchestrates, controls, limits, organizes, orders, distributes, partitions, transforms and/or regulates data and/or information or the transfer of data and/or information to and from one or more other modules, peripherals or devices. A data display organization module can receive data and/or information form a logic processing module and/or plotting module and transfer data and/or information to a logic processing module, plotting module, display, peripheral or device. An apparatus comprising a logic processing module, sequencing module or data display organization module can comprise at least one processor. In some embodiments, data and/or information are provided by an apparatus that includes a processor (e.g., one or more processors) which processor can perform and/or implement one or more instructions (e.g., processes, routines and/or subroutines) from the logic processing module, sequencing module and/or data display organization module. In some embodiments, a logic processing module, sequencing module or data display organization module operates with one or more external processors (e.g., an internal or external network, server, storage device and/or storage network (e.g., a cloud)).

Software often is provided on a program product containing program instructions recorded on a computer readable medium, including, but not limited to, magnetic media including floppy disks, hard disks, and magnetic tape; and optical media including CD-ROM discs, DVD discs, magneto-optical discs, flash drives, RAM, floppy discs, the like, and other such media on which the program instructions can be recorded. In online implementation, a server and web site maintained by an organization can be configured to provide software downloads to remote users, or remote users may access a remote system maintained by an organization to remotely access software. Software may obtain or receive input information. Software may include a module that specifically obtains or receives data (e.g., a data receiving module that receives sequence read data and/or mapped read data) and may include a module that specifically processes the data (e.g., a processing module that processes received data (e.g., filters, normalizes, provides an outcome and/or report). The terms "obtaining" and "receiving" input information refers to receiving data (e.g., sequence reads, mapped reads) by computer communication means from a local, or remote site, human data entry, or any other method of receiving data. The input information may be generated in the same location at which it is received, or it may be generated in a different location and transmitted to the receiving location. In some embodiments, input information is modified before it is processed (e.g., placed into a format amenable to processing (e.g., tabulated)).

In some embodiments, provided are computer program products, such as, for example, a computer program product comprising a computer usable medium having a computer readable program code embodied therein, the computer readable program code adapted to be executed to implement a method comprising: (a) obtaining sequence reads of sample nucleic acid from a test subject; (b) mapping the sequence reads obtained in (a) to a known genome, which known genome has been divided into genomic sections; (c) counting the mapped sequence reads within the genomic sections; (d) generating a sample normalized count profile by normalizing the counts for the genomic sections obtained in (c); and (e) determining the presence or absence of a genetic variation from the sample normalized count profile in (d).

Software can include one or more algorithms in certain embodiments. An algorithm may be used for processing data and/or providing an outcome or report according to a finite sequence of instructions. An algorithm often is a list of defined instructions for completing a task. Starting from an initial state, the instructions may describe a computation that proceeds through a defined series of successive states, eventually terminating in a final ending state. The transition from one state to the next is not necessarily deterministic (e.g., some algorithms incorporate randomness). By way of example, and without limitation, an algorithm can be a search algorithm, sorting algorithm, merge algorithm, numerical algorithm, graph algorithm, string algorithm, modeling algorithm, computational genometric algorithm, combinatorial algorithm, machine learning algorithm, cryptography algorithm, data compression algorithm, parsing algorithm and the like. An algorithm can include one algorithm or two or more algorithms working in combination. An algorithm can be of any suitable complexity class and/or parameterized complexity. An algorithm can be used for calculation and/or data processing, and in some embodiments, can be used in a deterministic or probabilistic/predictive approach. An algorithm can be implemented in a computing environment by use of a suitable programming language, non-limiting examples of which are C, C++, Java, Perl, Python, Fortran, and the like. In some embodiments, an algorithm can be configured or modified to include margin of errors, statistical analysis, statistical significance, and/or comparison to other information or data sets (e.g., applicable when using a neural net or clustering algorithm).

In certain embodiments, several algorithms may be implemented for use in software. These algorithms can be trained with raw data in some embodiments. For each new raw data sample, the trained algorithms may produce a representative processed data set or outcome. A processed data set sometimes is of reduced complexity compared to the parent data set that was processed. Based on a processed set, the performance of a trained algorithm may be assessed based on sensitivity and specificity, in some embodiments. An algorithm with the highest sensitivity and/or specificity may be identified and utilized, in certain embodiments.

In certain embodiments, simulated (or simulation) data can aid data processing, for example, by training an algorithm or testing an algorithm. In some embodiments, simulated data includes hypothetical various samplings of different groupings of sequence reads. Simulated data may be based on what might be expected from a real population or may be skewed to test an algorithm and/or to assign a correct classification. Simulated data also is referred to herein as "virtual" data. Simulations can be performed by a computer program in certain embodiments. One possible step in using a simulated data set is to evaluate the confidence of an identified results, e.g., how well a random sampling matches or best represents the original data. One approach is to calculate a probability value (p-value), which estimates the probability of a random sample having better score than the selected samples. In some embodiments, an empirical model may be assessed, in which it is assumed that at least one sample matches a reference sample (with or without resolved variations). In some embodiments, another distribution, such as a Poisson distribution for example, can be used to define the probability distribution.

A system may include one or more processors in certain embodiments. A processor can be connected to a communication bus. A computer system may include a main memory, often random access memory (RAM), and can also include a secondary memory. Memory in some embodiments comprises a non-transitory computer-readable storage medium. Secondary memory can include, for example, a hard disk drive and/or a removable storage drive, representing a floppy disk drive, a magnetic tape drive, an optical disk drive, memory card and the like. A removable storage drive often reads from and/or writes to a removable storage unit. Non-limiting examples of removable storage units include a floppy disk, magnetic tape, optical disk, and the like, which can be read by and written to by, for example, a removable storage drive. A removable storage unit can include a computer-usable storage medium having stored therein computer software and/or data.

A processor may implement software in a system. In some embodiments, a processor may be programmed to automatically perform a task described herein that a user could perform. Accordingly, a processor, or algorithm conducted by such a processor, can require little to no supervision or input from a user (e.g., software may be programmed to implement a function automatically). In some embodiments, the complexity of a process is so large that a single person or group of persons could not perform the process in a timeframe short enough for determining the presence or absence of a genetic variation.

In some embodiments, secondary memory may include other similar means for allowing computer programs or other instructions to be loaded into a computer system. For example, a system can include a removable storage unit and an interface device. Non-limiting examples of such systems include a program cartridge and cartridge interface (such as that found in video game devices), a removable memory chip (such as an EPROM, or PROM) and associated socket, and other removable storage units and interfaces that allow software and data to be transferred from the removable storage unit to a computer system.

One entity can generate counts of sequence reads, map the sequence reads to genomic sections, count the mapped reads, and utilize the counted mapped reads in a method, system, apparatus or computer program product described herein, in some embodiments. Counts of sequence reads mapped to genomic sections sometimes are transferred by one entity to a second entity for use by the second entity in a method, system, apparatus or computer program product described herein, in certain embodiments.

In some embodiments, one entity generates sequence reads and a second entity maps those sequence reads to genomic sections in a reference genome in some embodiments. The second entity sometimes counts the mapped reads and utilizes the counted mapped reads in a method, system, apparatus or computer program product described herein. In some embodiments, the second entity transfers the mapped reads to a third entity, and the third entity counts the mapped reads and utilizes the mapped reads in a method, system, apparatus or computer program product described herein. In some embodiments, the second entity counts the mapped reads and transfers the counted mapped reads to a third entity, and the third entity utilizes the counted mapped reads in a method, system, apparatus or computer program product described herein. In embodiments involving a third entity, the third entity sometimes is the same as the first entity. That is, the first entity sometimes transfers sequence reads to a second entity, which second entity can map sequence reads to genomic sections in a reference genome and/or count the mapped reads, and the second entity can transfer the mapped and/or counted reads to a third entity. A third entity sometimes can utilize the mapped and/or counted reads in a method, system, apparatus or computer program product described herein, where the third entity sometimes is the same as the first entity, and sometimes the third entity is different from the first or second entity.

In some embodiments, one entity obtains blood from a pregnant female, optionally isolates nucleic acid from the blood (e.g., from the plasma or serum), and transfers the blood or nucleic acid to a second entity that generates sequence reads from the nucleic acid.

FIG. 158 illustrates a non-limiting example of a computing environment 510 in which various systems, methods, algorithms, and data structures described herein may be implemented. The computing environment 510 is only one example of a suitable computing environment and is not intended to suggest any limitation as to the scope of use or functionality of the systems, methods, and data structures described herein. Neither should computing environment 510 be interpreted as having any dependency or requirement relating to any one or combination of components illustrated in computing environment 510. A subset of systems, methods, and data structures shown in FIG. 158 can be utilized in certain embodiments. Systems, methods, and data structures described herein are operational with numerous other general purpose or special purpose computing system environments or configurations. Examples of known computing systems, environments, and/or configurations that may be suitable include, but are not limited to, personal computers, server computers, thin clients, thick clients, hand-held or laptop devices, multiprocessor systems, microprocessor-based systems, set top boxes, programmable consumer electronics, network PCs, minicomputers, mainframe computers, distributed computing environments that include any of the above systems or devices, and the like.

The operating environment 510 of FIG. 158 includes a general purpose computing device in the form of a computer 520, including a processing unit 521, a system memory 522, and a system bus 523 that operatively couples various system components including the system memory 522 to the processing unit 521. There may be only one or there may be more than one processing unit 521, such that the processor of computer 520 includes a single central-processing unit (CPU), or a plurality of processing units, commonly referred to as a parallel processing environment. The computer 520 may be a conventional computer, a distributed computer, or any other type of computer.

The system bus 523 may be any of several types of bus structures including a memory bus or memory controller, a peripheral bus, and a local bus using any of a variety of bus architectures. The system memory may also be referred to as simply the memory, and includes read only memory (ROM) 524 and random access memory (RAM). A basic input/output system (BIOS) 526, containing the basic routines that help to transfer information between elements within the computer 520, such as during start-up, is stored in ROM 524. The computer 520 may further include a hard disk drive interface 527 for reading from and writing to a hard disk, not shown, a magnetic disk drive 528 for reading from or writing to a removable magnetic disk 529, and an optical disk drive 530 for reading from or writing to a removable optical disk 531 such as a CD ROM or other optical media.

The hard disk drive 527, magnetic disk drive 528, and optical disk drive 530 are connected to the system bus 523 by a hard disk drive interface 532, a magnetic disk drive interface 533, and an optical disk drive interface 534, respectively. The drives and their associated computer-readable media provide nonvolatile storage of computer-readable instructions, data structures, program modules and other data for the computer 520. Any type of computer-readable media that can store data that is accessible by a computer, such as magnetic cassettes, flash memory cards, digital video disks, Bernoulli cartridges, random access memories (RAMs), read only memories (ROMs), and the like, may be used in the operating environment.

A number of program modules may be stored on the hard disk, magnetic disk 529, optical disk 531, ROM 524, or RAM, including an operating system 535, one or more application programs 536, other program modules 537, and program data 538. A user may enter commands and information into the personal computer 520 through input devices such as a keyboard 540 and pointing device 542. Other input devices (not shown) may include a microphone, joystick, game pad, satellite dish, scanner, or the like. These and other input devices are often connected to the processing unit 521 through a serial port interface 546 that is coupled to the system bus, but may be connected by other interfaces, such as a parallel port, game port, or a universal serial bus (USB). A monitor 547 or other type of display device is also connected to the system bus 523 via an interface, such as a video adapter 548. In addition to the monitor, computers typically include other peripheral output devices (not shown), such as speakers and printers.

The computer 520 may operate in a networked environment using logical connections to one or more remote computers, such as remote computer 549. These logical connections may be achieved by a communication device coupled to or a part of the computer 520, or in other manners. The remote computer 549 may be another computer, a server, a router, a network PC, a client, a peer device or other common network node, and typically includes many or all of the elements described above relative to the computer 520, although only a memory storage device 550 has been illustrated in FIG. 158. The logical connections depicted in FIG. 158 include a local-area network (LAN) 551 and a wide-area network (WAN) 552. Such networking environments are commonplace in office networks, enterprise-wide computer networks, intranets and the Internet, which all are types of networks.

When used in a LAN-networking environment, the computer 520 is connected to the local network 551 through a network interface or adapter 553, which is one type of communications device. When used in a WAN-networking environment, the computer 520 often includes a modem 554, a type of communications device, or any other type of communications device for establishing communications over the wide area network 552. The modem 554, which may be internal or external, is connected to the system bus 523 via the serial port interface 546. In a networked environment, program modules depicted relative to the personal computer 520, or portions thereof, may be stored in the remote memory storage device. It is appreciated that the network connections shown are non-limiting examples and other communications devices for establishing a communications link between computers may be used.

Certain System, Apparatus and Computer Program Product Embodiments

In certain aspects provided is a computer implemented method for identifying the presence or absence of a sex chromosome aneuploidy in a fetus, determining fetal gender, and/or determining sex chromosome karyotype in a fetus, comprising (a) obtaining counts of nucleotide sequence reads mapped to genomic sections of a reference genome, which sequence reads are reads of circulating cell-free nucleic acid from a pregnant female bearing a fetus; (b) determining an experimental bias for each of the sections of the reference genome for multiple samples from a fitted relation for each sample between (i) the counts of the sequence reads mapped to each of the sections of the reference genome, and (ii) a mapping feature for each of the sections; (c) calculating a genomic section level for each of the sections of the reference genome from a fitted relation between the experimental bias and the counts of the sequence reads mapped to each of the sections of the reference genome, thereby providing calculated genomic section levels; and (d) identifying the presence or absence of a sex chromosome aneuploidy for the fetus, determining fetal gender, and/or determining sex chromosome karyotype for the fetus according to the calculated genomic section levels.

Provided also in certain aspects is a system comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to (a) determine an experimental bias for each of the sections of the reference genome for multiple samples from a fitted relation for each sample between (i) the counts of the sequence reads mapped to each of the sections of the reference genome, and (ii) a mapping feature for each of the sections; (b) calculate a genomic section level for each of the sections of the reference genome from a fitted relation between the experimental bias and the counts of the sequence reads mapped to each of the sections of the reference genome, thereby providing calculated genomic section levels; and (c) identify the presence or absence of a sex chromosome aneuploidy for the fetus, determine fetal gender, and/or determine sex chromosome karyotype for the fetus according to the calculated genomic section levels.

Also provided in certain aspects is an apparatus comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to (a) determine an experimental bias for each of the sections of the reference genome for multiple samples from a fitted relation for each sample between (i) the counts of the sequence reads mapped to each of the sections of the reference genome, and (ii) a mapping feature for each of the sections; (b) calculate a genomic section level for each of the sections of the reference genome from a fitted relation between the experimental bias and the counts of the sequence reads mapped to each of the sections of the reference genome, thereby providing calculated genomic section levels; and (c) identify the presence or absence of a sex chromosome aneuploidy for the fetus, determine fetal gender, and/or determine sex chromosome karyotype for the fetus according to the calculated genomic section levels.

Provided also in certain embodiments is a computer program product tangibly embodied on a computer-readable medium, comprising instructions that when executed by one or more processors are configured to (a) access counts of nucleotide sequence reads mapped to genomic sections of a reference genome, which sequence reads are reads of circulating cell-free nucleic acid from a pregnant female bearing a fetus; (b) determine an experimental bias for each of the sections of the reference genome for multiple samples from a fitted relation for each sample between (i) the counts of the sequence reads mapped to each of the sections of the reference genome, and (ii) a mapping feature for each of the sections; (c) calculate a genomic section level for each of the sections of the reference genome from a fitted relation between the experimental bias and the counts of the sequence reads mapped to each of the sections of the reference genome, thereby providing calculated genomic section levels; and (d) identify the presence or absence of a sex chromosome aneuploidy for the fetus, determine fetal gender, and/or determine sex chromosome karyotype for the fetus according to the calculated genomic section levels.

In certain embodiments, a system, apparatus and/or computer program product comprises a counting module configured to count reads mapped to genomic sections of a reference genome or portion thereof (e.g., subset of genomic sections, selected set of genomic sections). A counting module often is configured to count reads from nucleic acid fragments having lengths that are less than a selected fragment length. The counts sometimes are raw, filtered, normalized counts or combination of the foregoing. In some embodiments, a counting module can normalize the counts, for example, using any suitable normalization process described herein or known in the art.

In some embodiments, a system, apparatus and/or computer program product comprises a count comparison module. A count comparison module often is configured to compare the number of counts of reads counted by a counting module, thereby making a count comparison. A count comparison module often is configured to access, receive, utilize, store, search for and/or align counts of reads (e.g., from a counting module or normalization module). A count comparison module often is configured to provide a suitable comparison between counts, non-limiting examples of which comparison include a simple comparison (e.g., match or no match between counts of reads mapped to a first set of genomic sections compared to a second set of genomic sections), mathematical comparison (e.g., ratio, percentage), statistical comparison (e.g., multiple comparisons, multiple testing, standardization (e.g., z-score analyses)), the like and combinations thereof. A suitable count comparison value can be provided by a count comparison module, non-limiting examples of which include presence or absence of a match between counts, a ratio, percentage, z-score, a value coupled with a measure of variance or uncertainty (e.g., standard deviation, median absolute deviation, confidence interval), the like and combinations thereof. A count comparison module sometimes is configured to transmit a comparison value to another module or apparatus, such as a genetic variation module, display apparatus or printer apparatus, for example.

In certain embodiments, a system, apparatus and/or computer program product comprises a genetic variation module. A genetic variation module sometimes is configured to provide a determination of the presence or absence of a genetic variation according to counts of reads mapped to genomic sections of a reference genome. A genetic variation module sometimes is configured to provide a determination of the presence or absence of a genetic variation according to a comparison of counts. A genetic variation module often is configured to access, receive, utilize, store, search for and/or align one or more comparisons from a count comparison module and/or counts from a counting module. A genetic variation module can determine the presence or absence of a genetic variation from one or more comparisons or from counts in a suitable manner. A genetic variation module sometimes determines whether there is a significant difference between counts for different sets of genomic sections in a reference genome. The significance of a difference can be determined by a genetic variation module in a suitable manner (e.g., percent difference, z-score analysis). A genetic variation module sometimes determines whether a count determination or a comparison of counts is in a particular category. For example, a genetic variation module may categorize a particular comparison to a particular ratio threshold or a range of ratios associated with a euploid determination, or a particular ratio threshold or range of ratios associated with an aneuploid determination. In another non-limiting example, a genetic variation module may categorize a particular count determination to a particular count threshold or a range of counts associated with a euploid determination, or a particular count threshold or range of counts associated with an aneuploid determination. A genetic variation module can provide an outcome in a suitable format, which sometimes is a call pertaining to a genetic variation optionally associated with a measure of variance or uncertainty (e.g., standard deviation, median absolute deviation, accuracy (e.g., within a particular confidence interval). A genetic variation module sometimes is configured to transmit a determination of the presence or absence of a genetic variation to another module or apparatus, such as a display apparatus or printer, for example.

An apparatus or system comprising a module described herein (e.g., a reference comparison module) can comprise one or more processors. In some embodiments, an apparatus or system can include multiple processors, such as processors coordinated and working in parallel. A processor (e.g., one or more processors) in a system or apparatus can perform and/or implement one or more instructions (e.g., processes, routines and/or subroutines) in a module described herein. A module described herein sometimes is located in memory or associated with an apparatus or system. In some embodiments, a module described herein operates with one or more external processors (e.g., an internal or external network, server, storage device and/or storage network (e.g., a cloud)). In some embodiments, a module described herein is configured to access, gather, assemble and/or receive data and/or information from another module, apparatus or system (e.g., component, peripheral). In some embodiments, a module described herein is configured to provide and/or transfer data and/or information to another module, apparatus or system (e.g., component, peripheral). In some embodiments, a module described herein is configured to access, accept, receive and/or gather input data and/or information from an operator of an apparatus or system (i.e., user). For example, sometimes a user provides a constant, a threshold value, a formula and/or a predetermined value to a module. A module described herein sometimes is configured to transform data and/or information it accesses, receives, gathers and/or assembles.

In certain embodiments, a system, apparatus and/or computer program product comprises (i) a sequencing module configured to obtain and/or access nucleic acid sequence reads and/or partial nucleotide sequence reads; (ii) a mapping module configured to map nucleic acid sequence reads to portions of a reference genome; (iii) a counting module configured to provide counts of nucleic acid sequence reads mapped to portions of a reference genome; (iv) a normalization module configured to provide normalized counts; (v) a comparison module configured to provide an identification of a first elevation that is significantly different than a second elevation; (vi) a range setting module configured to provide one or more expected level ranges; (vii) a categorization module configured to identify an elevation representative of a copy number variation; (viii) an adjustment module configured to adjust a level identified as a copy number variation; (ix) a plotting module configured to graph and display a level and/or a profile; (x) an outcome module configured to determine the presence or absence of a genetic variation, or determine an outcome (e.g., outcome determinative of the presence or absence of a fetal aneuploidy); (xi) a data display organization module configured to display a genetic variation determination; (xii) a logic processing module configured to perform one or more of map sequence reads, count mapped sequence reads, normalize counts and generate an outcome; (xiii) a count comparison module, (xiv) fetal fraction module configured to provide a fetal fraction determination; (xv) a genetic variation module configured to provide a determination of the presence or absence of a genetic variation; or (xvi) combination of two or more of the foregoing.

In some embodiments a sequencing module and mapping module are configured to transfer sequence reads from the sequencing module to the mapping module. The mapping module and counting module sometimes are configured to transfer mapped sequence reads from the mapping module to the counting module. In some embodiments, the normalization module and/or comparison module are configured to transfer normalized counts to the comparison module and/or range setting module. The comparison module, range setting module and/or categorization module independently are configured to transfer (i) an identification of a first elevation that is significantly different than a second elevation and/or (ii) an expected level range from the comparison module and/or range setting module to the categorization module, in some embodiments. In certain embodiments, the categorization module and the adjustment module are configured to transfer an elevation categorized as a copy number variation from the categorization module to the adjustment module. In some embodiments, the adjustment module, plotting module and the outcome module are configured to transfer one or more adjusted levels from the adjustment module to the plotting module or outcome module. The normalization module sometimes is configured to transfer mapped normalized sequence read counts to one or more of the comparison module, range setting module, categorization module, adjustment module, outcome module or plotting module.

Genetic Variations and Medical Conditions

The presence or absence of a genetic variance can be determined using a method or apparatus described herein. In certain embodiments, the presence or absence of one or more genetic variations is determined according to an outcome provided by methods and apparatuses described herein. A genetic variation generally is a particular genetic phenotype present in certain individuals, and often a genetic variation is present in a statistically significant sub-population of individuals. In some embodiments, a genetic variation is a chromosome abnormality (e.g., aneuploidy), partial chromosome abnormality or mosaicism, each of which is described in greater detail herein. Non-limiting examples of genetic variations include one or more deletions (e.g., micro-deletions), duplications (e.g., micro-duplications), insertions, mutations, polymorphisms (e.g., single-nucleotide polymorphisms), fusions, repeats (e.g., short tandem repeats), distinct methylation sites, distinct methylation patterns, the like and combinations thereof. An insertion, repeat, deletion, duplication, mutation or polymorphism can be of any length, and in some embodiments, is about 1 base or base pair (bp) to about 250 megabases (Mb) in length. In some embodiments, an insertion, repeat, deletion, duplication, mutation or polymorphism is about 1 base or base pair (bp) to about 1,000 kilobases (kb) in length (e.g., about 10 bp, 50 bp, 100 bp, 500 bp, 1 kb, 5 kb, 10 kb, 50 kb, 100 kb, 500 kb, or 1000 kb in length).

A genetic variation is sometime a deletion. In some embodiments, a deletion is a mutation (e.g., a genetic aberration) in which a part of a chromosome or a sequence of DNA is missing. A deletion is often the loss of genetic material. Any number of nucleotides can be deleted. A deletion can comprise the deletion of one or more entire chromosomes, a segment of a chromosome, an allele, a gene, an intron, an exon, any non-coding region, any coding region, a segment thereof or combination thereof. A deletion can comprise a microdeletion. A deletion can comprise the deletion of a single base.

A genetic variation is sometimes a genetic duplication. In some embodiments, a duplication is a mutation (e.g., a genetic aberration) in which a part of a chromosome or a sequence of DNA is copied and inserted back into the genome. In some embodiments, a genetic duplication (i.e. duplication) is any duplication of a region of DNA. In some embodiments a duplication is a nucleic acid sequence that is repeated, often in tandem, within a genome or chromosome. In some embodiments a duplication can comprise a copy of one or more entire chromosomes, a segment of a chromosome, an allele, a gene, an intron, an exon, any non-coding region, any coding region, segment thereof or combination thereof. A duplication can comprise a microduplication. A duplication sometimes comprises one or more copies of a duplicated nucleic acid. A duplication sometimes is characterized as a genetic region repeated one or more times (e.g., repeated 1, 2, 3, 4, 5, 6, 7, 8, 9 or 10 times). Duplications can range from small regions (thousands of base pairs) to whole chromosomes in some instances. Duplications frequently occur as the result of an error in homologous recombination or due to a retrotransposon event. Duplications have been associated with certain types of proliferative diseases. Duplications can be characterized using genomic microarrays or comparative genetic hybridization (CGH).

A genetic variation is sometimes an insertion. An insertion is sometimes the addition of one or more nucleotide base pairs into a nucleic acid sequence. An insertion is sometimes a microinsertion. In some embodiments, an insertion comprises the addition of a segment of a chromosome into a genome, chromosome, or segment thereof. In some embodiments, an insertion comprises the addition of an allele, a gene, an intron, an exon, any non-coding region, any coding region, segment thereof or combination thereof into a genome or segment thereof. In some embodiments, an insertion comprises the addition (i.e., insertion) of nucleic acid of unknown origin into a genome, chromosome, or segment thereof. In some embodiments, an insertion comprises the addition (i.e. insertion) of a single base.

As used herein a "copy number variation" generally is a class or type of genetic variation or chromosomal aberration. A copy number variation can be a deletion (e.g. micro-deletion), duplication (e.g., a micro-duplication) or insertion (e.g., a micro-insertion). Often, the prefix "micro" as used herein sometimes is a segment of nucleic acid less than 5 Mb in length. A copy number variation can include one or more deletions (e.g. micro-deletion), duplications and/or insertions (e.g., a micro-duplication, micro-insertion) of a segment of a chromosome. In some embodiments, a duplication comprises an insertion. In some embodiments, an insertion is a duplication. In some embodiments, an insertion is not a duplication. For example, often a duplication of a sequence in a genomic section increases the counts for a genomic section in which the duplication is found. Often a duplication of a sequence in a genomic section increases the elevation. In some embodiments, a duplication present in genomic sections making up a first elevation increases the elevation relative to a second elevation where a duplication is absent. In some embodiments, an insertion increases the counts of a genomic section and a sequence representing the insertion is present (i.e., duplicated) at another location within the same genomic section. In some embodiments, an insertion does not significantly increase the counts of a genomic section or elevation and the sequence that is inserted is not a duplication of a sequence within the same genomic section. In some embodiments, an insertion is not detected or represented as a duplication and a duplicate sequence representing the insertion is not present in the same genomic section.

In some embodiments a copy number variation is a fetal copy number variation. Often, a fetal copy number variation is a copy number variation in the genome of a fetus. In some embodiments a copy number variation is a maternal copy number variation. In some embodiments, a maternal and/or fetal copy number variation is a copy number variation within the genome of a pregnant female (e.g., a female subject bearing a fetus), a female subject that gave birth or a female capable of bearing a fetus. A copy number variation can be a heterozygous copy number variation where the variation (e.g., a duplication or deletion) is present on one allele of a genome. A copy number variation can be a homozygous copy number variation where the variation is present on both alleles of a genome. In some embodiments a copy number variation is a heterozygous or homozygous fetal copy number variation. In some embodiments a copy number variation is a heterozygous or homozygous maternal and/or fetal copy number variation. A copy number variation sometimes is present in a maternal genome and a fetal genome, a maternal genome and not a fetal genome, or a fetal genome and not a maternal genome.

"Ploidy" refers to the number of chromosomes present in a fetus or mother. In some embodiments, "Ploidy" is the same as "chromosome ploidy". In humans, for example, autosomal chromosomes are often present in pairs. For example, in the absence of a genetic variation, most humans have two of each autosomal chromosome (e.g., chromosomes 1-22). The presence of the normal complement of 2 autosomal chromosomes in a human is often referred to as euploid. "Microploidy" is similar in meaning to ploidy. "Microploidy" often refers to the ploidy of a segment of a chromosome. The term "microploidy" sometimes refers to the presence or absence of a copy number variation (e.g., a deletion, duplication and/or an insertion) within a chromosome (e.g., a homozygous or heterozygous deletion, duplication, or insertion, the like or absence thereof). "Ploidy" and "microploidy" sometimes are determined after normalization of counts of an elevation in a profile (e.g., after normalizing counts of an elevation to an NRV of 1). Thus, an elevation representing an autosomal chromosome pair (e.g., a euploid) is often normalized to an NRV of 1 and is referred to as a ploidy of 1. Similarly, an elevation within a segment of a chromosome representing the absence of a duplication, deletion or insertion is often normalized to an NRV of 1 and is referred to as a microploidy of 1. Ploidy and microploidy are often bin-specific (e.g., genomic section specific) and sample-specific. Ploidy is often defined as integral multiples of ½, with the values of 1, ½, 0, 3/2, and 2 representing euploidy (e.g., 2 chromosomes), 1 chromosome present (e.g., a chromosome deletion), no chromosome present, 3 chromosomes (e.g., a trisomy) and 4 chromosomes, respectively. Likewise, microploidy is often defined as integral multiples of ½, with the values of 1, ½, 0, 3/2, and 2 representing euploidy (e.g., no copy number variation), a heterozygous deletion, homozygous deletion, heterozygous duplication and homozygous duplication, respectively.

In some embodiments, the microploidy of a fetus matches the microploidy of the mother of the fetus (i.e., the pregnant female subject). In some embodiments, the microploidy of a fetus matches the microploidy of the mother of the fetus and both the mother and fetus carry the same heterozygous copy number variation, homozygous copy number variation or both are euploid. In some embodiments, the microploidy of a fetus is different than the microploidy of the mother of the fetus. For example, sometimes the microploidy of a fetus is heterozygous for a copy number variation, the mother is homozygous for a copy number variation and the microploidy of the fetus does not match (e.g., does not equal) the microploidy of the mother for the specified copy number variation.

A microploidy is often associated with an expected elevation. For example, sometimes an elevation (e.g., an elevation in a profile, sometimes an elevation that includes substantially no copy number variation) is normalized to an NRV of 1 and the microploidy of a homozygous duplication is 2, a heterozygous duplication is 1.5, a heterozygous deletion is 0.5 and a homozygous deletion is zero.

A genetic variation for which the presence or absence is identified for a subject is associated with a medical condition in certain embodiments. Thus, technology described herein can be used to identify the presence or absence of one or more genetic variations that are associated with a medical condition or medical state. Non-limiting examples of medical conditions include those associated with intellectual disability (e.g., Down Syndrome), aberrant cell-proliferation (e.g., cancer), presence of a micro-organism nucleic acid (e.g., virus, bacterium, fungus, yeast), and preeclampsia.

Non-limiting examples of genetic variations, medical conditions and states are described hereafter.

Fetal Gender

In some embodiments, the prediction of a fetal gender or gender related disorder (e.g., sex chromosome aneuploidy) can be determined by a method or apparatus described herein. In some embodiments, a method in which fetal gender is determined can also comprise determining fetal fraction and/or presence or absence of a fetal genetic variation (e.g., fetal chromosome aneuploidy). Determining presence or absence of a fetal genetic variation can be performed in a suitable manner, non-limiting examples of which include karyotype analysis, amniocentesis, circulating cell-free nucleic acid analysis, cell-free fetal DNA analysis, nucleotide sequence analysis, sequence read quantification, targeted approaches, amplification-based approaches, mass spectrometry-based approaches, differential methylation-based approaches, differential digestion-based approaches, polymorphism-based approaches, hybridization-based approaches (e.g., using probes), and the like.

Gender determination generally is based on a sex chromosome. In humans, there are two sex chromosomes, the X and Y chromosomes. The Y chromosome contains a gene, SRY, which triggers embryonic development as a male. The Y chromosomes of humans and other mammals also contain other genes needed for normal sperm production. Individuals with XX are female and XY are male and non-limiting variations, often referred to as sex chromosome aneuploidies, include X0, XYY, XXX and XXY. In some instances, males have two X chromosomes and one Y chromosome (XXY; Klinefelter's Syndrome), or one X chromosome and two Y chromosomes (XYY syndrome; Jacobs Syndrome), and some females have three X chromosomes (XXX; Triple X Syndrome) or a single X chromosome instead of two (X0; Turner Syndrome). In some instances, only a portion of cells in an individual are affected by a sex chromosome aneuploidy which may be referred to as a mosaicism (e.g., Turner mosaicism). Other cases include those where SRY is damaged (leading to an XY female), or copied to the X (leading to an XX male).

In certain cases, it can be beneficial to determine the gender of a fetus in utero. For example, a patient (e.g., pregnant female) with a family history of one or more sex-linked disorders may wish to determine the gender of the fetus she is carrying to help assess the risk of the fetus inheriting such a disorder. Sex-linked disorders include, without limitation, X-linked and Y-linked disorders. X-linked disorders include X-linked recessive and X-linked dominant disorders. Examples of X-linked recessive disorders include, without limitation, immune disorders (e.g., chronic granulomatous disease (CYBB), Wiskott-Aldrich syndrome, X-linked severe combined immunodeficiency, X-linked agammaglobulinemia, hyper-IgM syndrome type 1, IPEX, X-linked lymphoproliferative disease, Properdin deficiency), hematologic disorders (e.g., Hemophilia A, Hemophilia B, X-linked sideroblastic anemia), endocrine disorders (e.g., androgen insensitivity syndrome/Kennedy disease, KAL1 Kallmann syndrome, X-linked adrenal hypoplasia congenital), metabolic disorders (e.g., ornithine transcarbamylase deficiency, oculocerebrorenal syndrome, adrenoleukodystrophy, glucose-6-phosphate dehydrogenase deficiency, pyruvate dehydrogenase deficiency, Danon disease/glycogen storage disease Type IIb, Fabry's disease, Hunter syndrome, Lesch-Nyhan syndrome, Menkes disease/occipital horn syndrome), nervous system disorders (e.g., Coffin-Lowry syndrome, MASA syndrome, X-linked alpha thalassemia mental retardation syndrome, Siderius X-linked mental retardation syndrome, color blindness, ocular albinism, Norrie disease, choroideremia, Charcot-Marie-Tooth disease (CMTX2-3), Pelizaeus-Merzbacher disease, SMAX2), skin and related tissue disorders (e.g., dyskeratosis congenital, hypohidrotic ectodermal dysplasia (EDA), X-linked ichthyosis, X-linked endothelial corneal dystrophy), neuromuscular disorders (e.g., Becker's muscular dystrophy/Duchenne, centronuclear myopathy (MTM1), Conradi-Hünermann syndrome, Emery-Dreifuss muscular dystrophy 1), urologic disorders (e.g., Alport syndrome, Dent's disease, X-linked nephrogenic diabetes insipidus), bone/tooth disorders (e.g., AMELX Amelogenesis imperfecta), and other disorders (e.g., Barth syndrome, McLeod syndrome, Smith-Fineman-Myers syndrome, Simpson-Golabi-Behmel syndrome, Mohr-Tranebjaerg syndrome, Nasodigitoacoustic syndrome). Examples of X-linked dominant disorders include, without limitation, X-linked hypophosphatemia, Focal dermal hypoplasia, Fragile X syndrome, Aicardi syndrome, Incontinentia pigmenti, Rett syndrome, CHILD syndrome, Lujan-Fryns syndrome, and Orofaciodigital syndrome 1. Examples of Y-linked disorders include, without limitation, male infertility, retinits pigmentosa, and azoospermia.

Chromosome Abnormalities

In some embodiments, the presence or absence of a fetal chromosome abnormality can be determined by using a method or apparatus described herein. Chromosome abnormalities include, without limitation, a gain or loss of an entire chromosome or a region of a chromosome comprising one or more genes. Chromosome abnormalities include monosomies, trisomies, polysomies, loss of heterozygosity, deletions and/or duplications of one or more nucleotide sequences (e.g., one or more genes), including deletions and duplications caused by unbalanced translocations. The terms "aneuploidy" and "aneuploid" as used herein refer to an abnormal number of chromosomes in cells of an organism. As different organisms have widely varying chromosome complements, the term "aneuploidy" does not refer to a particular number of chromosomes, but rather to the situation in which the chromosome content within a given cell or cells of an organism is abnormal. In some embodiments, the term "aneuploidy" herein refers to an imbalance of genetic material caused by a loss or gain of a whole chromosome, or part of a chromosome. An "aneuploidy" can refer to one or more deletions and/or insertions of a segment of a chromosome.

The term "monosomy" as used herein refers to lack of one chromosome of the normal complement. Partial monosomy can occur in unbalanced translocations or deletions, in which only a segment of the chromosome is present in a single copy. Monosomy of sex chromosomes (45, X) causes Turner syndrome, for example.

The term "disomy" refers to the presence of two copies of a chromosome. For organisms such as humans that have two copies of each chromosome (those that are diploid or "euploid"), disomy is the normal condition. For organisms that normally have three or more copies of each chromosome (those that are triploid or above), disomy is an aneuploid chromosome state. In uniparental disomy, both copies of a chromosome come from the same parent (with no contribution from the other parent).

The term "euploid", in some embodiments, refers a normal complement of chromosomes.

The term "trisomy" as used herein refers to the presence of three copies, instead of two copies, of a particular chromosome. The presence of an extra chromosome 21, which is found in human Down syndrome, is referred to as "Trisomy 21." Trisomy 18 and Trisomy 13 are two other human autosomal trisomies. Trisomy of sex chromosomes can be seen in females (e.g., 47, XXX in Triple X Syndrome) or males (e.g., 47, XXY in Klinefelter's Syndrome; or 47, XYY in Jacobs Syndrome).

The terms "tetrasomy" and "pentasomy" as used herein refer to the presence of four or five copies of a chromosome, respectively. Although rarely seen with autosomes, sex chromosome tetrasomy and pentasomy have been reported in humans, including XXXX, XXXY, XXYY, XYYY, XXXXX, XXXXY, XXXYY, XXYYY and XYYYY.

Chromosome abnormalities can be caused by a variety of mechanisms. Mechanisms include, but are not limited to (i) nondisjunction occurring as the result of a weakened mitotic checkpoint, (ii) inactive mitotic checkpoints causing non-disjunction at multiple chromosomes, (iii) merotelic attachment occurring when one kinetochore is attached to both mitotic spindle poles, (iv) a multipolar spindle forming when more than two spindle poles form, (v) a monopolar spindle forming when only a single spindle pole forms, and (vi) a tetraploid intermediate occurring as an end result of the monopolar spindle mechanism.

The terms "partial monosomy" and "partial trisomy" as used herein refer to an imbalance of genetic material caused by loss or gain of part of a chromosome. A partial monosomy or partial trisomy can result from an unbalanced translocation, where an individual carries a derivative chromosome formed through the breakage and fusion of two different chromosomes. In this situation, the individual would have three copies of part of one chromosome (two normal copies and the segment that exists on the derivative chromosome) and only one copy of part of the other chromosome involved in the derivative chromosome.

The term "mosaicism" as used herein refers to aneuploidy in some cells, but not all cells, of an organism. Certain chromosome abnormalities can exist as mosaic and non-mosaic chromosome abnormalities. For example, certain trisomy 21 individuals have mosaic Down syndrome and some have non-mosaic Down syndrome. Different mechanisms can lead to mosaicism. For example, (i) an initial zygote may have three 21st chromosomes, which normally would result in simple trisomy 21, but during the course of cell division one or more cell lines lost one of the 21st chromosomes; and (ii) an initial zygote may have two 21st chromosomes, but during the course of cell division one of the 21st chromosomes were duplicated. Somatic mosaicism likely occurs through mechanisms distinct from those typically associated with genetic syndromes involving complete or mosaic aneuploidy. Somatic mosaicism has been identified in certain types of cancers and in neurons, for example. In certain instances, trisomy 12 has been identified in chronic lymphocytic leukemia (CLL) and trisomy 8 has been identified in acute myeloid leukemia (AML). Also, genetic syndromes in which an individual is predisposed to breakage of chromosomes (chromosome instability syndromes) are frequently associated with increased risk for various types of cancer, thus highlighting the role of somatic aneuploidy in carcinogenesis. Methods and protocols described herein can identify presence or absence of non-mosaic and mosaic chromosome abnormalities.

Tables 1A and 1B present a non-limiting list of chromosome conditions, syndromes and/or abnormalities that can be potentially identified by methods and apparatus described herein. Table 1B is from the DECIPHER database as of Oct. 6, 2011 (e.g., version 5.1, based on positions mapped to GRCh37; available at uniform resource locator (URL) dechipher.sanger.ac.uk).

TABLE 1A

| Chromosome | Abnormality | Disease Association |
|---|---|---|
| X | XO | Turner's Syndrome |
| Y | XXY | Klinefelter syndrome |
| Y | XYY | Double Y syndrome |
| Y | XXX | Trisomy X syndrome |
| Y | XXXX | Four X syndrome |
| Y | Xp21 deletion | Duchenne's/Becker syndrome, congenital adrenal hypoplasia, chronic granulomatus disease |
| Y | Xp22 deletion | steroid sulfatase deficiency |
| Y | Xq26 deletion | X-linked lymphproliferative disease |
| 1 | 1p (somatic) monosomy trisomy | neuroblastoma |
| 2 | monosomy trisomy 2q | growth retardation, developmental and mental delay, and minor physical abnormalities |

TABLE 1A-continued

| Chromosome | Abnormality | Disease Association |
|---|---|---|
| 3 | monosomy trisomy (somatic) | Non-Hodgkin's lymphoma |
| 4 | monosomy trisomy (somatic) | Acute non lymphocytic leukemia (ANLL) |
| 5 | 5p | Cri du chat; Lejeune syndrome |
| 5 | 5q (somatic) monosomy trisomy | myelodysplastic syndrome |
| 6 | monosomy trisomy (somatic) | clear-cell sarcoma |
| 7 | 7q11.23 deletion | William's syndrome |
| 7 | monosomy trisomy | monosomy 7 syndrome of childhood; somatic: renal cortical adenomas; myelodysplastic syndrome |
| 8 | 8q24.1 deletion | Langer-Giedon syndrome |
| 8 | monosomy trisomy | myelodysplastic syndrome; Warkany syndrome; somatic: chronic myelogenous leukemia |
| 9 | monosomy 9p | Alfi's syndrome |
| 9 | monosomy 9p partial trisomy | Rethore syndrome |
| 9 | trisomy | complete trisomy 9 syndrome; mosaic trisomy 9 syndrome |
| 10 | Monosomy trisomy (somatic) | ALL or ANLL |
| 11 | 11p- | Aniridia; Wilms tumor |
| 11 | 11q- | Jacobsen Syndrome |
| 11 | monosomy (somatic) trisomy | myeloid lineages affected (ANLL, MDS) |
| 12 | monosomy trisomy (somatic) | CLL, Juvenile granulosa cell tumor (JGCT) |
| 13 | 13q- | 13q-syndrome; Orbeli syndrome |
| 13 | 13q14 deletion | retinoblastoma |
| 13 | monosomy trisomy | Patau's syndrome |
| 14 | monosomy trisomy (somatic) | myeloid disorders (MDS, ANLL, atypical CML) |
| 15 | 15q11-q13 deletion monosomy | Prader-Willi, Angelman's syndrome |
| 15 | trisomy (somatic) | myeloid and lymphoid lineages affected, e.g., MDS, ANLL, ALL, CLL) |
| 16 | 16q13.3 deletion | Rubenstein-Taybi |
|  | monosomy trisomy (somatic) | papillary renal cell carcinomas (malignant) |
| 17 | 17p-(somatic) | 17p syndrome in myeloid malignancies |
| 17 | 17q11.2 deletion | Smith-Magenis |
| 17 | 17q13.3 | Miller-Dieker |
| 17 | monosomy trisomy (somatic) | renal cortical adenomas |
| 17 | 17p11.2-12 trisomy | Charcot-Marie Tooth Syndrome type 1; HNPP |
| 18 | 18p- | 18p partial monosomy syndrome or Grouchy Lamy Thieffry syndrome |
| 18 | 18q- | Grouchy Lamy Salmon Landry Syndrome |
| 18 | monosomy trisomy | Edwards Syndrome |
| 19 | monosomy trisomy |  |
| 20 | 20p- | trisomy 20p syndrome |
| 20 | 20p11.2-12 deletion | Alagille |
| 20 | 20q- | somatic: MDS, ANLL, polycythemia vera, chronic neutrophilic leukemia |
| 20 | monosomy trisomy (somatic) | papillary renal cell carcinomas (malignant) |
| 21 | monosomy trisomy | Down's syndrome |
| 22 | 22q11.2 deletion | DiGeorge's syndrome, velocardiofacial syndrome, conotruncal anomaly face syndrome, autosomal dominant Opitz G/BBB syndrome, Caylor cardiofacial syndrome |
| 22 | monosomy trisomy | complete trisomy 22 syndrome |

TABLE 1B

| Syndrome | Chromosome | Start | End | Interval (Mb) | Grade |
|---|---|---|---|---|---|
| 12q14 microdeletion syndrome | 12 | 65,071,919 | 68,645,525 | 3.57 |  |
| 15q13.3 microdeletion syndrome | 15 | 30,769,995 | 32,701,482 | 1.93 |  |
| 15q24 recurrent microdeletion syndrome | 15 | 74,377,174 | 76,162,277 | 1.79 |  |

TABLE 1B-continued

| Syndrome | Chromosome | Start | End | Interval (Mb) | Grade |
|---|---|---|---|---|---|
| 15q26 overgrowth syndrome | 15 | 99,357,970 | 102,521,392 | 3.16 | |
| 16p11.2 microduplication syndrome | 16 | 29,501,198 | 30,202,572 | 0.70 | |
| 16p11.2-p12.2 microdeletion syndrome | 16 | 21,613,956 | 29,042,192 | 7.43 | |
| 16p13.11 recurrent microdeletion (neurocognitive disorder susceptibility locus) | 16 | 15,504,454 | 16,284,248 | 0.78 | |
| 16p13.11 recurrent microduplication (neurocognitive disorder susceptibility locus) | 16 | 15,504,454 | 16,284,248 | 0.78 | |
| 17q21.3 recurrent microdeletion syndrome | 17 | 43,632,466 | 44,210,205 | 0.58 | 1 |
| 1p36 microdeletion syndrome | 1 | 10,001 | 5,408,761 | 5.40 | 1 |
| 1q21.1 recurrent microdeletion (susceptibility locus for neurodevelopmental disorders) | 1 | 146,512,930 | 147,737,500 | 1.22 | 3 |
| 1q21.1 recurrent microduplication (possible susceptibility locus for neurodevelopmental disorders) | 1 | 146,512,930 | 147,737,500 | 1.22 | 3 |
| 1q21.1 susceptibility locus for Thrombocytopenia-Absent Radius (TAR) syndrome | 1 | 145,401,253 | 145,928,123 | 0.53 | 3 |
| 22q11 deletion syndrome (Velocardiofacial/ DiGeorge syndrome) | 22 | 18,546,349 | 22,336,469 | 3.79 | 1 |
| 22q11 duplication syndrome | 22 | 18,546,349 | 22,336,469 | 3.79 | 3 |
| 22q11.2 distal deletion syndrome | 22 | 22,115,848 | 23,696,229 | 1.58 | |
| 22q13 deletion syndrome (Phelan-Mcdermid syndrome) | 22 | 51,045,516 | 51,187,844 | 0.14 | 1 |
| 2p15-16.1 microdeletion syndrome | 2 | 57,741,796 | 61,738,334 | 4.00 | |
| 2q33.1 deletion syndrome | 2 | 196,925,089 | 205,206,940 | 8.28 | 1 |
| 2q37 monosomy | 2 | 239,954,693 | 243,102,476 | 3.15 | 1 |
| 3q29 microdeletion syndrome | 3 | 195,672,229 | 197,497,869 | 1.83 | |
| 3q29 microduplication syndrome | 3 | 195,672,229 | 197,497,869 | 1.83 | |
| 7q11.23 duplication syndrome | 7 | 72,332,743 | 74,616,901 | 2.28 | |
| 8p23.1 deletion syndrome | 8 | 8,119,295 | 11,765,719 | 3.65 | |
| 9q subtelomeric deletion syndrome | 9 | 140,403,363 | 141,153,431 | 0.75 | 1 |
| Adult-onset autosomal dominant leukodystrophy (ADLD) | 5 | 126,063,045 | 126,204,952 | 0.14 | |
| Angelman syndrome (Type 1) | 15 | 22,876,632 | 28,557,186 | 5.68 | 1 |

TABLE 1B-continued

| Syndrome | Chromosome | Start | End | Interval (Mb) | Grade |
|---|---|---|---|---|---|
| Angelman syndrome (Type 2) | 15 | 23,758,390 | 28,557,186 | 4.80 | 1 |
| ATR-16 syndrome | 16 | 60,001 | 834,372 | 0.77 | 1 |
| AZFa | Y | 14,352,761 | 15,154,862 | 0.80 | |
| AZFb | Y | 20,118,045 | 26,065,197 | 5.95 | |
| AZFb + AZFc | Y | 19,964,826 | 27,793,830 | 7.83 | |
| AZFc | Y | 24,977,425 | 28,033,929 | 3.06 | |
| Cat-Eye Syndrome (Type I) | 22 | 1 | 16,971,860 | 16.97 | |
| Charcot-Marie-Tooth syndrome type 1A (CMT1A) | 17 | 13,968,607 | 15,434,038 | 1.47 | 1 |
| Cri du Chat Syndrome (5p deletion) | 5 | 10,001 | 11,723,854 | 11.71 | 1 |
| Early-onset Alzheimer disease with cerebral amyloid angiopathy | 21 | 27,037,956 | 27,548,479 | 0.51 | |
| Familial Adenomatous Polyposis | 5 | 112,101,596 | 112,221,377 | 0.12 | |
| Hereditary Liability to Pressure Palsies (HNPP) | 17 | 13,968,607 | 15,434,038 | 1.47 | 1 |
| Leri-Weill dyschondrostosis (LWD) - SHOX deletion | X | 751,878 | 867,875 | 0.12 | |
| Leri-Weill dyschondrostosis (LWD) - SHOX deletion | X | 460,558 | 753,877 | 0.29 | |
| Miller-Dieker syndrome (MDS) | 17 | 1 | 2,545,429 | 2.55 | 1 |
| NF1-microdeletion syndrome | 17 | 29,162,822 | 30,218,667 | 1.06 | 1 |
| Pelizaeus-Merzbacher disease | X | 102,642,051 | 103,131,767 | 0.49 | |
| Potocki-Lupski syndrome (17p11.2 duplication syndrome) | 17 | 16,706,021 | 20,482,061 | 3.78 | |
| Potocki-Shaffer syndrome | 11 | 43,985,277 | 46,064,560 | 2.08 | 1 |
| Prader-Willi syndrome (Type 1) | 15 | 22,876,632 | 28,557,186 | 5.68 | 1 |
| Prader-Willi Syndrome (Type 2) | 15 | 23,758,390 | 28,557,186 | 4.80 | 1 |
| RCAD (renal cysts and diabetes) | 17 | 34,907,366 | 36,076,803 | 1.17 | |
| Rubinstein-Taybi Syndrome | 16 | 3,781,464 | 3,861,246 | 0.08 | 1 |
| Smith-Magenis Syndrome | 17 | 16,706,021 | 20,482,061 | 3.78 | 1 |
| Sotos syndrome | 5 | 175,130,402 | 177,456,545 | 2.33 | 1 |
| Split hand/foot malformation 1 (SHFM1) | 7 | 95,533,860 | 96,779,486 | 1.25 | |
| Steroid sulphatase deficiency (STS) | X | 6,441,957 | 8,167,697 | 1.73 | |
| WAGR 11p13 deletion syndrome | 11 | 31,803,509 | 32,510,988 | 0.71 | |
| Williams-Beuren Syndrome (WBS) | 7 | 72,332,743 | 74,616,901 | 2.28 | 1 |
| Wolf-Hirschhorn Syndrome | 4 | 10,001 | 2,073,670 | 2.06 | 1 |
| Xq28 (MECP2) duplication | X | 152,749,900 | 153,390,999 | 0.64 | |

Grade 1 conditions often have one or more of the following characteristics; pathogenic anomaly; strong agreement amongst geneticists; highly penetrant; may still have variable phenotype but some common features; all cases in the literature have a clinical phenotype; no cases of healthy individuals with the anomaly; not reported on DVG databases or found in healthy population; functional data confirming single gene or multi-gene dosage effect; confirmed or strong candidate genes; clinical management implications defined; known cancer risk with implication for surveillance; multiple sources of information (OMIM, GeneReviews, Orphanet, Unique, Wikipedia); and/or available for diagnostic use (reproductive counseling).

Grade 2 conditions often have one or more of the following characteristics; likely pathogenic anomaly; highly penetrant; variable phenotype with no consistent features other than DD; small number of cases/reports in the literature; all reported cases have a clinical phenotype; no functional data or confirmed pathogenic genes; multiple sources of information (OMIM, Genereviews, Orphanet, Unique, Wikipedia); and/or may be used for diagnostic purposes and reproductive counseling.

Grade 3 conditions often have one or more of the following characteristics; susceptibility locus; healthy individuals or unaffected parents of a proband described; present in control populations; non penetrant; phenotype mild and not specific; features less consistent; no functional data or confirmed pathogenic genes; more limited sources of data; possibility of second diagnosis remains a possibility for cases deviating from the majority or if novel clinical finding present; and/or caution when using for diagnostic purposes and guarded advice for reproductive counseling.

Preeclampsia

In some embodiments, the presence or absence of preeclampsia is determined by using a method or apparatus described herein. Preeclampsia is a condition in which hypertension arises in pregnancy (i.e. pregnancy-induced hypertension) and is associated with significant amounts of protein in the urine. In some instances, preeclampsia also is associated with elevated levels of extracellular nucleic acid and/or alterations in methylation patterns. For example, a positive correlation between extracellular fetal-derived hypermethylated RASSF1A levels and the severity of preeclampsia has been observed. In certain examples, increased DNA methylation is observed for the H19 gene in preeclamptic placentas compared to normal controls.

Preeclampsia is one of the leading causes of maternal and fetal/neonatal mortality and morbidity worldwide. Circulating cell-free nucleic acids in plasma and serum are novel biomarkers with promising clinical applications in different medical fields, including prenatal diagnosis. Quantitative changes of cell-free fetal (cff)DNA in maternal plasma as an indicator for impending preeclampsia have been reported in different studies, for example, using real-time quantitative PCR for the male-specific SRY or DYS 14 loci. In cases of early onset preeclampsia, elevated levels may be seen in the first trimester. The increased levels of cffDNA before the onset of symptoms may be due to hypoxia/reoxygenation within the intervillous space leading to tissue oxidative stress and increased placental apoptosis and necrosis. In addition to the evidence for increased shedding of cffDNA into the maternal circulation, there is also evidence for reduced renal clearance of cffDNA in preeclampsia. As the amount of fetal DNA is currently determined by quantifying Y-chromosome specific sequences, alternative approaches such as measurement of total cell-free DNA or the use of gender-independent fetal epigenetic markers, such as DNA methylation, offer an alternative. Cell-free RNA of placental origin is another alternative biomarker that may be used for screening and diagnosing preeclampsia in clinical practice. Fetal RNA is associated with subcellular placental particles that protect it from degradation. Fetal RNA levels sometimes are ten-fold higher in pregnant females with preeclampsia compared to controls, and therefore is an alternative biomarker that may be used for screening and diagnosing preeclampsia in clinical practice.

Pathogens

In some embodiments, the presence or absence of a pathogenic condition is determined by a method or apparatus described herein. A pathogenic condition can be caused by infection of a host by a pathogen including, but not limited to, a bacterium, virus or fungus. Since pathogens typically possess nucleic acid (e.g., genomic DNA, genomic RNA, mRNA) that can be distinguishable from host nucleic acid, methods and apparatus provided herein can be used to determine the presence or absence of a pathogen. Often, pathogens possess nucleic acid with characteristics unique to a particular pathogen such as, for example, epigenetic state and/or one or more sequence variations, duplications and/or deletions. Thus, methods provided herein may be used to identify a particular pathogen or pathogen variant (e.g. strain).

Cancers

In some embodiments, the presence or absence of a cell proliferation disorder (e.g., a cancer) is determined by using a method or apparatus described herein. For example, levels of cell-free nucleic acid in serum can be elevated in patients with various types of cancer compared with healthy patients. Patients with metastatic diseases, for example, can sometimes have serum DNA levels approximately twice as high as non-metastatic patients. Patients with metastatic diseases may also be identified by cancer-specific markers and/or certain single nucleotide polymorphisms or short tandem repeats, for example. Non-limiting examples of cancer types that may be positively correlated with elevated levels of circulating DNA include breast cancer, colorectal cancer, gastrointestinal cancer, hepatocellular cancer, lung cancer, melanoma, non-Hodgkin lymphoma, leukemia, multiple myeloma, bladder cancer, hepatoma, cervical cancer, esophageal cancer, pancreatic cancer, and prostate cancer. Various cancers can possess, and can sometimes release into the bloodstream, nucleic acids with characteristics that are distinguishable from nucleic acids from non-cancerous healthy cells, such as, for example, epigenetic state and/or sequence variations, duplications and/or deletions. Such characteristics can, for example, be specific to a particular type of cancer. Thus, it is further contemplated that a method provided herein can be used to identify a particular type of cancer.

EXAMPLES

The examples set forth below illustrate certain embodiments and do not limit the technology.

Example 1: General Methods for Detecting Conditions Associated with Genetic Variations The methods and underlying theory described herein can be utilized to detect various conditions associated with genetic variation and determine the presence or absence of a genetic variation. Non-limiting examples of genetic variations that can be detected with the methods described herein include, segmental chromosomal aberrations (e.g., deletions, duplications), aneuploidy, gender, sample identification, disease conditions associated with genetic variation, the like or combinations of the foregoing.

Bin Filtering

Figure 1:
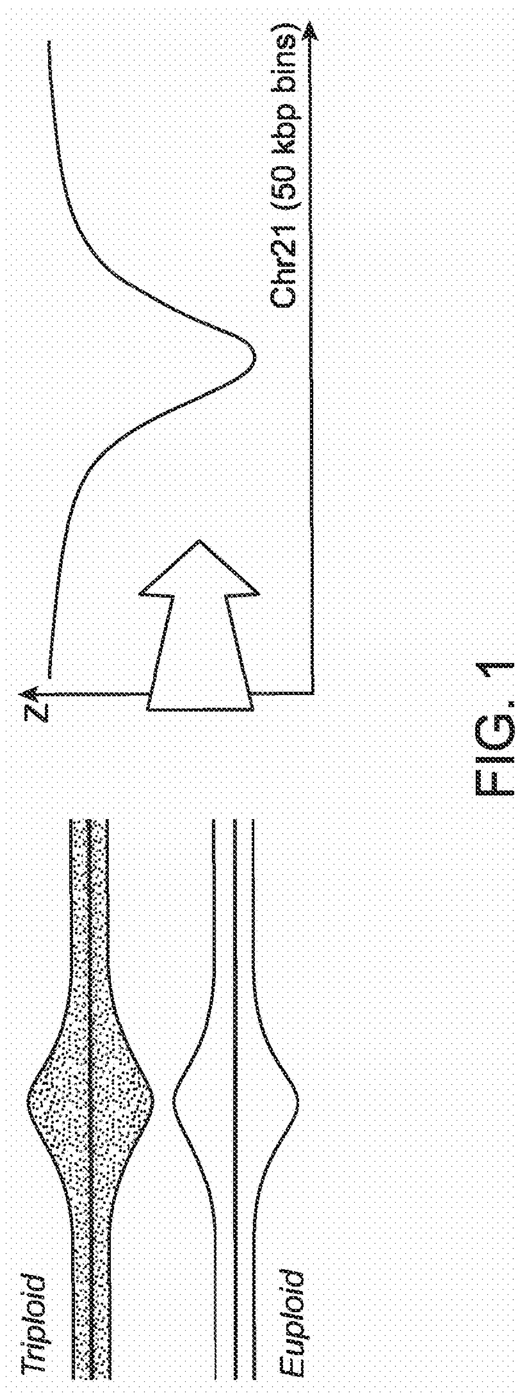
FIG. 1 graphically illustrates how increased uncertainty in bin counts within a genomic region sometimes reduces gaps between euploid and trisomy Z-values.
Figure 2:
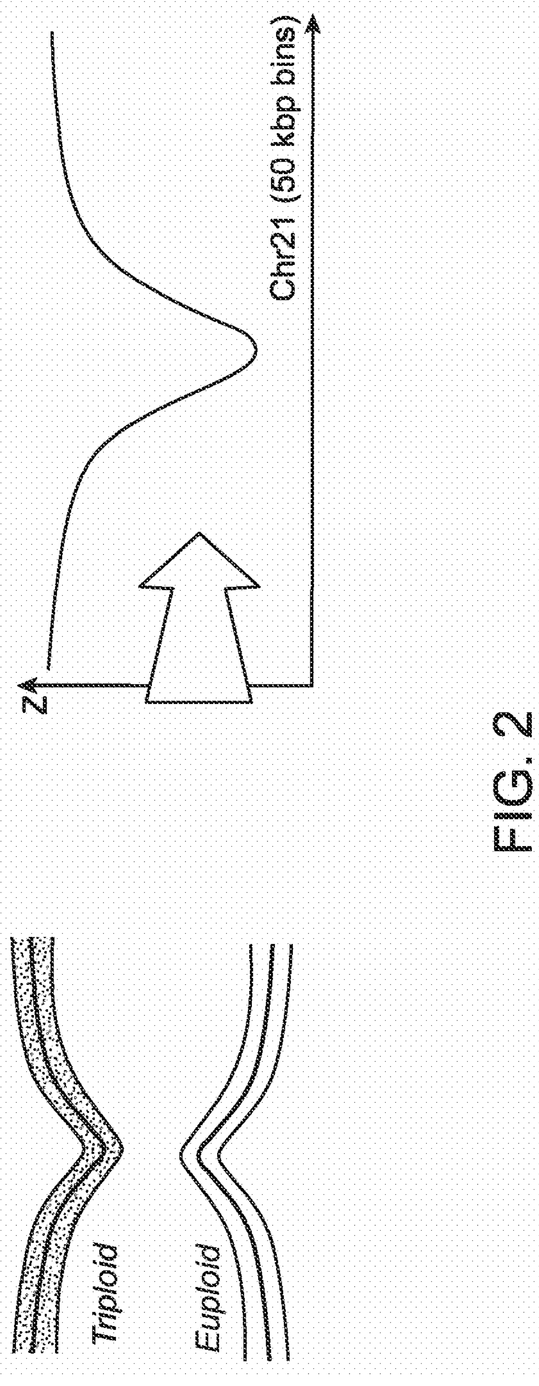
FIG. 2 graphically illustrates how decreased differences between triploid and euploid number of counts within a genomic region sometimes reduces predictive power of Z-scores. See Example 1 for experimental details and results.

The information content of a genomic region in a target chromosome can be visualized by plotting the result of the average separation between euploid and trisomy counts normalized by combined uncertainties, as a function of chromosome position. Increased uncertainty (see FIG. 1) or reduced gap between triploids and euploids (e.g. triploid pregnancies and euploid pregnancies)(see FIG. 2) both result in decreased Z-values for affected cases, sometimes reducing the predictive power of Z-scores.

Figure 3:
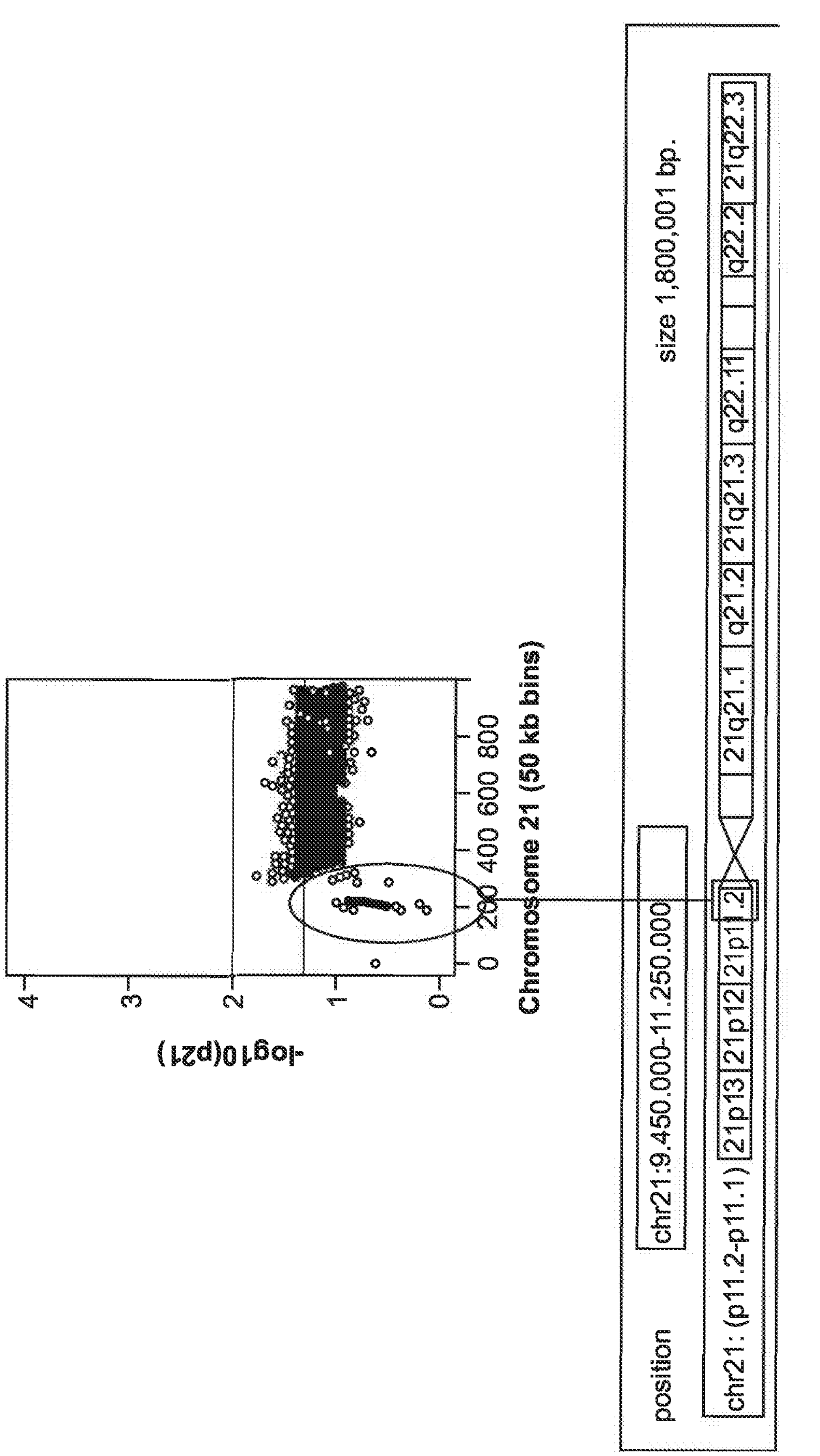
FIG. 3 graphically illustrates the dependence of p-values on the position of genomic bins within chromosome 21.

FIG. 3 graphically illustrates a p-value profile, based on t-distribution, plotted as a function of chromosome position along chromosome 21. Analysis of the data presented in FIG. 3 identifies 36 uninformative chromosome 21 bins, each about 50 kilo-base pairs (kbp) in length. The uninformative region is located in the p-arm, close to centromere (21p11.2-21p11.1). Removing all 36 bins from the calculation of Z-scores, as schematically outlined in FIG. 4, sometimes can significantly increase the Z-values for all trisomy cases, while introducing only random variations into euploid Z-values.

Figure 5:
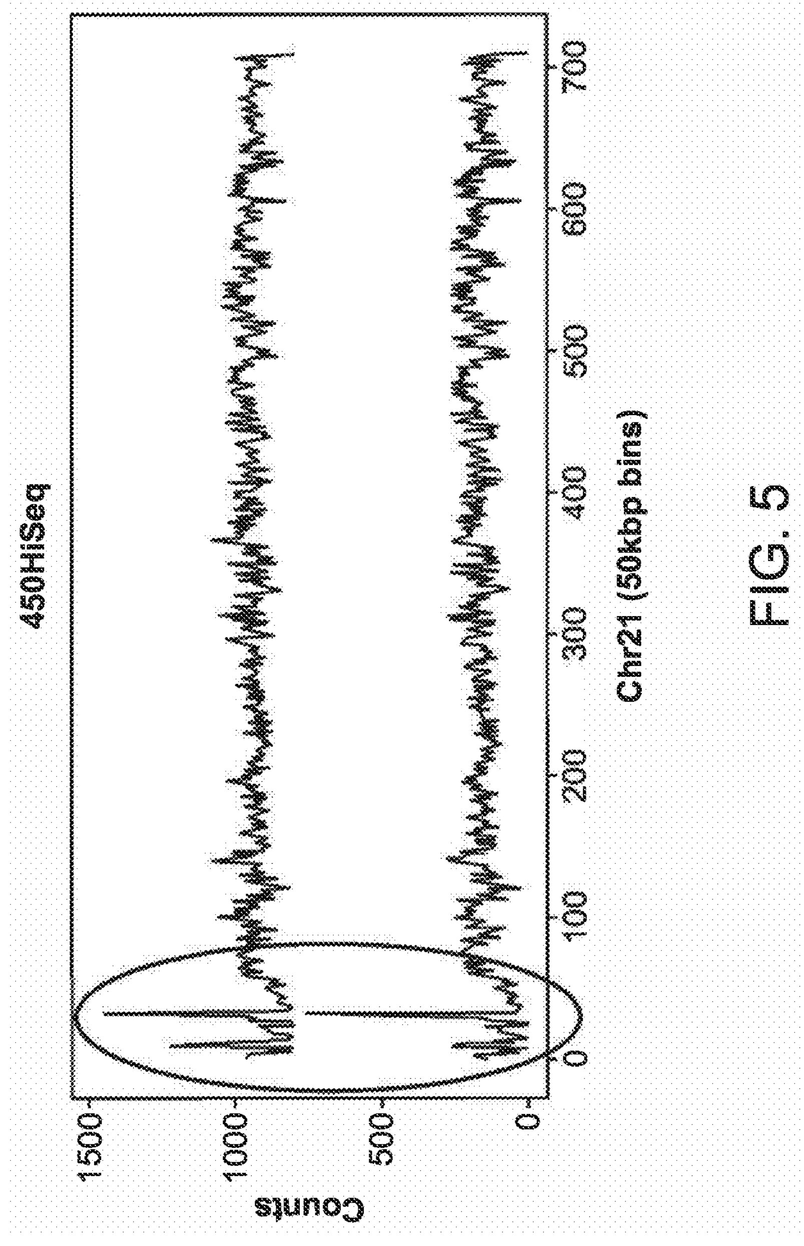
FIG. 5 graphically illustrates count profiles for chromosome 21 in two patients.

The improvement in predictive power afforded by removal of the 36 uninformative bins can be explained by examining the count profile for chromosome 21 (see FIG. 5). In FIG. 5, two arbitrarily chosen samples demonstrate the general tendency of count versus (vs) bin profiles to follow substantially similar trends, apart from short-range noise. The profiles shown in FIG. 5 are substantially parallel. The highlighted region of the profile plot presented in FIG. 5 (e.g., the region in the ellipse), while still exhibiting parallelism, also exhibit large fluctuations relative to the rest of chromosome. Removal of the fluctuating bins (e.g., the 36 uninformative bins) can improve precision and consistency of Z statistics, in some embodiments.

Bin Normalization

Filtering out uninformative bins, as described in Example 1, sometimes does not provide the desired improvement to the predictive power of Z-values. When chromosome 18 data is filtered to remove uninformative bins, as described in Example 1, the z-values did not substantially improve (see FIG. 6). As seen with the chromosome 21 count profiles presented in Example 1, the chromosome 18 count profiles also are substantially parallel, disregarding short range noise. However, two chromosome 18 samples used to evaluate binwise count uncertainties (see the bottom of FIG. 6) significantly deviate from the general parallelism of count profiles. The dips in the middle of the two traces, highlighted by the ellipse, represent large deletions. Other samples examined during the course of the experiment did not exhibit this deletion. The deletion coincides with the location of a dip in p-value profiles for chromosome 18, illustrated in by the ellipse shown in FIG. 7. That is, the dip observed in the p-value profiles for chromosome 18 are explained by the presence of the deletion in the chromosome 18 samples, which cause an increase in the variance of counts in the affected region. The variance in counts is not random, but represents a rare event (e.g., the deletion of a segment of chromosome 18), which, if included with other, random fluctuations from other samples, decreases the predictive power bin filtering procedure.

Two questions arise from this example; (1) how are p-value signals determined to be meaningful and/or useful, and (2) can the p-value approach described herein be generalized for use with any bin data (e.g., from within any chromosome, not only bins from within chromosomes 13, 18 or 21). A generalized procedure could be used to remove variability in the total counts for the entire genome, which can often be used as the normalization factor when evaluating Z-scores. The data presented in FIG. 8 can be used to investigate the answers to the questions above by reconstructing the general contour of the data by assigning the median reference count to each bin, and normalizing each bin count in the test sample with respect to the assigned median reference count.

The medians are extracted from a set of known euploid references. Prior to computing the reference median counts, uninformative bins throughout the genome are filtered out. The remaining bin counts are normalized with respect to the total residual number of counts. The test sample is also normalized with respect to the sum of counts observed for bins that are not filtered out. The resulting test profile often centers around a value of 1, except in areas of maternal deletions or duplication, and areas in which the fetus is triploid (see FIG. 9). The bin-wise normalized profile illustrated in FIG. 10 confirms the validity of the normalization procedure, and clearly reveals the heterozygous maternal deletion (e.g., central dip in the gray segment of the profile tracing) in chromosome 18 and the elevated chromosomal representation of chromosome 18 of the tested sample (see the gray area of profile tracing in FIG. 10). As can be seen from FIG. 10, the median value for the gray segment of the tracing centers around about 1.1, where the median value for the black segment of the tracing centers around 1.0.

Peak Elevation

Figure 11:
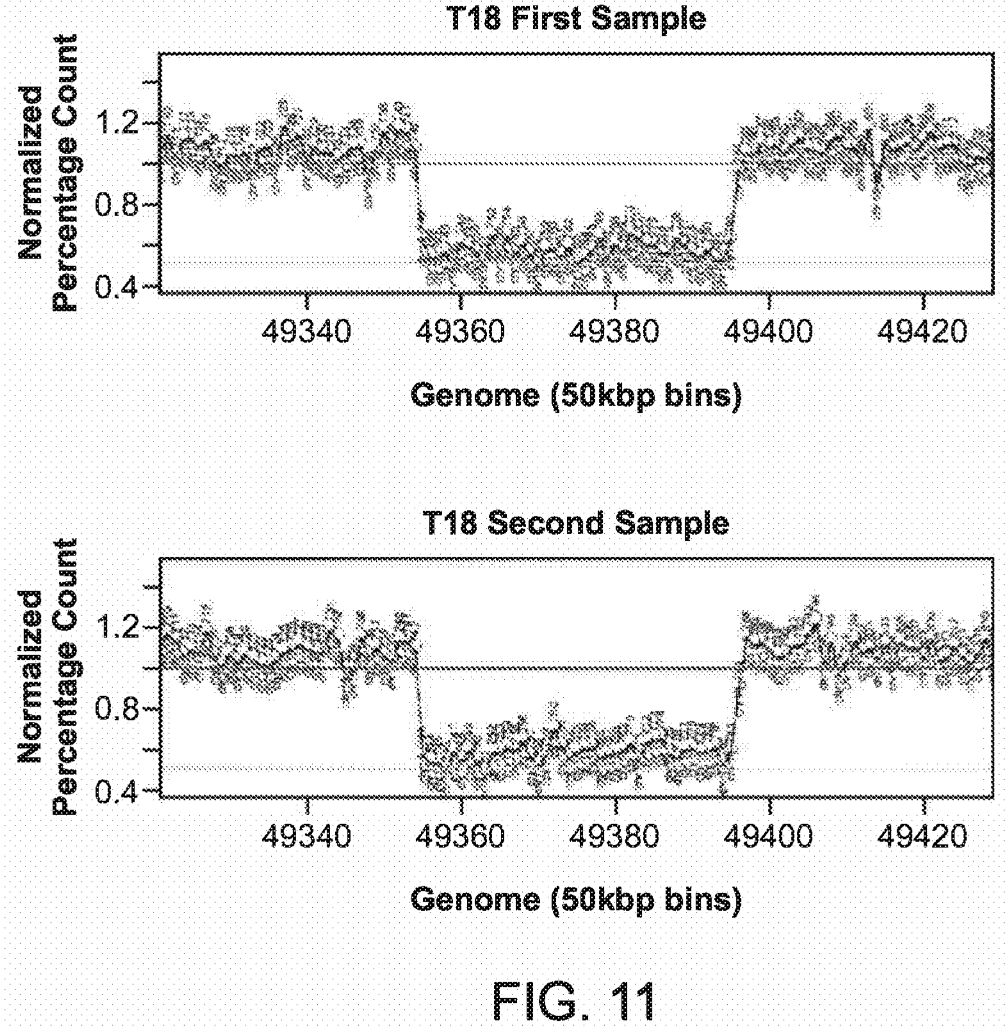
FIG. 11 graphically illustrates normalized binwise count profiles for two samples collected from the same patient with heterozygous maternal deletion in chromosome 18. The substantially identical tracings can be used to determine if two samples are from the same donor.

FIG. 11 graphically illustrates the results of analyzing multiple samples using bin-wise normalization, from a patient with a discernible feature or trait (e.g., maternal duplication, maternal deletion, the like or combinations thereof). The identities of the samples often can be determined by comparing their respective normalized count profiles. In the example illustrated in FIG. 11, the location of the dip in the normalized profile and its elevation, as well as its rarity, indicate that both samples originate from the same patient. Forensic panel data often can be used to substantiate these findings.

Figure 12:
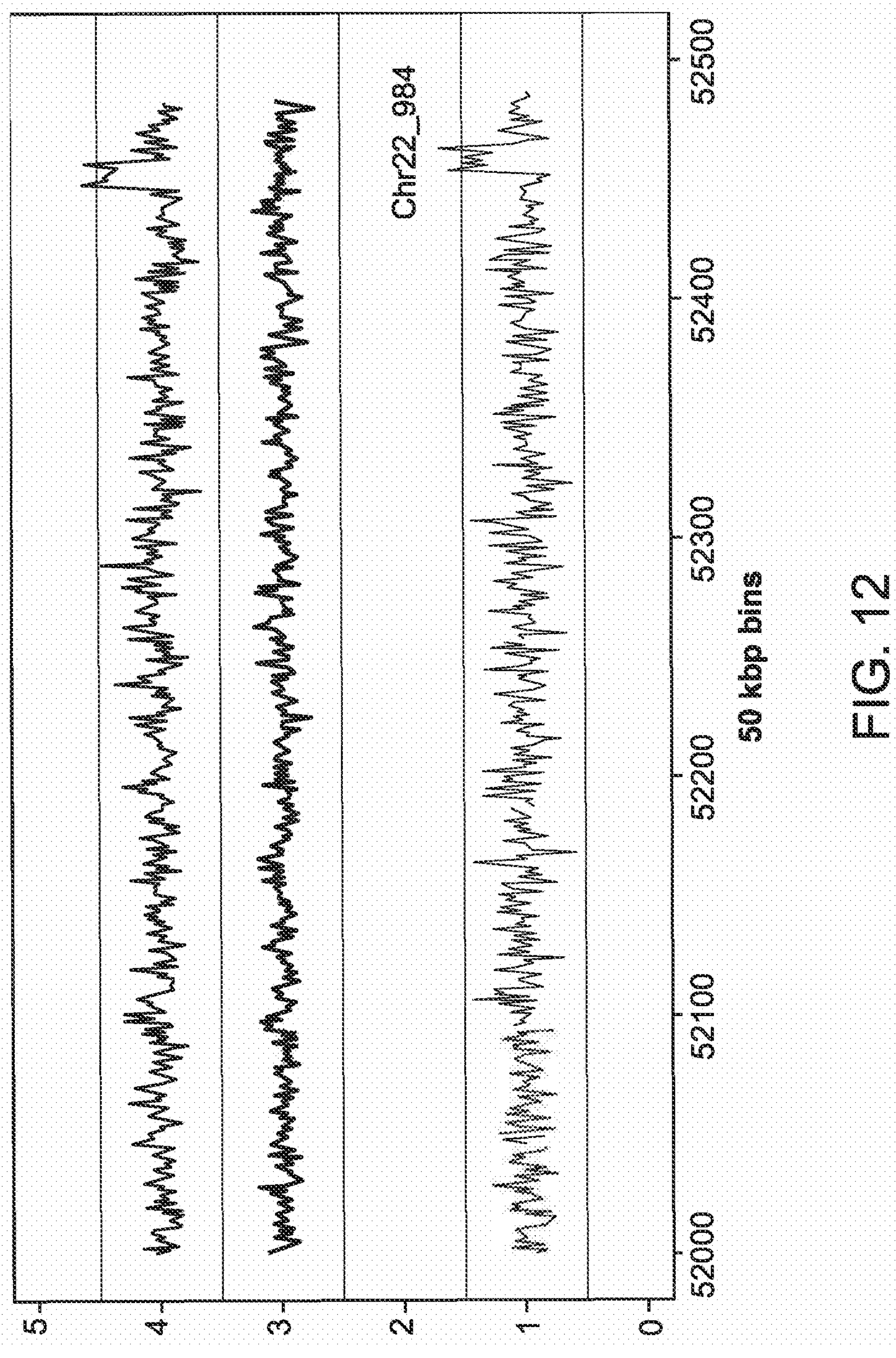
FIG. 12 graphically illustrates normalized binwise count profiles of a sample from one study, compared with two samples from a previous study. The duplication in chromosome 22 unambiguously points out the patient's identity.
Figure 13:
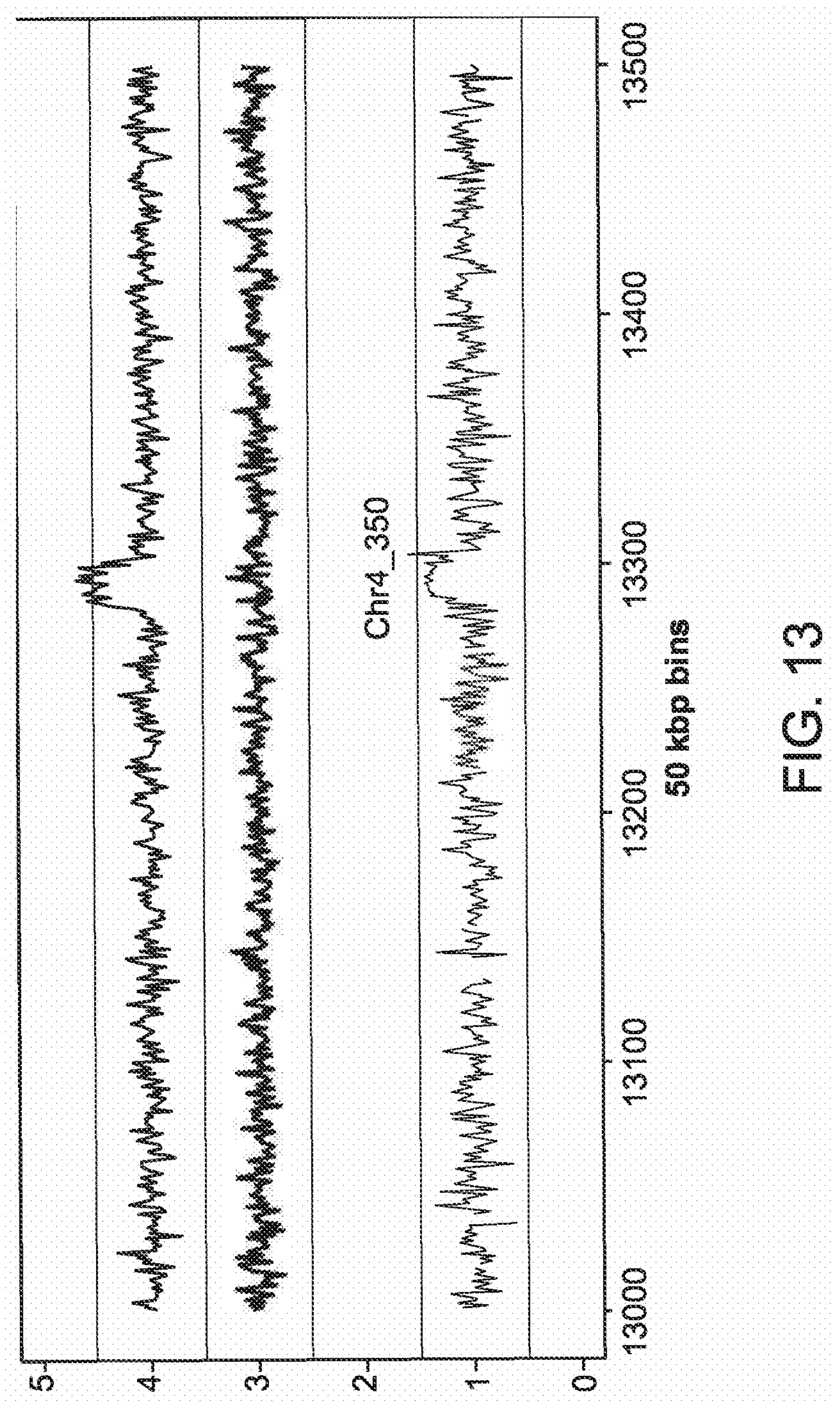
FIG. 13 graphically illustrates normalized binwise count profiles of chromosome 4 in the same three patients presented in FIG. 12. The duplication in chromosome 4 confirms the patient's identity established in FIG. 12. See Example 1 for experimental details and results.

FIGS. 12 and 13 graphically illustrate the results of the use of normalized bin profiles for identifying patient identity, or sample identity. The samples analyzed in FIGS. 12 and 13 carry wide maternal aberrations in chromosomes 4 and 22, which are absent in the other samples in the profile tracings, confirming the shared origin of the top and bottom traces. Results such as this can lead to the determination that a particular sample belongs to a specific patient, and also can be used to determine if a particular sample has already been analyzed.

Bin-wise normalization facilitates the detection of aberrations, however, comparison of peaks from different samples often is further facilitated by analyzing quantitative measures of peak elevations and locations (e.g., peak edges). The most prominent descriptor of a peak often is its elevation, followed by the locations of its edges. Features from different count profiles often can be compared using the following non-limiting analysis.

(a) Determine the confidence in a features detected peaks in a single test sample. If the feature is distinguishable from background noise or processing artifacts, the feature can be further analyzed against the general population.

(b) Determine the prevalence of the detected feature in the general population. If the feature is rare, it can be used as a marker for rare aberrations. Features that are found frequently in the general population are less useful for analysis. Ethnic origins can play a role in determining the relevance of a detected features peak elevation. Thus, some features provide useful information for samples from certain ethnic origins.

(c) Derive the confidence in the comparison between features observed in different samples.

Figure 14:
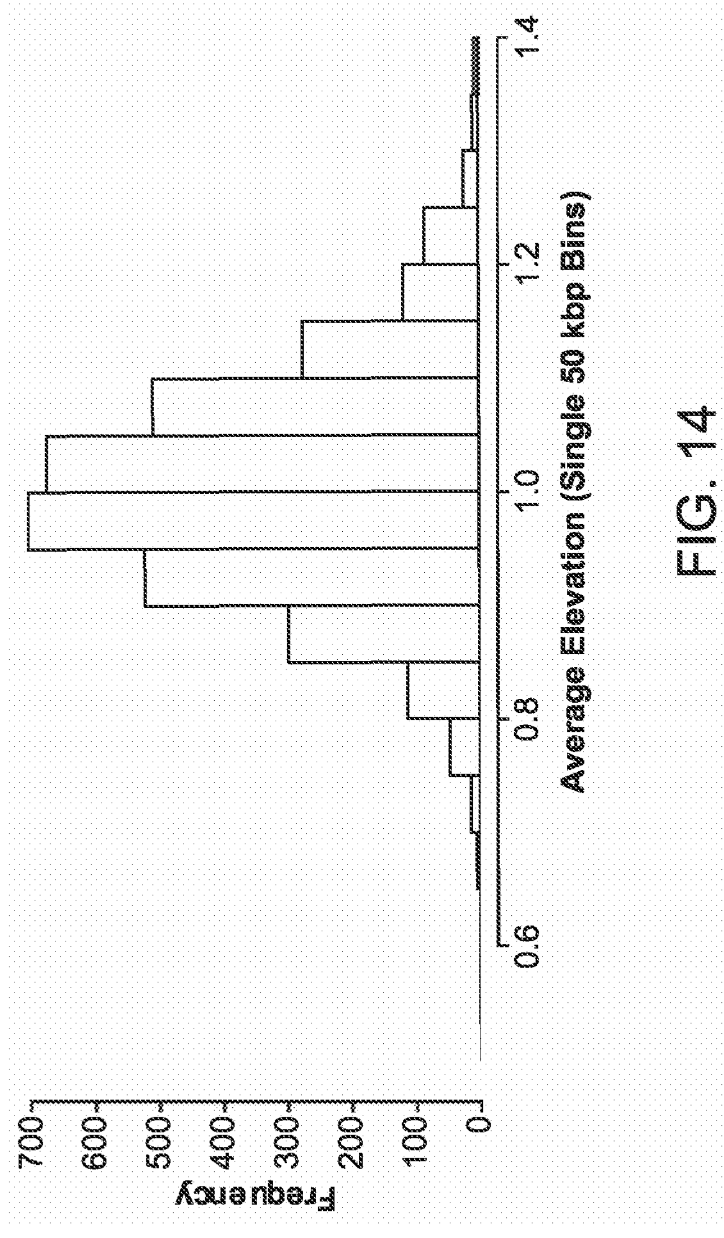
FIG. 14 graphically illustrates the distribution of normalized bin counts in chromosome 5 from a euploid sample.
Figure 15:
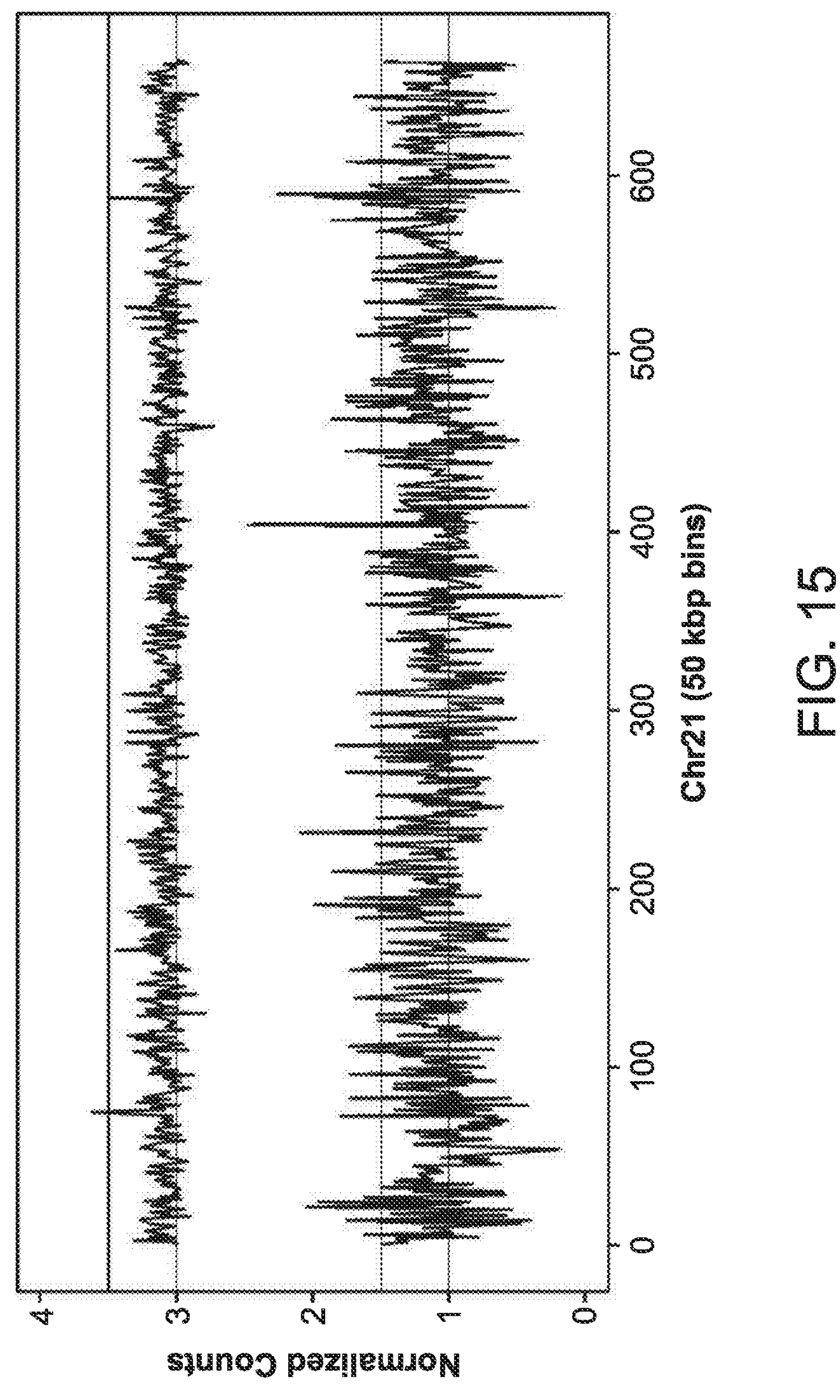
FIG. 15 graphically illustrates two samples with different levels of noise in their normalized count profiles.
Figure 16:
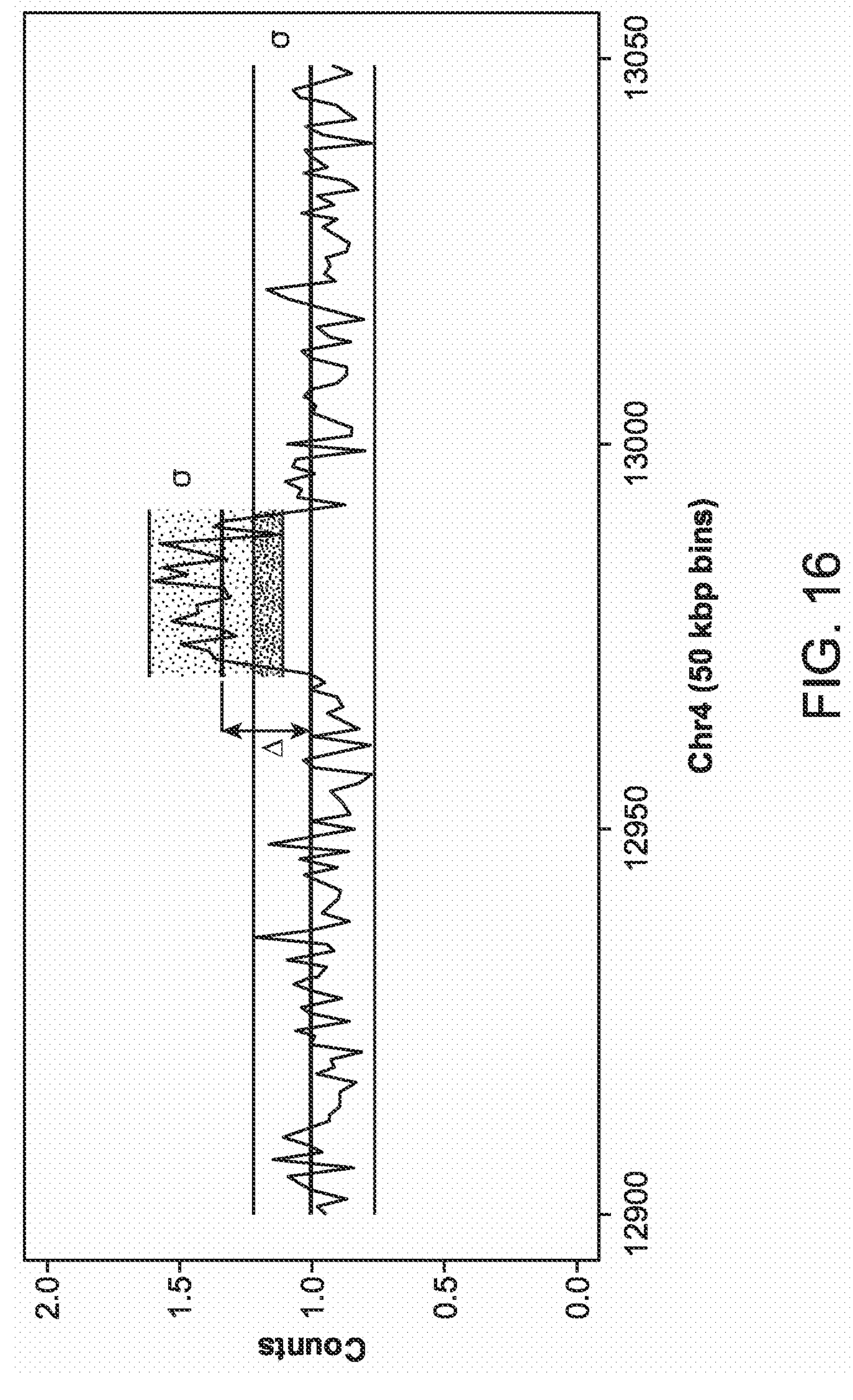
FIG. 16 schematically represents factors determining the confidence in peak elevation: noise standard deviation (e.g., $\sigma$) and average deviation from the reference baseline (e.g., $\Delta$). See Example 1 for experimental details and results.
Figure 17:
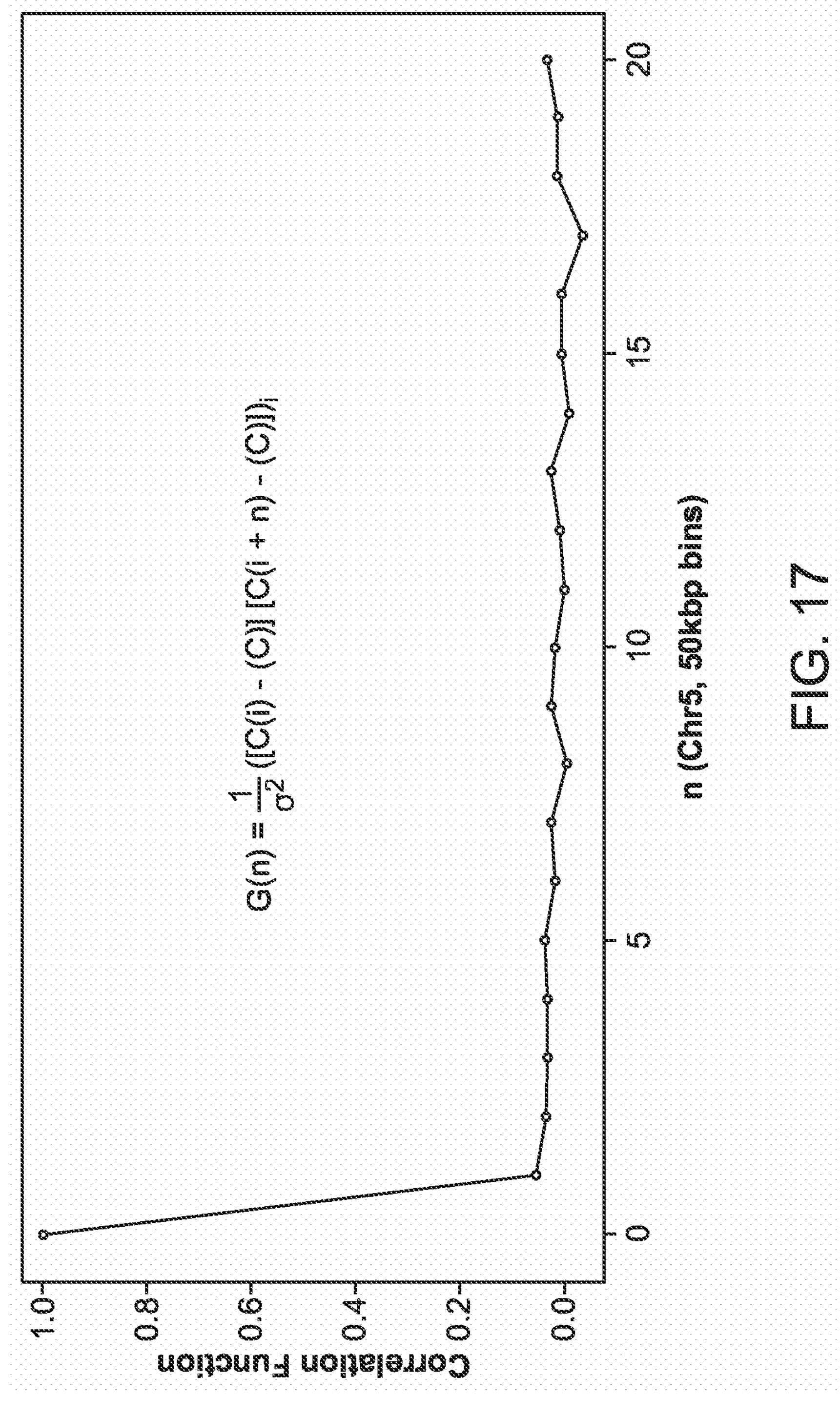
FIG. 17 graphically illustrates the results of applying a correlation function to normalized bin counts. The correlation function shown in FIG. 17 was used to normalize bin counts in chromosome 5 of an arbitrarily chosen euploid patient.
Figure 18:
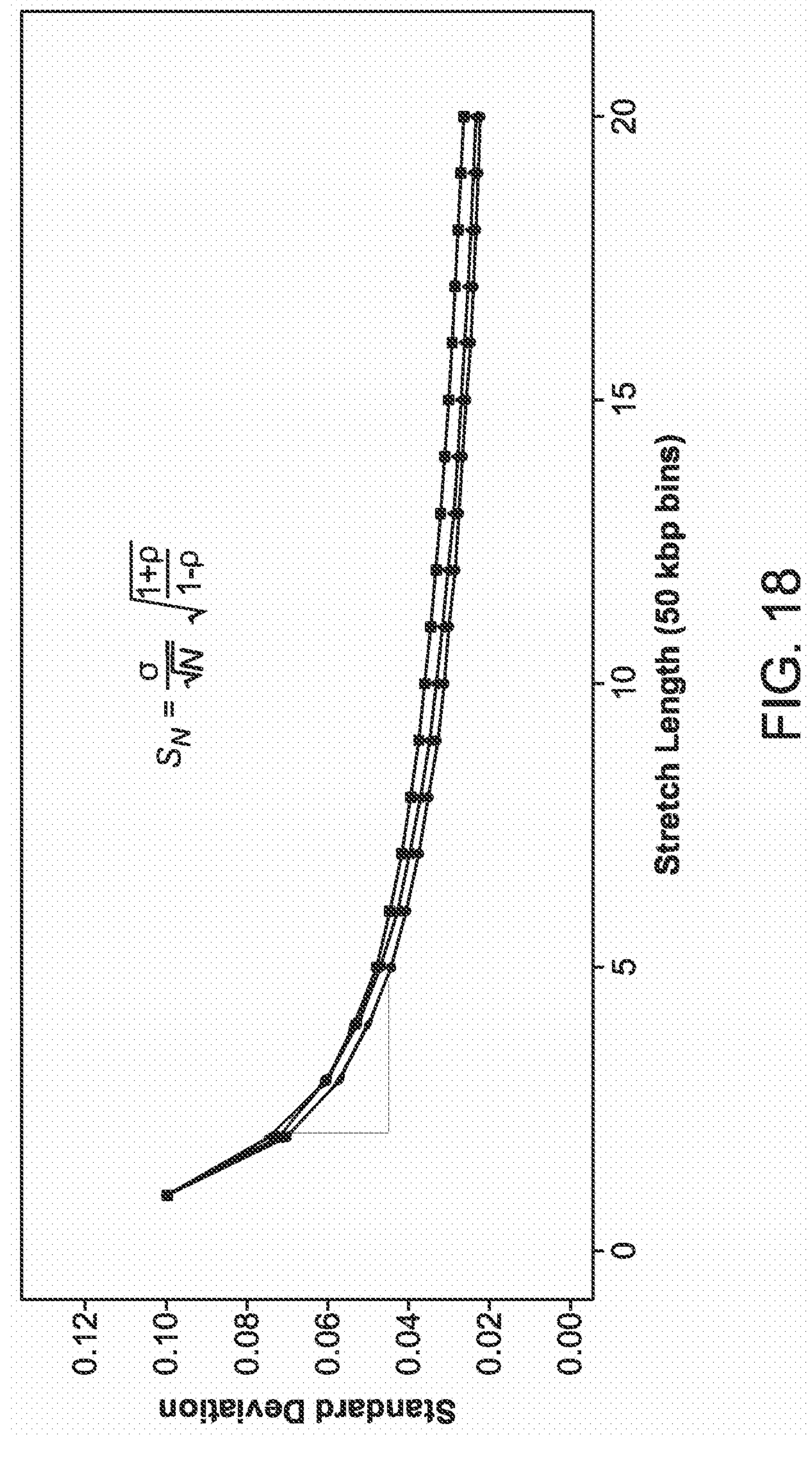
FIG. 18 graphically illustrates the standard deviation for the average stretch elevation in chromosome 5, evaluated as a sample estimate (square data points) and compared with the standard error of the mean (triangle data points) and with the estimate corrected for auto-correlation $\rho=0.5$ (circular data points). The aberration depicted in FIG. 18 is about 18 bins long. See Example 1 for experimental details and results.
Figure 19:
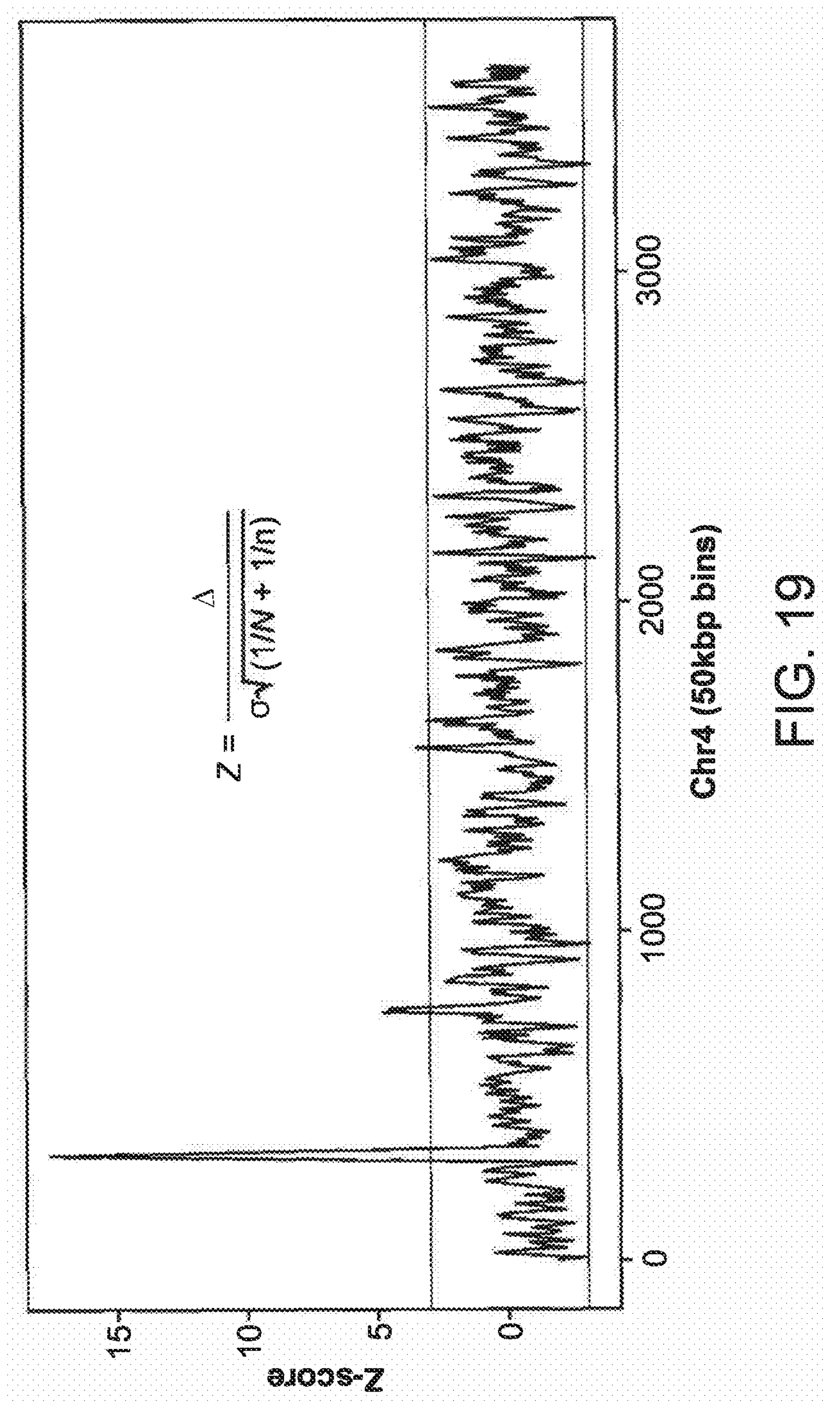
FIG. 19 graphically illustrates Z-values calculated for average peak elevation in chromosome 4. The patient has a heterozygous maternal duplication in chromosome 4 (see FIG. 13).
Figure 20:
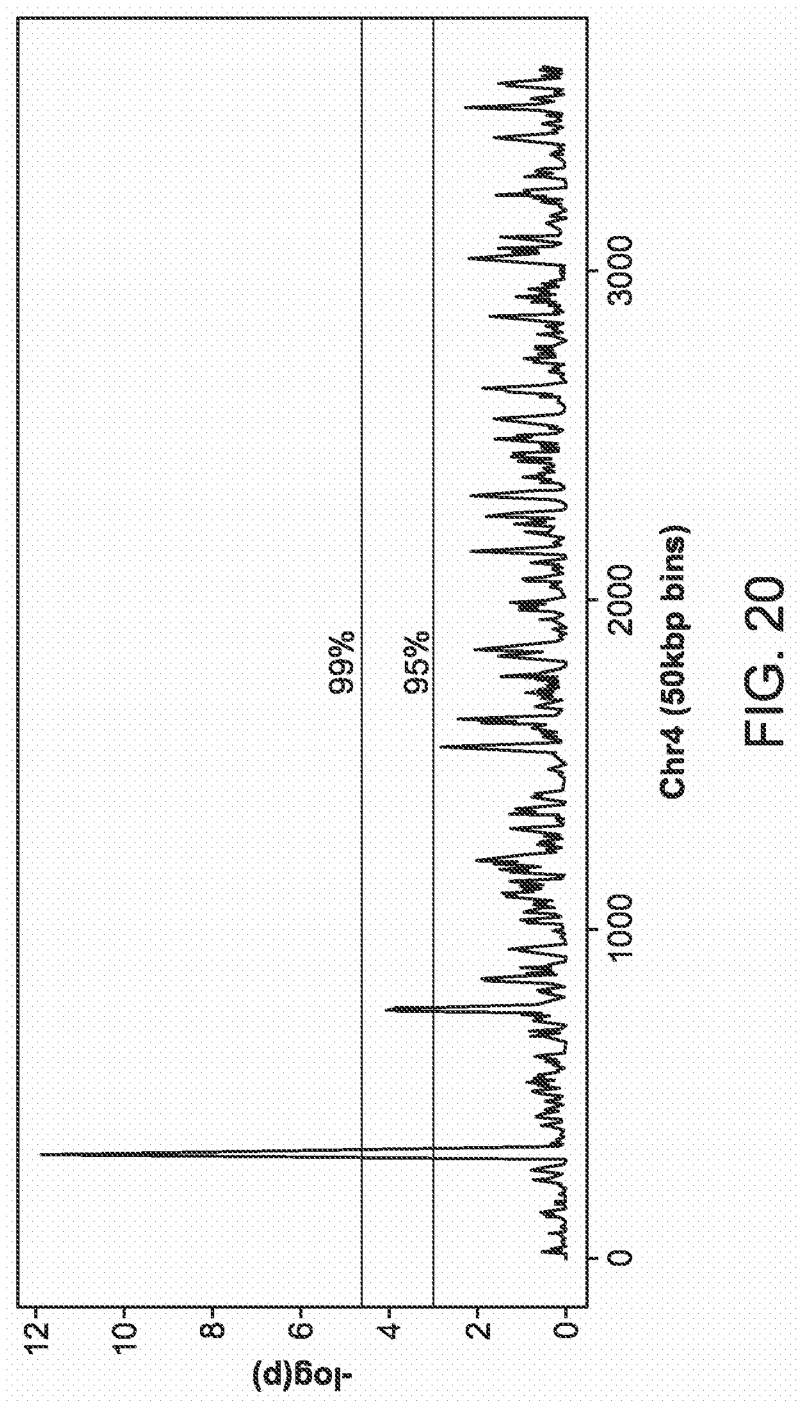
FIG. 20 graphically illustrates p-values for average peak elevation, based on a t-test and the Z-values from FIG. 19. The order of the t-distribution is determined by the length of the aberration. See Example 1 for experimental details and results.

Illustrated in FIG. 14 are the normalized bin counts in chromosome 5, from a euploid subject. The average elevation generally is the reference baseline from which the elevations of aberrations are measured, in some embodiments. Small and/or narrow deviations are less reliable predictors than wide, pronounced aberrations. Thus, the background noise or variance from low fetal contribution and/or processing artifacts is an important consideration when aberrations are not large or do not have a significant peak elevation above the background. An example of this is presented in FIG. 15, where a peak that would be significant in the upper trace, can be masked in the background noise observed in the bottom profile trace. The confidence in the peak elevation (see FIG. 16) can be determined by the average deviation from the reference (shown as the delta symbol), relative to the width of the euploid distribution (e.g., combined with the variance (shown as the sigma symbol) in the average deviation). The error in the average stretch elevation can be derived from the known formula for the error of the mean. If a stretch longer than one bin is treated as a random (non-contiguous) sample of all bins within a chromosome, the error in the average elevation decreases with the square root of the number of bins within the aberration. This reasoning neglects the correlation between neighboring bins, an assumption confirmed by the correlation function shown in FIG. 17 (e.g., the equation for G(n)). Non-normalized profiles sometimes exhibit strong medium-range correlations (e.g., the wavelike variation of the baseline), however, the normalized profiles smooth out the correlation, leaving only random noise. The close match between the standard error of the mean, the correction for autocorrelation, and the actual sample estimates of the standard deviation of the mean elevation in chromosome 5 (see FIG. 18) confirms the validity of the assumed lack of correlation. Z-scores (see FIG. 19) and p-values calculated from Z-scores associated with deviations from the expected elevation of 1 (see FIG. 20) can then be evaluated in light of the estimate for uncertainty in the average elevation. The p-values are based on a t-distribution whose order is determined by the number of bins in a peak. Depending on the desired level of confidence, a cutoff can suppress noise and allow unequivocal detection of the actual signal.

$$Z = \frac{\Delta_1 - \Delta_2}{\sqrt{\sigma_1^2\left(\frac{1}{N_1} + \frac{1}{n_1}\right) + \sigma_2^2\left(\frac{1}{N_2} + \frac{1}{n_2}\right)}} \quad (1)$$

Equation 1 can be used to directly compare peak elevation from two different samples, where N and n refer to the numbers of bins in the entire chromosome and within the aberration, respectively. The order of the t-test that will yield a p-value measuring the similarity between two samples is determined by the number of bins in the shorter of the two deviant stretches.

Peak Edge

Figure 21:
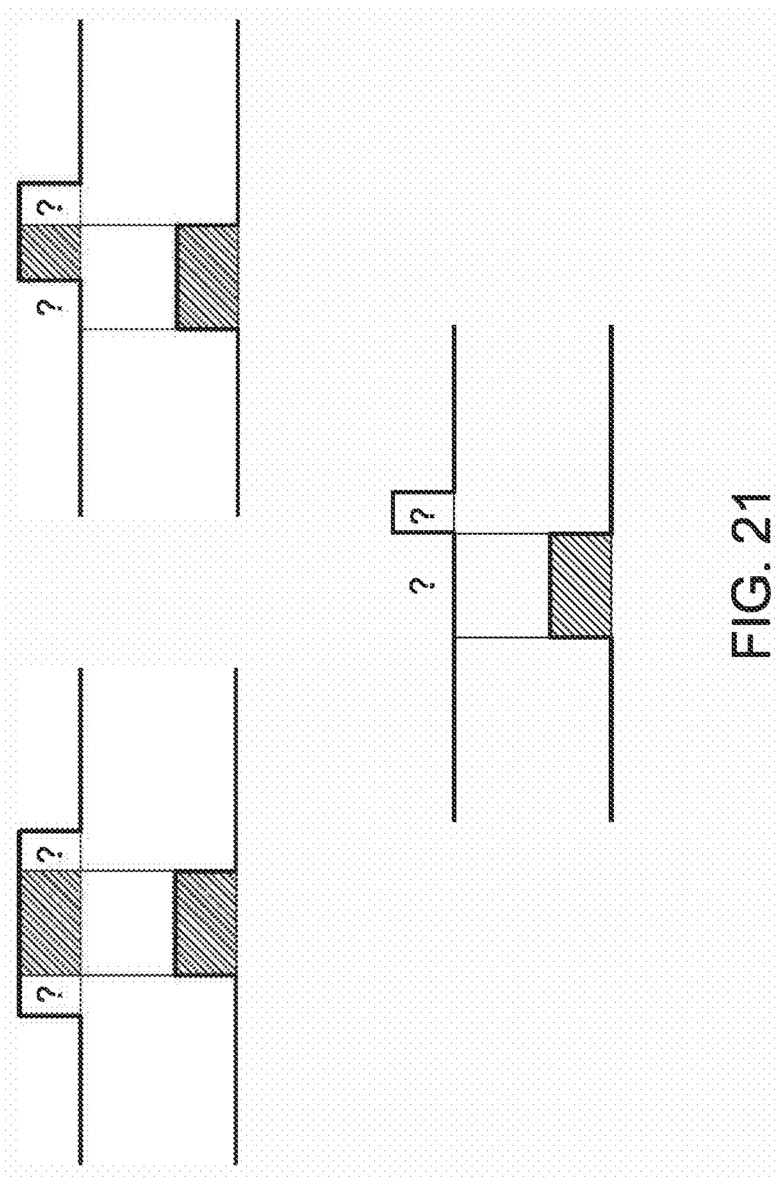
FIG. 21 schematically represents edge comparisons between matching aberrations from different samples. Illustrated in FIG. 21 are overlaps, containment, and neighboring deviations.
Figure 22:
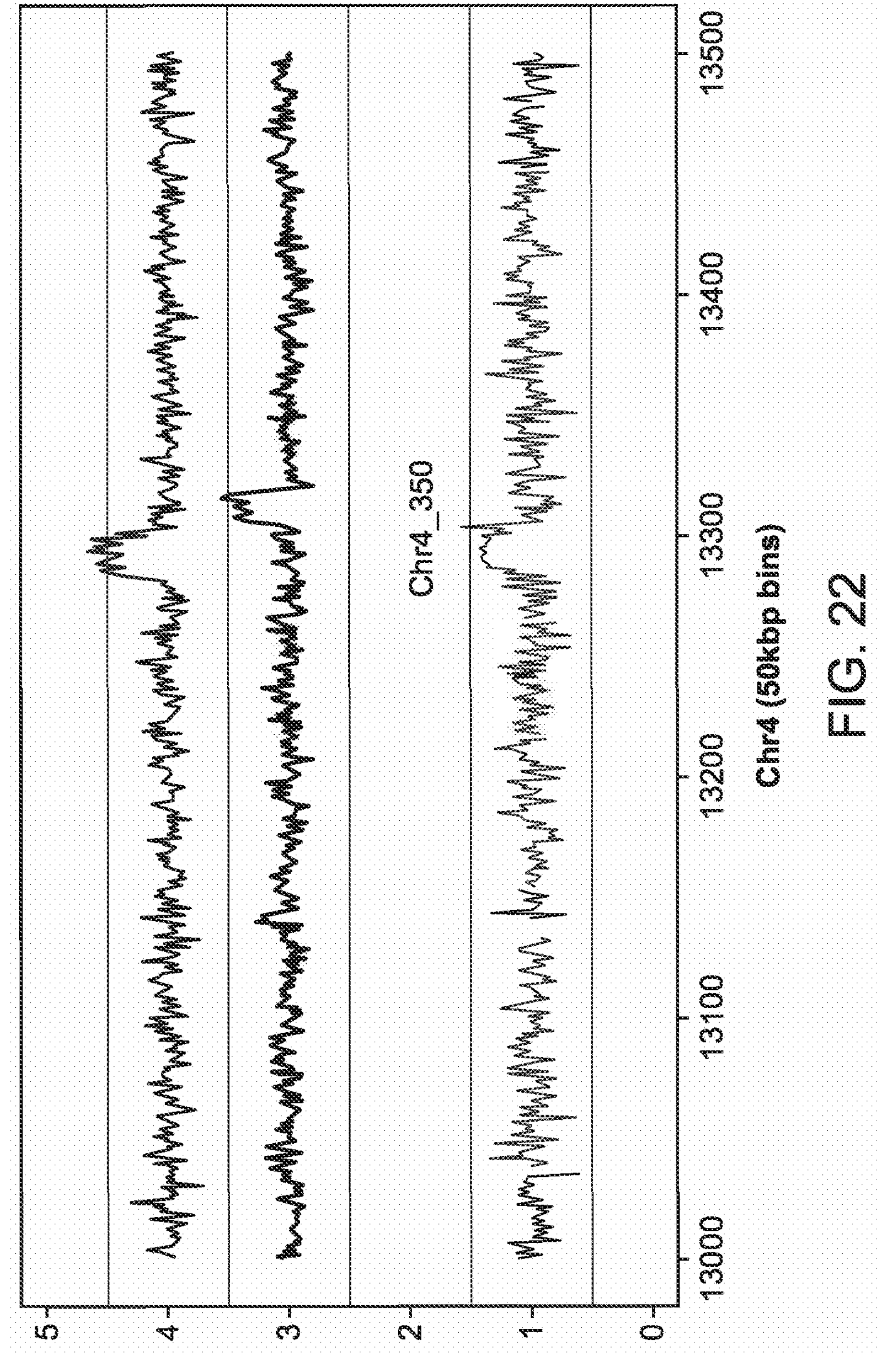
FIG. 22 graphically illustrates matching heterozygous duplications in chromosome 4 (top trace and bottom trace), contrasted with a marginally touching aberration in an unrelated sample (middle trace). See Example 1 for experimental details and results.
Figure 23:
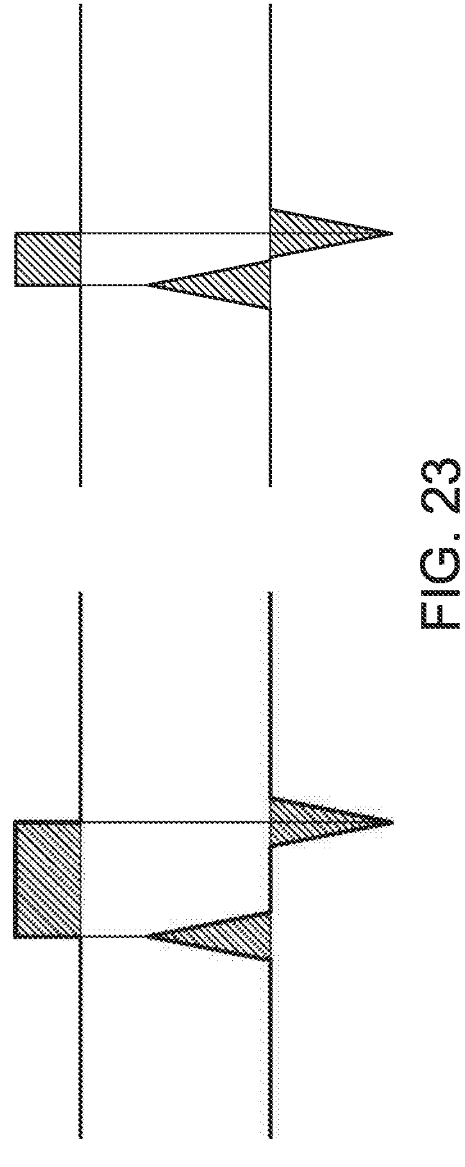
FIG. 23 schematically represents edge detection by means of numerically evaluated first derivatives of count profiles.

In addition to comparing average elevations of aberrations in a sample, the beginning and end of the compared stretches also can provide useful information for statistical analysis. The upper limit of resolution for comparisons of peak edges often is determined by the bin size (e.g., 50 kbps in the examples described herein). FIG. 21 illustrates 3 possible peak edge scenarios; (a) a peak from one sample can be completely contained within the matching peak from another sample, (b) the edges from one sample can partially overlap the edges of another sample, or (c) the leading edge from one sample can just marginally touch or overlap the trailing edge of another sample. FIG. 22 illustrates and example of the scenario described in (c) (e.g., see the middle trace, where the trailing edge of the middle trace marginally touches the leading edge of the upper trace). The lateral tolerance associated with an edge often can be used to distinguish random variations from true, aberration edges. The position and the width of an edge can be quantified by numerically evaluating the first derivative of the aberrant count profile, as shown in FIG. 23. If the aberration is represented as a composite of two Heaviside functions, its derivative will be the sum of two Dirac's delta functions. The starting edge corresponds to an upward absorption-shaped peak, while the ending edge is a downward, 180 degree-shifted absorption peak. If the aberration is narrow, the two spikes are close to one another, forming a dispersion-like contour. The locations of the edges can be approximated by the extrema of the first derivative spikes, while the edge tolerance is determined by their widths.

Figure 24:
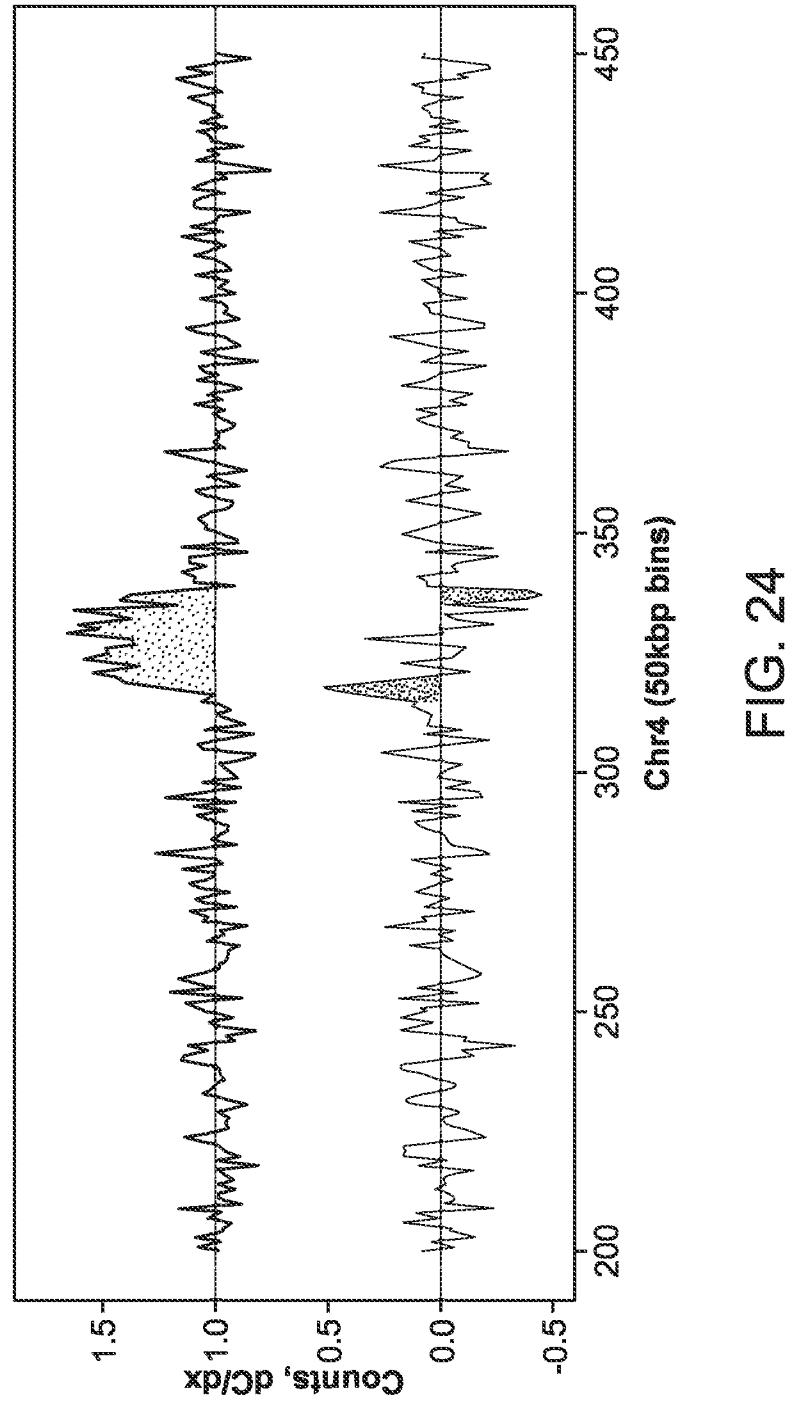
FIG. 24 graphically illustrates that first derivative of count profiles, obtained from real data, are difficult to distinguish from noise.
Figure 25:
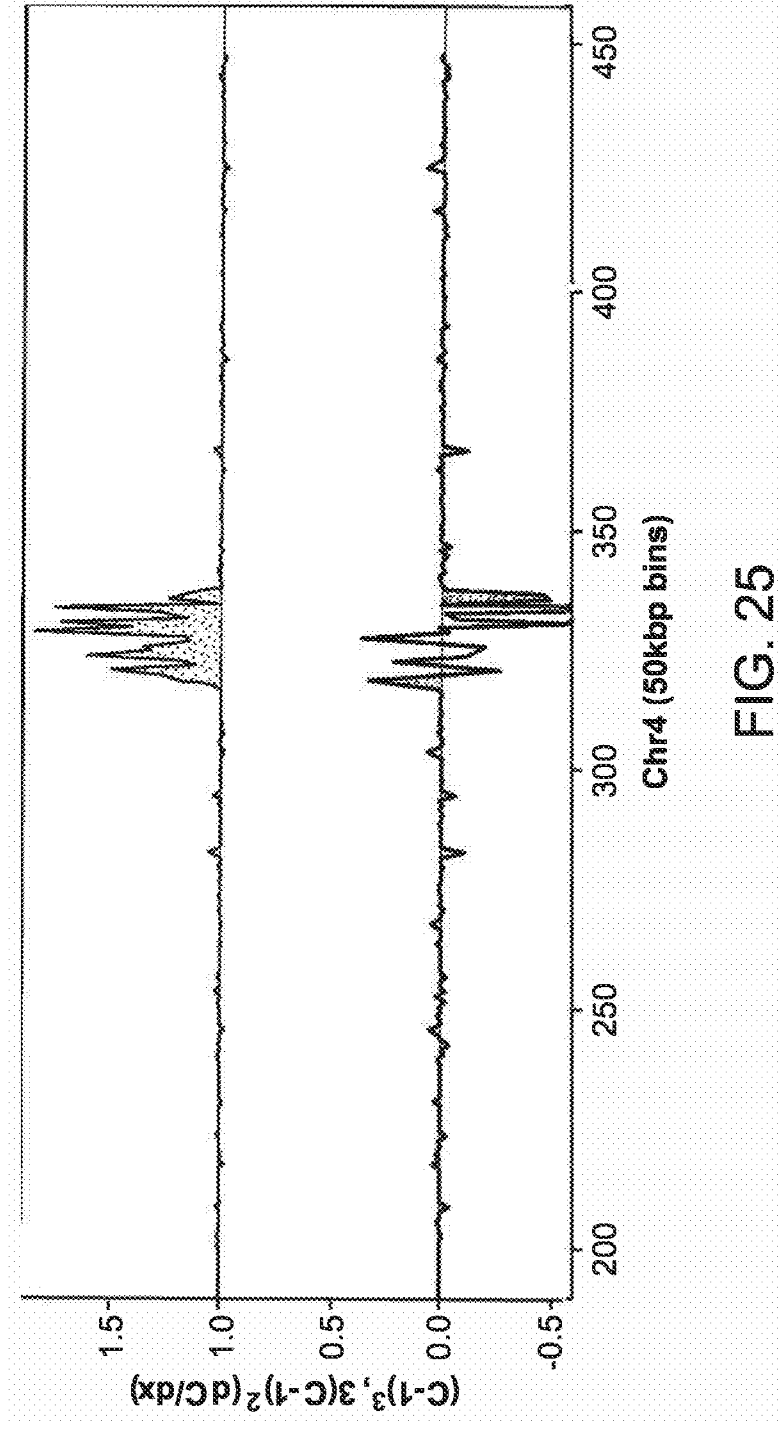
FIG. 25 graphically illustrates the third power of the count profile, shifted by 1 to suppress noise and enhance signal (see top trace). Also illustrated in FIG. 25 (see bottom trace) is a first derivative of the top trace. Edges are unmistakably detectable. See Example 1 for experimental details and results.

Comparison between different samples often can be reduced to determining the difference between two matching edge locations, divided by the combined edge uncertainties. However, the derivatives sometimes are lost in background noise, as illustrated in FIG. 24. While the aberration itself benefits from the collective information contributed from all its bins, the first derivative only can afford information from the few points at the edge of the aberration, which can be insufficient to overcome the noise. Sliding window averaging, used to create FIG. 24, is of limited value in this situation. Noise can be suppressed by combining the first derivative (e.g., akin to a point estimate) with the peak elevation (e.g., comparable to an integral estimate). In some embodiments the first derivative and the peak elevation can be combined by multiplying them together, which is equivalent to taking the first derivative of a power of the peak elevation, as shown in FIG. 25. The results presented in FIG. 25 successfully suppress noise outside of the aberration, however, noise within the aberration is enhanced by the manipulation. The first derivative peaks are still clearly discernible, allowing them to be used to extract edge locations and lateral tolerances, thereby allowing the aberration to be clearly identified in the lower profile tracing.

Median Chromosomal Elevation

Figure 9:
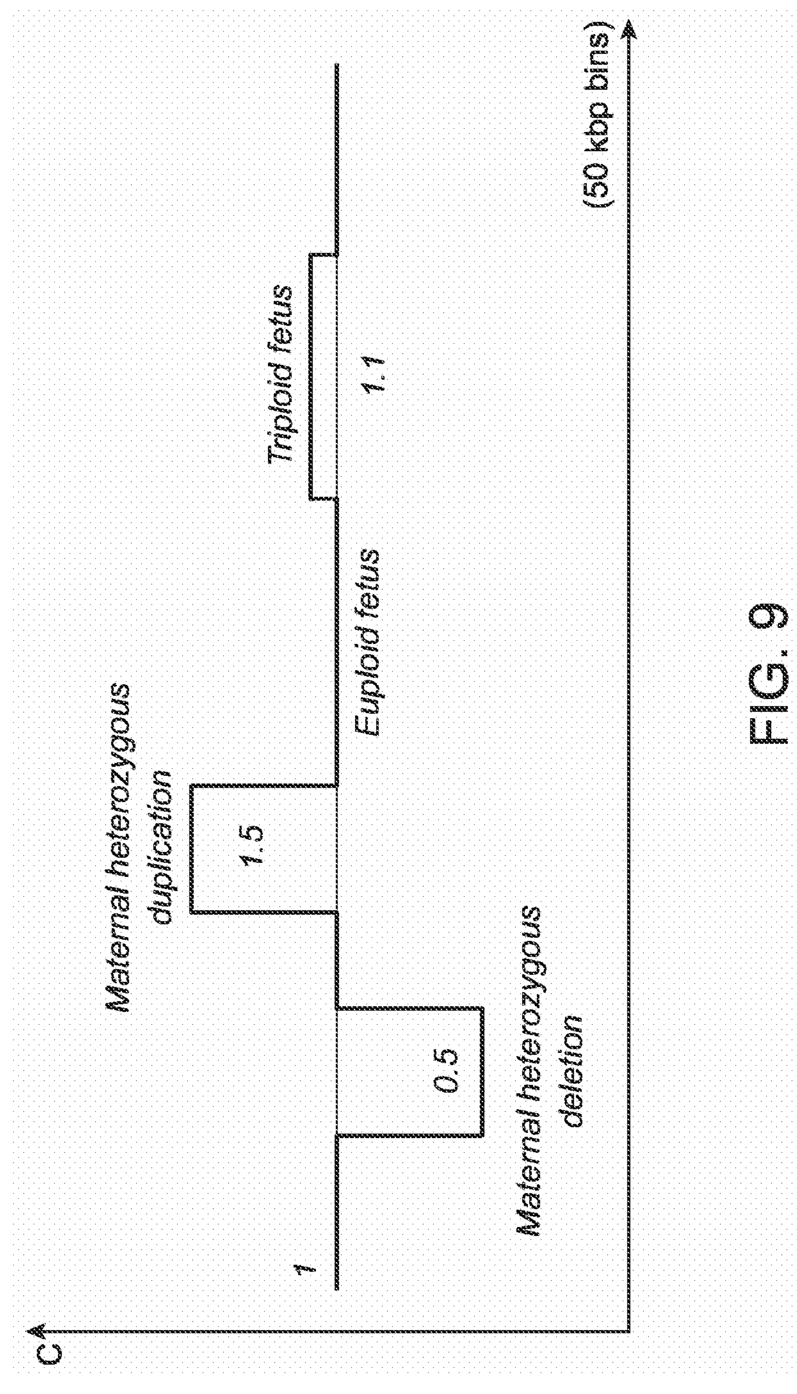
FIG. 9 graphically illustrates the expected behavior of normalized count profiles. The majority of normalized bin counts often will center on 1, with random noise superimposed. Deletions and duplications (e.g., maternal or fetal, or maternal and fetal, deletions and duplications) sometimes shifts the elevation to an integer multiple of 0.5. Profile elevations corresponding to a triploid fetal chromosome often shifts upward in proportion to the fetal fraction. See Example 1 for experimental details and results.
Figure 10:
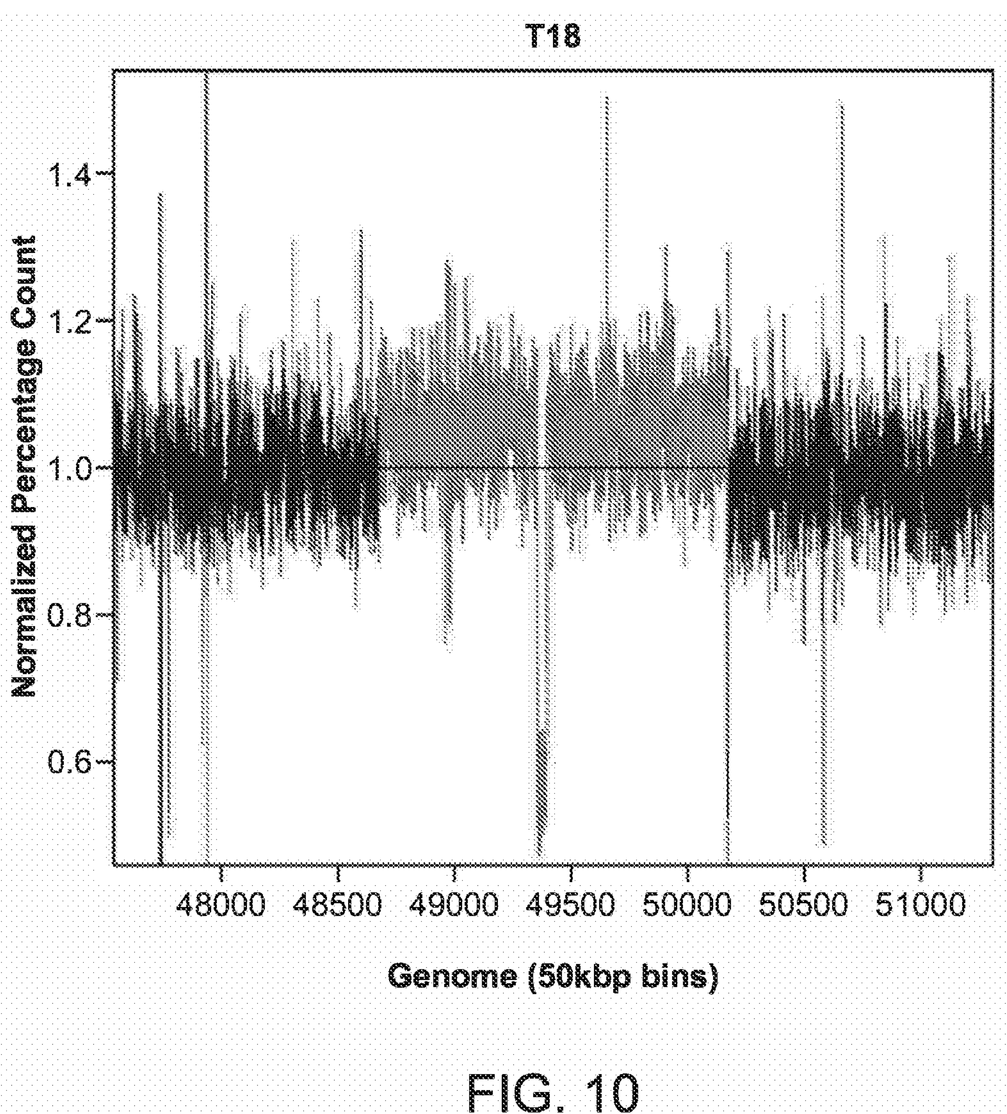
FIG. 10 graphically illustrates a normalized T18 count profile with a heterozygous maternal deletion in chromosome 18. The light gray segment of the graph tracing shows a higher average elevation than the black segment of the graph tracing. See Example 1 for experimental details and results.
Figure 26:
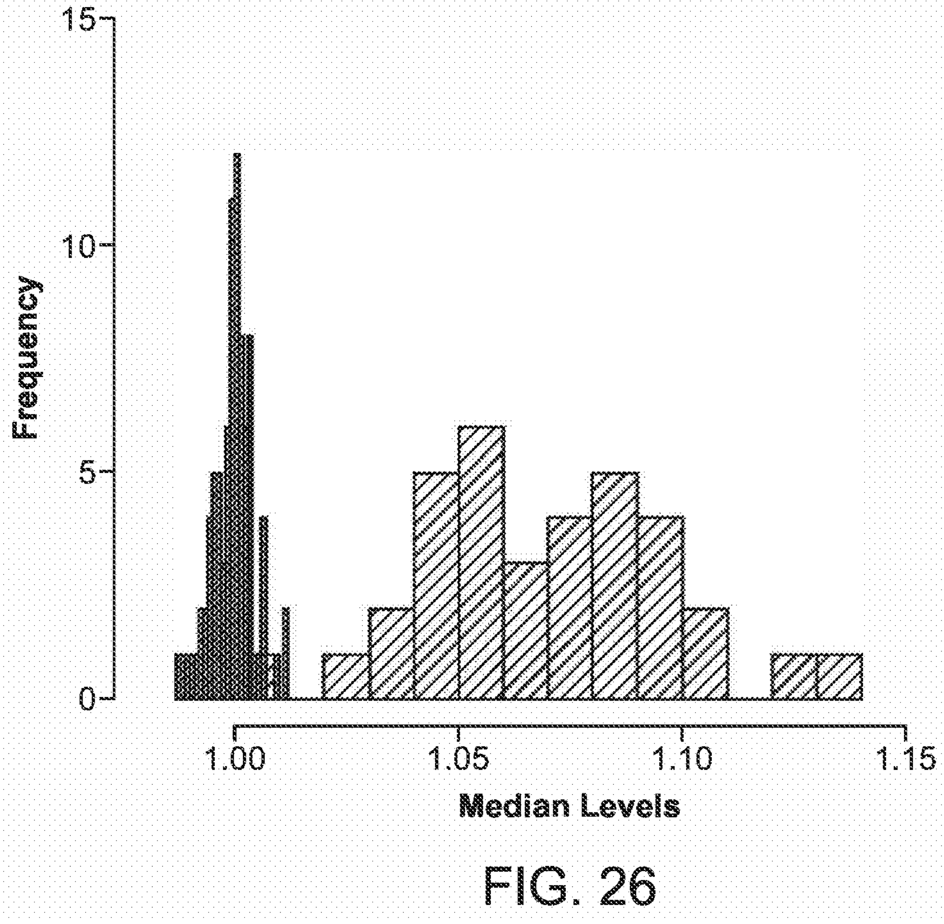
FIG. 26 graphically illustrates histograms of median chromosome 21 elevations for various patients. The dotted histogram illustrates median chromosome 21 elevations for 86 euploid patients. The hatched histogram illustrates median chromosome 21 elevations for 35 trisomy 21 patients. The count profiles were normalized with respect to a euploid reference set prior to evaluating median elevations.

The median normalized elevation within the target chromosome in a euploid patient is expected to remain close to 1 regardless of the fetal fraction. However, as shown in FIGS. 9 and 10, median elevations in trisomy patients increase with the fetal fraction. The increase generally is substantially linear with a slope of 0.5. Experimental measurements confirm these expectations. FIG. 26 illustrates a histogram of median elevations for 86 euploid samples (shown in dotted bars in FIG. 26). The median values are tightly clustered around 1 (median=1.0000, median absolute deviation (MAD)=0.0042, mean=0.9996, standard deviation (SD)=0.0046). None of the euploid median elevations exceeds 1.012, as shown in the histogram presented in FIG. 26. In contrast, out of 35 trisomy samples shown (hatched bars) in FIG. 26, all but one have median elevations exceeding 1.02, significantly above the euploid range. The gap between the two groups of patients in this example is large enough to allow classification as euploid or aneuploid.

Fetal Fraction as the Limiting Factor in Classification Accuracy

The ratio between the fetal fraction and the width of the distribution of median normalized counts in euploids (e.g. euploid pregnancies) can be used to determine the reliability of classification using median normalized elevations, in some embodiments. Since median normalized counts, as well as other descriptors such as Z-values, linearly increase with the fetal fraction with the proportionality constant of 0.5, the fetal fraction must exceed four standard deviations of the distribution of median normalized counts to achieve 95% confidence in classification, or six standard deviations to achieve 99% confidence in classification. Increasing the number of aligned sequences tags can serve to decrease the error in measured profiles and sharpen the distribution of median normalized elevations, in certain embodiments. Thus, the effect of increasingly precise measurements is to improve the ratio between fetal fraction and the width of the distribution of euploid median normalized elevations.

Area Ratio

Figure 27:
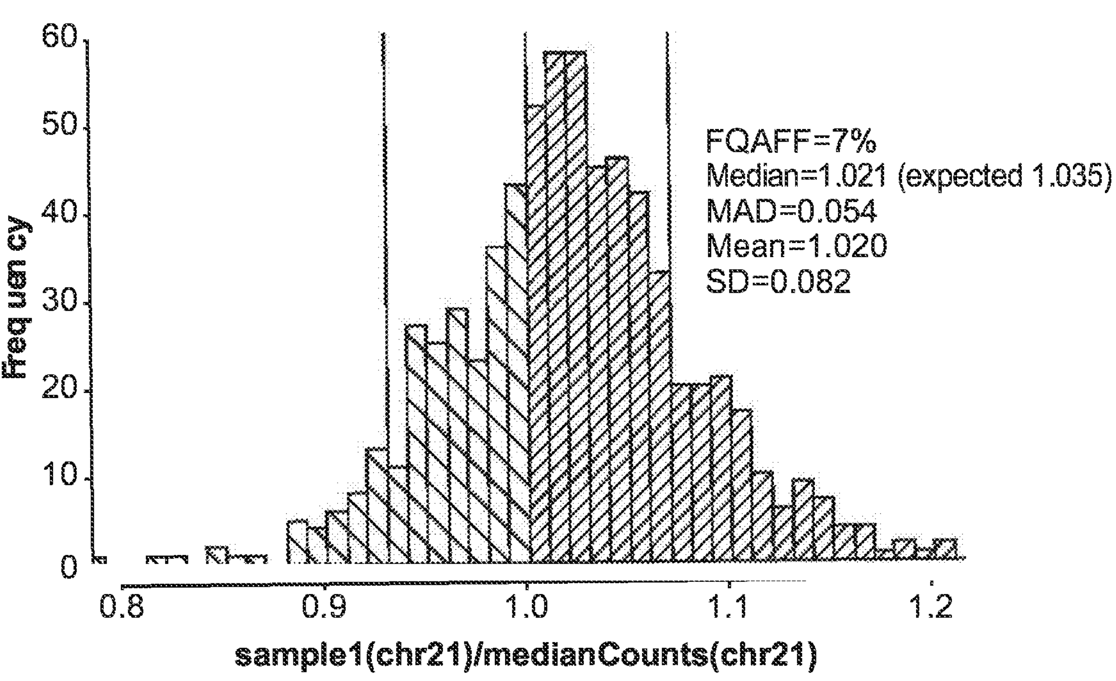
FIG. 27 graphically illustrates a distribution of normalized counts for chromosome 21 in a trisomy sample.

The median of the distribution of normalized counts generally is a point estimate and, as such, often is a less reliable estimate than integral estimates, such as areas under the distribution (e.g., area under the curve. Samples containing high fetal level fractions are not as affected by using a point estimate, however at low fetal fraction values, it becomes difficult to distinguish a truly elevated normalized profile from a euploid sample that has a slightly increased median count due to random errors. A histogram illustrating the median distribution of normalized counts from a trisomy case with a relatively low fetal fraction (e.g., F=about 7%; F(7%)) is shown in FIG. 27. The median of the distribution is 1.021, not far from 1+F/2=1.035. However, the width of the distribution (MAD=0.054, SD=0.082) far exceeds the deviation of the median from the euploid value of 1, precluding any claims that the sample is abnormal. Visual inspection of the distribution suggests an alternative analysis: although the shift of the peak to the right is relatively small, it significantly perturbs the balance between the areas to the left (backward slashed) and to the right (forward slashed) from the euploid expectation of 1. Thus the ratio between the two areas, being an integral estimate, can be advantageous in cases where classification is difficult due to low fetal fraction values. Calculation of the integral estimate for the forward slashed and backward slashed areas under the curve is explained in more detail below.

If a Gaussian distribution of normalized counts is assumed, then $$P(q) = \frac{1}{\sigma\sqrt{2\pi}}\exp\left[-(q-q_0)/(2\sigma^2)\right]. \tag{2}$$

In euploid cases, the expectation for the normalized counts is 1. For trisomy patients, the expectation is $$q_0 = 1 + F/2. \tag{3}$$

Since the reference point for calculating the area ratio is 1, the argument to the exponential function is $z^2$, where $$z = -F/(2\sigma\sqrt{2}). \tag{4}$$

The area to the left of the reference point is $$B = \int_{-\infty}^{1} P(q)dq = \frac{1}{2}[1 + \operatorname{erf}(z)]. \tag{5}$$

The error function erf(z) can be evaluated using its Taylor expansion:

$$\operatorname{erf}(z) = \frac{2}{\sqrt{\pi}}\sum_{n=0}^{\infty}\frac{(-1)^n Z^{2n+1}}{n!(2n+1)}. \tag{6}$$

The area to the right from the reference point is 1-B. The ratio between two areas is therefore $$R = \frac{1-B}{B} = \frac{1-\operatorname{erf}(z)}{1+\operatorname{erf}(z)} = \frac{1-\operatorname{erf}\left[-F/(2\sigma\sqrt{2})\right]}{1+\operatorname{erf}\left[-F/(2\sigma\sqrt{2})\right]}. \tag{7}$$

Figure 28:
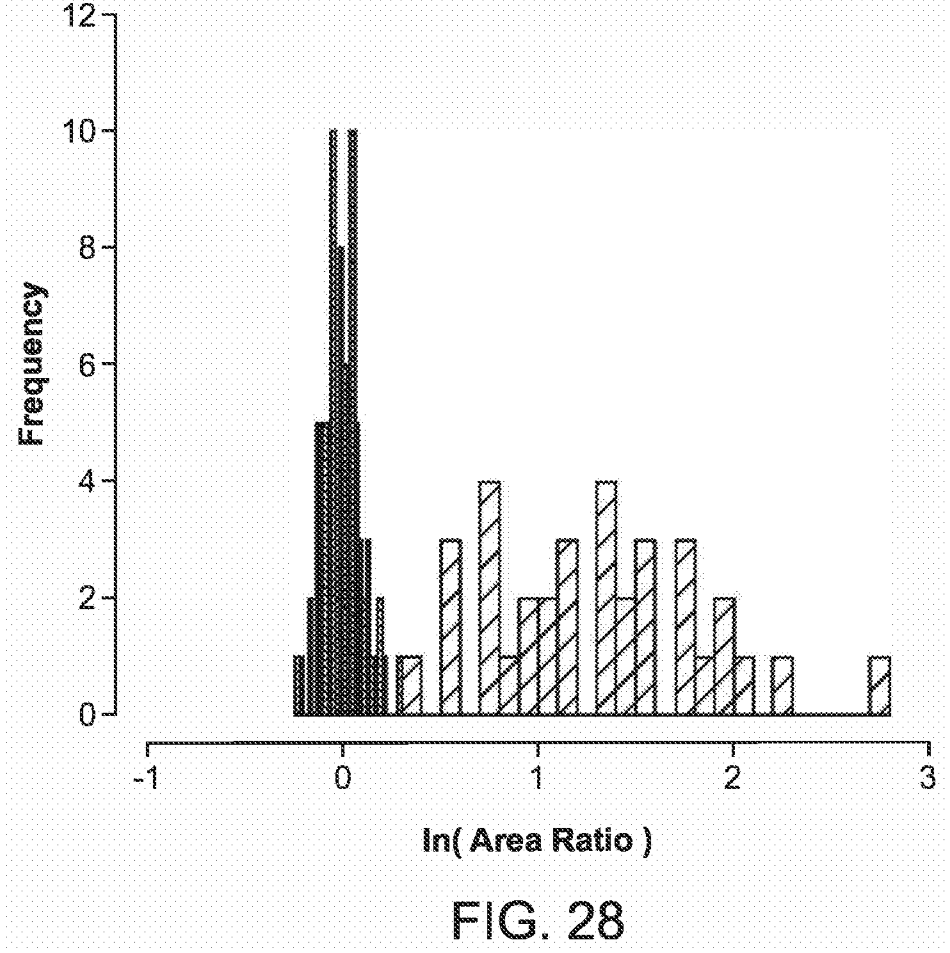
FIG. 28 graphically represents area ratios for various patients. The dotted histogram illustrates chromosome 21 area ratios for 86 euploid patients. The hatched histogram illustrates chromosome 21 area ratios for 35 trisomy 21 patients. The count profiles were normalized with respect to a euploid reference set prior to evaluating area ratios. See Example 1 for experimental details and results.

Error propagation from measured fetal fractions into area ratios R can be estimated by simply replacing F in equation 7 with F−ΔF and F+ΔF. FIG. 28 shows the frequencies of euploid and trisomy area ratios in a set of 480 samples. The overlap between two groups involves trisomy samples with low fetal fractions.

Combined Classification Criteria

Figure 29:
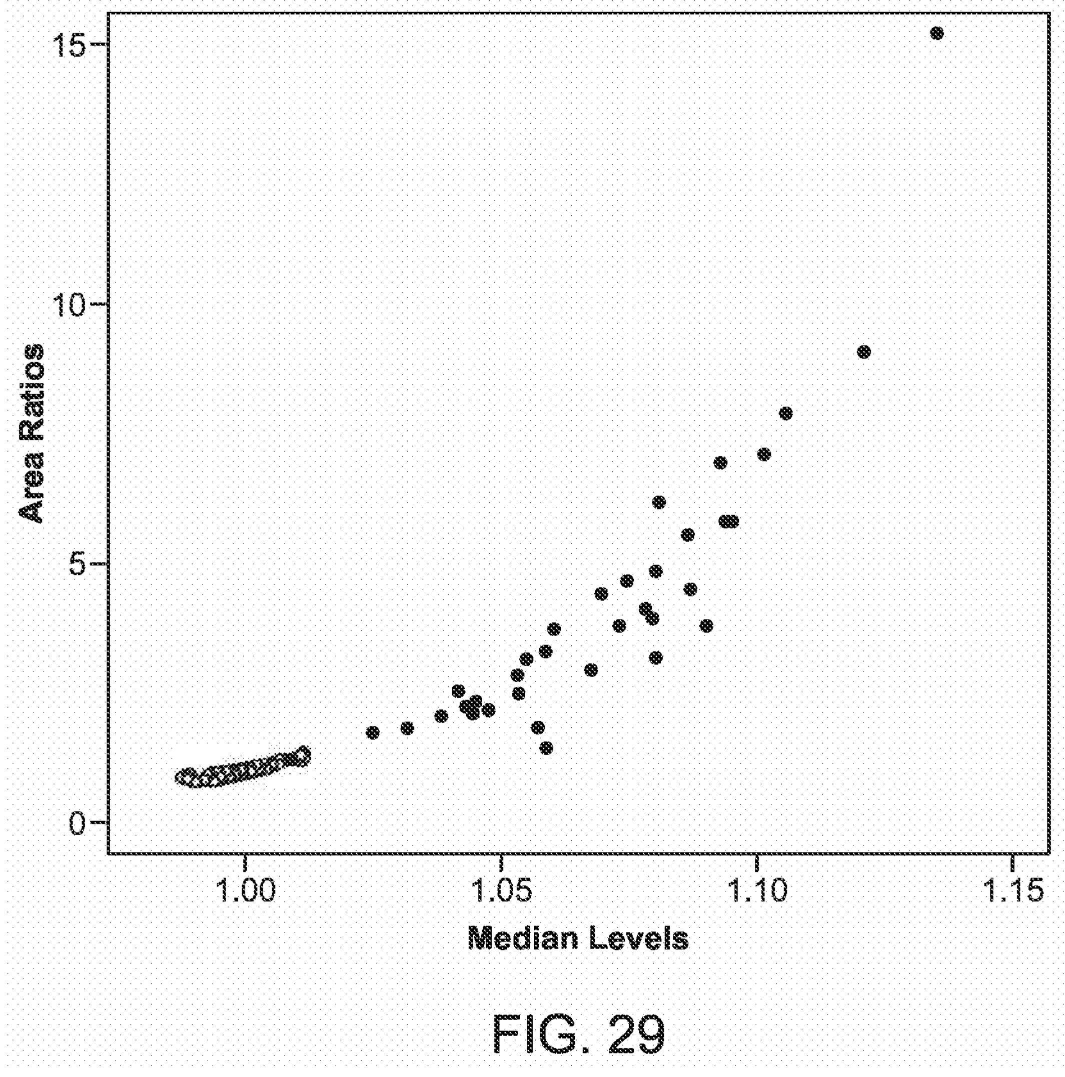
FIG. 29 graphically illustrates area ratio in chromosome 21 plotted against median normalized count elevations. The open circles represent about 86 euploid samples. The filled circles represent about 35 trisomy patients. See Example 1 for experimental details and results.
Figure 30:
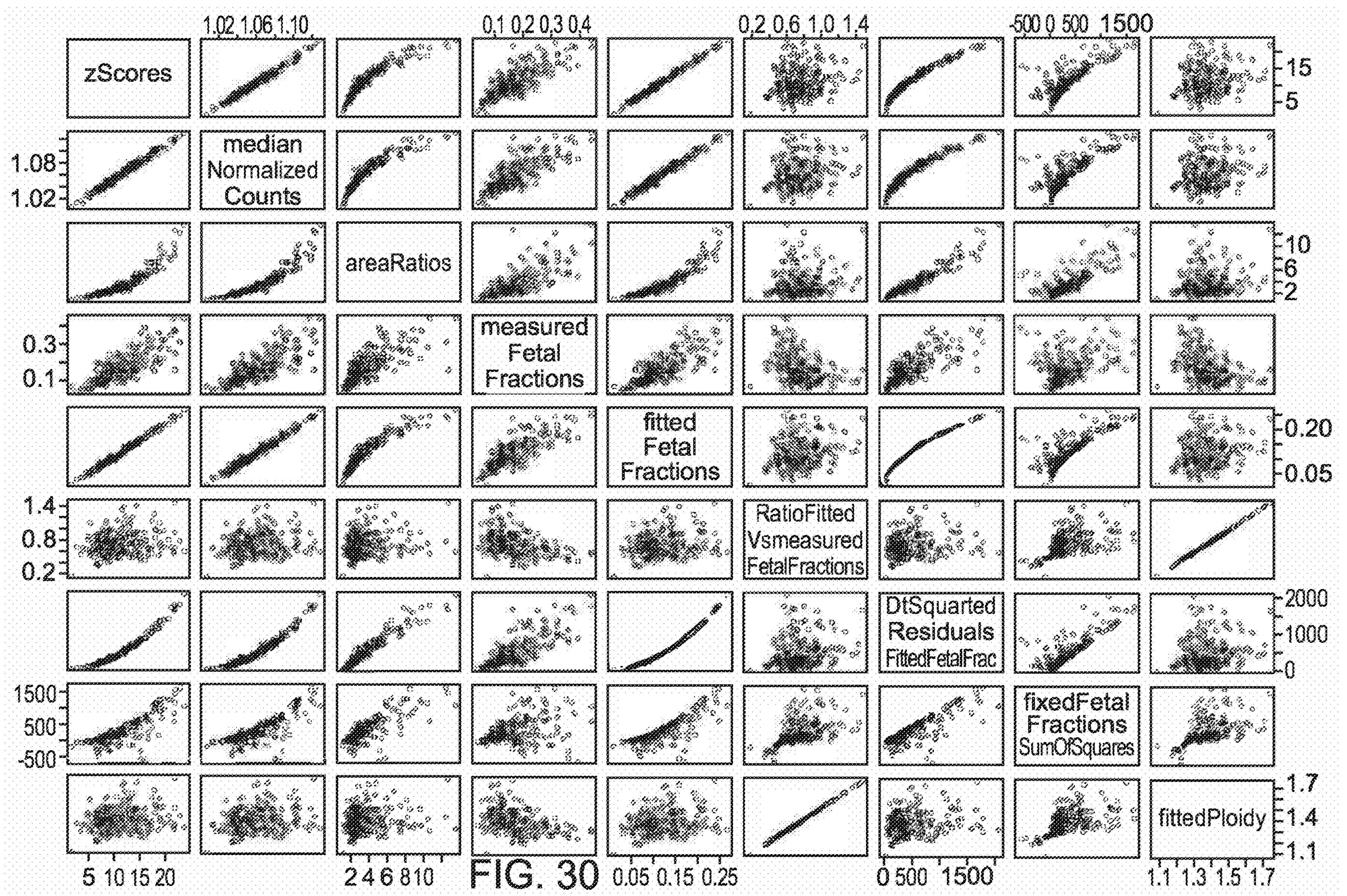
FIG. 30 graphically illustrates relationships among 9 different classification criteria, as evaluated for a set of trisomy patients. The criteria involve Z-scores, median normalized count elevations, area ratios, measured fetal fractions, fitted fetal fractions, the ratio between fitted and measured fetal fractions, sum of squared residuals for fitted fetal fractions, sum of squared residuals with fixed fetal fractions and fixed ploidy, and fitted ploidy values. See Example 1 for experimental details and results.

FIG. 29 illustrates the interrelation and interdependence of median elevations and area ratios, both of which described substantially similar phenomena. Similar relationships connect median elevations and area ratios with other classification criteria, such as Z-scores, fitted fetal fractions, various sums of squared residuals, and Bayesian p-values (see FIG. 30). Individual classification criteria can suffer from ambiguity stemming from partial overlap between euploid and trisomy distributions in gap regions, however, a combination of multiple criteria can reduce or eliminate any ambiguities. Spreading the signal along multiple dimensions can have the same effect as measuring NMR frequencies of different nuclei, in some embodiments, resolving overlapping peaks into well-defined, readily identifiable entities. Since no attempt is made to quantitatively predict any theoretical parameter using mutually correlated descriptors, the cross-correlations observed between different classification criteria do not interfere. Defining a region in multidimensional space that is exclusively populated by euploids, allows classification of any sample that is located outside of the limiting surface of that region. Thus the classification scheme is reduced to a consensus vote for euploidy.

In some embodiments utilizing a combined classification criteria approach, classification criteria described herein can be combined with additional classification criteria known in the art. Certain embodiments can use a subset of the classification criteria listed here. Certain embodiments can mathematically combine (e.g., add, subtract, divide, multiply, and the like) one or more classification criteria among themselves and/or with fetal fraction to derive new classification criteria. Some embodiments can apply principal components analysis to reduce the dimensionality of the multidimensional classification space. Some embodiments can use one or more classification criteria to define the gap between affected and unaffected patients and to classify new data sets. Any combination of classification criteria can be used to define the gap between affected and unaffected patients and to classify new data sets. Non-limiting examples of classification criteria that can be used in combination with other classification criteria to define the gap between affected and unaffected patients and to classify new data sets include: linear discriminant analysis, quadratic discriminant analysis, flexible discriminant analysis, mixture discriminant analysis, k Nearest Neighbors, classification tree, bagging, boosting, neural networks, support vector machines, and/or random forest.

Example 2: Methods for Detection of Genetic Variations Associated with Fetal Aneuploidy Using Measured Fetal Fractions and Bin-Weighted Sums of Squared Residuals Z-value statistics and other statistical analysis of sequence read data frequently are suitable for determining or providing an outcome determinative of the presence or absence of a genetic variation with respect to fetal aneuploidy, however, in some instances it can be useful to include additional analysis based on fetal fraction contribution and ploidy assumptions. When including fetal fraction contribution in a classification scheme, a reference median count profile from a set of known euploids (e.g. euploid pregnancies) generally is utilized for comparison. A reference median count profile can be generated by dividing the entire genome into N bins, where N is the number of bins. Each bin i is assigned two numbers: (i) a reference count $F_i$ and (ii) the uncertainty (e.g., standard deviation or σ) for the bin reference counts.

The following relationship can be utilized to incorporate fetal fraction, maternal ploidy, and median reference counts into a classification scheme for determining the presence or absence of a genetic variation with respect to fetal aneuploidy, $$y_i = (1-F)M_i f_i + FXf_i \tag{8}$$

where $Y_i$ represents the measured counts for a bin in the test sample corresponding to the bin in the median count profile, F represents the fetal fraction, X represents the fetal ploidy, and $M_i$ represents maternal ploidy assigned to each bin. Possible values used for X in equation (8) are: 1 if the fetus is euploid; 3/2, if the fetus is triploid; and, 5/4, if there are twin fetuses and one is affected and one is not. 5/4 is used in the case of twins where one fetus is affected and the other not, because the term F in equation (8) represents total fetal DNA, therefore all fetal DNA must be taken into account. In some embodiments, large deletions and/or duplications in the maternal genome can be accounted for by assigning maternal ploidy, $M_i$, to each bin or genomic section. Maternal ploidy often is assigned as a multiple of ½, and can be estimated using bin-wise normalization, in some embodiments. Because maternal ploidy often is a multiple of ½, maternal ploidy can be readily accounted for, and therefore will not be included in further equations to simplify derivations.

Fetal ploidy can be assessed using any suitable approach. In some embodiments, fetal ploidy can be assessed using equation (8), or derivations thereof. In certain embodiments, fetal ploidy can be classified using one of the following, equation (8) based, non-limiting approaches:

1) Measure fetal fraction F and use the value to form two sums of squared residuals. To calculate the sum of squared residuals, subtract the right hand side (RHS) of equation (8) from its left hand side (LHS), square the difference, and sum over selected genomic bins, or in those embodiments using all bins, sum over all bins. This process is performed to calculate each of the two sums of squared residuals. One sum of square residuals is evaluated with fetal ploidy set to 1 (e.g., X=1) and the other sum of squared residuals is evaluated with fetal ploidy set to 3/2 (e.g., X=3/2). If the fetal test subject is euploid, the difference between the two sums of squared residuals is negative, otherwise the difference is positive.
2) Fix fetal fraction at its measured value and optimize ploidy value. Fetal ploidy generally can take on only 1 of two discrete values, 1 or 3/2, however, the ploidy sometimes can be treated as a continuous function. Linear regression can be used to generate an estimate for ploidy. If the estimate resulting from linear regression analysis is close to 1, the fetal test sample can be classified as euploid. If the estimate is close to 3/2, the fetus can be classified as triploid.
3) Fix fetal ploidy and optimize fetal fraction using linear regression analysis. The fetal fraction can be measured and a restraint term can be included to keep the fitted fetal fraction close to the measured fetal fraction value, with a weighting function that is reciprocally proportional to the estimated error in the measure fetal fraction. Equation (8) is solved twice, once with ploidy set at 3/2, and once for fetal ploidy set to 1. When solving equation (8) with ploidy set to 1, the fetal fraction need not be fitted. A sum of square residuals is formed for each result and the sum of squared residuals subtracted. If the difference is negative, the fetal test subject is euploid. If the difference is positive, the fetal test subject is triploid.

The generalized approaches described in 1), 2) and 3) are described in further detail herein.

Fixed Ploidy, Fixed Fetal Fraction: Sums of Squared Residuals

In some embodiments, fetal aneuploidy can be determined using a model which analyzes two variables, fetal ploidy (e.g., X) and fetal nucleic acid fraction (e.g., fetal fraction; F). In certain embodiments, fetal ploidy can take on discrete values, and in some embodiments, fetal fraction can be a continuum of values. Fetal fraction can be measured, and the measured valued used to generate a result for equation (8), for each possible value for fetal ploidy. Fetal ploidy values that can be used to generate a result for equation (8) include land 3/2 for a single fetus pregnancy, and in the case of a twin fetus pregnancy where one fetus is affected and the other fetus unaffected, 5/4 can be used. The sum of squared residuals obtained for each fetal ploidy value measures the success with which the method reproduces the measurements, in some embodiments. When evaluating equation (8) at X=1, (e.g., euploid assumption), the fetal fraction is canceled out and the following equation results for the sum of squared residuals:

$$\varphi_E = \sum_{i=1}^{N} \frac{1}{\sigma_i^2}(y_i - f_i)^2 = \sum_{i=1}^{N} \frac{y_i^2}{\sigma_i^2} - 2\sum_{i=1}^{N} \frac{y_i f_i}{\sigma_i^2} + \sum_{i=1}^{N} \frac{f_i^2}{\sigma_i^2} = \Xi_{yy} - 2\Xi_{fy} + \Xi_{ff} \tag{9}$$

To simplify equation (9) and subsequent calculations, the following notion is utilized:

$$\Xi_{yy} = \sum_{i=1}^{N} \frac{y_i^2}{\sigma_i^2} \tag{10}$$

-continued $$\Xi_{ff}=\sum_{i=1}^{N}\frac{f_i^2}{\sigma_i^2} \tag{11}$$

$$\Xi_{fy}=\sum_{i=1}^{N}\frac{y_i f_i}{\sigma_i^2} \tag{12}$$

When evaluating equation (8) at X=3/2 (e.g., triploid assumption), the following equation results for the sum of the squared residuals:

$$\varphi_T=\sum_{i=1}^{N}\frac{1}{\sigma_i^2}\left(y_i-f_i-\frac{1}{2}Ff_i\right)^2=\Xi_{yy}-2\Xi_{fy}+\Xi_{ff}+F(\Xi_{ff}-\Xi_{fy})+\frac{1}{4}F^2\Xi_{ff} \tag{13}$$

The difference between equations (9) and (13) forms the functional result (e.g., phi) that can be used to test the null hypothesis (e.g., euploid, X=1) against the alternative hypothesis (e.g., trisomy singleton, X=3/2):

$$\varphi=\varphi_E-\varphi_T=F(\Xi_{fy}-\Xi_{ff})-\frac{1}{4}F^2\Xi_{ff} \tag{14}$$

The profile of phi with respect to F is a parabola defined to the right of the ordinate (since F is greater than or equal to 0). Phi converges to the origin as F approaches zero, regardless of experimental errors and uncertainties in the model parameters.

In some embodiments, the functional Phi is dependent on the measured fetal fraction F with a negative second-order quadratic coefficient (see equation (14)). Phi's dependence on the measured fetal fraction would seem to imply a convex shape for both euploid and triploid cases. If this analysis were correct, trisomy cases would reverse the sign at high F values, however equation (12) depends on F. Combining equations (8) and (14), disregarding maternal ploidy, setting X=3/2 and neglecting experimental errors, the equation for trisomy cases becomes:

$$\Xi_{fy}=\sum_{i=1}^{N}\frac{y_i f_i}{\sigma_i^2}=\sum_{i=1}^{N}\frac{f_i}{\sigma_i^2}[(1-F)f_i+FXf_i]=\left(1+\frac{1}{2}F\right)\sum_{i=1}^{N}\frac{f_i^2}{\sigma_i^2}=\left(1+\frac{1}{2}F\right)\Xi_{ff} \tag{15}$$

The relationship between equations (11) and (12) for triploids holds under ideal circumstances, in the absence of any measurement errors. Combining equations (14) and (15) results in the following expression, which often yields a concave parabola in triploid cases:

$$\varphi=F(\Xi_{fy}-\Xi_{ff})-\frac{1}{4}F^2\,\Xi_{ff}=F\left[\left(1+\frac{1}{2}F\right)\Xi_{ff}-\Xi_{ff}\right]-\frac{1}{4}F^2\,\Xi_{ff}=\frac{1}{4}F^2\,\Xi_{ff}\text{(Trisomy)} \tag{16}$$

For euploids, equations (11) and (12) should have the same value, with the exception of measurement errors, which sometimes yields a convex parabola:

$$\varphi=F(\Xi_{fy}-\Xi_{ff})-\frac{1}{4}F^2\,\Xi_{ff}=-\frac{1}{4}F^2\,\Xi_{ff}\text{(Euploids)} \tag{17}$$

Figure 31:
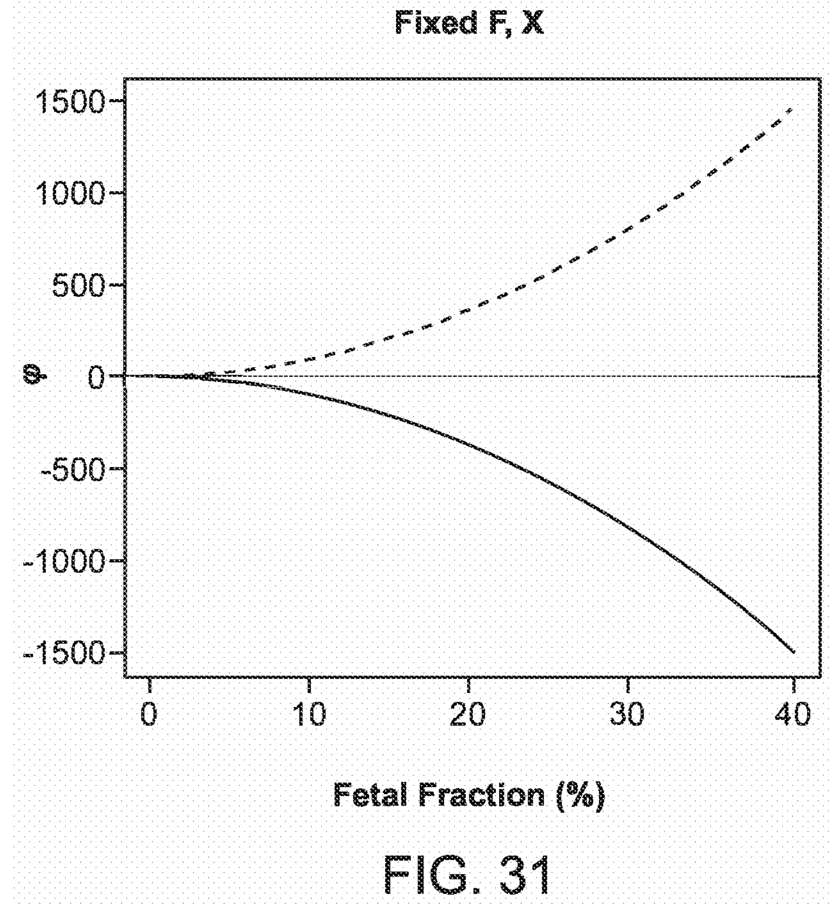
FIG. 31 graphically illustrates simulated functional Phi profiles for trisomy (dashed line) and euploid cases (solid line, bottom).
Figure 32:
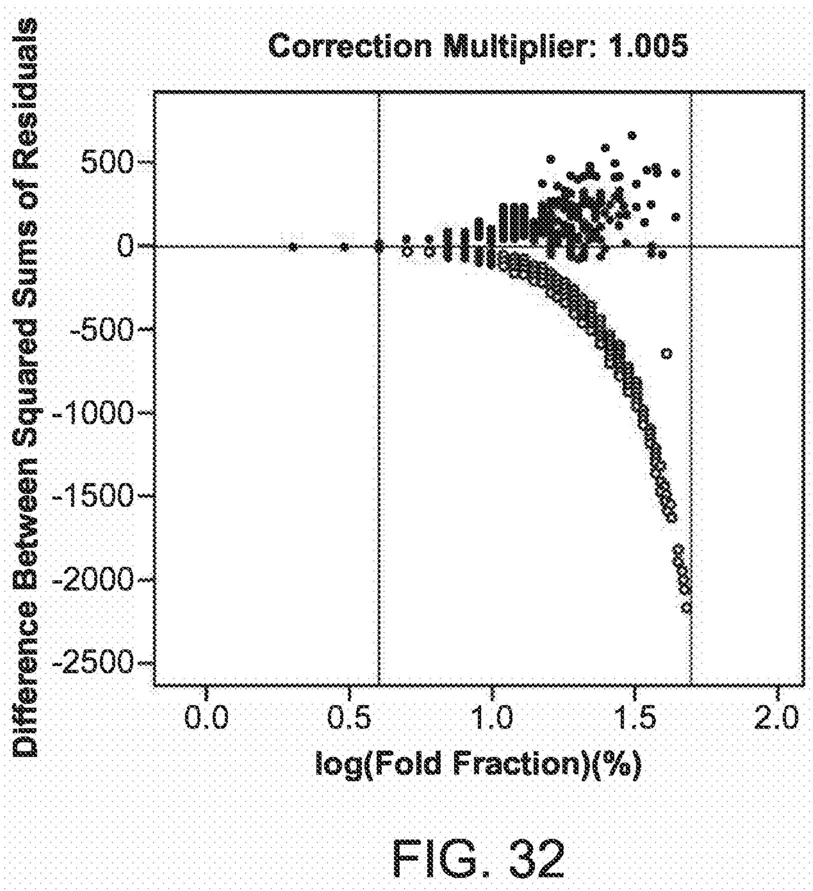
FIG. 32 graphically illustrates functional Phi values derived from measured trisomy (filled circles) and euploid data sets (open circles). See Example 2 for experimental details and results.

Simulated functional phi profiles for typical model parameter values are shown in FIG. 31, for trisomy (dashed line) and euploid (solid line, bottom) cases. FIG. 32 shows an example using actual data. In FIGS. 31 and 32, data points below the abscissa generally represent cases classified as euploids. Data points above the abscissa generally represent cases classified as trisomy 21 (T21) cases. In FIG. 32, the solitary data point in the fourth quadrant (e.g., middle lower quadrant) is a twin pregnancy with one affected fetus. The data set utilized to generate FIG. 32 includes other affected twin samples as well, explaining the spread of T21 data points toward the abscissa.

Equations (9) and (10) often can be interpreted as follows: For triploids, the euploid model sometimes generates larger errors, implying that phi$_E$ (see equation (9)) is greater than phi$_T$ (see equation (13)). As a result, functional phi (see equation (7)) occupies the first quadrant (e.g., upper left quadrant). For euploids, the trisomy model sometimes generates larger errors, the rank of equations (2) and (6) reverses and functional phi (equation (7)) occupies in the fourth quadrant. Thus, in principle, classification of a sample as euploid or triploid sometimes reduces to evaluating the sign of phi.

Figure 33:
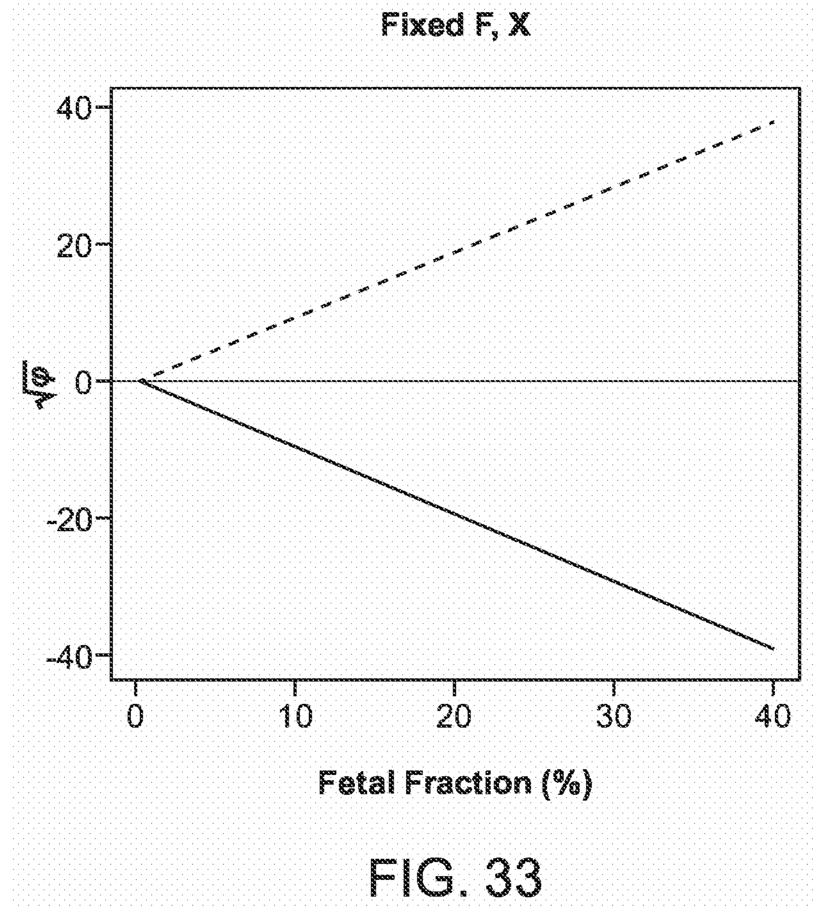
FIG. 33 graphically illustrates linearized sum of squared differences as a function of measured fetal fraction.

In some embodiments, the curvature of the data points shown in FIGS. 31 and 32 can be reduced or eliminated by replacing functional phi (equation (7)) with the square root of functional phi's absolute value, multiplied by its sign. The linear relationship generated with respect to F sometimes can improve separation between triploids and euploids at low fetal fraction values, as shown in FIG. 33. Linearizing the relationship with respect to F sometimes results in increase uncertainty intervals at low fetal fraction (e.g., F) values, therefore, the gains realized from this process are related to making visual inspection of the differences substantially easier; the gray area remains unchanged. Extension of the process to analysis of twin pregnancies is relatively straightforward. The reason used to generate equation (9) implies that in a twin pregnancy with one affected and one normal fetus, functional phi should reduce to zero, plus or minus experimental error, regardless of F. Twin pregnancies generally produce more fetal DNA than single pregnancies.

Optimized Ploidy, Fixed Fetal Fraction: Linear Regression

In certain embodiments, fetal aneuploidy can be determined using a model in which the fetal fraction is fixed at its measured value and ploidy is varied to optimize the sum of squared residuals. In some embodiments, the resulting fitted fetal fraction value can be used to classify a case as trisomy or euploid, depending on whether the value is close to 1, 3/2, or 5/4 in the case of twins. Starting from equation (8), the sum of squared residuals can be formed as follows:

$$\varphi=\sum_{i=1}^{N}\frac{1}{\sigma_i^2}[y_i-(1-F)M_i f_i-FXf_i]_2=\sum_{i=1}^{N}\frac{1}{\sigma_i^2}\left[y_i^2-2(1-F)M_i f_i y_i-2FXf_i y_i+(1-F)^2M_i^2f_i^2+2F(1-F)XM_i f_i^2+F^2X^2f_i^2\right] \tag{18}$$

To minimize phi as a function of X, the first derivative of phi with respect to X is generated, set equal to zero, and the resulting equation solved for X. The resulting expression is presented in equation (19).

$$\frac{1}{2}\left(\frac{d\varphi}{dX}\right) = 0 = XF^2\sum_{i=1}^{N}\frac{f_i^2}{\sigma_i^2} - F\sum_{i=1}^{N}\frac{f_i y_i}{\sigma_i^2} + F(1-F)\sum_{i=1}^{N}\frac{M_i f_i^2}{\sigma_i^2} \tag{19}$$

The optimal ploidy value sometimes is given by the following expression:

$$X = \frac{\sum_{i=1}^{N}\frac{f_i y_i}{\sigma_i^2} - (1-F)\sum_{i=1}^{N}\frac{M_i f_i^2}{\sigma_i^2}}{F\sum_{i=1}^{N}\frac{f_i^2}{\sigma_i^2}} \tag{20}$$

As noted previously, the term for maternal ploidy, $M_i$, can be omitted from further mathematical derivations. The resulting expression for X corresponds to the relatively simple, and often most frequently occurring, special case of when the mother has no deletions or duplications in the chromosome or chromosomes being evaluated. The resulting expression is presented in FIG. 21.

$$X = \frac{\Xi_{fy} - (1-F)\Xi_{ff}}{F\Xi_{ff}} = \frac{\Xi_{fy}}{F\Xi_{ff}} - \frac{1-F}{F} = 1 + \frac{1}{F}\left(\frac{\Xi_{fy}}{\Xi_{ff}} - 1\right) \tag{21}$$

$Xi_{ff}$ and $Xi_{fy}$ are given by equations (11) and (12), respectively. In embodiments where all experimental errors are negligible, solving equation (21) results in a value of 1 for euploids where $Xi_{ff}=Xi_{fy}$. In certain embodiments where all experimental errors are negligible, solving equation (21) results in a value of 3/2 for triploids (see equation (15) for triploid relationship between $Xi_{ff}$ and $Xi_{fy}$.

Optimized Ploidy, Fixed Fetal Fraction: Error Propagation

Optimized ploidy often is inexact due to various sources of error. Three, non-limiting examples of error sources include: reference bin counts $f_i$, measured bin counts $y_i$, and fetal fraction F. The contribution of the non-limiting examples of error will be examined separately.

Errors in Measured Fetal Fractions: Quality of Fitted Fetal Fraction

Figure 34:
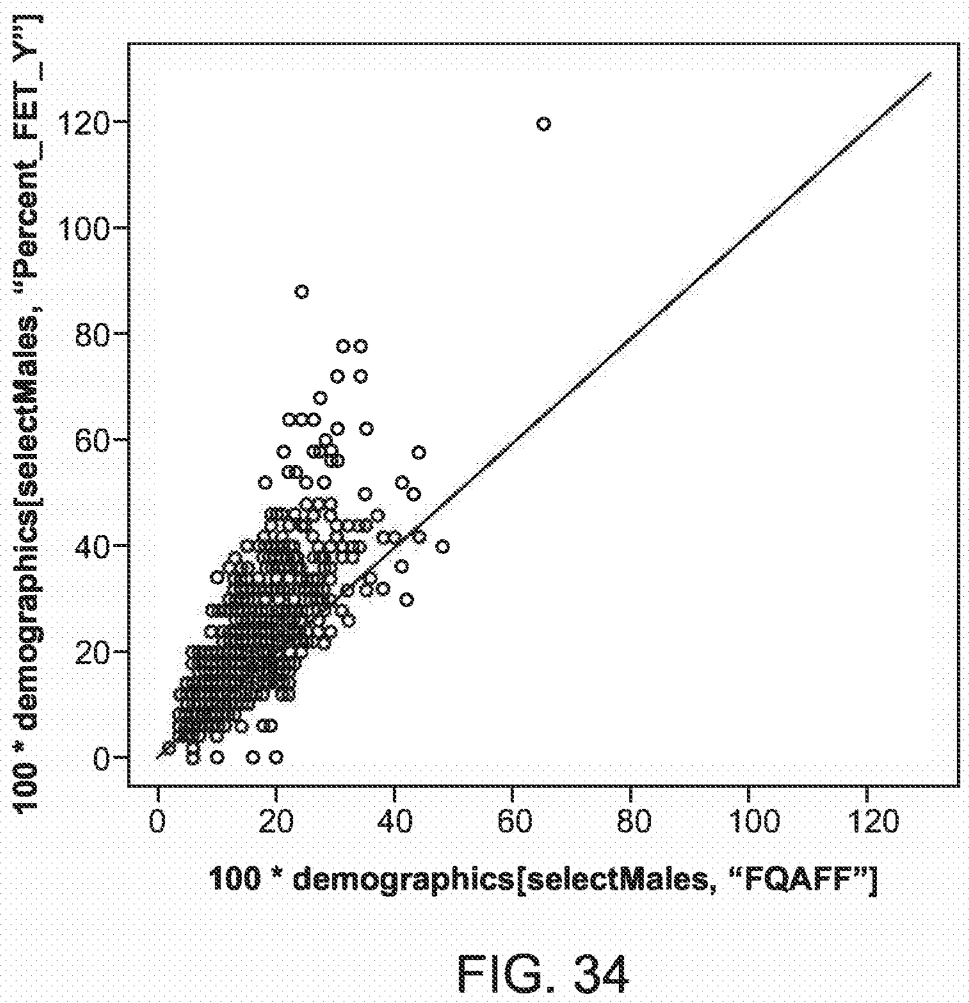
FIG. 34 graphically illustrates fetal fraction estimates based on Y-counts plotted against values obtained from a fetal quantifier assay (e.g., FQA) fetal fraction values.
Figure 35:
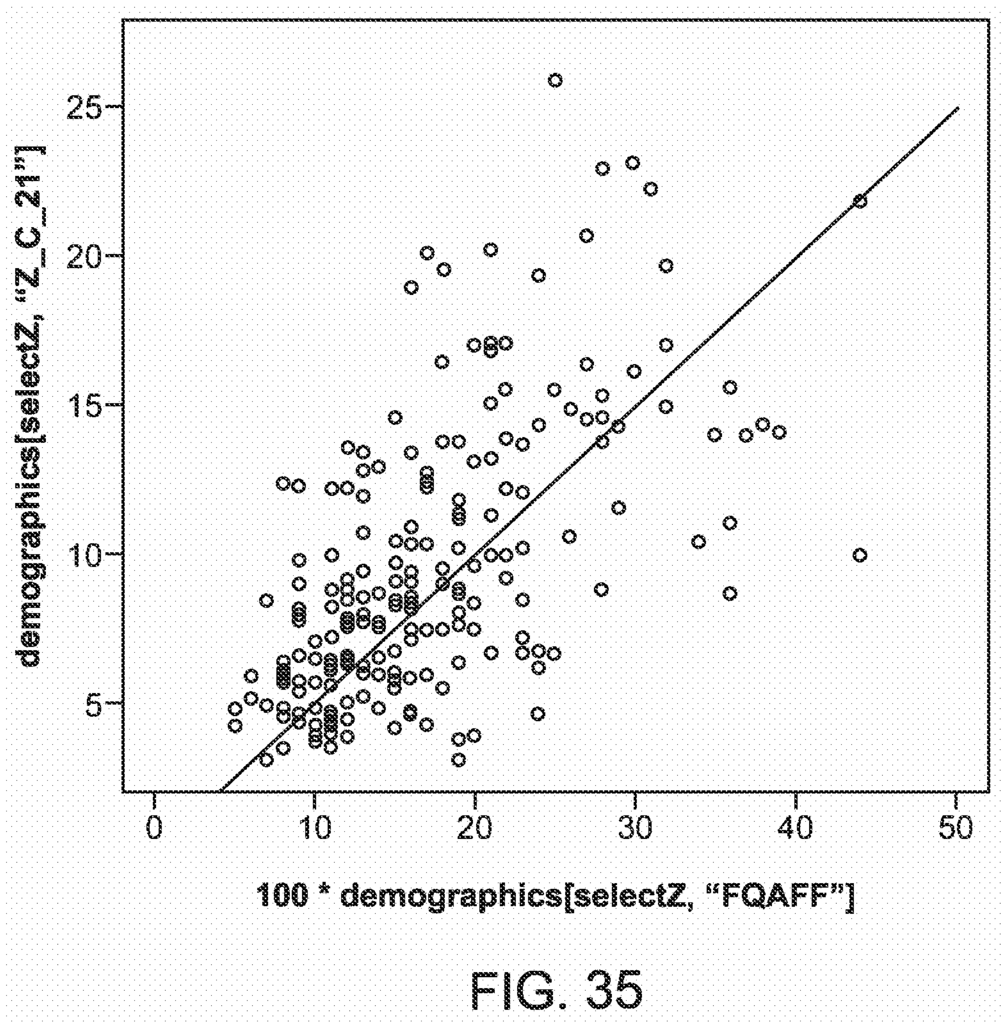
FIG. 35 graphically illustrates Z-values for T21 patients plotted against FQA fetal fraction measurements. For FIG. 33-35 see Example 2 for experimental details and results.
Figure 36:
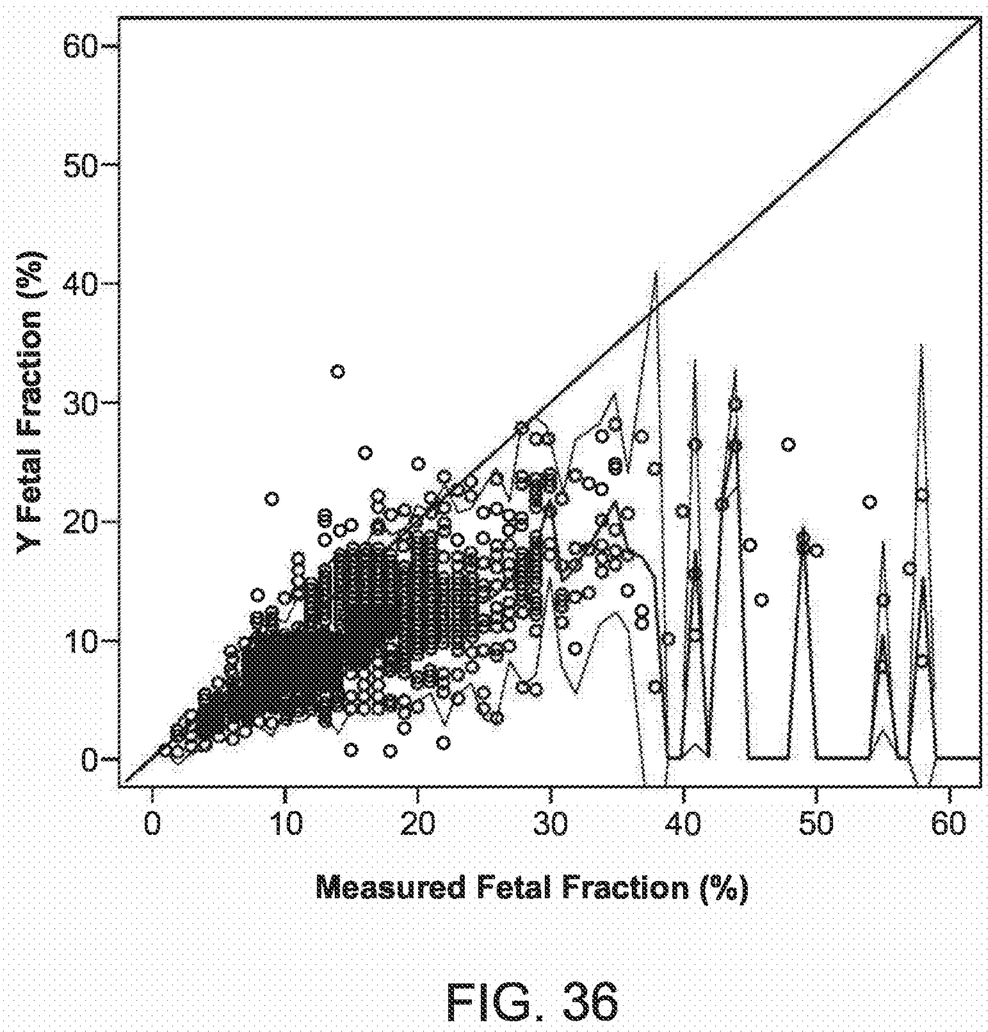
FIG. 36 graphically illustrates fetal fraction estimates based on chromosome Y plotted against measured fetal fractions.
Figure 37:
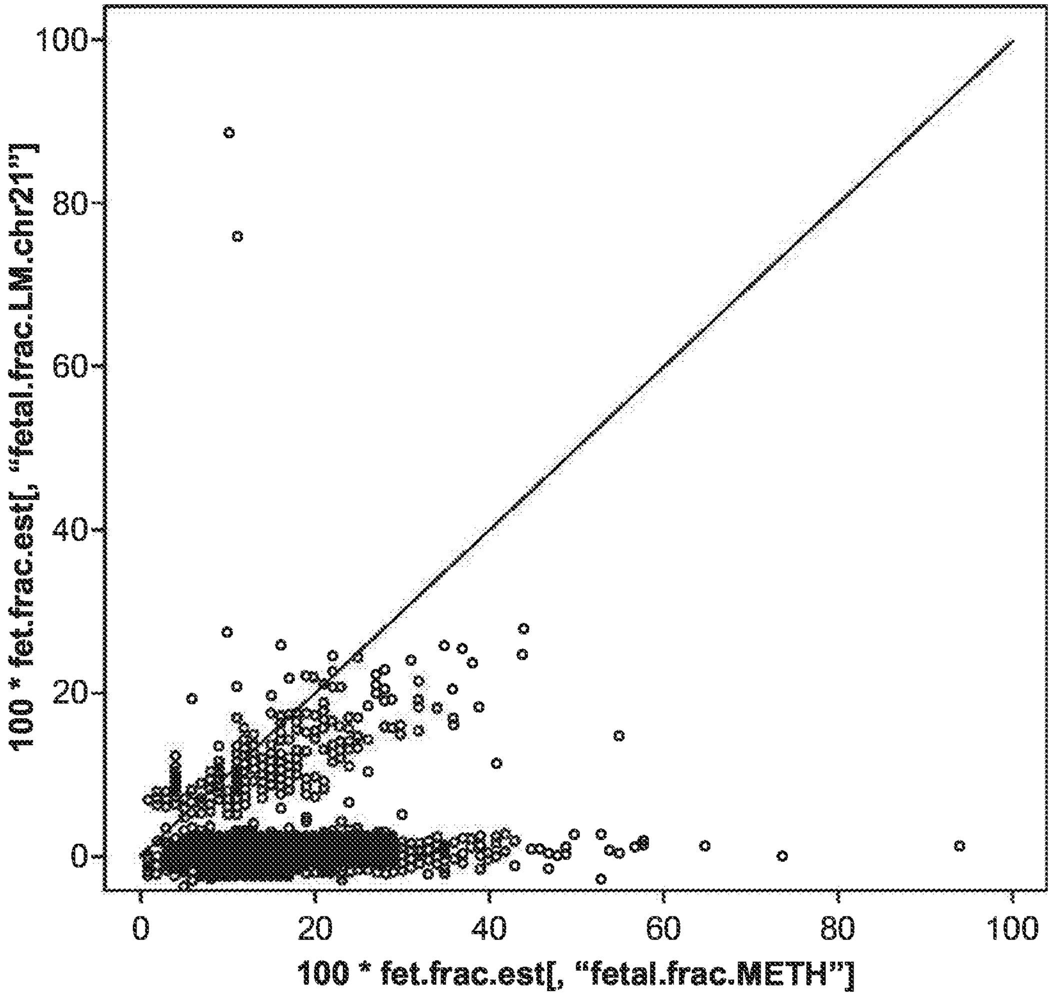
FIG. 37 graphically illustrates fetal fraction estimates based on chromosome 21 (Chr21) plotted against measured fetal fractions.
Figure 38:
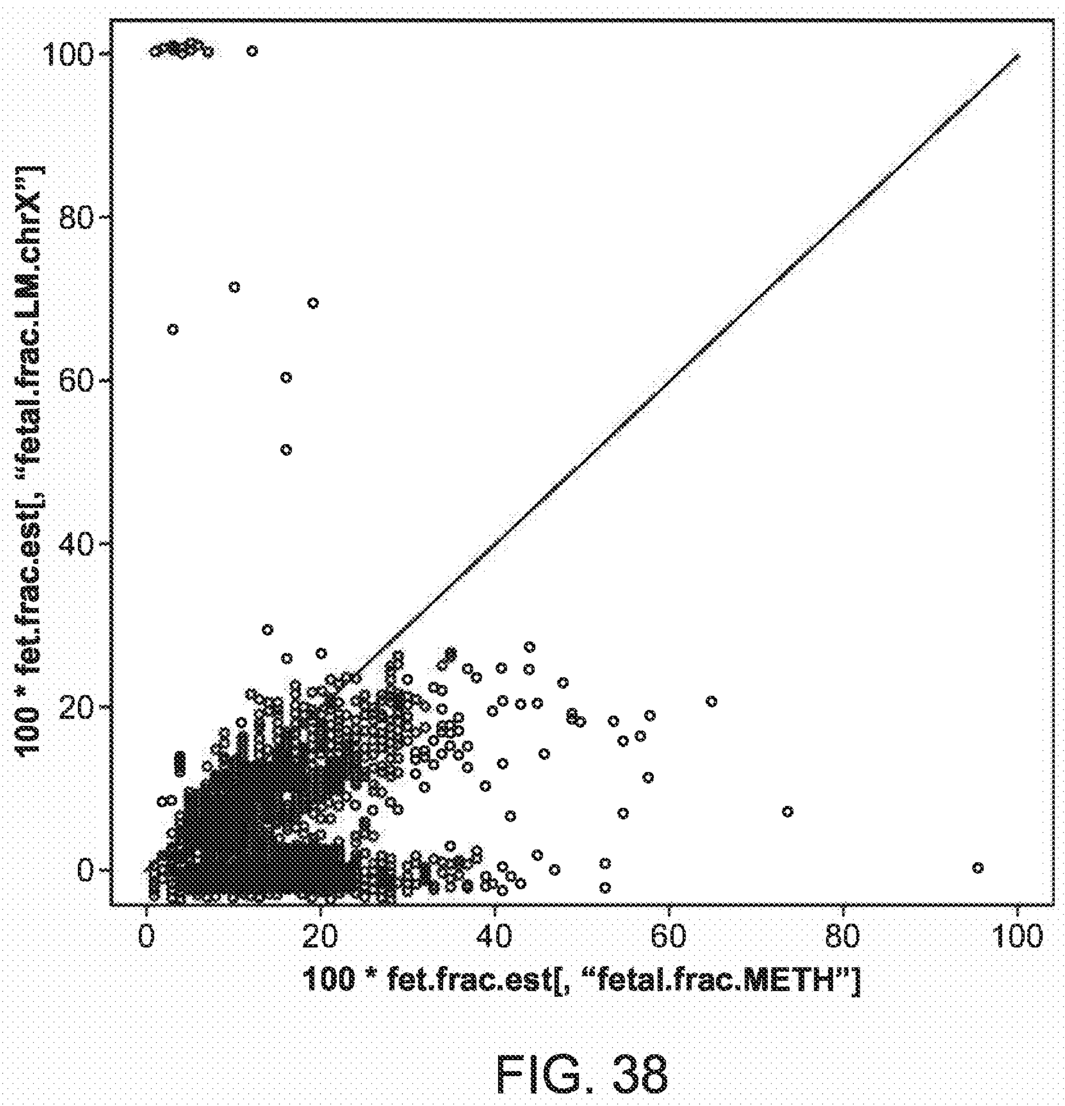
FIG. 38 graphically illustrates fetal fraction estimates derived from chromosome X counts plotted against measured fetal fractions.
Figure 39:
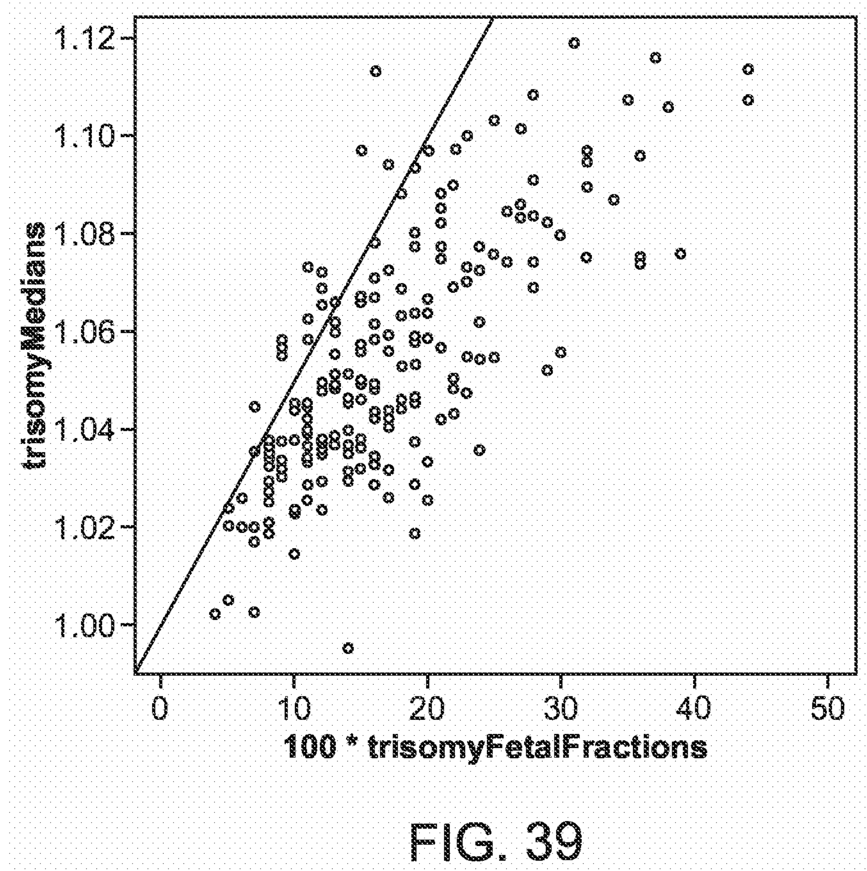
FIG. 39 graphically illustrates medians of normalized bin counts for T21 cases plotted against measured fetal fractions. For FIG. 36-39 see Example 2 for experimental details and results.

Fetal fraction estimates based on the number of sequence tags mapped to the Y chromosome (e.g., Y-counts) sometimes show relatively large deviations with respect to FQA fetal fraction values (see FIG. 34). Z-values for triploid often also exhibit a relatively wide spread around the diagonal shown in FIG. 35. The diagonal line in FIG. 35 represents a theoretically expected increase of the chromosomal representation for chromosome 21 with increasing fetal fraction in trisomy 21 cases. Fetal fraction can be estimated using a suitable method. A non-limiting example of a method that can be utilized to estimate fetal fraction is the fetal quantifier assay (e.g., FQA). Other methods for estimating fetal fraction are known in the art. Various methods utilized to estimate fetal fraction sometimes also show a substantially similar spread around the central diagonal, as shown in FIG. 36-39. In FIG. 36, the deviations are substantially similar (e.g., negative at high $F_0$) to those observed in fitted fetal fraction (see equation (33)). In some embodiments, the slope of the linear approximation to the average chromosome Y (e.g., chromosome Y) fetal fraction (see the middle histogram line in FIG. 36) in the range between 0% and 20% is about ¾. In certain embodiments, the linear approximation for standard deviation (see FIG. 36, upper and lower histogram lines) is about $2/3+F_0/6$. In some embodiments, fetal fraction estimates based on chromosome 21 (e.g., chromosome 21) are substantially similar to those obtained by fitting fetal fractions (see FIG. 37). Another qualitatively similar set of gender-based fetal fraction estimates is shown in FIG. 38. FIG. 39 illustrates the medians of normalized bin counts for T21 cases, which are expected to have a slope whose linear approximation is substantially similar to $1+F_0/2$ (see gray line from origin to the midpoint of the top of the graph in FIG. 39).

FIG. 36-39 share the following common features:

a) slope not equal to 1 (either greater or less than 1, depending on the method, with the exception of Z-values), b) large spread fetal fraction estimation, and c) the extent of spread increases with fetal fraction.

To account for these observations, errors in measured fetal fraction will be modeled using the formula $\Delta F = 2/3 + F_0/6$, in some embodiments.

Errors in Measured Fetal Fractions: Error Propagation from Measured Fetal Fractions to Fitted Ploidy If the assumption is made that $f_i$ and $y_i$ are errorless, to simplify analysis, the measured fetal fraction F is composed of $F_v$ (e.g., the true fetal fraction) and $\Delta F$ (e.g., the error in measured fetal fraction):

$$F = F_V + \Delta F. \tag{22}$$

In some instances, uncertainties in fitted X values originate from errors in measured fetal fraction, F. Optimized values for X are given by equation (21), however the true ploidy value is given by $X_V$, where $X_V=1$ or 3/2. $X_V$ varies discretely, whereas X varies continuously and only accumulates around $X_V$ under favorable conditions (e.g., relatively low error).

Assuming again that $f_i$ and $y_i$ are errorless, equation (8) becomes:

$$y_i = (1-F_V)M_i f_i + F_V X f_i. \tag{23}$$

Combining equations (21) to (23) generates the following relationship between true ploidy $X_V$ and the ploidy estimate X that includes the error $\Delta F$. The relationship also includes the assumption that maternal ploidy equals 1 (e.g., euploid), and the term for maternal ploidy, $M_i$, is replaced by 1.

$$X = 1 + \frac{1}{F_V + \Delta F}\left\{\frac{\sum_{i=1}^{N}\frac{f_i}{\sigma_i^2}[(1-F_V)f_i + F_V X_V f_i]}{\sum_{i=1}^{N}\frac{f_i^2}{\sigma_i^2}} - 1\right\} = 1 + \frac{F_V(X_V - 1)}{F_V + \Delta F} \tag{24}$$

In some instances, the term $X_V-1$ is substantially identical to zero in euploids, and $\Delta F$ does not contribute to errors in X. In triploid cases, the error term does not reduce to zero (e.g., is not substantially identical to zero). Thus, in some embodiments, ploidy estimates can be viewed as a function of the error ΔF:

$$X = g(\Delta F) \tag{25}$$

Figure 40:
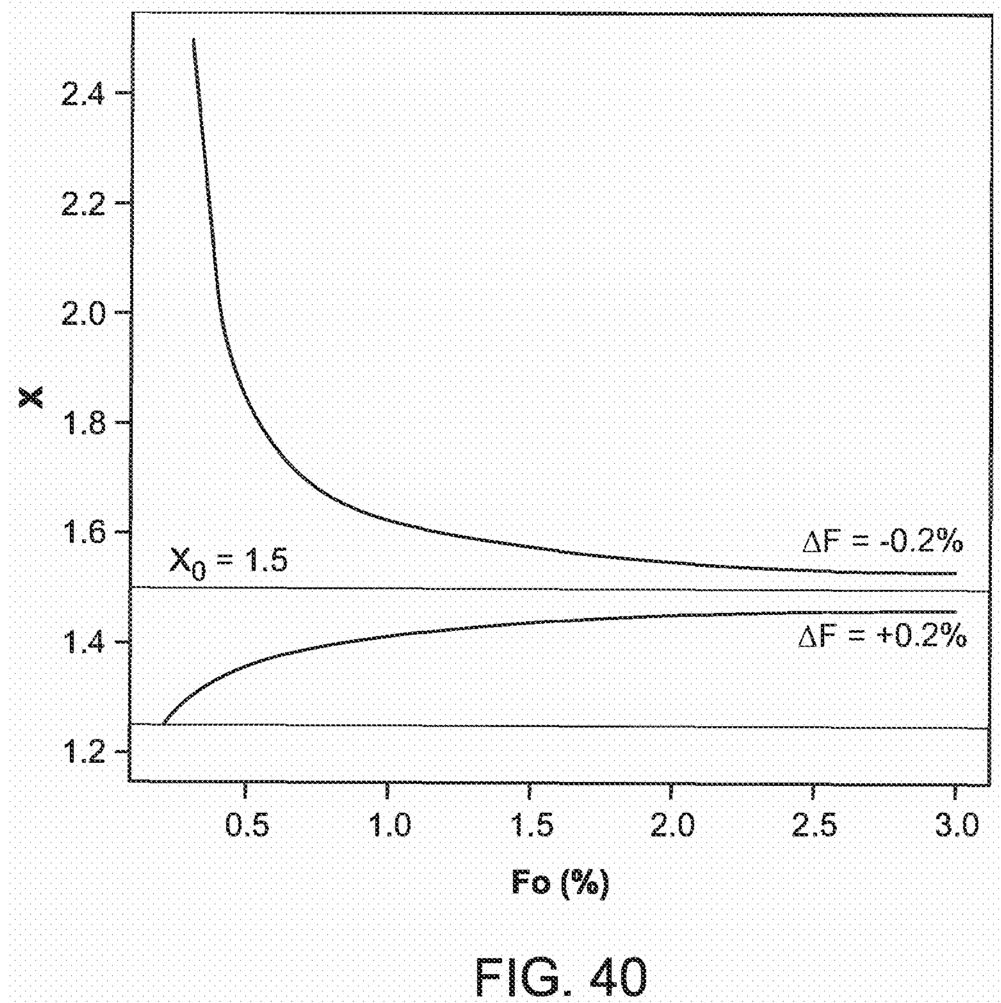
FIG. 40 graphically illustrates simulated profiles of fitted triploid ploidy (e.g., X) as a function of $F_0$ with fixed errors $\Delta F=+/-0.2\%$.
Figure 41:
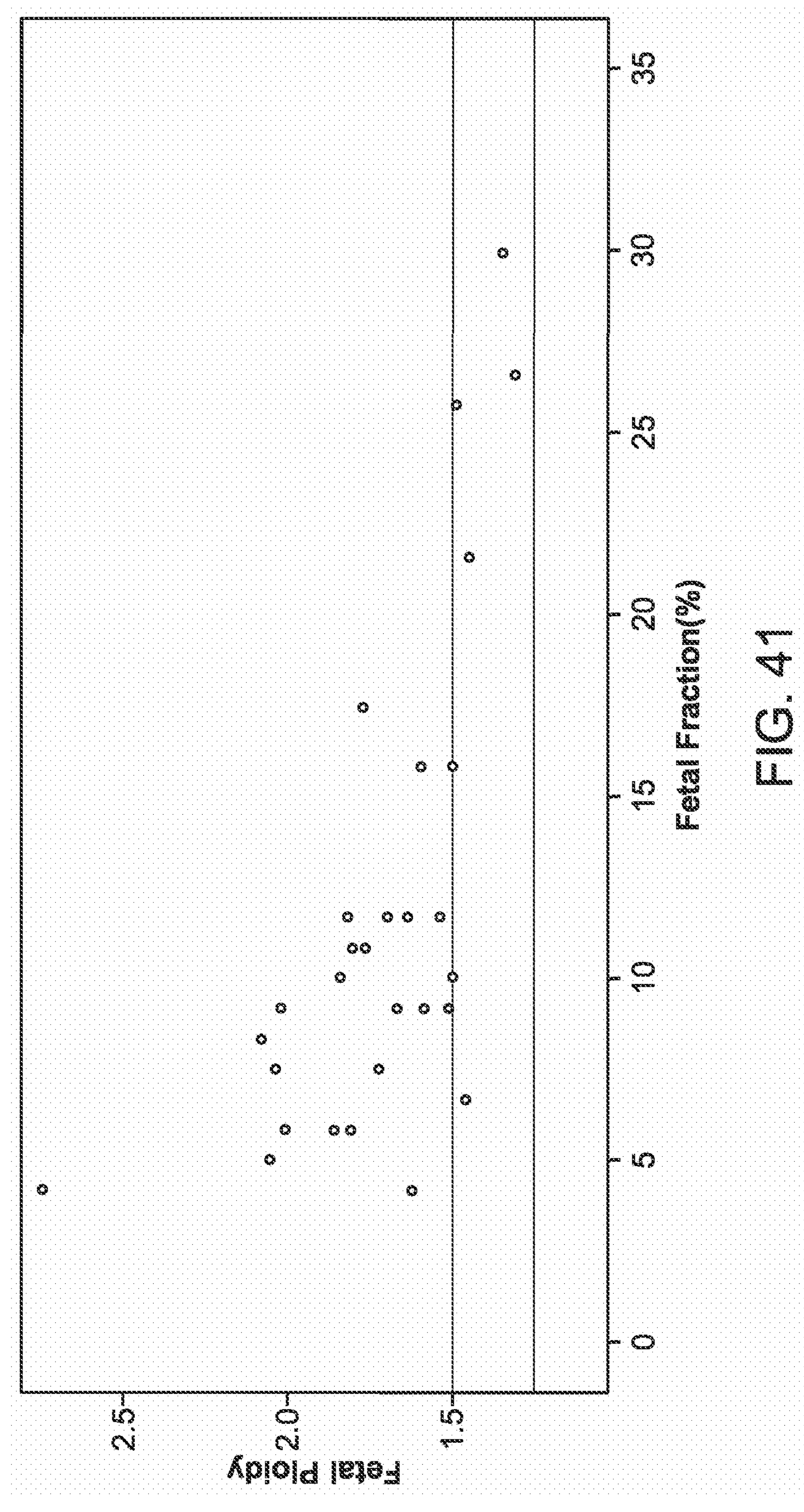
FIG. 41 graphically illustrates fitted triploid ploidy values as a function of measured fetal fractions. For FIGS. 40 and 41 see Example 2 for experimental details and results.

Simulated profiles of fitted triploid X as a function of $F_0$ with fixed errors ΔF=plus or minus 0.2% are shown in FIG. 40. Results obtained using actual data are shown in FIG. 41. The data points generally conform to the asymmetric trumpet-shaped contour predicted by equation (24).

Smaller fetal fractions often are qualitatively associated with larger ploidy errors. Underestimated fetal fraction sometimes is compensated by ploidy overestimates; overestimated fetal fraction often is linked to underestimates in ploidy. The effect frequently is stronger when fetal fraction is underestimated. This is consistent with the asymmetry seen in the graphs presented in FIGS. 40 and 41, (e.g., as F decreases, the growth of the upper branch is substantially faster than the decay of the lower branch). Simulations with different levels of error in F follow the same pattern, with the extent of the deviations from $X_V$ increasing with ΔF.

A probability distribution for X can be used to quantify these observations. In some embodiments, the distribution of ΔF can be used to derive the density function for X using the following expression:

$$f_Y(y) = \left|\frac{1}{g'(g^{-1}(y))}\right| f_X(g^{-1}(y)) \tag{26}$$

where, $f_Y(y)$ is the unknown density function for y=g(x)

$f_X$ (x) is the given density function for x g'(x) is the first derivative of the given function y=g(x)

$g^{-1}(y)$ is the inverse of the given function $g:x=g^{-1}(y)$ $g'(g^{-1}(y))$ is the value of the derivative at the point $g^{-1}(y)$ In equation 26 x is ΔF, y is X (e.g., ploidy estimate), and g(x) is given by equation (24). The derivative is evaluated according to the following expression:

$$\frac{dg}{d\Delta F} = -\frac{F_V(X_V-1)}{(F_V+\Delta F)^2} \tag{27}$$

The inverse $g^{-1}(y)$ can be obtained from equation (24), in some embodiments:

$$\Delta F = \frac{F_V(X_V-X)}{X-1} \tag{28}$$

If the error in F conforms to a Gaussian distribution, $f_x(x)$ in equation (26) can be replaced with the following expression:

$$P(\Delta F) = \frac{\exp[-(\Delta F)^2/(2\sigma^2)]}{\sigma\sqrt{2\pi}} \tag{29}$$

In certain embodiments, combining equations (26) to (29) results in a probability distribution for X at different levels of ΔF, as shown in FIG. 42.

Figure 43:
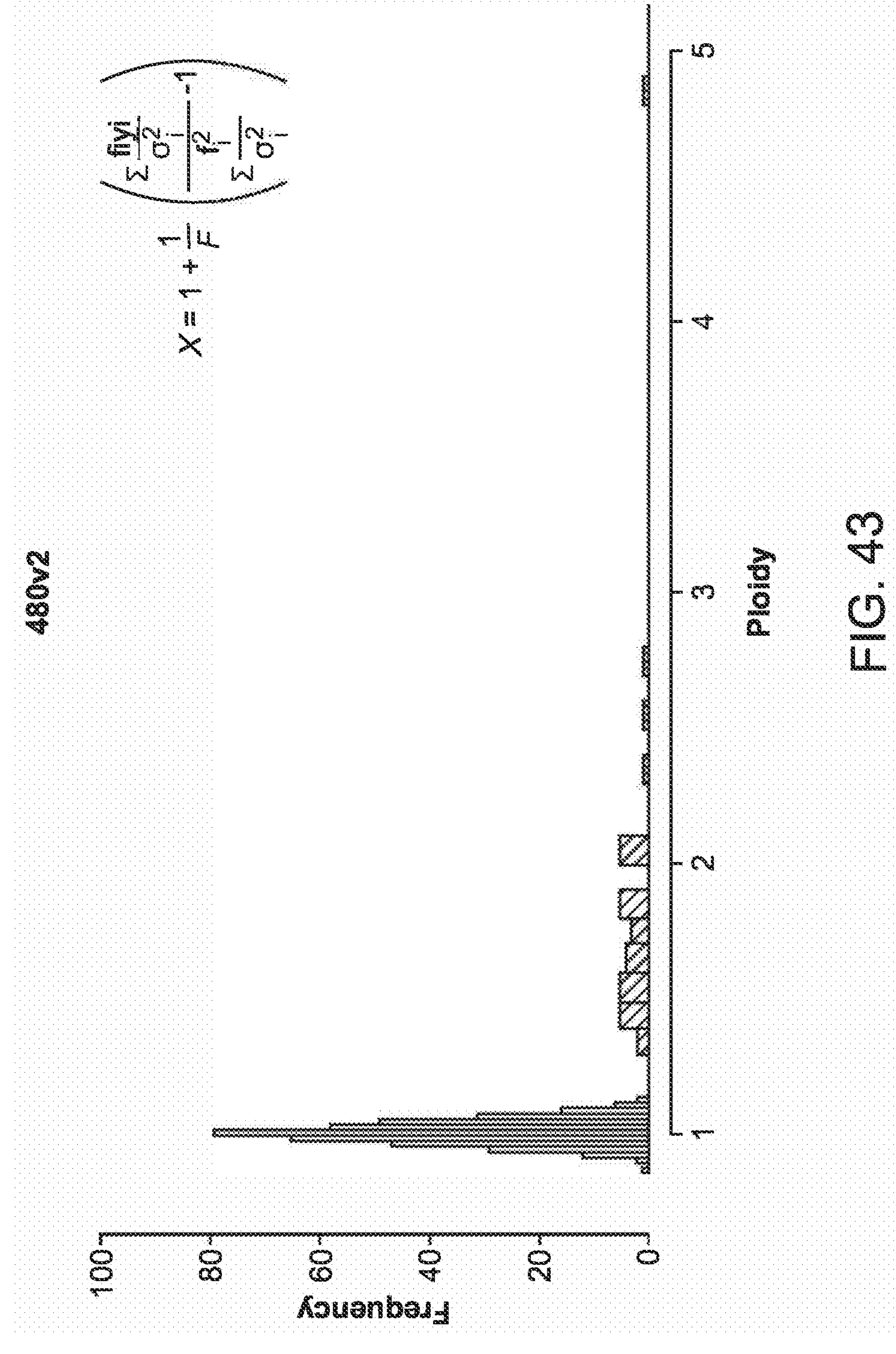
FIG. 43 graphically illustrates euploid and trisomy distributions of fitted ploidy values for a data set derived from patient samples.

In some instances, a bias towards higher ploidy values, which sometimes are prominent at high levels of errors in F, often is reflected in the asymmetric shape of the density function: a relatively long, slowly decaying tail to the right of the right vertical line, vertically in line with X, along the X axis, as shown in FIG. 42, panels A-C. In some embodiments, for any value of ΔF, the area under the probability density function to the left of the right vertical line ($X_V$=3/2) equals the area to the right of the right vertical line. That is, one half of all fitted ploidy values often are overestimates, while the other half of all fitted ploidy values sometimes are underestimates. In some instances, the bias generally only concerns the extent of errors in X, not the prevalence of one or the other direction. The median of the distribution remains equal to $X_V$, in some embodiments. FIG. 43 illustrates euploid and trisomy distributions obtained for actual data. Uncertainties in measured fetal fraction values sometimes explain part of the variance seen in the fitted ploidy values for triploids, however errors in estimated X values for euploids often require examining error propagation from bin counts.

Fixed Ploidy, Optimized Fetal Fraction: Linear Regression

A continuously varying fetal fraction often can be optimized while keeping ploidy fixed at one of its possible values (e.g., 1 for euploids, 3/2 for singleton triploids, 5/4 for twin triploids), as opposed to fitting ploidy that often can take on a limited number of known discrete values. In embodiments in which the measured fetal fraction ($F_0$) is known, optimization of the fetal fraction can be restrained such that the fitted F remains close to $F_0$, within experimental error (e.g., ΔF). In some instances, the observed (e.g., measured) fetal fraction $F_0$, sometimes differs from fetal fraction, $F_V$, described in equations (22) to (28). A robust error propagation analysis should be able to distinguish between $F_0$ and $F_V$. To simplify the following derivations, difference between the observed fetal fraction and the true fetal fraction will be ignored.

Equation (8) is presented below in a rearranged format that also omits the maternal ploidy term (e.g., $M_i$).

$$y_i = F(X-1)f_i + f_i \tag{30}$$

A functional term that needs to be minimized is defined as follows, in some embodiments:

$$\begin{aligned}\varphi(F) &= \frac{(F-F_0)^2}{(\Delta F)^2} + \sum_{i=1}^{N}\frac{1}{\sigma_i^2}[y_i - F(X-1)f_i - f_i]^2 = \\ &\frac{(F-F_0)^2}{(\Delta F)^2} + \sum_{i=1}^{N}\frac{1}{\sigma_i^2}\big[y_i^2 + F^2(X-1)^2 f_i^2 + f_i^2 - \\ &2F(X-1)f_i y_i - 2f_i y_i + 2F(X-1)f_i^2\big] = \frac{(F-F_0)^2}{(\Delta F)^2} + \\ &F^2(X-1)^2\sum_{i=1}^{N}\frac{f_i^2}{\sigma_i^2} + 2F(X-1)\sum_{i=1}^{N}\frac{f_i^2 - f_i y_i}{\sigma_i^2} + \sum_{i=1}^{N}\frac{(y_i-f_i)^2}{\sigma_i^2}\end{aligned} \tag{31}$$

When equation (31) is evaluated for euploids (e.g., X=1), the term $$\frac{(F-F_0)^2}{(\Delta F)^2}$$

often depends on F, thus fitted F frequently equals $F_0$. In some instances, when equation (24) is evaluated for euploids, the equation sometimes reduces to $$\sum_{i=1}^{N} \frac{(y_i - f_i)^2}{\sigma_i^2}.$$

When equation (24) is evaluated for singleton trisomy cases (e.g., X=3/2), the coefficients that multiply F contain both fetal fraction measurements and bin counts, therefore the optimized value for F often depends on both parameters. The first derivative of equation (24) with respect to F reduces to zero in some instances:

$$\frac{1}{2}\left(\frac{d\varphi}{dF}\right) = 0 = \frac{(F - F_0)}{(\Delta F)^2} + F(X-1)^2 \sum_{i=1}^{N} \frac{f_i^2}{\sigma_i^2} + (X-1) \sum_{i=1}^{N} \frac{f_i^2 - f_i y_i}{\sigma_i^2} \tag{32}$$

In some embodiments, replacing X=3/2 and solving equation (32) for F yields an optimized value for F:

$$F = \frac{F_0 + \frac{(\Delta F)^2}{2} \sum_{i=1}^{N} \frac{1}{\sigma_i^2}(f_i y_i - f_i^2)}{1 + \frac{(\Delta F)^2}{4} \sum_{i=1}^{N} f_i^2/\sigma_i^2}. \tag{33}$$

To simplify further calculations and/or derivations, the following auxiliary variables will be utilized:

$$S_0 = \frac{(\Delta F)^2}{4} \sum_{i=1}^{N} \frac{1}{\sigma_i^2} \tag{34}$$

$$S_f = \frac{(\Delta F)^2}{4} \sum_{i=1}^{N} \frac{f_i}{\sigma_i^2} \tag{35}$$

$$S_y = \frac{(\Delta F)^2}{4} \sum_{i=1}^{N} \frac{y_i}{\sigma_i^2} \tag{36}$$

$$S_{yy} = \frac{(\Delta F)^2}{4} \sum_{i=1}^{N} \frac{y_i^2}{\sigma_i^2} \tag{37}$$

$$S_{ff} = \frac{(\Delta F)^2}{4} \sum_{i=1}^{N} \frac{f_i^2}{\sigma_i^2} \tag{38}$$

$$S_{fy} = \frac{(\Delta F)^2}{4} \sum_{i=1}^{N} \frac{y_i f_i}{\sigma_i^2} \tag{39}$$

Utilizing the auxiliary variables, the optimized fetal fraction for X=3/2 for equation (33) then reduces to:

$$F = \frac{F_0 + 2S_{fy} - 2S_{ff}}{1 + S_{ff}} \tag{40}$$

Fitted F often is linearly proportional to the measured value $F_0$, but sometimes is not necessarily equal to $F_0$. The ratio between errors in fetal fraction measurements and uncertainties in bin counts determines the relative weight given to the measured $F_0$ versus individual bins, in some embodiments. In some instances, the larger the error ΔF, the stronger the influence that bin counts will exert on the fitted F. Alternatively, small ΔF generally implies that the fitted value F will be dominated by $F_0$. In some embodiments, if a data set comes from a trisomy sample, and all errors are negligible, equation (40) reduces to identity between F and $F_0$. By way of mathematic proof, using fetal ploidy set to X=3/2, and assuming that $F_0$ (observed) and $F_V$ (true) have the same value, equation (30) becomes:

$$y_i = \frac{1}{2} = F_0 f_i + f_i \tag{41}$$

The assumption that $F_0$ and $F_V$ generally is an acceptable assumption for the sake of the qualitative analysis presented herein. Combing equations (39) and (41) yields $$S_{fy} = \frac{(\Delta F)^2}{4} \sum_{i=1}^{N} \frac{y_i f_i}{\sigma_i^2} = \frac{(\Delta F)^2}{4} \sum_{i=1}^{N} \frac{\left(\frac{1}{2}F_0 f_i + f_i\right) f_i}{\sigma_i^2} = \left(\frac{1}{2}F_0 + 1\right) S_{ff} \tag{42}$$

Combining equations (40) and (42) results in identity between $F_0$ and $F_V$:

$$F = \frac{F_0 + 2S_{fy} - 2S_{ff}}{1 + S_{ff}} = \frac{F_0 + 2\left(\frac{1}{2}F_0 + 1\right) S_{ff} - 2S_{ff}}{1 + S_{ff}} = \frac{F_0(1 + S_{ff})}{1 + S_{ff}} \equiv F_0 \ QED \tag{43}$$

To further illustrate the theoretical model, if the true ploidy is 1 (e.g., euploid) but the ploidy value use in equation (40) is set to X=3/2 (e.g., triploid singleton), the resulting fitted F does not equal $F_0$, nor does it reduce to zero, and the following expression generally is true:

$$y_i = f_i \Rightarrow S_{fy} = \frac{(\Delta F)^2}{4} \sum_{i=1}^{N} \frac{y_i f_i}{\sigma_i^2} = \frac{(\Delta F)^2}{4} \sum_{i=1}^{N} \frac{f_i^2}{\sigma_i^2} = S_{ff} \Rightarrow F = \frac{F_0 + 2S_{fy} - 2S_{ff}}{1 + S_{ff}} = \frac{F_0}{1 + S_{ff}}. \tag{44}$$

Figure 44:
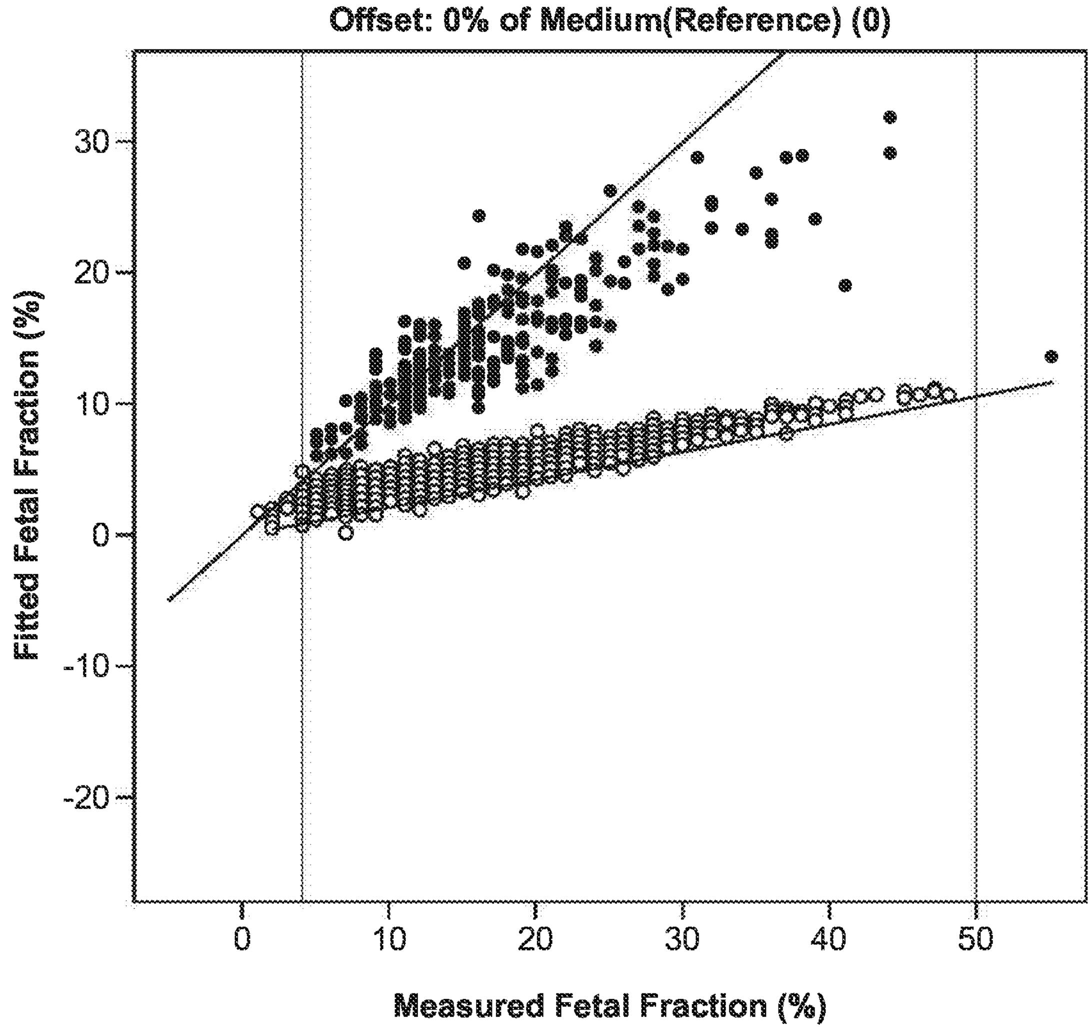
FIG. 44 graphically illustrates fitted fetal fractions plotted against measured fetal fractions. For FIGS. 43 and 44 see Example 2 for experimental details and results.

Thus, application of triploid equations when testing a euploid case generally results in a non-zero fitted F that is proportional to $F_0$ with a coefficient of proportionality between 0 and 1 (exclusive), depending on reference bin counts and associated uncertainties (cf. equation (38)), in certain embodiments. A similar analysis is shown in FIG. 44, using actual data from 86 know euploids as reference. The slope of the straight line from equation (44) is close to 20 degrees, as shown in FIG. 44.

The solitary data point between euploid and T21 cases (e.g., measured fetal fraction approximately 40%, fitted fraction approximately 20%) represents a T21 twin. When a constant ΔF is assumed the euploid branch of the graph shown in FIG. 44 generally is sloped, however when $\Delta F = 2/3 + F_0/6$ is used the euploid branch of the graph often becomes substantially horizontal, as described herein in the section entitled “Fixed ploidy, optimized fetal fraction, error propagation: fitted fetal fractions”.

Fixed Ploidy, Optimized Fetal Fraction: Sums of Squared Residuals

In some instances for euploid cases, were fitted F for equation (32) equals $F_0$ and X=1, the sum of square residuals for a euploid model follows from equation (31):

$$\varphi_E = \sum_{i=1}^{N} \frac{1}{\sigma_i^2}(y_i - f_i)^2 = \Xi_{yy} - 2\Xi_{fy} + \Xi_{ff} \tag{45}$$

which is substantially the same result as equation (9). In certain instances for euploid cases, equation (40) can be combined into equation (31). The resulting mathematical expression quadratically depends on $F_0$, in some embodiments. In certain embodiments, classification of a genetic variation is performed by subtracting the triploid sum of squared residuals from the euploid sum of squared residuals. The result of the classification obtained by subtracting the triploid sum of squared residuals from the euploid sum of squared residuals also frequently depends on $F_0$:

$$\begin{aligned}
\varphi_E - \varphi_T = & \frac{-1}{(\Delta F)^2}\left[\left(\frac{F_0 + 2S_{fy} - 2S_{ff}}{1 \prime S_{ff}} - F_0\right)^2 + \right. \\
& \left(\frac{F_0 + 2S_{fy} - 2S_{ff}}{1 + S_{ff}}\right)^2 \frac{(\Delta F)^2}{4} \sum_{i=1}^{N} \frac{f_i^2}{\sigma_i^2} + \\
& \left.\left(\frac{F_0 + 2S_{fy} - 2S_{ff}}{1 + S_{ff}}\right)(\Delta F)^2 \sum_{i=1}^{N} \frac{f_i^2 - f_i y_i}{\sigma_i^2}\right] \\
= & \frac{-1}{(\Delta F)^2}\left[\left(\frac{F_0 + 2S_{fy} - 2S_{ff}}{1 + S_{ff}} - F_0\right)^2 + \right. \\
& \left(\frac{F_0 + 2S_{fy} - 2S_{ff}}{1 + S_{ff}}\right)^2 S_{ff} + \\
& \left. 4\left(\frac{F_0 + 2S_{fy} - 2S_{ff}}{1 + S_{ff}}\right)(S_{ff} - S_{fy})\right] \\
= & \frac{-[(2S_{fy} - 2S_{ff} - F_0 S_{ff})^2 + (F_0 + 2S_{fy} - 2S_{ff})^2 S_{ff} + 4(F_0 + 2S_{fy} - 2S_{ff})(1 + S_{ff})(S_{ff} - S_{fy})]}{(\Delta F)^2(1 + S_{ff})^2} \\
= & \frac{-1}{(\Delta F)^2(1 + S_{ff})^2}\left[\left(4S_{fy}^2 + 4S_{ff}^2 + F_0^2 S_{ff}^2 - \right.\right. \\
& \left. 8S_{fy}S_{ff} - 4F_0 S_{fy} S_{ff} + 4F_0 S_{ff}^2\right) + \\
& \left(F_0^2 S_{ff} + 4S_{fy}^2 S_{ff} + 4S_{ff}^3 + \right. \\
& \left. 4F_0 S_{fy} S_{ff} - 4F_0 S_{ff}^2 - 8S_{fy} S_{ff}^2\right) + \\
& \left(4F_0 S_{ff} + 8S_{fy} S_{ff} - 8S_{ff}^2 - \right. \\
& 4F_0 S_{fy} - 8F_0 S_{fy} + 8S_{fy} S_{ff} + \\
& 4F_0 S_{ff}^2 + 8S_{fy} S_{ff}^2 - 8S_{ff}^3 - 4F_0 S_{fy} S_{ff} - \\
& \left.\left. 8S_{fy}^2 S_{ff} + 8S_{fy} S_{ff}^2\right)\right] \\
= & \frac{-1}{(\Delta F)^2(1 + S_{ff})}\left[F_0^2 S_{ff} + 4F_0(S_{ff} - S_{fy}) - 4(S_{ff} - S_{fy})^2\right]
\end{aligned} \tag{46}$$

The term $S_{fy}$ generally depends on fetal fraction, as also seen for equation (14). The dependence of $\varphi_E - \varphi_T$ on the measured fetal fraction can be analyzed by accounting for the fetal fraction, in some embodiments. The fetal fraction often can be accounted for by assuming that measured fetal fraction $F_0$ equals true fetal fraction $F_V$. In some embodiments, if the sample's karyotype is euploid, $S_{fy}$ and $S_{ff}$ have the same values (e.g., with the exception of experimental errors). As a result, the difference between the two sums of squared residuals often reduces to:

$$\varphi_E - \varphi_T = \frac{-F_0^2 S_{ff}}{(\Delta F)^2(1 + S_{ff})} \text{ (Euploids)} \tag{47}$$

In certain embodiments, if the sample's karyotype is triploid, equations (41) and (42) can be combined with equation (46), yielding:

$$\varphi_E - \varphi_T = \frac{F_0^2 S_{ff}}{(\Delta F)^2} \text{ (Triploids)} \tag{48}$$

Thus, if the difference of $\varphi_E - \varphi_T'$ is positive, the fetus is triploid, in some embodiments, and in certain embodiments, if the difference is negative, the fetus is unaffected. The graphical representation for the positive or negative result frequently is a parabola; concave for triploids and convex for euploids. Both branches tend towards zero as $F_0$ decreases, with experimental error having little effect on the shape of the graph. Neither branch has a substantially linear or free term, but the second order coefficients differ in size in addition to having different signs, in many instances. With $\Delta$F approximately 2%, the value of the term $S_{ff}$ is close to 3.7, using the reference counts and uncertainties extracted from the 86 euploid set (see FIG. 45).

Figure 45:
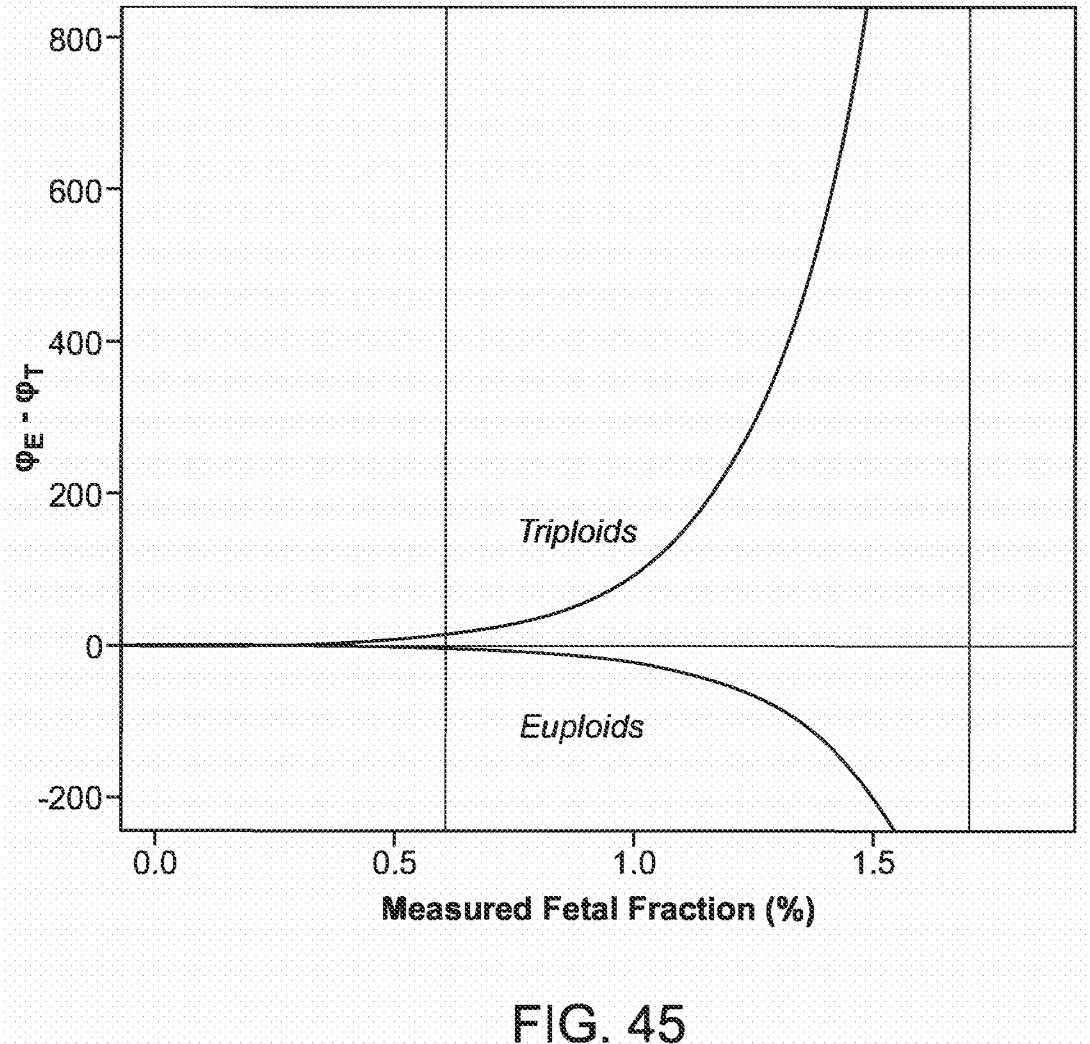
FIG. 45 schematically illustrates the predicted difference between euploid and trisomy sums of squared residuals for fitted fetal fraction as a function of the measured fetal fraction.
Figure 46:
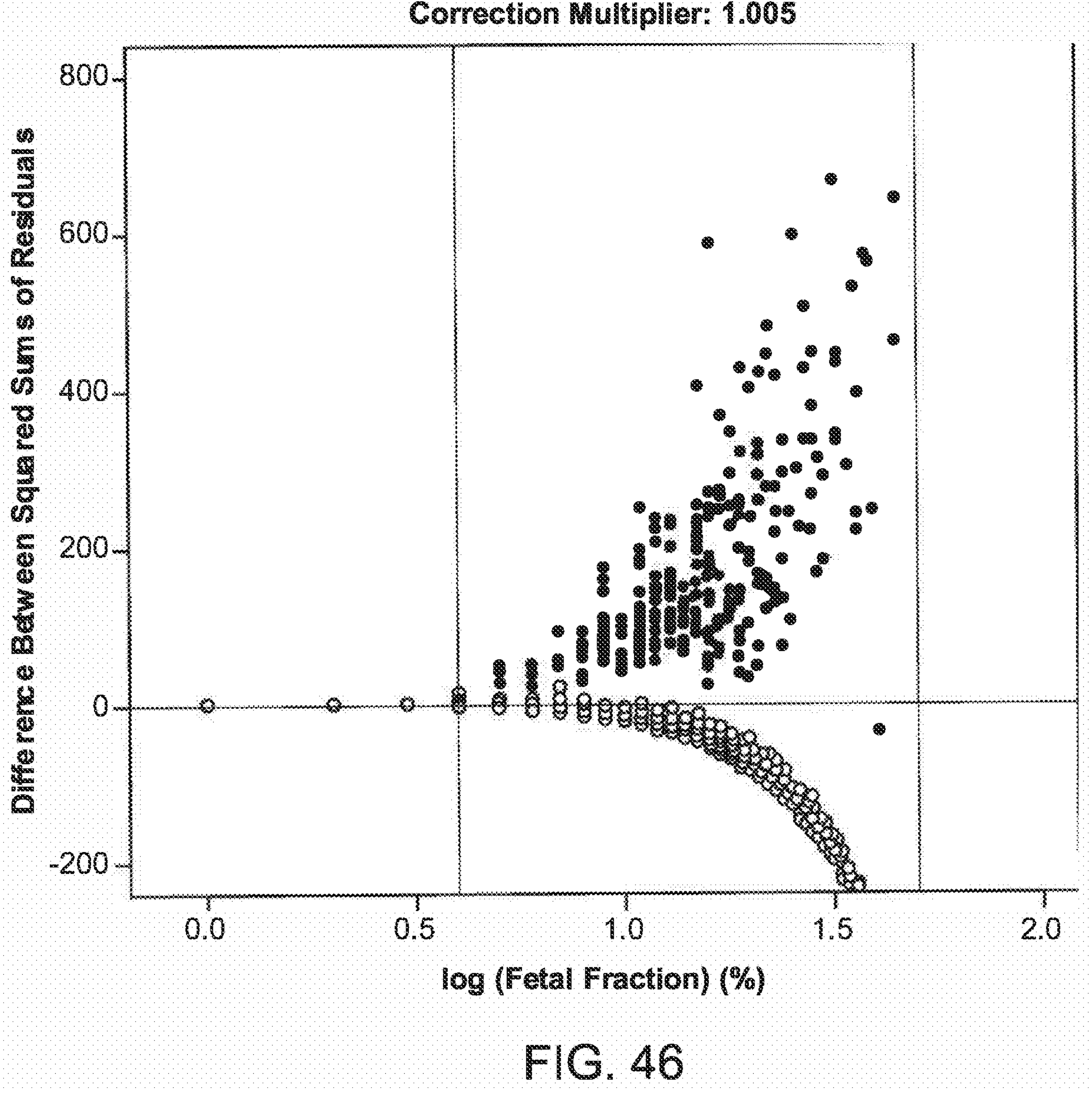
FIG. 46 graphically illustrates the difference between euploid and trisomy sums of squared residuals as a function of the measured fetal fraction using a data set derived from patient samples. The data points are obtained by fitting fetal fraction values assuming fixed uncertainties in fetal fraction measurements.

In the example shown in FIG. 45, the two branches often are asymmetric due to the different coefficients multiplying the square of the measured fetal fraction in equations (47) and (48). The triploid (e.g., positive) branch increases relatively quickly, becoming distinguishable from zero substantially earlier than the euploid branch. FIG. 46, obtained using a real data set, confirms the qualitative results shown in FIG. 45. In FIG. 46 the solitary dark gray point in the fourth quadrant (e.g., lower middle quadrant) is an affected twin. In the data set used to generate FIG. 46, both the euploid and T21 branches of the graph show curvature because both show quadratic dependence on $F_0$ from the trisomy version of equation (31)

Figure 47:
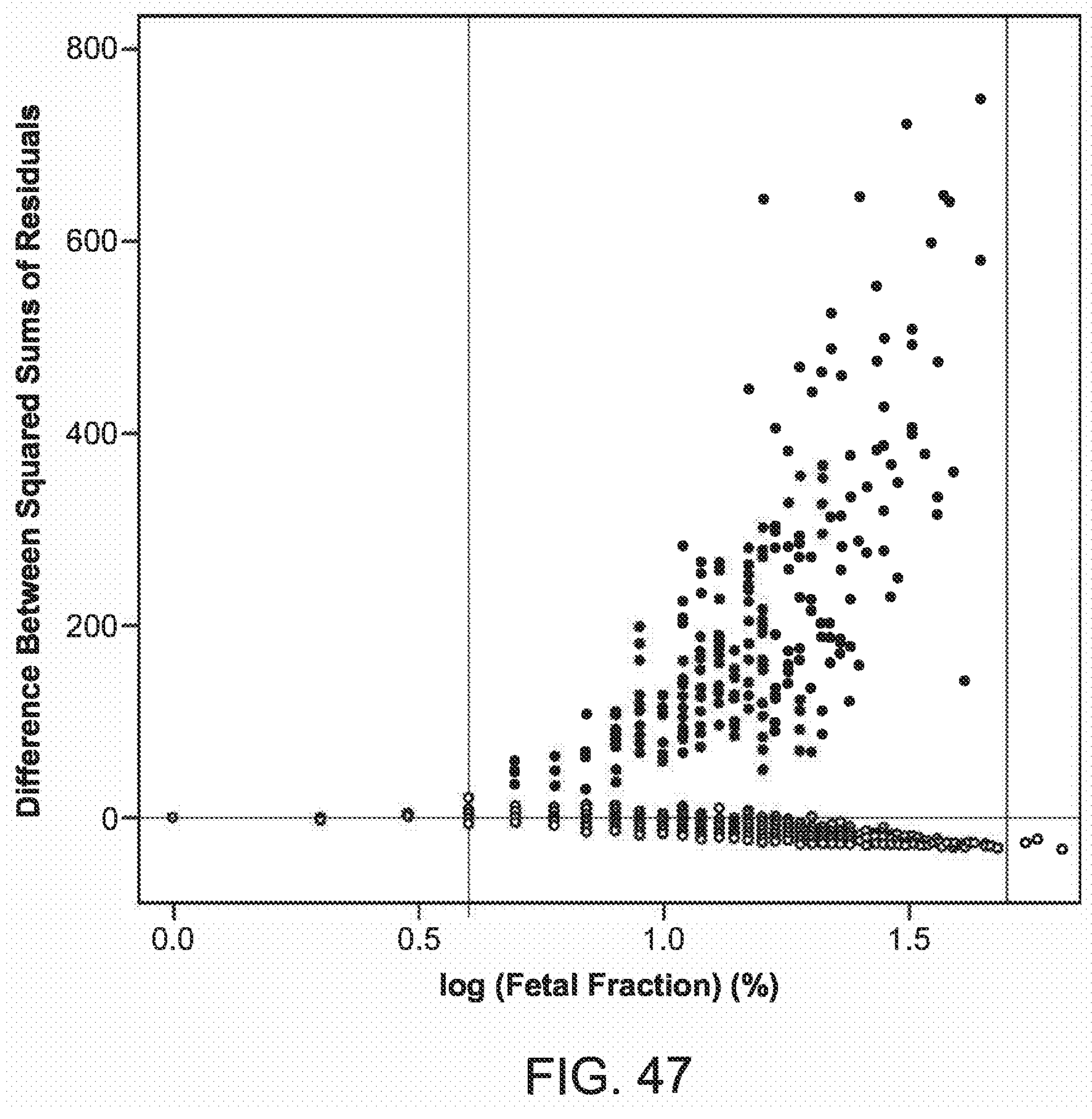
FIG. 47 graphically illustrates the difference between euploid and trisomy sums of squared residuals as a function of the measured fetal fraction. The data points are obtained by fitting fetal fraction values assuming that uncertainties in fetal fraction measurements are proportional to fetal fractions: $\Delta F=\frac{2}{3}+F_0/6$. For FIG. 45-47 see Example 2 for experimental details and results.

In some embodiments, both branches of the graph can be linearized to facilitate visual inspection. The value of the linearization often is conditioned on the error propagation analysis. The results presented in FIGS. 45 and 46 were based on the assumption that the error in measured fetal fractions is uniform the entire range of fetal fractions. However, the assumption is not always the case. In some instances, the more realistic assumption, based on a linear relationship between error $\Delta$F and measured fetal fraction $F_0$($\Delta F = 2/3 + F_0/6$), produces the results presented in FIG. 47. In FIG. 47, the euploid branch is substantially flat, almost constant (e.g., the parabolic character is substantially lost), however, the trisomy branch remains parabolic. The three light gray points interspersed in the dark gray points of the trisomy branch represent data from twins. Twin data sometimes are elevated relative to the fixed error model.

Classification of whether or not a sample is affected by a genetic variation often is carried out using one of three processes: (1) classification based on parabolic differences of summed squares of residuals, (see FIGS. 45 and 46), (2)

classification based on linear differences of summed squares of residuals, (see FIGS. 47 and 48), and (3) classification based on fitted fetal fraction (see equation (33)). In some embodiments, the chosen approach takes error propagation into account.

Fixed Ploidy, Optimized Fetal Fraction: Systematic Error—Reference Offset

Ideally, reference and measured bin counts should contain zero systematic error (e.g., offset), however, in practice, reference and measured bin counts sometimes are shifted with respect to one another. In some instances, the effect of the shift with respect to one another can be analyzed using equation (33), assuming the shift Δ is constant across the chromosome of interest. For euploid cases, if random errors are neglected, the following relationships hold, in some embodiments:

$$f_i = f_i^0 + \Delta \tag{49}$$

$$y_i = f_i^0 = f_i - \Delta \tag{50}$$

$$f_i^0$$

represents the true reference bin count i, and $f_i$ represents the reference bin counts used, including any systematic error Δ. In certain embodiments, replacing equations (49) and (50) into equation (33) generates the following expression for the euploid branch of the fitted fetal fraction graph:

$$F_E = \frac{F_0 + \frac{(\Delta F)^2}{2}\sum_{i=1}^{N}\frac{1}{\sigma_i^2}(f_i y_i - f_i^2)}{1 + \frac{(\Delta F)^2}{4}\sum_{i=1}^{N} f_i^2/\sigma_i^2} = \tag{51}$$

$$\frac{F_0 + \frac{(\Delta F)^2}{2}\sum_{i=1}^{N}\frac{1}{\sigma_i^2}\left[(f_i^0+\Delta)f_i^0 - (f_i^0+\Delta)^2\right]}{1 + \frac{(\Delta F)^2}{4}\sum_{i=1}^{N}(f_i^0+\Delta)^2/\sigma_i^2} =$$

$$\frac{F_0 - \frac{(\Delta F)^2}{2}\left(\Delta\sum_{i=1}^{N}\frac{f_i^0}{\sigma_i^2} + \Delta^2\sum_{i=1}^{N}\frac{1}{\sigma_i^2}\right)}{1 + \frac{(\Delta F)^2}{4}\left(\sum_{i=1}^{N}\frac{1}{\sigma_i^2}(f_i^0)^2 + 2\Delta\sum_{i=1}^{N}\frac{f_i^0}{\sigma_i^2} + \Delta^2\sum_{i=1}^{N}\frac{1}{\sigma_i^2}\right)} =$$

$$\frac{F_0 - 2S_f^0\Delta - 2S_0^0\Delta^2}{1 + S_{ff}^0 + 2S_f^0\Delta + S_0^0\Delta^2}$$

The coefficients $$S_0^0,\ S_f^0 \text{ and } S_{ff}^0,$$

are generated from equations (33) to (39) by replacing $f_i$ with $$f_i^0,$$

in some embodiments. In certain embodiments, the reciprocal slope of the linear functional relationship between fitted euploid value $F_E$ and measured $F_0$ equals $$1 + S_{ff}^0 + 2S_f^0\Delta + S_0^0\Delta^2,$$

which often allows estimation of the systematic error Δ by solving a relatively simple quadratic equation. For triploids, assuming $F_0$ equals $F_V$, measured bin counts sometimes become:

$$y_i = f_i^0 + \frac{1}{2}F_0 f_i^0$$

Combining equations (52), (49) and (33) generates the following expression for the triploid branch of the fitted fetal fraction graph:

$$F_T = \frac{F_0 + \frac{(\Delta F)^2}{2}\sum_{i=1}^{N}\frac{1}{\sigma_i^2}(f_i y_i - f_i^2)}{1 + \frac{(\Delta F)^2}{4}\sum_{i=1}^{N} f_i^2/\sigma_i^2} = \tag{53}$$

$$\frac{F_0 + \frac{(\Delta F)^2}{2}\sum_{i=1}^{N}\frac{1}{\sigma_i^2}\left[(f_i^0+\Delta)\left(f_i^0 + \frac{1}{2}F_0 f_i^0\right) - (f_i^0+\Delta)^2\right]}{1 + \frac{(\Delta F)^2}{4}\sum_{i=1}^{N}(f_i^0+\Delta)^2/\sigma_i^2} =$$

$$\frac{F_0 + \frac{(\Delta F)^2}{2}\left(\frac{1}{2}F_0\sum_{i=1}^{N}\frac{1}{\sigma_i^2}(f_i^0)^2 + \frac{1}{2}F_0\Delta\sum_{i=1}^{N}\frac{f_i^0}{\sigma_i^2} - \Delta\sum_{i=1}^{N}\frac{f_i^0}{\sigma_i^2} - \Delta^2\sum_{i=1}^{N}\frac{1}{\sigma_i^2}\right)}{1 + \frac{(\Delta F)^2}{4}\left(\sum_{i=1}^{N}\frac{1}{\sigma_i^2}(f_i^0)^2 + 2\Delta\sum_{i=1}^{N}\frac{f_i^0}{\sigma_i^2} + \Delta^2\sum_{i=1}^{N}\frac{1}{\sigma_i^2}\right)} =$$

$$\frac{F_0(1 + S_{ff}^0 + S_f^0\Delta) - S_f^0\Delta - S_0^0\Delta^2}{1 + S_{ff}^0 + 2S_f^0\Delta + S_0^0\Delta^2}$$

Figure 48:
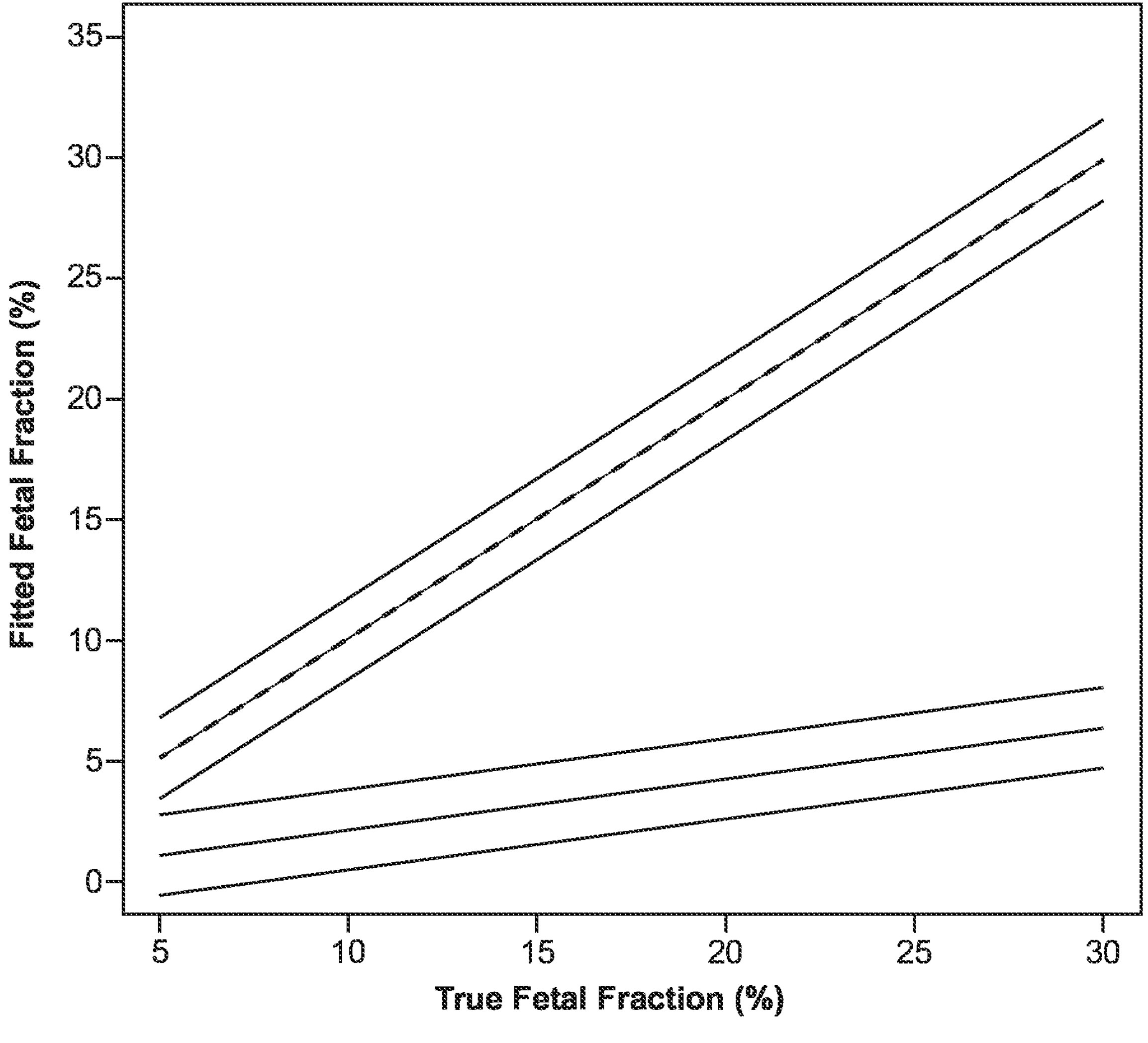
FIG. 48 schematically illustrates the predicted dependence of the fitted fetal fraction plotted against measured fetal fraction profiles on systematic offsets in reference counts. The lower and upper branches represent euploid and triploids cases, respectively.
Figure 49:
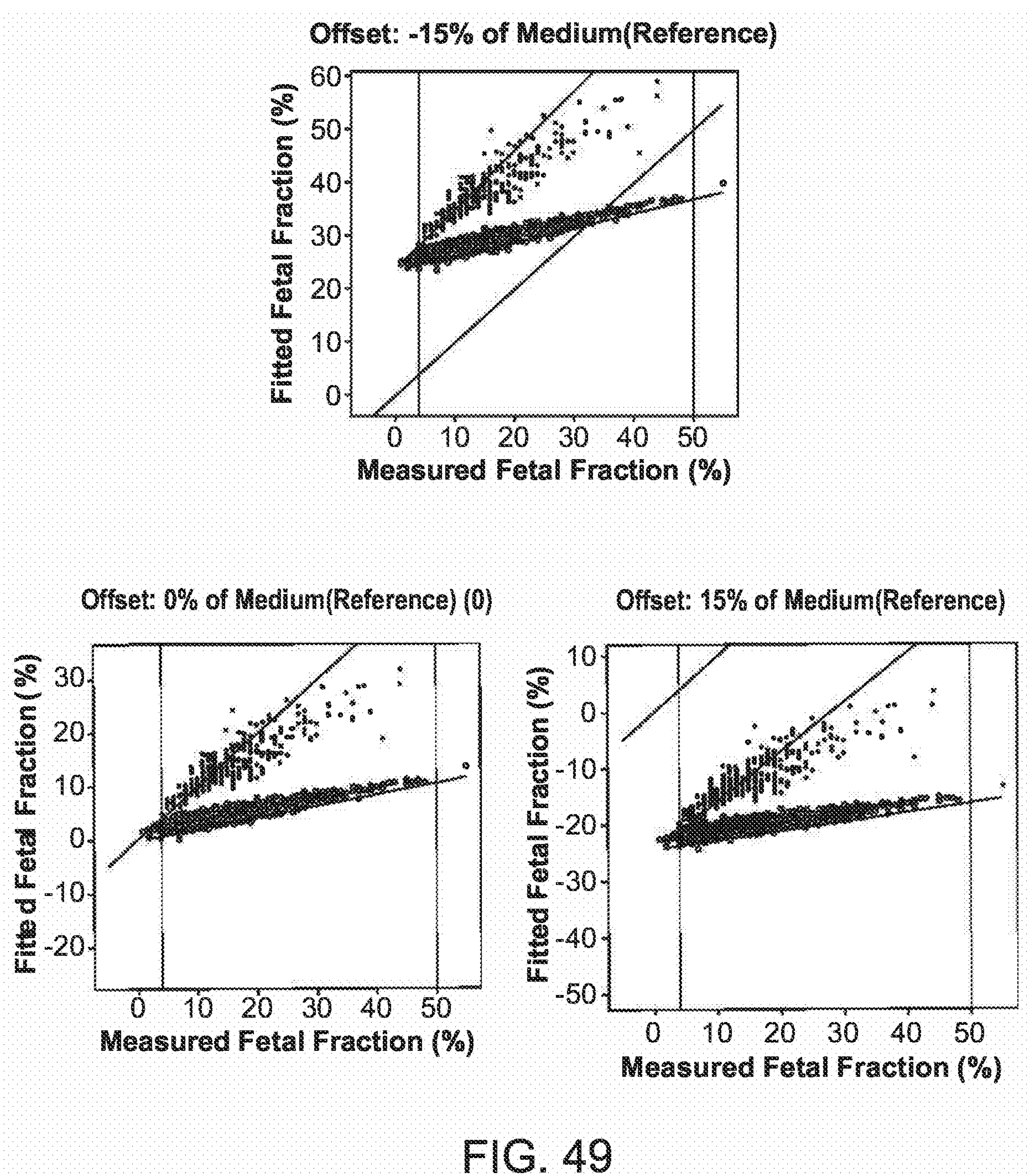
FIG. 49 graphically represents the effects of simulated systematic errors $\Delta$ artificially imposed on actual data. The main diagonal in the upper panel and the upper diagonal in the lower right panel represent ideal agreement. The dark gray line in all panels represents equations (51) and (53) for euploid and triploid cases, respectively. The data points represent actual measurements incorporating various levels of artificial systematic shifts. The systematic shifts are given as the offset above each panel. For FIGS. 48 and 49 see Example 2 for experimental details and results.

In some embodiments, equations (51) and (53) predict that fitted triploid and euploid fetal fractions will behave as shown in FIG. 48. In FIG. 48 black lines (e.g., upper lines in each set of 3 lines) correspond to negative offset Δ, dark gray lines (e.g., bottom lines in each set of 3 lines) correspond to positive offset Δ, and light gray lines (e.g., middle lines in each set of 3 lines) correspond to the absence of offset. FIG. 49 illustrates the effects of simulated systematic errors Δ artificially imposed on actual data.

FIG. 50 illustrates the dependence of fitted fetal fraction on systematic error offset for euploid and triploid data sets.

For both euploid and triploid cases, the theoretical expressions of equations (51) and (53) often capture the qualitative dependence of fitted fetal fraction on measured fetal fraction and on systematic error offset. Coefficients used for the graphs in FIGS. 49 and 50 were obtained from raw reference bin counts, without removing any potential systematic bias.

Fixed Ploidy, Optimized Fetal Fraction, Error Propagation: Fitted Fetal Fraction Contributions to errors in fitted fetal fractions often fall into one of two types of errors: 1) from measured fetal fractions, and 2) from measured and reference bin counts. The two types of errors will be analyzed separately, using different approaches, and later combined to generate final error ranges. Errors propagated from measure fetal fractions can be evaluated by replacing $F_0$ in equation (40) first with $F_0$−2⊿F (e.g., for the lower error boundary) and then with $F_0$+2⊿F (e.g., for the upper error boundary). This relatively simple approach produces correct qualitative behavior at 95% confidence intervals, in certain embodiments. For a different desired level of confidence, a more general pair of bounds, $F_0$−n⊿F and $F_0$+n⊿F, can be utilized. The terms used to generate upper and lower error boundaries sometimes underestimates the total error because the contributions from errors in measure and reference bin counts often are neglected.

To better assess the contribution from measured and reference bin counts on error in fitted fetal fraction, equations (38) to (40) can be utilized, in some embodiments. In certain embodiments, equation (33) can be expanded for fitted fetal fraction into a Taylor series with respect to $f_i$ and $y_i$, truncated to the first order, square and average. In some instances, it can be assumed that uncertainties in $y_i$ often are the same as uncertainties in $f_i$. To simply analysis, cross-terms and higher-order terms are assumed to reduce to zero upon averaging. Taylor expansion coefficients often are obtained utilizing the chain rule. The mean squared variation in the fitted fetal fraction is then given by equation (54) shown below. The model represented by equation ignores contributions from estimates for ⊿F, in some embodiments. Partial derivatives can be evaluated using the expressions presented below equation (54).

$$(\delta F)^2 = \sum_{i=1}^{N}\left(\frac{\partial F}{\partial f_i}\right)^2\sigma_i^2 + \sum_{i=1}^{N}\left(\frac{\partial F}{\partial y_i}\right)^2\sigma_i^2 = \sum_{i=1}^{N}\left[\left(\frac{\partial F}{\partial S_{ff}}\right)\left(\frac{\partial S_{ff}}{\partial f_i}\right)+\left(\frac{\partial F}{\partial S_{fy}}\right)\left(\frac{\partial S_{fy}}{\partial f_i}\right)\right]^2\sigma_i^2 + \sum_{i=1}^{N}\left[\left(\frac{\partial F}{\partial S_{fy}}\right)\left(\frac{\partial S_{fy}}{\partial y_i}\right)\right]^2\sigma_i^2 \tag{54}$$

$$\left(\frac{\partial F}{\partial S_{ff}}\right) = -\frac{F_0+2S_{fy}+2}{(1+S_{ff})^2} \tag{55}$$

$$\left(\frac{\partial F}{\partial S_{fy}}\right) = \frac{2}{1+S_{ff}} \tag{56}$$

$$\left(\frac{\partial S_{ff}}{\partial f_i}\right) = \frac{(\Delta F)^2}{2}\left(\frac{f_i}{\sigma_i^2}\right) \tag{57}$$

$$\left(\frac{\partial S_{fy}}{\partial f_i}\right) = \frac{(\Delta F)^2}{4}\left(\frac{y_i}{\sigma_i^2}\right) \tag{58}$$

$$\left(\frac{\partial S_{fy}}{\partial y_i}\right) = \frac{(\Delta F)^2}{4}\left(\frac{f_i}{\sigma_i^2}\right) \tag{59}$$

Combining equations (54) to (59) generates the following expression:

$$(\delta F)^2 = \left[\frac{(\Delta F)^2}{4}\right]^2\left\{\sum_{i=1}^{N}\frac{1}{\sigma_i^2}\left[\frac{2y_i}{1+S_{ff}} - 2f_i\frac{F_0+2S_{fy}+2}{(1+S_{ff})^2}\right]^2 + \sum_{i=1}^{N}\frac{1}{\sigma_i^2}\left(\frac{2f_i}{1+S_{ff}}\right)^2\right\} = \left[\frac{(\Delta F)^2}{4}\right]^2\sum_{i=1}^{N}\frac{1}{\sigma_i^2}\left[\left(\frac{2y_i}{1+S_{ff}}\right)^2 - 8f_iy_i\frac{F_0+2S_{fy}+2}{(1+S_{ff})^2} + 4f_i^2\frac{(F_0+2S_{fy}+2)^2}{(1+S_{ff})^2} + \left(\frac{2f_i}{1+S_{ff}}\right)^2\right] = \left[\frac{(\Delta F)^2}{4}\right]^2\left\{\frac{4}{(1+S_{ff})^2}\sum_{i=1}^{N}\frac{y_i^2}{\sigma_i^2} - 8\frac{F_0+2S_{fy}+2}{(1+S_{ff})^2}\sum_{i=1}^{N}\frac{f_iy_i}{\sigma_i^2} + 4\left[\frac{(F_0+2S_{fy}+2)^2}{(1+S_{ff})^4} + \frac{1}{(1+S_{ff})^2}\right]\sum_{i=1}^{N}\frac{f_i^2}{\sigma_i^2}\right\} = (\Delta F)^2\left\{\frac{S_{yy}}{(1+S_{ff})^2} - 2S_{fy}\frac{F_0+2S_{fy}+2}{(1+S_{ff})^2} + S_{ff}\left[\frac{(F_0+2S_{fy}+2)^2}{(1+S_{ff})^2} + \frac{1}{(1+S_{ff})^2}\right]\right\} \tag{60}$$

To evaluate equation (60) at a 95% confidence interval, the following upper and lower bounds can be used, in some embodiments:

$$\begin{bmatrix} F_{Lower} \\ F_{Upper} \end{bmatrix} = \frac{F_0+2S_{fy}-2S_{ff}}{1+S_{ff}} + \begin{bmatrix} -2 \\ 2 \end{bmatrix}\Delta F\left\{\frac{1}{1+S_{ff}} + \sqrt{\frac{S_{yy}}{(1+S_{ff})^2} - 2S_{fy}\frac{F_0+2S_{fy}+2}{(1+S_{ff})^2} + S_{ff}\left[\frac{(F_0+2S_{fy}+2)^2}{(1+S_{ff})^2} + \frac{1}{(1+S_{ff})^2}\right]}\right\} \tag{61}$$

Figure 51:
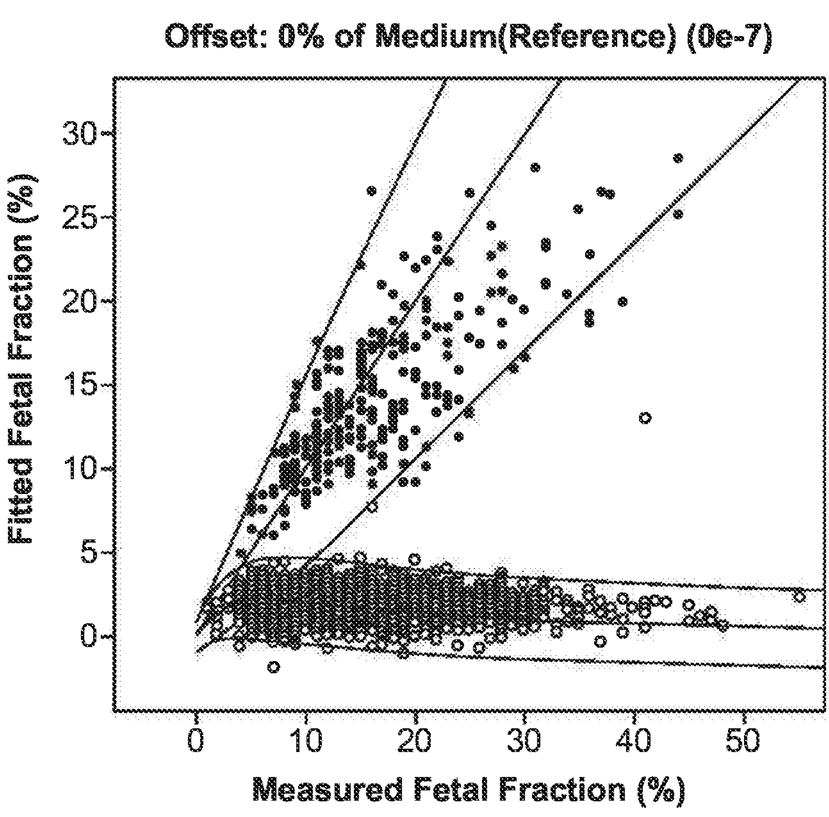
FIG. 51 graphically illustrates simulations based on equation (61), along with fitted fetal fractions for actual data. Black lines represent two standard deviations (obtained as square root of equation (61)) above and below equation (40). $\Delta F$ is set to $\frac{2}{3}+F_0/6$. For FIGS. 50 and 51 see Example 2 for experimental details and results.

In embodiments in which substantially all possible sources of error (e.g., $F_0$, $f_i$, $y_i$) are included in the Taylor expansion series, the same equation often is obtained. In some instances, dependence of F on $F_0$, can be accounted for through $S_{fy}$. In some embodiments, power series terms corresponding to $F_0$ often take the form;

$$\left[\left(\frac{\partial F}{\partial F_0}\right)+\left(\frac{\partial F}{\partial S_{fy}}\right)\left(\frac{\partial S_{fy}}{\partial F_0}\right)\right]^2(\Delta F)^2,\text{ but }\left[\left(\frac{\partial F}{\partial F_0}\right)+\left(\frac{\partial F}{\partial S_{fy}}\right)\left(\frac{\partial S_{fy}}{\partial F_0}\right)\right]^2$$

equals 1 for triploids. Thus, relatively simple subtraction and addition of ⊿F to $F_0$ often is justified, even though ⊿F often increases with $F_0$ and becomes large at high $F_0$. The outcome is due to both F and $S_{fy}$ depending linearly on $F_0$, in some embodiments. Simulations based on equation (61) are shown in FIG. 51, along with fitted fetal fractions obtained from test subject derived data. In the simulations presented in FIG. 51, ⊿F=⅔+$F_0$/6, as described herein.

Example 3: Sliding Window Analysis and Cumulative Sums as a Function of Genomic Position Identification of recognizable features (e.g., regions of genetic variation, regions of copy number variation) in a normalized count profile sometimes is a relatively time consuming and/or relatively expensive process. The process of identifying recognizable features often is complicated by data sets containing noisy data and/or low fetal nucleic acid contribution. Identification of recognizable features that represent true genetic variations or copy number variations can help avoid searching large, featureless regions of a genome. Identification of recognizable features can be achieved by removing highly variable genomic sections from a data set being searched and obtaining, from the remaining genomic sections, data points that deviate from the mean profile elevation by a predetermined multiple of the profile variance.

In some embodiments, obtaining data points that deviate from the mean profile elevation by a predetermined multiple of the profile variance can be used to reduce the number of candidate genomic sections from greater than 50,000 or 100,000 genomic sections to in the range of about 100 to about 1000 candidate genomic sections that represent true signals or solitary noise spikes (e.g., about 100 genomic sections, about 200 genomic sections, about 300 genomic sections, about 400 genomic sections, about 500 genomic sections, about 600 genomic sections, about 700 genomic sections, about 800 genomic sections, about 900 genomic sections, or about 1000 genomic sections). The reduction in the number of candidate genomic sections can be achieved relatively quickly and easily and often speeds up the search for and/or identification of genetic aberrations by two or more orders of magnitude. Reduction in the number of genomic sections searched for the presence or absence of candidate regions of genomic variation often reduces the complexity and/or dimensionality of a data set.

After a reduced data set containing data points that deviate from the mean profile elevation by a predetermined multiple of the profile variance is generated, the reduced data set is filtered to eliminate solitary noise spikes, in some embodiments. Filtering a reduced data set to remove solitary noise spikes often generates a filtered, reduced data set. In some embodiments, a filtered, reduced data set retains contiguous clusters of data points, and in certain embodiments, a filtered, reduced data set retains clusters of data points that are largely contiguous with allowance for a predetermined number and/or size of gaps. Data points from the filtered, reduced data set that deviate from the average profile elevation in substantially the same direction are grouped together, in some embodiments.

Due to the background noise often present in nucleic acid samples (e.g., ratio of regions of interest compared to the total nucleic acid in a sample), distinguishing regions of genetic variation or genetic aberration from background noise often is challenging. Methods that improve the signal-to-noise ratio often are useful for facilitating the identification of candidate regions representative of regions of true genetic variation and/or genetic aberration. Any method that improves the signal-to-noise ratio of regions of true genetic variation with respect to the genomic background noise can be used. A non-limiting example of a method suitable for use in improving the signal-to-noise ratio of regions of true genetic variation with respect to the genomic background noise is the use of integrals over the suspected aberration and its immediate surroundings. In some embodiments, the use of integrals over the suspected aberration and its immediate surroundings is beneficial, because summation cancel out random noise. After noise has been reduced or eliminated, even relatively minor signals can become readily detectable using a cumulative sum of the candidate peak and its surroundings, in some embodiments. A cumulative sum sometimes is defined with respect to an arbitrarily chosen origin outside (e.g., on one side or the other) of the peak. A cumulative sum often is a numerical estimate of the integral of the normalized count profile over the selected genetic section or sections.

In the absence of aberrations, the cumulative sum as a function of the genomic position often behaves as a straight line with unit slope (e.g., slope equal to 1). If deletions or duplications are present, the cumulative sum profile often consists of two or more line segments. In some embodiments, areas outside of aberrations map to line segments with unit slopes. For areas within aberrations, the line segments are connected by other line segments whose slopes equal the count profile elevation or depression within the aberration, in certain embodiments.

In those samples having maternal aberrations, the slopes (e.g., equivalent to the count profile elevation) are relatively easily determined: 0 for homozygous maternal deletions, 0.5 for heterozygous maternal deletions, 1.5 for heterozygous duplications, 2.0 for homozygous duplications. In those samples having fetal aberrations, the actual slopes depend both on the type of the aberration (e.g., homozygous deletion, heterozygous deletion, homozygous duplication or heterozygous duplication) and on the fetal fraction. In some embodiments, inheritance of a maternal aberration by the fetus also is taken into account when evaluating fetal samples for genetic variations.

In some embodiments, line segments with unit slopes, corresponding to normal genomic areas to the left and to the right of an aberration, are vertically shifted with respect to one another. The difference (e.g., subtractive result) between their intercepts equals the product between the width of the aberration (number of affected genomic sections) and the aberration level (e.g., −1 for homozygous maternal deletion, −0.5 for heterozygous maternal deletion, +0.5 for heterozygous duplication, +1 for homozygous duplication, and the like). Refer to FIGS. 52-61F for examples of data sets processed using cumulative sums as a function of genomic position (e.g., sliding window analysis).

Example 4: Parameterized Error Removal and Unbiased Normalization (PERUN)

Variability of Measured Counts

Ideally, the measured chromosomal elevation is a straight horizontal line with the elevation of 1 for euploids, as in FIG. 62. For trisomy pregnancies, the desired behavior of the measured chromosomal elevation is a step-function, with the deviation from 1 proportional to the fetal fraction, as simulated in FIG. 63 for fetal fraction equal to 15%. Exceptions arise out of maternal deletions/duplications, which are readily recognized and distinguished from fetal abnormalities based on their magnitudes, which are multiples of one-half.

What was actually measured was not ideal. FIG. 64 shows overlaid raw counts for chromosomes 20, 21, and 22 collected from 1093 euploid pregnancies and FIG. 65 shows overlaid raw counts for chromosomes 20, 21, and 22 collected from 134 trisomy 21 pregnancies. Visual inspection of the two sets of profiles failed to confirm that chromosome 21 traces in trisomy cases were elevated. Stochastic noise and systematic bias both made the elevation of chromosome 21 difficult to visualize. Furthermore, the far right segment of chromosome 21 incorrectly suggested that euploid chromosome 21 traces were elevated, rather than the trisomy profiles. A large part of the systematic bias originated from the GC content associated with a particular genomic region.

Attempts to remove the systematic bias due to GC content included multiplicative LOESS GC smoothing, Repeat Masking (RM), combination of LOESS and RM (GCRM), and others, such as cQN. FIG. 66 shows the results of a GCRM procedure as applied to 1093 euploid traces and FIG. 67 shows the GCRM profiles for 134 trisomy cases. GCRM successfully flattened the elevated, GC-rich, rightmost segment of chromosome 21 in euploids. However, the procedure evidently increased the overall stochastic noise. Moreover, it created a new systematic bias, absent from the raw measurements (leftmost region of chromosome 20 (Chr20)). The improvements that were due to GCRM were offset by increased noise and bias, rendering the usefulness of the procedure questionable. The tiny elevation from chromosome 21 as observed in FIG. 63 was lost in the high noise as shown in FIG. 66 and FIG. 67.

PERUN (Parameterized Error Removal and Unbiased Normalization) was developed as a viable alternative to previously described GC normalization methods. FIG. 68 and FIG. 69 contrast the PERUN method results against those presented in FIG. 64 through 67. PERUN results were obtained on the same two subpopulations of data that was analyzed in FIG. 64 through 67. Most of the systematic bias was absent from PERUN traces, only leaving stochastic noise and biological variation, such as the prominent deletion in chromosome 20 of one of the euploid samples (FIG. 68). The chromosome 20 deletion was also observable in raw count profiles (FIG. 64), but completely masked in the GCRM traces. The inability of GCRM to reveal this huge deviation clearly disqualifies it for the purposes of measuring the miniscule fetal T21 elevations. PERUN traces contain fewer bins than raw or GCRM profiles. As shown in FIG. 62-63, the PERUN results look at least as good as the measurement errors permit.

Normalization with Respect to Reference Median Count Profile

Figure 4:
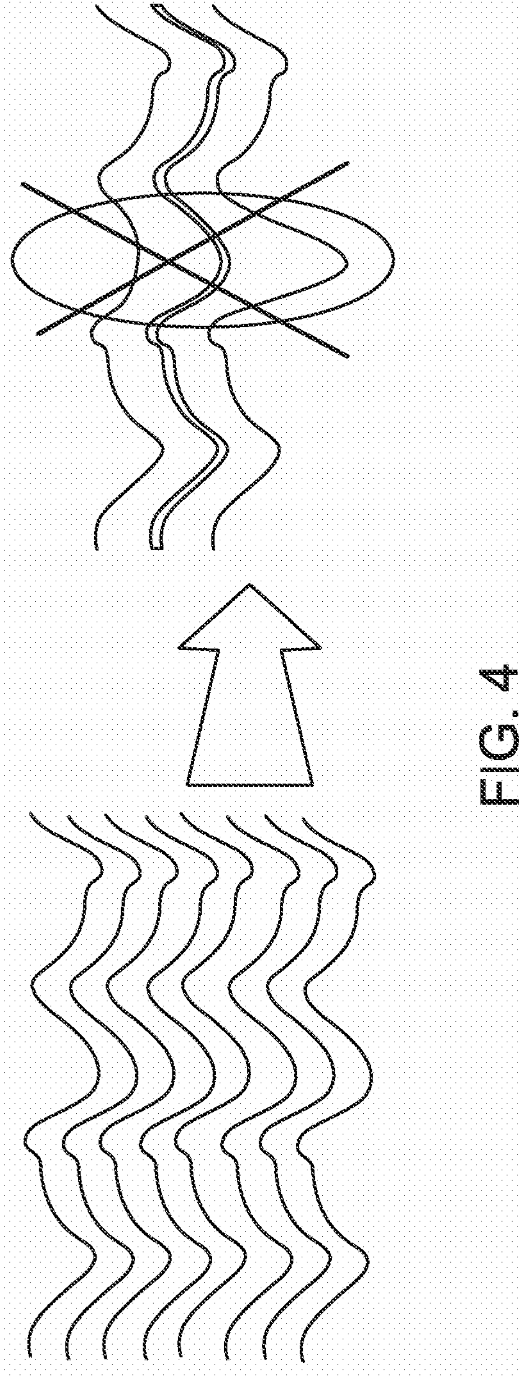
FIG. 4 schematically represents a bin filtering procedure. A large number of euploid samples are lined up, bin count uncertainties (SD or MAD values) are evaluated, and bins with largest uncertainties sometimes are filtered out.
Figure 6:
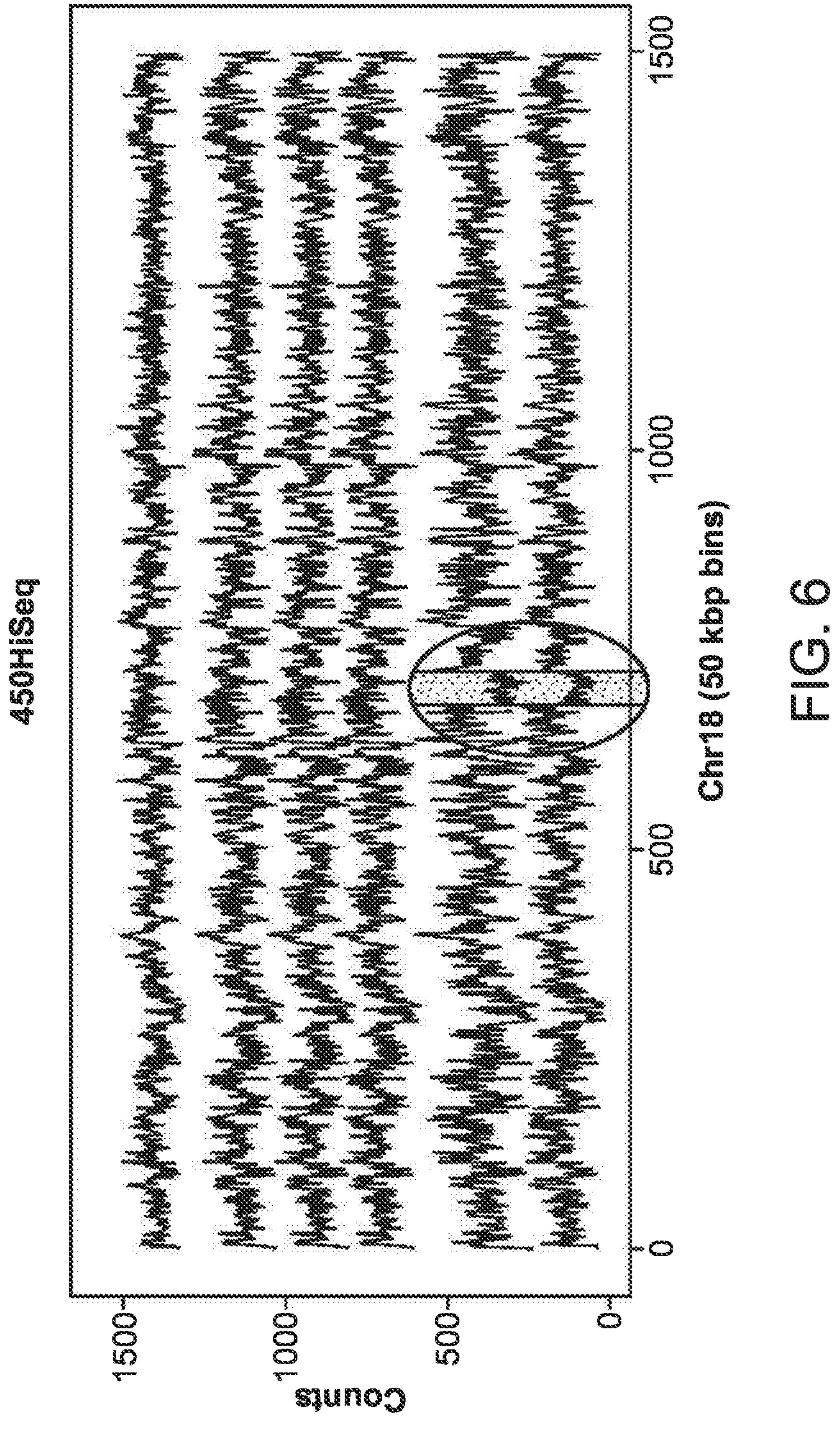
FIG. 6 graphically illustrates count profiles for patients used to filter out uninformative bins from chromosome 18.
Figure 7:
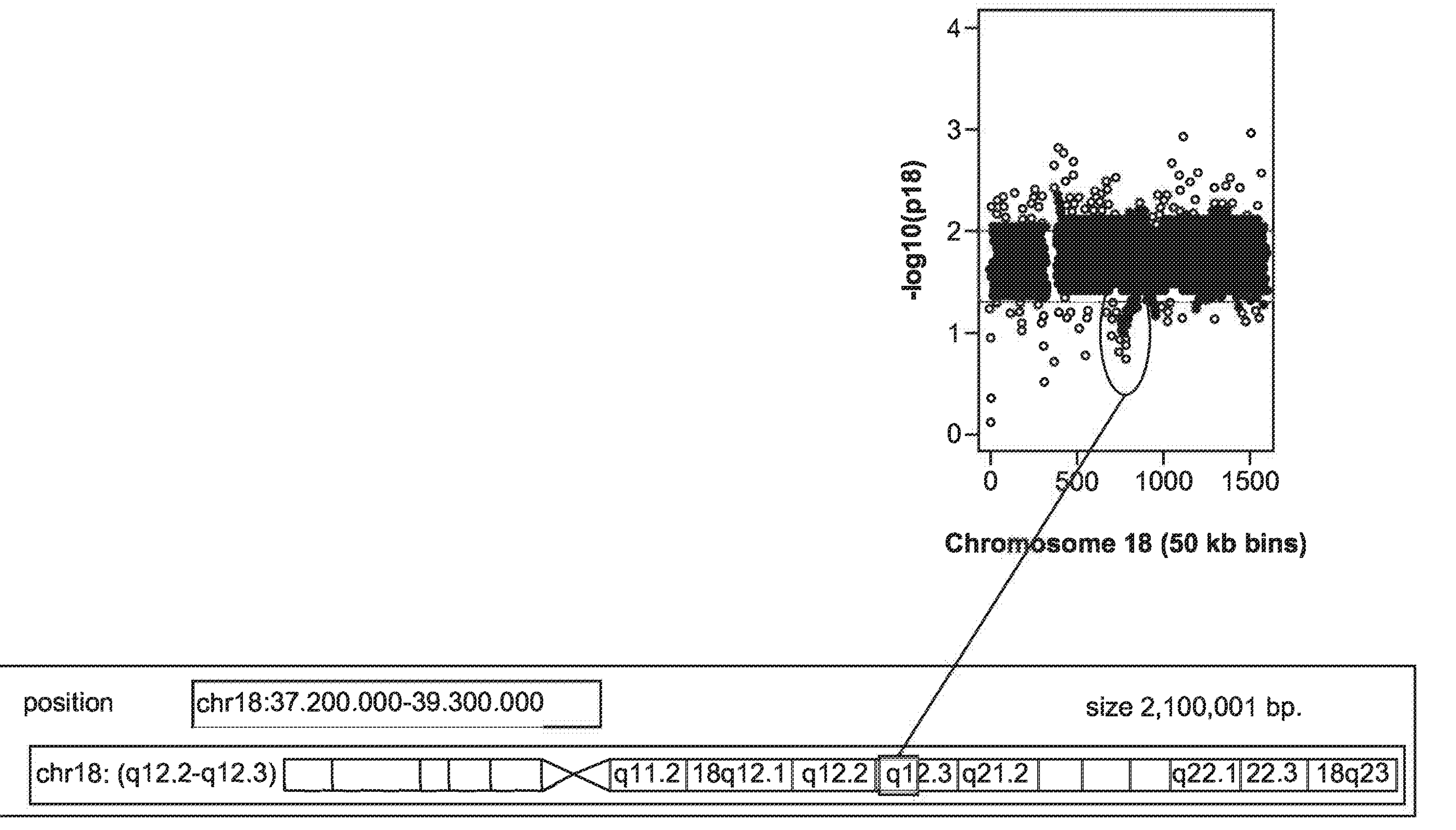
FIG. 7 graphically illustrates the dependence of p-values on the position of genomic bins within chromosome 18.
Figure 8:
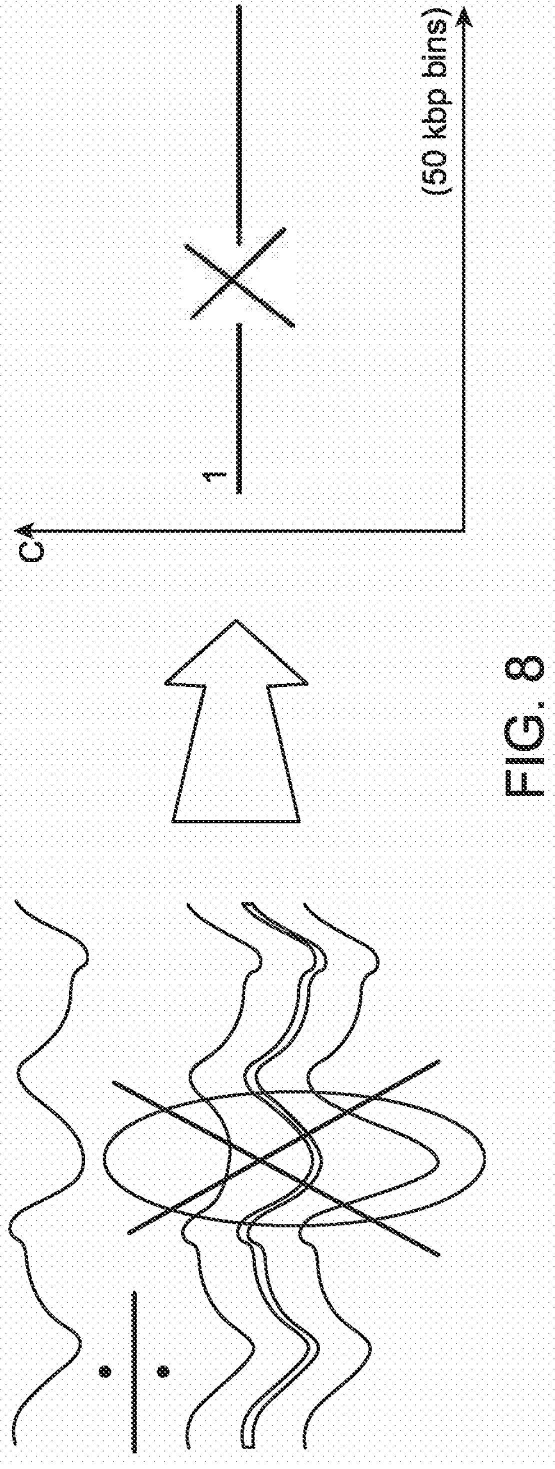
FIG. 8 schematically represents bin count normalization. The procedure first lines up known euploid count profiles, from a data set, and normalizes them with respect to total counts. For each bin, the median counts and deviations from the medians are evaluated. Bins with too much variability (exceeding 3 mean absolute deviations (e.g., MAD)) sometimes are eliminated. The remaining bins are normalized again with respect to residual total counts, and medians are re-evaluated following the renormalization, in some embodiments. Finally, the resulting reference profile (see bottom trace, left panel) is used to normalize bin counts in test samples (see top trace, left panel), smoothing the count contour (see trace on the right) and leaving gaps where uninformative bins have been excluded from consideration.

Conventional GC normalization procedures can perform suboptimally. A part of the reason has been that GC bias is not the only source of variation. A stack plot of many individual raw count profiles revealed parallelism between different samples. While some genomic regions were consistently over-represented, others were consistently under-represented, as illustrated by the traces from a 480v2 study (FIG. 6). While GC bias varied from one sample to another, the systematic, bin-specific bias observed in these profiles followed the same pattern for all samples. All the profiles in FIG. 6 zigzagged in a coordinated fashion. The only exceptions were the middle portions of the bottom two samples, which turned out to originate from maternal deletions. To correct for this bin-specific bias, a median reference profile was used. The median reference profile was constructed from a set of known euploids (e.g. euploid pregnancies) or from all the samples in a flow cell. The procedure generated the reference profile by evaluating median counts per bin for a set of reference samples. The MAD associated with a bin measured the reliability of a bin. Highly variable bins and bins that consistently have vanishing representations were removed from further analysis (FIG. 4). The measured counts in a test data set were then normalized with respect to the median reference profile, as illustrated in FIG. 8. The highly variable bins are removed from the normalized profile, leaving a trace that is approximately 1 in the diploid sections, 1.5 in the regions of heterozygous duplication, 0.5 in the areas of heterozygous deletion, and so on (FIG. 9). The resulting normalized profiles reasonably reduced the variability, enabling detection of maternal deletions and duplications and tracing of sample identities (FIG. 12, 22, 13, 11). Normalization based on median count profile can clarify outcomes, but GC bias still has a negative effect on such methods. PERUN methods described here can be used to address GC bias and provide outcomes with higher sensitivity and specificity.

Detrimental Effects of Multiplicative LOESS Correction

FIG. 11. illustrated why binwise counts fluctuate more after application of GC-LOESS or GCRM (FIG. 66-67) than before (FIG. 64-65). LOESS GC correction removed the trend from the raw counts (FIG. 70, upper panel) by dividing the raw counts with the regression line (straight line, FIG. 70, upper panel). The point defined by the median counts and the median genome GC content was kept immobile. On average, counts below the median count were divided by small numbers, while counts exceeding the median count were divided by large numbers. In either case, on average, counts were scaled up or down to match 1 (FIG. 70, lower panel). The scaling of small counts, in addition to inflating the counts, also inflated their variability. The end result (FIG. 70, lower panel) to the left from the median GC genome content displayed a larger spread than the corresponding raw counts (FIG. 70, upper panel), forming the typical triangular shape (FIG. 70, lower panel, triangle). To detrend the counts, GC LOESS/GCRM sacrificed precision as such corrective processes generally are multiplicative and not additive. Normalization provided by PERUN generally is additive in nature and enhances precision over multiplicative techniques.

Inadequacy of a Genome-Wide Pivot for GC-Bias Scaling

An alternative approach applied the LOESS correction separately to individual chromosomes instead of subjecting the entire genome to a collective GC-Bias scaling. The scaling of individual chromosomes was impractical for purposes of classifying samples as euploid or trisomy because it canceled out the signal from over-represented chromosomes. However, the conclusions from this study were eventually useful as catalyzers for developing the PERUN algorithm. FIG. 71 illustrates the fact that LOESS curves obtained for the same chromosome from multiple samples share a common intersection (pivot).

FIG. 72 demonstrated that tilting chromosome-specific LOESS curves around the pivot by an angle proportional to the GC bias coefficients measured in those samples caused all the curves to coalesce. The tilting of the chromosome-specific LOESS curves by the sample-specific GC bias coefficients significantly reduced the spread of the family of LOESS curves obtained for multiple samples, as shown in FIG. 73 (filled circles (before tilting) and open circles (after tilting)). The point where the filled circles and open circles touch coincided with the pivot. In addition, it became evident that the location on the GC content axis of the chromosome-specific pivot coincided with the median GC content of the given chromosome (FIG. 74, left vertical line: median, right vertical line: mean). Similar results were obtained for all chromosomes, as shown in FIG. 75A through FIG. 75F (left vertical grey line: median, right vertical bold line: mean). All autosomes and chromosome X were ordered according to their median GC content.

The genome-wide GC LOESS scaling pivoted the transformation on the median GC content of the entire genome, as shown in FIG. 76. That pivot was acceptable for chromosomes that have median GC content similar to the GC content of the entire genome, but became suboptimal for chromosomes with extreme GC contents, such as chromosomes 19, 20, 17, and 16 (extremely high GC content). The pivoting of those chromosomes centered on the median GC content of the entire genome maintained the spread observed within the left box in FIG. 76, missing the low-variability region enclosed by the right box in FIG. 76 (the chromosome-specific pivot).

Pivoting on the chromosome-specific median GC content, however, significantly reduced the variability (FIG. 75). The following observations were made:

1) GC correction should be done on small genomic sections or segments, rather than on the entire genome, to reduce the variability. The smaller the section or segment, the more focused GC correction becomes, minimizing the residual error.
2) In this particular instance, those small genomic sections or segments are identical to chromosomes. In principle, the concept is more general: the sections or segments could be any genomic regions, including 50 kbp bins.
3) The GC bias within individual genomic regions can be rectified using the sample-specific, genome-wide GC coefficient evaluated for the entire genome. This concept is important: while some descriptors of the genomic sections (such as the location of the pivot point, GC content distribution, median GC content, shape of the LOESS curve, and so on) are specific to each section and independent of the sample, the GC coefficient value used to rectify the bias is the same for all the sections and different for each sample.

These general conclusions guided the development of PERUN, as will become apparent from the detailed description of its processes.

Separability of Sources of Systematic Bias

Careful inspection of a multitude of raw count profiles measured using different library preparation chemistries, clustering environments, sequencing technologies, and sample cohorts consistently confirmed the existence of at least two independent sources of systematic variability:

1) sample-specific bias based on GC-content, affecting all bins within a given sample in the same manner, varying from sample to sample, and
2) bin-specific attenuation pattern common to all samples.

The two sources of variability are intermingled in the data. Thorough removal of both required their deconvolution. The deficiencies of the error-removal procedures predating PERUN stem from the fact that they only correct for one of the two sources of systematic bias, while neglecting the other.

For example, the GCRM (or GC LOESS) method treated identically all the bins with GC content values falling within a narrow GC content range. The bins belonging to that subset may be characterized by a wide range of different intrinsic elevations, as reflected by the reference median count profile. However, GCRM was blind to their inherent properties other than their GC content. GCRM therefore maintains (or even enlarges) the spread already present in the bin subset. On the other hand, the binwise reference median count disregarded the modulation of the bin-specific attenuation pattern by the GC bias, maintaining the spread caused by the varying GC content.

The sequential application of the methods dealing with the opposite extremes of the error spectrum unsuccessfully attempts to resolve the two biases globally (genome-wide), ignoring the need to dissociate the two biases on the bin elevation. Without being limited by theory, PERUN apparently owes its success to the fact that it separates the two sources of bias locally, on the bin elevation.

Removal of Uninformative Bins

Multiple attempts to remove uninformative bins have indicated that bin selection has the potential to improve classification. The first such approach evaluated the mean chromosome 21, chromosome 18, and chromosome 13 counts per bin for all 480v2 trisomy cases and compared it with the mean counts per bin for all 480v2 euploids. The gap between affected and unaffected cases was scaled with the combined binwise uncertainty derived from bin counts measured in both groups. The resulting t-statistic was used to evaluate binwise p-value profile, shown in FIG. 77. In the case of chromosome 21, the procedure identified 36 uninformative bins (center panel, labeled with ellipse on FIG. 77). Elimination of those bins from calculation of Z scores noticeably increased the Z-values for affected cases, while randomly perturbing the unaffected Z-scores (FIG. 78), thereby increasing the gap between euploids and trisomy 21 cases.

In chromosome 18, the procedure only improved Z scores for two affected cases (FIG. 79).

A post-hoc analysis showed that the improvement of the Z-scores in those two samples resulted from removal of the large maternal deletion in chromosome 18 (FIG. 11) and that the two samples actually come from the same patient. These improvements were sample-specific, with no generalizing power. In chromosome 13, the procedure did not lead to any improvements of Z-scores.

An alternative bin filtering scheme removes bins with extremely low or extremely high GC content. This approach yielded mixed results, with noticeably reduced variance in chromosomes 9, 15, 16, 19, and 22 (depending on the cutoffs), but adverse effects on chromosomes 13 and 18.

Yet another simple bin selection scheme eliminates bins with consistently low counts. The procedure corrected two LDTv2CE chromosome 18 false negatives (FIG. 80) and two chromosome 21 false negatives (FIG. 81). It also corrected at least three chromosome 18 false positives, but created at least one new chromosome 18 false positive (FIG. 80):

In conclusion, the different criteria used to filter out uninformative bins made it clear that data processing will benefit from bin selection based on how much useful information the bins contribute to the classification.

Separation of GC Bias from Systematic Binwise Bias

To resolve and eliminate the different systematic biases found in the measured counts, the data processing workflow needed to optimally combine the partial procedures described from the previous section entitled "Normalization with Respect to Reference Median Count Profile" to the section entitled "Removal of Uninformative Bias". The first step is to order different samples according to their GC bias coefficient values and then stack their plots of counts-vs.-GC content. The result is a three-dimensional surface that twists like a propeller, schematically shown on FIG. 82.

Thus arranged, the measurements suggest that a set of sample-specific GC bias coefficient can be applied to rectify errors within an individual genomic section or segment. In FIG. 82, the sections or segments are defined by their GC content. An alternative partition of the genome gives contiguous, non-overlapping bins. The successive starting locations of the bins uniformly cover the genome. For one such 50 kbp long bin, FIG. 83 explores the behavior of the count values measured within that bin for a set of samples. The counts are plotted against the GC bias coefficients observed in those samples. The counts within the bin evidently increase linearly with the sample-specific GC bias. The same pattern in observed in an overwhelming majority of bins. The observations can be modeled using the simple linear relationship:

$$M = LI + GS \quad \text{(A)}$$

The various terms in Eq. A have the following meanings:

M: measured counts, representing the primary information polluted by unwanted variation.

L: chromosomal elevation—this is the desired output from the data processing procedure. L indicates fetal and/or maternal aberrations from euploidy. This is the quantity that is masked both by stochastic errors and by the systematic biases. The chromosomal elevation L is both sample specific and bin-specific.

G: GC bias coefficient measured using linear model, LOESS, or any equivalent approach. G represents secondary information, extracted from M and from a set of bin-specific GC content values, usually derived from the reference genome (but may be derived from actually observed GC contents as well). G is sample specific and does not vary along the genomic position. It encapsulates a portion of the unwanted variation.

I: Intercept of the linear model (diagonal line in FIG. 83). This model parameter is fixed for a given experimental setup, independent on the sample, and bin-specific.

S: Slope of the linear model (diagonal line in FIG. 83). This model parameter is fixed for a given experimental setup, independent on the sample, and bin specific.

The quantities M and G are measured. Initially, the bin-specific values I and S are unknown. To evaluate unknown I and S, we must assume that L=1 for all bins in euploid samples. The assumption is not always true, but one can reasonably expect that any samples with deletions/duplications will be overwhelmed by samples with normal chromosomal elevations. A linear model applied to the euploid samples extracts the I and S parameter values specific for the selected bin (assuming L=1). The same procedure is applied to all the bins in the human genome, yielding a set of intercepts I and slopes S for every genomic location. Cross-validation randomly selects a work set containing 90% of all LDTv2CE euploids and uses that subset to train the model. The random selection is repeated 100 times, yielding a set of 100 slopes and 100 intercepts for every bin. The previous section entitled "Cross-Validation of PERUN Parameters" describes the cross-validation procedure in more detail.

FIG. 84-85 show 100 intercept values and 100 slope values, respectively, evaluated for bin #2404 in chromosome 2. The two distributions correspond to 100 different 90% subsets of 1093 LDTv2CE euploids shown in FIG. 83. Both distributions are relatively narrow and irregularly shaped. Their spreads are similar to the errors in the coefficient as reported by the linear model. As a rule, the slope is less reliable than the intercept because fewer samples populate the extreme sections of the GC-bias range.

Interpretation of PERUN Parameters I and S

The meaning of the intercept I is illustrated by FIG. 86. The graph correlates the estimated bin intercepts with the data extracted from a set of technical replicates, obtained when one LDTv2CE flow cell was subjected to three separate sequencing runs. The y-axis contains median values of binwise counts from those three measurements. These median values are related conceptually to the median reference profile, previously used to normalize profiles as described in the section entitled "Normalization with Respect to Reference Median Count Profile". The binwise intercepts are plotted along the x-axis. The striking correlation between the two quantities reveals the true meaning of the intercepts as the expected counts per bin in the absence of GC bias. The problem with the median reference count profile is that it fails to account for the GC bias (see section entitled "Normalization with Respect to Reference Median Count Profile"). In PERUN, without being limited by theory, the task of an intercept I is to deal with the bin-specific attenuation, while the GC bias is relegated to the other model parameter, the slope S.

FIG. 86 excludes chromosome Y from the correlation because the set of technical replicates does not reflect the general population of male pregnancies.

The distribution of the slope S (FIG. 87) illustrates the meaning of that model parameter.

The marked semblance between the distribution from FIG. 87 and the distribution of the genome-wide GC content (FIG. 88) indicates that the slope S approximates the GC content of a bin, shifted by the median GC content of the containing chromosome. The thin vertical line in FIG. 88 marks the median GC content of the entire genome.

FIG. 89 reaffirms the close relationship between the slope S and the GC content per bin. While slightly bent, the observed trend is extremely tight and consistent, with only a handful of notable outlier bins.

Extraction of Chromosomal Elevation from Measured Counts

Assuming that the model parameter values I and S are available for every bin, measurements M collected on a new test sample are used to evaluate the chromosomal elevation according to the following expression:

$$L = (M - GS)/I \quad \text{(B)}$$

As in Eq. A, the GC bias coefficient G is evaluated as the slope of the regression between the binwise measured raw counts M and the GC content of the reference genome. The chromosomal elevation L is then used for further analyses (Z-values, maternal deletions/duplications, fetal microdeletions/microduplications, fetal gender, sex aneuploidies, and so on). The procedure encapsulated by Eq. B is named Parameterized Error Removal and Unbiased Normalization (PERUN).

Cross-Validation of PERUN Parameters

As inferred in the section entitled "Separation of GC Bias from Systematic Binwise Bias", the evaluation of I and S randomly selects 10% of known euploids (a set of 1093 LDTv2 in FIG. 83) and sets them aside for cross-validation. Linear model applied to the remaining 90% of euploids extracts the I and S parameter values specific for the selected bin (assuming L=1). Cross validation then uses the I and S estimates for a given bin to reproduce measured M values from measured G values both in the work set and in the remaining 10% euploids (again assuming L=1). The random selection of the cross-validation subset is repeated many times (100 times in FIG. 83, although 10 repetitions would suffice). 100 diagonal straight lines in FIG. 83 represent the linear models for 100 different 90% work subset selections. The same procedure is applied to all the bins in the human genome, yielding a set of intercepts I and slopes S for every genomic location.

To quantify the success of the model and avoid biasing the results, we use the R-factor, defined as follows:

$$R = \frac{\sum_{i=1}^{N} |M_i - P_i|}{\sum_{i=1}^{N} |M_i|} \tag{C}$$

The numerator in Eq. B sums up the absolute deviations of the predicted count values (P, Eq. B) from the actual measurements (M). The numerator simply sums up the measurements. The R factor may be interpreted as the residual error in the model, or the unexplained variation. The R factor is directly borrowed from the crystallographic model refinement practice, which is vulnerable to bias. In crystallography, the bias is detected and measured by the R-factor evaluated within the cross-validation subset of observables. The same concepts are applied in the context of genome-wide count bias removal.

FIG. 90 shows the R-factors evaluated for the cross-validation subset (y-axis) plotted against R-factors evaluated for the work (training) set for bin #2404 from chromosome 2. There are 100 data points since the random selection of the cross-validation subset was repeated 100 times. Typical linear relationship is observed, with the increasing $R_{cv}$ values (measuring bias) accompanying the decreasing $R_{work}$.

FIG. 90 may be interpreted in terms of the percentage error (or relative error) of the model for this particular bin. $R_{cv}$ always exceeds $R_{work}$, usually by ~1%. Here, both $R_{cv}$ and $R_{work}$ remain below 6%, meaning that one can expect ~6% error in the predicted M values using the measured GC bias coefficient G and the model parameters I and S from the procedure described above.

Cross-Validation Error Values

FIG. 90-91 show cross-validation errors for bins chr2_2404 and chr2_2345, respectively. For those and many other bins, the errors never exceed 6%. Some bins, such as chr1_31 (FIG. 92) have cross-validation errors approaching 8%. Still others (FIG. 93-95) have much larger cross-validation errors, at times exceeding 100% (40% for chr1_10 in FIG. 93, 350% for chr1_9 in FIG. 94, and 800% for chr1_8 in FIG. 95).

FIG. 96 shows the distribution of max($R_{cv}$, $R_{work}$) for all bins. Only a handful of bins have errors below 5%. Most bins have errors below 7% (48956 autosomes out of 61927 total including X and Y). A few bins have errors between 7% and 10%. The tail consists of bins with errors exceeding 10%.

FIG. 97 correlates the cross-validation errors with the relative errors per bin estimated from the set of technical replicates. Data points in the center region (i.e., data points located between the two vertical lines) correspond to cross-validation errors between 7% and 10%. Data points in the region to the right of the two vertical lines denote bins with cross-validation error exceeding 10%. Data points in the region to the left of the two vertical lines (error <7%) represent the bulk of bins.

In FIG. 91-95, the number in parentheses following the bin name above the top right inset indicates the ratio between the intercept found for that particular bin and the genome-wise median count per bin. The cross-validation errors evidently increase with the decreasing value of that ratio. For example, the bin chr1_8 never gets more than 3 counts and its relative error approaches 800%. The smaller the expected number of counts for a given bin, the less reliable that bin becomes.

Bin Selection Based on Cross-Validation

Based on the observations described in the previous section entitled "Removal of Uninformative Bins" (FIG. 78 and FIG. 80-81), cross-validation errors were used as a criterion for bin filtering. The selection procedure throws away all bins with cross-validation errors exceeding 7%. The filtering also eliminates all bins that consistently contain zero counts. The remaining subset contains 48956 autosomal bins. Those are the bins used to evaluate chromosomal representations and to classify samples as affected or euploid. The cutoff of 7% is justified by the fact that the gap separating euploid Z-scores from trisomy Z-scores plateaus at the 7% cross-validation error (FIG. 98).

FIGS. 99A (all bins) and 99B (cross-validated bins) demonstrate that the bin selection described above mostly removes bins with low mappability.

As expected, most removed bins have intercepts far smaller than the genome-wide median bin count. Not surprisingly, the bin selection largely overlaps with the selection described in the previous section entitled "Removal of Uninformative Bins" (FIGS. 25 and 27-28).

Errors in Model Parameters

FIG. 100-101 show the 95% confidence intervals (curved lines) of the fitted linear model (thin straight line) for two bins (chr18_6 and chr18_8). The thick grey straight lines are obtained by replacing the S parameter with the difference between the GC contents of these two bins and the median GC content of chromosome 18. The error range is evaluated based on errors in the model parameters I and S for those two bins, as reported by the linear model. In addition, larger GC bias coefficients also contain larger errors. The large uncertainty corresponding to extremely large GC bias coefficients suggests that the range of applicability of the unmodified PERUN is limited to modest GC bias coefficients. Beyond that range, additional measures need to be taken to remove the residual GC bias. Fortunately, only very few samples are affected (roughly 10% of the LDTv2CE population).

FIG. 102-104 show the errors in the model parameters I and S and the correlation between the error in S and the value of the intercept.

Secondary Normalization

High values of GC bias coefficients exceed the linear range assumed by the PERUN model and are remedied by an additional LOESS GC normalization step after PERUN normalization. The multiplicative nature of the LOESS procedure does not significantly inflate the variability since the normalized counts are already very close to 1. Alternatively, LOESS can be replaced with an additive procedure that subtracts residuals. The optional secondary normalization often is utilized only required for a minority of samples (roughly 10%).

Hole Padding (Padding)

FIG. 68-69 confirm the presence of a large number of maternal deletions and duplications that have the potential to create false positives or false negatives, depending on their sizes and locations. An optional procedure called hole-padding has been devised to eliminate the interferences from these maternal aberrations. The procedure simply pads the normalized profile to remain close to 1 when it deviates above 1.3 or below 0.7. In LDTv2CE, hole padding (i.e., padding) did not significantly affect the classification. However, FIG. 105 shows a WI profile that contains a large deletion in chromosome 4. Hole padding converts that profile from chromosome 13 false positive to chromosome 13 true negative.

Results

This section discusses PERUN results for trisomy 13, trisomy 18 and trisomy 21 (T13, T18 and T21, respectively), gender determination, and sex aneuploidy.

Reduced Variability

FIG. 106 compares the distribution of standard deviations of the binwise count profiles before and after PERUN normalization. The resulting distributions of chromosome representations for euploids and trisomy cases are shown in FIG. 107.

Improved T13, T18, and T21 Classification

FIG. 108-111 compare LDTv2CE PERUN classification results with those obtained using GCRM counts. In addition to removing two chromosome 18 false positives, two chromosome 18 false negatives, and two chromosome 21 false negatives, PERUN almost doubles the gap between the euploids and the affected cases, in spite of the fact that the higher plexing elevation decreased the number of counts per sample (ELAND data). Similar results are obtained when PERUN parameters trained on LDTv2CE Eland data are applied to WI measurements. Bowtie alignments require a different set of parameters and additional bin filtering, accounting for low mappability in some bins, but its results approach those seen with ELAND alignments.

Example 5: Additional Description of PERUN

Examples of parameterized Error Removal and Unbiased Normalization (PERUN) methods are described in Example 4, and an additional description of such methods is provided in this Example 5.

Massive parallel sequencing of cell-free circulating DNA (e.g. from maternal plasma) can, under ideal conditions, quantify chromosomal elevations by counting sequenced reads if unambiguously aligned to a reference human genome. Such methods that incorporate massive amounts of replicate data can, in some instances, show statistically significant deviations between the measured and expected chromosomal elevations that can imply aneuploidy [Chiu et al., Noninvasive prenatal diagnosis of fetal chromosomal aneuploidy by massively parallel genomic sequencing of DNA in maternal plasma. *Proc. Natl. Acad. Sci USA* 2008; 105:20458-20463; Fan et al., Noninvasive diagnosis of fetal aneuploidy by shotgun sequencing DNA from maternal blood. *Proc. Natl. Acad. Sci USA* 2008; 105:16266-16271; Ehrich et al., Noninvasive detection of fetal trisomy 21 by sequencing of DNA in maternal blood: a study in a clinical setting, *American Journal of Obstetrics and Gynecology—AMER J OBSTET GYNECOL*, vol. 204, no. 3, pp. 205.e1-205.e11, 2011 DOI: 10.1016/j.ajog.2010.12.060]. Ideally, the distribution of aligned reads should cover euploid sections of the genome at a constant level (FIG. 62 and FIG. 63). In practice, uniformity can be difficult to attain because multiplexed Next Generation Sequencing (NGS) measurements typically yield low coverage (about 0.1) with sparsely scattered read start positions. In some embodiments, this problem is partially overcome by partitioning the genome into non-overlapping sections (bins) of equal lengths and assigning to each bin the number of the reads that align within it. In some embodiments, residual unevenness stemming from GC bias [Dohm J C, Lottaz C, Borodina T, Himmelbauer H. Substantial biases in ultra-short read data sets from high-throughput DNA sequencing. Nucleic Acids Res. 2008 September; 36(16):e105. Epub 2008 Jul. 26.] is largely suppressed using multiplicative detrending with respect to the binwise GC content (Fan HC, Quake SR (2010) Sensitivity of Noninvasive Prenatal Detection of Fetal Aneuploidy from Maternal Plasma Using Shotgun Sequencing Is Limited Only by Counting Statistics. PLoS ONE 5(5): e10439. doi:10.1371/journal.pone.0010439). In some embodiments, the resulting flattening of the count profile allows for successful classification of fetal trisomies in a clinical setting using quadruplex barcoding [Palomaki et al., DNA sequencing of maternal plasma to detect Down syndrome: an international clinical validation study. *Genet Med.*, 2011 November; 13(11):913-20.].

The transition from a quadruplex (i.e. 4 simultaneous sample reads) to higher sample plexing levels (e.g., dodecaplex (i.e. 12 simultaneous sample reads)) pushes the limits of NGS-based detection of genetic variations (e.g. aneuploidy, trisomy, and the like) in a test subject (e.g. a pregnant female), reducing both the number of reads per sample and the gap separating genetic variations (e.g. euploid from trisomy samples). The downsampling driven by increased multiplexing can impose new, more stringent requirements on data processing algorithms (FIG. 64, FIG. 65 and Example 4). In some embodiments, GC detrending, even when coupled with repeat masking, requires some improvement (FIG. 66, FIG. 67 and Example 4). In some embodiments, to maintain the sensitivity achieved with quadruplex barcoding (e.g., quadruplex indexing), methods and algorithms are presented that are capable of extracting a minute signal of interest from an overwhelming background noise as illustrated and described below and in FIG. 7, FIG. 8 and Example 4. In some embodiments, a novel method termed "PERUN" (Parameterized Error Removal and Unbiased Normalization) is described.

Conventional GC detrending can be multiplicative in nature (FIG. 17 and Example 4) and may not address additional sources of systematic bias, illustrated in FIG. 6. A reference median count profile constructed from a set of known euploid samples can eliminate additional bias and lead to qualitative improvements. In some instances, a reference median count profile constructed from a set of known euploid samples can inherit a mixture of residual GC biases from the reference samples. In some embodiments, a normalization removes one or more orthogonal types of bias by separating them from one another at the bin elevation, rather than tackling them in bulk. In some embodiments GC bias is removed and binwise separation of the GC bias from the position-dependent attenuation is achieved (FIG. 68. FIG. 69 and Example 4). In some embodiments, substantially increased gaps between euploid and trisomy Z-scores are obtained relative to both quadruplex and dodecaplex GCRM results. In some embodiments, maternal and fetal microdeletions and duplications are detected. In some embodiments fetal fractions are accurately measured. In some embodiments gender is determined reliably. In some embodiments sex aneuploidy (e.g. fetal sex aneuploidy) is identified.

PERUN Method and Definitions

In some embodiments the entire reference genome is partitioned into an ordered set B of J bins:

$$B=\{b_j|j=1,\ldots,J\} \tag{D}$$

Bin lengths can be constrained to accommodate genomic stretches of relatively uniform GC content. In some embodiments adjacent bins can overlap. In some embodiments adjacent bins do not overlap. In some embodiments the bin edges can be equidistant or can vary to offset systematic biases, such as nucleotide composition or signal attenuation. In some embodiments a bin comprises genomic positions within a single chromosome. Each bin $b_j$ is characterized by the GC content $$g_j^0$$

of the corresponding portion of the reference genome. In some embodiments, the $$g^0 = \lfloor g_1^0 \ g_2^0 \ \cdots \ g_J^0 \rfloor \quad \text{(E)}$$

The same $g^0$ profile can apply to all samples aligned to the chosen reference genome.

A proper or trivial subset of bins b, $$b \subseteq B \quad \text{(F)}$$

can be selected to satisfy certain criteria, such as to exclude bins with $$g_j^0 = 0,$$

bins with extreme $$g_j^0$$

values, bins characterized by low complexity or low mappability (Derrien T, Estelle' J, Marco Sola S, Knowles DG, Raineri E, et al. (2012) Fast Computation and Applications of Genome Mappability. PLoS ONE 7(1): e30377, doi: 10.1371/journal.pone.0030377), highly variable or otherwise uninformative bins, regions with consistently attenuated signal, observed maternal aberrations, or entire chromosomes (X, Y, triploid chromosomes, and/or chromosomes with extreme GC content). The symbol ||b|| denotes the size of b.

All sequenced reads from sample i unambiguously aligned within a bin $b_j$ form a set $a_{ij}$ whose cardinality $M_{ij}$ represents raw measured counts assigned to that bin. In some embodiments, the vector of measured bin counts for sample i constitutes the raw count profile for that sample. In some embodiments this is the primary observation for the purposes of PERUN:

$$M_i = [M_{i1} M_{i2} \ \cdots \ M_{iJ}] \quad \text{(G)}$$

To enable comparisons among different samples, the scaling constant $N_i$ is evaluated as the sum of raw bin counts over a subset of the bins:

$$N_i = \sum_{b \subseteq B} M_{ij} \quad \text{(H)}$$

In some embodiments b in Eq. H is restricted to autosomal bins. In some embodiments b in Eq. H is not restricted to autosomal bins. Division of $M_i$ by the total counts $N_i$ yields the scaled raw bin counts $m_{ij}$:

$$m_i[m_{i1} m_{i2} \ \cdots \ m_{iJ}] = M_i / N_i \quad \text{(I)}$$

The nucleotide composition of the set $a_{ij}$ is described by the bin's observed GC content $g_{ij}$. The sample-specific observed GC content profile $g_i$ gathers individual bin-specific GC contents into a vector:

$$g_i[g_{i1} g_{i2} \ \cdots \ g_{iJ}] \quad \text{(J)}$$

In some embodiments, $g_i \neq g^0$ and $g_{i_1} \neq g_{i_2 \neq i_1}$. The symbol g denotes the GC content profile regardless of its origin, i.e. whether it is derived from the reference genome or from the sample-specific read alignments. In some embodiments model equations use g. In some embodiments, actual implementations can substitute g with either $g^0$ or $g_i$.

For a single sample i, a linear relationship between $m_i$ and g is assumed, with $G_i$ and $r_i$ denoting the sample-specific slope of the regression line and the array of residuals, respectively:

$$m_i = G_i g + r_i \quad \text{(K)}$$

The regression can extend over the entire set B (Eq. D) or its proper subset b (Eq. F). The observed slope $G_i$ is also referred to as the scaled GC bias coefficient. $G_i$ expresses the bulk of the vulnerability of the sample i to the systematic GC bias. In some embodiments, to minimize the number of model parameters, higher-order terms, linked with curvature of the relationship $m_i$ (g) and encapsulated in the residuals $r_i$ are not explicitly addressed. In some embodiments, since sample-specific total counts $N_i$ confound the interactions among observables recorded on different samples, the unscaled equivalent of $G_i$, relating $M_i$ to g, is less useful and will not be considered.

The vector of true chromosomal elevations $l_{ij}$ corresponding to bins $b_j \in b$ in sample i form the sample-specific chromosomal elevation profile:

$$l_i[l_{i1} l_{i2} \ \cdots \ l_{iJ}] \quad \text{(L)}$$

In some embodiments, the goal is to derive estimates for $l_i$ from $m_i$ by removing systematic biases present in $m_i$.

The values $l_{ij}$ are bin-specific and also sample-specific. They comprise both maternal and fetal contributions, proportional to their respective ploidies $$P_{ij}^M \text{ and } P_{ij}^F.$$

The bin-specific and sample-specific ploidy $P_{ij}$ can be defined as an integral multiple of one-half, with the values of 1, ½, 0, 3/2, and 2 representing euploidy, heterozygous deletion, homozygous deletion, heterozygous duplication, and homozygous duplication, respectively. In some instances, trisomy of a given chromosome implies ploidy values of 3/2 along the entire chromosome or its substantial portion.

When both the mother and the fetus are diploid $$(P_{ij}^M = P_{ij}^F = 1),\ l_{ij}$$

equals some arbitrarily chosen euploid elevation E. In some embodiments, a convenient choice sets E to 1/||b||, thus ensuring that the profile $l_i$ is normalized. In the absence of bin selection, ||b||=||B||=J⇒E=1/J. In some embodiments, E can be set to 1 for visualization. In some embodiments, the following relationship is satisfied:

$$l_{ij} = E\left[(1-f_i)P_{ij}^M + f_i P_{ij}^F\right] \tag{M}$$

The symbol $f_i$ stands for the fraction of the fetal DNA present in the cell-free circulating DNA from maternal plasma in sample i. Any deviations from euploidy, either fetal $$(P_{ij}^F \neq 1)$$

or maternal $$(P_{ij}^M \neq 1),$$

cause differences between $l_{ij}$ and E that can be exploited to estimate $f_i$ and detect microdeletions/microduplications or trisomy.

To achieve the goal of extracting $l_i$ from $m_i$, a linear relationship is postulated between the bin-specific scaled raw counts $m_{ij}$ measured on a given sample and the sample-specific scaled GC bias coefficients:

$$m_i = l_i I + G_i S \tag{N}$$

The diagonal matrix I and the vector S gather bin-specific intercepts and slopes of the set of linear equations summarized by Eq. N:

$$I = \begin{bmatrix} I_1 & 0 & \cdots & 0 \\ 0 & I_2 & \cdots & 0 \\ \vdots & \vdots & \ddots & \vdots \\ 0 & 0 & \cdots & I_J \end{bmatrix} \tag{O}$$

$$S = [S_1\ S_2\ \cdots\ S_J] \tag{P}$$

Both I and S are sample-independent. The intercepts $I_j$ can be viewed as expected euploid values for scaled row counts in the absence of GC bias (i.e. when $G_i$=0). Their actual values reflect the convention and for E (vide supra). The intercepts $S_j$ are non-linearly related to the differences $$g_j^0 - \langle g_k^0 \rangle, \text{ where } \langle g_k^0 \rangle$$

represents the median GC content of the chromosome containing the bin j.

Once the values for the parameters I and S are known, the true chromosomal elevation profile $l_i$ is estimated from the scaled raw count profile $m_i$ and the scaled GC bias coefficient $G_i$ by rearranging Eq. N:

$$l_i = (m_i - G_i S)I^{-1} \tag{Q}$$

The diagonal character of the intercept matrix I provides for the matrix inversion in Eq. Q.

Parameter Estimation

Model parameters I and S are evaluated from a set of N scaled raw count profiles collected on samples karyotyped as euploid pregnancies. N is of the order of $10^3$. Scaled GC bias coefficients $G_i$ are determined for each sample (i=1, . . . , N). All samples are segregated into a small number of classes according to the sizes and signs of their $G_i$ values. The stratification balances the opposing needs to include sufficiently large numbers of representatives and a sufficiently small range of $G_i$ values within each shell. The compromise of four strata accommodates negative, near-zero, moderately positive, and extreme positive GC biases, with the near-zero shell being most densely populated. A fraction of samples (typically 10%) from each stratum can be randomly selected and set aside for cross-validation. The remaining samples make up the work set, used to train the model. Both the training and the subsequent cross-validation assume that all samples are free of maternal and fetal deletions or duplications along the entire genome:

$$P_{ij}^M = P_{ij}^F = 1,\ \forall\, i = 1, \ldots N,\ \forall\, j = 1, \ldots, J \tag{R}$$

The large number of samples compensates for the occasional maternal deviations from the assumption R. For each bin j, $l_{ij}$ is set to E, allowing evaluation of the intercept $I_j$ and the slope $S_j$ as the coefficients of the linear regression applied to the training set according to Eq. N. The uncertainty estimates for $I_j$ and $S_j$ are recorded as well.

The random partitioning into the working and the cross-validation subsets is repeated multiple times (e.g. $10^2$), yielding distributions of values for the $I_j$ and $S_j$ parameters. In some embodiments the random partitioning is repeated between about 10 and about $10^5$ times. In some embodiments the random partitioning is repeated about 10, about $10^2$, about $10^3$, about $10^4$ or about $10^5$ times.

Cross-Validation

Once derived from the work set, the model parameters $I_j$ and $S_j$ are employed to back-calculate scaled raw counts from the scaled GC bias coefficients using Eq. N and assumption R. The symbol $p_{ij}$ denotes the predicted scaled raw counts for the bin $b_j$ in the sample i. The indices W and CV in further text designate the work and the cross-validation subsets, respectively. The back-calculation is applied to all samples, both from W and CV. R-factors, borrowed from the crystallographic structure refinement practice (Brunger, Free R value: a novel statistical quantity for assessing the accuracy of crystal structures, *Nature* 355, 472-475 (30 Jan. 1992); doi:10.1038/355472a0), are separately defined for the two subsets of samples:

$$R_j^W = \frac{\sum_{i \in W} |m_{ij} - p_{ij}|}{\sum_{i \in W} |m_{ij}|} \quad \text{(S)}$$

$$R_j^{CV} = \frac{\sum_{i \in CV} |m_{ij} - p_{ij}|}{\sum_{i \in CV} |m_{ij}|} \quad \text{(T)}$$

Both R-factors are bin-specific. As in crystallography, R-factors 16-17 can be interpreted as residual relative errors in the model. Having been excluded from the parameter estimation, the cross-validation R-factor $$R_j^{CV}$$

provides a true measure of the error for the given W/CV division, while the difference between $$R_j^{CV} \text{ and } R_j^W$$

reflects the model bias for the bin j. A separate pair of R-values is evaluated for each bin and for each random partitioning of the set of samples into W and CV. The maximum of all $$R_j^{CV} \text{ and } R_j^W$$

values obtained for the different random partitionings into W and CV is assigned to the bin j as its overall model error $\varepsilon_j$.

Bin Selection

All the bins with zero GC content $$g_j^0$$

are eliminated from further consideration, as is the set $\{b_j:M_{ij} \equiv 0, \forall i=1, \ldots, N\}$ of bins that consistently receive zero counts across a large number of samples. In addition, a maximum tolerable cross-validation error value ε can be imposed on all bins. In some embodiments the bins with model errors $\varepsilon_j$ exceeding the upper limit E are rejected. In some embodiments, filtering uses bin mappability scores $\mu_j \in [0,1]$ and imposes a minimum acceptable mappability μ, rejecting bins with $\mu_j < \mu$ (Derrien T, Estelle' J, Marco Sola S, Knowles DG, Raineri E, et al. (2012) Fast Computation and Applications of Genome Mappability. PLoS ONE 7(1): e30377, doi:10.1371/journal.pone.0030377). For the purposes of determining fetal trisomy of chromosomes 21, 18, and 13, the sex chromosomes can be excluded as well. The subset β of bins that survive all the phases of the bin selection can undergo further computations. In some embodiments, the same subset β is used for all samples.

Normalization and Standardization

In some embodiments, for a given sample i, the chromosomal elevations $l_{ij}$ corresponding to the bin selection β are estimated according to Eq. Q. In some embodiments, a secondary normalization is applied to remove any curvature from the $l_{ij}$-vs.-GC content correlation. In some embodiments $l_{ij}$ is already nearly unbiased, the secondary detrending is robust and is immune to error boosting. In some embodiments, standard textbook procedures suffice.

In some embodiments, the results of the normalization are summed up within each chromosome:

$$L_{in} = \sum_{b_j \in \beta \cap Chr_n} l_{ij}, \, n = 1, \ldots, 22 \quad \text{(U)}$$

The total autosomal material in sample i can be evaluated as the sum of all individual $L_{in}$ terms:

$$L_i = \sum_{n=1}^{22} L_{in} \quad \text{(V)}$$

The chromosomal representation of each chromosome of interest can be obtained by dividing $L_{in}$ with $L_i$:

$$\chi_{in} = L_{in} / L_i \quad \text{(W)}$$

The variability $\sigma_n$ of the representation of the chromosome n can be estimated as an uncensored MAD of $\chi_{in}$ values across a election of samples spanning multiple flow cells. In some embodiments, the expectation $\langle \chi_n \rangle$ is evaluated as the median of $\chi_{in}$ values corresponding to a selection of samples from the same flow cell as the tested sample. Both sample selections can exclude high positive controls, low positive controls, high negative controls, blanks, samples that fail QC criteria, and samples with $SD(l_i)$ exceeding a predefined cutoff (typically 0.10). Together, the values $\sigma_n$ and $\langle \chi_n \rangle$ can provide the context for standardization and comparison of chromosomal representations among different samples using Z-scores:

$$Z_{in} = (\chi_{in} - \langle \chi_n \rangle) / \sigma_n \quad \text{(X)}$$

In some embodiments, aberrations such as trisomies 13, 18, and 21 are indicated by Z-values exceeding a predefined value, dictated by the desired confidence level.

Example 6: Examples of Formulas

Provided below are non-limiting examples of mathematical and/or statistical formulas that can be used in methods described herein.

$$Z = \frac{\Delta_1 - \Delta_2}{\sqrt{\sigma_1^2\left(\frac{1}{N_1} + \frac{1}{n_1}\right) + \sigma_2^2\left(\frac{1}{N_2} + \frac{1}{n_2}\right)}}$$

$$P(q) = \frac{1}{\sigma\sqrt{2\pi}} \exp\left[-(q - q_0)/(2\sigma^2)\right]$$

-continued $$q_0 = 1 + F/2$$

$$z = -F/(2\sigma\sqrt{2})$$

$$B = \int_{-\infty}^{1} P(q)dq = \frac{1}{2}[1 + \text{erf}(z)]$$

$$\text{erf}(z) = \frac{2}{\sqrt{\pi}} \sum_{n=0}^{\infty} \frac{(-1)^n z^{2n+1}}{n!(2n+1)}$$

$$R = \frac{1-B}{B} = \frac{1-\text{erf}(z)}{1+\text{erf}(z)} = \frac{1-\text{erf}[-F/(2\sigma\sqrt{2})]}{1+\text{erf}[-F/(2\sigma\sqrt{2})]}$$

Example 7: Identifying and Adjusting (Padding) Elevations

Maternal deletions and duplications, often represented as first elevations in a profile, can be removed from count profiles normalized with PERUN to reduce variability when detecting T21, T18, or T13. The removal of deletions and duplication from a profile can reduce the variability (e.g., biological variability) found in measured chromosomal representations that originates from maternal aberrations.

All bins that significantly deviate from the expected chromosomal elevation of 1 are first identified. In this example some isolated bins are removed from the selection. This is optional. In this example only large enough groups of contiguous outlier bins are kept. This is also optional. Depending on the elevation assigned to an outlier bin or a group of contiguous outlier bins, a correction factor is added to the measured elevation to adjust it closer to the expected elevation of 1. The PAV values used in this example are +1 (for homozygous maternal deletions), +0.5 (for heterozygous maternal deletions), −0.5 (for heterozygous duplications), −1 (for homozygous duplications), or more (for large spikes). Large spikes are often not identified as maternal deletions and duplications.

This padding procedure corrected the classification (e.g., the classification as an aneuploidy, e.g., a trisomy) for samples that contains large maternal aberrations. Padding converted the WI sample from false positive T13 to true negative due to removal of a large maternal deletion in Chr4 (FIG. 112-115).

Past simulations with experimental data have shown that depending on the chromosome, fetal fraction, and the type of aberration (homozygous or heterozygous, duplication or deletion), maternal aberrations in 20-40 bins long may push the Z-value over the classification edge (e.g., threshold) and result in a false positive or a false negative. Padding (e.g., adjusting) can circumvent this risk.

This padding procedure can remove uninteresting maternal aberrations (a confounding factor), reduce euploid variability, create tighter sigma-values used to standardize Z-scores and therefore enlarge the gap between euploids and trisomy cases.

Example 8: Determining Fetal Fractions from Maternal and/or Fetal Copy Number Variations A distinguishing feature of the method described herein is the use of maternal aberrations (e.g., maternal and/or fetal copy number variations) as a probe providing insight into the fetal fraction in the case of a pregnant female bearing a fetus (e.g., a euploid fetus). The detection and quantitation of maternal aberrations typically is aided by normalization of raw counts. In this example raw counts are normalized using PERUN. Alternatively, normalization with respect to a reference median count profile can be used in a similar manner and for the same purpose.

PERUN normalization of raw counts yields sample-specific binwise chromosomal levels $l_{ij}$ (i counts samples, j counts bins). They comprise both maternal and fetal contributions, proportional to their respective ploidy $$P_{ij}^M \text{ and } P_{ij}^F.$$

The bin-specific and sample-specific ploidy $P_{ij}$ is defined as an integral multiple of ½, with the values of 1, ½, 0, 3/2, and 2 representing euploidy, heterozygous deletion, homozygous deletion, heterozygous duplication, and homozygous duplication, respectively. In particular, trisomy of a given chromosome implies ploidy values of 3/2 along the entire chromosome or its substantial portion.

When both the mother and the fetus are diploid $$(P_{ij}^M = P_{ij}^F = 1),\ l_{ij}$$

equals some arbitrarily chosen euploid level E. A convenient choice sets E to 1/||b||, where b denotes a proper or trivial subset of the set of all bins (B). thus ensuring that the profile $l_i$ is normalized. In the absence of bin selection, ||b||=||B||=J⇒E=1/J. Alternatively and preferentially, E may be set to 1 for visualization. In general, the following relationship is satisfied:

$$l_{ij} = E\lfloor(1-f_i)P_{ij}^M + f_i P_{ij}^F\rfloor \tag{Y}$$

The symbol $f_i$ stands for the fraction of the fetal DNA present in the cell-free circulating DNA from maternal plasma in sample i. Any deviations from euploidy, either fetal $$(P_{ij}^F \neq 1)$$

or maternal $$(P_{ij}^M \neq 1),$$

cause differences between $l_{ij}$ and E that can be exploited to estimate $f_i$ and detect microdeletions/microduplications or trisomy.

Four different types of maternal aberrations are considered separately. All four account for possible fetal genotypes, as the fetus may (or in homozygous cases must) inherit the maternal aberration. In addition, the fetus may inherit a matching aberration from the father as well. In general, fetal fraction can only be measured when $$P_{ij}^M \neq P_{ij}^F.$$

A) Homozygous maternal deletion $$(P_{ij}^{M}=0).$$

Two possible accompanying fetal ploidies include:

a.

$$P_{ij}^{F}=0,$$

in which case $l_{ij}=0$ and the fetal fraction cannot be evaluated from the deletion.

b.

$$P_{ij}^{F}=1/2,$$

in which case $l_{ij}=f_i/2$ and the fetal fraction is evaluated as twice the average elevation within the deletion.

B) Heterozygous maternal deletion $$(P_{ij}^{M}=1/2).$$

Three possible accompanying fetal ploidies include:

a.

$$P_{ij}^{F}=0,$$

in which case $l_{ij}=(1-f_i)/2$ and the fetal fraction is evaluated as twice the difference between ½ and the average elevation within the deletion.

b.

$$P_{ij}^{F}=1/2,$$

in which case $l_{ij}=½$ and the fetal fraction cannot be evaluated from the deletion.

c.

$$P_{ij}^{F}=1,$$

in which case $l_{ij}=(1+f_i)/2$ and the fetal fraction is evaluated as twice the difference between ½ and the average elevation within the deletion.

C) Heterozygous maternal duplication $$(P_{ij}^{M}=3/2).$$

Three possible accompanying fetal ploidies include:

a.

$$P_{ij}^{F}=1,$$

in which case $l_{ij}=(3-f_i)/2$ and the fetal fraction is evaluated as twice the difference between 3/2 and the average elevation within the duplication.

b.

$$P_{ij}^{F}=3/2,$$

in which case $l_{ij}=3/2$ and the fetal fraction cannot be evaluated from the duplication.

c.

$$P_{ij}^{F}=2,$$

in which case $l_{ij}=(3+f_i)/2$ and the fetal fraction is evaluated as twice the difference between 3/2 and the average elevation within the duplication.

D) Homozygous maternal duplication $$(P_{ij}^{M}=2).$$

Two possible accompanying fetal ploidies include:

a.

$$P_{ij}^{F}=2,$$

in which case $l_{ij}=2$ and the fetal fraction cannot be evaluated from the duplication.

b.

$$P_{ij}^{F}=3/2,$$

in which case $l_{ij}=2-f_i/2$ and the fetal fraction is evaluated as twice the difference between 2 and the average elevation within the duplication.

The following LDTv2CE samples (FIG. 116-131) illustrate the application of determining fetal fraction from maternal and/or fetal copy number variations. The patients were not selected randomly and any agreement with FQA fetal fraction values should not be construed as the measure of merit of either technique.

Example 9: Karyotype Determinations Using Normalized Read Counts Mapped to Chromosome X and Chromosome Y In this example, maternal samples containing cell-free nucleic acid were classified as carrying a fetus with a karyotype of XX (euploid female), XY (euploid male), XXX (Triple X Syndrome), X (Turner Syndrome), XXY (Klinefelter Syndrome), or XYY (Jacobs Syndrome) based on nucleotide sequence read counts mapped to chromosome X (ChrX) and chromosome Y (ChrY). Samples were obtained from the Women and Infants Hospital (WI study;

Palomaki et al. (2011) Genet. Med. 13(11):913-20). Nucleotide sequence reads for each sample were obtained using an Illumina HISEQ 2000 platform (Illumina, Inc., San Diego, CA). In some instances, nucleotide sequence reads were aligned to a reference genome (build 37 (hg19)) using a BOWTIE 2 aligner. In some instances, nucleotide sequence reads were aligned to a reference genome using the ELAND aligner.

PERUN was used to normalize read counts for both chromosome X and chromosome Y. Genomic section (e.g., bin) parameters for chromosome Y were derived from 20 adult male controls. Genomic section (e.g., bin) parameters for chromosome X were derived from sample measurements from pregnant females carrying female fetuses (female pregnancies). About 300 chromosome Y bins where the median male pregnancy counts exceeded median female pregnancy counts by a factor of 6 or more were selected. In some instances, 226 chromosome Y bins were selected. Genomic section levels (L) were determined for chromosome X genomic sections and chromosome Y genomic sections for each sample according to the formula: $L_i=(m_i-G_iS)I^{-1}$, as defined herein.

In some instances, PERUN-normalized autosomal counts were used as a reference for additional GC smoothing. Such additional GC smoothing was applied to chromosome X, and not to chromosome Y, to remove residual systematic GC bias left after PERUN normalization, in some instances. Autosomal elevations (e.g., nucleotide sequence read counts or derivative thereof (e.g., L values)) and chromosome X (ChrX) elevations (e.g., L values) were plotted against GC content. The LOESS smoothing, which included autosomal counts, describing a trend was used to rectify chromosome X data (i.e., remove any residual trend). In this case, the implemented correction was multiplicative, with very few bins deviating significantly from 1.

Chromosome X bins (nearly 2800 bins) were selected based on PERUN cross-validation errors. Specifically, chromosome X bins having cross-validation errors exceeding 7% were removed from analysis. The success of the chromosome Y classification depended, in part, on the selection of male-specific chromosome Y bins.

Chromosome X representations were calculated according to the following formula:

$$\left(\sum L \text{ values for } ChrX\right)/\left(\sum L \text{ values for autosomes}\right)$$

Chromosome Y representations were calculated according to the following formula:

$$\left(\sum L \text{ values for } ChrY\right)/\left(\sum L \text{ values for autosomes}\right)$$

where L is defined above as a genomic section level.

Median (i.e., a value separating the higher half of chromosome representation values from the lower half; the median of chromosome representation values can be determined, in some instances, by arranging the values from lowest value to highest value and selecting the middle one or calculating the mean of the two middle values) and median absolute deviation (MAD) values were calculated for chromosome X representations (ChrX median; MAD ChrX) for female pregnancies and chromosome Y representations (ChrY median; MAD ChrY) for female pregnancies. Median and MAD values were used to standardize all chromosome X and chromosome Y representations for samples from the WI study. Median and MAD statistics for both chromosome X and chromosome Y were based on an XX karyotype null hypothesis. Z scores for chromosome X and chromosome Y were calculated for each sample according to the formulas below and plotted as Z score chromosome Y (y-axis) versus Z score chromosome X score (x-axis) shown in FIG. 132.

For chromosome X:

$$Z\text{-score} = \frac{[(\text{sample } ChrX \text{ representation}) - (ChrX \text{ median for female pregnancies})]}{(MAD\ ChrX \text{ for female pregnancies})}$$

For chromosome Y:

$$Z\text{-score} = \frac{[(\text{sample } ChrY \text{ representation}) - (ChrY \text{ median for female pregnancies})]}{(MAD\ ChrY \text{ for female pregnancies})}$$

The resulting plot showed that plot points for samples having certain fetal karyotypes (e.g., normal karyotypes and various sex chromosome aneuploidy karyotypes) segregated to substantially distinct areas of the graph. For example, the plot of the resulting Y chromosome Z scores versus X chromosome Z scores segregated various karyotypes as follows: XX karyotype (euploid female fetuses) at the origin; XY karyotype (euploid male fetuses) along the main diagonal, second quadrant (negative X-axis, positive Y-axis); XXX karyotype (Triple X Syndrome) along the positive X-axis; X karyotype (Turner Syndrome) along the negative X-axis; XXY karyotype (Klinefelter Syndrome) along the positive Y-axis; XYY karyotype (Jacobs Syndrome) along the secondary diagonal, second quadrant, having a slope about twice as large as the slope for euploid male pregnancies.

The segregation of karyotypes is illustrated in FIG. 132. Karyotype classification decisions were made by carving the plane into karyotype-specific areas as dictated by the chromosome X and chromosome Y spreads. FIG. 133 illustrates certain karyotype-specific areas on a plot of chromosome X means versus chromosome Y means. FIG. 135 illustrates XX and XY specific (e.g., gender determinative) areas on a plot of chromosome X means versus chromosome Y means. Karyotype classification decisions were compared to a karyotype truth table provided by the Women and Infants Hospital (WI study; FIG. 134).

Example 10: Noninvasive Prenatal Detection of Sex Chromosomal Aneuploidies by Sequencing Circulating Cell-Free DNA from Maternal Plasma In this example, a comprehensive bioinformatics model was used to demonstrate accurate detection of certain sex chromosome aneuploidies (SCA) through whole-genome massively parallel sequencing. The SCA detection method can complement other methods for detection of autosomal trisomies. For example, whole-genome sequencing of circulating cell free (ccf) DNA from maternal plasma has enabled noninvasive prenatal testing for certain autosomal aneuploidies. In this example, detection was extended to include certain sex chromosome aneuploidies: Trisomy X [47,XXX], Turner [45,X], Klinefelter [47,XXY], and [47, XYY] syndromes. A training set was established for SCA detection and for testing of a newly developed assay and algorithm on a blinded validation set. In this example, SCAs were detected noninvasively with high sensitivity and a low false positive rate.

Methods

Massively parallel sequencing using an improved assay format was performed on ccf DNA isolated from the plasma of 1564 pregnant women with known fetal karyotype. Data from this cohort were used as a training set to construct a classification algorithm for sex chromosome aneuploidy detection. A separate study of 420 maternal samples from women with blinded-to-laboratory fetal karyotypes was then performed to determine the accuracy of the classification algorithm.

Study Design and Sample Collection

A training cohort was composed of frozen plasma sample aliquots from 1564 pregnant women collected as part of an independently developed and coordinated study (Palomaki et al. (2011) Genet Med 13:913-20; Palomaki et al. (2012) Genet Med 14:296-305; Canick et al. (2012) Prenat Diagn 32:730-4). These samples were selected from a residual bank of aliquots collected for a prior nested case-control study of pregnant women at high risk for fetal aneuploidy. Samples involved were collected between 10.5 and 20 weeks gestation, prior to invasive amniocentesis or chorionic villus sampling (CVS). Karyotype results, including sex chromosomal abnormalities, were obtained for all samples. This cohort was employed as part of a laboratory development process of an improved assay for detection of autosomal aneuploidy. A separate blinded clinical validation cohort included samples from 420 pregnancies, and was collected within a similar gestational period (i.e., from pregnant women at high risk for fetal aneuploidy and prior to invasive sampling). Demographic information for these samples is presented in FIG. 137.

Samples from patients with multiple gestations, mosaic for sex chromosomes, or having no documented karyotype report available were excluded from the clinical performance analysis (n=9). The remaining set of 411 samples included 21 [45,X] samples, 1 [47,XXX] sample, 5 [47, XXY] samples and 3 [47,XYY] samples. All samples used for the validation cohort had at least two 4 mL plasma aliquots available per patient.

Samples were obtained from subjects 18 years of age or older who provided Institutional Review Board (or equivalent) approved informed consent. Samples for the training cohort were collected as described in Palomaki et al. (2011) Genet Med 13:913-20. Samples for the validation cohort were collected under the following Investigational Review Board approved clinical studies: Western IRB no. 20091396, Western IRB no. 20080757, Compass IRB no. 00351.

Blood Collection and Plasma Fractionation

Up to 50 mL of whole blood was collected from patients into EDTA-K2 spray-dried 10 mL Vacutainers (EDTA tubes; Becton Dickinson, Franklin Lakes, NJ). Whole blood samples were refrigerated or stored on wet ice and were processed to plasma within 6 hours of the blood draw. The maternal whole blood in EDTA tubes was centrifuged (EPPENDORF 5810R plus swing out rotor) at 4° C. at 2500 g for 10 minutes, and the plasma was collected. The EDTA plasma was centrifuged a second time (EPPENDORF 5810R plus fixed angle rotor) at 4° C. at 15,500 g for 10 minutes. After the second spin, the EDTA plasma was removed from the pellet that formed at the bottom of the tube and distributed into 4 mL barcoded plasma aliquots and immediately stored frozen at less than or equal to −70° C. until DNA extraction.

Circulating Cell Free (Ccf) Plasma DNA Isolation and Purification

Circulating cell free (ccf) DNA was isolated from up to 4 mL plasma using the QIAAMP Circulating Nucleic Acid Kit (QIAGEN Inc., Valencia, CA) as described, for example, in Chiu et al. (2009) Clin Chem 56:459-63 and Nygren et al. (2010) Clin Chem 56:1627-35. A minimum of 3.5 mL initial plasma volume was required for final classification of fetal sex chromosome aneuploidy (SCA). The ccf DNA was eluted in a final volume of 55 μL.

The quantity of ccf DNA in each sample was assessed using the Fetal Quantifier Assay (FQA) as described, for example, in Nygren et al. (2010) Clin Chem 56:1627-35; Ehrich et al. (2011) Am J Obstet Gynecol 204:205.e1-.e11; and Palomaki et al. (2011) Genet Med 13:913-20.

Sequencing Library Preparation

Circulating cell-free DNA libraries were prepared in 96-well plate format from 40 μL of ccf DNA per donor following the Illumina TRUSEQ library preparation protocol (Illumina, Inc., San Diego, CA) with AMPURE XP magnetic bead clean-up (Beckman Coulter, Inc., Brea, CA) on a CALIPER ZEPHYR liquid handler (PerkinElmer Inc., Santa Clara, CA). TRUSEQ indexes 1 through 12 were incorporated into libraries. No size fractionation of ccf DNA libraries was required due to the characteristic fragmentation of ccf DNA. Libraries were quantified on the CALIPER LABCHIP GX (PerkinElmer Inc., Santa Clara, CA) and normalized to the same concentration.

Multiplexing, Clustering and Sequencing

The ccf DNA libraries were pooled row-wise at a 12-plex level, clustered to Illumina HISEQ 2000 v3 flow cells, and the ccf DNA insert sequenced for 36 cycles on a HISEQ 2000. Index sequences were identified with 7 cycles of sequencing.

Quality Control

Prior to sequencing, each sample library was assessed for DNA content. The results were translated to a concentration measure. Samples with the DNA concentrations greater than 7.5 nM/L were accepted in the final analysis. Samples with fetal DNA fractions less than the detection limit of 4% were rejected. Furthermore, since the contribution of the fetal DNA in the maternal plasma typically is less than 50%, samples with reported fetal fraction exceeding 50% were deemed invalid and were also excluded. In order to assure quality of the sequencing step, a set of post-sequencing quality control (QC) metrics were imposed. The QC criteria included (a) a minimum number of total sequenced reads per sample, (b) a lower cut-off for the aligned reads partitioned into 50 kBp sections as filtered for the sections with repeated DNA sequences, subjected to GC content correction, and divided by the total raw counts, and (c) the observed curvature of the counts-versus-GC content estimated in the context of the 50 kBp sections.

Bioinformatics Analysis

Following sequencing, adapters were removed from the qualified reads. The reads were then de-multiplexed according to their barcodes and aligned to human reference genome build 37 (hg.19) using the BOWTIE 2 short read aligner. Only perfect matches within the seed regions were allowed for the final analysis.

To remove systematic biases from raw measurements, a normalization procedure was applied to sex chromosomes. All chromosomes were partitioned into contiguous, non-overlapping 50 kBp genomic sections and parameterized. The normalization parameters for chromosome X were derived from a subset of 480 euploid samples corresponding to known female fetuses. Filtering of genomic sections yielded a subsection comprising 76.7% of chromosome X. This subsection was employed to quantify the amount of chromosome X present in the sample. A similar procedure was used for chromosome Y, using a separate training set of 23 pooled adult male samples. A subset of sections representing 2.2% of chromosome Y was found to be specific to males. Those sections were then used to quantify the representation of chromosome Y. The normalization method used for genomic section selection also enabled detection of sub-chromosomal abnormalities and generally did not depend on any study-specific optimized normalized chromosomal ratio.

To remove systematic biases from raw measurements, in some instances, a parameterized error removal and unbiased normalization (PERUN) protocol, as described herein, was applied to sex chromosomes. Both chromosomes X and Y were partitioned into contiguous, non-overlapping 50 kBp genomic sections and parameterized as described herein for autosomes. The parameterization and normalization began by extracting the GC content of each section from the reference human genome. For each sequenced sample, linear regression was applied to the measured numbers of aligned reads per section (counts) as a function of the section-specific GC content. Sections which exhibited outlier behavior in either counts or GC content were not included in the linear model. Sample-specific GC bias coefficients were evaluated as the slopes of the straight lines relating the counts to the GC content. For each genomic section, a regression of measured read counts versus sample-specific GC bias coefficient values yielded the section-specific model parameters. The parameters were employed to flatten the systematic variations in measured read counts.

Model parameters for chromosome X were derived from 752 euploid samples corresponding to female fetuses. Section filtering for chromosome X was based on 10-fold cross-validation, stratified with respect to the levels of the GC bias coefficient. The final genomic section selection represented 76.7% of chromosome X and was used to evaluate chromosome X representation.

Model parameters for chromosome Y were extracted from a separate set of adult male samples. To identify informative chromosome Y sections, all euploid count profiles were first normalized according to the PERUN procedure. For each chromosome Y section, the median and mean absolute deviation (MAD) of the normalized counts were calculated for the subset of 752 female samples and for the subset of 757 male samples. The two medians and MADs were then combined to yield a single, section-specific t-statistic value. A subset of sections representing 2.2% of chromosome Y generated t-values that exceeded a predefined cutoff of 50. Those sections were used to evaluate the representation of chromosome Y.

Classification Method

The sex chromosome aneuploidy (SCA) detection method herein generally is sex-specific. Fetal sex was predicted using a massively parallel sequencing method. SCA was then assessed separately for male and female pregnancies. X chromosome aneuploidies ([45,X] and [47,XXX]) were considered for putative female fetuses, while Y chromosome aneuploidies ([47,XXY] and [47,XYY]) were evaluated for putative male fetuses. For both sexes, chromosome representations were evaluated as the ratios of normalized chromosome X and Y read counts in the genomic sections described above, versus the total autosomal read counts.

Samples identified as representing female fetuses were labeled as [XX] if they fell within a range compatible with the [46,XX] samples from the training set. Under-representation of chromosome X led to a labeling of [45,X] while over-representation of chromosome X led to a labeling of [47,XXX]. To avoid maternal interference with the chromosome X fetal sex aneuploidy calls, lower and upper boundaries were enforced on chromosome X representations for the prediction of [45,X] and [47,XXX]. Such lower and upper thresholds were determined by calculating the maximum theoretical chromosomal representation of a sample with 70% fetal fraction. Determination of SCA for the putative female samples for which the chromosome X representation fell within borderline ranges was not performed. In z-score space, these ranges corresponded to [−3.5; −2.5] and [2.5; 3.5].

Samples identified as representing male fetuses were labeled as [XY] provided they followed a pattern of chromosome X and Y distribution compatible with the [46,XY] samples in the training set. Over-representation of chromosome X in putative male samples, if comparable with the distribution of chromosome X for [46,XX] samples, led to a labeling of [47,XXY]. Over-representation of chromosome Y in putative male samples led to a labeling of [47,XYY]. Determination of SCA was not performed for putative male samples for which the fetal contribution was insufficient.

A non-reportable category included samples affected either by analytical failures (fetal fraction less than 4% or greater than 50%, library concentration less than 7.5 nM/L, or QC requirements not satisfied), or by a region in which a sex aneuploidy assessment cannot be performed. Such regions are described in further detail in Example 11.

Sex Chromosome Aneuploidy Detection in the Training Set

The performance of the classification method herein is summarized in FIG. 138. Data for the training set are shown in FIG. 143 (panels A and B). In this set, there were 740 samples with a karyotype result that indicated female sex and data that allowed for assessment of fetal sex aneuploidy. Of these, 732 were correctly classified (720 XX, 8 X, 4 XXX) while 8 reportedly euploid samples were not classified as XX (3 were identified as X, 1 as XXX and 4 as XY). Additionally there were 729 samples with a karyotype result that indicated male sex. Of these, 725 were correctly classified (718 XY, 6 XXY, and 1 XYY) while 4 euploid male samples were annotated as euploid female samples. Thus, overall sensitivity for the detection of SCA was 100% (95% confidence interval 82.3%-100%) and specificity was 99.9% (95% confidence interval 99.7%-100%). The non-reportable rate relating to SCA determination was 6%.

Sex Chromosome Aneuploidy Detection in the Validation Set

Data for the validation set are shown in FIG. 143 (panels C and D). In this set, there were 191 samples with a karyotype result that indicated female sex and data that allowed for assessment of fetal sex aneuploidy. Of these, a total of 185 were correctly classified (167 XX, 17 X, 1 XXX). There was 1 false positive and 1 false negative for [45,X], and 4 XX samples were predicted to be XY. Of the 199 samples with a karyotype result indicating male sex, 198 were correctly classified (191 XY, 5 XXY, 2 XYY) and 1 was annotated as a female sample. Thus the overall sensitivity for the detection of SCA was 96.2% (95% confidence interval 78.4%-99.8%) and the specificity was 99.7% (95% confidence interval 98.2%-100%). The non-reportable rate relating to SCA determination was 5%.

The results from the training set were comparable with the results from the validation set. The non-reportable rate was higher among samples pertaining to male fetuses. This was likely due to inclusion of fewer genomic sections from chromosome Y, which lead to a weaker signal-to-noise ratio.

CONCLUSION

The method presented in this example for detection of fetal sex chromosome aneuploidies (SCA) had a combined sensitivity of 96.2% and specificity of 99.7% with a non-reportable rate of 5%. Thus, noninvasive prenatal testing (NIPT), which can be used for detecting certain autosomal trisomies, also can be used for detecting certain sex chromosome aneuploidies with a high detection rate and a low false positive rate.

Example 11: Non-Reportable Zones for PERUN-Based Chromosomal Representations of Chromosomes X and Y This example describes a method for determining non-reportable (i.e., no-call) zones for sex chromosome aneuploidy (SCA) detection Distribution of Chromosome X Representations The distribution of chromosome X representations for euploid female pregnancies in the training cohort (shown in a comparative manner to the normal distribution by means of a quintile-quintile plot in FIG. 139) was markedly asymmetrical, with a heavy tail on the left. The observed skew may have resulted from putative maternal and/or fetal mosaicism of monosomy X, as well as technological imperfections (GC bias and other systematic errors). Such distribution can increase the complexity associated with detection of fetal chromosome X abnormalities. For example, the deviation from the Gaussian distribution can reduce the classification accuracy in certain female pregnancies with marginal chromosome X representations (near the [45,X] and [47,XXX] cutoffs, i.e. ±3σ □ away from the mode of the distribution). Consequently, most misclassified female pregnancies from the training set were located close to the two cutoffs.

Standardized Chromosome X Representations

To express chromosome X representations in terms of standardized Z-scores, the width of a censored chromosome X distribution was estimated for normal female samples from the training set. First, a linear model was established relating the theoretical standard normal quintiles (the predictor) to the observed chromosome X quintiles (the response variable). FIG. 140 illustrates the distribution of the residuals from the point estimates based on the linear model. The samples whose residuals deviated more than 5σ to the left or more than 3σ to the right of mode of the distribution (FIG. 140, horizontal lines) were excluded, yielding a censored distribution of the chromosome X representation. The unbiased width, ŝ, of this censored distribution was then used to standardize female chromosome X representations as follows:

$$Z_X = \frac{chrX - \hat{X}}{\hat{s}}$$

In the above equation, chrX is the chromosome X representation for female pregnancies, $Z_X$ is the standardized equivalent of chrX, $\hat{X}$ represents the median of chrX, and $\hat{s}$ stands for the median absolute deviation of the censored distribution of chromosome X representations.

Non-Reportable SCA Zones for Female Pregnancies

To illustrate the complexity of chromosome X aneuploidy detection and to avoid misclassification of female sex aneuploidies, two non-reportable regions were introduced, centered on the ±3 cutoffs on the $Z_X$ scale. The two non-reportable regions included $Z_X$ values within the segments ±[2.5, 3.5]. The female pregnancies with chromosome X representations within these two regions were considered unclassifiable (i.e., non-reportable) for sex aneuploidies (FIG. 141, shaded regions).

Non-Reportable SCA Zones for Male Pregnancies

Classification of a male fetus as normal [46,XY] or aneuploid (Klinefelter syndrome, [47,XXY]; or Jacobs syndrome, [47,XYY]) with respect to chromosome Y relied on both X and Y chromosomal representations. The depletion of chromosome X in normal male fetuses typically is accompanied by the proportional elevation of chromosome Y. Doubling of the ratio between chromosomes Y and X indicated a [47,XYY] fetal aneuploidy (Jacobs syndrome). An elevation of chromosome Y in the absence of chromosome X depletion indicated a [47,XXY] fetal aneuploidy (Klinefelter syndrome). A two-dimensional XY scatter plot relating the two chromosomal representations (chromosome X on the abscissa (i.e. x-axis) and chromosome Y on the ordinate (i.e. y-axis) formed the basis of a classifier for male fetal aneuploidies.

Both the measured elevation of fetal chromosome Y representation and the depletion of chromosome X representation in male pregnancies were proportional to the fraction of fetal DNA in the maternal plasma. An insufficient amount of fetal DNA can adversely affect the signal to noise ratio. The problem can be exacerbated by the routine appearance of a non-zero background chromosome Y signal in all pregnancies, for both male and female fetuses, in addition to certain stochastic errors, in spite of the absence of chromosome Y from the maternal genome. Artifacts may partially be attributed to miss-alignments, but a significant contribution to the noise typically stems from the homology between chromosome Y and other chromosomes (e.g., chromosome X, e.g., 3.5 Mb of TGIFL X/Y).

The scarcity of [47,XXY] and [47,XYY] aneuploidies can impede both the training of a male sex aneuploidy classifier and the assessment of the classifier's accuracy. Furthermore, at low fetal fraction values, the areas on the XY scatter plot occupied by the two male sex aneuploidies can partially overlap. In certain instances, low fetal fractions can cause both Klinefelter and Jacobs syndromes to overlap with normal male pregnancies.

To illustrate the complexity of chromosome Y aneuploidy detection and to avoid faulty classification due to insufficient fetal DNA levels, two non-reportable zones were introduced for samples pertaining to male fetuses. The first non-reportable zone was defined by the euploid control samples containing pooled male fetal DNA at a median level of 4%. This zone included the semi-plane defined by the chromosome Y levels below the 0.15 percentile of the euploid control measurements (FIG. 142, horizontal dotted line).

The second non-reportable zone outlined the overlap between XXY, XYY and euploid male areas. It is shaped as a right-angled triangle just above the origin of the XY scatter plot. The triangle touches the first non-reportable zone with its horizontal cathetus (FIG. 142). The location of its vertical cathetus was determined by the Turner syndrome cutoff ($Z_X$=−3). The hypotenuse of the triangle coincided with the straight line defining the upper $99^{th}$ percentile confidence interval for the normal male area (FIG. 142, upper diagonal dotted line). The line's intersection with the euploid male control cutoff (FIG. 142, horizontal dotted line) marked the right extremity of the triangle.

The cutoffs described above are summarized in Table 2 below. The decision tree which implements the SCA method described herein is presented in FIG. 144 which includes variable names provided in Table 2 below.

TABLE 2

| Variable | Description |
|---|---|
| | Description of cutoffs used in a sex chromosome aneuploidy (SCA) decision tree |
| $x_s$ | Chromosome X representation for sample s |
| $y_s$ | Chromosome Y representation for sample s |
| $g_s$ | Predicted fetal sex for sample s |
| $G_x$ | Gray zone for chromosome X $\{z \in R: 2.5 \leq |z| \leq 3.5\}$ |
| $Z_{x,s}$ | Standardized chromosome X representation for sample s as described above |
| $X_{45}$ | 0.15 percentile of chromosome X representations in female pregnancies of the training cohort |
| $X_{47}$ | 99.85 percentile of chromosome X representations in female pregnancies of the training cohort |
| $X_{m45}$ | Threshold for maternal monosomy 45, X |
| $X_{m47}$ | Threshold for maternal trisomy 47, XXX |
| $\hat{X}_{46}$ | 99.7% Cl of euploid female chromosome X representation |
| $\hat{Y}_{46}(x)$ | 99% Cl of the point estimate of chromosome Y representation at x level of chromosome X |
| $\tilde{Y}(x)$ | 0.05 percentile confidence level of the point estimate of chromosome Y representation at x level of chromosome X |
| $\tilde{Y}_{Ctrl}$ | The 0.15 percentile of the chromosome Y representation level of the pooled male control samples |
| Δ | The shaded zone for the male pregnancies with a right-angle triangular geometry in chromosome-XY representation plane |

Example 12: Selection of Genomic Sections for Chromosomes X and Y

This example describes selection of informative genomic sections of chromosome X and male-specific genomic sections of chromosome Y.

To remove systematic biases from measured numbers of sequenced reads aligned in sex chromosomes (aligned using BOWTIE aligner), the Parameterized Error Removal and Unbiased Normalization (PERUN) protocol was applied to sex chromosomes, as described in Example 10. Both chromosomes X and Y were partitioned into contiguous, non-overlapping 50 kBp genomic sections and parameterized as described herein for autosomes. The parameterization and normalization began by extracting the GC content of each section from the reference human genome. For each sequenced sample, censored linear regression was applied to the measured numbers of aligned reads per section (counts) as a function of the section-specific GC content.

The sample-specific GC bias coefficients were evaluated as the slopes of the straight lines relating the counts to the GC content. For each genomic section, a linear regression of measured read counts versus sample-specific GC bias coefficient values yielded the section-specific PERUN parameters. Two parameters were obtained for each genomic section: the slope and the intercept. The parameters were employed to flatten the systematic variations in measured read counts as described herein for autosomal genomic sections.

The PERUN parameters for chromosome X were derived from 752 euploid female pregnancies. Section filtering for chromosome X was based on 10-fold cross-validation. The random selection of the cross-validation subset was stratified according to the sample-specific GC bias coefficient values and repeated 100 times. Chromosome X sections whose cross-validation R factor values exceeded 7% were eliminated. Additional mappability/repeatability filtering yielded the final selection of 2382 bins, representing 76.7% of chromosome X. The selected 2382 bins were used to evaluate chromosome X representation. The PERUN parameters for chromosome Y were extracted from a set of 23 adult male samples.

To identify informative chromosome Y sections, euploid count profiles were normalized according to the PERUN procedure. The PERUN profiles were segregated according to fetal gender into two subsets, comprising 752 female and 757 male histograms, respectively. For each chromosome Y section, the median and the MAD were evaluated separately for each subset. The two medians and MADs were then combined to yield a single, genomic section-specific t-statistics value, which was determined according to the equation below:

$$t = \frac{Y_m - Y_f}{\sqrt{\frac{S_m^2}{N_m} + \frac{S_f^2}{N_f}}}$$

where:

t=t-value for a given ChrY bin.

$N_m$=the number of male euploid pregnancies.

$Y_m$=median PERUN-normalized counts evaluated for all $N_m$ male pregnancies for a given ChrY bin. The median can be replaced with mean, in certain instances. The PERUN-normalized counts can be replaced by raw counts or GCRM counts or any other unnormalized or normalized counts.

$S_m$=MAD PERUN-normalized counts evaluated for all $N_m$ male pregnancies for a given ChrY bin. The MAD can be replaced with standard deviation, in certain instances. The PERUN-normalized counts can be replaced by raw counts or GCRM counts or any other unnormalized or normalized counts.

$N_f$=The number of female euploid pregnancies $Y_f$=Median PERUN-normalized counts evaluated for all $N_f$ female pregnancies for a given ChrY bin. The median can be replaced with mean, in certain instances. The PERUN-normalized counts can be replaced by raw counts or GCRM counts or any other unnormalized or normalized counts.

$S_f$=MAD PERUN-normalized counts evaluated for all $N_f$ female pregnancies for a given ChrY bin. The MAD can be replaced with standard deviation, in certain instances. The PERUN-normalized counts can be replaced by raw counts or GCRM counts or any other unnormalized or normalized counts.

A bin was selected if the t-value was greater than or equal to 50 (t≥50). A subset of 26 genomic sections representing 2.2% of chromosome Y generated t-values that exceeded the predefined cutoff of 50. Those sections were used to evaluate chromosome Y representation.

The procedure described above also was modified to use raw chromosome Y counts. The protocol was successfully applied using raw counts derived from ELAND alignments. The bin selection based on raw ELAND counts yielded 226 chromosome Y bins. The cutoff used for t-values based on raw counts was 60, which was slightly higher than the cutoff used for BOWTIE aligned, PERUN-normalized chromosome Y counts described above. Raw counts resulting from BOWTIE alignments also can be used in some instances. Normalizing the counts with PERUN before evaluating t-values, however, can improve the precision of certain chromosomal representations. For that reason, the following 26 bins based on BOWTIE/PERUN treatment (t-value cutoff of 50) were selected for evaluating chromosome Y representation: chrY_125, chrY_169, chrY_170, chrY_171, chrY_172, chrY_182, chrY_183, chrY_184, chrY_186, chrY_187, chrY_192, chrY_417, chrY_448, chrY_449, chrY_473, chrY_480, chrY_481, chrY_485, chrY_491, chrY_502, chrY_519, chrY_535, chrY_559, chrY_1176, chrY_1177, chrY_1178. Genome coordinates for the selected chromosome Y bins are provided in Table 3 below.

TABLE 3

Bins selected for determining chromosome Y representation

| Bin number | Start coordinate* | End coordinate |
|---|---|---|
| "ChrY_125" | 6250001 | 6300000 |
| "ChrY_169" | 8450001 | 8500000 |
| "ChrY_170" | 8500001 | 8550000 |
| "ChrY_171" | 8550001 | 8600000 |
| "ChrY_172" | 8600001 | 8650000 |
| "ChrY_182" | 9100001 | 9150000 |
| "ChrY_183" | 9150001 | 9200000 |
| "ChrY_184" | 9200001 | 9250000 |
| "ChrY_186" | 9300001 | 9350000 |
| "ChrY_187" | 9350001 | 9400000 |
| "ChrY_192" | 9600001 | 9650000 |
| "ChrY_417" | 20850001 | 20900000 |
| "ChrY_448" | 22400001 | 22450000 |
| "ChrY_449" | 22450001 | 22500000 |
| "ChrY_473" | 23650001 | 23700000 |
| "ChrY_480" | 24000001 | 24050000 |
| "ChrY_481" | 24050001 | 24100000 |
| "ChrY_485" | 24250001 | 24300000 |
| "ChrY_491" | 24550001 | 24600000 |
| "ChrY_502" | 25100001 | 25150000 |
| "ChrY_519" | 25950001 | 26000000 |
| "ChrY_535" | 26750001 | 26800000 |
| "ChrY_559" | 27950001 | 28000000 |
| "ChrY_1176" | 58800001 | 58850000 |
| "ChrY_1177" | 58850001 | 58900000 |
| "ChrY_1178" | 58900001 | 58950000 |

*coordinate positions are relative to the first (5') nucleotide in chromosome Y (i.e., position "1")

Example 13: Special Treatment of Certain Genomic Sections of Chromosome Y

This example describes special treatment of genomic sections (i.e., bins) chrY_1176, chrY_1177, and chrY_1178 when evaluating chromosomal representations for chromosome Y in female pregnancies.

The following method was applied in certain instances to prevent overestimates of chromosome Y representations in female pregnancies with elevated bins chrY_1176, chrY_1177, and chrY_1178. The previous example details a procedure to select male specific genomic sections in chromosome Y. Briefly, to identify informative chromosome Y sections, the method began by normalizing all euploid count profiles according to the PERUN procedure. Next, the PERUN profiles were segregated according to fetal gender into two subsets. In the case of the LDTv2CE training set, the two subsets included 752 female histograms and 757 male histograms. For each chromosome Y section, the median and the MAD are evaluated separately for each subset. The two medians and MADs were then combined to yield a single, section-specific t-statistics value. A subset of sections representing 2.2% of chromosome Y generated t-values that exceeded a predefined cutoff of 50. Those sections were used to evaluate the representation of chromosome Y. Using this method, the following 26 chromosome Y bins were identified as useful for discriminating between male and female pregnancies: chrY_125, chrY_169, chrY_170, chrY_171, chrY_172, chrY_182, chrY_183, chrY_184, chrY_186, chrY_187, chrY_192, chrY_417, chrY_448, chrY_449, chrY_473, chrY_480, chrY_481, chrY_485, chrY_491, chrY_502, chrY_519, chrY_535, chrY_559, chrY_1176, chrY_1177, chrY_1178.

The last three bins in the set of selected bins (i.e., chrY_1176, chrY_1177, and chrY_1178) showed the smallest degree of variability among all female pregnancies. Additionally, these three bins tended to reach the highest elevation in male pregnancies. Thus, these three bins can be particularly useful for detecting the presence of chromosome Y in a sample. However, in very few female pregnancies, these three bins were elevated, while the rest of the chromosome Y profile was not. The possible reason for sporadic elevation of these three bins is their immediate proximity to the pseudoautosomal region 2 (PAR2) in chromosome Y. These female fetuses may have inherited a piece of paternal chromosome Y, recombined with their paternally inherited chromosome X. In those rare cases (roughly 0.5% or less), chromosome Y representation appeared increased due to the last three bins. These deviations, illustrated in FIGS. 145 to 148, have the potential to interfere with sex aneuploidy assessment, fetal fraction evaluation, and gender determination based on sequencing measurements. This example describes a method for removing or reducing interference from bins chrY_1176, chrY_1177, and chrY_1178 for situations where they are elevated in a female pregnancy.

One method to correct for the elevation of the three bins described above included eliminating them from consideration. However, because these bins were highly informative for both male and female pregnancies, it was beneficial to retain them. Thus, instead of removing these bins, the median elevation of these three bins was compared to the median elevation of the remaining 23 chromosome Y bins. In addition to the two medians, the MAD values were evaluated for the two subsets of chromosome Y bins (bins 1-23 and bins 24-26). The two medians and the two MADs were combined to form a t-value. If the t-value exceeded 3, we replaced the normalized counts in the bins chrY_1176, chrY_1177, and chrY_1178 with the median of chromosome Y bins 1-23 prior to evaluating chromosome Y representation. A code that performs these operations is presented in FIG. 149.

When the R-script in FIG. 149 was used to evaluate chromosome Y representations in female pregnancies that had elevated bins chrY_1176, chrY_1177, and chrY_1178, the results were consistent with chromosome Y representations observed in a larger population of female pregnancies (all LDTv2CE samples with female fetuses).

Example 14: Secondary GC Correction Applied to PERUN-Based Chromosome X and Y Representations This example describes application of a secondary GC correction to PERUN-based chromosomal representations of chromosomes X and Y to increase the accuracy of fetal sex aneuploidy detection. Chromosome Y and chromosome X representations were corrected for any systematic GC biases that were not removed from count profiles generated by an initial GC normalization (e.g., PERUN, Hybrid Additive LOESS, Additive LOESS with division by medians, GCRM, GC-LOESS, or variants of these techniques). The results included increased accuracy of fetal sex aneuploidy detection, improved fetal fraction estimates based on chromosome X and Y representations measured in male fetuses, and improved fetal fraction estimates based on chromosome X representations observed in female fetuses with Turner and XXX syndromes.

Certain examples above describe application of the PERUN algorithm to sex chromosomes, bin selection for chromosomes X and Y, and special treatment of certain chromosome Y sections adjacent to the PAR2 region. When evaluated according to the methods described in certain examples above, chromosomal representations of sex chromosomes generally contained residual GC bias. FIG. 150 illustrates the dependence of chromosome X representation on a sample-specific GC bias coefficient (scaled with respect to the total autosomal counts). FIG. 151 correlates chromosome Y representation with GC bias coefficients. Both FIGS. 150 and 151 show chromosomal representations measured in female fetuses to remove certain confounding effects of fetal fraction, sometimes observed in male fetuses. FIGS. 152 and 153 show chromosome X and chromosome Y representations for LDTv2CE pregnancies, both male and female, as functions of sample-specific GC bias coefficients. The female data points in FIGS. 152 and 153 are the same as in FIGS. 150 and 151. The chromosomal representations in FIGS. 150-153 were obtained from PERU N profiles without any secondary GC corrections.

The linear regression between chromosome X representations in female pregnancies and the corresponding GC bias coefficients (divided by the total autosomal counts) yielded a slope of 2.1783 and an intercept of 0.0477, with an $r^2=5\times10^{-4}$. The p-value for the slope was 0.5669 (FIG. 150, diagonal line). The standard error for the chromosome X slope was 3.802.

The linear regression between chromosome Y representations in female pregnancies and the corresponding GC bias coefficients (divided by the total autosomal counts) yielded a slope of −1.6692 and an intercept of $1\times10^{-4}$, with an $r^2=0.4091$. The p-value for the slope was $2.2\times10^{-16}$ (FIG. 151, diagonal line). The standard error for the chromosome Y slope was $7.993\times10^{-2}$.

A secondary correction for GC bias was applied to chromosome Y representations by subtracting the product of the GC coefficient (divided by the total autosomal counts) and the slope of the linear regression (−1.6692) from the chromosome Y representation estimate derived from the PERUN profile. The value of the chromosome Y-vs-GC bias slope can be periodically updated on larger data sets to account for drifts in the measurements. The correction factor of −1.6692 should therefore be interpreted as a representative example, not the sole possible value. The range of the correction factor for chromosome Y can be estimated from the standard error. Subtraction and addition of three standard errors to the slope estimate yielded a range of [−1.9088, −1.4292].

Although insignificant relative to the spread of chromosome X representations, the secondary correction for GC bias was applied to chromosome X representations by subtracting the product of the GC coefficient (divided by the total autosomal counts) and the slope of the linear regression (2.1783) from the chromosome X representation estimate derived from the PERUN profile. The value of the chromosome X-vs-GC bias slope can be periodically updated on larger data sets to account for drifts in the measurements. The correction factor of 2.1783 should therefore be interpreted as a representative example, not the sole possible value. The range of the correction factor for chromosome X can be estimated from the standard error. Subtraction and addition of three standard errors to the slope estimate yielded a range of [−9.2277, 13.5843].

FIGS. 154 and 155 show corrected chromosome X representations and chromosome Y representations, respectively, for female fetuses. The corrections follow the method described above. The solid lines indicate complete absence of correlation between chromosomal representations and GC bias coefficients following the secondary correction. In addition to the data points shown in FIGS. 154 and 155, FIGS. 156 and 157 also include corrected chromosome X and chromosome Y representations obtained for male pregnancies. FIGS. 154-157 confirm successful removal of residual GC biases from chromosome X representations and chromosome Y representations derived from PERUN profiles.

Example 15: Examples of Embodiments

Listed hereafter are non-limiting examples of certain embodiments of the technology.

A1. A method for identifying the presence or absence of a sex chromosome aneuploidy in a fetus, comprising:
- (a) obtaining counts of sequence reads mapped to sections of a reference genome, which sequence reads are reads of circulating cell-free nucleic acid from a pregnant female bearing a fetus;
- (b) determining a guanine and cytosine (GC) bias for each of the sections of the reference genome for multiple samples from a fitted relation for each sample between (i) the counts of the sequence reads mapped to each of the sections of the reference genome, and (ii) GC content for each of the sections;
- (c) calculating a genomic section level for each of the sections of the reference genome from a fitted relation between the GC bias and the counts of the sequence reads mapped to each of the sections of the reference genome, thereby providing calculated genomic section levels; and
- (d) identifying the presence or absence of a sex chromosome aneuploidy for the fetus according to the calculated genomic section levels.

A2. The method of embodiment A1, wherein the sections of the reference genome are in a sex chromosome.

A3. The method of embodiment A2, wherein the sex chromosome is an X chromosome.

A4. The method of embodiment A2, wherein the sex chromosome a Y chromosome.

A5. The method of embodiment A1, wherein some sections of the reference genome are in an X chromosome and some sections of the reference genome are in a Y chromosome.

A6. The method of embodiment A1, wherein the sections of the reference genome are in a segment of a sex chromosome.

A7. The method of embodiment A1 or A6, wherein the sex chromosome aneuploidy is an aneuploidy of a segment of a sex chromosome.

A8. The method of any one of embodiments A1 to A5, wherein the sex chromosome aneuploidy is selected from XXX, XXY, X, and XYY.

A9. The method of any one of embodiments A1 to A8, which comprises prior to (b) calculating a measure of error for the counts of sequence reads mapped to some or all of the sections of the reference genome and removing or weighting the counts of sequence reads for certain sections of the reference genome according to a threshold of the measure of error.

A10. The method of embodiment A9, wherein the measure of error is an R factor.

A11. The method of embodiment A10, wherein the counts of sequence reads for a section of the reference genome having an R factor of about 7% to about 10% is removed prior to (b).

A12. The method of any one of embodiments A1 to A11, wherein the fitted relation in (b) is a fitted linear relation.

A13. The method of embodiment A12, wherein the slope of the relation is determined by linear regression.

A14. The method of embodiment A12 or A13, wherein each GC bias is a GC bias coefficient.

A15. The method of embodiment A14, wherein the GC bias coefficient is the slope of the linear relationship between (i) the counts of the sequence reads mapped to each of the sections of the reference genome, and (ii) the read counts and GC content for each of the sections.

A16. The method of any one of embodiments A1 to A11, wherein the fitted relation in (b) is a fitted non-linear relation.

A17. The method of embodiment A16, wherein each GC bias comprises a GC curvature estimation.

A18. The method of any one of embodiments A1 to A17, wherein the fitted relation in (c) is linear.

A19. The method of embodiment A18, wherein the slope of the relation is determined by linear regression.

A20. The method of any one of embodiments A1 to A19, wherein the fitted relation in (b) is linear, the fitted relation in (c) is linear and the genomic section level $L_i$ is determined for each of the sections of the reference genome according to Equation α:

$$L_i = (m_i - G_i S) I^{-1} \quad \text{Equation } \alpha$$

wherein $G_i$ is the GC bias, I is the intercept of the fitted relation in (c), S is the slope of the relation in (c), $m_i$ is measured counts mapped to each section of the reference genome and i is a sample.

A21. The method of any one of embodiments A1 to A20, wherein the number of sections of the reference genome is about 220 or more sections for chromosome Y.

A22. The method of any one of embodiments A1 to A20, wherein the number of sections of the reference genome is about 2750 or more sections for chromosome X.

A23. The method of any one of embodiments A1 to A22, wherein the presence or absence of a sex chromosome aneuploidy is identified for the fetus with a sensitivity of 80% or greater and a specificity of 98% or greater.

A24. The method of any one of embodiments A1 to A22, wherein the presence or absence of a sex chromosome aneuploidy is identified for the fetus with a sensitivity of 80% or greater and a specificity of 99% or greater.

A25. The method of any one of embodiments A1 to A22, wherein the presence or absence of a sex chromosome aneuploidy is identified for the fetus with a sensitivity of 99% or greater and a specificity of 98% or greater.

A26. The method of any one of embodiments A1 to A22, wherein the presence or absence of a sex chromosome aneuploidy is identified for the fetus with a sensitivity of 99% or greater and a specificity of 99% or greater.

A27. The method of any one of embodiments A1 to A22, wherein the presence or absence of a sex chromosome aneuploidy is identified for the fetus with a sensitivity of 100% and a specificity of 98% or greater.

A28. The method of any one of embodiments A1 to A22, wherein the presence or absence of a sex chromosome aneuploidy is identified for the fetus with a sensitivity of 100% and a specificity of 99% or greater.

A29. The method of any one of embodiments A1 to A28, wherein the reference genome is from a male subject.

A30. The method of any one of embodiments A1 to A28, wherein the reference genome is from a female subject.

A31. The method of embodiment A29 or A30, wherein the female subject is a pregnant female.

A32. The method of embodiment A31, wherein the pregnant female is carrying a female fetus.

A32.1 The method of embodiment A31, wherein the pregnant female is carrying a male fetus.

A33. A system comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(b) calculate a genomic section level for each of the sections of the reference genome from a fitted relation between the GC bias and the counts of the sequence reads mapped to each of the sections of the reference genome, thereby providing calculated genomic section levels; and (c) identify the presence or absence of a sex chromosome aneuploidy for the fetus according to the calculated genomic section levels.

A34. An apparatus comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(b) calculate a genomic section level for each of the sections of the reference genome from a fitted relation between the GC bias and the counts of the sequence reads mapped to each of the sections of the reference genome, thereby providing calculated genomic section levels; and (c) identify the presence or absence of a sex chromosome aneuploidy for the fetus according to the calculated genomic section levels.

A35. A computer program product tangibly embodied on a computer-readable medium, comprising instructions that when executed by one or more processors are configured to:

(a) access counts of nucleotide sequence reads mapped to genomic sections of a reference genome, which sequence reads are reads of circulating cell-free nucleic acid from a pregnant female bearing a fetus;

(b) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(c) calculate a genomic section level for each of the sections of the reference genome from a fitted relation between the GC bias and the counts of the sequence reads mapped to each of the sections of the reference genome, thereby providing calculated genomic section levels; and (d) identify the presence or absence of a sex chromosome aneuploidy for the fetus according to the calculated genomic section levels.

B1. A method for determining fetal gender, comprising:

(a) obtaining counts of sequence reads mapped to sections of a reference genome, which sequence reads are reads of circulating cell-free nucleic acid from a pregnant female bearing a fetus;

(b) determining a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(c) calculating a genomic section level for each of the sections of the reference genome from a fitted relation between the GC bias and the counts of the sequence reads mapped to each of the sections of the reference genome, thereby providing calculated genomic section levels; and (d) determining fetal gender according to the calculated genomic section levels.

B2. The method of embodiment B1, wherein the sections of the reference genome are in a sex chromosome.

B3. The method of embodiment B2, wherein the sex chromosome is an X chromosome.

B4. The method of embodiment B2, wherein the sex chromosome a Y chromosome.

B5. The method of embodiment B1, wherein some sections of the reference genome are in an X chromosome and some sections of the reference genome are in a Y chromosome.

B6. The method of any one of embodiments B1 to B5, which comprises prior to (b) calculating a measure of error for the counts of sequence reads mapped to some or all of the sections of the reference genome and removing or weighting the counts of sequence reads for certain sections of the reference genome according to a threshold of the measure of error.

B7. The method of embodiment B6, wherein the measure of error is an R factor.

B8. The method of embodiment B7, wherein the counts of sequence reads for a section of the reference genome having an R factor of about 7% to about 10% is removed prior to (b).

B9. The method of any one of embodiments B1 to B8, wherein the fitted relation in (b) is a fitted linear relation.

B10. The method of embodiment B9, wherein the slope of the relation is determined by linear regression.

B11. The method of embodiment B9 or B10, wherein each GC bias is a GC bias coefficient.

B12. The method of embodiment B11, wherein the GC bias coefficient is the slope of the linear relationship between (i) the counts of the sequence reads mapped to each of the sections of the reference genome, and (ii) the read counts and GC content for each of the sections.

B13. The method of any one of embodiments B1 to B8, wherein the fitted relation in (b) is a fitted non-linear relation.

B14. The method of embodiment B13, wherein each GC bias comprises a GC curvature estimation.

B15. The method of any one of embodiments B1 to B14, wherein the fitted relation in (c) is linear.

B16. The method of embodiment B15, wherein the slope of the relation is determined by linear regression.

B17. The method of any one of embodiments B1 to B16, wherein the fitted relation in (b) is linear, the fitted relation in (c) is linear and the genomic section level $L_i$ is determined for each of the sections of the reference genome according to Equation α:

$$L_i = (m_i - G_i S) I^{-1} \qquad \text{Equation } \alpha$$

wherein $G_i$ is the GC bias, I is the intercept of the fitted relation in (c), S is the slope of the relation in (c), $m_i$ is measured counts mapped to each section of the reference genome and i is a sample.

B18. The method of any one of embodiments B1 to B17, wherein the number of sections of the reference genome is about 220 or more sections for chromosome Y.

B19. The method of any one of embodiments B1 to B17, wherein the number of sections of the reference genome is about 2750 or more sections for chromosome X.

B20. The method of any one of embodiments B1 to B19, wherein fetal gender is determined with a sensitivity of 99% or greater and a specificity of 99% or greater.

B21. The method of any one of embodiments B1 to B20 wherein the reference genome is from a male subject.

B22. The method of any one of embodiments B1 to B20, wherein the reference genome is from a female subject.

B23. The method of embodiment B21 or B22, wherein the female subject is a pregnant female.

B24. The method of embodiment B23, wherein the pregnant female is carrying a female fetus.

B24.1 The method of embodiment B23, wherein the pregnant female is carrying a male fetus.

B25. A system comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(b) calculate a genomic section level for each of the sections of the reference genome from a fitted relation between the GC bias and the counts of the sequence reads mapped to each of the sections of the reference genome, thereby providing calculated genomic section levels; and (c) determine fetal gender according to the calculated genomic section levels.

B26. An apparatus comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(b) calculate a genomic section level for each of the sections of the reference genome from a fitted relation between the GC bias and the counts of the sequence reads mapped to each of the sections of the reference genome, thereby providing calculated genomic section levels; and (c) determine fetal gender according to the calculated genomic section levels.

B27. A computer program product tangibly embodied on a computer-readable medium, comprising instructions that when executed by one or more processors are configured to:

(a) access counts of nucleotide sequence reads mapped to genomic sections of a reference genome, which sequence reads are reads of circulating cell-free nucleic acid from a pregnant female bearing a fetus;

(b) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(c) calculate a genomic section level for each of the sections of the reference genome from a fitted relation between the GC bias and the counts of the sequence reads mapped to each of the sections of the reference genome, thereby providing calculated genomic section levels; and (d) determine fetal gender according to the calculated genomic section levels.

C1. A method for determining sex chromosome karyotype in a fetus, comprising:

(a) obtaining counts of sequence reads mapped to sections of a reference genome, which sequence reads are reads of circulating cell-free nucleic acid from a pregnant female bearing a fetus;

(b) determining a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(c) calculating a genomic section level for each of the sections of the reference genome from a fitted relation between the GC bias and the counts of the sequence reads mapped to each of the sections of the reference genome, thereby providing calculated genomic section levels; and (d) determining sex chromosome karyotype for the fetus according to the calculated genomic section levels.

C2. The method of embodiment C1, wherein the sections of the reference genome are in a sex chromosome.

C3. The method of embodiment C2, wherein the sex chromosome is an X chromosome.

C4. The method of embodiment C2, wherein the sex chromosome a Y chromosome.

C5. The method of embodiment C1, wherein some sections of the reference genome are in an X chromosome and some sections of the reference genome are in a Y chromosome.

C6. The method of any one of embodiments C1 to C5, which comprises prior to (b) calculating a measure of error for the counts of sequence reads mapped to some or all of the sections of the reference genome and removing or weighting the counts of sequence reads for certain sections of the reference genome according to a threshold of the measure of error.

C7. The method of embodiment C6, wherein the measure of error is an R factor.

C8. The method of embodiment C7, wherein the counts of sequence reads for a section of the reference genome having an R factor of about 7% to about 10% is removed prior to (b).

C9. The method of any one of embodiments C1 to C8, wherein the fitted relation in (b) is a fitted linear relation.

C10. The method of embodiment C9, wherein the slope of the relation is determined by linear regression.

C11. The method of embodiment C9 or C10, wherein each GC bias is a GC bias coefficient.

C12. The method of embodiment C11, wherein the GC bias coefficient is the slope of the linear relationship between (i) the counts of the sequence reads mapped to each of the sections of the reference genome, and (ii) the read counts and GC content for each of the sections.

C13. The method of any one of embodiments C1 to C8, wherein the fitted relation in (b) is a fitted non-linear relation.

C14. The method of embodiment C13, wherein each GC bias comprises a GC curvature estimation.

C15. The method of any one of embodiments C1 to C14, wherein the fitted relation in (c) is linear.

C16. The method of embodiment C15, wherein the slope of the relation is determined by linear regression.

C17. The method of any one of embodiments C1 to C16, wherein the fitted relation in (b) is linear, the fitted relation in (c) is linear and the genomic section level $L_i$ is determined for each of the sections of the reference genome according to Equation α:

$$L_i = (m_i - G_i S) I^{-1} \quad \text{Equation } \alpha$$

wherein $G_i$ is the GC bias, I is the intercept of the fitted relation in (c), S is the slope of the relation in (c), $m_i$ is measured counts mapped to each section of the reference genome and i is a sample.

C18. The method of any one of embodiments C1 to C17, wherein the number of sections of the reference genome is about 220 or more sections for chromosome Y.

C19. The method of any one of embodiments C1 to C17, wherein the number of sections of the reference genome is about 2750 or more sections for chromosome X.

C20. The method of any one of embodiments C1 to C19, wherein the sex chromosome karyotype is selected from XX, XY, XXX, X, XXY, and XYY.

C21. The method of any one of embodiments C1 to C20, wherein the reference genome is from a male subject.

C22. The method of any one of embodiments C1 to C20, wherein the reference genome is from a female subject.

C23. The method of embodiment C21 or C22, wherein the female subject is a pregnant female.

C24. The method of embodiment C23, wherein the pregnant female is carrying a female fetus.

C24.1 The method of embodiment C23, wherein the pregnant female is carrying a male fetus.

C25. A system comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(b) calculate a genomic section level for each of the sections of the reference genome from a fitted relation between the GC bias and the counts of the sequence reads mapped to each of the sections of the reference genome, thereby providing calculated genomic section levels; and (c) determine sex chromosome karyotype for the fetus according to the calculated genomic section levels.

C26. An apparatus comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(b) calculate a genomic section level for each of the sections of the reference genome from a fitted relation between the GC bias and the counts of the sequence reads mapped to each of the sections of the reference genome, thereby providing calculated genomic section levels; and (c) determine sex chromosome karyotype for the fetus according to the calculated genomic section levels.

C27. A computer program product tangibly embodied on a computer-readable medium, comprising instructions that when executed by one or more processors are configured to:

(a) access counts of nucleotide sequence reads mapped to genomic sections of a reference genome, which sequence reads are reads of circulating cell-free nucleic acid from a pregnant female bearing a fetus;

(b) determine a guanine and cytosine (GC) bias for each of the sections of the reference genome for multiple samples from a fitted relation for each sample between (i) the counts of the sequence reads mapped to each of the sections of the reference genome, and (ii) GC content for each of the sections;

(c) calculate a genomic section level for each of the sections of the reference genome from a fitted relation between the GC bias and the counts of the sequence reads mapped to each of the sections of the reference genome, thereby providing calculated genomic section levels; and (d) determine sex chromosome karyotype for the fetus according to the calculated genomic section levels.

D1. A method for identifying the presence or absence of a sex chromosome aneuploidy in a fetus, comprising:

(a) obtaining counts of sequence reads mapped to sections of a reference genome, which sequence reads are reads of circulating cell-free nucleic acid from a pregnant female bearing a fetus;

(b) determining an experimental bias for each of the sections of the reference genome for multiple samples from a fitted relation for each sample between (i) the counts of the sequence reads mapped to each of the sections of the reference genome, and (ii) a mapping feature for each of the sections;

(c) calculating a genomic section level for each of the sections of the reference genome from a fitted relation between the experimental bias and the counts of the sequence reads mapped to each of the sections of the reference genome, thereby providing calculated genomic section levels; and (d) identifying the presence or absence of a sex chromosome aneuploidy for the fetus according to the calculated genomic section levels.

D1.1 The method of embodiment D1, wherein the sex chromosome aneuploidy is selected from XXX, XXY, X, and XYY.

D1.2 The method of embodiment D1 or D1.1, wherein the sex chromosome aneuploidy is an aneuploidy of a segment of a sex chromosome.

D2. A method for determining fetal gender, comprising:

(a) obtaining counts of sequence reads mapped to sections of a reference genome, which sequence reads are reads of circulating cell-free nucleic acid from a pregnant female bearing a fetus;

(b) determining an experimental bias for each of the sections of the reference genome for multiple samples from a fitted relation for each sample between (i) the counts of the sequence reads mapped to each of the sections of the reference genome, and (ii) a mapping feature for each of the sections;

(c) calculating a genomic section level for each of the sections of the reference genome from a fitted relation between the experimental bias and the counts of the sequence reads mapped to each of the sections of the reference genome, thereby providing calculated genomic section levels; and (d) determining fetal gender according to the calculated genomic section levels.

D3. A method for determining sex chromosome karyotype in a fetus, comprising:

(a) obtaining counts of sequence reads mapped to sections of a reference genome, which sequence reads are reads of circulating cell-free nucleic acid from a pregnant female bearing a fetus;

(b) determining an experimental bias for each of the sections of the reference genome for multiple samples from a fitted relation for each sample between (i) the counts of the sequence reads mapped to each of the sections of the reference genome, and (ii) a mapping feature for each of the sections;

(c) calculating a genomic section level for each of the sections of the reference genome from a fitted relation between the experimental bias and the counts of the sequence reads mapped to each of the sections of the reference genome, thereby providing calculated genomic section levels; and (d) determining sex chromosome karyotype for the fetus according to the calculated genomic section levels.

D3.1 The method of embodiment D3, wherein the sex chromosome karyotype is selected from XX, XY, XXX, X, XXY and XYY.

D4. The method of any one of embodiments D1 to D3.1, wherein the fitted relation in (b) is a fitted linear relation.

D5. The method of embodiment D4, wherein the slope of the relation is determined by linear regression.

D6. The method of embodiment D4 or D5, wherein each experimental bias is an experimental bias coefficient, which experimental bias coefficient is the slope of the linear relationship between (i) the counts of the sequence reads mapped to each of the sections of the reference genome, and (ii) the mapping feature for each of the sections.

D7. The method of any one of embodiments D1 to D3, wherein the fitted relation in (b) is a fitted non-linear relation.

D8. The method of embodiment D7, wherein each experimental bias comprises an experimental bias curvature estimation.

D9. The method of any one of embodiments D1 to D8, wherein the fitted relation in (c) is linear.

D10. The method of embodiment D9, wherein the slope of the relation is determined by linear regression.

D11. The method of any one of embodiments D1 to D10, wherein the fitted relation in (b) is linear, the fitted relation in (c) is linear and the genomic section level $L_i$ is determined for each of the sections of the reference genome according to Equation α:

$$L_i = (m_i - G_i S) I^{-1} \quad \text{Equation } \alpha$$

wherein $G_i$ is the experimental bias, I is the intercept of the fitted relation in (c), S is the slope of the relation in (c), $m_i$ is measured counts mapped to each section of the reference genome and i is a sample.

D12. The method of any one of embodiments D1 to D11, wherein the number of sections of the reference genome is about 40,000 or more sections.

D13. The method of any one of embodiments D1 to D12, wherein the mapping feature is GC content and the experimental bias is GC bias.

D14. The method of any one of embodiments D1 to D12, wherein the mapping feature is a measure of mapability and the experimental bias is mapability bias.

D15. The method of any one of embodiments D1 to D14, wherein the relation in (c) is non-linear.

D16. The method of any one of embodiments D1 to D15, which comprises prior to (b) calculating a measure of error for the counts of sequence reads mapped to some or all of the sections of the reference genome and removing or weighting the counts of sequence reads for certain sections of the reference genome according to a threshold of the measure of error.

D17. The method of embodiment D16, wherein the threshold is selected according to a standard deviation gap between a first genomic section level and a second genomic section level of 3.5 or greater.

D18. The method of embodiment D16 or D17, wherein the measure of error is an R factor.

D19. The method of embodiment D18, wherein the counts of sequence reads for a section of the reference genome having an R factor of about 7% to about 10% is removed prior to (b).

D20. The method of any one of embodiments D1 to D19, wherein the sections of the reference genome are in a sex chromosome.

D21. The method of embodiment D20, wherein the sex chromosome is an X chromosome.

D22. The method of embodiment D20, wherein the sex chromosome is a Y chromosome.

D23. The method of any one of embodiments D1 to D19, wherein some sections of the reference genome are in an X chromosome and some sections of the reference genome are in a Y chromosome.

D23.1 The method of embodiment D23, wherein a subset of sections for chromosome Y is selected.

D23.2 The method of embodiment D23.1, wherein the subset of sections for chromosome Y is selected according to a t-value determined for each section.

D23.3 The method of embodiment D23.2, wherein the t-value is determined for each section according to Equation β:

$$t = \frac{Y_m - Y_f}{\sqrt{\frac{S_m^2}{N_m} + \frac{S_f^2}{N_f}}} \quad \text{Equation } \beta$$

wherein t is the t-value for a given ChrY bin; $N_m$ is the number of male euploid pregnancies; $Y_m$ is the median PERUN-normalized counts evaluated for all $N_m$ male pregnancies for a given ChrY bin; $S_m$ is the MAD PERUN-normalized counts evaluated for all $N_m$ male pregnancies for a given ChrY bin; $N_f$ is the number of female euploid pregnancies; $Y_f$ is the median PERUN-normalized counts evaluated for all $N_f$ female pregnancies for a given ChrY bin; and $S_f$ is the MAD PERUN-normalized counts evaluated for all $N_f$ female pregnancies for a given ChrY bin.

D23.4 The method of embodiment D23.3, wherein sections having a t-value of greater than or equal to 50 are selected.

D24. The method of any one of embodiments D1 to D23.4, wherein the number of sections of the reference genome is about 220 or more sections for chromosome Y.

D24.1 The method of any one of embodiments D1 to D23.4, wherein the number of sections of the reference genome is about 20 or more sections for chromosome Y.

D24.2 The method of embodiment D24.1, wherein the number of sections of the reference genome is about 26 sections for chromosome Y.

D24.3 The method of embodiment D24.1, wherein the number of sections of the reference genome is about 23 sections for chromosome Y.

D24.4 The method of embodiment D24.1, D24.2 or D24.3, wherein the sections are chosen from among the genomic sections of Table 3.

D24.5 The method of any one of embodiments D24.1 to D24.4, wherein the sections do not comprise ChrY_1176, ChrY_1177, and ChrY_1176.

D25. The method of any one of embodiments D1 to D23, wherein the number of sections of the reference genome is about 2750 or more sections for chromosome X.

D25.1 The method of any one of embodiments D1 to D23, wherein the number of sections of the reference genome is about 2350 or more sections for chromosome X.

D25.2 The method of embodiment D25.1, wherein the number of sections of the reference genome is about 2382 sections for chromosome X.

D26. The method of any one of embodiments D1 to D25.2, wherein the reference genome is from a male subject.

D27. The method of any one of embodiments D1 to D25.2, wherein the reference genome is from a female subject.

D28. The method of embodiment D26 or D27, wherein the female subject is a pregnant female.

D29. The method of embodiment D28, wherein the pregnant female is carrying a female fetus.

D29.1 The method of embodiment D28, wherein the pregnant female is carrying a male fetus.

D30. The method of any one of embodiments D1 to D29.1, wherein each section of the reference genome comprises a nucleotide sequence of a predetermined length.

D31. The method of embodiment D30, wherein the predetermined length is about 50 kilobases.

D32. The method of any one of embodiments D1 to D31, comprising applying a secondary normalization to the genomic section level calculated in (c).

D33. The method of embodiment D32, wherein the secondary normalization comprises GC normalization.

D34. The method of any one of embodiments D1 to D33, comprising determining a chromosome X elevation and a chromosome Y elevation from a plurality genomic section levels calculated in (c).

D35. The method of embodiment D34, comprising plotting the chromosome X elevation, or derivative thereof, versus the chromosome Y elevation, or derivative thereof, on a two-dimensional graph, thereby generating a plot position.

D36. The method of embodiment D35, comprising determining sex chromosome karyotype for the fetus according to the plot position.

D37. The method of embodiment D35, comprising not determining sex chromosome karyotype for the fetus according to the plot position.

D38. A system comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine an experimental bias for each of the sections of the reference genome for multiple samples from a fitted relation for each sample between
  (i) the counts of the sequence reads mapped to each of the sections of the reference genome, and
  (ii) a mapping feature for each of the sections;
(b) calculate a genomic section level for each of the sections of the reference genome from a fitted relation between the experimental bias and the counts of the sequence reads mapped to each of the sections of the reference genome, thereby providing calculated genomic section levels; and
(c) identify the presence or absence of a sex chromosome aneuploidy for the fetus according to the calculated genomic section levels.

D39. An apparatus comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine an experimental bias for each of the sections of the reference genome for multiple samples from a fitted relation for each sample between
  (i) the counts of the sequence reads mapped to each of the sections of the reference genome, and
  (ii) a mapping feature for each of the sections;
(b) calculate a genomic section level for each of the sections of the reference genome from a fitted relation between the experimental bias and the counts of the sequence reads mapped to each of the sections of the reference genome, thereby providing calculated genomic section levels; and
(c) identify the presence or absence of a sex chromosome aneuploidy for the fetus according to the calculated genomic section levels.

D40. A computer program product tangibly embodied on a computer-readable medium, comprising instructions that when executed by one or more processors are configured to:

(a) access counts of nucleotide sequence reads mapped to genomic sections of a reference genome, which sequence reads are reads of circulating cell-free nucleic acid from a pregnant female bearing a fetus;
(b) determine an experimental bias for each of the sections of the reference genome for multiple samples from a fitted relation for each sample between
  (i) the counts of the sequence reads mapped to each of the sections of the reference genome, and (ii) a mapping feature for each of the sections;

(c) calculate a genomic section level for each of the sections of the reference genome from a fitted relation between the experimental bias and the counts of the sequence reads mapped to each of the sections of the reference genome, thereby providing calculated genomic section levels; and (d) identify the presence or absence of a sex chromosome aneuploidy for the fetus according to the calculated genomic section levels.

D41. A system comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine an experimental bias for each of the sections of the reference genome for multiple samples from a fitted relation for each sample between (i) the counts of the sequence reads mapped to each of the sections of the reference genome, and (ii) a mapping feature for each of the sections;

(b) calculate a genomic section level for each of the sections of the reference genome from a fitted relation between the experimental bias and the counts of the sequence reads mapped to each of the sections of the reference genome, thereby providing calculated genomic section levels; and (c) determine fetal gender according to the calculated genomic section levels.

D42. An apparatus comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine an experimental bias for each of the sections of the reference genome for multiple samples from a fitted relation for each sample between (i) the counts of the sequence reads mapped to each of the sections of the reference genome, and (ii) a mapping feature for each of the sections;

(b) calculate a genomic section level for each of the sections of the reference genome from a fitted relation between the experimental bias and the counts of the sequence reads mapped to each of the sections of the reference genome, thereby providing calculated genomic section levels; and (c) determine fetal gender according to the calculated genomic section levels.

D43. A computer program product tangibly embodied on a computer-readable medium, comprising instructions that when executed by one or more processors are configured to:

(a) access counts of nucleotide sequence reads mapped to genomic sections of a reference genome, which sequence reads are reads of circulating cell-free nucleic acid from a pregnant female bearing a fetus;

(b) determine an experimental bias for each of the sections of the reference genome for multiple samples from a fitted relation for each sample between (i) the counts of the sequence reads mapped to each of the sections of the reference genome, and (ii) a mapping feature for each of the sections;

(c) calculate a genomic section level for each of the sections of the reference genome from a fitted relation between the experimental bias and the counts of the sequence reads mapped to each of the sections of the reference genome, thereby providing calculated genomic section levels; and (d) determine fetal gender according to the calculated genomic section levels.

D44. A system comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine an experimental bias for each of the sections of the reference genome for multiple samples from a fitted relation for each sample between (i) the counts of the sequence reads mapped to each of the sections of the reference genome, and (ii) a mapping feature for each of the sections;

(b) calculate a genomic section level for each of the sections of the reference genome from a fitted relation between the experimental bias and the counts of the sequence reads mapped to each of the sections of the reference genome, thereby providing calculated genomic section levels; and (c) determine sex chromosome karyotype for the fetus according to the calculated genomic section levels.

D45. An apparatus comprising one or more processors and memory, which memory comprises instructions executable by the one or more processors and which memory comprises counts of nucleotide sequence reads mapped to genomic sections of a reference genome, which sequence reads are reads of circulating cell-free nucleic acid from a pregnant female bearing a fetus; and which instructions executable by the one or more processors are configured to:

(a) determine an experimental bias for each of the sections of the reference genome for multiple samples from a fitted relation for each sample between (i) the counts of the sequence reads mapped to each of the sections of the reference genome, and (ii) a mapping feature for each of the sections;

(b) calculate a genomic section level for each of the sections of the reference genome from a fitted relation between the experimental bias and the counts of the sequence reads mapped to each of the sections of the reference genome, thereby providing calculated genomic section levels; and (c) determine sex chromosome karyotype for the fetus according to the calculated genomic section levels.

D46. A computer program product tangibly embodied on a computer-readable medium, comprising instructions that when executed by one or more processors are configured to:

(a) access counts of nucleotide sequence reads mapped to genomic sections of a reference genome, which sequence reads are reads of circulating cell-free nucleic acid from a pregnant female bearing a fetus;

(b) determine an experimental bias for each of the sections of the reference genome for multiple samples from a fitted relation for each sample between (i) the counts of the sequence reads mapped to each of the sections of the reference genome, and (ii) a mapping feature for each of the sections;

(c) calculate a genomic section level for each of the sections of the reference genome from a fitted relation between the experimental bias and the counts of the sequence reads mapped to each of the sections of the reference genome, thereby providing calculated genomic section levels; and (d) determine sex chromosome karyotype for the fetus according to the calculated genomic section levels.

Example 16: Examples of Formulas

Provided below are non-limiting examples of mathematical and/or statistical formulas that can be used in methods described herein.

$$Z = \frac{\Delta_1 - \Delta_2}{\sqrt{\sigma_1^2\left(\frac{1}{N_1} + \frac{1}{n_1}\right) + \sigma_2^2\left(\frac{1}{N_2} + \frac{1}{n_2}\right)}}$$

$$P(q) = \frac{1}{\sigma\sqrt{2\pi}}\exp\left[-(q-q_0)/(2\sigma^2)\right]$$

$$q_0 = 1 + F/2$$

$$z = -F/(2\sigma\sqrt{2})$$

$$B = \int_{-\infty}^{1} P(q)dq = \frac{1}{2}[1 + \text{erf}(z)]$$

$$\text{erf}(z) = \frac{2}{\sqrt{\pi}}\sum_{n=0}^{\infty}\frac{(-1)^n z^{2n+1}}{n!(2n+1)}$$

$$R = \frac{1-B}{B} = \frac{1-\text{erf}(z)}{1+\text{erf}(z)} = \frac{1-\text{erf}\left[-F/(2\sigma\sqrt{2})\right]}{1+\text{erf}\left[-F/(2\sigma\sqrt{2})\right]}$$

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications can be made to the foregoing without departing from the basic aspects of the technology. Although the technology has been described in substantial detail with reference to one or more specific embodiments, those of ordinary skill in the art will recognize that changes can be made to the embodiments specifically disclosed in this application, yet these modifications and improvements are within the scope and spirit of the technology.

The technology illustratively described herein suitably can be practiced in the absence of any element(s) not specifically disclosed herein. Thus, for example, in each instance herein any of the terms "comprising," "consisting essentially of," and "consisting of" can be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed can be resorted to by those skilled in the art, and such modifications and variations are considered within the scope of this technology.

Certain embodiments of the technology are set forth in the claim(s) that follow(s).

What is claimed is:

1. A method for determining sex chromosome karyotype for a fetus, comprising:

(I) sequencing circulating cell-free nucleic acid in a test sample from a pregnant subject bearing a fetus by genome-wide massively parallel sequencing, thereby generating sequence reads;

(II) mapping, using a microprocessor, the sequence reads to portions of a reference genome;

(III) counting, using a microprocessor, the sequence reads mapped to the portions of the reference genome, thereby generating counts of the sequence reads;

(IV) normalizing the counts of the sequence reads according to a process comprising:

(a) determining, using a microprocessor, a guanine and cytosine (GC) bias coefficient for the test sample based on a linear regression of (i) the counts of the sequence reads mapped to each of the portions, and (ii) a GC content for each of the portions, wherein the GC bias coefficient is a slope of the linear regression;

(b) for each portion, receiving onto memory model parameters comprising a slope and an intercept from a linear regression of (i) a GC bias coefficient for each of multiple samples in a dataset, wherein the GC bias coefficient for each of the multiple samples in the dataset is the slope of a linear regression of (1) counts of sequence reads mapped to each of the portions of the reference genome for each of the multiple samples, and (2) GC content for each of the portions for each of the multiple samples, and (ii) counts of sequence reads mapped to the portion of the reference genome for each of the multiple samples, wherein the dataset comprises samples comprising circulating cell-free nucleic acid from multiple pregnant women with known fetal karyotype; and (c) generating, using a microprocessor, genomic section level (L) for each of the portions according to $L_i=(m_i-G_iS)I^{-1}$, wherein G is the GC bias coefficient determined in (a), I is the intercept provided in (b), S is the slope provided in (b), m is the counts of the sequence reads generated in (III), and i is the test sample;

(V) determining a sex chromosome karyotype for the fetus according to the genomic section levels generated in (c); and (VI) generating a report for the sex chromosome karyotype for the fetus based on the determination in (V).

2. The method of claim 1, wherein the sequencing is at about 1-fold coverage or less.

3. The method of claim 1, further comprising applying a secondary normalization to the genomic section level generated in (c).

4. The method of claim 3, wherein the secondary normalization comprises GC normalization.

5. The method of claim 1, further comprising determining a chromosome X elevation and a chromosome Y elevation from a plurality of genomic section levels generated in (e).

6. The method of claim 5, further comprising plotting the chromosome X elevation, or derivative thereof, versus the chromosome Y elevation, or derivative thereof, on a two-dimensional graph, thereby generating a plot position.

7. The method of claim 6, further comprising determining a sex chromosome karyotype for the fetus according to the plot position.

8. The method of claim 1, further comprising prior to (IV):

determining a measure of error for the counts of the sequence reads mapped to some or all of the portions of the reference genome; and removing or weighting the counts of sequence reads for certain portions of the reference genome according to a threshold of the measure of error, mappability, repeatability, genomic portion-specific t-statistic, or combination thereof.

9. The method of claim 8, wherein the threshold is selected according to a standard deviation gap between a first genomic section level and a second genomic section level of 3.5 or greater.

10. The method of claim 8, wherein the measure of error is an R factor and the sequence read count for a portion of the reference genome having an R factor of 7% or greater is removed.

11. The method of claim 1, wherein the portions of the reference genome are in one or more sex chromosomes.

12. The method of claim 11, wherein the number of portions of the reference genome is 20 or more portions for chromosome Y.

13. The method of claim 12, wherein the portions for chromosome Y are chosen from among chrY_125, chrY_169, chrY_170, chrY_171, chrY_172, chrY_182, chrY_183, chrY_184, chrY_186, chrY_187, chrY_192, chrY_417, chrY_448, chrY_449, chrY_473, chrY_480, chrY_481, chrY_485, chrY_491, chrY_502, chrY_519, chrY_535, chrY_559, chrY_1176, chrY_1177, and chrY_1178.

14. The method of claim 13, wherein the portions for chromosome Y comprise one or more of chrY_1176, chrY_1177, and chrY_1178.

15. The method of claim 13, wherein the portions for chromosome Y do not comprise one or more of chrY_1176, chrY_1177, and chrY_1178.

16. The method of claim 13, further comprising: comparing genomic section levels, or derivatives thereof, for one or more of chrY_1176, chrY_1177, and chrY_1178, to genomic section levels, or derivatives thereof, for one or more of chrY_125, chrY_169, chrY_170, chrY_171, chrY_172, chrY_182, chrY_183, chrY_184, chrY_186, chrY_187, chrY_192, chrY_417, chrY_448, chrY_449, chrY_473, chrY_480, chrY_481, chrY_485, chrY_491, chrY_502, chrY_519, chrY_535 and chrY_559, thereby generating a comparison.

17. The method of claim 16, wherein sequence read counts for one or more of chrY_1176, chrY_1177, and chrY_1178 are removed or replaced according to the comparison.

18. The method of claim 1, wherein a subset of portions in chromosome X in the reference genome is utilized for determining sex chromosome karyotype, wherein the subset comprises about 2350 or more portions for chromosome X.

19. The method of claim 1, wherein the reference genome is from a male subject.

20. The method of claim 1, wherein the reference genome is from a female subject.

21. The method of claim 1, wherein each portion of the reference genome comprises a nucleotide sequence of a predetermined length.

22. The method of claim 21, wherein the predetermined length is 50 kilobases.

23. The method of claim 1, wherein the sex chromosome karyotype is chosen from XX, XY, XXX, X, XXY and XYY.

24. The method of claim 1, wherein the nucleic acid is from blood plasma or blood serum.

25. The method of claim 1, further comprising after (c), generating a Z-score from the genomic section levels.

26. The method of claim 1, wherein (V) is performed using a microprocessor.

27. The method of claim 1, wherein the sequencing in (I) comprises simultaneous analysis of up to 96 samples in an 8-lane flow cell.

28. The method of claim 1, wherein the sequencing in (I) comprises simultaneous analysis of up to 384 samples in an 8-lane flow cell.

* * * * *